United States Patent
Childers et al.

(10) Patent No.: US 9,725,445 B2
(45) Date of Patent: *Aug. 8, 2017

(54) CYCLOALKYL NITRILE PYRAZOLO PYRIDONES AS JANUS KINASE INHIBITORS

(71) Applicant: Merck Sharp & Dohme Corp., Rahway, NJ (US)

(72) Inventors: Matthew Lloyd Childers, Medfield, MA (US); Christopher Dinsmore, Newton, MA (US); Peter Fuller, Ashland, MA (US); David Guerin, Natick, MA (US); Jason David Katz, Newton, MA (US); Qinglin Pu, Needham, MA (US); Mark E. Scott, Andover, MA (US); Christopher F. Thompson, Arlington, MA (US); Hongjun Zhang, Newton, MA (US); Danielle Falcone, Brookline, MA (US); Luis Torres, Norwood, MA (US); Jason Brubaker, Cambridge, MA (US); Hongbo Zeng, Westford, MA (US); Jiaqiang Cai, Shanghai (CN); Xiaoxing Du, Shanghai (CN); Chonggang Wang, Shanghai (CN); Yunfeng Bai, Beijing (CN); Norman Kong, Beijing (CN); Yumei Liu, Beijing (CN); Zhixiang Zheng, Beijing (CN)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/778,019

(22) PCT Filed: Mar. 19, 2014

(86) PCT No.: PCT/CN2014/000296
§ 371 (c)(1),
(2) Date: Sep. 17, 2015

(87) PCT Pub. No.: WO2014/146490
PCT Pub. Date: Sep. 25, 2014

(65) Prior Publication Data
US 2016/0280704 A1    Sep. 29, 2016

(30) Foreign Application Priority Data

Mar. 19, 2013 (WO) ............... PCT/CN2013/072867

(51) Int. Cl.
C07D 471/04  (2006.01)
C07D 519/00  (2006.01)

(52) U.S. Cl.
CPC ......... *C07D 471/04* (2013.01); *C07D 519/00* (2013.01)

(58) Field of Classification Search
CPC .......................... C07D 471/04; C07D 519/00
See application file for complete search history.

(56) References Cited

U.S. PATENT DOCUMENTS

| 2010/0105661 A1 | 4/2010 | Shirakami |
| 2012/0178740 A1 | 7/2012 | Nielsen et al. |
| 2016/0272634 A1 | 9/2016 | Dinsmore et al. |

FOREIGN PATENT DOCUMENTS

| CN | 102574857 | 7/2012 |
| EP | 2857400 | 4/2015 |
| WO | WO2009035575 A1 | 3/2009 |
| WO | 2011003418 | 1/2011 |
| WO | 2011112662 | 9/2011 |
| WO | 2012127506 | 9/2012 |
| WO | 2013180265 | 12/2013 |

OTHER PUBLICATIONS

International Search Report—PCT/CN2011/000296—Mail date: Jun. 30, 2014.
Smyth et al., Synthesis and reactivity of 3-amino-1H-pyrazolo[4,3-c]pyridin-4(5H)-ones: development of a novel kinase-focussed library. Tetrahedron, Elsevier Science Publishers, Amsterdam, NL, vol. 66, No. 15, pp. 2843-2854.
Supplementary European Search Report—EP14767371—Mail Date: Aug. 1, 2016.
Huisman, Gjalt, W. et al., Practical chiral alcohol manufacture using ketoreductases, Current Opinion in Chemical Biology, 2010, p. 122-129, vol. 14.
Keystone et al., 12-Week Results of a Phase 2B Dose-Ranging Study of LY3009104 (INCB028050) an oral JAJ/JAK2 inhibitor, in combination with traditional DMARDs in patients wit rheumatoid arthritis. (Abstract LB0005), Ann. Rheum. Dis, 2012, pp. 152-154, vol. 71 (S31).
Kwatra et al., JAK Inhibitors i Psoriasis: A Promising new Treatment Modality, Journal of Drugs in Dermatology, 2012, pp. 913-918, vol. 11, Issue 8.

(Continued)

*Primary Examiner* — Samira Jean-Louis
(74) *Attorney, Agent, or Firm* — Patricia A. Shatynski; Catherine D. Fitch

(57) ABSTRACT

Compounds of formula I are provided, which are JAK inhibitors and are useful for the treatment of JAK-mediated diseases such as rheumatoid arthritis, asthma, COPD and cancer.

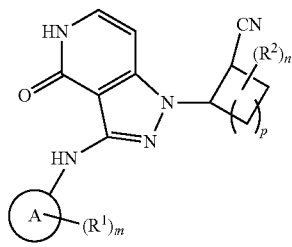

I

17 Claims, No Drawings

(56) References Cited

OTHER PUBLICATIONS

Matsunaga et al., Effects of a Junus kinase inhibitor, pyridone 6, on airway responses in a murine model of asthma, Biochemical and Biophysical Research Communications, 2011, pp. 261-267, vol. 404.

O'Shea et al., Janus kinase inhibitors in autoimmune diseases, Ann Rheum Dis, 2013, pp. 111-115, vol. 71.

Stump et al., A highly selective, orally active inhibitor of Janus kinase 2, CEP-33779, ablates disease in two mouse models of sheumatoid arthritis, Arthritis Research Therapy, 2011, pp. 1-15, vol. 13.

Vanhoutte et al., Efficacy and Safety of GLPG0634, a SelectiveJAK1 Inhibitor, as Monotherapy in Patients With Active Rheumatoid Arthritis, Ann. Rheum. Dis, 2012, pp. 145-146, vol. 71, (S3).

Williams et al., A Randomized Placebo-Controlled Study of INCB018824, a Selective Janus Kinase 1&2 (JAK1&2) Inhibitor in Rheumatoid Arthritis, Arthritis Rheum. (Abstract), 2008, pp. S431, vol. 58.

CYCLOALKYL NITRILE PYRAZOLO PYRIDONES AS JANUS KINASE INHIBITORS

CROSS REFERENCE TO RELATED APPLICATIONS

This application is a U.S. National Phase application under 35 U.S.C. §371 of PCT Application No. PCT/CN2014/000296, filed Mar. 19, 2014 which claims priority under 35 U.S.C. §365 from PCT Application No. PCT/CN2013/072867 filed on Mar. 19, 2013.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)).

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts, or stereoisomers thereof:

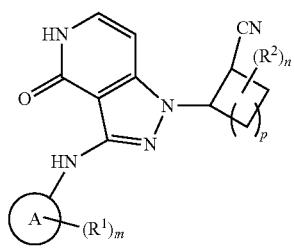

I

A is selected from aryl and heteroaryl;
n is 0, 1, 2, 3, or 4;
m is 0, 1, 2, 3, or 4;
p is 0, 1, 2, 3, or 4;
$R^1$ is selected from:
  halogen,
  Oxo (=O),
  $C_{1-10}$ alkyl(oxy)$_{0-1}$(carbonyl)$_{0-1}C_{0-10}$ alkyl,
  $C_{1-10}$ heteroalkyl(oxy)$_{0-1}$(carbonyl)$_{0-1}C_{0-10}$ alkyl,
  $C_{2-10}$ alkenyl(oxy)$_{0-1}$(carbonyl)$_{0-1}C_{0-10}$ alkyl,
  aryl $C_{0-10}$ alkyl(oxy)$_{0-1}$(carbonyl)$_{0-1}C_{0-10}$ alkyl,
  $C_{3-12}$ cycloalkyl $C_{0-10}$ alkyl(oxy)$_{0-1}$(carbonyl)$_{0-1}C_{0-10}$ alkyl,
  heteroaryl $C_{0-10}$ alkyl(oxy)$_{0-1}$(carbonyl)$_{0-1}C_{0-10}$ alkyl,
  $(C_{3-12})$heterocycloalkyl $C_{0-10}$ alkyl(oxy)$_{0-1}$(carbonyl)$_{0-1}C_{0-10}$ alkyl,
  $C_{0-10}$ alkyl(oxy)$_{0-1}$(carbonyl)$_{0-1}$amino$C_{0-10}$ alkyl,
  $(C_{1-10})$heteroalkyl(oxy)$_{0-1}$(carbonyl)$_{0-1}$amino$C_{0-10}$ alkyl,
  $C_{3-12}$ cycloalkyl $C_{0-10}$ alkyl(oxy)$_{0-1}$(carbonyl)$_{0-1}$amino$C_{0-10}$ alkyl,
  aryl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl,
($C_{3-12}$)heterocycloalkyl $C_{0-10}$ alkyl(oxy)$_{0-1}$(carbonyl)$_{0-1}$amino$C_{0-10}$ alkyl,
$C_{0-10}$ alkylamino(carbonyl)$_{0-1}$$C_{0-10}$ alkyl,
($C_{1-10}$)heteroalkylamino(carbonyl)$_{0-1}$$C_{0-10}$ alkyl,
$C_{3-12}$ cycloalkylamino(carbonyl)$_{0-1}$$C_{0-10}$ alkyl,
aryl $C_{0-10}$ alkylaminoamino(carbonyl)$_{0-1}$$C_{0-10}$ alkyl,
heteroaryl $C_{0-10}$ alkylamino(carbonyl)$_{0-1}$$C_{0-10}$ alkyl,
($C_{3-12}$)heterocycloalkylamino(carbonyl)$_{0-1}$$C_{0-10}$ alkyl,
$C_{1-10}$ alkylsulfonyl$C_{0-10}$ alkyl,
$C_{1-10}$ heteroalkylsulfonyl$C_{0-10}$ alkyl,
($C_{3-12}$)cycloalkyl$C_{0-10}$alkylsulfonyl$C_{0-10}$ alkyl,
($C_{3-12}$)cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
($C_{3-12}$)cycloalkyl$C_{0-10}$ alkylsulfamoyl$C_{0-10}$ alkyl,
($C_{3-12}$)cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$C_{1-10}$ alkylsulfonimidoyl$C_{0-10}$ alkyl,
$C_{1-10}$ heteroalkylsulfonimidoyl$C_{0-10}$ alkyl,
($C_{3-12}$)cycloalkyl$C_{0-10}$ alkylsulfonimidoyl$C_{0-10}$ alkyl,
($C_{3-12}$)cycloheteroalkyl$C_{0-10}$alkysulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$C_{1-10}$ alkylthio$C_{0-10}$ alkyl,
($C_{0-10}$ alkyl)$_{1-2}$ amino,
—$CO_2$($C_{0-10}$ alkyl),
—($C_{0-10}$ alkyl)$CO_2H$,
—$SO_2NH_2$,
—$SO_2NH$($C_{1-10}$ alkyl),
—$SO_2N$($C_{1-10}$ alkyl)$_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
($C_{3-12}$)cycloalkyl$C_{0-10}$alkylsulfinyl$C_{0-10}$alkyl,
($C_{3-12}$)cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$ alkyl,
$C_{0-10}$ alkylsulfinylamino$C_{0-10}$ alkyl,
$C_{1-4}$acylamino $C_{0-10}$ alkyl,
hydroxy,
—($C_{1-10}$ alkyl)OH,
—$C_{1-10}$ alkylalkoxy,
cyano,
($C_{1-6}$alkyl)cyano, and
$C_{1-6}$haloalkyl; and
wherein two $R^1$ may optionally join together with the ring atom to
which each is attached to form a 3 to 6 membered saturated ring;
$R^2$ is selected from:
halogen,
Oxo (═O),
$C_{1-10}$ alkyl(oxy)$_{0-1}$(carbonyl)$_{0-1}$$C_{0-10}$ alkyl,
$C_{3-12}$ cycloalkyl,
($C_{3-12}$)heterocycloalkyl $C_{0-10}$ alkyl(oxy)$_{0-1}$(carbonyl)$_{0-1}$$C_{0-10}$ alkyl,
$C_{0-10}$ alkylamino$C_{0-10}$alkyl,
($C_{1-10}$)heteroalkylamino$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
($C_{3-12}$)heterocycloalkyl $C_{0-10}$ alkylamino$C_{0-10}$ alkyl,
$C_{1-10}$ alkylsulfonyl,
($C_{3-12}$)cycloalkyl$C_{0-10}$alkylsulfonyl,
($C_{3-12}$)cycloheteroalkyl$C_{0-10}$alkylsulfonyl,
($C_{0-10}$ alkyl)$_{1-2}$ amino,
—$CO_2$($C_{0-10}$ alkyl),
—($C_{0-10}$ alkyl)$CO_2H$,
—$SO_2CF_3$,
—$SO_2CF_2H$,
$C_{1-10}$ alkylsulfinyl,
hydroxy,
—($C_{1-10}$ alkyl)OH,
—$C_{1-10}$ alkylalkoxy,
cyano,
($C_{1-6}$alkyl)cyano, and
$C_{1-6}$haloalkyl, and
wherein two $R^2$ may optionally join together with the ring atom to
which each is attached to form a 3 to 6 membered saturated ring; and
wherein $R^1$ and $R^2$ are each optionally substituted with 1, 2, 3, or 4 $R^3$ substituents;
$R^3$ is independently selected from:
halogen,
$C_{1-10}$ alkyl(oxy)$_{0-1}$(carbonyl)$_{0-1}$$C_{0-10}$ alkyl, and
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
($C_{3-12}$)heterocycloalkyl $C_{0-10}$ alkyl(oxy)$_{0-1}$(carbonyl)$_{0-1}$$C_{0-10}$ alkyl,
(($C_{0-10}$)alkyl)$_{1-2}$aminocarbonyloxy,
aryl ($C_{0-10}$)alkylaminocarbonyloxy,
—$CO_2$($C_{0-10}$ alkyl),
—($C_{0-10}$ alkyl)$CO_2H$,
Oxo (═O),
—$SO_2NH_2$,
—$SO_2NH$($C_{1-10}$ alkyl),
—$SO_2N$($C_{1-10}$ alkyl)$_2$,
—$SO_2CF_3$,
—$SO_2CF_2H$,
$C_{1-10}$ alkylsulfinyl,
amino,
($C_{0-10}$ alkyl)$_{1-2}$ amino,
-(oxy)$_{0-1}$(carbonyl)$_{0-1}$N($C_{0-10}$ alkyl)$_{1-2}$
hydroxy,
($C_{1-10}$ alkyl)OH,
$C_{1-10}$ alkoxy,
($C_{1-10}$ alkyl)cyano,
cyano, and
$C_{1-6}$haloalkyl; and
$R^3$ is optionally substituted with 1, 2, or 3 $R^4$ substituents selected from hydrogen, ($C_{1-6}$)alkyl, ($C_{1-6}$) alkoxy, ($C_{1-10}$ alkyl)OH, halogen, $CO_2H$, —($C_{0-6}$)alkylCN, —O(C═O)$C_1$-$C_6$ alkyl, $NO_2$, trifluoromethoxy, trifluoroethoxy, trifluoromethyl, trifluoroethyl, —N—C(O)O($C_{0-6}$) alkyl, $C_{1-10}$ alkylsulfonyl, oxo (O═), aminosulfonyl, —$SO_2NH_2$, —$SO_2NH$($C_{1-10}$ alkyl), —$SO_2N$($C_{1-10}$ alkyl)$_2$, —$SO_2C_{1-6}$alkyl, —$SO_2CF_3$, —$SO_2CF_2H$, —$C_{1-10}$ alkylsulfinyl, —$O_{(0-1)}$($C_{1-10}$)haloalkyl, amino($C_{1-6}$alkyl)$_{0-2}$ and $NH_2$.

Representative compounds of the instant invention include, but are not limited to the following compounds and their pharmaceutically acceptable salts and stereoisomers thereof:

2-{3-[(4-fluorophenyl)amino]-4-oxo-4,5-dihydro-1H-pyrazolo[4,3-c]pyridin-1-yl}cyclohexanecarbonitrile;

2-(3-{[4-(methylsulfonyl)phenyl]amino}-4-oxo-4,5-dihydro-1H-pyrazolo[4,3-c]pyridin-1-yl)cyclohexanecarbonitrile;

2-{3-[(2-fluoropyridin-4-yl)amino]-4-oxo-4,5-dihydro-1H-pyrazolo[4,3-c]pyridin-1-yl}cyclohexanecarbonitrile;

2-{3-[(4-chlorophenyl)amino]-4-oxo-4,5-dihydro-1H-pyrazolo[4,3-c]pyridin-1-yl}cyclohexanecarbonitrile;

2-{3-[(4-chlorophenyl)amino]-4-oxo-4,5-dihydro-1H-pyrazolo[4,3-c]pyridin-1-yl}-5-{[1-cyclopropylethyl]amino}cyclohexanecarbonitrile;

5-hydroxy-2-(4-oxo-3-{[4-(trifluoromethyl)phenyl]amino}-4,5-dihydro-1H-pyrazolo[4,3-c]pyridin-1-yl)cyclohexanecarbonitrile;

5-azetidin-1-yl-2-(4-oxo-3-{[4-(trifluoromethyl)phenyl]amino}-4,5-dihydro-1H-pyrazolo[4,3-c]pyridin-1-yl)cyclohexanecarbonitrile;

5-{[1-cyclopropylethyl]amino}-2-(4-oxo-3-{[4-(trifluoromethyl)phenyl]amino}-4,5-dihydro-1H-pyrazolo[4,3-c]pyridin-1-yl)cyclohexanecarbonitrile;

5-{[1-cyclopropylethyl]amino}-2-(4-oxo-3-{[4-(trifluoromethyl)phenyl]amino}-4,5-dihydro-1H-pyrazolo[4,3-c]pyridin-1-yl)cyclohexanecarbonitrile;

5-azetidin-1-yl-2-{3-[(4-chloro-3-fluorophenyl)amino]-4-oxo-4,5-dihydro-1H-pyrazolo[4,3-c]pyridin-1-yl}cyclohexanecarbonitrile;

2-{3-[(4-chloro-3-fluorophenyl)amino]-4-oxo-4,5-dihydro-1H-pyrazolo[4,3-c]pyridin-1-yl}-5-(dimethylamino)cyclohexanecarbonitrile;

2-{3-[(4-chloro-3-fluorophenyl)amino]-4-oxo-4,5-dihydro-1H-pyrazolo[4,3-c]pyridin-1-yl}-5-{[1-cyclopropylethyl]amino}cyclohexanecarbonitrile;

5-azetidin-1-yl-2-{3-[(4-chlorophenyl)amino]-4-oxo-4,5-dihydro-1H-pyrazolo[4,3-c]pyridin-1-yl}cyclohexanecarbonitrile;

2-{3-[(4-chlorophenyl)amino]-4-oxo-4,5-dihydro-1H-pyrazolo[4,3-c]pyridin-1-yl}-5-(dimethylamino)cyclohexanecarbonitrile;

5-azetidin-1-yl-2-(4-oxo-3-{[4-(trifluoromethoxy)phenyl]amino}-4,5-dihydro-1H-pyrazolo[4,3-c]pyridin-1-yl)cyclohexanecarbonitrile;

5-{[1-cyclopropylethyl]amino}-2-(4-oxo-3-{[4-(trifluoromethoxy)phenyl]amino}-4,5-dihydro-1H-pyrazolo[4,3-c]pyridin-1-yl)cyclohexanecarbonitrile;

5-(dimethylamino)-2-(4-oxo-3-{[4-(trifluoromethoxy)phenyl]amino}-4,5-dihydro-1H-pyrazolo[4,3-c]pyridin-1-yl)cyclohexanecarbonitrile;

2-{4-oxo-3-[(2,2,2-trifluoroethyl)amino]-4,5-dihydro-1H-pyrazolo[4,3-c]pyridin-1-yl}cyclohexanecarbonitrile;

2-{3-[(4-chlorophenyl)amino]-4-oxo-4,5-dihydro-1H-pyrazolo[4,3-c]pyridin-1-yl}-5-(3-hydroxy-3-methylazetidin-1-yl)cyclohexanecarbonitrile;

2-{3-[(4-chlorophenyl)amino]-4-oxo-4,5-dihydro-1H-pyrazolo[4,3-c]pyridin-1-yl}-5-(3-hydroxyazetidin-1-yl)cyclohexanecarbonitrile;

4-({1-[2-cyanocyclohexyl]-4-oxo-4,5-dihydro-1H-pyrazolo[4,3-c]pyridin-3-yl}amino)-N,N-dimethylbenzenesulfonamide;

4-({1-[2-cyanocyclohexyl]-4-oxo-4,5-dihydro-1H-pyrazolo[4,3-c]pyridin-3-yl}amino)benzenesulfonamide;

(2-{3-[(2-fluoropyridin-4-yl)amino]-4-oxo-4,5-dihydro-1H-pyrazolo[4,3-c]pyridin-1-yl}cyclopentanecarbonitrile;

(2-(3-{[4-(methylsulfonyl)phenyl]amino}-4-oxo-4,5-dihydro-1H-pyrazolo[4,3-c]pyridin-1-yl)cyclopentanecarbonitrile;

2-[4-oxo-3-({4-[2,2,2-trifluoro-1-hydroxyethyl]phenyl}amino)-4,5-dihydro-1H-pyrazolo[4,3-c]pyridin-1-yl]cyclohexanecarbonitrile;

2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclohexanecarbonitrile;

4-({1-[2-cyanocyclopentyl]-4-oxo-4,5-dihydro-1H-pyrazolo[4,3-c]pyridin-3-yl}amino)-N,N-dimethylbenzenesulfonamide;

2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclopentanecarbonitrile;

2-(4-oxo-3-{[4-(2,2,2-trifluoro-1-hydroxyethyl)phenyl]amino}-4,5-dihydro-1H-pyrazolo[4,3-c]pyridin-1-yl)cyclopentanecarbonitrile;

4-({1-[2-cyanocyclopentyl]-4-oxo-4,5-dihydro-1H-pyrazolo[4,3-c]pyridin-3-yl}amino)benzenesulfonamide;

2-[3-({1-[2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide;

N-[3-({1-[2-cyanocyclohexyl]-4-oxo-4,5-dihydro-1H-pyrazolo[4,3-c]pyridin-3-yl}amino)benzyl]-1,3-oxazole-5-carboxamide;

N-[3-({1-[2-cyanocyclohexyl]-4-oxo-4,5-dihydro-1H-pyrazolo[4,3-c]pyridin-3-yl}amino)benzyl]pyrimidine-2-carboxamide;

2-[3-({1-[2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide;

tert-butyl [3-({1-[2-cyanocyclohexyl]-4-oxo-4,5-dihydro-1H-pyrazolo[4,3-c]pyridin-3-yl}amino)benzyl]carbamate;

2-(3-{[3-(aminomethyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-N-(1-methylethyl)benzenesulfonamide;

N-benzyl-4-({1-[2-cyanocyclohexyl]-4-oxo-4,5-dihydro-1H-pyrazolo[4,3-c]pyridin-3-yl}amino)benzenesulfonamide;

4-({1-[2-cyanocyclohexyl]-4-oxo-4,5-dihydro-1H-pyrazolo[4,3-c]pyridin-3-yl}amino)-N-(cyclopropylmethyl)benzenesulfonamide;

4-({1-[2-cyanocyclohexyl]-4-oxo-4,5-dihydro-1H-pyrazolo[4,3-c]pyridin-3-yl}amino)-N-(2-methoxyethyl)benzenesulfonamide;

4-({1-[2-cyanocyclohexyl]-4-oxo-4,5-dihydro-1H-pyrazolo[4,3-c]pyridin-3-yl}amino)-N-cyclohexylbenzenesulfonamide;

2-(3-{[4-(morpholin-4-ylsulfonyl)phenyl]amino}-4-oxo-4,5-dihydro-1H-pyrazolo[4,3-c]pyridin-1-yl)cyclohexanecarbonitrile;

2-[4-oxo-3-(phenylamino)-4,5-dihydro-1H-pyrazolo[4,3-c]pyridin-1-yl]cyclohexanecarbonitrile; 2-(3-{[3-methyl-4-(pyrrolidin-1-ylcarbonyl)phenyl]amino}-4-oxo-4,5-dihydro-1H-pyrazolo[4,3-c]pyridin-1-yl)cyclohexanecarbonitrile;

2-(4-oxo-3-{[3-(2H-1,2,3-triazol-2-ylmethyl)phenyl]amino}-4,5-dihydro-1H-pyrazolo[4,3-c]pyridin-1-yl)cyclohexanecarbonitrile;

N-[4-({1-[2-cyanocyclohexyl]-4-oxo-4,5-dihydro-1H-pyrazolo[4,3-c]pyridin-3-yl}amino)benzyl]-1,3-oxazole-5-carboxamide;

N-[4-({1-[2-cyanocyclohexyl]-4-oxo-4,5-dihydro-1H-pyrazolo[4,3-c]pyridin-3-yl}amino)benzyl]pyrimidine-2-carboxamide;

2-(3-{[3-(1-hydroxyethyl)phenyl]amino}-4-oxo-4,5-dihydro-1H-pyrazolo[4,3-c]pyridin-1-yl)cyclohexanecarbonitrile;

tert-butyl [4-({1-[2-cyanocyclohexyl]-4-oxo-4,5-dihydro-1H-pyrazolo[4,3-c]pyridin-3-yl}amino)benzyl]carbamate;

2-(3-{[4-(aminomethyl)phenyl]amino}-4-oxo-4,5-dihydro-1H-pyrazolo[4,3-c]pyridin-1-yl)cyclohexanecarbonitrile;

2-(3-{[3-(aminomethyl)-4-fluorophenyl]amino}-4-oxo-4,5-dihydro-1H-pyrazolo[4,3-c]pyridin-1-yl)cyclohexanecarbonitrile;

2-(3-{[3-(morpholin-4-ylmethyl)phenyl]amino}-4-oxo-4,5-dihydro-1H-pyrazolo[4,3-c]pyridin-1-yl)cyclohexanecarbonitrile;

tert-butyl [5-({1-[2-cyanocyclohexyl]-4-oxo-4,5-dihydro-1H-pyrazolo[4,3-c]pyridin-3-yl}amino)-2-fluorobenzyl]carbamate;

tert-butyl [3-({1-[2-cyanocyclohexyl]-4-oxo-4,5-dihydro-1H-pyrazolo[4,3-c]pyridin-3-yl}amino)-5-fluorobenzyl]carbamate;

2-{3-[(3-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile;

2-(3-{[3-(1-hydroxy-2-methoxy-1-methylethyl)-4-(methylsulfonyl)phenyl]amino}-4-oxo-4,5-dihydro-1H-pyrazolo[4,3-c]pyridin-1-yl)cyclohexanecarbonitrile;

2-(3-{[3-(1,3-dihydroxy-1-methylpropyl)-4-(methylsulfonyl)phenyl]amino}-4-oxo-4,5-dihydro-1H-pyrazolo[4,3-c]pyridin-1-yl)cyclohexanecarbonitrile;

2-(3-{[3-(1,2-dihydroxy-1-methylethyl)-4-(methylsulfonyl)phenyl]amino}-4-oxo-4,5-dihydro-1H-pyrazolo[4,3-c]pyridin-1-yl)cyclohexanecarbonitrile;

2-[3-(2,3-dihydro-1H-isoindol-5-ylamino)-4-oxo-4,5-dihydro-1H-pyrazolo[4,3-c]pyridin-1-yl]cyclohexanecarbonitrile;

2-[3-({3-[(4-methyl-1H-1,2,3-triazol-1-yl)methyl]phenyl}amino)-4-oxo-4,5-dihydro-1H-pyrazolo[4,3-c]pyridin-1-yl]cyclohexanecarbonitrile;

2-[3-({3-[1-amino-2,2,2-trifluoroethyl]phenyl}amino)-4-oxo-4,5-dihydro-1H-pyrazolo[4,3-c]pyridin-1-yl]cyclohexanecarbonitrile;

N-{1-[3-({1-[2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide;

2-(4-oxo-3-{[3-(2,2,4-trimethyl-1,3-dioxolan-4-yl)phenyl]amino}-4,5-dihydro-1H-pyrazolo[4,3-c]pyridin-1-yl)cyclohexanecarbonitrile;

2-{4-oxo-3-[(3-{[(2,2,2-trifluoroethyl)amino]methyl}phenyl)amino]-4,5-dihydro-1H-pyrazolo[4,3-c]pyridin-1-yl}cyclohexanecarbonitrile;

2-(3-{[3-(aminomethyl)-4-(methylsulfonyl)phenyl]amino}-4-oxo-4,5-dihydro-1H-pyrazolo[4,3-c]pyridin-1-yl)cyclohexanecarbonitrile;

6-(3-{[4-(methylsulfonyl)phenyl]amino}-4-oxo-4,5-dihydro-1H-pyrazolo[4,3-c]pyridin-1-yl)spiro[2.5]octane-5-carbonitrile;

N-[5-({1-[2-cyanocyclohexyl]-4-oxo-4,5-dihydro-1H-pyrazolo[4,3-c]pyridin-3-yl}amino)-2-(dimethylsulfamoyl)benzyl]acetamide;

2-[3-({3-[(dimethylamino)methyl]phenyl}amino)-4-oxo-4,5-dihydro-1H-pyrazolo[4,3-c]pyridin-1-yl]cyclohexanecarbonitrile;

2-(3-{[3-(1,2-dihydroxy-1-methylethyl)phenyl]amino}-4-oxo-4,5-dihydro-1H-pyrazolo[4,3-c]pyridin-1-yl)cyclohexanecarbonitrile;

4-{[1-(5-cyanospiro[2.5]oct-6-yl)-4-oxo-4,5-dihydro-1H-pyrazolo[4,3-c]pyridin-3-yl]amino}-N,N-dimethylbenzenesulfonamide;

2-(aminomethyl)-4-({1-[2-cyanocyclohexyl]-4-oxo-4,5-dihydro-1H-pyrazolo[4,3-c]pyridin-3-yl}amino)-N,N-dimethylbenzenesulfonamide;

2-(4-oxo-3-{[3-(1H-pyrazol-1-ylmethyl)phenyl]amino}-4,5-dihydro-1H-pyrazolo[4,3-c]pyridin-1-yl)cyclohexanecarbonitrile;

2-(4-oxo-3-{[4-(pyrrolidin-1-ylcarbonyl)phenyl]amino}-4,5-dihydro-1H-pyrazolo[4,3-c]pyridin-1-yl)cyclohexanecarbonitrile;

2-(4-oxo-3-{[4-(1H-1,2,3-triazol-1-ylmethyl)phenyl]amino}-4,5-dihydro-1H-pyrazolo[4,3-c]pyridin-1-yl)cyclohexanecarbonitrile;

2-(3-{[3-(1H-imidazol-1-ylmethyl)phenyl]amino}-4-oxo-4,5-dihydro-1H-pyrazolo[4,3-c]pyridin-1-yl)cyclohexanecarbonitrile;

6-(3-{[4-(methylsulfonyl)phenyl]amino}-4-oxo-4,5-dihydro-1H-pyrazolo[4,3-c]pyridin-1-yl)spiro[2.5]octane-5-carbonitrile;

2-(3-{[4-hydroxy-4-(hydroxymethyl)-1,1-dioxido-3,4-dihydro-2H-thiochromen-6-yl]amino}-4-oxo-4,5-dihydro-1H-pyrazolo[4,3-c]pyridin-1-yl)cyclohexanecarbonitrile;

2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-(4-oxo-3-{[3-(1H-1,2,4-triazol-1-ylmethyl)phenyl]amino}-4,5-dihydro-1H-pyrazolo[4,3-c]pyridin-1-yl)cyclohexanecarbonitrile;

2-(4-oxo-3-{[3-(1H-1,2,4-triazol-4-ylmethyl)phenyl]amino}-4,5-dihydro-1H-pyrazolo[4,3-c]pyridin-1-yl)cyclohexanecarbonitrile;

2-{3-[(4-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-{3-[(1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

N-{1-[4-({1-[2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide;

2-[3-({4-[1-amino-2,2,2-trifluoroethyl]phenyl}amino)-4-oxo-4,5-dihydro-1H-pyrazolo[4,3-c]pyridin-1-yl]cyclohexanecarbonitrile;

2-{4-oxo-3-[(4-{[(2,2,2-trifluoroethyl)amino]methyl}phenyl)amino]-4,5-dihydro-1H-pyrazolo[4,3-c]pyridin-1-yl}cyclohexanecarbonitrile;

2-[4-oxo-3-({4-[(pyrrolidin-1-ylsulfonyl)methyl]phenyl}amino)-4,5-dihydro-1H-pyrazolo[4,3-c]pyridin-1-yl]cyclohexanecarbonitrile;

2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{3-[(1,1-dioxido-2,3-dihydro-1-benzothiophen-5-yl)amino]-4-oxo-4,5-dihydro-1H-pyrazolo[4,3-c]pyridin-1-yl}cyclohexanecarbonitrile;

2-{3-[(2-ethyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile;

2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclopentanecarbonitrile;

2-(4-oxo-3-{[2-(2,2,2-trifluoroethyl)-2,3-dihydro-1H-isoindol-5-yl]amino}-4,5-dihydro-1H-pyrazolo[4,3-c]pyridin-1-yl)cyclohexanecarbonitrile;

5-({1-[2-cyanocyclohexyl]-4-oxo-4,5-dihydro-1H-pyrazolo[4,3-c]pyridin-3-yl}amino)-2,3-dihydro-1H-indene-2-carboxylic acid;

2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile;

2-(3-{[2-(cyclopropylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{3-[(2-methyl-2,3-dihydro-1H-isoindol-5-yl)amino]-4-oxo-4,5-dihydro-1H-pyrazolo[4,3-c]pyridin-1-yl}cyclohexanecarbonitrile;

2-[3-({4-[1-(dimethylamino)-2,2,2-trifluoroethyl]phenyl}amino)-4-oxo-4,5-dihydro-1H-pyrazolo[4,3-c]pyridin-1-yl]cyclohexanecarbonitrile;

2-(3-{[2-(cyclopentylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{4-oxo-3-[(4-{1-[(2,2,2-trifluoroethyl)amino]ethyl}phenyl)amino]-4,5-dihydro-1H-pyrazolo[4,3-c]pyridin-1-yl}cyclopentanecarbonitrile;

4-({1-[2-cyanocyclohexyl]-4-oxo-4,5-dihydro-1H-pyrazolo[4,3-c]pyridin-3-yl}amino)-N,N,2-trimethylbenzamide;

2-(3-{[3-methyl-4-(morpholin-4-ylcarbonyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-2-cyclopropyl-N,N-dimethylbenzamide;

2-[3-({4-[1-amino-2,2-difluoroethyl]phenyl}amino)-4-oxo-4,5-dihydro-1H-pyrazolo[4,3-c]pyridin-1-yl]cyclohexanecarbonitrile;

2-(3-{[4-(2,2-difluoro-1-hydroxyethyl)phenyl]amino}-4-oxo-4,5-dihydro-1H-pyrazolo[4,3-c]pyridin-1-yl)cyclohexanecarbonitrile;

2-[4-oxo-3-({4-[pyrrolidin-2-yl]phenyl}amino)-4,5-dihydro-1H-pyrazolo[4,3-c]pyridin-1-yl]cyclohexanecarbonitrile;

2-{4-oxo-3-[(4-{1-[(2,2,2-trifluoroethyl)amino]ethyl}phenyl)amino]-4,5-dihydro-1H-pyrazolo[4,3-c]pyridin-1-yl}cyclohexanecarbonitrile;

2-(3-{[2-(1-methylethyl)-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[2-(2-methylpropyl)-2,3-dihydro-1H-isoindol-5-yl]amino}-4-oxo-4,5-dihydro-1H-pyrazolo[4,3-c]pyridin-1-yl)cyclohexanecarbonitrile;

2-{3-[(2-ethyl-2,3-dihydro-1H-isoindol-5-yl)amino]-4-oxo-4,5-dihydro-1H-pyrazolo[4,3-c]pyridin-1-yl}cyclohexanecarbonitrile;

2-(3-{[2-(cyclopropylmethyl)-2,3-dihydro-1H-isoindol-5-yl]amino}-4-oxo-4,5-dihydro-1H-pyrazolo[4,3-c]pyridin-1-yl)cyclohexanecarbonitrile;

2-[3-({3-[(methylsulfanyl)methyl]-5-(1H-1,2,3-triazol-1-ylmethyl)phenyl}amino)-4-oxo-4,5-dihydro-1H-pyrazolo[4,3-c]pyridin-1-yl]cyclohexanecarbonitrile;

2-(3-{[2-(1-methylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(2-hydroxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(3-hydroxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-[4-oxo-3-({4-[1-(1H-1,2,3-triazol-1-yl)ethyl]phenyl}amino)-4,5-dihydro-1H-pyrazolo[4,3-c]pyridin-1-yl]cyclohexanecarbonitrile;

2-[3-({4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile;

2-(3-{[2-(3-hydroxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-[3-({4-[1-amino-2,2,2-trifluoroethyl]phenyl}amino)-4-oxo-4,5-dihydro-1H-pyrazolo[4,3-c]pyridin-1-yl]cyclopentanecarbonitrile;

2-[3-({4-[1-amino-2,2,2-trifluoroethyl]phenyl}amino)-4-oxo-4,5-dihydro-1H-pyrazolo[4,3-c]pyridin-1-yl]cyclopentanecarbonitrile;

2-(3-{[2-(2-methoxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-(aminomethyl)phenyl]amino}-4-oxo-4,5-dihydro-1H-pyrazolo[4,3-c]pyridin-1-yl)cyclohexanecarbonitrile;

2-[3-({4-[(1-methylethyl)sulfonyl]phenyl}amino)-4-oxo-4,5-dihydro-1H-pyrazolo[4,3-c]pyridin-1-yl]cyclopentanecarbonitrile;

2-(3-{[4-(tert-butylsulfonyl)phenyl]amino}-4-oxo-4,5-dihydro-1H-pyrazolo[4,3-c]pyridin-1-yl)cyclopentanecarbonitrile;

N-tert-butyl-4-({1-[2-cyanocyclopentyl]-4-oxo-4,5-dihydro-1H-pyrazolo[4,3-c]pyridin-3-yl}amino)benzenesulfonamide;

2-(4-oxo-3-((4-(propan-2-ylsulfonimidoyl)phenyl)amino)-4,5-dihydro-1H-pyrazolo[4,3-c]pyridin-1-yl)cyclopentanecarbonitrile;

2-(3-{[4-(methylsulfonimidoyl)phenyl]amino}-4-oxo-4,5-dihydro-1H-pyrazolo[4,3-c]pyridin-1-yl)cyclohexanecarbonitrile;

4-({1-[2-cyanocyclopentyl]-4-oxo-4,5-dihydro-1H-pyrazolo[4,3-c]pyridin-3-yl}amino)benzonitrile;

2-[3-({4-[1-(ethylamino)-2,2,2-trifluoroethyl]phenyl}amino)-4-oxo-4,5-dihydro-1H-pyrazolo[4,3-c]pyridin-1-yl]cyclopentanecarbonitrile;

2-(4-oxo-3-((4-(2,2,2-trifluoro-1-(isopropylamino)ethyl)phenyl)amino)-4,5-dihydro-1H-pyrazolo[4,3-c]pyridin-1-yl)cyclopentanecarbonitrile;

ethyl 3-(4-((1-(2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate;

isopropyl 3-(4-((1-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate;

2-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)cyclohexanecarbonitrile;

2-(3-((1'-hydroxy-1'-(trifluoromethyl)-1',3'-dihydrospiro[cyclopropane-1,2'-inden]-5'-yl)amino)-4-oxo-4,5-dihydro-1H-pyrazolo[4,3-c]pyridin-1-yl)cyclohexanecarbonitrile 2-(4-oxo-3-((4-(1,1,1-trifluoro-2-methoxypropan-2-yl)phenyl)amino)-4,5-dihydro-1H-pyrazolo[4,3-c]pyridin-1-yl)cyclohexanecarbonitrile;

2-(3-((2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-((3-methyl-1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-((4-(4,4-difluoropiperidine-1-carbonyl)-3-methylphenyl)amino)-4-oxo-4,5-dihydro-1H-pyrazolo[4,3-c]pyridin-1-yl)cyclohexanecarbonitrile;

2-(3-((2-(2,5-dimethylmorpholino)quinolin-6-yl)amino)-4-oxo-4,5-dihydro-1H-pyrazolo[4,3-c]pyridin-1-yl)cyclohexanecarbonitrile;

tert-butyl 4-(5-((1-2-cyanocyclohexyl)-4-oxo-4,5-dihydro-1H-pyrazolo[4,3-c]pyridin-3-yl)amino)-1-oxoisoindolin-2-yl)cyclohexanecarboxylate;

2-[3-({4-[1-amino-2,2,2-trifluoroethyl]phenyl}amino)-4-oxo-4,5-dihydro-1H-pyrazolo[4,3-c]pyridin-1-yl]cyclopentanecarbonitrile;

2-(4-oxo-3-((4-(1,1,1-trifluoro-2-hydroxypropan-2-yl)phenyl)amino)-4,5-dihydro-1H-pyrazolo[4,3-c]pyridin-1-yl)cyclopentanecarbonitrile;

N-tert-butyl-4-({1-2-cyanocyclohexyl]-4-oxo-4,5-dihydro-1H-pyrazolo[4,3-c]pyridin-3-yl}amino)benzenesulfonamide;

2-[3-({4-[(1-methylethyl)sulfonyl]phenyl}amino)-4-oxo-4,5-dihydro-1H-pyrazolo[4,3-c]pyridin-1-yl]cyclohexanecarbonitrile;

N-tert-butyl-4-({1-[2-cyanocyclohexyl]-4-oxo-4,5-dihydro-1H-pyrazolo[4,3-c]pyridin-3-yl}amino)-N-methylbenzenesulfonamide;

2-(3-{[4-(tert-butylsulfonyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-N-methylbenzenesulfonamide;

2-[3-({4-[1-(2-methoxyethyl)-1H-pyrazol-4-yl]phenyl}amino)-4-oxo-4,5-dihydro-1H-pyrazolo[4,3-c]pyridin-1-yl]cyclohexanecarbonitrile;

2-(3-{[3-chloro-4-(1-methyl-1H-pyrazol-4-yl)phenyl]amino}-4-oxo-4,5-dihydro-1H-pyrazolo[4,3-c]pyridin-1-yl)cyclohexanecarbonitrile;

2-[3-({4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile;

2-[3-({2-[1,2-dimethylpropyl]-2,3-dihydro-1H-isoindol-5-yl}amino)-4-oxo-4,5-dihydro-1H-pyrazolo[4,3-c]pyridin-1-yl]cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]propanoate;

tert-butyl [5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]acetate;

tert-butyl 2-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-2-methylpropanoate;

2-(3-{[2-(1-methylethyl)-1-oxo-2,3-dihydro-1H-isoindol-5-yl]amino}-4-oxo-4,5-dihydro-1H-pyrazolo[4,3-c]pyridin-1-yl)cyclohexanecarbonitrile;

2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-3-methylbutanoate;

2-[4-oxo-3-(1,2,3,4-tetrahydroisoquinolin-6-ylamino)-4,5-dihydro-1H-pyrazolo[4,3-c]pyridin-1-yl]cyclohexanecarbonitrile;

2-[4-oxo-3-(1,2,3,4-tetrahydroisoquinolin-7-ylamino)-4,5-dihydro-1H-pyrazolo[4,3-c]pyridin-1-yl]cyclohexanecarbonitrile;

2-[4-oxo-3-({2-[(5-piperidin-1-ylpyrazin-2-yl)carbonyl]-2,3-dihydro-1H-isoindol-5-yl}amino)-4,5-dihydro-1H-pyrazolo[4,3-c]pyridin-1-yl]cyclohexanecarbonitrile;

2-(3-((2-(3-methoxy-2,2-dimethylpropyl)-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-{[2-(2-methoxy-1,1-dimethylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(3-methoxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(cyclopentylmethyl)-2,3-dihydro-1H-isoindol-5-yl]amino}-4-oxo-4,5-dihydro-1H-pyrazolo[4,3-c]pyridin-1-yl)cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,3-dihydro-2H-isoindol-2-yl]propanoate;

tert-butyl [5-({1-[2-cyanocyclohexyl]-4-oxo-4,5-dihydro-1H-pyrazolo[4,3-c]pyridin-3-yl}amino)-1,3-dihydro-2H-isoindol-2-yl]acetate;

tert-butyl 3-(4-((1-(2-cyanocyclohexyl)-4-oxo-4,5-dihydro-1H-pyrazolo[4,3-c]pyridin-3-yl)amino)phenyl)-8-azabicyclo[3.2.1]octane-8-carboxylate;

2-(3-{[4-(tert-butylsulfonyl)phenyl]amino}-4-oxo-4,5-dihydro-1H-pyrazolo[4,3-c]pyridin-1-yl)cycloheptanecarbonitrile;

2-{3-[(2,2-dimethyl-1,1-dioxido-3-oxo-2,3-dihydro-1-benzothiophen-5-yl)amino]-4-oxo-4,5-dihydro-1H-pyrazolo[4,3-c]pyridin-1-yl}cyclohexanecarbonitrile;

2-(3-{[3-hydroxy-2,2-dimethyl-1,1-dioxido-2,3-dihydro-1-benzothiophen-5-yl]amino}-4-oxo-4,5-dihydro-1H-pyrazolo[4,3-c]pyridin-1-yl)cyclohexanecarbonitrile;

2-(3-{[3-hydroxy-1,1-dioxido-3H-spiro[1-benzothiophene-2,1'-cyclohexan]-5-yl]amino}-4-oxo-4,5-dihydro-1H-pyrazolo[4,3-c]pyridin-1-yl)cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile;

2-(3-{[1-methyl-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[4-(1,3-oxazol-2-yl)phenyl]amino}-4-oxo-4,5-dihydro-1H-pyrazolo[4,3-c]pyridin-1-yl)cyclohexanecarbonitrile;

2-(4-oxo-3-{[4-(1,3-thiazol-2-yl)phenyl]amino}-4,5-dihydro-1H-pyrazolo[4,3-c]pyridin-1-yl)cyclohexanecarbonitrile;

2-(3-{[4-(1,2,4-oxadiazol-3-yl)phenyl]amino}-4-oxo-4,5-dihydro-1H-pyrazolo[4,3-c]pyridin-1-yl)cyclohexanecarbonitrile;

2-{3-[(4-isoxazol-3-ylphenyl)amino]-4-oxo-4,5-dihydro-1H-pyrazolo[4,3-c]pyridin-1-yl}cyclohexanecarbonitrile;

2-{3-[(4-isoxazol-5-ylphenyl)amino]-4-oxo-4,5-dihydro-1H-pyrazolo[4,3-c]pyridin-1-yl}cyclohexanecarbonitrile;

2-(3-{[4-(1,2,4-oxadiazol-5-yl)phenyl]amino}-4-oxo-4,5-dihydro-1H-pyrazolo[4,3-c]pyridin-1-yl)cyclohexanecarbonitrile;

2-{3-[(3,3-dimethyl-2-oxo-2,3-dihydro-1H-indol-6-yl)amino]-4-oxo-4,5-dihydro-1H-pyrazolo[4,3-c]pyridin-1-yl}cyclohexanecarbonitrile;

2-(3-{[4-(1,3-oxazol-5-yl)phenyl]amino}-4-oxo-4,5-dihydro-1H-pyrazolo[4,3-c]pyridin-1-yl)cyclohexanecarbonitrile;

2-(3-{[4-(3-hydroxyoxetan-3-yl)phenyl]amino}-4-oxo-4,5-dihydro-1H-pyrazolo[4,3-c]pyridin-1-yl)cyclohexanecarbonitrile;

2-{3-[(2-methyl-1,3-benzothiazol-6-yl)amino]-4-oxo-4,5-dihydro-1H-pyrazolo[4,3-c]pyridin-1-yl}cyclohexanecarbonitrile;

2-(4-oxo-3-((4-(1,1,1-trifluoro-2-hydroxypropan-2-yl)phenyl)amino)-4,5-dihydro-1H-pyrazolo[4,3-c]pyridin-1-yl)cyclohexanecarbonitrile;

2-(3-{[4-(3-methyloxetan-3-yl)phenyl]amino}-4-oxo-4,5-dihydro-1H-pyrazolo[4,3-c]pyridin-1-yl)cyclohexanecarbonitrile;

2-[3-({4-[1-(2-cyanoethyl)-1H-pyrazol-4-yl]phenyl}amino)-4-oxo-4,5-dihydro-1H-pyrazolo[4,3-c]pyridin-1-yl]cyclohexanecarbonitrile;

ethyl 1-[4-({1-[2-cyanocyclohexyl]-4-oxo-4,5-dihydro-1H-pyrazolo[4,3-c]pyridin-3-yl}amino)-2-methylphenyl]-1H-pyrazole-4-carboxylate;

isopropyl 6-((1-(2-cyanocyclohexyl)-4-oxo-4,5-dihydro-1H-pyrazolo[4,3-c]pyridin-3-yl)amino)quinoline-2-carboxylate;

2-(4-oxo-3-{[4-(5-oxo-4,5-dihydro-1,2,4-oxadiazol-3-yl)phenyl]amino}-4,5-dihydro-1H-pyrazolo[4,3-c]pyridin-1-yl)cyclohexanecarbonitrile;

2-[3-({4-[1-(2-cyanoethyl)-1H-pyrazol-4-yl]-3-methylphenyl}amino)-4-oxo-4,5-dihydro-1H-pyrazolo[4,3-c]pyridin-1-yl]cyclohexanecarbonitrile;

2-[4-oxo-3-({4-[1-trifluoromethyl)cyclopropyl]phenyl}amino)-4,5-dihydro-1H-pyrazolo[4,3-c]pyridin-1-yl]cyclohexanecarbonitrile;

2-{3-[(2-tert-butyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

2-[4-oxo-3-({4-[1-(2H-1,2,3-triazol-2-yl)ethyl]phenyl}amino)-4,5-dihydro-1H-pyrazolo[4,3-c]pyridin-1-yl]cyclohexanecarbonitrile;

2-[3-({4-[2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile;

2-{4-oxo-3-[(4-piperidin-4-ylphenyl)amino]-4,5-dihydro-1H-pyrazolo[4,3-c]pyridin-1-yl}cyclohexanecarbonitrile;

2-{3-[(2-acetyl-2,3-dihydro-1H-isoindol-5-yl)amino]-4-oxo-4,5-dihydro-1H-pyrazolo[4,3-c]pyridin-1-yl}cyclohexanecarbonitrile;

2-(3-{[1-(difluoromethyl)-2,3-dihydro-1H-isoindol-5-yl]amino}-4-oxo-4,5-dihydro-1H-pyrazolo[4,3-c]pyridin-1-yl)cyclohexanecarbonitrile;

2-[3-({4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile;

2-[3-({4-[2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile;

2-[3-({3-methyl-4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile;

2-{3-[(2-cyclohexyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

2-[3-({3-methyl-4-[2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile;

2-[3-({3-methyl-4-[2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile;

tert-butyl 4-(4-((1-(2-cyanocyclohexyl)-4-oxo-4,5-dihydro-1H-pyrazolo[4,3-c]pyridin-3-yl)amino)phenyl)-4-hydroxycyclohexanecarboxylate;

2-[4-oxo-3-({4-[1-(1H-1,2,3-triazol-1-yl)ethyl]phenyl}amino)-4,5-dihydro-1H-pyrazolo[4,3-c]pyridin-1-yl]cyclohexanecarbonitrile;

tert-butyl 4-(5-((1-(2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylate;

2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-methyl-4-(pyrrolidin-1-ylcarbonyl)phenyl]amino}-4-oxo-4,5-dihydro-1H-pyrazolo[4,3-c]pyridin-1-yl)cycloheptanecarbonitrile;

2-(3-{[2-(3-methoxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cycloheptanecarbonitrile;

N-tert-butyl-4-({1-[2-cyanocycloheptyl]-4-oxo-4,5-dihydro-1H-pyrazolo[4,3-c]pyridin-3-yl}amino)-N-methylbenzenesulfonamide;

2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cycloheptanecarbonitrile;

2-(4-oxo-3-{[2-(piperidin-1-ylcarbonyl)-2,3-dihydro-1H-isoindol-5-yl]amino}-4,5-dihydro-1H-pyrazolo[4,3-c]pyridin-1-yl)cycloheptanecarbonitrile;

2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cycloheptanecarbonitrile;

2-[3-({4-[1-(4-tert-butyl-1H-1,2,3-triazol-1-yl)-2-methylpropyl]phenyl}amino)-4-oxo-4,5-dihydro-1H-pyrazolo[4,3-c]pyridin-1-yl]cyclohexanecarbonitrile;

tert-butyl 1-{1-[4-({1-[2-cyanocyclohexyl]-4-oxo-4,5-dihydro-1H-pyrazolo[4,3-c]pyridin-3-yl}amino)phenyl]-2-methylpropyl}-1H-1,2,3-triazole-4-carboxylate;

2-(4-oxo-3-{[1-oxo-2-(tetrahydro-2H-pyran-4-yl)-2,3-dihydro-1H-isoindol-5-yl]amino}-4,5-dihydro-1H-pyrazolo[4,3-c]pyridin-1-yl)cyclohexanecarbonitrile;

2-(4-oxo-3-{[1-oxo-2-(tetrahydro-2H-thiopyran-4-yl)-2,3-dihydro-1H-isoindol-5-yl]amino}-4,5-dihydro-1H-pyrazolo[4,3-c]pyridin-1-yl)cyclohexanecarbonitrile;

2-[4-oxo-3-({4-[2-(trifluoromethyl)pyrrolidin-2-yl]phenyl}amino)-4,5-dihydro-1H-pyrazolo[4,3-c]pyridin-1-yl]cyclohexanecarbonitrile;

2-(3-{[2-(4-methyltetrahydro-2H-pyran-4-yl)-1-oxo-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[2-(4-methyltetrahydro-2H-pyran-4-yl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-hydroxy-1,1-dioxido-2',3',5',6'-tetrahydro-3H-spiro[1-benzothiophene-2,4'-pyran]-5-yl]amino}-4-oxo-4,5-dihydro-1H-pyrazolo[4,3-c]pyridin-1-yl)cyclohexanecarbonitrile;

2-(3-((3-methyl-4-(2,2,2-trifluoro-1-hydroxyethyl)phenyl)
amino)-4-oxo-4,5-dihydro-1H-pyrazolo[4,3-c]pyridin-1-
yl)cycloheptanecarbonitrile;
4-((1-(2-cyanocyclohexyl)-4-oxo-4,5-dihydro-1H-pyrazolo
[4,3-c]pyridin-3-yl)amino)benzoic acid;
4-(5-((1-(2-cyanocyclohexyl)-4-oxo-4,5-dihydro-1H-pyra-
zolo[4,3-c]pyridin-3-yl)amino)-1,1-dioxidobenzo[d]iso-
thiazol-2(3H)-yl)cyclohexanecarboxylic acid;
4-(4-(1-(2-cyanocyclohexyl)-4-oxo-4,5-dihydro-1H-pyra-
zolo[4,3-c]pyridin-3-ylamino)phenyl)-4-hydroxycyclo-
hexanecarboxylic acid;
tert-butyl 5-((1-(2-cyanocyclohexyl)-4-oxo-4,5-dihydro-
1H-pyrazolo[4,3-c]pyridin-3-yl)amino)-1-methylisoindo-
line-2-carboxylate;
2-(3-((2-isopropyl-1-methylisoindolin-5-yl)amino)-4-oxo-
4,5-dihydro-1H-pyrazolo[4,3-c]pyridin-1-yl)cyclohexan-
ecarbonitrile;
2-(3-((4-(8-azabicyclo[3.2.1]octan-3-yl)phenyl)amino)-4-
oxo-4,5-dihydro-1H-pyrazolo[4,3-c]pyridin-1-yl)cyclo-
hexanecarbonitrile;
2-(3-((2,2-dimethyl-1,1-dioxido-2,3-dihydrobenzo[b]thio-
phen-5-yl)amino)-4-oxo-4,5-dihydro-1H-pyrazolo[4,3-c]
pyridin-1-yl)cyclohexanecarbonitrile;
2-(3-((1,1-dioxido-3H-spiro[benzo[b]thiophene-2,1'-cyclo-
hexan]-5-yl)amino)-4-oxo-4,5-dihydro-1H-pyrazolo[4,3-
c]pyridin-1-yl)cyclohexanecarbonitrile;
2-{3-[(1,1-dioxido-2',3',5',6'-tetrahydro-3H-spiro[1-benzo-
thiophene-2,4'-pyran]-5-yl)amino]-4-oxo-4,5-dihydro-
1H-pyrazolo[4,3-c]pyridin-1-yl}cyclohexanecarbonitrile;
2-(3-((4-(tert-butylsulfonyl)phenyl)amino)-4-oxo-4,5-di-
hydro-1H-pyrazolo[4,3-c]pyridin-1-yl)-4,4-difluorocy-
clopentanecarbonitrile;
4,4-difluoro-2-(3-{[3-methyl-4-(pyrrolidin-1-ylcarbonyl)
phenyl]amino}-4-oxo-4,5-dihydro-1H-pyrazolo[4,3-c]
pyridin-1-yl)cyclopentanecarbonitrile;
2-[4-oxo-3-({4-2-(trifluoromethyl)piperidin-2-yl]
phenyl}amino)-4,5-dihydro-1H-pyrazolo[4,3-c]pyridin-
1-yl]cycloheptanecarbonitrile;
2-[4-oxo-3-({4-2-(trifluoromethyl)piperidin-2-yl]
phenyl}amino)-4,5-dihydro-1H-pyrazolo[4,3-c]pyridin-
1-yl]cyclopentanecarbonitrile;
2-(3-{[2-(4,4-difluoro-1-methylcyclohexyl)-1,1-dioxido-2,
3-dihydro-1,2-benzisothiazol-5-yl]amino}-4-oxo-4,5-di-
hydro-1H-pyrazolo[4,3-c]pyridin-1-yl)cyclohexanecar-
bonitrile; and
2-[4-oxo-3-({4-[2-(trifluoromethyl)piperidin-2-yl]
phenyl}amino)-4,5-dihydro-1H-pyrazolo[4,3-c]pyridin-
1-yl]cyclohexanecarbonitrile.

The invention also encompasses pharmaceutical compo-
sitions containing a compound of formula I or II, and
methods for treatment or prevention of JAK mediated dis-
eases using compounds of formula I or II.

The invention is described using the following definitions
unless otherwise indicated.

As used herein except where noted, "alkyl" is intended to
include both branched- and straight-chain saturated aliphatic
hydrocarbon groups, including all isomers, having the speci-
fied number of carbon atoms. Commonly used abbreviations
for alkyl groups are used throughout the specification, e.g.
methyl may be represented by "Me" or $CH_3$, ethyl may be
represented by "Et" or $CH_2CH_3$, propyl may be represented
by "Pr" or $CH_2CH_2CH_3$, butyl may be represented by "Bu"
or $CH_2CH_2CH_2CH_3$, etc. "$C_{1-6}$ alkyl" (or "$C_1$-$C_6$ alkyl") for
example, means linear or branched chain alkyl groups,
including all isomers, having the specified number of carbon
atoms. $C_{1-6}$ alkyl includes all of the hexyl alkyl and pentyl
alkyl isomers as well as n-, iso-, sec- and t-butyl, n- and
isopropyl, ethyl and methyl. "$C_{1-4}$ alkyl" means n-, iso-, sec-
and t-butyl, n- and isopropyl, ethyl and methyl.

The term "alkylene" refers to both branched- and straight-
chain saturated aliphatic hydrocarbon groups, including all
isomers, having the specified number of carbons, and having
two terminal end chain attachments. For illustration, the
term "unsubstituted A-$C_4$alkylene-B" represents A-$CH_2$—
$CH_2$—$CH_2$—$CH_2$—B.

The term "alkoxy" represents a linear or branched alkyl
group of indicated number of carbon atoms attached through
an oxygen bridge.

"Acyl" means a —C(O)R radical Where R is optionally
substituted alkyl, alkenyl, cycloalkyl, heterocycloalkyl, aryl
heteroaryl, etc.

"Acylamino" means a —NRR' radical where R is H, OH,
or alkoxy and R' is acyl, as defined herein.

The term "alkyl" refers to an aliphatic hydrocarbon group
which may be straight or branched and having the indicated
number of carbon atoms. Non-limiting examples of alkyl
groups include methyl, ethyl, propyl, isopropyl, butyl, s- and
t-butyl, pentyl, hexyl, and the like.

The term "heteroalkyl" refers to an alkyl group where 1,
2, or 3 of the carbon atoms is substituted by a heteroatom
independently chosen from N, O, or S.

"Alkenyl" refers to an aliphatic hydrocarbon group con-
taining at least one carbon-carbon double bond and which
may be straight or branched and having the indicated
number of carbon atoms. Preferably alkenyl contains one
carbon to carbon double bond, and up to four nonaromatic
carbon-carbon double bonds may be present. Examples of
alkenyl groups include ethenyl, propenyl, n-butenyl,
2-methyl-1-butenyl, 3-methylbut-2-enyl, n-pentenyl, octe-
nyl and decenyl.

"Alkynyl" refers to an aliphatic hydrocarbon group con-
taining at least one carbon-carbon triple bond and which
may be straight or branched and having the indicated
number of carbon atoms. Non-limiting examples of suitable
alkynyl groups include ethynyl, propynyl, 2-butynyl and
3-methylbutynyl.

"Alkoxy" refers to an alkyl-O— group in which the alkyl
group is as described above. $C_{1-6}$alkoxy, for example,
includes methoxy, ethoxy, propoxy, isopropoxy, and the like.

"Alkoxyalkyl" refers to an alkyl group as described above
in which one or more (in particular 1 to 3) hydrogen atoms
have been replaced by alkoxy groups. Examples include
$CH_2OCH_3$, $CH_2CH_2OCH_3$ and $CH(OCH_3)CH_3$.

"Aminoalkyl" refers to an alkyl group as described above
in which one hydrogen atom has been replaced by an amino,
monoalkylamino or dialkylamino group. Examples include
$CH_2NH_2$, $CH_2CH_2NHCH_3$ and $CH(N(CH_3)_2)CH_3$.

The term "$C_0$" as employed in expressions such as "$C_{0-6}$
alkyl" means a direct covalent bond; or when the term
appears at the terminus of a substituent, $C_{0-6}$ alkyl means
hydrogen or $C_{1-6}$alkyl. Similarly, when an integer defining
the presence of a certain number of atoms in a group is equal
to zero, it means that the atoms adjacent thereto are con-
nected directly by a bond. For example, in the structure

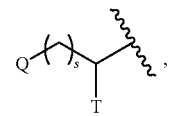

wherein s is an integer equal to zero, 1 or 2, the structure is

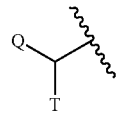

when s is zero.

The term "C$_{3-8}$ cycloalkyl" (or "C$_3$-C$_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "C$_{3-7}$ cycloalkyl", "C$_{3-6}$ cycloalkyl", "C$_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system.

Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with C$_{1-6}$ alkyl, C$_{1-6}$ alkenyl, C$_{1-6}$ alkynyl, aryl, halogen, NH$_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

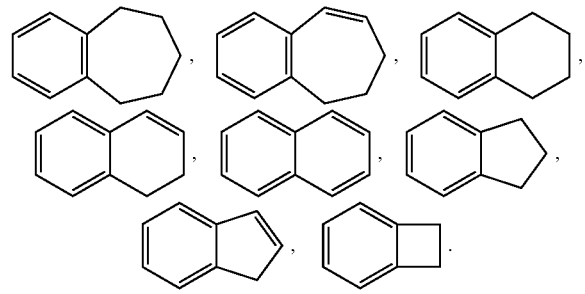

"Cyanoalkyl" refers to an alkyl group as described above in which one hydrogen atom has been replaced by a cyano group. Examples include CH$_2$CN, CH$_2$CH$_2$CN and CH(CN)CH$_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. C$_{1-6}$haloalkyl, for example, includes —CF$_3$, —CF$_2$CF$_3$, CHFCH$_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. For a bicyclic system, the rings may be fused across two adjacent ring atoms (e.g., quinoline), at one ring carbon atom (e.g., 1,4-dioxaspiro[4.5]decane), or are bridged groups (e.g. 8-azabicyclo[3.2.1]octanyl,). "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and (C$_{3-12}$)heterocycloalkyl" generally refers to a heterocycle as defined above in which the entire ring system (whether mono- or polycyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

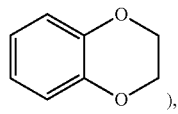
), imidazo(2,1-b)(1,3)thiazole, (i.e.,

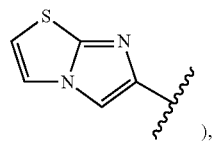
), and benzo-1,3-dioxolyl (i.e.,

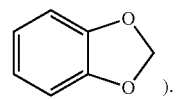
).

In certain contexts herein,

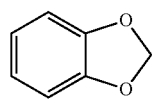

is alternatively referred to as phenyl having as a substituent methylenedioxy attached to two adjacent carbon atoms.

Non-limiting examples of substituted heteroaryls include: isoindolinone, isoindolin-1-one, 2,3-dihydro-1H-pyrazolo[4,3-c]pyridin-4(5H)-one, 2,3,4,5-tetrahydrobenzo[d]isothiazole 1,1-dioxide, and 2,3,4,5-tetrahydrobenzo[b]thiophene 1,1-dioxide.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "sulfamoyl" is a suffix to denote radicals derived from sulfamide such as $-SO_2NH_2$, and $-SO_2N(RR^1)$.

The term "sulfonimidoyl" is a suffix to denote the radical

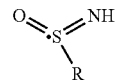

where R is $C_{(1-10)}$ alkyl, aryl, heteroaryl, cycloalkyl, heterocycloalkyl and the like, such as for example methyl, ethyl, isopropy. and propyl, The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formula I or formula II its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

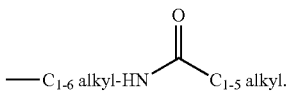

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "CH$_3$", e.g. "—CH$_3$" or using a straight line representing the presence of the methyl group, e.g. " ⎯⎯ ", i.e.,

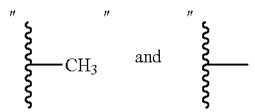

have equivalent meanings.

For variable definitions containing terms having repeated terms, e.g., $(R^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

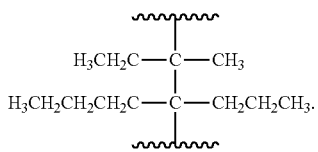

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I or II, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group $—(CR^3R^3)_2—$, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

In one embodiment of the invention, A is selected from: phenyl, isoindolinyl, 2,3-dihydro-1H-isoindolyl, quinolinyl, pyridinyl,

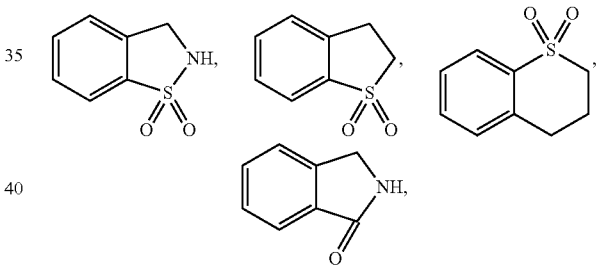

2,3-dihydro-1H-indenyl, benzothazolyl, 1,3-benzothiazolyl, and 1,2,3,4-tetrahydroisoquinolinyl.

In one embodiment of the invention, p is 2, 3, or 4. In a variant of this embodiment, p is 3, or 4. In yet another embodiment, p is 2.

In one embodiment of the invention, m is 1, 2, 3, or 4. In another embodiment, m is 0, 1, 2, or 3. In yet another embodiment, m is 4.

In one embodiment of the invention, n is 0, 1, 2, or 3. In a variant of this embodiment, n is 0, 1, or 2.

In one embodiment of the invention, $R^1$ is selected from: halogen, Oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{0-10}$ alkyl(oxy)$_{0-1}$(carbonyl)$_{0-1}$amino$C_{0-10}$ alkyl, $(C_{1-10})$heteroalkyl(oxy)$_{0-1}$(carbonyl)$_{0-1}$amino$C_{0-10}$ alkyl, $C_{3-12}$ cycloalkyl $C_{0-10}$ alkyl(oxy)$_{0-1}$(carbonyl)$_{0-1}$amino$C_{0-10}$ alkyl, aryl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl, $(C_{3-12})$heterocycloalkyl $C_{0-10}$ alkyl(oxy)$_{0-1}$(carbonyl)$_{0-}$ ₁aminoC$_{0-10}$ alkyl, C$_{0-10}$ alkylamino(carbonyl)$_{0-1}$C$_{0-10}$ alkyl, (C$_{1-10}$)heteroalkylamino(carbonyl)$_{0-1}$C$_{0-10}$ alkyl, C$_{3-12}$ cycloalkylamino(carbonyl)$_{0-1}$C$_{0-10}$ alkyl, aryl C$_{0-10}$ alkylaminoamino(carbonyl)$_{0-1}$C$_{0-10}$ alkyl, heteroaryl C$_{0-10}$ alkylamino(carbonyl)$_{0-1}$C$_{0-10}$ alkyl, (C$_{3-12}$)heterocycloalkylamino(carbonyl)$_{0-1}$C$_{0-10}$ alkyl, C$_{1-10}$ alkylsulfonylC$_{0-10}$ alkyl, (C$_{3-12}$)cycloalkylC$_{0-10}$alkylsulfonylC$_{0-10}$ alkyl, (C$_{3-12}$)cycloheteroalkylC$_{0-10}$alkylsulfonylC$_{0-10}$ alkyl, heteroarylC$_{0-10}$ alkylsulfonylC$_{0-10}$ alkyl, arylC$_{0-10}$ alkylsulfonylC$_{0-10}$ alkyl, C$_{1-10}$ alkylsulfamoylC$_{0-10}$ alkyl, C$_{1-10}$ heteroalkylsulfamoylC$_{0-10}$ alkyl, (C$_{3-12}$)cycloalkylC$_{0-10}$ alkylsulfamoylC$_{0-10}$ alkyl, (C$_{3-12}$)cycloheteroalkylC$_{0-10}$alkylsulfamoylC$_{0-10}$ alkyl, heteroarylC$_{0-10}$ alkylsulfamoylC$_{0-10}$ alkyl, arylC$_{0-10}$ alkylsulfamoylC$_{0-10}$ alkyl, C$_{1-10}$ alkylsulfonimidoylC$_{0-10}$ alkyl, C$_{1-10}$ heteroalkylsulfonimidoylC$_{0-10}$ alkyl, (C$_{3-12}$)cycloalkylC$_{0-10}$ alkylsulfonimidoylC$_{0-10}$ alkyl, (C$_{3-12}$)cycloheteroalkyl C$_{0-10}$alkysulfonimidoylC$_{0-10}$ alkyl, heteroarylC$_{0-10}$ alkylsulfonimidoylC$_{0-10}$ alkyl, arylC$_{0-10}$ alkylsulfonimidoylC$_{0-10}$ alkyl, C$_{1-10}$ alkylthioC$_{0-10}$ alkyl, (C$_{0-10}$ alkyl)$_{1-2}$ amino, —CO$_2$(C$_{0-10}$ alkyl), —(C$_{0-10}$ alkyl)CO$_2$H, —SO$_2$NH$_2$, —SO$_2$NH(C$_{1-10}$ alkyl), —SO$_2$N(C$_{1-10}$ alkyl)$_2$, —SO$_2$CF$_3$, —SO$_2$CF$_2$H, C$_{1-10}$ alkylsulfinylC$_{0-10}$ alkyl, hydroxy, —(C$_{1-10}$ alkyl)OH, —C$_{1-10}$ alkylalkoxy, cyano, (C$_{1-6}$alkyl) cyano, and C$_{1-6}$haloalkyl; wherein two R$^1$ may optionally join together with the ring atom to which each is attached to form a 3 to 6 membered saturated ring and wherein R$^1$ is optionally substituted with 1, 2, 3, or 4 R$^3$ substituents.

In one embodiment of the invention, R$^1$ is selected from: halogen, Oxo (=O), C$_{1-10}$ alkyl(oxy)$_{0-1}$(carbonyl)$_{0-1}$C$_{0-10}$ alkyl, C$_{1-10}$ heteroalkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkyl(oxy)$_{0-1}$(carbonyl)$_{0-1}$aminoC$_{0-10}$ alkyl, (C$_{1-10}$)heteroalkyl(oxy)$_{0-1}$(carbonyl)$_{0-1}$aminoC$_{0-10}$ alkyl, (C$_{3-12}$)heterocycloalkyl C$_{0-10}$ alkyl(oxy)$_{0-1}$(carbonyl)$_{0-1}$aminoC$_{0-10}$ alkyl, heteroaryl C$_{0-10}$ alkyl(oxy)$_{0-1}$(carbonyl)$_{0-1}$aminoC$_{0-10}$ alkyl, C$_{0-10}$ alkylamino(carbonyl)$_{0-1}$C$_{0-10}$ alkyl, heteroaryl C$_{0-10}$ alkylamino(carbonyl)$_{0-1}$C$_{0-10}$ alkyl, C$_{1-10}$ alkylsulfonylC$_{0-10}$ alkyl, (C$_{3-12}$)cycloheteroalkylC$_{0-10}$alkylsulfonylC$_{0-10}$ alkyl, C$_{1-10}$ alkylsulfamoylC$_{0-10}$ alkyl, (C$_{3-12}$)cycloalkylC$_{0-10}$ alkylsulfamoylC$_{0-10}$ alkyl, (C$_{3-12}$)cycloheteroalkylC$_{0-10}$ alkylsulfamoylC$_{0-10}$ alkyl, arylC$_{0-10}$ alkylsulfamoylC$_{0-10}$ alkyl, C$_{1-10}$ alkylsulfonimidoylC$_{0-10}$ alkyl, C$_{1-10}$ alkylthioC$_{0-10}$ alkyl, (C$_{0-10}$ alkyl)$_{1-2}$ amino, —CO$_2$(C$_{0-10}$ alkyl), —(C$_{0-10}$ alkyl)CO$_2$H, —SO$_2$NH$_2$, —SO$_2$NH(C$_{1-10}$ alkyl), —SO$_2$N(C$_{1-10}$ alkyl)$_2$, hydroxy, —(C$_{1-10}$ alkyl)OH, —C$_{1-10}$ alkylalkoxy, cyano, and C$_{1-6}$haloalkyl; and wherein two R$^1$ may optionally join together with the ring atom to which each is attached to form a 3 to 6 membered saturated ring; and wherein R is each optionally substituted with 1, 2, 3, or 4 R$^3$ substituents.

In one embodiment, R$^1$ is chosen from: aminomethyl, 1-aminoethyl, isopropylsulfonyl, tert-butylsulfonyl, tert-butylsulfamoyl, methyl, pyrrolidinylcarbonyl, ethylaminomethyl, isopropylaminomethyl, isopropyl, tert-butyl, isobutyl, ethyl, propyl, cyclopropylmethyl, fluoro, methylcarbonyl, methylthiomethyl, triazolyl methyl, oxo, hydroxyethyl, methoxyethyl, tert-butyloxycarbonyl, 2-methoxy-1,1-dimethylethyl, 3-methoxy-1,1-dimethylpropyl, 3-methoxy-2,2-dimethylpropyl, dimethylsulfamoyl, cyclopentylmethyl, tert-butyloxycarbonylethyl, tert-butyloxycarbonylmethyl, tert-butyloxycarbonylisopropyl, cyclohexyl, cyclopentyl, methylaminomethyl, pyrrolidinylcarbonyl, piperidinyl, methoxy, difluoromethyl, ethoxycarbonyldimethyleth-2yl, (isopropoxy)carbonyldimethyleth-2yl, tetrahydropyranyl, oxazolyl, pyrazolyl, chloro, oxetanyl, oxadiazolyl, 1,2,4-oxadiazolyl, piperidinylcarbonyl, isoxazolyl, pyrrolidinyl, isopropylcarboxy, cyclopropyl, trifluoroethyl, 2,2,2-trifluoroethyl, morpholinyl, propyl, cyclobutyl, carboxy, methylsulfonyl, sulfamoyl, hydroxymethyl, pyrazolylaminocarbonylmethyl, 1,3-oxazolylcarbonylaminomethyl, pyrimidinylcarbonylaminomethyl, tert-butyloxycarbonylaminomethyl, isopropylsulfonyl, pyrrolidinylsulfonylmethyl, pyrazolylcarbonylaminomethyl, oxazolylcarbonylaminomethyl, pyrimidinylcarbonylaminomethyl, isopropylsulfamoyl, phenylmethylsulfamoyl, (cyclopropylmethyl)sulfamoyl, ethylsulfamoyl, cyclohexylsulfamoyl, piperidinylsulfonyl, morpholinylsulfonyl, 1,2,3-triazolylmethyl, morpholinylmethyl, dioxolanyl, trifluoroethylaminomethyl, methylsulfonyl, methylcarbonylaminomethyl, pyrazolylmethyl, imidazolylmethyl, (2,2,2-trifluoroethyl)aminomethyl, dimethylaminocarbonyl, morpholinylcarbonyl, pyrrolidinyl, 3-hydroxy-1,1-dimethylpropyl, 3-hydroxy-2,2-dimethylpropyl, 2-methoxy-1-methylethyl, hydroxypropyl, 2-hydroxypropyl, 1-hydroxy-1-methylethyl, trifluoromethyl, triazolyisopropyl, 1,2-dimethylpropyl, tert-butyloxycarbonyldimethyleth-2-yl, pyrazinylcarbonyl, 8-azabicyclo[3.2.1]octanyl, trifluoromethoxy, difluoroethyl, thiazolyl, 1,3-thiazolyl, triazolylisobutyl, tetrahydrothiopyranyl, ethoxycarbonyl, isopropylsulfonimidoyl, methylsulfonimidoyl, hydroxy, cyano, methoxyisopropyl, and 4,5-dihydro-1,2,4-oxadiazolyl; and wherein two R$^1$ may optionally join together with the ring atom to which each is attached to form a 3 to 6 membered saturated ring; and wherein R$^1$ is each optionally substituted with 1, 2, 3, or 4 R$^3$ substituents.

In one embodiment of the invention, R$^2$ is selected from: halogen, Oxo (=O), C$_{1-10}$alkyl(oxy)$_{0-1}$(carbonyl)$_{0-1}$C$_{0-10}$ alkyl, C$_{3-12}$ cycloalkyl, (C$_{3-12}$)heterocycloalkyl C$_{0-10}$ alkyl (oxy)$_{0-1}$(carbonyl)$_{0-1}$C$_{0-10}$ alkyl, C$_{0-10}$ alkylaminoC$_{0-10}$ alkyl, C$_{3-12}$ cycloalkyl C$_{0-10}$ alkylaminoC$_{0-10}$ alkyl, (C$_{3-12}$) heterocycloalkyl C$_{0-10}$ alkylaminoC$_{0-10}$ alkyl, C$_{1-10}$ alkylsulfonyl, (C$_{0-10}$ alkyl)$_{1-2}$ amino, —(C$_{0-10}$ alkyl)CO$_2$H, hydroxy, —(C$_{1-10}$ alkyl)OH, —C$_{1-10}$ alkylalkoxy, (C$_{1-6}$ alkyl)cyano, and C$_{1-6}$haloalkyl; wherein two R$^2$ may optionally join together with the ring atom to which each is attached to form a 3 to 6 membered saturated ring; and wherein R$^2$ is each optionally substituted with 1, 2, 3, or 4 R$^3$ substituents;

In one embodiment of the invention, R$^2$ is selected from: halogen, C$_{1-10}$ alkyl(oxy)$_{0-1}$(carbonyl)$_{0-1}$C$_{0-10}$ alkyl, C$_{3-12}$ cycloalkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkylaminoC$_{0-10}$ alkyl, C$_{3-12}$ cycloalkyl C$_{0-10}$ alkylaminoC$_{0-10}$ alkyl, (C$_{0-10}$ alkyl)$_{1-2}$ amino, and hydroxy; wherein two R$^2$ may optionally join together with the ring atom to which each is attached to form a 3 to 6 membered saturated ring; and wherein R$^2$ is each optionally substituted with 1, 2, 3, or 4 R$^3$ substituents.

In another embodiment of the invention, R$^2$ is chosen from: fluoro, hydroxy, 1-cyclopropylethylamino, dimethylamino, azetidinyl, ethylamino, methyl; wherein two R$^2$ may optionally join together with the ring atom to which each is attached to form a 3 to 6 membered saturated ring; and wherein R$^2$ is each optionally substituted with 1, 2, 3, or 4 R$^3$ substituents.

In one embodiment of the invention, R$^3$ is independently selected from: halogen, C$_{1-10}$ alkyl(oxy)$_{0-1}$(carbonyl)$_{0-1}$C$_{0-10}$ alkyl, C$_{1-10}$ heteroalkyl(oxy)$_{0-1}$(carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-12}$)

heterocycloalkyl $C_{0-10}$ alkyl(oxy)$_{0-1}$(carbonyl)$_{0-1}$$C_{0-10}$ alkyl, —$CO_2$($C_{0-10}$ alkyl), —($C_{0-10}$ alkyl)$CO_2H$, Oxo (=O), —$SO_2NH_2$, —$SO_2NH$($C_{1-10}$ alkyl), —$SO_2N$($C_{1-10}$ alkyl)$_2$, $C_{1-10}$ alkylsulfinyl, amino, ($C_{0-10}$ alkyl)$_{1-2}$ amino, hydroxy, ($C_{1-10}$ alkyl)OH, $C_{1-10}$ alkoxy, ($C_{1-10}$alkyl)cyano, cyano, and $C_{1-6}$haloalkyl; and $R^3$ is optionally substituted with 1, 2, or 3 $R^4$ substituents selected from hydrogen, hydroxy, ($C_{1-6}$)alkyl, ($C_{1-6}$)alkoxy, ($C_{1-10}$ alkyl)OH, halogen, $CO_2H$, —($C_{0-6}$)alkylCN, —O(C=O)$C_1$-$C_6$ alkyl, $NO_2$, trifluoromethoxy, trifluoroethoxy, trifluoromethyl, trifluoroethyl, —N=C(O)O($C_{0-6}$)alkyl, $C_{1-10}$ alkylsulfonyl, oxo (O=), aminosulfonyl, —$SO_2NH_2$, —$SO_2NH$($C_{1-10}$ alkyl), —$SO_2N$($C_{1-10}$ alkyl)$_2$, —$SO_2C_{1-6}$alkyl, —$SO_2CF_3$, —$SO_2CF_2H$, —$C_{1-10}$ alkylsulfinyl, —$O_{(0-1)}$($C_{1-10}$)haloalkyl, amino($C_{1-6}$alkyl)$_{0-2}$ and $NH_2$.

In one embodiment of the invention, $R^3$ is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, —$CO_2$($C_{0-10}$ alkyl), Oxo (=O), $C_{1-10}$ alkylsulfinyl, amino, ($C_{0-10}$ alkyl)$_{1-2}$ amino, hydroxy, ($C_{1-10}$ alkyl)OH, $C_{1-10}$ alkoxy, ($C_{1-10}$ alkyl)cyano, cyano, and $C_{1-6}$haloalkyl.

In one embodiment, $R^3$ is independently selected from: trifluoromethyl, hydroxy, methyl, piperidinyl, carboxy, tert-butyloxycarbonyl, tert-butyl, methoxyethyl, cyano, methoxy, fluoro, amino, phenyl, cyclopropyl, tert-butylsulfinyl, 1-hydroxymethylethyl, difluoromethyl, dimethylamino, cyanoethyl, oxo, isopropyl, and trifluoroethyl.

In one embodiment, $R^4$ is hydrogen, hydroxy, and ($C_{1-6}$) alkyl. In a variant of this embodiment, $R^4$ is hydrogen.

In one embodiment of the invention, is a compound of formula I wherein: A is selected from aryl and heteroaryl; n is 0, 1, 2, 3, or 4; m is 0, 1, 2, 3, or 4; p is 0, 1, 2, 3, or 4; $R^1$ is independently selected from: is selected from: halogen, Oxo (=O), $C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, $C_{0-10}$ alkyl(oxy)$_{0-1}$(carbonyl)$_{0-1}$amino$C_{0-10}$ alkyl, ($C_{1-10}$)heteroalkyl(oxy)$_{0-1}$(carbonyl)$_{0-1}$amino$C_{0-10}$ alkyl, ($C_{3-12}$)heterocycloalkyl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl, $C_{0-10}$ alkylamino(carbonyl)$_{0-1}$$C_{0-10}$ alkyl, heteroaryl $C_{0-10}$ alkylamino(carbonyl)$_{0-1}$$C_{0-10}$ alkyl, $C_{0-10}$ alkylsulfonyl$C_{0-10}$ alkyl, ($C_{3-12}$)cycloheteroalkyl$C_{0-10}$alkylsulfonyl$C_{0-10}$ alkyl, $C_{1-10}$ alkylsulfamoyl$C_{0-10}$ alkyl, ($C_{3-12}$)cycloalkyl$C_{0-10}$ alkylsulfamoyl$C_{0-10}$ alkyl, ($C_{3-12}$)cycloheteroalkyl$C_{0-10}$alkylsulfamoyl$C_{0-10}$ alkyl, aryl$C_{0-10}$ alkylsulfamoyl$C_{0-10}$ alkyl, $C_{1-10}$ alkylsulfonimidoyl$C_{0-10}$ alkyl, Cl-10 alkylthio$C_{0-10}$ alkyl, ($C_{0-10}$ alkyl)$_{1-2}$ amino, —$CO_2$($C_{0-10}$ alkyl), —($C_{0-10}$ alkyl)$CO_2H$, —$SO_2NH_2$, —$SO_2NH$($C_{1-10}$ alkyl), —$SO_2N$($C_{1-10}$ alkyl)$_2$, hydroxy, —($C_{1-10}$ alkyl)OH, —$C_{1-10}$ alkylalkoxy, cyano, and $C_{1-6}$haloalkyl; and wherein two $R^1$ may optionally join together with the ring atom to which each is attached to form a 3 to 6 membered saturated ring; and wherein $R^1$ is each optionally substituted with 1, 2, 3, or 4 $R^3$ substituents;

$R^2$ is selected from: halogen, $C_{1-10}$ alkyl(oxy)$_{0-1}$(carbonyl)$_{0-1}$$C_{0-10}$ alkyl, $C_{3-12}$ cycloalkyl, ($C_{3-12}$)heterocycloalkyl $C_{0-10}$ alkyl(oxy)$_{0-1}$(carbonyl)$_{0-1}$$C_{0-10}$ alkyl, $C_{0-10}$ alkylamino$C_{0-10}$ alkyl, $C_{3-12}$ cycloalkyl $C_{0-10}$ alkylamino$C_{0-10}$ alkyl, ($C_{0-10}$ alkyl)$_{1-2}$ amino, and hydroxy; wherein two $R^2$ may optionally join together with the ring atom to which each is attached to form a 3 to 6 membered saturated ring; wherein $R^1$ and $R^2$ are each optionally substituted with 1, 2, 3, or 4 $R^3$ substituents; and $R^3$ is independently selected from: halogen, $C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl (oxy)$_{0-1}$(carbonyl)$_{0-1}$$C_{0-10}$ alkyl, $C_{3-12}$ cycloalkyl $C_{0-10}$ alkyl (oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, —$CO_2$($C_{0-10}$ alkyl), Oxo (=O), $C_{1-10}$ alkylsulfinyl, amino, ($C_{0-10}$ alkyl)$_{1-2}$ amino, hydroxy, ($C_{1-10}$ alkyl)OH, $C_{1-10}$ alkoxy, ($C_{1-10}$ alkyl)cyano, cyano, and $C_{1-6}$haloalkyl.

In one embodiment of the invention, A is selected from phenyl, pyridinyl, 2,3-dihydro-1H-isoindolyl, thiochromanenyl, 2,3-dihydro-1,2-benzisothiazolyl, 2,3 dihydro-1-benzothiophenyl, and 2,3-dihydro-1H-indenyl; $R^1$ is selected from: halogen, Oxo (=O), $C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$ $C_{0-10}$ alkyl, aryl $C_{0-10}$ alkyl(oxy)$_{0-1}$(carbonyl)$_{0-1}$$C_{0-10}$ alkyl, $C_{3-8}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, ($C_{3-8}$)heterocycloalkyl $C_{0-10}$ alkyl(oxy)$_{0-1}$(carbonyl)$_{0-1}$$C_{0-10}$ alkyl, $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl, $C_{0-10}$ alkylamino(carbonyl)$_{0-1}$$C_{0-10}$ alkyl, heteroaryl $C_{0-10}$ alkylamino(carbonyl)$_{0-1}$$C_{0-10}$ alkyl, $C_{0-10}$ alkylsulfonyl $C_{0-10}$ alkyl, ($C_{3-8}$)cycloheteroalkyl$C_{0-10}$alkylsulfonyl$C_{0-10}$ alkyl, $C_{1-10}$ alkylsulfamoyl$C_{0-10}$ alkyl, ($C_{3-8}$)cycloalkyl $C_{0-10}$ alkylsulfamoyl$C_{0-10}$ alkyl, ($C_{3-8}$)cycloheteroalkyl $C_{0-10}$alkylsulfamoyl$C_{0-10}$alkyl, aryl$C_{0-10}$ alkylsulfamoyl $C_{0-10}$ alkyl, —($C_{0-10}$ alkyl)$CO_2H$, —$SO_2NH_2$, —$SO_2NH$ ($C_{1-10}$ alkyl) —$SO_2N$($C_{1-10}$ alkyl)$_2$, $C_{0-10}$ alkylsulfinylamino$C_{0-10}$ alkyl, —($C_{1-10}$ alkyl)OH, —$C_{1-10}$ alkylalkoxy, and $C_{1-6}$haloalkyl; wherein $R^1$ is optionally substituted with 1, 2, 3, or 4 $R^3$ substituents.

In an variant of this embodiment of the invention, $R^1$ is selected from: fluoro, methylsulfonyl, chloro, trifluoromethyl, trifluoromethoxy, dimethylsulfamoyl, sulfamoyl, hydroxyethyl, trifluoroethyl, pyrazolylcarbamoylmethyl, pyrazolylcarbonylaminomethyl, tert-butyloxycarbonylaminomethyl, aminomethyl,
isopropylsulfamoyl, benzylsulfamoyl, (cyclopropylmethyl) sulfamoyl, ethylsulfomoyl, cyclohexylsulfamoyl, piperidinylsulfonyl, morpholinylsulfonyl, triazolylmethyl, pyrrolidinylcarbonyl,
oxazolylcarbonylaminomethyl, pyrimidinylcarbonylaminomethyl, hydroxyethyl, 1-hydroxyethyl, morpholinylmethyl,
1-hydroxymethylethyl, hydroxy(methylpropyl), 1-hydroxy (methylpropyl),
hydroxypropyl, ethylhydroxy, (tert-butyl)sulfinylaminomethyl, dioxolanyl, methylaminomethyl, methylcarbonylaminomethyl, (dimethylamino)methyl, pyrazolylmethyl, imidazolylmethyl, oxo, hydroxy, hydroxymethyl, methyl, tert-butyl, (tert-butyl)sulfinylaminomethyl, (ethyl)aminomethyl, pyrrolidinylsulfonylmethyl, trifluoroethyl, (2,2,2,-trifluoroethyl),
carboxy, cyclopropylmethyl, dimethylaminomethyl, cyclopentylmethyl, methylaminoethyl, 1-(methylamino)ethyl, ethylaminomethyl, dimethylaminocarbonyl,
dimethylcarbamoyl, morpholinylcarbonyl, cyclopropyl, aminoethyl, 1-aminoethyl, pyrrolidinyl, methylethyl, isobutyl, cyclopropylmethyl, methylsulfanylmethyl, 3-hydroxy (dimethylpropyl), triazolylmethyl, 3-hydroxy-2,2,-dimethylpropyl, and methoxyethyl; wherein $R^1$ is optionally substituted with 1, 2, 3, or 4 $R^3$ substituents;

$R^2$ selected from: cyclopropylethylamino, 1-cylopropylethylamino, hydroxy, azetidinyl, dimethylamino, trifluoroethyl, methyl, ethyl; wherein two $R^2$ may optionally join together with the ring atom to which each is attached to form a 3 to 6 membered saturated ring; and wherein $R^2$ is optionally substituted with 1, 2, 3, or 4 $R^3$ substituents. and $R^3$ is independently selected from: chloro, fluoro, methoxy, methyl, trifluoroethyl, hydroxymethylethyl, hydroxy, isopropyl, ethyl; wherein $R^3$ is optionally substituted with 1, 2, or 3 $R^4$ substituents.

In one embodiment, the present invention is selected from compounds of formula II or pharmaceutically acceptable salts, or stereoisomers thereof:

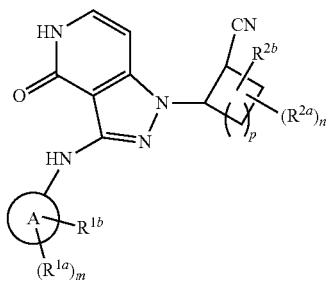

II

A is selected from aryl and heteroaryl;
n is 0, 1, or 2;
m is 0, 1, 2, or 3;
p is 0, 1, 2, 3, or 4;
$R^{1a}$ is selected from:
  halogen,
  Oxo (=O),
  $C_{1-10}$ alkyl(oxy)$_{0-1}$(carbonyl)$_{0-1}C_{0-10}$ alkyl,
  $C_{3-12}$ cycloalkyl $C_{0-10}$ alkyl(oxy)$_{0-1}$(carbonyl)$_{0-1}C_{0-10}$ alkyl,
  $C_{0-10}$ alkyl(oxy)$_{0-1}$(carbonyl)$_{0-1}$amino$C_{0-10}$ alkyl,
  $(C_{1-10})$heteroalkyl(oxy)$_{0-1}$(carbonyl)$_{0-1}$amino$C_{0-10}$ alkyl,
  $C_{0-10}$ alkylamino(carbonyl)$_{0-1}C_{0-10}$ alkyl,
  $(C_{0-10}$ alkyl)$_{1-2}$ amino,
  $C_{1-10}$ alkylthio$C_{0-10}$ alkyl,
  $C_{1-10}$ alkylsulfonyl$C_{0-10}$ alkyl,
  —SO$_2$NH$_2$,
  —SO$_2$NH($C_{1-10}$ alkyl),
  —SO$_2$N($C_{1-10}$ alkyl)$_2$,
  hydroxy,
  —($C_{1-10}$ alkyl)OH,
  —$C_{1-10}$ alkylalkoxy, and
  $C_{1-6}$haloalkyl, and
  wherein two $R^{1a}$ may optionally join together with the ring atom to which each is attached to form a 3 to 6 membered saturated ring;
$R^{2a}$ is selected from:
  halogen,
  Oxo (=O),
  $C_{1-10}$ alkyl(oxy)$_{0-1}$(carbonyl)$_{0-1}C_{0-10}$ alkyl,
  $C_{0-10}$ alkylamino$C_{0-10}$ alkyl,
  $(C_{3-12})$heterocycloalkyl $C_{0-10}$ alkylamino$C_{0-10}$ alkyl,
  $(C_{0-10}$ alkyl)$_{1-2}$ amino,
  —CO$_2$($C_{0-10}$ alkyl),
  —($C_{0-10}$ alkyl)CO$_2$H,
  hydroxy,
  —($C_{1-10}$ alkyl)OH,
  —$C_{1-10}$ alkylalkoxy, and
  $C_{1-6}$haloalkyl, wherein two $R^{2a}$ may optionally join together with the ring atom to which each is attached to form a 3 to 6 membered saturated ring;
wherein $R^{1a}$ and $R^{2a}$ are independently optionally substituted with 1, 2, 3, or 4 $R^{3a}$ substituents;
$R^{3a}$ is independently selected from:
  halogen,
  $C_{1-10}$ alkyl(oxy)$_{0-1}$(carbonyl)$_{0-1}C_{0-10}$ alkyl, and
  $C_{1-10}$ heteroalkyl(oxy)$_{0-1}$(carbonyl)$_{0-1}C_{0-10}$ alkyl,
  Oxo (=O),
  hydroxy,
  ($C_{1-10}$ alkyl)OH,
  $C_{1-10}$ alkoxy, and
  $C_{1-6}$haloalkyl;
$R^{3a}$ is optionally substituted with 1, 2, or 3 $R^{4a}$ substituents selected from hydrogen, hydroxy, ($C_{1-6}$)alkyl, ($C_{1-6}$) alkoxy, ($C_{1-10}$ alkyl)OH, halogen, CO$_2$H, —($C_{0-6}$)alkylCN, —O(C=O)$C_1$-$C_6$ alkyl, NO$_2$, trifluoromethoxy, trifluoroethoxy, trifluoromethyl, trifluoroethyl, —N=C(O) O($C_{0-6}$)alkyl, $C_{1-10}$ alkylsulfonyl, oxo (O=), aminosulfonyl, —SO$_2$NH$_2$, —SO$_2$NH($C_{1-10}$ alkyl), —SO$_2$N($C_{1-10}$ alkyl)$_2$, —SO$_2C_{1-6}$alkyl, —SO$_2$CF$_3$, —SO$_2$CF$_2$H, —$C_{1-10}$ alkylsulfinyl, —O$_{(0-1)}$($C_{1-10}$)haloalkyl, amino($C_{1-6}$alkyl)$_{0-2}$ and NH$_2$;
$R^{1b}$ is selected from:
  hydrogen,
  halogen,
  Oxo (=O),
  $C_{1-10}$ alkyl(oxy)$_{0-1}$(carbonyl)$_{0-1}C_{0-10}$ alkyl,
  $C_{1-10}$ heteroalkyl(oxy)$_{0-1}$(carbonyl)$_{0-1}C_{0-10}$ alkyl,
  $C_{2-10}$ alkenyl(oxy)$_{0-1}$(carbonyl)$_{0-1}C_{0-10}$ alkyl,
  aryl $C_{0-10}$ alkyl(oxy)$_{0-1}$(carbonyl)$_{0-1}C_{0-10}$ alkyl,
  $C_{3-12}$ cycloalkyl $C_{0-10}$ alkyl(oxy)$_{0-1}$(carbonyl)$_{0-1}C_{0-10}$ alkyl,
  heteroaryl $C_{0-10}$ alkyl(oxy)$_{0-1}$(carbonyl)$_{0-1}C_{0-10}$ alkyl,
  $(C_{3-12})$heterocycloalkyl $C_{0-10}$ alkyl(oxy)$_{0-1}C_{0-10}$ alkyl,
  $C_{0-10}$ alkyl(oxy)$_{0-1}$(carbonyl)$_{0-1}$amino$C_{0-10}$ alkyl,
  $(C_{1-10})$heteroalkyl(oxy)$_{0-1}$(carbonyl)$_{0-1}$amino$C_{0-10}$ alkyl,
  $C_{3-12}$ cycloalkyl $C_{0-10}$ alkyl(oxy)$_{0-1}$(carbonyl)$_{0-1}$amino$C_{0-10}$ alkyl,
  aryl $C_{0-10}$ alkyl(oxy)$_{0-1}$(carbonyl)$_{0-1}$amino$C_{0-10}$ alkyl,
  heteroaryl $C_{0-10}$ alkyl(oxy)$_{0-1}$(carbonyl)$_{0-1}$amino$C_{0-10}$ alkyl,
  $(C_{3-12})$heterocycloalkyl $C_{0-10}$ alkyl(oxy)$_{0-1}$(carbonyl)$_{0-1}$amino$C_{0-10}$ alkyl,
  $C_{0-10}$ alkylamino(carbonyl)$_{0-1}C_{0-10}$ alkyl,
  $(C_{1-10})$heteroalkylamino(carbonyl)$_{0-1}C_{0-10}$ alkyl,
  $C_{3-12}$ cycloalkylamino(carbonyl)$_{0-1}C_{0-10}$ alkyl,
  aryl $C_{0-10}$ alkylaminoamino(carbonyl)$_{0-1}C_{0-10}$ alkyl,
  heteroaryl $C_{0-10}$ alkylamino(carbonyl)$_{0-1}C_{0-10}$ alkyl,
  $(C_{3-12})$heterocycloalkylamino(carbonyl)$_{0-1}C_{0-10}$ alkyl,
  $C_{1-10}$ alkylsulfonyl$C_{0-10}$ alkyl, $C_{1-10}$ heteroalkylsulfonyl$C_{0-10}$ alkyl,
  $(C_{3-12})$cycloalkyl$C_{0-10}$alkylsulfonyl$C_{0-10}$ alkyl,
  $(C_{3-12})$cycloheteroalkyl$C_{0-10}$alkylsulfonyl$C_{0-10}$ alkyl,
  heteroaryl$C_{0-10}$ alkylsulfonyl$C_{0-10}$ alkyl,
  aryl$C_{0-10}$ alkylsulfonyl$C_{0-10}$ alkyl,
  $C_{1-10}$ alkylsulfamoyl$C_{0-10}$ alkyl,
  $C_{1-10}$ heteroalkylsulfamoyl$C_{0-10}$ alkyl,
  $(C_{3-12})$cycloalkyl$C_{0-10}$ alkylsulfamoyl$C_{0-10}$ alkyl,
  $(C_{3-12})$cycloheteroalkyl$C_{0-10}$alkylsulfamoyl$C_{0-10}$ alkyl,
  heteroaryl$C_{0-10}$ alkylsulfamoyl$C_{0-10}$ alkyl,
  aryl$C_{0-10}$ alkylsulfamoyl$C_{0-10}$ alkyl,
  $C_{1-10}$ alkylsulfonimidoyl$C_{0-10}$ alkyl,
  $C_{1-10}$ heteroalkylsulfonimidoyl$C_{0-10}$ alkyl,
  $(C_{3-12})$cycloalkyl$C_{0-10}$ alkylsulfonimidoyl$C_{0-10}$ alkyl, ($C_{3-12}$)cycloheteroalkyl$C_{0-10}$alkysulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$C_{1-10}$ alkylthio$C_{0-10}$ alkyl,
($C_{0-10}$ alkyl)$_{1-2}$ amino,
—$CO_2$($C_{0-10}$ alkyl),
—($C_{0-10}$ alkyl)$CO_2H$,
—$SO_2NH_2$,
—$SO_2NH$($C_{1-10}$ alkyl),
—$SO_2N$($C_{1-10}$ alkyl)$_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
($C_{3-12}$)cycloalkyl$C_{0-10}$alkylsulfinyl$C_{0-10}$alkyl,
($C_{3-12}$)cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$ alkyl,
$C_{0-10}$ alkylsulfinylamino$C_{0-10}$ alkyl,
$C_{1-4}$acylamino $C_{0-10}$ alkyl,
hydroxy,
—($C_{1-10}$ alkyl)OH,
—$C_{1-10}$ alkylalkoxy,
cyano,
($C_{1-6}$alkyl)cyano, and
$C_{1-6}$haloalkyl;
$R^{2b}$ is selected from:
hydrogen,
halogen,
Oxo (=O),
$C_{1-10}$ alkyl(oxy)$_{0-1}$(carbonyl)$_{0-1}$$C_{0-10}$ alkyl,
$C_{3-12}$ cycloalkyl,
($C_{3-12}$)heterocycloalkyl $C_{0-10}$ alkyl(oxy)$_{0-1}$(carbonyl)$_{0-1}$ $C_{0-10}$ alkyl,
$C_{0-10}$ alkylamino$C_{0-10}$ alkyl,
($C_{1-10}$)heteroalkylamino$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
($C_{3-12}$)heterocycloalkyl $C_{0-10}$ alkylamino$C_{0-10}$ alkyl,
$C_{1-10}$ alkylsulfonyl,
($C_{3-12}$)cycloalkyl$C_{0-10}$alkylsulfonyl,
($C_{3-12}$)cycloheteroalkyl$C_{0-10}$ alkylsulfonyl,
($C_{0-10}$ alkyl)$_{1-2}$ amino,
—$CO_2$($C_{0-10}$ alkyl),
—($C_{0-10}$ alkyl)$CO_2H$,
—$SO_2CF_3$,
—$SO_2CF_2H$,
$C_{1-10}$ alkylsulfinyl,
hydroxy,
—($C_{1-10}$ alkyl)OH,
—$C_{1-10}$ alkylalkoxy,
cyano,
($C_{1-6}$alkyl)cyano, and
$C_{1-6}$haloalkyl; wherein $R^{1b}$ and $R^{2b}$ are each optionally substituted with 1, 2, or 3 $R^{3b}$ substituents;
$R^{3b}$ is independently selected from: is independently selected from: halogen, $C_{1-10}$ alkyl(oxy)$_{0-1}$(carbonyl)$_{0-1}$ $C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$ $C_{0-10}$ alkyl, $C_{3-12}$ cycloalkyl $C_{0-10}$ alkyl(oxy)$_{0-1}$(carbonyl)$_{0-1}$ $C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, —$CO_2$($C_{0-10}$ alkyl), Oxo (=O), $C_{1-10}$ alkylsulfinyl, amino, ($C_{0-10}$ alkyl)$_{1-2}$ amino, hydroxy, ($C_{1-10}$ alkyl)OH, $C_{1-10}$ alkoxy, ($C_{1-10}$ alkyl)cyano, cyano, and $C_{1-6}$haloalkyl, halogen, $C_{1-10}$ alkyl(oxy)$_{0-1}$(carbonyl)$_{0-1}$$C_{0-10}$ alkyl, Oxo (=O), amino, hydroxy, ($C_{1-10}$ alkyl)OH, $C_{1-10}$alkoxy, and $C_{1-6}$haloalkyl; wherein $R^{3b}$ is optionally substituted with 1, 2, or 3 $R^{4b}$ substituents; and $R^{4b}$ is independently selected from hydrogen, hydroxy, ($C_{1-6}$)alkyl, ($C_{1-6}$)alkoxy, ($C_{1-10}$ alkyl)OH, halogen, —O(C=O)$C_1$-$C_6$ alkyl, trifluoromethoxy, trifluoroethoxy, trifluoromethyl, trifluoroethyl, oxo (O=), —$O_{(0-1)}$($C_{1-10}$)haloalkyl, amino($C_{1-6}$alkyl)$_{0-2}$ and $NH_2$.

In an embodiment of this invention of formula II, $R^{1b}$ is selected from: halogen, Oxo (=O), $C_{1-10}$ alkyl(oxy)$_{0-1}$(carbonyl)$_{0-1}$$C_{0-10}$ alkyl, $C_{1-10}$ heteroalkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, ($C_{3-12}$)heterocycloalkyl $C_{0-10}$ alkyl(oxy)$_{0-1}$(carbonyl)$_{0-1}$$C_{0-10}$ alkyl, $C_{0-10}$ alkyl(oxy)$_{0-1}$(carbonyl)$_{0-1}$ amino$C_{0-10}$ alkyl, ($C_{1-10}$)heteroalkyl(oxy)$_{0-1}$(carbonyl)$_{0-1}$ amino$C_{0-10}$ alkyl, ($C_{3-12}$)heterocycloalkyl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$ alkyl, $C_{0-10}$ alkylamino(carbonyl)$_{0-1}$$C_{0-10}$ alkyl, heteroaryl $C_{0-10}$ alkylamino(carbonyl)$_{0-1}$$C_{0-10}$ alkyl, $C_{0-10}$ alkylsulfonyl$C_{0-10}$ alkyl, ($C_{3-12}$)cycloheteroalkyl$C_{0-10}$alkylsulfonyl$C_{0-10}$ alkyl, $C_{1-10}$ alkylsulfamoyl$C_{0-10}$ alkyl, ($C_{3-12}$)cycloalkyl$C_{0-10}$ alkylsulfamoyl$C_{0-10}$ alkyl, ($C_{3-12}$)cycloheteroalkyl$C_{0-10}$alkylsulfamoyl$C_{0-10}$ alkyl, aryl$C_{0-10}$ alkylsulfamoyl$C_{0-10}$ alkyl, $C_{1-10}$ alkylsulfonimidoyl$C_{0-10}$ alkyl, $C_{1-10}$ alkylthio$C_{0-10}$ alkyl, ($C_{0-10}$ alkyl)$_{1-2}$ amino, —$CO_2$($C_{0-10}$ alkyl), —($C_{0-10}$ alkyl)$CO_2H$, —$SO_2NH_2$, —$SO_2NH$($C_{1-10}$ alkyl), —$SO_2N$($C_{1-10}$ alkyl)$_2$, hydroxy, —($C_{1-10}$ alkyl)OH, —$C_{1-10}$ alkylalkoxy, cyano, and $C_{1-6}$haloalkyl; and wherein $R^{1b}$ is each optionally substituted with 1, 2, 3, or 4 $R^{3b}$ substituents.

In another embodiment of the invention of formula II, $R^{1b}$ is selected from: aminomethyl, 1-aminoethyl, isopropylsulfonyl, tert-butylsulfonyl, tert-butylsulfamoyl, methyl, pyrrolidinylcarbonyl, ethylaminomethyl, isopropylaminomethyl, isopropyl, tert-butyl, isobutyl, ethyl, propyl, cyclopropylmethyl, fluoro, methylcarbonyl, methylthiomethyl, triazolyl methyl, oxo, hydroxyethyl, methoxyethyl, tert-butyloxycarbonyl, 2-methoxy-1,1-dimethylethyl, 3-methoxy-1,1-dimethylpropyl, 3-methoxy-2.2-dimethylpropyl, dimethylsulfamoyl, cyclopentylmethyl, tert-butyloxycarbonylethyl, tert-butyloxycarbonylmethyl, tert-butyloxycarbonylisopropyl, cyclohexyl, cyclopentyl, methylaminomethyl, pyrrolidinylcarbonyl, piperidinyl, methoxy, difluoromethyl, ethoxycarbonyldimethyleth-2yl, (isopropoxy)carbonyldimethyleth-2yl, tetrahydropyranyl, oxazolyl, pyrazolyl, chloro, oxetanyl, oxadiazolyl, 1,2,4-oxadiazolyl, piperidinylcarbonyl, isoxazolyl, pyrrolidinyl, isopropylcarboxy, cyclopropyl, trifluoroethyl, 2,2,2-trifluoroethyl, morpholinyl, propyl, cyclobutyl, carboxy, methylsulfonyl, sulfamoyl, hydroxymethyl, pyrazolylaminocarbonylmethyl, 1,3-oxazolylcarbonylaminomethyl, pyrimidinylcarbonylaminomethyl, tert-butyloxycarbonylaminomethyl, isopropylsulfonyl, pyrrolidinylsulfonylmethyl, pyrazolylcarbonylaminomethyl, oxazolylcarbonylaminomethyl, pyrimidinylcarbonylaminomethyl, isopropylsulfamoyl, phenylmethylsulfamoyl, (cyclopropylmethyl)sulfamoyl, ethylsulfamoyl, cyclohexylsulfamoyl, piperidinylsulfonyl, morpholinylsulfonyl, 1,2,3-triazolylmethyl, morpholinylmethyl, dioxolanyl, trifluoroethylaminomethyl, methylsulfonyl, methylcarbonylaminomethyl, pyrazolylmethyl, imidazolylmethyl, (2,2,2-trifluoroethyl)aminomethyl, dimethylaminocarbonyl, morpholinylcarbonyl, pyrrolidinyl, 3-hydroxy-1,1-dimethylpropyl, 3-hydroxy-2,2-dimethylpropyl, 2-methoxy-1-methylethyl, hydroxypropyl, 2-hydroxypropyl, 1-hydroxy-1-methylethyl, trifluoromethyl, triazolyisopropyl, 1,2-dimethylpropyl, tertbutyloxycarbonyldimethyleth-2-yl, pyrazinylcarbonyl, 8-azabicyclo[3.2.1]octanyl, trifluoromethoxy, difluoroethyl, thiazolyl, 1,3-thiazolyl, triazolylisobutyl, tetrahydrothiopyranyl, ethoxycarbonyl, isopropylsulfonimidoyl, methylsulfonimidoyl, hydroxy, cyano, methoxyisopropyl, and 4,5-dihydro-1,2,4-oxadiazolyl; and wherein $R^{1b}$ is each optionally substituted with 1, 2, 3, or 4 $R^{3b}$ substituents.

In another embodiment of the invention, $R^{2b}$ is selected from: hydrogen, In another embodiment of the invention, $R^{2b}$ is halogen, $C_{1-10}$ alkyl(oxy)$_{0-1}$(carbonyl)$_{0-1}C_{0-10}$ alkyl, $C_{3-12}$ cycloalkyl, $(C_{3-12})$heterocycloalkyl $C_{0-10}$ alkyl (oxy)$_{0-1}$(carbonyl)$_{0-1}C_{0-10}$ alkyl, $C_{0-10}$ alkylamino$C_{0-10}$ alkyl, $C_{3-12}$ cycloalkyl $C_{0-10}$ alkylamino$C_{0-10}$ alkyl, $(C_{0-10}$ alkyl)$_{1-2}$ amino, and hydroxy; and wherein $R^{2b}$ is each optionally substituted with 1, 2, 3, or 4 $R^{3b}$ substituents.

In another embodiment of the invention, $R^{2b}$ is chosen from: fluoro, hydroxy, 1-cyclopropylethylamino, dimethylamino, azetidinyl, ethylamino, methyl; wherein $R^{2b}$ is each optionally substituted with 1, 2, 3, or 4 $R^{3b}$ substituents.

In one embodiment of the invention, $R^{2a}$ is selected from: hydrogen, methyl and fluoro.

In one embodiment of the invention, $R^{1a}$ is selected from: hydrogen, oxo, methyl, fluoro, dimethyl sulfamoyl, hydroxy, hydroxymethyl, cyclopropyl, (methylthio)methyl, isopropyl, methylsulfonyl, chloro, propyl, and ethyl.

In one embodiment of the invention $R^{3a}$ is chosen from oxo, methyl, fluoro, trifluoromethyl, hydroxymethyl, hydroxy, ethyl, cyclopropyl, (methylsulfanyl)methyl, hydroxypropyl, hydroxyethyl, methoxyethyl, chloro, aminomethyl, difluoromethyl, and (methylcarbonyl)aminomethyl.

In one embodiment of the invention, $R^{4a}$ is selected from hydrogen, hydroxy, methyl, oxo, trifluoromethyl, methoxy, 1-hydroxy-1-methylethyl, amino, methoxyethyl, difluoromethyl, dimethylamino, and ethyl.

In one embodiment of the invention of formula II, $R^{3b}$ is independently selected from: trifluoromethyl, hydroxy, methyl, piperidinyl, carboxy, tert-butyloxycarbonyl, tert-butyl, methoxyethyl, cyano, methoxy, fluoro, amino, phenyl, cyclopropyl, tert-butylsulfinyl, 1-hydroxymethylethyl, difluoromethyl, dimethylamino, cyanoethyl, oxo, isopropyl, and trifluoroethyl.

Optical Isomers—Diastereomers—Geometric Isomers—Tautomers

Compounds of the present invention may contain one or more asymmetric centers and can thus occur as racemates and racemic mixtures, single enantiomers, diastereomeric mixtures and individual diastereomers. The present invention is meant to comprehend all such isomeric forms of the compounds of the present invention, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I or formula II.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers.

Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of the present invention may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, 1-Bromo-4-((S and R)-propan-2-ylsulfonimidoyl)benzene, the "and" indicates a racemic mixture of the enantiomers. That is, the individual enantiomers were not individually isolated.

When the stereomeric nomenclature includes "or", for example, (1S,2S or 1R,2R)-2-(3-{[4-(tert-butylsulfonyl)phenyl]amino}-4-oxo-4,5-dihydro-H-pyrazolo[4,3-c]pyridin-1-yl)cycloheptanecarbonitrile, the "or" indicates that chiral resolution of racemate into individual enantiomers was accomplished but the actual optical activity of the specific enantiomer was not necessarily determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, 1-hydroxy-2-naphthoic acid (xinafoate) and the like. Particularly preferred are citric, hydrobromic, hydrochloric, maleic, phosphoric, sulfuric, and tartaric acids.

It will be understood that, unless otherwise specified, references to the compound of formula I subsets thereof, embodiments thereof, as well as specific compounds are meant to also include the pharmaceutically acceptable salts and stereoisomers thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis. In another embodiment, such diseases include recurrent airway obstruction, and chronic obstruction pulmonary disease (COPD), or obstructive airways diseases. In a variant of this embodiment the disease is COPD.

Another aspect of the present invention provides for the use of a compound of formula I in the manufacture of a medicament for the treatment or prevention of a JAK-mediated diseases or disorder.

One aspect of the invention is the use of a compound of Formula I or a pharmaceutically acceptable salt or a stereoisomer thereof in the manufacture of a medicament for the treatment of a disease or a disorder ameliorated by selective inhibition of Janus kinases JAK1 and JAK2.

Another aspect of the invention is the use of a compound of Formula I or a pharmaceutically acceptable salt or a stereoisomer thereof and a second active agent in the manufacture of a medicament for the treatment of a disease or a disorder ameliorated by selective inhibition of Janus kinases JAK1 and JAK2.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g, of active agent compounded with an appropriate and convenient amount of carrier material which may vary from about 5 to about 99.95 percent of the total composition. In some cases, the dosage unit forms may contain from about 0.05 to about 3 g of active ingredient. Dosage unit forms will generally contain between from about 0.1 mg to about 0.4 g of an active ingredient, typically 0.1 mg, 0.2 mg, 0.3 mg, 0.4 mg, 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

METHODS OF SYNTHESIS

SCHEMES AND EXAMPLES

The abbreviations used herein have the following tabulated meanings. Abbreviations not tabulated below have their meanings as commonly used unless specifically stated otherwise.

| | |
|---|---|
| ACN, MeCN | acetonitrile |
| AcOH | Acetic acid |
| AIBN | 2,2'-Azobis(2-methylpropionitrile) |
| BAST | bis(2-methoxyethyl)aminosulfur trifluoride |
| BuOH (n-BuOH) | butanol |
| Chiral SFC | chiral super critical fluid chromatography |
| $CO_2$ | carbon dioxide |
| $Cs_2CO_3$ | cesium carbonate |
| Dba | dibenzylideneacetone |
| DBU | 1,8-diazabicyclo[5.4.0]undec-7-ene |
| DCE | 1,2-dichloroethane |
| DCM | dichloromethane |
| DEA | diethylamine |
| DIPEA | N,N-diisopropylethylamine |
| DMAP | 4-Dimethylaminopyridine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |

-continued

| | |
|---|---|
| EtOH | ethanol |
| ESI | Electrospray ionization |
| HATU | O-(7-aza-1H-benzotriazol-1-yl)-N,N,N',N'-tetramethyluronium hexafluorophosphate |
| hr or h | hour |
| $H_2$ | Hydrogen |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LCMS | Liquid chromatography mass spectrometry |
| LRMS | low resolution mass spectrometry |
| MeI | iodomethane |
| Me-THF | 2-methyltetrahydrofuran |
| MgSO4 | magnesium sulfate |
| MP-(OAc)$_3$BH | solid supported (macro porous) triacetoxyborohydride |
| MPLC | medium pressure liquid chromatography |
| NaBH$_3$CN | Sodium cyanoborohydride |
| NaH | sodium hydride |
| Na$_2$SO$_4$ | sodium sulfate |
| NaBH$_4$ | sodium borohydride |
| NaHCO$_3$ | sodium bicarbonate |
| NaOH | Sodium hydroxide |
| NaOMe | sodium methoxide |
| Pd | palladium |
| Pd/C | Palladium on carbon |
| Pd$_2$(dba)$_3$ | tris(dibenzylideneacetone)dipalladium(0) |
| POCl$_3$ | phosphorus (V) oxychloride |
| Prep | preparative |
| PyBOP | (7-azabenzotriazol-1-yloxy)tripyrrolidinophosphonium hexafluorophosphate |
| Sat. | saturated |
| SEM-Cl | 2-(trimethylsilyl)ethoxymethyl chloride |
| SiliaCat ® DPP-Pd | silica bound diphenylphosphine palladium (II) |
| TBAF | tetra-n-butylammonium fluoride |
| TBS-Cl | tert-butyldimethylsilyl chloride |
| t-BuOH (tert-BuOH) | tent-butanol |
| t-Bu Xphos | 2-di-tert-butylphosphino-2',4',6'-triisopropylbiphenyl |
| TEA | triethylamine |
| TFA | trifluoroacetic acid |
| TFAA | Trifluoroacetic anhydride |
| THF | tetrahydrofuran |
| X-Phos | 2-dicyclohexylphosphino-2',4',6'-triisopropylbiphenyl |
| Me$_4$-$^t$Bu-X-Phos | di-tert-butyl[3,4,5,6-tetramethyl-2',4',6'-tri(propan-2-yl)biphenyl-2-yl]phosphane |
| MeOH | methanol |
| NH$_4$Cl | Ammonium chloride |
| NMP | N-Methylpyrrolidone |
| NMO | 4-methylmorpholine N-oxide |
| rt or RT | Room temperature |
| Sat. aq. | Saturated, aqueous |
| TPAP | tetra-n-propylammonium perruthenate (VII) |
| HCOOH | formic acid |
| K$^t$OBu | potassium tert-butoxide |
| Na$_2$S$_2$O$_5$ | sodium metabisulfite |
| NMR | nuclear magnetic resonance |
| TLC | thin layer chromatography |
| (EtO)$_2$P(O)CH$_2$CN | diethyl (cyanomethyl)phosphonate |
| MsCl | methanesulfonyl chloride |
| TsOH | p-toluenesulfonic acid |
| KCN | potassium cyanide |
| Si-DMT | silica supported Dimercaptotriazine |
| TMS | trimethylsilane |
| CF$_3$TMS | (trifluoromethyl)trimethylsilane |
| PhI(OAc)$_2$ | Iodosobenzene diacetate |
| Ti(OEt)$_4$ | Titanium (IV) ethoxide |
| Ti(Oi-Pr)$_4$ | Titanium (IV) isopropoxide |
| TMSCF$_3$ | trimethyl(trifluoromethyl)silane |
| BH3 | borane |
| SOCl$_2$ | Thionyl chloride |
| LiHMDS | Lithium bis(trimethylsilyl)amide |
| BOC$_2$O | Boc-anhydride, or di-tent-butyl dicarbonate |
| K$_2$CO$_3$ | Potassium carbonate |

-continued

| | |
|---|---|
| KI | Potassium iodide |
| i-PrMgCl | Isopropylmagnesium chloride |
| KOAc | Potassium acetate |
| KOH | Potassium hydroxide |
| K$_3$PO$_4$ | Potassium phosphate tribasic |
| PG | Protecting group |
| IBX | 2-Iodoxybenzoic acid |
| HNRR | A disubstituted amine |
| Ph$_3$PMeBr | Methyltriphenylphosphonium bromide |
| AlCl$_3$ | Aluminum trichloride |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-P | encyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted.

Ambient temperature is 15-25° C.

Most compounds were purified by reverse-phase preparative HPLC, MPLC on silica gel, SFC, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

Method 1

General procedures to prepare intermediates of the instant invention are described in Scheme 1. Using an appropriate base, such as DBU, in a suitable solvent, such as MeCN, EtOH, n-BuOH or tert-BuOH, at a temperature between 25-110° C. either protected pyrazolopyridone 1A (PG=a suitable protecting group) can undergo conjugate addition to optionally substituted nitriles 1B to yield adduct 1C, typically as a mixture of optical isomers, intermediates in the synthesis of examples of the instant invention. The isomers of intermediate IC can be separated into its respective individual optical isomers using the appropriate chromatographic method (achiral and/or chiral). Intermediate 1C is cross coupled to substituted aryl and heteroaryl halides 1D using an appropriate catalytic palladium/ligand system, such as $Pd_2(dba)_3$ or $Pd_2(dba)_3.CHCl_3$, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane ($Me_4{}^tBu$-XPhos), or 2-dicyclohexylphosphino-2',4',6'-triisopropylbiphenyl (XPhos), or [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3). Typical conditions employ 1-2 equivalents of the aryl/heteroaryl halide relative to the pyrazolopyrimidine with 10-25% Pd precatalyst loading, using an approximate Pd:ligand ratio of 1:2 to 1:2.5. Typically, the cross coupling is carried out using either 2-propanol or t-amyl alcohol solvents, and between 1-3.1 equivalents of KOAc or $K_3PO_4$ base. Reactions were typically carried out between 65-80° C., to yield intermediates 1E of the instant invention. Intermediates 1E can be deprotected using either hydrogenolysis conditions ($H_2$ gas, Pd/C, in a suitable solvent such as EtOAc, EtOH, MeOH, or using combinations of solvents thereof), or promoted by a suitable acid to afford Examples 1F of the instant invention. Alternatively, Intermediates 1C can be deprotected using either hydrogenolysis conditions ($H_2$ gas, Pd/C, in a suitable solvent such as EtOAc, EtOH, MeOH, or using combinations of solvents thereof), or promoted by a suitable acid to afford Intermediate 1G. Intermediate 1G is cross coupled to substituted aryl and heteroaryl halides 1D using an appropriate catalytic palladium/ligand system, such as $Pd_2(dba)_3$ or $Pd_2(dba)_3.CHCl_3$, and 2-di-tert-butylphosphino-2',4',6'-triisopropylbiphenyl (t-Bu XPhos) or di-tert-butyl[3,4,5,6-tetramethyl-2',4',6'-tri(propan-2-yl)biphenyl-2-yl]phosphane ($Me_4{}^tBu$-XPhos), or 2-dicyclohexylphosphino-2',4',6'-triisopropylbiphenyl (XPhos), or [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3). Typical conditions employ 1-2 equivalents of the aryl/heteroaryl halide relative to the pyrazolopyrimidine with 10-25% Pd precatalyst loading, using an approximate Pd:ligand ratio of 1:2 to 1:2.5. Typically, the cross coupling is carried out using either 2-propanol or t-amyl alcohol solvents, and between 1-3.1 equivalents of KOAc or $K_3PO_4$ base. Reactions were typically carried out between 65–80° C., to yield Examples 1F of the instant invention.

SCHEME 1

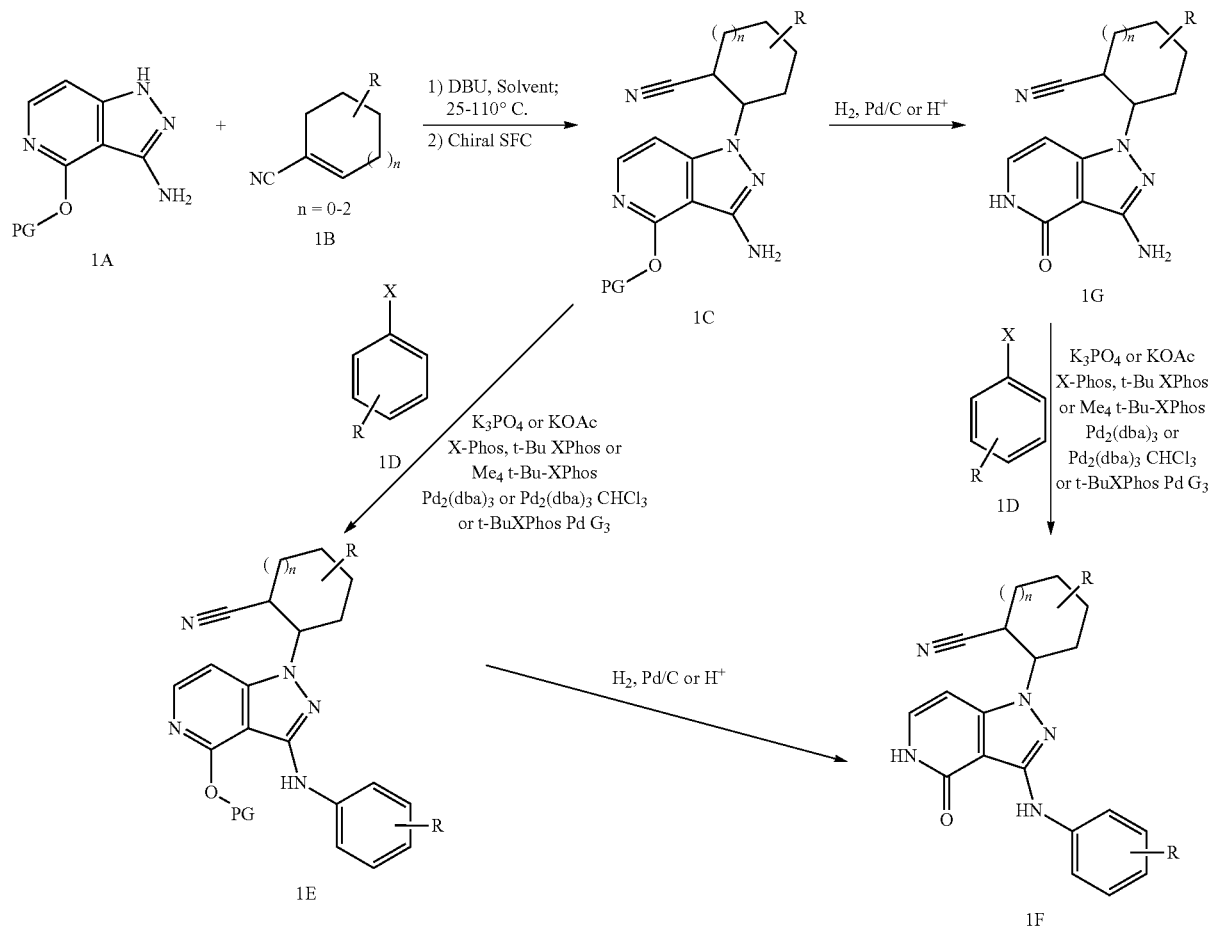

n = 0-2

Method 2

General procedures to prepare intermediates of the instant invention are described in Scheme 2. Pyrazolo-pyridone 2A is oxidized using an appropriate oxidant such as IBX or Jones reagent in a suitable solvent such as DMSO or acetone at a temperature between 0-50° C. to afford ketone 2B. Ketone 2B can further be reacted with a substituted amine under reductive amination conditions using a borohydride such as NaBH$_3$CN in a suitable solvent system such as MeOH/THF/AcOH to afford Examples 2C of the instant invention. Alternatively, ketone 2B can be reacted with BAST in a suitable solvent such as DCM at a temperature of 0° C. to afford Intermediate 2D. Intermediates 2D can be deprotected using either hydrogenolysis conditions (H$_2$ gas, Pd/C, in a suitable solvent such as EtOAc, EtOH, MeOH, or using combinations of solvents thereof), or promoted by a suitable acid to afford Examples 2E of the instant invention.

SCHEME 2

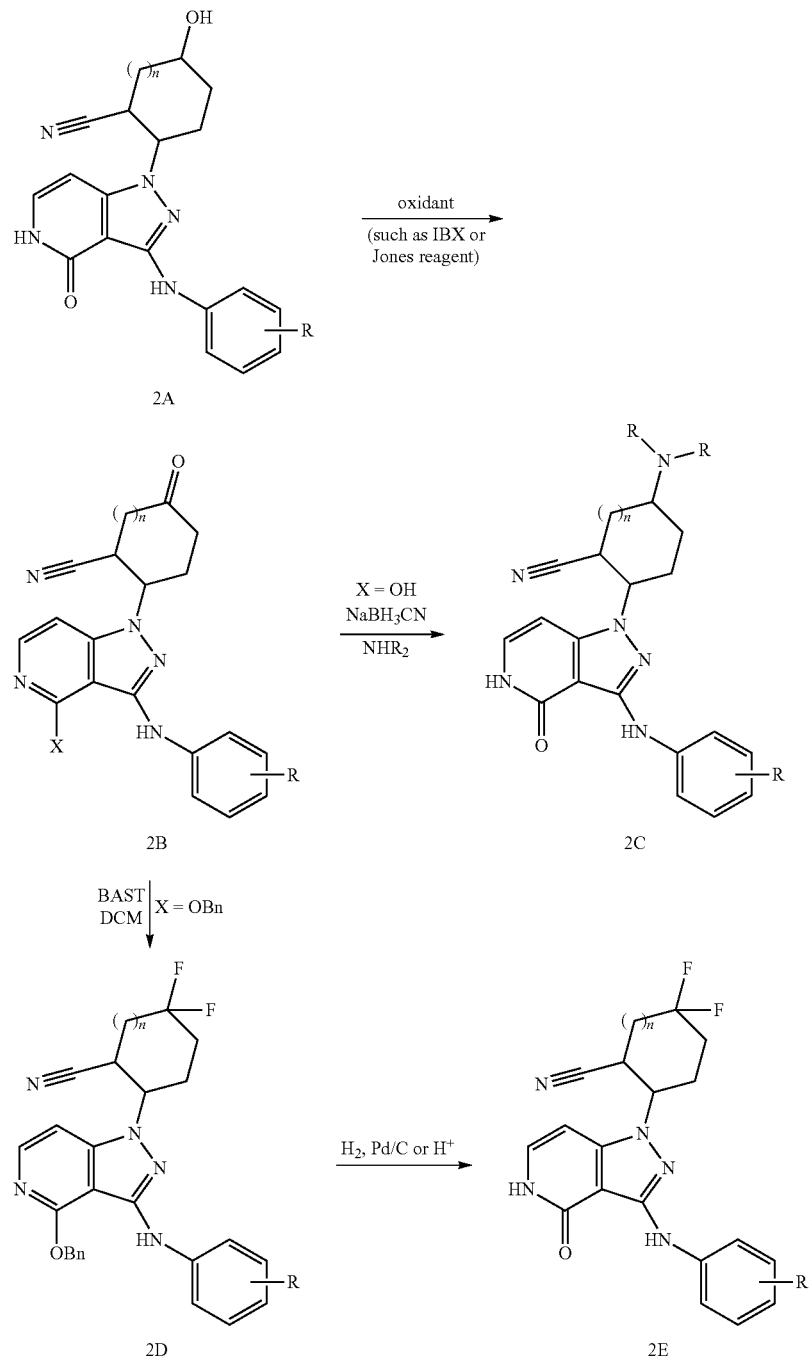

n = 0-2

Method 3

General procedures to prepare intermediates of the instant invention are described in Scheme 3. Pyrazolo-pyridone 3A can be treated with a suitable acid such as TFA or HCl in an appropriate solvent such as DCM, EtOAc, or MeOH at approximately ambient temperature to afford the corresponding amine-containing Examples 3B of the instant invention. Alternatively, protected intermediates 3C may be reacted in a similar manner to afford Examples 3B of the instant invention.

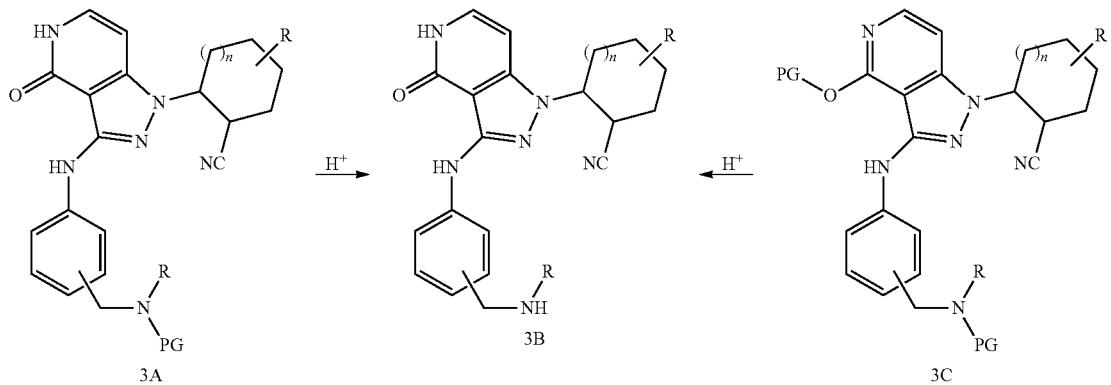

Method 4

General procedures to prepare intermediates of the instant invention are described in Scheme 4. Intermediates 4B can be treated with 2-methylpropane-2-sulfinamide (or another suitable ammonia surrogate) in the presence of a lewis acid such as titanium isopropoxide followed by a reductant such as sodium borohydride to afford Examples 4A after hydrogenolysis in the presence of an acid source (such as HCl) in a solvent such as EtOAc. Alternatively, Intermediates 4B can be treated with appropriately substituted amines using analogous conditions to afford Examples 4C of the instant invention. Intermediates 4B can also be treated with sodium borohydride in an appropriate solvent such as MeOH, followed by standard hydrogenolysis to afford alcohol-containing Examples 4D of the instant invention.

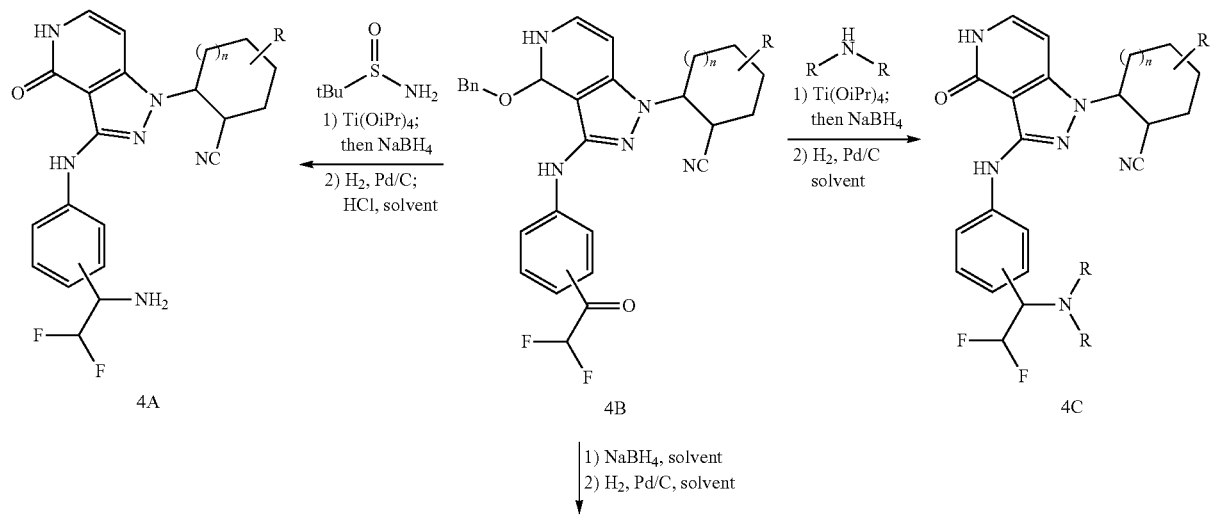

-continued

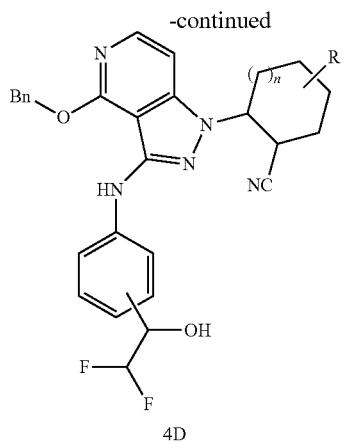

4D n = 0-2

Method 5

General procedures to prepare intermediates of the instant invention are described in Scheme 5. Dioxolane containing Intermediates 5A can be treated with a suitable acid such as HCl in a solvent (THF) to afford diol-containing Examples 5B of the instant invention.

Method 6

General procedures to prepare intermediates of the instant invention are described in Scheme 6. Ester-containing Intermediates 6A can be treated with an appropriate base such as sodium hydroxide in a solvent system such as MeOH/water at ambient temperature to afford Examples 6B of the instant invention following hydrogenolysis.

SCHEME 5

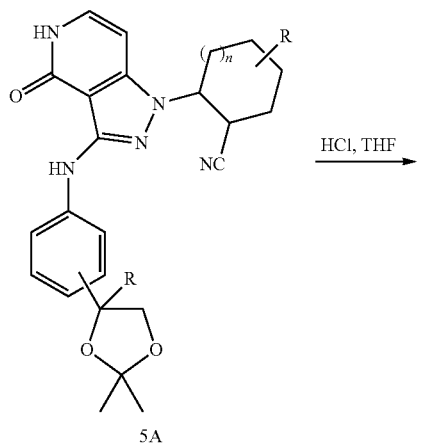

5A

HCl, THF →

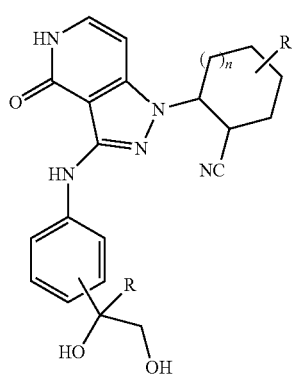

5B n = 0-2

SCHEME 6

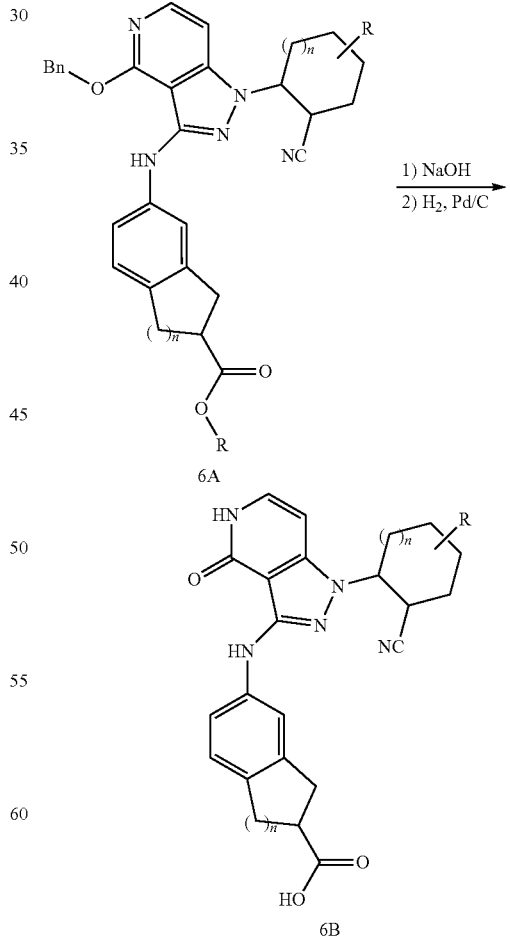

6A

1) NaOH
2) H₂, Pd/C →

6B n = 0-2

Method 7

General procedures to prepare intermediates of the instant invention are described in Scheme 7. Lactone Intermediates 7A are reacted with amines in the presence of a lewis acid such as aluminum trichloride at or around 80° C. to afford the corresponding amide Intermediates 7B, which can then be further treated with i-PrMgCl in a suitable solvent system such as THF/NMP followed by bis(dimethylamino)phosphoryl chloride at reflux temperature to afford Intermediates 7C of the instant invention.

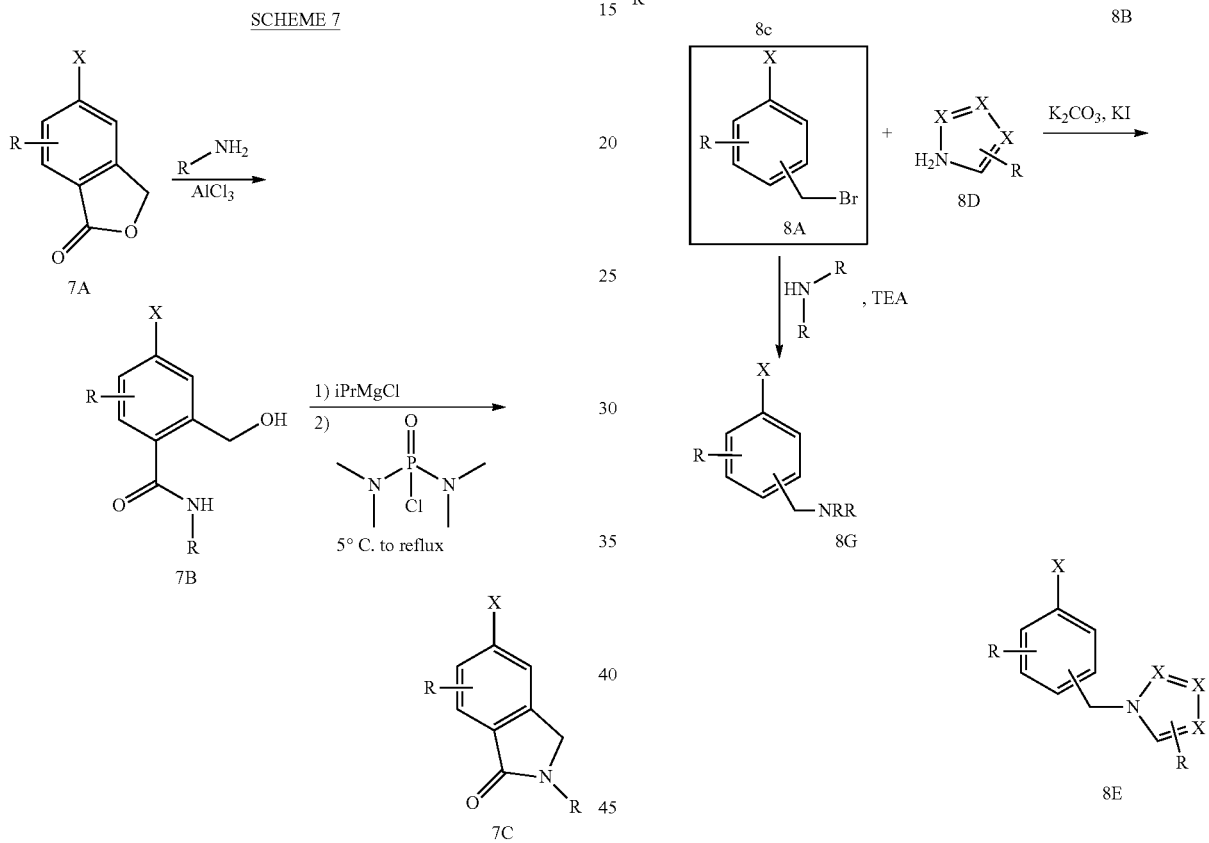

Method 8

General procedures to prepare intermediates of the instant invention are described in Scheme 8. Intermediates 8A can be reacted with an appropriately substituted heterocycle in the presence of a base such as potassium carbonate with an additive such as potassium iodide in a suitable solvent (such as acetone) at refluxing temperature to afford Examples 8E of the instant invention. Alternatively, Intermediates 8A can be reacted first with sodium azide in a solvent such as DMSO to afford an intermediate azide that can be further reacted with an appropriately substituted alkyne 8B in the presence of a copper salt (such as copper sulfate pentahydrate) and sodium ascorbate to afford the corresponding triazole Intermediates 8C to be used in the synthesis of examples of the instant invention. Alternatively, Intermediates 8A can be reacted with an appropriately substituted amine 8F in the presence of a base such as TEA in an appropriate solvent such as THF to afford Intermediates 8G which can be used in the synthesis of examples of the instant invention.

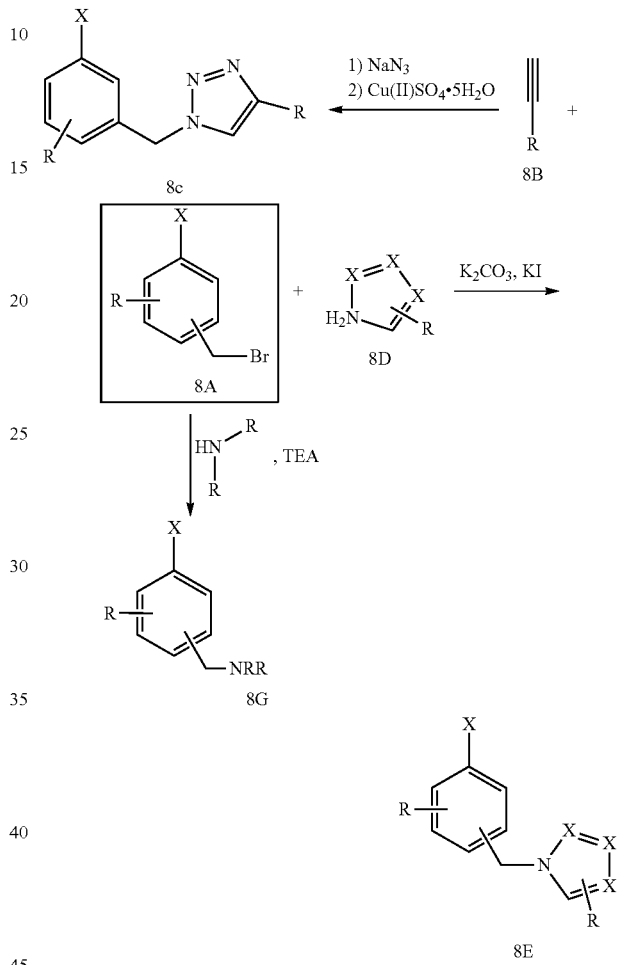

Method 9

General procedures to prepare intermediates of the instant invention are described in Scheme 9. Trifluoromethyl ketone containing Intermediates 9A can be reduced with a suitable reducing agent such as sodium borohydride in a solvent such as MeOH to afford the corresponding alcohol Intermediates 9B to be used in the synthesis of examples of the instant invention. Optical isomers may further be separated using appropriate chiral chromatographic methods to afford the corresponding diastereomers/enantiomers. Alternatively, Intermediates 9A can be reacted with LiHMDS followed by a reducing agent such as borane-THF complex to afford the corresponding amine Intermediates 9C. Optical isomers may further be separated using appropriate chiral chromatographic methods to afford the corresponding diastereomers/enantiomers to be used as intermediates in the syntheses of examples of the instant invention.

SCHEME 9

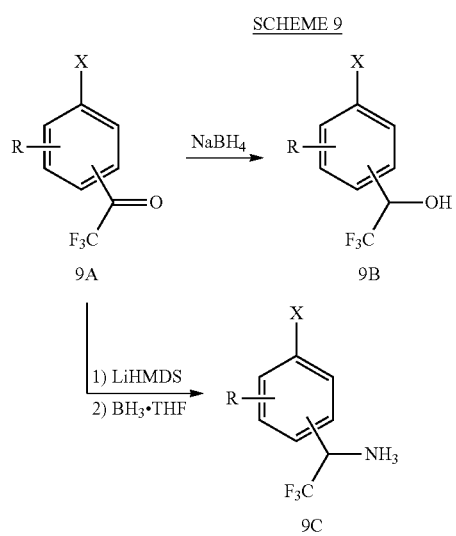

Method 10

General procedures to prepare intermediates of the instant invention are described in Scheme 10. Amine-containing Intermediates 10A can be reacted with an appropriately substituted carboxylic acid 10B in the presence of amide coupling reagents (such as EDC and HOBt) in a solvent such as DCM to afford the corresponding amide Intermediates 10C to be used in the synthesis of examples of the instant invention. Alternatively, Intermediates 10A can be reacted with BOC$_2$O in a solvent such as EtOH or DCM to provide carbamate Intermediates 10D to be used in the synthesis of examples of the instant invention.

SCHEME 10

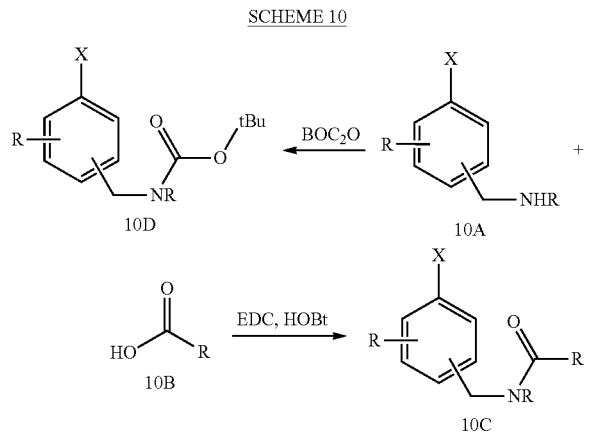

Method 11

General procedures to prepare intermediates of the instant invention are described in Scheme 11. Sulfonyl chloride Intermediates 11A can be reacted with an appropriately substituted amine in the presence of a suitable base (such as DIPEA) in a solvent such as DCM to afford Intermediates 11B that can be used in the synthesis of examples of the instant invention.

SCHEME 11

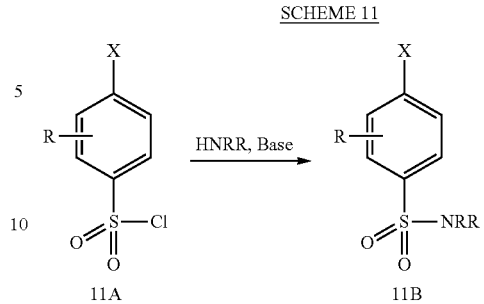

Method 12

General procedures to prepare intermediates of the instant invention are described in Scheme 12. Carboxylic acid Intermediates 12A can be reacted under amide coupling conditions using reagents such as EDC or HOBt, or alternatively can be converted to the corresponding acid chloride using a reagent such as thionyl chloride to afford amide Intermediates 12C that can be used in the synthesis of examples of the instant invention.

SCHEME 12

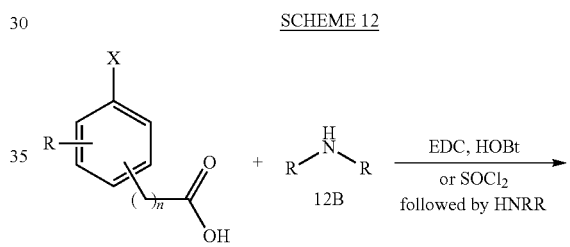

n = 0-3

Method 13

General procedures to prepare intermediates of the instant invention are described in Scheme 13. Amine Intermediates 13A or 13B can be reacted with an appropriate anhydride (or under suitable amide coupling conditions) to afford an intermediate amide that can further be reduced using a reductant such as borane-dimethylsulfide complex at approximately 75° C. to afford Intermediates 13C or 13D which can be used in the synthesis of examples of the instant invention.

SCHEME 13

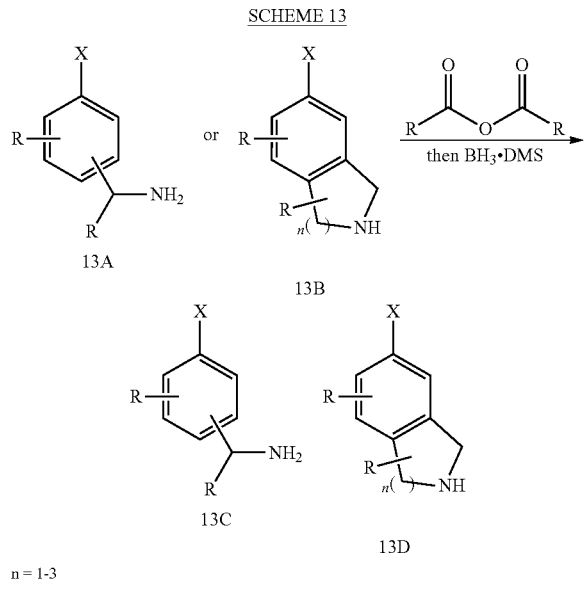

n = 1-3

Method 14

General procedures to prepare intermediates of the instant invention are described in Scheme 14. Amine Intermediates 14A can be reacted with an appropriately substituted aldehyde in the presence of a reductant such as sodium borohydride in a suitable solvent (such as MeOH) to afford Intermediates 14B that can be used in the synthesis of examples of the instant invention. Alternatively, Intermediates 14A can be reacted with an appropriately substituted alkyl halide in the presence of a base such as sodium hydride in DMF solvent to afford Intermediates 14C that can be used in the synthesis of examples of the instant invention.

SCHEME 14

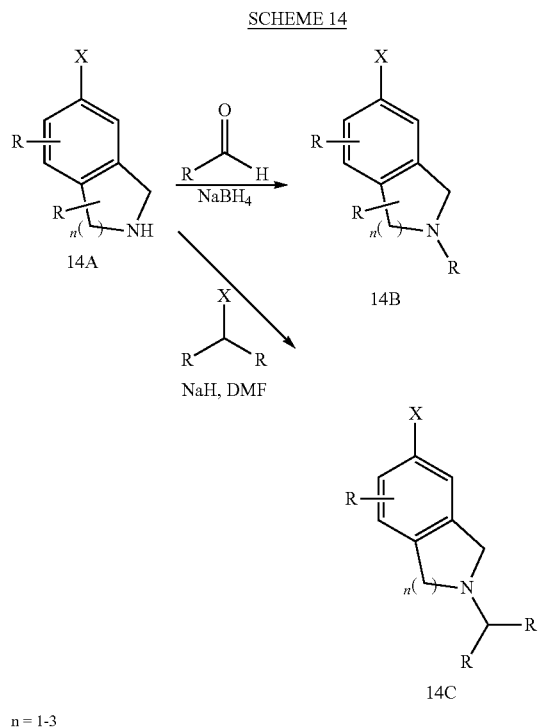

n = 1-3

Method 15

General procedures to prepare intermediates of the instant invention are described in Scheme 15. Appropriately substituted aldehydes 15A can be reacted with 2-methylpropane-2-sulfinamide (racemate or optically pure enantiomers may be used) in the presence of a lewis acid such as titanium ethoxide in a solvent such as THF at reflux temperature to afford the corresponding Intermediates 15B that can further be treated with trimethyl(trifluoromethyl)silane and a fluoride source such as TBAF to afford Intermediates 15C that can be used in the synthesis of examples of the instant invention. Optical isomers may further be separated using appropriate chiral chromatographic methods to afford the corresponding individual diastereomers/enantiomers.

SCHEME 15

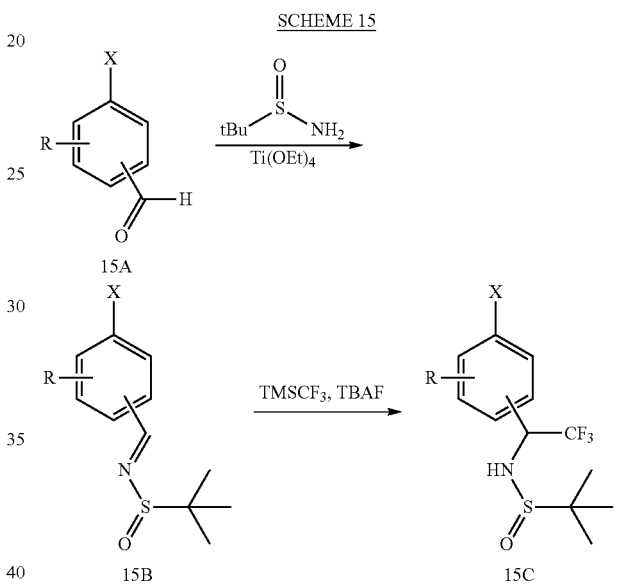

Method 16

General procedures to prepare intermediates of the instant invention are described in Scheme 16. Sulfonyl chloride 16A can be reacted with an appropriately substituted amine in the presence of a suitable base such as triethylamine in a solvent such as dichloromethane to afford sulfonamide Intermediates 16B. Intermediates 16B can be treated with oxidative conditions to affect intramolecular cyclization to afford Intermediates 16C or 16E (protocols such as periodic acid with chromium trioxide and acetic acid; or iodobenzene diacetate and iodine can be used). Intermediates 16C can be reduced using a suitable reducing agent such as borane-tetrahydrofuran or borane-dimethylsulfide complex to afford Intermediates 16D which can be used in the synthesis of examples of the instant invention. Alternatively, Intermediates 16E can be reacted with an appropriately substituted alkyl halide in the presence of a base such as cesium carbonate to afford Intermediates 16D following reduction with either borane-tetrahydrofuran or borane-dimethylsulfide complex.

SCHEME 16

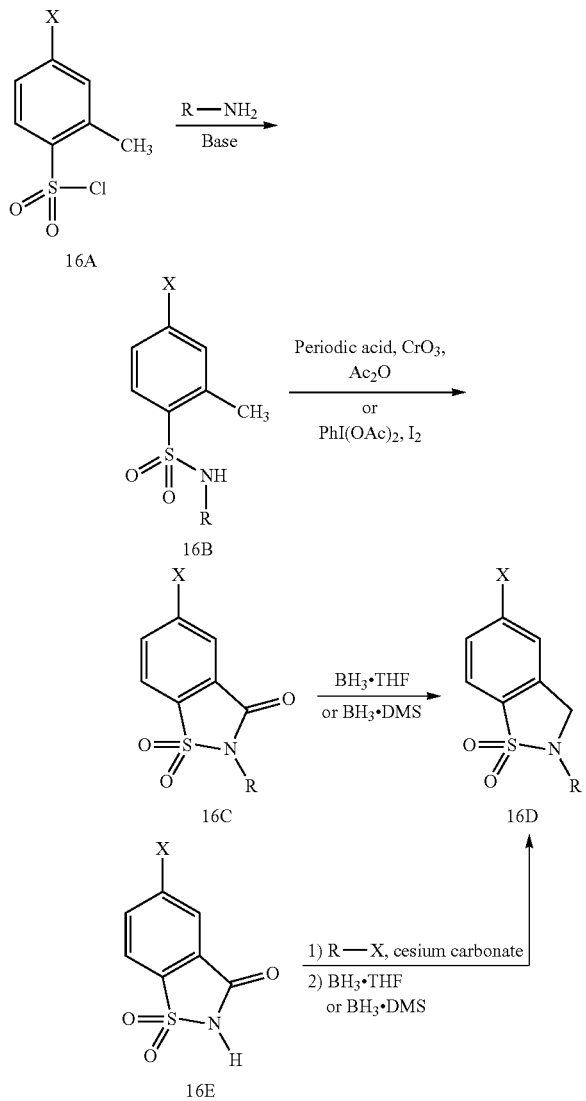

INTERMEDIATES

The following experimental procedures detail the preparation of chemical materials used in the synthesis of Examples of the instant invention. The exemplified procedures are for illustrative purposes only, and are not intended to limit the scope of the instant invention in any way.

Intermediate 1

4-(Benzyloxy)-1H-pyrazolo[4,3-c]pyridin-3-amine

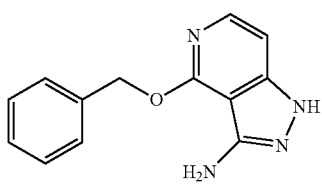

I-1

Step 1: 2-(Benzyloxy)-4-methoxynicotinonitrile

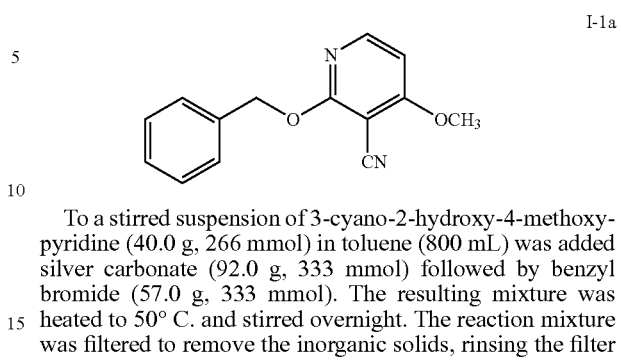

I-1a

To a stirred suspension of 3-cyano-2-hydroxy-4-methoxy-pyridine (40.0 g, 266 mmol) in toluene (800 mL) was added silver carbonate (92.0 g, 333 mmol) followed by benzyl bromide (57.0 g, 333 mmol). The resulting mixture was heated to 50° C. and stirred overnight. The reaction mixture was filtered to remove the inorganic solids, rinsing the filter cake with DCM. The filtrate was concentrated in vacuo. Petroleum ether (100 mL) was added to the crude residue, and the triturated solids were collected by filtration to afford 2-(benzyloxy)-4-methoxynicotinonitrile. LRMS (ESI) calc'd for $C_{14}H_{13}N_2O_2$ [M+H]$^+$: 241, found: 241. $^1$H NMR (600 MHz CDCl$_3$) δ 8.21 (d, J=6.6 Hz, 1H), 7.48 (d, J=7.8 Hz, 2H), 7.38 (m, 2H), 7.32 (m, 1H), 6.58 (d, J=6.0 Hz, 1H), 5.51 (s, 2H), 3.99 (s, 3H).

Step 2: 4-(Benzyloxy)-1H-pyrazolo[4,3-c]pyridin-3-amine

A stirred suspension of 2-(benzyloxy)-4-methoxynicotinonitrile (63 g, 0.26 mol) in a solvent mixture of hydrazine hydrate (210 mL) and anhydrous ethanol (420 mL) was heated to reflux at approximately 110° C. The reaction was refluxed for 3 days. The mixture was then concentrated in vacuo and diluted with EtOAc (200 mL), and washed with water (20 mL) and brine (20 mL). The organic layer was dried over Na$_2$SO$_4$, filtered and concentrated in vacuo to afford a residue that was purified by silica gel column chromatography (Petroleum ether/EtOAc=10:1-1:1) to afford 4-(benzyloxy)-1H-pyrazolo[4,3-c]pyridin-3-amine. LRMS (ESI) calc'd for $C_{13}H_{13}N_4O$ [M+H]$^+$: 241, found 241. $^1$H NMR (DMSO-d$_6$, 400 MHz): δ 11.87 (br s, 1H), δ 7.67 (d, 1H, J=6.0 Hz), 7.38-7.49 (m, 2H), 7.34-7.38 (m, 2H), 7.28-7.31 (m, 1H), 6.80 (d, 1H, J=4.0 Hz), 5.49 (s, 2H), 5.15 (s, 2H).

Intermediate 2

(cis)-2-[3-Amino-4-(benzyloxy)-1H-pyrazolo[4,3-c]pyridin-1-yl]cyclohexanecarbonitrile (racemate)

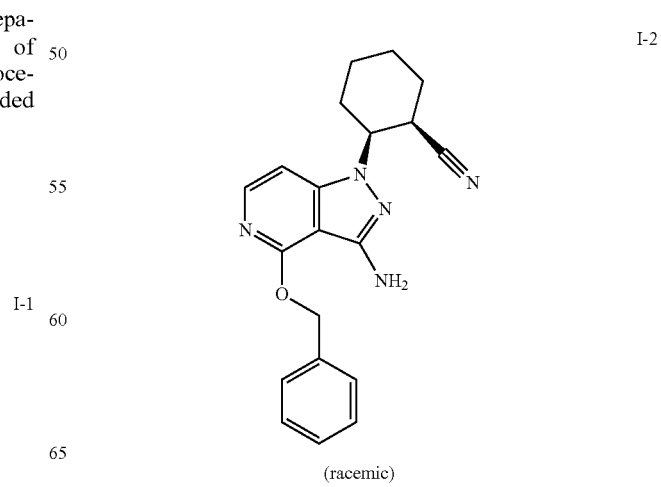

I-2

(racemic)

To a solution of 4-(benzyloxy)-1H-pyrazolo[4,3-c]pyridin-3-amine (I-1; 15 mg, 0.062 mmol) in ethanol (0.2 mL) in a sealable tube was added 1-cyanocyclohexene (0.070 mL, 0.624 mmol) and DBU (0.019 mL, 0.125 mmol). The tube was sealed and heated at 90° C. for 24 hours. The reaction was then cooled to room temperature, concentrated in vacuo, and purified by silica gel chromatography (0-100% EtOAc/hexanes). The first eluting product is the minor (trans)-2-[3-amino-4-(benzyloxy)-1H-pyrazolo[4,3-c]pyridin-1-yl]cyclohexanecarbonitrile and the second eluting product is the major (cis)-2-[3-amino-4-(benzyloxy)-1H-pyrazolo[4,3-c]pyridin-1-yl]cyclohexanecarbonitrile (racemate). LRMS (ESI) calc'd for $C_{20}H_{22}N_5O$ [M+H]$^+$: 348, found 348. $^1$H NMR (600 MHz, CDCl$_3$): δ 7.80 (d, J=6.6 Hz, 1H), 7.45 (d, J=7.2 Hz, 2H), 7.37 (t, J=7.2 Hz, 2H), 7.32 (t, J=7.2 Hz, 1H), 6.79 (d, J=6.6 Hz, 1H), 5.51 (s, 2H), 4.45 (br s, 2H), 4.24 (m, 1H), 3.32 (s, 1H), 2.52 (qd, J=12.6, 3.6 Hz, 1H), 2.12-2.18 (m, 2H), 2.07 (m, 1H), 1.71-1.78 (m, 3H), 1.46 (m, 1H).

Intermediate 3

(trans)-2-[3-Amino-4-(benzyloxy)-1H-pyrazolo[4,3-c]pyridin-1-yl]cyclohexanecarbonitrile (racemate)

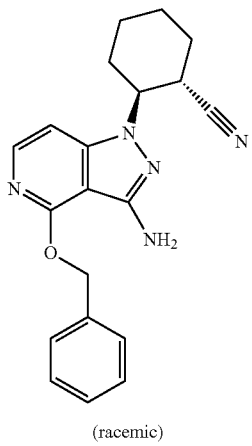

I-3

(racemic)

4-(Benzyloxy)-1H-pyrazolo[4,3-c]pyridin-3-amine (I-1; 20.0 g, 83.0 mmol) was placed in a thick-wall reaction flask (500 mL) followed by the addition of acetonitrile (167 ml), cyclohex-1-enecarbonitrile (71.0 g, 0.670 mol), and DBU (25.0 g, 0.170 mol). The flask was sealed and heated at 120° C. for 4 days. After 4 days, nearly ~80% conversion to the major trans-isomer took place with a minor amount of the cis-product detected. The mixture was cooled down, concentrated in vacuo and the residue was purified by gel silica chromatography (petroleum ether/EtOAc loaded with 1% DCM) to afford the product (trans)-2-[3-amino-4-(benzyloxy)-1H-pyrazolo[4,3-c]pyridin-1-yl]cyclohexanecarbonitrile (racemate). LRMS (ESI) calc'd for $C_{20}H_{22}N_5O$ [M+H]$^+$: 348, found 348; 1H NMR (600 MHz, CDCl$_3$): δ 7.83 (d, J=6.0 Hz, 1H), 7.46 (d, J=7.8 Hz, 2H), 7.38 (t, J=7.8 Hz, 2H), 7.32 (t, J=7.2 Hz, 1H), 6.77 (d, J=6.6 Hz, 1H), 5.50 (s, 2H), 4.44 (s, 2H), 4.18 (m, 1H), 3.19 (m, 1H), 2.30 (m, 1H), 1.90-1.98 (m, 3H), 1.84 (m, 1H), 1.74 (m, 1H), 1.44 (m, 1H), 1.32 (m, 1H).

Intermediates 4 and 5

(1R,2R)-2-(3-Amino-4-(benzyloxy)-1H-pyrazolo[4,3-c]pyridin-1-yl)cyclohexanecarbonitrile and (1S,2S)-2-(3-Amino-4-(benzyloxy)-1H-pyrazolo[4,3-c]pyridin-1-yl)cyclohexanecarbonitrile

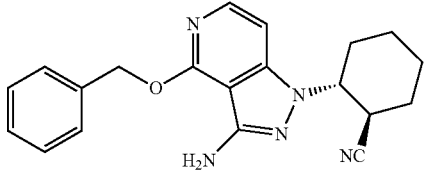

I-4

I-5

The title compounds, I-4 and I-5, were separated from the racemic mixture following the procedure below:

Column Used: Chiral Technology IC 2.1×25 cm, 5 μM.

Mobile phase: 28%/72% 2-Propanol/CO$_2$ (no other modifiers).

Flow rate: 65 mL/min, 8 min run time, 10 minutes with impurity.

Wavelength: 220 nm.

Injection preparation: 7 grams of racemate was dissolved into methanol/DMF, 3:1 (80 mL), and filtered to remove any particulates. Injections of 0.30 mL were performed and elution of the individual enantiomers was observed at 4.97 minutes (1R,2R; I-4 LRMS (ESI) calc'd for $C_{20}H_{22}N_5O$ [M+H]$^+$: 348, found 348) and 6.02 minutes (1S,2S; I-5 LRMS (ESI) calc'd for $C_{20}H_{22}N_5O$ [M+H]$^+$: 348, found 348).

Intermediates 6 and 7

(1R,2R)-2-(3-Amino-4-(benzyloxy)-1H-pyrazolo[4,3-c]pyridin-1-yl)cyclopentanecarbonitrile and (1S,2S)-2-(3-Amino-4-(benzyloxy)-1H-pyrazolo[4,3-c]pyridin-1-yl)cyclopentanecarbonitrile

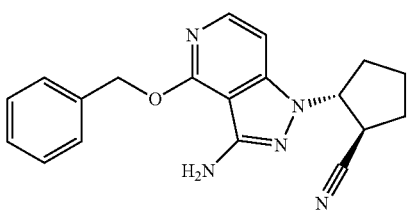

I-6

-continued

I-7

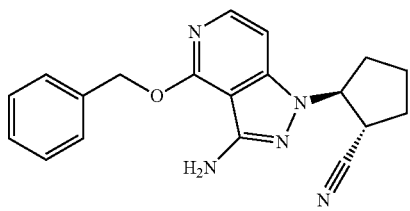

Into a 5000-mL 4-necked round-bottom flask purged and maintained with an inert atmosphere of nitrogen was placed 4-(benzyloxy)-1H-pyrazolo[4,3-c]pyridin-3-amine (I-1; 250 g, 1.04 mol), ethanol (3000 mL), cyclopent-1-ene-1-carbonitrile (300 g, 3.22 mol), and DBU (317 g, 2.08 mol). The resulting solution was heated to reflux and stirred overnight. The reaction mixture was cooled and concentrated in vacuo, and the resulting residue was applied onto a silica gel column and eluted with ethyl acetate/petroleum ether (1:10-1:2) to afford racemic-2-[3-amino-4-(benzyloxy)-1H-pyrazolo[4,3-c]pyridin-1-yl]cyclopentane-1-carbonitrile.

The racemic 2-[3-amino-4-(benzyloxy)-1H-pyrazolo[4,3-c]pyridin-1-yl]cyclopentane-1-carbonitrile (100 g, 300 mmol) was purified using Chiral Prep-SFC with the following conditions:
Column Used: Phenomenex Lux Cellulose-4, 2×25 cm, 5 μm
Mobile phase: $CO_2$ (80%), methanol with 0.1% DEA (20%)
Wavelength: UV 254 nm.
Peak A, I-6: (1R,2R)-2-[3-amino-4-(benzyloxy)-1H-pyrazolo[4,3-c]pyridin-1-yl]cyclopentane-1-carbonitrile LRMS (ESI) calc'd for $C_{19}H_{20}N_5O$ [M+H]$^+$: 334, found 334. $^1$H-NMR (300 MHz, $CDCl_3$): δ 7.86-6.84 (m, 7H), 5.55 (s, 2H), 4.94-4.86 (s, 2H), 4.49 (s, 1H), 3.34-3.26 (m, 1H), 2.39-2.01 (m, 6H).
Peak B, I-7: (1S,2S)-2-[3-amino-4-(benzyloxy)-1H-pyrazolo[4,3-c]pyridin-1-yl]cyclopentane-1-carbonitrile LRMS (ESI) calc'd for $C_{19}H_{20}N_5O$ [M+H]$^+$: 334, found 334. $^1$H-NMR (300 MHz, $CDCl_3$): δ 7.86-6.84 (m, 7H), 5.55 (s, 2H), 4.94-4.86 (s, 2H), 4.49 (s, 1H), 3.34-3.26 (m, 1H), 2.39-2.01 (m, 6H).

Intermediates 8 and 9

(1R,2R,5S)-2-(3-Amino-4-(benzyloxy)-1H-pyrazolo[4,3-c]pyridin-1-yl)-5-hydroxycyclohexanecarbonitrile and (1S,2S,5R)-2-(3-Amino-4-(benzyloxy)-1H-pyrazolo[4,3-c]pyridin-1-yl)-5-hydroxycyclohexanecarbonitrile

I-8

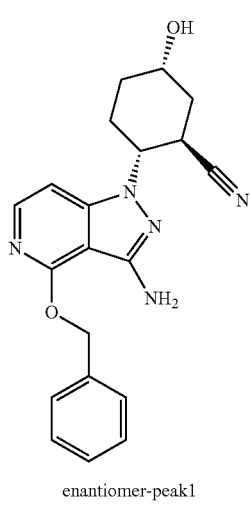

enantiomer-peak1

I-9

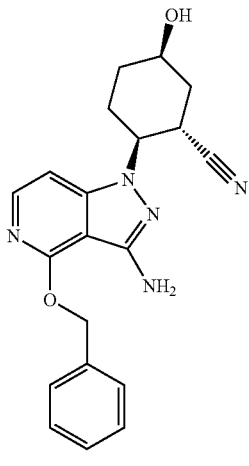

enantiomer-peak2

To a flask was added 4-(benzyloxy)-1H-pyrazolo[4,3-c]pyridin-3-amine, (I-1; 6.00 g, 25.0 mmol), 5-hydroxycyclohex-1-enecarbonitrile (9.23 g, 74.9 mmol), DBU (7.53 mL, 49.9 mmol), and EtOH (50 mL). The resulting mixture was heated at 85° C. for 50 h, then was cooled, concentrated in vacuo, and diluted with EtOAc/$H_2O$. The layers were separated and the organic layer was washed with $H_2O$ and brine. The organic layer was dried over $Na_2SO_4$, filtered and concentrated in vacuo to afford a residue that was subjected to silica gel chromatography (0-50% acetone/DCM) to afford the major diastereomer as a racemic mixture of (1R,2R,5S) and (1S,2S,5R)-2-(3-amino-4-(benzyloxy)-1H-pyrazolo[4,3-c]pyridin-1-yl)-5-hydroxycyclohexanecarbonitrile. The individual enantiomers were separated by preparative chiral SFC using the following conditions to afford the two enantiomers:

Column Used: Chiral Technology AZ-H 2.1×25 cm, 5 μM.
Mobile phase: 29%/71% Methanol/$CO_2$
Flow rate: 63 mL/min
Wavelength: 220 nm Peak A, I-8: (1R,2R,5S)-2-(3-amino-4-(benzyloxy)-1H-pyrazolo[4,3-c]pyridin-1-yl)-5-hydroxycyclohexanecarbonitrile. LRMS (ESI) calc'd for $C_{20}H_{22}N_5O_2$ [M+H]$^+$: 364, found 364. $^1$H NMR (600 MHz, $CDCl_3$): δ 7.86 (d, J=6.0 Hz, 1H), 7.50 (d, J=7.2 Hz, 2H), 7.41 (t, J=7.2 Hz, 2H), 7.36 (t, J=7.2 Hz, 2H), 6.80 (d, J=6.0 Hz, 1H), 5.54 (s, 2H), 4.55 (s, 2H), 4.24-4.27 (m, 2H), 3.76 (t, J=10.8 Hz, 1H), 2.44-2.50 (m, 1H), 2.37 (d, J=13.2 Hz, 1H), 1.94-2.00 (m, 2H), 1.61-1.82 (m, 2H).

Peak B, I-9: (1S,2S,5R)-2-(3-amino-4-(benzyloxy)-1H-pyrazolo[4,3-c]pyridin-1-yl)-5-hydroxycyclohexane carbonitrile. LRMS (ESI) calc'd for $C_{20}H_{22}N_5O_2$ [M+H]$^+$: 364, found 364. $^1$H NMR (600 MHz, $CDCl_3$): δ 7.86 (d, J=6.0 Hz, 1H), 7.50 (d, J=7.2 Hz, 2H), 7.41 (t, J=7.2 Hz, 2H), 7.36 (t, J=7.2 Hz, 2H), 6.80 (d, J=6.0 Hz, 1H), 5.54 (s, 2H), 4.55 (s, 2H), 4.24-4.27 (m, 2H), 3.76 (t, J=10.8 Hz, 1H), 2.44-2.50 (m, 1H), 2.37 (d, J=13.2 Hz, 1H), 1.94-2.00 (m, 2H), 1.61-1.82 (m, 2H).

Intermediate 10

(1S,2S)-2-(3-Amino-4-oxo-4,5-dihydro-1H-pyrazolo[4,3-c]pyridin-1-yl)cyclohexanecarbonitrile

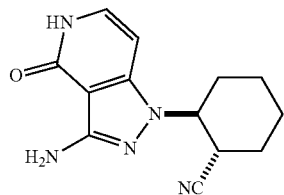

I-10

10% Palladium on carbon (213 mg, 10 wt. %) was added to a solution of (1S,2S)-2-(3-amino-4-(benzyloxy)-1H-pyrazolo[4,3-c]pyridin-1-yl)cyclohexanecarbonitrile (I-5; 695 mg, 2.00 mmol) in EtOAc (10.0 mL) at room temperature. The flask was sealed and degassed by evacuation and backfill with hydrogen (3×) and stirred under a hydrogen balloon at room temperature for 2 hours. The mixture was diluted with 25% MeOH/CH$_2$Cl$_2$, filtered through celite, and the filtrate was concentrated in vacuo. The residue was triturated with CH$_2$Cl$_2$ and the solid was collected by filtration to give the title compound. LRMS(ESI) calc'd for CH$_3$H$_{16}$N$_5$O [M+H]$^+$: 258, found 258.

Table 1 discloses an Intermediate which was prepared in an analogous manner to that of Intermediate 10, using Intermediate 7 as the starting material.

TABLE 1

| Intermediate | Structure | Compound Name | LRMS [M + H]$^+$ |
|---|---|---|---|
| I-11 | 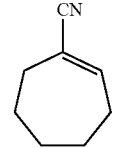 | (1S,2S)-2-(3-amino-4-oxo-4,5-dihydro-1H-pyrazolo[4,3-c]pyridin-1-yl)cyclopentanecarbonitrile | Calc'd 244, found 244 |

Intermediate 12

2-(3-Amino-4-(benzyloxy)-1H-pyrazolo[4,3-c]pyridin-1-yl)cycloheptanecarbonitrile

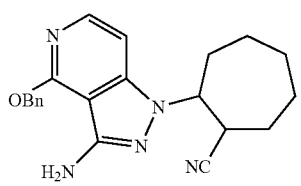

I-12

Step 1: 1-((Trimethylsilyl)oxy)cycloheptanecarbonitrile

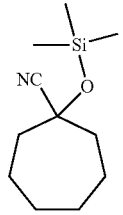

I-12a

Into a 500-mL round-bottom flask, was placed cycloheptanone (20.0 g, 178 mmol) in dichloromethane (250 mL). Diiodozinc (0.57 g, 1.8 mmol) and trimethylsilane-carbonitrile (21.21 g, 213.8 mmol) were added respectively at 0° C. The resulting solution was stirred for 1 h at ambient temperature and then diluted with dichloromethane (200 mL). The resulting mixture was washed with water (3×100 mL) and brine (3×100 mL), dried over anhydrous sodium sulfate and filtered. The filtrate was concentrated in vacuo to afford the crude title compound.

Step 2: Cyclohept-1-enecarbonitrile

I-12b

Into a 500 mL round bottom flask purged and maintained with an inert atmosphere of nitrogen, were placed 1-[(trimethylsilyl)oxy]cycloheptane-1-carbonitrile (35.0 g, 166 mmol), phosphoroyl trichloride (127 g, 828 mmol) and pyridine (200 mL). The resulting solution was stirred for 16 h at 100° C. The reaction was quenched by ice water (500 mL) and the resulting solution extracted with ethyl acetate (3×200 mL). The organic layers were combined, washed with water (3×200 mL) and brine (3×200 mL), dried over anhydrous sodium sulfate and filtered. The filtrate was concentrated in vacuo and the residue purified on silica, eluting with ethyl acetate/petroleum ether (1:10) to afford the title compound. GCMS (ES) calc'd for C$_8$H$_{11}$N [M]$^+$: 121, found 121.

Step 3: 2-(3-Amino-4-(benzyloxy)-1H-pyrazolo[4,3-c]pyridin-1-yl)cycloheptanecarbonitrile Into a 100 mL round bottom flask, were placed 4-(benzyloxy)-1H-pyrazolo[4,3-c]pyridin-3-amine (I-1; 2.0 g, 8.3 mmol), cyclohept-1-ene-1-carbonitrile (2.02 g, 16.7 mmol), 1,8-diazabicyclo[5,4,0]undec-7-ene (2.65 g, 16.7 mmol) and acetonitrile (15 mL). The resulting solution was stirred for 16 h at 80° C. Water (100 mL) was added and the mixture extracted with ethyl acetate (3×200 mL). The organic layers were combined, washed with water (3×200 mL) and brine (3×200 mL), dried over anhydrous sodium sulfate and filtered. The filtrate was concentrated in vacuo and the residue purified on silica, eluting with ethyl acetate/petroleum ether (1:5) to afford the title compound. LRMS (ESI) calc'd for $C_{21}H_{24}N_5O$ [M+H]$^+$ 362, found 362. $^1$H NMR (300 MHz, CDCl$_3$) δ 7.88-7.83 (m, 1H), 7.50-7.48 (m, 2H), 7.44-7.35 (m, 3H), 6.81 (d, J=6.0 Hz, 1H), 5.55 (s, 2H), 4.50 (brs, 2H), 3.54-3.26 (m, 1H), 2.61-2.51 (m, 0.3H), 2.28-2.11 (m, 1.7H), 2.06-1.61 (m, 9H).

Intermediates 13 and 14

(cis)-2-(3-Amino-4-oxo-4,5-dihydro-1H-pyrazolo[4,3-c]pyridin-1-yl)cycloheptanecarbonitrile (racemic) and (trans)-2-(3-Amino-4-oxo-4,5-dihydro-1H-pyrazolo[4,3-c]pyridin-1-yl)cycloheptanecarbonitrile (racemic)

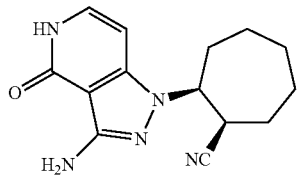

I-13

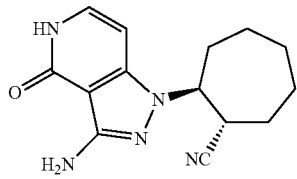

I-14

Deprotection was preceded in a similar procedure as described above for Intermediate 10. The diastereomers were separated by mass triggered reverse phase HPLC (XBridge Phenyl; 35-60% ACN/Water containing 0.05% TFA) to afford the title compounds.

Peak A (I-13): (cis)-2-(3-Amino-4-oxo-4,5-dihydro-1H-pyrazolo[4,3-c]pyridin-1-yl)cycloheptanecarbonitrile (racemic). Tr=11.2 min. LRMS (ESI) calc'd for $C_{14}H_{18}N_5O$ [M+H]$^+$: 272, found 272.

Peak B (I-14): (trans)-2-(3-Amino-4-oxo-4,5-dihydro-1H-pyrazolo[4,3-c]pyridin-1-yl)cycloheptanecarbonitrile (racemic). Tr=12.5 min. LRMS (ESI) calc'd for $C_{14}H_{18}N_5O$ [M+H]$^+$: 272, found 272.

Intermediates 15 and 16

(1S,2S or 1R,2R)-2-(3-Amino-4-oxo-4,5-dihydro-1H-pyrazolo[4,3-c]pyridin-1-yl)cycloheptanecarbonitrile and (1R,2R or 1S,2S)-2-(3-Amino-4-oxo-4,5-dihydro-1H-pyrazolo[4,3-c]pyridin-1-yl)cycloheptanecarbonitrile

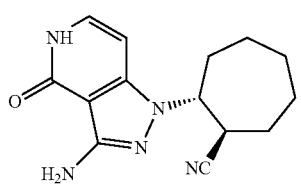

I-15

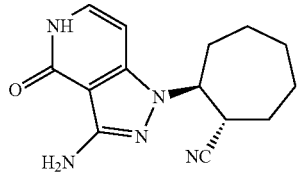

I-16

The title compounds were separated by Chiral Prep-HPLC from the racemic mixture (trans)-2-(3-Amino-4-oxo-4,5-dihydro-1H-pyrazolo[4,3-c]pyridin-1-yl)cycloheptanecarbonitrile (I-14) following the procedure below:
Column used: ChiralPak IA, 2×25 cm, 5 μM
Mobile Phase: 40% EtOH in Hexanes Peak A (I-15): (1S,2S or 1R,2R)-2-(3-Amino-4-oxo-4,5-dihydro-1H-pyrazolo[4,3-c]pyridin-1-yl)cycloheptanecarbonitrile. Tr=8.0 mins. LRMS (ESI) calc'd for $C_{14}H_{18}N_5O$ [M+H]$^+$: 272, found 272. $^1$H NMR (400 MHz, DMSO-d$_6$) δ10.75 (brs, 1H), 7.10-7.07 (m, 1H), 6.54 (d, J=7.2 Hz, 1H), 5.39 (s, 2H), 4.71-4.66 (m, 1H), 3.45-3.39 (m, 1H), 2.02-1.85 (m, 3H), 1.76-1.73 (m, 3H), 1.61-1.58 (m, 4H).

Peak B (I-16): (1R,2R or 1S,2S)-2-(3-Amino-4-oxo-4,5-dihydro-1H-pyrazolo[4,3-c]pyridin-1-yl)cycloheptanecarbonitrile. Tr=11.0 mins. LRMS (ESI) calc'd for $C_{14}H_{18}N_5O$ [M+H]$^+$: 272, found 272. $^1$H NMR (400 MHz, DMSO-d$_6$) δ10.75 (brs, 1H), 7.10-7.07 (m, 1H), 6.54 (d, J=7.2 Hz, 1H), 5.39 (s, 2H), 4.71-4.66 (m, 1H), 3.44-3.39 (m, 1H), 2.08-1.85 (m, 3H), 1.76-1.73 (m, 3H), 1.61-1.58 (m, 4H).

Intermediate 17

5-Bromo-2-(2,2,2-trifluoroethyl)isoindolin-1-one

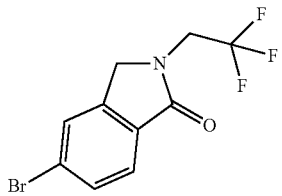

I-17

Step 1: 4-Bromo-2-(hydroxymethyl)-N-(2,2,2-trifluoroethyl)benzamide

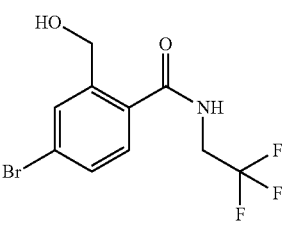

I-17a

To a stirred suspension of aluminum chloride (8.14 g, 61.0 mmol) in CH$_2$Cl$_2$ at 0° C. under argon was added 2,2,2-trifluoroethanamine (6.08 mL, 77 mmol). The reaction mixture was allowed to warm up to room temperature and stirred for 4 h. 5-bromoisobenzofuran-1(3H)-one (10.0 g, 46.9 mmol) was added to the reaction mixture, and heated at 80°

C. overnight. The reaction was carefully quenched with ice water (150 mL) and stirred until the ice was melted. The resulting mixture was diluted with $CH_2Cl_2$ (150 mL) and filtered through a pad of silica, eluting with additional $CH_2Cl_2$. The layers were separated, and the aqueous layer was extracted with $CH_2Cl_2$ (3×100 mL). The combined organic layers were dried over sodium sulfate and concentrated in vacuo to afford 4-bromo-2-(hydroxymethyl)-N-(2,2,2-trifluoroethyl)benzamide. LRMS (ESI) calc'd for $C_{10}H_{10}BrF_3NO_2$ [M+H]$^+$: 312, 314 (1:1). found 312, 314 (1:1).

Step 2:
5-Bromo-2-(2,2,2-trifluoroethyl)isoindolin-1-one

To a stirred solution (cooled to 5° C.) of 4-bromo-2-(hydroxymethyl)-N-(2,2,2-trifluoroethyl)benzamide (6.79 g, 21.8 mmol) in anhydrous THF (100 mL) and N-methyl-2-pyrrolidinone (40.0 mL) under argon was added a solution of isopropylmagnesium chloride (50 mL, 100 mmol) slowly to keep temperature under 10° C. After the addition was complete, the reaction mixture was stirred at a temperature below 10° C. for 1 h, and then at room temperature for an additional hour. The reaction mixture was then cooled to 5° C. and bis(dimethylamino)phosphoryl chloride (4.19 mL, 28.3 mmol) was added dropwise. The resulting reaction mixture was heated at reflux for 24 hr, then concentrated in vacuo to afford a residue that was purified by column chromatography on silica gel (hexanes/EtOAc: 2/1) to afford the title compound. LRMS (ESI) calc'd for $C_{10}H_8BrF_3NO$ [M+H]$^+$: 294, found 294. $^1$H NMR (600 MHz, DMSO-d$_6$): δ 7.93 (d, J=1.1 Hz 1H), 7.72 (d, J=1.1 Hz, 1H), 7.67-7.68 (s, 1H), 4.58 (s, 2H), 4.35 (q, 2H).

Intermediate 18

2-[1-(3-Bromobenzyl)-1H-1,2,3-triazol-4-yl]propan-2-ol

I-18

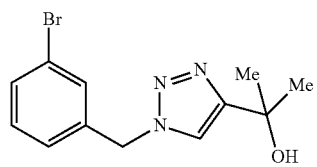

To a solution of 1-bromo-3-(bromomethyl)benzene (5.0 g, 20 mmol) in DMSO (40 mL) was added sodium azide (1.3 g, 20 mmol). The resulting mixture was allowed to stir at ambient temperature for 18 hours before it was diluted with water and extracted with diethyl ether (2×). The combined organic extracts were washed with brine, dried over anhydrous $Na_2SO_4$, filtered, and concentrated in vacuo. The crude residue was dissolved in t-BuOH (65 mL) and water (39 mL) and to this mixture was added 2-methylbut-3-yn-2-ol (2.3 g, 27 mmol). Then a solution of copper (II) sulfate pentahydrate (0.26 g, 1.0 mmol) in water (10 mL) was added, followed by a solution of sodium ascorbate (0.83 g, 4.2 mmol) in water (8 mL). The resulting mixture was allowed to stir at ambient temperature for 2 hours and then was diluted with water and extracted with EtOAc (2×). The combined organic extracts were washed with brine, dried over anhydrous $Na_2SO_4$, filtered, and concentrated in vacuo to afford the title compound which was carried onto the next step without further purification. LRMS (ESI) calc'd for $C_{12}H_{15}BrN_3O$ [M+H]$^+$: 296, 298 (1:1). found: 296, 298 (1:1).

Table 2 discloses an Intermediate which was prepared in an analogous manner to that of Intermediate 18, using 1-bromo-4-(bromomethyl)benzene as the starting material.

TABLE 2

| Intermediate | Structure | Compound Name | $^1$H NMR |
|---|---|---|---|
| I-19 | Br-[structure with N=N triazole, Me, Me, OH] | 2-(1-(4-bromobenzyl)-1H-1,2,3-triazol-4-yl)propan-2-ol | (CDCl$_3$, 400 MHz): δ 7.51 (d, J = 8.4 Hz, 2H), 7.34 (s, 1H), 7.15 (d, J = 8.4 Hz, 2H), 5.44 (s, 2H), 2.51 (br s, 1H), 1.61 (s, 6H) |

Intermediates 20 and 21

(S or R)-1-(4-Bromophenyl)-2,2,2-trifluoroethanol and (S or R)-1-(4-Bromophenyl)-2,2,2-trifluoroethanol

I-20

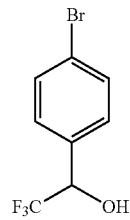

I-21

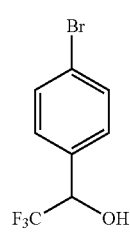

4'-Bromo-2,2,2-trifluoroacetophenone (3.00 mL, 19.8 mmol) was stirred in MeOH (66 mL) at 0° C. Sodium borohydride (0.748 g, 19.8 mmol) was added and the mixture was allowed to warm to ambient temperature. The mixture was stirred for 3 hours, then quenched with saturated aqueous ammonium chloride and extracted with ethyl acetate. The organic layer was then washed with brine, dried over anhydrous MgSO$_4$, filtered, and concentrated in vacuo. The residue was purified by silica gel chromatography (5% EtOAc/hexanes) to afford a racemic mixture of the title compounds. The racemic residue was resolved by Chiral SFC purification using the following method:

mmol), TEA (2.2 g, 22 mmol) and EDCI (1.7 g, 8.8 mmol). The resulting mixture was stirred at r.t. overnight, then partitioned between water and DCM. The organic phase was dried over NaSO$_4$, filtered and concentrated in vacuo to afford a residue that was purified by column chromatography on silica gel (1:1 pet ether/EtOAc) to afford the title compound. $^1$H NMR (400 MHz, CDCl$_3$): δ7.83 (s, 1H), 7.70 (s, 1H), 7.41 (d, J=1.6 Hz, 1H), 7.37 (dt, J=7.6 Hz, 1.6 Hz, 1H), 7.21-7.14 (m, 1H), 7.16 (t, J=7.6 Hz, 1H), 6.57 (br, 1H), 4.53 (d, J=6.0 Hz, 2H).

Table 3 discloses Intermediates which were prepared in an analogous manner to that of Intermediate 22.

TABLE 3

| Intermediate | Structure | Compound Name | $^1$H NMR |
|---|---|---|---|
| I-23 | ![structure] | N-(3-bromobenzyl)pyrimidine-2-carboxamide | (400 MHz, CDCl$_3$): δ 8.86 (d, J = 4.8 Hz, 2H), 8.33 (br, 1H), 7.49 (t, J = 1.6 Hz, 1H), 7.43 (t, J = 5.2 Hz, 1H), 7.38 (dt, J = 5.2 Hz, 1.6 Hz, 1H), 7.29-7.27 (m, 1H), 7.19 (t, J = 7.6 Hz, 1H), 4.67 (d, J = 6.0 Hz, 2H). |
| I-24 | ![structure] | 2-(3-bromophenyl)-N-(1-methyl-1H-pyrazol-3-yl)acetamide | (400 MHz, CDCl$_3$): δ 7.67 (br, 1H), 7.56 (s, 1H), 7.45-7.41 (m, 1H), 7.24-7.21 (m, 3H), 6.64 (d, J = 2.4 Hz, 1H), 3.75 (s, 3H), 3.66 (s, 2H). |

Column Used: Chiral Technology OJ-H 2.1×25 cm, 5 µM
Mobile Phase: 5% isopropyl alcohol/CO$_2$ Peak A, I-19: (S or R)-1-(4-bromophenyl)-2,2,2-trifluoroethanol: $^1$H NMR (500 MHz, CDCl$_3$) δ 7.55 (d, J=8.5 Hz, 2H), 7.36 (d, J=8.5 Hz, 2H), 5.03-4.98 (m, 1H), 2.79 (br s, 1H).

Peak B, I-20: (S or R)-1-(4-bromophenyl)-2,2,2-trifluoroethanol: $^1$H NMR (500 MHz, CDCl$_3$) δ7.55 (d, J=8.5 Hz, 2H), 7.36 (d, J=8.5 Hz, 2H), 5.03-4.98 (m, 1H), 2.79 (br s, 1H).

Intermediate 22

N-(3-Bromobenzyl)oxazole-5-carboxamide

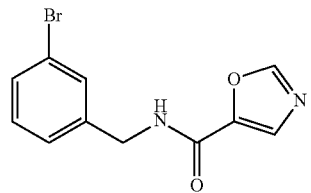

I-22

To a solution of (3-bromophenyl)methanamine (820 mg, 4.4 mmol) and oxazole-5-carboxylic acid (500 mg, 4.4 mmol) in DCM (50 mL), was added HOBt (1.2 g, 8.8

Intermediate 25 tert-Butyl 4-bromobenzylcarbamate

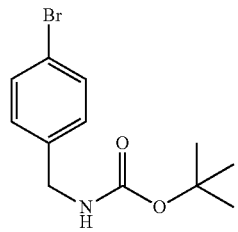

I-25

To a solution of (4-bromophenyl)methanamine (1.0 g, 5.4 mmol) in ethanol (20 mL) was added Boc$_2$O (2.0 g, 6.4 mmol). The resulting mixture was stirred overnight at room temperature. The solvent was removed in vacuo and the resulting residue purified by column chromatography on silica gel (petroleum ether/EtOAc: 4/1) to afford tert-butyl 4-bromobenzylcarbamate. LRMS (ESI) calc'd. for $C_{12}H_{17}BrNO_2$ [M+H]$^+$: 286, found 286. $^1$H NMR (400 MHz, CDCl$_3$): δ 7.44 (d, J=6.0 Hz, 2H), 7.14 (d, J=8.4 Hz, 2H), 4.85 (br s, 1H), 4.25 (d, J=6.0 Hz, 2H), 1.45 (s, 9H).

Table 4 discloses Intermediates that were prepared in an analogous manner to that of Inter mediate 25.

TABLE 4

| Intermediate | Structure | Compound Name | ¹HNMR |
|---|---|---|---|
| I-26 | (structure: 5-bromo-2-fluorobenzyl carbamate) | tert-butyl 5-bromo-2-fluorobenzylcarbamate | (400 MHz, CDCl₃): δ 7.44-7.42 (m, 1H), 7.35-7.31 (m, 1H), 6.9 (d, J = 8.8 Hz, 1H), 4.95 (br, 1H), 4.31 (d, J = 5.6 Hz, 2H), 1.44 (s, 9H) |
| I-27 | (structure: 3-bromo-5-fluorobenzyl carbamate) | tert-butyl 3-bromo-5-fluorobenzylcarbamate | (400 MHz, CDCl₃): δ 7.20 (s, 1H), 7.14-7.11 (m, 1H), 6.93 (d, J = 9.2 Hz, 1H), 4.98 (br, 1H), 4.27 (d, J = 5.6 Hz, 2H), 1.45 (s, 9H) |

Intermediate 28

4-Bromo-N-isopropylbenzenesulfonamide

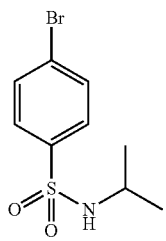

I-28

To a solution of propan-2-amine (160 mg, 2.6 mmol) and DIPEA (780 mg, 6.0 mmol) in CH₂Cl₂ (7 mL) was added a solution of 4-bromobenzene-1-sulfonyl chloride (510 mg, 2.0 mmol) in CH₂Cl₂ (14 mL). The resulting reaction mixture was stirred at rt overnight, then was poured into water (20 mL), and extracted with CH₂Cl₂ (3×15 mL). The combined organic layers were concentrated in vacuo to afford a residue that was purified by column chromatography on silica (petroleum ether/EtOAc: 20/1) to give 4-bromo-N-isopropylbenzenesulfonamide. ¹H NMR (400 MHz, CDCl₃): δ 7.75-7.72 (m, 2H), 7.65-7.62 (m, 2H), 4.43 (d, J=7.52 Hz, 1H), 3.49-3.44 (m, 1H), 1.08 (d, J=6.4 Hz, 6H).

Table 5 discloses Intermediates that were prepared in an analogous manner to that of Intermediate 28. In certain instances the sulfonylation was performed in the absence of DIPEA using excess amine coupling partner instead (1.75-5 equiv.).

TABLE 5

| Intermediate | Structure | Compound Name | ¹H NMR |
|---|---|---|---|
| I-29 | (structure: N-benzyl sulfonamide) | N-benzyl-4-bromobenzenesulfonamide | (400 MHz, CDCl₃): δ 7.78 (d, J = 5.8 Hz, 2H), 7.70 (d, J = 5.8 Hz, 2H), 7.46-7.44 (m, 3H), 7.27-7.17 (m, 2H), 4.78-4.75 (m, 1H), 4.14 (d, J = 6 Hz, 2H) |
| I-30 | (structure: N-cyclopropylmethyl sulfonamide) | 4-bromo-N-(cyclopropylmethyl)benzenesulfonamide | (400 MHz, CDCl₃): δ 7.65 (d, J = 5.6 Hz, 2H), 7.63 (d, J = 5.6 Hz, 2H), 4.48-4.45 (m, 1H), 2.77-2.73 (m, 2H), 0.81-0.76 (m, 1H) 0.47-0.38 (m, 2H), 0.27-0.25 (m, 2H). |
| I-31 | (structure: N-(2-methoxyethyl) sulfonamide) | 4-bromo-N-(2-methoxyethyl)benzenesulfonamide | (400 MHz, CDCl₃): δ 7.72 (d, J = 5.8 Hz, 2H), 7.70 (d, J = 5.8 Hz, 2H), 4.48-4.45 (m, 1H), 3.49-3.84 (m, 2H), 3.30 (s, 3H), 3.13-3.09 (m, 2H). |

TABLE 5-continued

| Intermediate | Structure | Compound Name | ¹H NMR |
|---|---|---|---|
| I-32 | 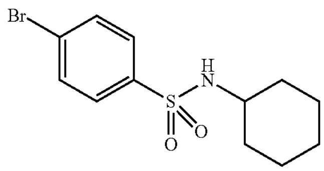 [SMILES: O=S(=O)(NC1CCCCC1)c1ccc(Br)cc1] | 4-bromo-N-cyclohexylbenzenesulfonamide | (400 MHz, CDCl₃): δ 7.75-7.73 (m, 2H), 7.64-7.61 (m, 2H), 4.70 (d, J = 7.6 Hz, 1H), 3.17-3.09 (m, 1H), 1.75-1.72 (m, 2H), 1.64-1.59 (m, 2H), 1.52-1.48 (m, 1H), 1.24-1.14 (m, 2H). |
| I-33 | 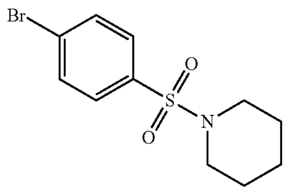 [SMILES: O=S(=O)(c1ccc(Br)cc1)N1CCCCC1] | 1-((4-bromophenyl)sulfonyl)piperidine | (400 MHz CDCl₃): δ 7.66-7.63 (m, 2H), 7.61-7.58 (m, 2H), 2.98-2.95 (m, 4H), 1.66-1.57 (m, 4H), 1.44-1.40 (m, 2H). |
| I-34 | 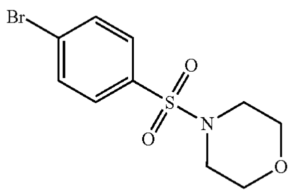 [SMILES: O=S(=O)(c1ccc(Br)cc1)N1CCOCC1] | 4-((4-bromophenyl)sulfonyl)morpholine | (400 MHz CDCl₃): δ 7.70-7.67 (m, 2H), 7.62-7.59 (m, 2H), 3.74-3.72 (m, 4H), 2.30-2.97 (m, 4H). |
| I-35 | 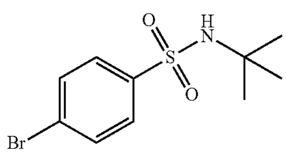 | 4-bromo-N-(tert-butyl)benzenesulfonamide | (600 MHz, CDCl₃): δ 7.75 (d, 2H, J = 8.5 Hz), 7.62 (d, 2H, J = 8.5 Hz), 4.53 (s, 1H), 1.24 (s, 9H). |

Intermediates 36 and 37

1-(3-Bromobenzyl)-1H-1,2,3-triazole and 2-(3-bromobenzyl)-2H-1,2,3-triazole

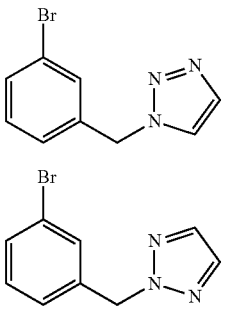

I-36

I-37

To a stirred solution of 1-bromo-3-(bromomethyl)benzene (5.0 g, 20.0 mmol) in acetone (200 mL) under N₂ was added 1H-1,2,3-triazole (2.1 g, 30.0 mmol) followed by K₂CO₃ (4.1 g, 30.0 mmol), and KI (0.16 g, 1.0 mmol). The reaction mixture was refluxed for 12 h, then it was diluted with H₂O (200 mL) and extracted with EtOAc (200 mL×2). The combined organic layers were washed with aq. KOH (10%, 50 mL) followed by brine (200 mL). The organic layers were dried over Na₂SO₄, filtered and concentrated in vacuo to afford a residue that was purified by column chromatograph on silica gel (petroleum ether/EtOAc: 50:1) to afford 1-(3-bromobenzyl)-1H-1,2,3-triazole ¹H NMR (CDCl₃, 400 MHz): δ 7.70 (s, 1H), 7.50 (t, J=3.2 Hz, 1H), 7.41 (d, J=7.1 Hz, 1H), 7.22 (d, J=3.2 Hz, 1H), 7.20-7.15 (m, 2H), 5.51 (s, 2H) and 2-(3-bromobenzyl)-2H-1,2,3-triazole ¹H NMR (CDCl₃, 400 MHz): δ 7.63 (s, 2H), 7.43 (d, J=4.8 Hz, 2H), 7.20 (t, J=3.4 Hz, 2H), 5.56 (s, 2H).

Table 6 discloses Intermediates that were prepared in an analogous manner to that of Intermediates 36 and 37.

TABLE 6

| Intermediate | Structure | Compound Name | ¹H NMR |
|---|---|---|---|
| I-38 | 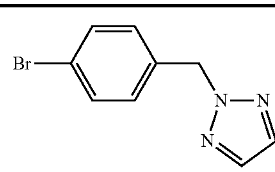 | 2-(4-bromobenzyl)-2H-1,2,3-triazole | (400 MHz, CDCl₃): δ 7.62 (s, 2H), 7.46 (d, J = 8.4 Hz, 2H), 7.17 (d, J = 8.0 Hz, 2H), 5.55 (s, 2H). |

TABLE 6-continued

| Intermediate | Structure | Compound Name | $^1$H NMR |
|---|---|---|---|
| I-39 | 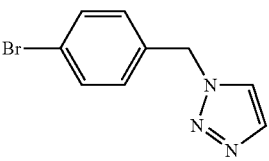 [SMILES: Brc1ccc(Cn2ccnn2)cc1] | 1-(4-bromobenzyl)-1H-1,2,3-triazole | (400 MHz, CDCl$_3$): δ 7.66 (s, 1H), 7.41-7.45 (m, 3H), 7.07 (d, J = 6.0 Hz, 2H), 5.46 (s, 2H) |
| I-40 | 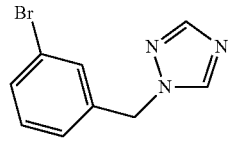 [SMILES: Brc1cccc(Cn2cncn2)c1] | 1-(3-bromobenzyl)-1H-1,2,4-triazole | (400 MHz, DMSO-d$_6$): δ 8.08 (s, 1H), 7.96 (s, 1H), 7.46-7.44 (m, 1H), 7.37 (t, J = 1.7 Hz, 1H), 7.22 (t, J = 7.8 Hz, 1H), 7.16 (d, J = 7.7 Hz, 1H), 5.29 (s, 2H) |
| I-41 | 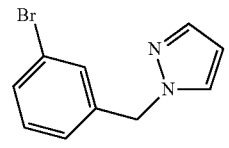 [SMILES: Brc1cccc(Cn2cccn2)c1] | 1-(3-bromobenzyl)-1H-pyrazole | (400 MHz, CDCl$_3$): δ 7.56 (d, J = 1.7 Hz, 1H), 7.43-7.40 (m, 2H), 7.33 (s, 1H), 7.20 (t, J = 7.8 Hz, 1H), 7.12 (d, J = 7.8 Hz, 1H), 6.30 (t, J = 2.0 Hz, 1H), 5.29 (s, 2H) |
| I-42 | 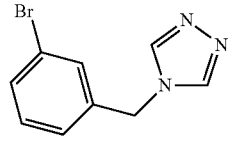 [SMILES: Brc1cccc(Cn2cnnc2)c1] | 4-(3-bromobenzyl)-4H-1,2,4-triazole | (400 MHz, DMSO-d$_6$): δ 8.12 (s, 2H), 7.47-7.44 (m, 1H), 7.28 (t, J = 1.8 Hz, 1H), 7.21-7.19 (m, 1H), 7.05-7.03 (m, 1H), 5.10 (s, 2H) |
| I-43 | 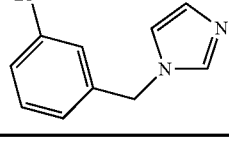 | 1-(3-bromobenzyl)-1H-imidazole | (400 MHz, CDCl$_3$): δ 7.52 (s, 1H), 7.44-7.41 (m, 1H), 7.27-7.26 (m, 1H), 7.20 (t, J = 7.9 Hz, 1H), 7.08 (t, J = 1.1 Hz, 1H), 7.05-7.02 (m, 1H), 6.87 (t, J = 1.3 Hz, 1H), 5.06 (s, 2H) |

Intermediate 44

1-(3-Bromobenzyl)-4-methyl-1H-1,2,3-triazole

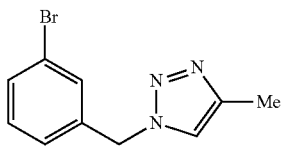

I-44

Step 1: 1-(Azidomethyl)-3-bromobenzene

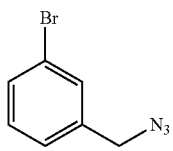

I-44a

To a solution of 1-bromo-3-(bromomethyl)benzene (2.0 g, 8.0 mmol) in DMSO (50 mL) was added NaN$_3$ (0.65 g, 10 mmol). The resulting reaction mixture was stirred overnight at rt. The reaction was quenched with water (50 mL) and extracted with DCM (2×50 mL). The combined organic layers were washed with brine (50 mL), then dried over Na$_2$SO$_4$, filtered and concentrated in vacuo to afford 1-(azidomethyl)-3-bromobenzene that was carried on without further purification.

Step 2: 1-(3-Bromobenzyl)-4-methyl-1H-1,2,3-triazole

A mixture of 1-(azidomethyl)-3-bromobenzene (3.2 g, 15 mmol), trimethyl(prop-1-yn-1-yl)silane (1.6 mL, 14 mmol) and Et$_3$N (2.2 mL, 4.5 mmol) in DMF (50 mL) was stirred at 100° C. overnight. The reaction mixture was cooled to rt, then sat. aq. NH$_4$Cl (25 mL) was added and extracted with EtOAc (50 mL×2). The combined organic layers were washed with H$_2$O (50 mL×3), then dried over Na$_2$SO$_4$, and concentrated in vacuo to afford the title compound. $^1$H NMR (CDCl$_3$, 400 MHz): δ 7.63 (s, 2H), 7.43 (d, J=4.8 Hz, 2H), 7.20 (t, J=3.4 Hz, 2H), 5.56 (s, 2H).

Intermediate 45

(4-Bromophenyl)(pyrrolidin-1-yl)methanone

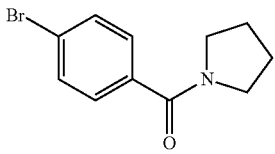

I-45

To a suspension of 4-bromobenzoic acid (150 mg, 0.75 mmol) in DCM (7.5 mL) were added pyrrolidine (53 mg, 0.75 mmol), HOBT (110 mg, 0.78 mmol), and Et₃N (190 mg, 1.9 mmol) successively at room temperature, then to the mixture was added EDCI (150 mg, 0.78 mmol) in portions. The resulting mixture was stirred overnight, then was poured into water and washed with dilute aq. HCl (5 mL), sat.aq. NaHCO₃ (15 mL) and brine (10 mL). The organic layer was dried over Na₂SO₄, filtered then concentrated in vacuo to afford the crude product which was purified by preparative TLC (petroleum ether/EtOAc: 3:1) to afford the title compound. LRMS (ESI) calc'd. for C₁₁H₁₃BrNO [M+H]⁺: 254, found: 254. ¹HNMR (400 MHz, CDCl₃): δ 7.46 (d, J=8.4 Hz, 2H), 7.33 (d, J=8.4 Hz, 2H), 3.55 (t, J=6.8 Hz, 2H), 3.33 (t, J=6.4 Hz, 2H), 1.92-1.77 (m, 4H).

Table 7 discloses an Intermediate that was prepared in analogous manner to that of Intermediate 45.

TABLE 7

| Intermediate | Structure | Compound Name | LRMS [M + H]⁺ |
|---|---|---|---|
| I-46 | 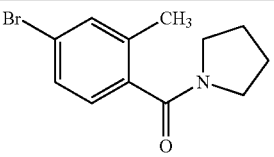 | (4-bromo-2-methylphenyl)(pyrrolidin-1-yl)methanone | Calc'd 268, found 268 |

Intermediate 47

4-Bromo-N,N,2-trimethylbenzamide

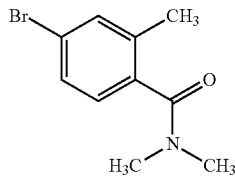

I-47

A solution of 4-bromo-2-methylbenzoic acid (2.15 g, 10.0 mmol) and thionyl chloride (3.6 g, 30 mmol) was heated at 80° C. for 3 h. The excess thionyl chloride was removed in vacuo, and the resulting residue was dissolved in dichloromethane (50 mL) and cooled to 0° C. (ice/water bath). Dimethylamine (gas) was bubbled to the reaction solution for 5 min. The resulting solution was stirred at 20° C. for 10 min, then was concentrated in vacuo, and diluted with ethyl acetate (100 mL). The reaction mixture was washed successively with aqueous sodium hydroxide (1.0 N, 20 mL), water (20 mL) and brine (20 mL). The organic layer was dried over sodium sulfate, filtered and concentrated in vacuo to afford 4-bromo-2-methyl-N,N,dimethylbenzamide. ¹H NMR (400 MHz, CDCl₃): δ 7.40-7.39 (m, 1H), 7.36 (dd, J=8.03, 1.51 Hz, 1H), 7.06 (d, J=8.03 Hz, 1H), 3.13 (s, 3H), 2.84 (s, 3H), 2.28 (s, 3H).

Table 8 discloses an Intermediate that was prepared in an analogous manner to that of Intermediate 47.

TABLE 8

| Intermediate | Structure | Compound Name | ¹H NMR |
|---|---|---|---|
| I-48 | 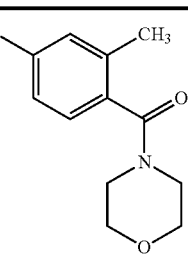 | (4-bromo-2-methylphenyl)(morpholino)methanone | (400 MHz, CDCl₃) δ 7.42-7.37 (m, 2H), 7.06 (d, J = 8.0 Hz, 1H), 3.84-3.78 (m, 4H), 3.76-3.60 (m, 2H), 3.26-3.24 (m, 2H), 2.32 (s, 3H) |

Intermediate 49

4-Chloro-2-cyclopropyl-N,N-dimethylbenzamide

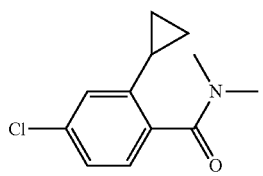

I-49

Into a 25-mL schlenk tube purged and maintained with an inert atmosphere of nitrogen, were added 2-bromo-4-chloro-N,N-dimethylbenzamide (0.26 g, 1.0 mmol), cyclopropylboronic acid (0.13 g, 1.5 mmol), toluene (5 mL), water (0.25 mL), tricyclohexylphosphine (14 mg, 0.050 mmol), palladium(II) acetate (22.4 mg, 0.10 mmol), and potassium phosphate (0.85 g, 4.0 mmol). The resulting mixture was stirred for 3 h at 100° C. in an oil bath, then was cooled down to 20° C., and diluted with ethyl acetate (100 mL), washed with water (2×20 mL) and brine (2×20 mL). The organic layer was dried over anhydrous sodium sulfate and filtered. The filtrate was concentrated in vacuo to afford a residue that was purified by chromatography (5%-10% ethyl acetate/petroleum ether) to afford the title compound. $^1$H NMR (300 MHz, CDCl$_3$) δ 7.18-7.03 (m, 2H), 6.85 (s, 1H), 3.14 (s, 3H), 2.87 (s, 3H), 1.91-1.82 (m, 1H), 1.00-0.90 (m, 2H), 0.88-0.64 (m, 2H).

Intermediate 50

(±) 1-(3-Bromophenyl)ethanol

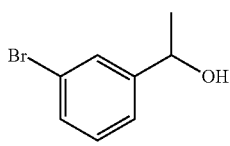

I-50

To a solution of 1-(3-bromophenyl)ethanone (1.0 g, 5.0 mmol) in EtOH (15 mL) was added NaBH$_4$ (470 mg, 12.0 mmol). The mixture was stirred at room temperature overnight. The reaction mixture was concentrated in vacuo, and the residue was purified by chromatography on silica gel (hexanes/EtOAc: 5/1) to afford (±)1-(3-bromophenyl)ethanol. LRMS (ESI) calc'd. for C$_8$H$_{10}$BrO [M+H]$^+$: 201, found 201. $^1$H NMR (CDCl$_3$, 400 MHz): δ 7.51-7.50 (m, 1H), 7.39-7.36 (m, 1H), 7.26-7.24 (m, 1H), 7.21-7.17 (m, 1H), 4.84-4.79 (m, 1H), 2.35 (s, 1H), 1.45 (d, J=6.48 Hz, 3H).

Table 9 discloses an Intermediate that was prepared in an analogous manner to that of Intermediate 50.

TABLE 9

| Intermediate | Structure | Compound Name | $^1$HNMR |
|---|---|---|---|
| I-51 | 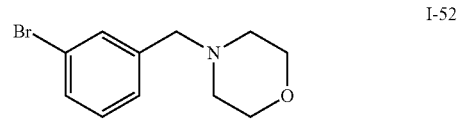 [SMILES: Brc1cccc(CN2CCOCC2)c1] | 1-(4-Bromo-2-methylphenyl)-2,2,2-trifluoroethanol | (600 MHz, CDCl$_3$) δ 7.48 (d, 1H, J = 7.8 Hz), 7.42 (dd, 1H, J = 8.4, 1.2 Hz), 7.37 (br s, 1H), 5.27 (m, 1H), 2.61 (d, 1H, J = 4.2 Hz), 2.36 (s, 3H). |

Intermediate 52

4-(3-Bromobenzyl)morpholine

I-52

To a suspension of 1-bromo-3-bromomethyl-benzene (530 mg, 2.10 mmol) in THF (10 mL) was added morpholine (200 mg, 1.80 mmol) and Et$_3$N (350 mg, 3.5 mmol). The resulting suspension was stirred at room temperature for 8 hours. Water (35 mL) was then added, and the mixture was extracted with EtOAc (50 mL), dried over sodium sulfate, filtered and concentrated in vacuo. The residue was purified by preparative TLC (petroleum ether/EtOAc: 5/1) to afford the title compound. LRMS (ESI) calc'd. for C$_{11}$H$_{15}$BrNO [M+H]$^+$: 255, found 255. $^1$H NMR (CDCl$_3$, 400 MHz): δ 7.51 (s, 1H), 7.40 (d, J=8.0 Hz, 1H), 7.29 (d, J=8.0 Hz, 1H), 7.19 (t, J=8.0 Hz, 1H), 3.66 (m, 4H), 3.47 (s, 2H), 2.41 (m, 4H).

Intermediate 53

N-(3-Bromobenzyl)-2,2,2-trifluoroethanamine

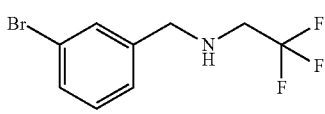

I-53

A suspension of 1,3-dibromo-benzene (500 mg, 2.00 mmol) in 2,2,2-Trifluoro-ethylamine (790 mg, 8.00 mmol) was stirred at 40–50° C. for 10 hours. The mixture was then concentrated in vacuo to afford the title compound. LRMS (ESI) calc'd. for C$_{11}$H$_{15}$BrNO [M+H]$^+$: 268, found 268.

Table 10 discloses an Intermediate that was prepared in an analogous manner to that of Intermediate 53.

TABLE 10

| Intermediate | Structure | Compound Name | $^1$H NMR |
|---|---|---|---|
| I-54 | 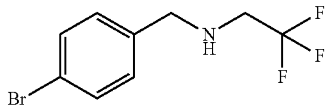 [SMILES: FC(F)(F)CNCc1ccc(Br)cc1] | N-(4-bromobenzyl)-2,2,2-trifluoroethanamine | (CDCl3, 400 MHz): δ 7.43 (d, J = 8.4 Hz, 2H), 7.19 (d, J = 8.4 Hz, 2H), 3.83 (m, 2H), 3.13 (q, J = 9.6 Hz, 2H) |

Intermediate 55

(R)—N-(1-(4-Bromophenyl)ethyl)-2,2,2-trifluoroethanamine

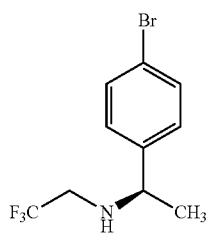

I-55

Step 1: (R)—N-(1-(4-Bromophenyl)ethyl)-2,2,2-trifluoroacetamide

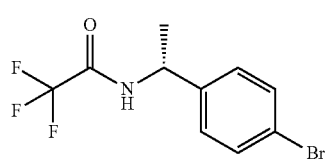

I-55a

To a solution of (R)-1-(4-bromophenyl)ethanamine (3.00 g, 15.0 mmol) in CH$_2$Cl$_2$ (70 mL) was added TFAA (3.78 g, 18.0 mmol) at 0° C. The resulting reaction mixture was stirred for 1 h at 20° C., then quenched by the addition of water. The organic layer was dried over anhydrous sodium sulfate, filtered and concentrated in vacuo to afford (R)—N-(1-(4-bromophenyl)ethyl)-2,2,2-trifluoroacetamide. $^1$H NMR (300 MHz, CDCl$_3$): δ 7.51 (d, J=8.4 Hz, 2H), 7.20 (d, J=8.4 Hz, 2H), 6.40 (s, br, 1H), 5.15-5.05 (m, 1H), 1.57 (d, J=6.9 Hz, 3H).

Step 2: (R)—N-(1-(4-Bromophenyl)ethyl)-2,2,2-trifluoroethanamine

To a stirred solution of (R)—N-(1-(4-bromophenyl)ethyl)-2,2,2-trifluoroacetamide (1.00 g, 3.38 mmol) in THF (20 mL) was added borane dimethylsulfide complex (2.0 M in THF, 8.4 mL, 17 mmol). The resulting solution was stirred for 4 h at 75° C. The mixture was poured carefully into an ice/water (50 mL) mixture and extracted with EtOAc (40 mL×2). The combined organic layers were dried over sodium sulfate, filtered and concentrated in vacuo to afford the title compound. $^1$H NMR (400 MHz, CDCl$_3$): δ 7.53 (d, J=8.4 Hz, 2H), 7.22 (d, J=8.4 Hz, 2H), 6.44 (s, br, 1H), 5.16-5.09 (m, 1H), 1.60 (d, J=7.2 Hz, 3H).

Table 11 discloses an Intermediate that was prepared in a similar manner to that described for Intermediate 55.

TABLE 11

| Intermediate | Structure | Compound Name | $^1$H NMR |
|---|---|---|---|
| I-56 | 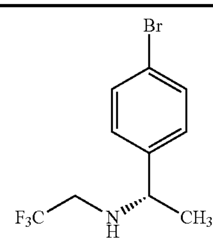 | (S)-N-(1-(4-bromophenyl)ethyl)-2,2,2-trifluoroethanamine | (400 MHz, CDCl$_3$): δ 7.53 (d, J = 8.4 Hz, 2H), 7.22 (d, J = 8.4 Hz, 2H), 6.44 (s, br, 1H), 5.16-5.09 (m, 1H), 1.60 (d, J = 7.2 Hz, 3H). |

Intermediate 57

5-Bromo-2-methylisoindoline

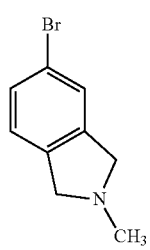

I-57

Into an 100-mL round-bottom flask was placed 5-bromo-2,3-dihydro-1H-isoindole (1.00 g, 5.05 mmol), formaldehyde (0.23 g, 40% in water, 7.60 mmol), sodium borohydride (0.29 g, 7.60 mmol) and methanol (50 mL). The resulting solution was stirred for 1 h at 15° C., then extracted with dichloromethane (3×50 mL). The combined organic layers were dried over anhydrous sodium sulfate, filtered and concentrated in vacuo to afford a residue that was purified by silica gel column chromatography with ethyl acetate/petroleum ether (1:1) to afford the title compound. LRMS (ESI) calc'd for: $C_9H_{10}BrN$ $[M+H]^+$: 212, 214 (1:1). found 212, 214 (1:1).

Intermediate 58

5-Bromo-2-ethylisoindoline

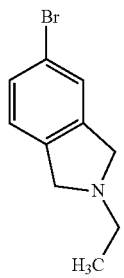

I-58

Step 1: 1-(5-Bromoisoindolin-2-yl)ethanone

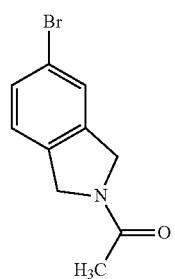

I-58a

Into a 50-mL three necked flask were placed 5-bromoisoindoline hydrochloride (0.234 g, 1.00 mmol), acetic acid (4 mL) and acetic anhydride (0.31 g, 3.0 mmol). The mixture was stirred at 20° C. for 2 h then diluted with ethyl acetate (50 mL). The solution was washed with water (3×15 mL), dried over anhydrous sodium sulfate and filtered. The filtrate was concentrated in vacuo to afford a residue that was purified by silica gel column chromatography (2-50% ethyl acetate in petroleum ether) to afford the title compound. $^1$H NMR (400 MHz, CD$_3$OD) δ7.54 (d, J=4.8 Hz, 1H), 7.48 (d, J=8.0 Hz, 1H), 7.27 (dd, J=8.0, 4.8 Hz, 1H), 4.88 (d, J=16.4 Hz, 2H), 4.72 (d, J=16.4 Hz, 2H), 2.18 (s, 3H).

Step 2: 5-Bromo-2-ethylisoindoline

Into a 50-mL three necked flask, were placed 1-(5-bromoisoindolin-2-yl)ethanone (0.17 g, 0.71 mmol), tetrahydrofuran (10 mL) and borane dimethylsulfite complex (0.35 mL, 1.0 M in tetrahydrofuran, 3.5 mmol). The solution was heated at reflux for 2 h, then was cooled to 20° C. and water (3 mL) was carefully added dropwise. The resulting mixture was concentrated in vacuo and diluted with ethyl acetate (50 mL). The solution was washed with water (15 mL) and brine (15 mL) respectively, dried over anhydrous sodium sulfate and filtered. The filtrate was concentrated in vacuo to afford the title compound. $^1$H NMR (400 MHz, CDCl$_3$) δ 7.44-7.38 (m, 2H), 7.11 (d, J=8.0 Hz, 1H), 4.52 (d, J=14.0 Hz, 1H), 4.49 (d, J=14.0 Hz, 1H), 4.16 (d, J=14.0 Hz, 1H), 4.13 (d, J=14.0 Hz, 1H), 3.12 (q, J=7.2 Hz, 2H), 1.30 (t, J=7.2 Hz, 3H).

Table 12 discloses Intermediates that were prepared in a manner analogous to that described for Intermediate 58.

TABLE 12

| Intermediate | Structure | Compound Name | $^1$HNMR |
|---|---|---|---|
| I-59 | ![structure] | 5-Bromo-2-isobutylisoindoline | (400 MHz, CDCl$_3$): δ 7.41 (d, J = 8.1 Hz, 1H), 7.35 (s, 1H), 7.07 (d, J = 8.1 Hz, 1H), 4.50 (q, J = 9.3 Hz, 2H), 4.14 (q, J = 10.2 Hz, 2H), 2.87 (q, J = 5.4 Hz, 2H), 2.40-2.35 (m, 1H), 1.03 (d, J = 6.9 Hz, 6H). |
| I-60 | ![structure] | 5-Bromo-2-(cyclopropylmethyl)isoindoline | (300 MHz, DMSO-d$_6$) δ7.52 (s, 1H), 7.45 (d, J = 8.1 Hz, 1H), 7.25 (d, J = 8.1 Hz, 1H), 4.40-4.20 (m, 4H), 2.87 (d, J = 6.9 Hz, 2H), 1.19-1.10 (m, 1H), 0.53-0.47 (m, 2H), 0.26-0.20 (m, 2H). |
| I-61 | ![structure] | 5-Bromo-2-(2,2,2-trifluoroethyl)isoindoline | (400 Hz, CDCl$_3$)δ7.49-7.45 (m, 2H), 7.10 (d, J = 4.4 Hz, 1H), 4.13-4.25 (m, 4H), 3.36(q, J = 5.6 Hz, 2H). |

TABLE 12-continued

| Intermediate | Structure | Compound Name | ¹HNMR |
|---|---|---|---|
| I-62 | (structure) | 5-bromo-2-(cyclopentylmethyl)isoindoline | (400 MHz, DMSO-$d_6$) δ 7.69 (s, 1H), 7.45 (d, J = 8.0 Hz, 1H), 7.21 (d, J = 8.0 Hz, 1H), 3.84 (s, 2H), 3.79 (s, 2H), 2.57 (d, J = 7.6 Hz, 2H), 2.12-2.01 (m, 1H), 1.79-1.69 (m, 2H), 1.67-1.52 (m, 4H), 1.28-1.09 (m, 2H). |

Intermediate 63

5-Bromo-2-isopropylisoindoline

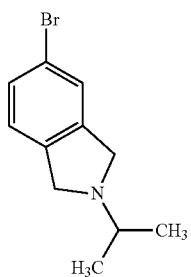

I-63

Into an 100-mL round-bottom flask was placed a solution of 5-bromo-2,3-dihydro-1H-isoindole hydrochloride (2.00 g, 8.53 mmol) in N,N-dimethylformamide (50 mL). Sodium hydride (0.85 g, 60% in mineral oil, 21 mmol) was added carefully and the resulting reaction mixture was stirred for 45 min at 20° C. 2-Iodopropane (2.17 g, 12.8 mmol) was added dropwise at the same temperature then the resulting solution was stirred for 16 h at 50° C. in an oil bath. The reaction was cooled down to ambient temperature then quenched carefully by water (80 mL) addition. The resulting mixture was extracted with ethyl acetate (3×40 mL). The organic layers were combined, washed with water (50 mL) and brine (50 mL) respectively, dried over anhydrous sodium sulfate and filtered. The filtrate was concentrated in vacuo to afford the title compound. LRMS (ESI) calc'd for: $C_{11}H_{15}BrN$ [M+H]⁺: 240, found: 240; ¹H NMR (300 MHz, CDCl₃) δ 7.46-7.32 (m, 2H), 7.07 (d, J=7.8 Hz, 1H), 4.92 (d, J=7.8 Hz, 4H), 2.79-2.71 (m, 1H), 1.19 (d, J=6.3 Hz, 6H).

Table 13 discloses an Intermediate prepared using similar procedures as described for Intermediate 63, using the appropriate alkylating agent. In select cases, the general procedure was modified to alternatively utilize 1.0-2.5 equivalents of TEA or NaH base and DCM or DMF as solvent.

TABLE 13

| Intermediate | Structure | Compound Name | LRMS [M + H]⁺ |
|---|---|---|---|
| I-64 | (structure) | tert-Butyl 2-(5-bromoisoindolin-2-yl)acetate | Calc'd 312, 314 (1:1), found 312, 314 (1:1) |

Intermediate 65

(R)—N—((S)-1-(3-Bromophenyl)-2,2,2-trifluoroethyl)-2-methylpropane-2-sulfinamide

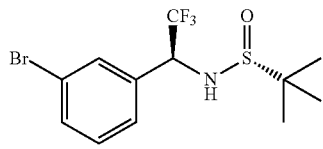

I-65

Step 1: (R,E)-N-(3-Bromobenzylidene)-2-methylpropane-2-sulfinamide

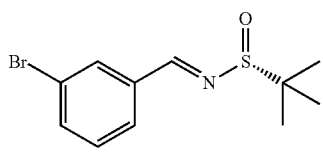

I-65a

To a suspension of 3-bromobenzaldehyde (2.00 g, 10.8 mmol) and (S)-2-methylpropane-2-sulfinamide (2.90 g, 21.6 mmol) in THF (50 mL) was added titanium ethoxide (3.10 g, 10.8 mmol). The mixture was heated to reflux for 5 h, then it was cooled to room temperature and quenched by the addition of water (30 mL). The resulting mixture was filtered, and the filtrate was extracted with EtOAc (30 mL×2). The combined organic layers were washed with brine (30 mL×2) dried over $NaSO_4$, filtered and concentrated in vacuo to afford a residue that was purified by column chromatography on silica gel (petroleum ether:EtOAc=40:1 to 10:1) to give (R,E)-N-(3-bromobenzylidene)-2-methylpropane-2-sulfinamide. LRMS (ESI) calc'd. for $C_{11}H_{15}BrNOS$ $[M+H]^+$: 288, found: 288. $^1H$ NMR (400 MHz, $CDCl_3$): δ 8.51 (s, 1H), 8.00 (s, 1H), 7.72 (d, J=8.0 Hz, 1H), 7.61 (d, J=8.0 Hz, 1H), 7.34 (t, J=8.0 Hz, 1H), 1.25 (s, 9H).

Step 2: (R)—N—((S)-1-(3-Bromophenyl)-2,2,2-trifluoroethyl)-2-methylpropane-2-sulfinamide To a suspension of (R,E)-N-(3-bromobenzylidene)-2-methylpropane-2-sulfinamide (150 mg, 0.520 mmol) and TBAF (210 mg, 1 mmol) in THF (15 mL) was added $TMSCF_3$ (0.84 mL, 1.7 mmol) dropwise at −55° C., and the resulting mixture was stirred for 1 h. The reaction was quenched by the addition of aq. $NH_4Cl$ and extracted with EtOAc (15 mL×2). The combined organic layers were washed with brine (15 mL×2), dried over $Na_2SO_4$, filtered and concentrated in vacuo to afford a residue that was purified by prep. TLC (silica gel, eluted by petroleum ether:EtOAc=10:1) to give (R)—N—((S)-1-(3-bromophenyl)-2,2,2-trifluoroethyl)-2-methylpropane-2-sulfinamide. LRMS (ESI) calc'd. for $C_{12}H_{16}BrF_3NOS$ $[M+H]^+$: 358, found 358.

Table 14 discloses Intermediates that were prepared in an analogous manner to that described for Intermediate 65. In select cases, (R)-2-methylpropane-2-sulfinamide was used to afford the alternative diastereomer.

TABLE 14

| Intermediate | Structure | Compound Name | LRMS [M + H]⁺ |
|---|---|---|---|
| I-66 | ![structure] | (S)-N-((R)-1-(3-bromophenyl)-2,2,2-trifluoroethyl)-2-methylpropane-2-sulfinamide | Calc'd 358, found 358 |
| I-67 | ![structure] | (S)-N-((R)-1-(4-bromophenyl)-2,2,2-trifluoroethyl)-2-methylpropane-2-sulfinamide | Calc'd 358, found 358 |
| I-68 | ![structure] | (R)-N-((S)-1-(4-bromophenyl)-2,2,2-trifluoroethyl)-2-methylpropane-2-sulfinamide | Calc'd 358, found 358 |

Intermediates 69 and 70

(R or S)-1-(4-Bromophenyl)-2,2,2-trifluoroethanamine and (R or S)-1-(4-Bromophenyl)-2,2,2-trifluoroethanamine

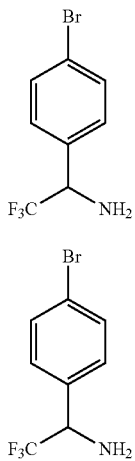

I-69

I-70

To a solution of 1-(4-bromophenyl)-2,2,2-trifluoroethanone (1.00 g, 3.95 mmol) in toluene (14 mL) at rt was added a solution of lithium bis(trimethylsilyl)amide in THF (4.35 mL, 4.35 mmol) dropwise. The reaction was stirred at rt for 15 min, then BH$_3$THF (7.90 mL, 7.90 mmol) was added and stirred for an additional 20 min. The reaction was cooled to 0° C., and was carefully quenched with aqueous sodium hydroxide (2.0 M; 5.93 mL, 11.9 mmol) over approximately 5 min. The resulting mixture was stirred at rt for 90 min, and then the layers were separated. The organic layer was washed with NaOH (1 N), dried over sodium sulfate, filtered and concentrated in vacuo to afford racemic 1-(4-bromophenyl)-2,2,2-trifluoroethanamine. The individual enantiomers were separated by preparative chiral SFC using the following conditions to afford the two enantiomers:
Column Used: Chiralpak AZ-H, 21×250 mm
UV wavelength: 220 nm
Flow Rate: 70 mL/min
Modifier: MeOH (7%)
Peak A (I-69): (R or S)-1-(4-bromophenyl)-2,2,2-trifluoroethanamine; LRMS (ESI) calc'd for C$_8$H$_8$BrF$_3$N [M+H]$^+$: 254, 256 (1:1). found: 254, 256 (1:1).
Peak B (I-70): (S or R)-1-(4-bromophenyl)-2,2,2-trifluoroethanamine; LRMS (ESI) calc'd for C$_8$H$_8$BrF$_3$N [M+H]$^+$: 254, 256 (1:1). found: 254, 256 (1:1).

Intermediate 71

N-(5-Bromo-2-(N,N-dimethylsulfamoyl)benzyl)acetamide

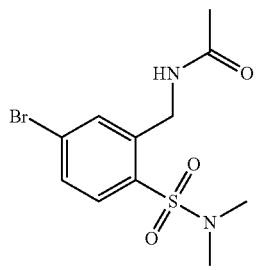

I-71

Step 1: N-(3-Bromobenzyl)acetamide

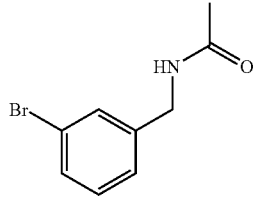

I-71a

A mixture of (3-bromophenyl)methanamine (5.4 g, 29 mmol), AcCl (2.7 g, 29 mmol) and Et$_3$N (5.9 g, 58 mmol) in DCM (100 mL) was stirred at rt for 3 h, then it was quenched with water (20 mL) and extracted with DCM (3×20 mL). The combined organic layers were concentrated in vacuo. The residue was recrystallized from hexanes/EtOAc (10/1, 55 mL) to afford the title compound. $^1$H NMR (CDCl$_3$, 400 MHz): δ 7.40-7.36 (m, 2H), 7.20-7.15 (m, 2H), 6.01 (br s, 1H), 4.37 (d, J=6.0 Hz, 2H), 2.01 (s, 3H).

Step 2: 2-(Acetamidomethyl)-4-bromobenzene-1-sulfonyl chloride

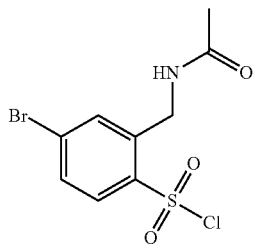

I-71b

A mixture of N-(3-bromobenzyl)acetamide (0.45 g, 2.0 mmol) in ClSO$_3$H (1.64 g, 14 mmol) was stirred at rt for 2 h. The reaction mixture was quenched by careful addition of water (20 mL) and then extracted with DCM (20 mL×3). The combined organic layers were concentrated in vacuo and the resulting residue triturated with DCM/Hex (1/25, 100 mL) to afford the title compound after filtration, which was used for the next step without further purification.

Step 3: N-(5-Bromo-2-(N,N-dimethylsulfamoyl)benzyl)acetamide

To a solution of 2-(acetamidomethyl)-4-bromobenzene-1-sulfonyl chloride (100 mg, 0.3 mmol) in DCM (1 mL) was added dimethylamine hydrochloride (50 mg, 0.6 mmol) and pyridine (0.13 g, 1.5 mmol). The reaction mixture was stirred at rt overnight, then concentrated in vacuo. The resulting residue was diluted with DCM (20 mL). The DCM solution was washed with H$_2$O (2×20 mL) and brine (20 mL), dried over Na$_2$SO$_4$, filtered and concentrated in vacuo. The residue was purified by preparative TLC to afford the title compound. $^1$H NMR (CDCl$_3$, 400 MHz): δ 7.81 (s, 1H), 7.67 (d, J=8.6 Hz, 1H), 7.55 (d, J=8.6 Hz, 1H), 6.43 (br s, 1H), 4.63 (d, J=6.6 Hz, 2H), 2.81 (s, 6H), 1.97 (s, 3H).

Intermediate 72

5-Bromo-2-(tert-butyl)-2,3-dihydrobenzo[d]isothiazole 1,1-dioxide

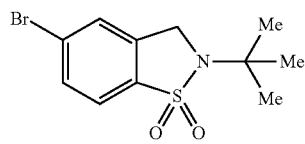

I-72

Step 1:
4-Bromo-N-(tert-butyl)-2-methylbenzenesulfonamide

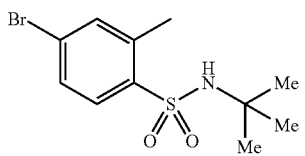

I-72a

To a solution of 4-bromo-2-methylbenzene-1-sulfonyl chloride (2.0 g, 7.4 mmol) in CH$_2$Cl$_2$ (15 mL) was added a solution of 2-methylpropan-2-amine (0.65 g, 8.9 mmol) and triethylamine (0.90 g, 8.9 mmol) in CH$_2$Cl$_2$ (30 mL) at 0° C. The reaction mixture was stirred at 0° C. for 2 h and then rt for 16 hours. The mixture was washed with HCl (0.1 M, 15 mL) and saturated aqueous NaHCO$_3$ (15 mL). The organic layer was dried over Na$_2$SO$_4$, filtered and concentrated in vacuo to afford the title compound. $^1$H NMR (400 MHz, DMSO-d$_6$) δ 7.78 (d, J=8.4 Hz, 1H), 7.63 (d, J=1.6 Hz, 1H), 7.59-7.56 (m, 2H), 2.57 (s, 3H), 1.09 (s, 9H).

Step 2: 5-Bromo-2-(tert-butyl)benzo[d]isothiazol-3(2H)-one 1,1-dioxide

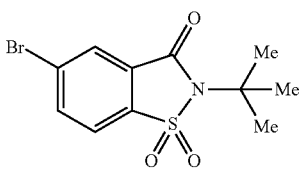

I-72b

A mixture of H$_5$IO$_6$ (5.9 g, 26 mmol) in acetonitrile (50 mL) was stirred at RT for 1 h, then CrO$_3$ (33 mg, 0.33 mmol) was added followed by acetic anhydride (2.7 g, 26 mmol).

The resulting solution was cooled to 0° C., and to it was added 4-bromo-N-(tert-butyl)-2-methylbenzenesulfonamide (1.0 g, 3.3 mmol). After stirring at 0° C. for 15 min, the reaction was allowed to warm to rt and stirred for 16 hours. The solvent was removed in vacuo, and the residue was extracted with EtOAc (100 mL). The ethyl acetate solution was washed with saturated aqueous NaHCO$_3$ (40 mL) and brine, and dried over Na$_2$SO$_4$. After filtration and concentration in vacuo, the residue was purified by column chromatography on silica gel (petroleum ether/EtOAc=20:1) to afford the title compound. $^1$H NMR (400 MHz, DMSO-d$_6$) δ 8.82-8.14 (m, 3H), 1.66 (s, 9H).

Step 3: 5-Bromo-2-(tert-butyl)-2,3-dihydrobenzo[d]isothiazole 1,1-dioxide

To a solution of 5-bromo-2-(tert-butyl)benzo[d]isothiazol-3(2H)-one 1,1-dioxide (0.20 g, 0.63 mmol) in THF (4 mL), was added BH$_3$.Me$_2$S (240 mg, 3.00 mmol). The reaction mixture was refluxed for 16 hours. After being cooled to rt, the reaction was quenched with HCl (2.0 M. 15 mL), then extracted with EtOAc (2×50 mL). The combined extracts were washed with brine, dried over Na$_2$SO$_4$, filtered and concentrated in vacuo. The resulting residue was purified by preparative TLC to afford the title compound. $^1$H NMR (400 MHz, DMSO-d$_6$) δ 7.83-7.56 (m, 3H), 4.55 (s, 2H), 1.46 (s, 9H).

Alternatively, Step 3 above can be conducted using BH$_3$-THF complex as the reducing agent (and heating to ~75° C.) to effect the carbonyl reduction (as described for Intermediate 72, Step 2).

Table 15 includes Intermediates that were prepared in an analogous manner to that disclosed for Intermediate 72.

TABLE 15

| Intermediate | Structure | Compound Name | $^1$H NMR |
|---|---|---|---|
| I-73 | 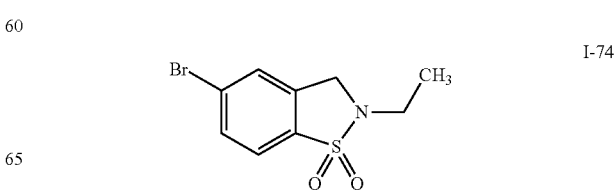 | 5-bromo-2-methyl-2,3-dihydrobenzo[d]isothiazole 1,1-dioxide | (CDCl$_3$, 400 MHz): δ 7.63-7.60 (m, 2H), 7.5 (s, 1H), 4.25 (s, 2H), 2.89 (s, 3H). |

Intermediate 74

5-Bromo-2-ethyl-2,3-dihydrobenzo[d]isothiazole 1,1-dioxide

I-74

Step 1: 4-Bromo-N-ethyl-2-methylbenzenesulfonamide

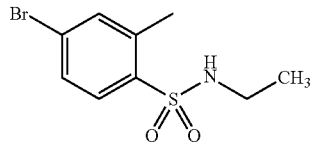
I-74a

Into a 100-mL 3-necked round-bottom flask were placed a solution of 4-bromo-2-methylbenzene-1-sulfonyl chloride (3.0 g, 9.7 mmol) in dichloromethane (30 mL), ethanamine (700 mg, 15.5 mmol) and DIPEA (4.32 g, 29.1 mmol). The resulting solution was stirred for 0.5 h at 25° C. The mixture was washed with water (10 mL), dried over sodium sulfate, filtered and concentrated in vacuo. The residue was purified by column chromatography on silica gel (5:1 petroleum ether/ethyl acetate) to afford the title compound. $^1$H NMR (400 MHz, CDCl$_3$) δ: 7.47-7.51 (m, 2H), 7.84 (d, J=8.4 Hz, 1H), 2.99-3.06 (m, 2H), 2.66 (s, 3H), 1.13 (t, J=2.4 Hz, 3H).

Step 2: 5-Bromo-2-ethylbenzo[d]isothiazol-3(2H)-one 1,1-dioxide

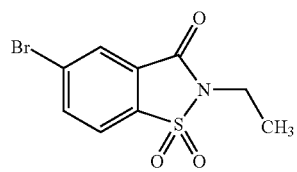
I-74b

To a solution of 4-bromo-N-ethyl-2-methylbenzene-1-sulfonamide (1.00 g, 3.59 mmol) in 1,2-dichloroethane (10 mL) was added iodobenzene diacetate (3.50 g, 10.9 mmol) and I$_2$ (900 mg, 3.54 mmol). The resulting solution was stirred for 16 h at 60° C. The mixture was washed with water (100 mL), and aqueous sodium sulfite (100 mL). The organic layer was dried over sodium sulfate, filtered and concentrated in vacuo. The residue was purified on silica, eluting with 5:1 petroleum ether/ethyl acetate to afford the title compound. $^1$H NMR (300 MHz, CDCl$_3$) δ: 7.70-7.79 (m, 1H), 7.97 (m, 1H), 8.18 (s, 1H), 3.84 (q, J=7.2 Hz, 2H), 1.45 (t, J=7.6 Hz, 3H).

Step 3: 5-Bromo-2-ethyl-2,3-dihydrobenzo[d]isothiazole 1,1-dioxide

To a solution of 5-bromo-2-ethylbenzo[d]isothiazol-3(2H)-one 1,1-dioxide (80 mg, 0.28 mmol) in tetrahydrofuran (5 mL) was added BH$_3$—S(Me)$_2$ (2.0 M in THF, 0.70 mL, 1.4 mmol). The resulting solution was stirred for 4 h at 70° C. and then quenched by the addition of ice water (30 mL). The mixture was then extracted with ethyl acetate (3×30 mL), and the combined organic layers were dried over anhydrous sodium sulfate, filtered and concentrated in vacuo to give crude 5-bromo-2-ethyl-2,3-dihydrobenzo[d]isothiazole 1,1-dioxide. LRMS (ESI) calc'd for C$_9$H$_{11}$BrNO$_2$S [M+H]$^+$: 276, found 276. $^1$H NMR (300 MHz, CDCl$_3$) δ: 7.77 (s, 2H), 7.57 (s, 1H), 4.34 (s, 2H), 3.21-3.41 (m, 2H), 1.38 (t, J=7.2 Hz, 3H).

The intermediates described in Table 16 were prepared in an analogous manner to that disclosed for Intermediate 74.

TABLE 16

| Intermediate | Structure | Compound Name | LRMS [M + H]$^+$ |
|---|---|---|---|
| I-75 | 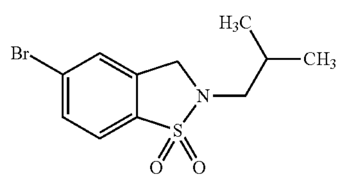 [SMILES: CC(C)CN1Cc2cc(Br)ccc2S1(=O)=O] | 5-bromo-2-isobutyl-2,3-dihydrobenzo[d]isothiazole 1,1-dioxide | Calc'd 304, found 304 |
| I-76 | 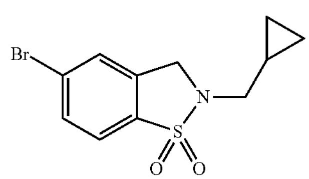 [SMILES: O=S1(=O)c2ccc(Br)cc2CN1CC1CC1] | 5-bromo-2-(cyclopropylmethyl)-2,3-dihydrobenzo[d]isothiazole 1,1-dioxide | Calc'd 302, found 302 |
| I-77 | 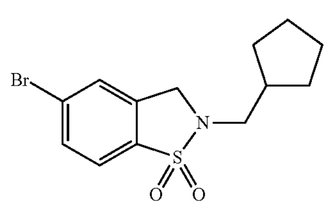 [SMILES: O=S1(=O)c2ccc(Br)cc2CN1CC1CCCC1] | 5-bromo-2-(cyclopentylmethyl)-2,3-dihydrobenzo[d]isothiazole 1,1-dioxide | Calc'd 330, found 330 |

Intermediate 78

5-Bromo-2-(2,2,2-trifluoroethyl)-2,3-dihydrobenzo[d]isothiazole 1,1-dioxide

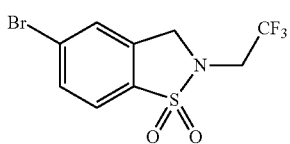

I-78

Step 1: 4-Bromo-2-methyl-N-(2,2,2-trifluoroethyl)benzenesulfonamide

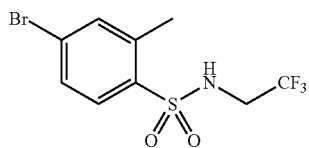

I-78a

Formation of 4-bromo-2-methyl-N-(2,2,2-trifluoroethyl)benzenesulfonamide was conducted in an analogous manner as described in Step 1 of the process for making I-74a.

Step 2: 5-Bromo-2-(2,2,2-trifluoroethyl)benzo[d]isothiazol-3(2H)-one 1,1-dioxide

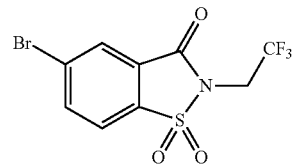

I-78b

A mixture of periodic acid (1.12 g, 4.91 mmol), 4-bromo-2-methyl-N-(2,2,2-trifluoroethyl)benzenesulfonamide (163 mg, 0.491 mmol), chromium trioxide (9.8 mg, 0.098 mmol) in acetonitrile (5 mL) was heated to reflux at 83° C. for 2 h. The reaction mixture was concentrated in vacuo to remove the acetonitrile. Water was then added, and the mixture was extracted with EtOAc (×3). The combined organic layers were washed with saturated aqueous NaHCO₃, followed by aq. Na₂S₂O₃ and brine. The organic layer was dried over Na₂SO₄, filtered and concentrated in vacuo. The residue was purified by silica gel chromatography (5-15% EtOAc/Hexanes) to afford the title compound. ¹H NMR (CDCl₃, 600 MHz): δ 8.24 (d, J=1.2 Hz, 1H), 8.04 (dd, J=8.1, 1.8 Hz, 1H), 7.83 (d, J=8.4 Hz, 1H), 4.30 (q, J=8.4 Hz, 2H).

Step 3: 5-Bromo-2-(2,2,2-trifluoroethyl)-2,3-dihydrobenzo[d]isothiazole 1,1-dioxide To a mixture of 5-bromo-2-(2,2,2-trifluoroethyl)benzo[d]isothiazol-3(2H)-one 1,1-dioxide (515 mg, 1.50 mmol) in THF (10 mL) was added BH₃THF (1.0 M, 15.0 mL, 15.0 mmol) and the reaction was heated in a sealed tube at 75° C. overnight. The reaction was then cooled to rt and quenched by careful addition of the reaction to a mixture of ice water and DCM. The resulting biphasic mixture was stirred for 2 hours, then extracted with DCM (×3). The combined organic layers were dried over Na₂SO₄, filtered and concentrated in vacuo. The residue was purified by silica gel chromatography (EtOAc/hexanes: 5-30%) to afford impure desired product. The product was repurified by silica gel chromatography (EtOAc/hexanes: 0-20%), to afford the title compound. ¹H NMR (CDCl₃, 600 MHz): δ 7.69 (br s, 2H), 7.58 (br s, 1H), 4.53 (s, 2H), 3.82 (q, J=9.0 Hz, 2H).

Intermediate 79

5-Bromo-2-(3-hydroxy-2,2-dimethylpropyl)-2,3-dihydrobenzo[d]isothiazole 1,1-dioxide

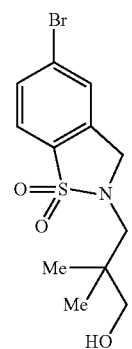

I-79

Step 1: 5-Bromo-2-(3-hydroxy-2,2-dimethylpropyl)benzo[d]isothiazol-3(2H)-one 1,1-dioxide

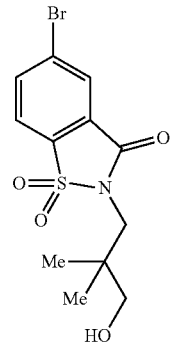

I-79a

To a stirred solution of 5-bromo-2,3-dihydro-1,2-benzothiazole-1,1,3-trione (0.10 g, 0.38 mmol,) in N-methyl-2-pyrrolidone (3 mL) was added 3-bromo-2,2-dimethylpropan-1-ol (0.19 g, 1.2 mmol) followed by cesium carbonate (0.37 g, 1.1 mmol). The resulting reaction mixture was stirred for 16 h at 130° C. The reaction was cooled down to ambient temperature and quenched by the addition of water (10 mL). The resulting mixture was extracted with ethyl acetate (2×20 mL). The organic layers were combined, dried over anhydrous sodium sulfate and filtered. The filtrate was concentrated in vacuo and the residue purified on silica, eluting with 1:1 ethyl acetate/petroleum ether to afford the title compound. LRMS (ESI) calc'd for $C_{12}H_{15}BrNO_4S$ [M+H]⁺: 348, 350 (1:1). found: 348, 350 (1:1).

Step 2: 5-Bromo-2-(3-hydroxy-2,2-dimethylpropyl)-2,3-dihydro-1,2-benzothiazole-1,1-dione To a stirred solution of 5-Bromo-2-(3-hydroxy-2,2-dimethylpropyl)benzo[d]isothiazol-3(2H)-one 1,1-dioxide (0.20 g, 0.57 mmol) in tetrahydrofuran (5.0 mL) was added a solution of borane dimethylsulfide (1.40 mL, 2.0 M in tetrahydrofuran, 2.8 mmol). The resulting solution was stirred for 2 h at 75° C. The reaction was quenched by the careful addition of water/ice (10 mL). The resulting mixture was extracted with ethyl acetate (2×30 mL). The organic layers were combined, dried over anhydrous sodium sulfate and filtered. The filtrate was concentrated in vacuo and the residue purified on silica, eluting with 1:1 ethyl acetate/petroleum ether to afford the title compound. LRMS (ESI) calc'd for $C_{12}H_{17}BrNO_3S$ [M+H]⁺: 334, 336 (1:1). found 334, 336 (1:1).

Table 17 discloses an Intermediate that was prepared in using similar procedures as described above for Intermediate 79.

TABLE 17

| Intermediate | Structure | Compound Name | LRMS [M + H]⁺ |
|---|---|---|---|
| I-80 | (structure) | 5-bromo-2-isopropyl-2,3-dihydrobenzo[d]isothiazole 1,1-dioxide | Calc'd 290, found 290 |

Intermediate 81

5-Bromo-2-(2-methoxyethyl)-2,3-dihydrobenzo[d]isothiazole 1,1-dioxide

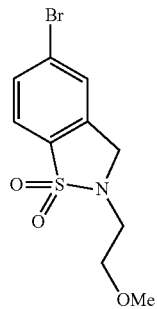

I-81

To a stirred solution of 5-bromo-2,3-dihydro-1,2-benzothiazole-1,1-dione (0.20 g, 0.81 mmol) in N,N-dimethylformamide (5 mL) was added 1-bromo-2-methoxyethane (0.13 g, 0.96 mmol) and cesium carbonate (0.39 g, 1.2 mmol). The reaction mixture was stirred for 4 h at 50° C., then was quenched by water (20 mL). The mixture was extracted with ethyl acetate (2×30 mL), the organic layers were combined, dried over anhydrous sodium sulfate, and filtered. The filtrate was concentrated in vacuo and the residue purified on silica, eluting with petroleum ether/ethyl acetate (1/1) to afford the title compound. LRMS (ESI) calc'd for $C_{10}H_{12}BrNO_3S$ [M+H]⁺: 306, found 306.

Table 18 discloses Intermediates prepared using similar procedures as described for Intermediate 81, starting with the appropriate benzothiazole or bromoisoindolinone and alkylating agent. In select cases, the general procedure was modified to alternatively utilize between 1.0-1.5 equivalents $CsCO_3$ or NaH base.

TABLE 18

| Intermediate | Structure | Compound Name | LRMS [M + H]⁺ |
|---|---|---|---|
| I-82 | (structure) | 5-bromo-2-(2-hydroxyethyl)-2,3-dihydrobenzo[d]isothiazole 1,1-dioxide | Calc'd 292, found 292 |

TABLE 18-continued

| Intermediate | Structure | Compound Name | LRMS [M + H]+ |
|---|---|---|---|
| I-83 | (5-Bromo, 3-Me, N-CH2CF3 dihydrobenzo[d]isothiazole 1,1-dioxide) | (R or S) 5-Bromo-3-methyl-2-(2,2,2-trifluoroethyl)-2,3-dihydrobenzo[d]isothiazole 1,1-dioxide (Derived from Peak A by SFC using AD-H, 85% MeOH in CO$_2$, Tr = 2.34 mins) | Calc'd 345, found 345 |
| I-84 | (5-Bromo, 3-Me, N-CH2CF3 dihydrobenzo[d]isothiazole 1,1-dioxide) | (R or S) 5-Bromo-3-methyl-2-(2,2,2-trifluoroethyl)-2,3-dihydrobenzo[d]isothiazole 1,1-dioxide (Derived from Peak B by SFC using AD-H, 85% MeOH in CO$_2$, Tr = 2.74 mins) | Calc'd 345, found 345 |
| I-85 | (5-Bromo-2,3-dimethyl dihydrobenzo[d]isothiazole 1,1-dioxide) | (R or S) 5-Bromo-2,3-dimethyl-2,3-dihydrobenzo[d]isothiazole 1,1-dioxide (Derived from Peak A by SFC using AS-H, 40% MeOH in ACN, Tr = 1.77 mins) | Calc'd 277, found 277 |
| I-86 | (5-Bromo-2,3-dimethyl dihydrobenzo[d]isothiazole 1,1-dioxide) | (R or S) 5-Bromo-2,3-dimethyl-2,3-dihydrobenzo[d]isothiazole 1,1-dioxide (Derived from Peak B by SFC using AS-H, 40% MeOH in ACN, Tr = 2.16 mins) | Calc'd 277, found 277 |
| I-87 | (tert-Butyl 2-(5-bromo-1,1-dioxidobenzo[d]isothiazol-2(3H)-yl)acetate) | tert-Butyl 2-(5-bromo-1,1-dioxidobenzo[d]isothiazol-2(3H)-yl)acetate | Calc'd 362, 364 (1:1), found 362, 364 (1:1) |
| I-88 | (5-Bromo-2-isopropyl isoindolinone) | 5-Bromo-2-(propan-2-yl)-2,3-dihydro-1H-isoindol-1-one | Calc'd 254, 256 (1:1), found 254, 256 (1:1) |

101

Intermediate 89

5-Bromo-2-(4-hydroxy-2-methylbutan-2-yl)-2,3-dihydrobenzo[d]isothiazole 1,1-dioxide

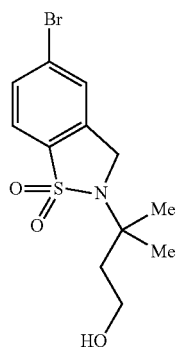

I-89

Step 1: Ethyl 3-(4-bromo-2-methylphenylsulfonamido)-3-methylbutanoate

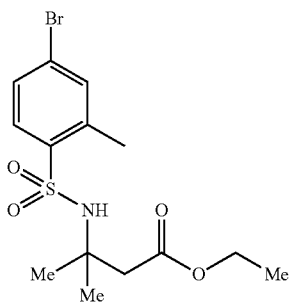

I-89a

To 4-bromo-2-methylbenzene-1-sulfonyl chloride (2.00 g, 7.42 mmol) in dichloromethane (40 mL) was added ethyl 3-amino-3-methylbutanoate hydrochloride (1.62 g, 8.92 mmol) and triethylamine (1.88 g, 18.6 mmol). The resulting solution was stirred for 4 h at ambient temperature, then concentrated in vacuo. The residue was purified by silica gel column chromatography (ethyl acetate/petroleum ether: 1/1) to afford the title compound.

Step 2: Ethyl 3-(5-bromo-1,1-dioxido-3-oxobenzo[d]isothiazol-2(3H)-yl)-3-methylbutanoate

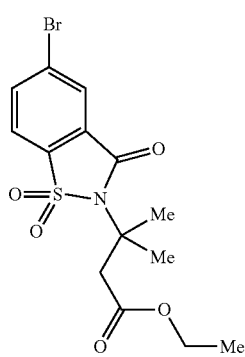

I-89b

102

To ethyl 3-(4-bromo-2-methylphenylsulfonamido)-3-methylbutanoate (0.50 g, 1.3 mmol) in acetonitrile (100 mL) was added periodic acid (2.40 g, 10.5 mmol) and chromium trioxide (26 mg, 0.26 mmol). The resulting mixture was stirred for 4 h at ambient temperature. The solids were removed by filtration and the filtrate was concentrated in vacuo. The residue was purified on silica, eluting with petroleum ether/ethyl acetate (1/1) to afford the title compound. $^1$H NMR (300 MHz, CDCl$_3$) δ 8.15 (d, J=1.8 Hz, 1H), 7.96 (dd, J=8.1, 1.8 Hz, 1H), 7.71 (d, J=8.1 Hz, 1H), 4.08 (q, J=7.2 Hz, 2H), 3.12 (s, 2H), 1.88 (s, 6H), 1.12 (t, J=7.2 Hz, 3H).

Step 3: 5-Bromo-2-(4-hydroxy-2-methylbutan-2-yl)-2,3-dihydrobenzo[d]isothiazole 1,1-dioxide To ethyl 3-(5-bromo-1,1-dioxido-3-oxobenzo[d]isothiazol-2(3H)-yl)-3-methylbutanoate (0.20 g, 0.51 mmol) in tetrahydrofuran (5 mL) was added borane-methyl sulfide complex (0.25 mL, 10 M in tetrahydrofuran, 2.50 mmol). The resulting solution was stirred for 16 h at 50° C., and carefully quenched by ice-water (10 mL). The mixture was extracted with ethyl acetate (3×30 mL), and the combined organic layers were dried over anhydrous sodium sulfate and filtered. The filtrate was concentrated in vacuo and the residue purified by silica gel column chromatography (ethyl acetate/petroleum ether: 1/1) to afford the title compound. LRMS (ESI) calc'd for C$_{12}$H$_{17}$BrNO$_3$S [M+H]$^+$: 334, 336 (1:1). found: 334, 336 (1:1).

Table 19 discloses an Intermediate prepared using similar procedures as described for Intermediate 89.

TABLE 19

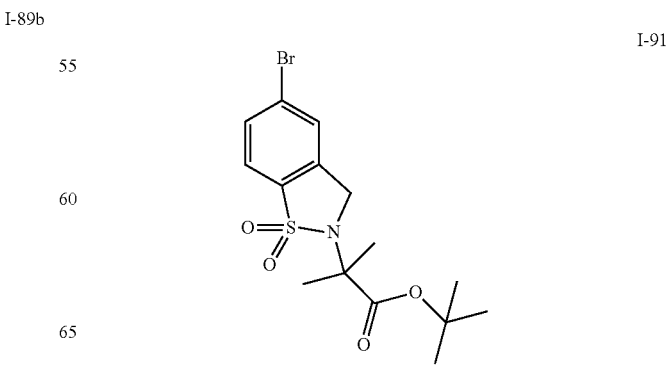

| Intermediate | Structure | Compound Name | $^1$H NMR |
|---|---|---|---|
| I-90 | 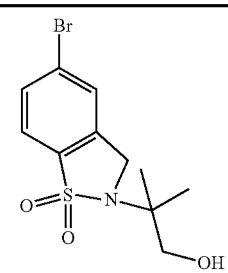 | 5-bromo-2-(1-hydroxy-2-methylpropan-2-yl)-2,3-dihydrobenzo[d]isothiazole 1,1-dioxide | (300 MHz, CDCl$_3$) δ 7.70-7.65 (m, 2H), 7.62 (s, 1H), 4.49 (s, 2H), 3.89 (s, 2H), 1.50 (s, 6H). |

Intermediate 91 tert-Butyl 2-(5-bromo-1,1-dioxidobenzo[d]isothiazol-2(3H)-yl)-2-methylpropanoate

I-91

Step 1: tert-Butyl 2-(4-bromo-2-methylphenylsulfonamido)-2-methylpropanoate

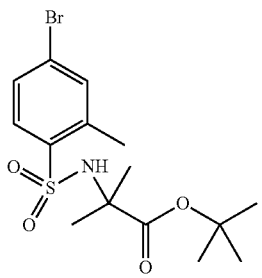

I-91a

Into a 100 mL round bottom flask, were placed 4-bromo-2-methylbenzene-1-sulfonyl chloride (4.00 g, 14.8 mmol) in dichloromethane (40 mL), tert-butyl 2-amino-2-methylpropanoate hydrochloride (3.47 g, 17.8 mmol) and triethylamine (3.74 g, 37.0 mmol). The resulting solution was stirred for 4 h at ambient temperature. The mixture was concentrated in vacuo and the residue purified on silica, eluting with ethyl acetate/petroleum ether (1:1) to give tert-butyl 2-(4-bromo-2-methylphenylsulfonamido)-2-methylpropanoate. LRMS (ESI) calc'd for $C_{15}H_{23}BrNO_4S$ [M+H]$^+$: 392, 394 (1:1). found 392, 394 (1:1).

Step 2: tert-Butyl 2-(4-bromo-2-(bromomethyl)phenylsulfonamido)-2-methylpropanoate

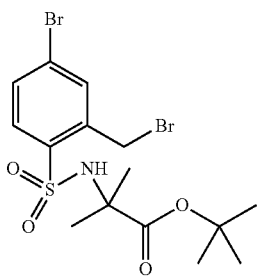

I-91b

Into a 250 mL round-bottom flask, were placed tert-butyl 2-(4-bromo-2-methylphenylsulfonamido)-2-methylpropanoate (3.00 g, 7.68 mmol) in carbontetrachloride (100 mL), N-bromosuccinimide (2.04 g, 11.4 mmol) and benzoyl peroxide (0.19 g, 0.76 mmol) was added at 80° C. The resulting solution was stirred for 24 h at 80° C. The resulting solution was concentrated in vacuo and water (30 mL) was added. The mixture was extracted with ethyl acetate (3×50 mL). The combined organic layers were dried over anhydrous sodium sulfate and filtered. The filtrate was concentrated in vacuo to afford the title compound which was carried onto the next step without further purification. LRMS (ESI) calc'd for $C_{15}H_{22}Br_2NO_4S$ [M+H]$^+$: 470, 472 (1:1). found 470, 472 (1:1).

Step 3: tert-Butyl 2-(5-bromo-1,1-dioxidobenzo[d]isothiazol-2(3H)-yl)-2-methylpropanoate Into a 250 mL round bottom flask, were placed tert-butyl 2-(4-bromo-2-(bromomethyl)phenylsulfonamido)-2-methylpropanoate (3.10 g, 6.35 mmol) and sodium bicarbonate (1.07 g, 12.7 mmol) in acetonitrile/water (5:1, 30 mL). The resulting solution was stirred for 3 h at 75° C. and then concentrated in vacuo. Water (30 mL) was added and extracted with ethyl acetate (3×50 mL). The combined organic layers were dried over anhydrous sodium sulfate and filtered. The filtrate was concentrated in vacuo and the residue purified on silica, eluting with ethyl acetate/petroleum ether (1:3) to give tert-butyl 2-(5-bromo-1,1-dioxidobenzo[d]isothiazol-2(3H)-yl)-2-methylpropanoate. LRMS (ESI) calc'd for $C_{15}H_{21}BrNO_4S$ [M+H]$^+$: 390, 392 (1:1). found 390, 392 (1:1); $^1$H NMR (300 MHz, CDCl$_3$) δ 7.64 (s, 1H), 7.53 (m, 2H), 4.75 (s, 2H), 1.77 (s, 6H), 1.38 (s, 9H).

Table 20 discloses Intermediates that were prepared in an analogous manner to that for Intermediate 91 using the appropriate amine.

TABLE 20

| Intermediate | Structure | Compound Name | LRMS [M + H]$^+$/$^1$H NMR |
|---|---|---|---|
| I-92 | 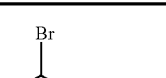 | 5-bromo-2-(tetrahydro-2H-pyran-4-yl)-2,3-dihydrobenzo[d]isothiazole 1,1-dioxide | Calc'd 332, 334 (1:1), found 332, 334 (1:1) |

TABLE 20-continued

| Intermediate | Structure | Compound Name | LRMS [M + H]⁺/¹H NMR |
|---|---|---|---|
| I-93 | (structure) | 5-bromo-2-(4-methyltetrahydro-2H-pyran-4-yl)-2,3-dihydrobenzo[d]isothiazole 1,1-dioxide | Calc'd 346, 348 (1:1), found 346, 348 (1:1) |
| I-94 | (structure) | 5-bromo-2-(4,4-difluoro-1-methylcyclohexyl)-2,3-dihydrobenzo[d]isothiazole 1,1-dioxide | (300 MHz, CDCl$_3$) δ7.69 (d, J = 8.4 Hz, 1H), 7.64 (d, J = 8.4 Hz, 1H), 7.56 (s, 1H), 4.37 (s, 2H), 2.43-2.33 (m, 2H), 2.31-2.11 (m, 2H), 2.09-1.92 (m, 2H), 1.88-1.78 (m, 2H), 1.51 (s, 3H). |

Intermediate 95 tert-Butyl 3-(5-bromo-1,1-dioxidobenzo[d]isothiazol-2(3H)-yl)-3-methylbutanoate

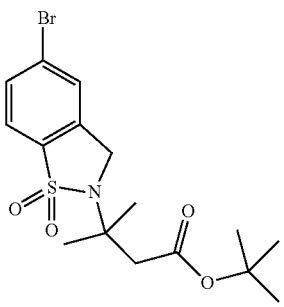

I-95

Step 1: 3-(5-Bromo-1,1-dioxidobenzo[d]isothiazol-2(3H)-yl)-3-methylbutanoic acid

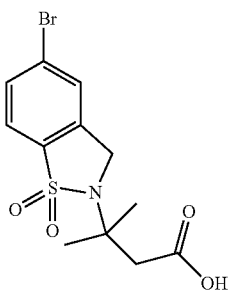

I-95a

Into a 50 mL round bottom flask, were placed 5-bromo-2-(4-hydroxy-2-methylbutan-2-yl)-2,3-dihydrobenzo[d]isothiazole-1,1-dioxide (I-89; 0.35 g, 1.05 mmol) and dichloromethane (2 mL). Jones reagent (0.60 mL, 1.57 mmol) was added and the reaction was stirred for 10 min at −5° C. Water (50 mL) was added and the mixture extracted with ethyl acetate (2×50 mL). The combined organic layers were washed with water (2×30 mL) and brine (2×30 mL), dried over sodium sulfate and filtered. The filtrate was concentrated in vacuo and the residue purified on silica, eluting with petroleum ether/ethyl acetate (1:3) to afford 3-(5-bromo-1,1-dioxidobenzo[d]isothiazol-2(3H)-yl)-3-methylbutanoic acid. LRMS (ESI) calc'd for C$_{12}$H$_{15}$BrNO$_4$S [M+H]⁺: 348, 350 (1:1). found 348, 350 (1:1).

Step 2: tert-Butyl 3-(5-bromo-1,1-dioxidobenzo[d]isothiazol-2(3H)-yl)-3-methylbutanoate Into a 10 mL round bottom flask, were placed 3-(5-bromo-1,1-dioxidobenzo[d]isothiazol-2(3H)-yl)-3-methylbutanoic acid (0.28 g, 0.80 mmol), tert-butyl 2,2,2-trichloroacetimidate (8.79 g, 40.2 mmol) and dichloromethane (2 mL). The mixture was stirred for 72 h at ambient temperature and then quenched by water (10 mL). The mixture was extracted with ethyl acetate (2×50 mL). The combined organic layers were washed with water (2×30 mL) and brine (2×30 mL), dried over sodium sulfate and filtered. The filtrate was concentrated in vacuo and the residue purified on silica, eluting with petroleum ether/ethyl acetate (1:5) to afford tert-butyl 3-(5-bromo-1,1-dioxidobenzo[d]isothiazol-2(3H)-yl)-3-methylbutanoate. LRMS (ESI) calc'd for C$_{16}$H$_{23}$BrNO$_4$S [M+H]⁺: 404, 406 (1:1). found 404, 406 (1:1).

Intermediate 96

5-Bromo-2-(3-methoxy-2,2-dimethylpropyl)-2,3-dihydrobenzo[d]isothiazole 1,1-dioxide

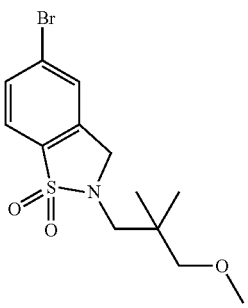

I-96

In a 100 mL round-bottom flask, 5-bromo-2-(3-hydroxy-2,2-dimethylpropyl)-2,3-dihydro-1,2-benzothiazole-1,1-dione (I-79; 0.14 g, 0.42 mmol) was combined with DCM (40 mL) and trimethyloxonium tetrafluoroborate (0.25 g, 1.7 mmol) at ambient temperature. The resulting mixture was stirred for 16 hours then quenched with water (30 mL). The resulting mixture was extracted with EtOAc (3×30 mL) and the combined organic layers were concentrated in vacuo. The residue was purified on silica, eluting with EtOAc/petroleum ether (1:1) to afford the title compound. LRMS (ESI) calc'd for $C_{13}H_{19}BrNO_3S$ [M+H]$^+$: 348, 350 (1:1). found 348, 350 (1:1).

Table 21 discloses Intermediates prepared using similar procedures as described for Intermediate 96.

TABLE 21

| Intermediate | Structure | Compound Name | LRMS [M + H]$^+$ |
|---|---|---|---|
| I-97 | 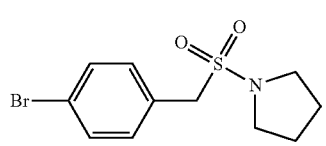 | 5-bromo-2-(1-methoxy-2-methylpropan-2-yl)-2,3-dihydrobenzo[d]isothiazole 1,1-dioxide (from I-90) | Calc'd 334, 336 (1:1), found 334, 336 (1:1) |
| I-98 | 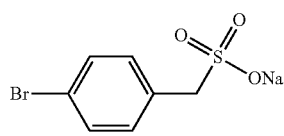 | 5-bromo-2-(4-methoxy-2-methylbutan-2-yl)-2,3-dihydrobenzo[d]isothiazole 1,1-dioxide (from I-89) | Calc'd 348, 350 (1:1), found 348, 350 (1:1) |

Intermediate 99

5-Bromo-2,3-dihydrobenzo[b]thiophene 1,1-dioxide

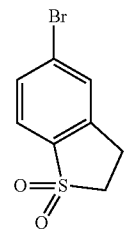

I-99

To a solution of 5-bromo-benzo[b]thiophene 1,1-dioxide (1.00 g, 4.08 mmol) in ethanol (14 mL) at 0° C., sodium borohydride (193 mg, 5.10 mmol) was added. The resulting reaction mixture was warmed to room temperature and stirred overnight. The reaction mixture was then cooled to 0° C., and quenched with HCl (1 N). The mixture was diluted with ethyl acetate (25 mL), the layers were separated, and the aqueous layer was extracted with ethyl acetate (3×25 mL). The combined organic layers were washed with brine, dried over $Na_2SO_4$, and concentrated in vacuo. The residue was purified by column chromatography on silica gel (Hexanes/EtOAc: 5:1) to give the title compound. $^1$H NMR (500 MHz, CDCl$_3$): δ 7.62-7.53 (m, 2H), 7.51 (s, 1H), 3.55-3.45 (m, 2H), 3.39-3.29 (m, 2H).

Intermediate 100

1-((4-Bromobenzyl)sulfonyl)pyrrolidine

I-100

Step 1: Sodium (4-bromophenyl)methanesulfonate

I-100a

To a boiling solution of 1-bromo-4-(bromomethyl)benzene (200 g, 0.8 mol) in EtOH (500 mL) was added a solution of sodium sulfite (101 g, 0.80 mol) in $H_2O$ (500 mL) over 60 min. The resulting reaction mixture was stirred at reflux for 2 h, then the mixture was cooled to 0° C., and stirred for 30 min. The mixture was filtered, and the solid was washed with EtOH, and dried in vacuo to afford the title compound. $^1$H NMR (300 MHz, D$_2$O) δ: 7.50 (d, 2H), 7.20 (d, 2H), 4.05 (s, 2H).

Step 2: (4-Bromophenyl)methanesulfonyl chloride

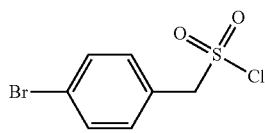

I-100b

To a vigorously stirred suspension of sodium (4-bromophenyl)methanesulfonate (167 g, 0.611 mol) in DMF (650 mL) at −10° C. was added thionyl dichloride (162 mL, 2.23 mol) drop-wise. The resulting reaction solution was stirred at rt for 2 h then was poured into ice with vigorous stirring. The mixture was filtered, and the resulting solid was dissolved in EtOAc, then washed with $H_2O$ and brine, dried over $Na_2SO_4$, filtered and concentrated in vacuo to give the title compound. $^1$H NMR (300 MHz, CDCl$_3$) δ: 7.66 (d, 2H), 7.39 (d, 2H), 4.87 (s, 2H).

Step 3: 1-((4-Bromobenzyl)sulfonyl)pyrrolidine

To a stirred mixture of potassium carbonate (74.8 g, 0.542 mol) in DCM (70 mL) and $H_2O$ (220 mL) at −10° C. was added pyrrolidine (21.2 g, 0.298 mol) in portions, and the resulting mixture was stirred for 20 min. Then (4-bromophenyl)methanesulfonyl chloride (73.0 g, 0.271 mol) in DCM (400 mL) was added drop-wise. The resultant mixture was stirred for 1 h at RT. The organic phase was separated, washed with $H_2O$, brine, dried over $Na_2SO_4$, and concentrated in vacuo. The residue was recrystallized from 5% EtOAc/petroleum ether to give the title compound. $^1$H NMR (300 MHz, CDCl3) δ: 7.52 (d, 2H), 7.25 (d, 2H), 4.20 (s, 2H), 3.20-3.30 (m, 4H), 1.80-1.92 (m, 4H).

Intermediate 101

(±)
4-(3-Bromophenyl)-2,2,4-trimethyl-1,3-dioxolane

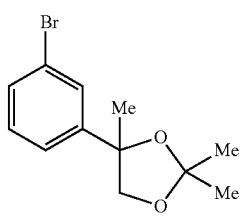

I-101

Step 1: 1-Bromo-3-(prop-1-en-2-yl)benzene

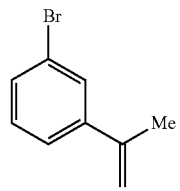

I-101a

To a suspension of Ph$_3$PMeBr (21.4 g, 60.0 mmol) in THF (500 mL) was added t-BuOK (6.72 g, 60.0 mmol) at 0° C. The resulting mixture was stirred at rt for 1 h. To the mixture was added 1-(4-bromophenyl)ethanone (10.0 g, 50.0 mmol) dropwise at 0° C., then was stirred for 24 h. $H_2O$ (300 mL) was added, and the mixture was extracted with EtOAc (300 mL×2). The combined organic layers were washed with brine (300 mL), dried over $Na_2SO_4$, filtered and concentrated in vacuo. The residue was purified by column chromatography on silica gel (Hexanes/EtOAc: 20:1) to afford 1-bromo-4-(prop-1-en-2-yl)benzene.

Step 2: 2-(3-Bromophenyl)propane-1,2-diol

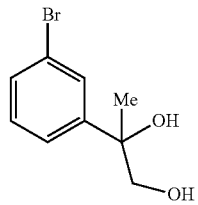

I-101b

To a solution of 1-Bromo-3-(prop-1-en-2-yl)benzene (10.0 g, 50.7 mmol) at 0° C. was added a mixture of $K_2O_sO_4 \cdot 2H_2O$ (930 mg, 2.50 mmol), $K_3Fe(CN)_6$ (83.0 g, 230 mmol) and $K_2CO_3$ (21.0 g, 150 mmol) in t-BuOH (300 mL) and $H_2O$ (300 mL). The reaction was quenched by the addition of aqueous saturated $Na_2S_2O_3$ (200 mL) and extracted with EtOAc (500 mL). The organic layer was washed with brine, dried over $Na_2SO_4$, filtered and concentrated in vacuo to afford the racemate of the title compound.

Step 3: 4-(3-Bromophenyl)-2,2,4-trimethyl-1,3-dioxolane

A suspension of 2-(4-bromophenyl)propane-1,2-diol (6.0 g, 26 mmol), 2,2-dimethoxypropane (6 mL), and TsOH (1.1 g, 6.5 mmol) in toluene (100 mL) was stirred overnight at rt. The mixture was quenched with $H_2O$ and extracted with EtOAc. The organic layer was washed with brine, dried over $Na_2SO_4$ and concentrated in vacuo to afford the racemate of the title compound. $^1$H NMR (CDCl$_3$, 400 MHz): δ 7.56 (s, 1H), 7.56-7.20 (m, 3H), 4.08-4.06 (m, 2H), 1.59-1.39 (m, 6H), 1.39 (d, J=5.2 Hz, 3H).

Intermediate 102

4-Bromo-2-(hydroxymethyl)benzenesulfonamide

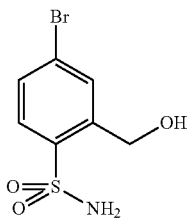

I-102

Step 1: 4-Bromo-2-methylbenzenesulfonamide

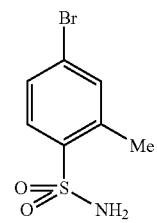

I-102a

Chlorosulfonic acid (63.0 g, 540 mmol) was added slowly to a cold solution (0° C.) of 1-bromo-3-methylbenzene (10 g, 58 mmol) in CHCl$_3$ (100 mL). The reaction was allowed to stir for 2 hours at 0° C. The reaction mixture was poured carefully into ice water (400 mL) and extracted with EtOAc (500 mL). The layers were separated and the organic layer was washed with brine, dried over NaSO₄, filtered and concentrated in vacuo. The crude product was dissolved in THF (100 mL) and cooled to 0° C., then to the solution was added NH₃/H₂O (25%, 150 mL). The mixture was stirred at the same temperature for 4 hours. The reaction was extracted with EtOAc (200 mL×2), and the combined organic layers were washed with water (2×200 mL) and brine (100 mL), dried over NaSO₄, filtered and concentrated in vacuo to afford 4-bromo-2-methylbenzenesulfonamide. $^1$H NMR (400 MHz, DMSO-d₆) δ 7.76 (d, J=8.4 Hz, 1H), 7.64 (s, 1H), 7.59 (dd, J=8.4, 2.0 Hz, 1H), 7.48 (br s, 2H), 2.58 (s, 3H).

Step 2:
N-((4-Bromo-2-methylphenyl)sulfonyl)acetamide

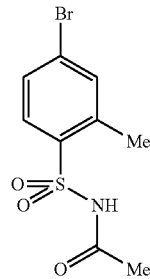

I-102b

To a solution of 4-bromo-2-methylbenzenesulfonamide (7.0 g, 28 mmol) in pyridine (70 mL) was added Ac₂O (5.7 g, 56 mmol) followed by DMAP (1.0 g, 8.4 mmol). The reaction mixture was stirred for 16 hours at rt, then quenched with saturated aqueous NH₄Cl and H₂O. The resulting mixture was extracted with EtOAc (200 mL×2). The combined organic layers were washed with HCl (1.0 M, 30 mL) and brine (50 mL), dried over Na₂SO₄, filtered and concentrated in vacuo to afford a residue that was recrystallized from EtOAc to afford the title compound. $^1$H NMR (400 MHz, DMSO-d₆) δ 12.26 (br s, 1H), 7.85 (d, J=8.4 Hz, 1H), 7.69-7.63 (m, 2H), 2.57 (s, 3H), 1.95 (s, 3H).

Step 3:
4-Bromo-2-(hydroxymethyl)benzenesulfonamide

KMnO₄ (2.7 g, 17 mmol) was added to a solution of N-((4-bromo-2-methylphenyl)sulfonyl)acetamide (0.50 g, 1.7 mmol) in aqueous NaOH (1.0 M, 24 mL) and the reaction was allowed to proceed at 80° C. with stirring for 16 hours. The reaction was quenched with acetone. The resulting insoluble material was remove by filtration, and the filtrate was diluted with H₂O, and acidified to pH=3 using HCl (1.0 M). The mixture was extracted with EtOAc (100 mL). The organic layer was washed with brine, dried over Na₂SO₄, filtered and concentrated in vacuo to afford 2-(N-acetylsulfamoyl)-5-bromobenzoic acid which was carried onto the reduction without further purification. To a solution of 5-bromo-2-sulfamoylbenzoic acid (0.14 g, 0.53 mmol) in THF (5 mL) was added BH₃.Me₂S (160 mg, 2.10 mmol). The reaction mixture was refluxed for 16 hours, cooled to rt, then carefully quenched with aq. HCl (2.0 M) to pH=3. The resulting mixture was extracted with EtOAc (2×50 mL). The combined organic layers were washed with brine, dried over Na₂SO₄, filtered and concentrated in vacuo. The residue was purified by preparative TLC to afford the title compound. $^1$H NMR (400 MHz, DMSO-d₆) δ 7.87-7.85 (m, 1H), 7.72 (d, J=8.4 Hz, 1H), 7.63 (dd, J=8.4, 2.0 Hz, 1H), 7.29 (s, 2H), 5.56 (t, J=5.6 Hz, 1H), 4.85 (d, J=5.6 Hz, 2H).

Intermediate 103

4-(Benzyloxy)-2-(5-chloro-2-(methylsulfonyl)phenyl)butan-2-ol

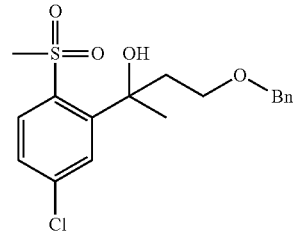

I-103

Step 1: (2-Bromo-4-chlorophenyl)(methyl)sulfane

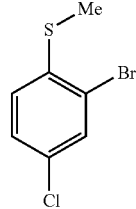

I-103a

A solution of 2-bromo-4-chloro-1-fluorobenzene (2.5 mL, 20 mmol) and sodium thiomethoxide (1.45 g, 20.7 mmol) in DMF (20 mL) was stirred at 100° C. for 2 h. The reaction mixture was added to water (20 mL) with stirring, and the aqueous mixture was extracted with ethyl acetate (3×50 mL). The combined organic layers were dried over sodium sulfate, filtered and concentrated in vacuo. The residue was purified by column chromatography on silica gel (hexanes/EtOAc: 20/1) to afford the title compound. $^1$H NMR (600 MHz, DMSO-d₆): δ 7.74 (d, J=8.6, 2.3 Hz, 1H), 7.49 (dd, J=8.6, 2.3 Hz, 1H), 7.28 (d, J=8.6 Hz, 1H), 2.51 (m, 3H).

Step 2: 4-(Benzyloxy)-2-(5-chloro-2-(methylthio)phenyl)butan-2-ol

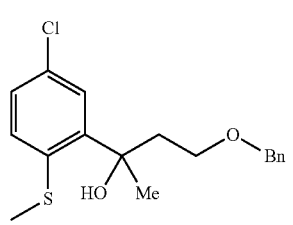

I-103b

To a THF solution of isopropylmagnesium chloride-lithium chloride complex (1.0 M, 2.43 mL, 3.16 mmol) in an oven dried vial was added (2-bromo-4-chlorophenyl)(methyl)sulfane (500 mg, 2.11 mmol; dried by passing through a plug of neat magnesium sulfate) dropwise under argon at 0° C. The ice bath was removed and the vial was allowed to warm to room temperature and stirred for 2 h. 4-(benzyloxy)butan-2-ol (1.12 g, 6.31 mmol) was added dropwise into the cooled reaction mixture. The resulting reaction was allowed to stir at room temperature overnight, then was concentrated in vacuo. The residue was purified by column chromatography on silica gel (hexanes/EtOAc: 10/1) to afford the title compound. $^1$H NMR (600 MHz, DMSO-$d_6$): δ 7.55 (d, J=2.4 Hz, 1H), 7.27-7.20 (m, 5H), 7.18 (d, J=7.4 Hz, 2H), 5.23 (s, 1H), 4.29 (s, 2H), 3.43-3.39 (m, 1H), 3.17-3.12 (m, 1H), 2.40 (s, 3H), 2.55-2.50 (m, 1H); 2.16-2.12 (m, 1H), 1.55 (s, 3H).

Step 3: 4-(Benzyloxy)-2-(5-chloro-2-(methylsulfonyl)phenyl)butan-2-ol

To a solution of 4-(benzyloxy)-2-(5-chloro-2-(methylthio)phenyl)butan-2-ol (297 mg, 0.880 mmol) in $CH_2Cl_2$ (7 mL) cooled in an ice bath was added meta-chloroperoxybenzoic acid (380 mg, 2.20 mmol). After stirring at room temperature overnight, the reaction mixture was diluted with $CH_2Cl_2$ (5 mL) and washed with saturated sodium bicarbonate solution, dried over sodium sulfate, filtered and concentrated in vacuo. The residue was purified by column chromatography on silica gel (hexanes/EtOAc: 20-30%) to give the title compound. LRMS (ESI) calc'd for $C_{18}H_{22}ClO_4S[M+H]^+$: 369, found 369. $^1$H NMR (600 MHz, DMSO-$d_6$): δ 8.08 (d, J=8.7 Hz, 1H), 7.65 (d, J=2.2 Hz, 1H), 7.54 (dd, J=8.7, 2.2 Hz, 1H), 7.24-7.25 (m, 3H), 7.16 (d, J=7.5 Hz, 2H), 5.47 (s, 1H), 4.29-4.30 (m, 2H), 3.46-3.43 (dt, J=9.7, 6.8 Hz, 1H), 3.37-3.33 (dt, J=9.7, 6.8 Hz, 1H), 3.32 (s, 3H), 2.43-2.38 (dt, J=14.0, 6.8 Hz, 1H), 2.18-2.15 (dt, J=14.0, 6.8 Hz, 1H), 1.60 (s, 3H).

Table 22 discloses an Intermediate which was prepared in analogous manner to that of Intermediate 103.

TABLE 22

| Intermediate | Structure | Compound Name | LRMS [M + H]$^+$ |
|---|---|---|---|
| I-104 | 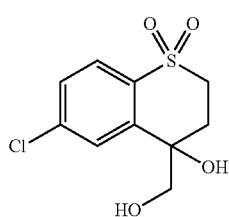 | 1-((tert-butyldimethylsilyl)oxy)-2-(5-chloro-2-(methylsulfonyl)phenyl)propan-2-ol | Calc'd 380, found 380. |

Intermediate 105

6-Chloro-4-hydroxy-4-(hydroxymethyl)thiochroman 1,1-dioxide

I-105

Step 1: 6-Chloro-4-hydroxy-4-((isopropoxydimethylsilyl)methyl)thiochroman 1,1-dioxide

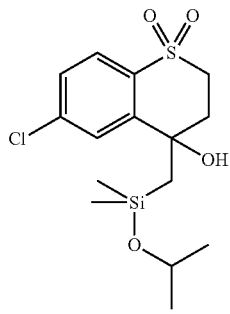

I-105a

A three-necked round-bottom flask was charged with magnesium turnings (71.1 mg, 2.93 mmol) that were dried under a rapid stream of $N_2$ with a heat gun. After cooling to room temperature, the flow rate of $N_2$ was reduced, and 1 mL of a solution of 6-chloro-4-hydroxy-4-((isopropoxydimethylsilyl)methyl)thiochroman 1,1-dioxide (470 mg, 2.82 mmol) in dry THF (3.5 mL) and two drops of 1,2-dibromoethane (2.0 μL, 0.022 mmol) were added. The mixture was stirred at room temperature and within a few min an exothermic reaction started. The remaining solution was added slowly at room temperature. After the addition was complete, the reaction mixture was stirred at room temperature. The mixture was cooled to 0° C., and a solution of 6-chlorothiochroman-4-one 1,1-dioxide (500 mg, 2.17 mmol) in THF (2.0 mL) was added dropwise at 0° C., then warmed to room temperature overnight. The resulting mixture was quenched with ammonium chloride solution (10% aqueous) and extracted with ethyl acetate (3×5 mL). The combined organic layers were washed with brine (3×10 mL), dried over sodium sulfate, filtered and concentrated in vacuo to afford the title compound that was carried on without further purification.

Step 2: 6-Chloro-4-hydroxy-4-(hydroxymethyl)thiochroman 1,1-dioxide

To a crude mixture of 6-Chloro-4-hydroxy-4-((isopropoxydimethylsilyl)methyl)thiochroman 1,1-dioxide (392 mg, 1.08 mmol), potassium fluoride (62.7 mg, 1.08 mmol) in THF (0.5 mL) and methanol (0.5 mL) was added hydrogen peroxide (30%; 0.29 mL, 3.24 mmol) in one portion at room temperature. The resulting cloudy solution was kept to maintain stirring under 50° C. and at room temperature for 2 h. The reaction was quenched with aqueous sodium thiosulfate solution, extracted with ethyl acetate (3×5 mL), and concentrated in vacuo. The residue was purified on silica, eluting with 0-100% hexanes/EtOAc to give the title compound. $^1$H NMR (600 MHz, DMSO-$d_6$): δ 7.74 (d, J=8.5 Hz, 1H), 7.65 (d, J=2.2 Hz, 1H), 7.58 (dd, J=8.5, 2.2 Hz, 1H), 5.10 (t, J=5.8 Hz, 1H), 3.68-3.62 (m, 2H), 3.54-3.50 (ddd, J=14.2, 8.3, 2.8 Hz, 1H), 3.46-3.42 (dd, J=11.3, 5.4 Hz, 1H), 2.62-2.56 (ddd, J=14.8, 8.3, 2.8 Hz, 1H), 2.36-2.28 (m, 1H) (note: could not assign one hydroxyl proton; likely due to overlap with solvent peaks).

Intermediate 106

Methyl 5-bromo-2,3-dihydro-1H-indene-2-carboxylate

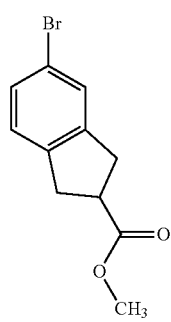

I-106

Step 1: Methyl 6-bromo-1-oxo-2,3-dihydro-1H-indene-2-carboxylate

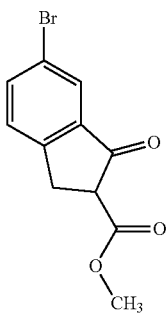

I-106a

Into a 50-mL round-bottom flask purged and maintained with an inert atmosphere of nitrogen, was placed a solution of 5-bromo-2,3-dihydro-1H-inden-1-one (1.00 g, 4.74 mmol) in tetrahydrofuran (15 mL). Sodium hydride (0.38 g, 60% in mineral oil, 9.48 mmol) was added followed by dimethyl carbonate (0.90 g, 10 mmol). The resulting mixture was stirred for 30 min at 50° C. then quenched by the addition of hydrochloric acid (20 mL, 1.0 M). The resulting mixture was extracted with ethyl acetate (2×50 mL). The organic layers were combined, dried over anhydrous sodium sulfate and filtered. The filtrate was concentrated in vacuo to afford the title compound. LRMS (ESI) calc'd for $C_{11}H_{10}BrO_3$ $[M+H]^+$: 269, 271 (1:1). found 269, 271 (1:1).

Step 2: Methyl 5-bromo-2,3-dihydro-1H-indene-2-carboxylate

Into a 25-mL round-bottom flask purged and maintained with an inert atmosphere of nitrogen, was placed a solution of methyl 6-bromo-1-oxo-2,3-dihydro-1H-indene-2-carboxylate (0.70 g, 2.6 mmol) in trifluoroacetic acid (10 mL). Triethylsilane (4 mL) was added dropwise at 0° C., and the resulting solution was stirred for 18 h at 10° C. The reaction mixture was concentrated in vacuo and the resulting residue was diluted with ethyl acetate (50 mL) and washed with water (100 mL). The organic layer was concentrated in vacuo to afford the title compound. GCMS (ESI) calc'd for $C_{11}H_{11}BrO_2$ $[M]^+$: 254, found 254.

Intermediate 107

1-({3-Bromo-5-[(methylsulfanyl)methyl]phenyl}methyl)-1H-1,2,3-triazole

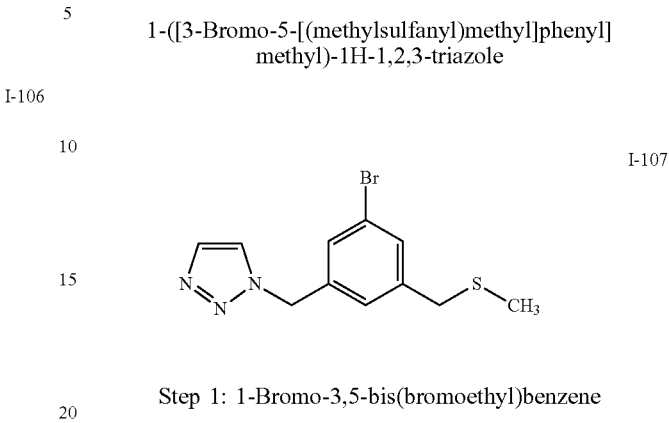

I-107

Step 1: 1-Bromo-3,5-bis(bromoethyl)benzene

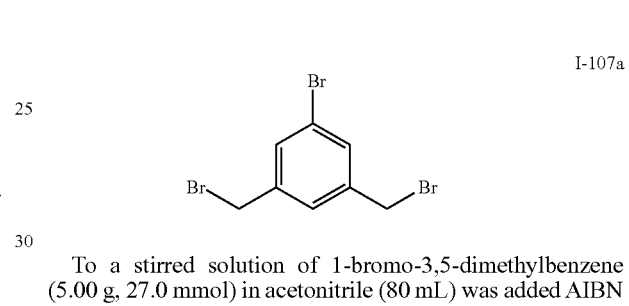

I-107a

To a stirred solution of 1-bromo-3,5-dimethylbenzene (5.00 g, 27.0 mmol) in acetonitrile (80 mL) was added AIBN (0.045 g, 0.27 mmol) and N-bromosuccinimide (7.20 g, 40.5 mmol). The reaction mixture was stirred for 1 h at 80° C. and then quenched by the addition of aqueous ammonium chloride (300 mL). The resulting solution was extracted with ethyl acetate (100 mL×3). The organic layers were combined, dried over anhydrous sodium sulfate, filtered and concentrated in vacuo. The residue was purified by silica gel column chromatography (ethyl acetate/petroleum ether: 1/100) to afford the title compound. $^1$H NMR (400 MHz, DMSO-d$_6$) δ7.70 (s, 2H), 7.64 (s, 1H), 4.70 (s, 4H).

Step 2: (3-Bromo-5-(bromomethyl)benzyl)(methyl)sulfane

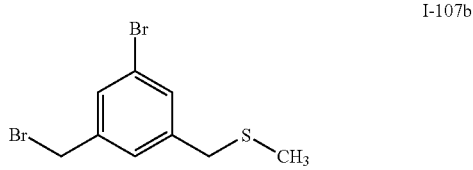

I-107b

1-Bromo-3,5-bis(bromomethyl)benzene (0.500 g, 1.46 mmol), (methylsulfanyl)sodium (0.102 g, 1.46 mmol), and ethanol (10 mL) were combined, and the resulting solution was stirred for 1 h at 60° C. The reaction mixture was concentrated in vacuo to afford a residue that was used for the next step without any further purification.

Step 3: 1-({3-Bromo-5-[(methylsulfanyl)methyl]phenyl}methyl)-1H-1,2,3-triazole To a stirred solution of (3-bromo-5-(bromomethyl)benzyl)(methyl)sulfane (0.500 g, 1.61 mmol) in acetonitrile (15 mL) was added 1H-1,2,3-triazole (0.220 g, 3.19 mmol) and potassium carbonate (0.442 g, 3.20 mmol). The reaction mixture was stirred for 1 h at 25° C. The reaction was then quenched by the addition of water (30 mL), and the resulting solution was extracted with ethyl acetate (50 mL×3). The organic layers were combined, washed with water (3×10 mL), dried over sodium sulfate, filtered and concentrated in vacuo. The residue was purified by silica gel chromatography (ethyl acetate/petroleum ether: 1:2) to give the title compound. $^1$H NMR (400 MHz, DMSO-$d_6$): δ8.24 (s, 1H), 7.77 (s, 1H), 7.49 (s, 1H), 7.39 (s, 1H), 7.23 (s, 1H), 5.64 (s, 2H), 1.93 (s, 3H).

Intermediate 108

1,1'-((5-Bromo-1,3-phenylene)bis(methylene))bis(1H-pyrazole)

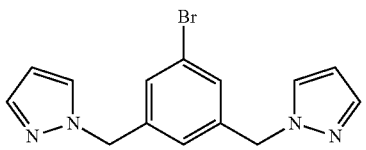

I-108

Step 1: 1-Bromo-3,5-bis(bromomethyl)benzene (alternate synthesis)

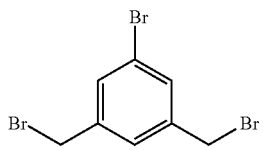

I-108a

1-Bromo-3,5-dimethylbenzene (5.00 g, 27.0 mmol), N-bromosuccinimide (7.20 g, 40.5 mmol), AIBN (0.045 g, 0.27 mmol) and acetonitrile (80 mL) were combined in a flask under a nitrogen atmosphere. The resulting solution was stirred for 1 h at 80° C., then diluted with aqueous ammonium chloride (50 mL) solution, and then extracted with dichloromethane (3×50 mL). The combined organic layers were concentrated in vacuo and the residue purified on silica, eluting with petroleum ether to afford the title compound. $^1$H NMR (400 MHz, DMSO-$d_6$) δ7.70 (s, 2H), 7.64 (s, 1H), 4.70 (s, 4H).

Step 2: 1,1'-((5-Bromo-1,3-phenylene)bis(methylene))bis(1H-pyrazole)

To a mixture of 1H-pyrazole (1.80 g, 26.4 mmol) in acetonitrile (120 mL) was added potassium carbonate (3.60 g, 26.1 mmol). The resulting mixture was stirred for 1 h at 25° C., then 1-bromo-3,5-bis(bromomethyl)benzene (3.00 g, 8.75 mmol) was added, and the solution was stirred for 16 h at 25° C. The reaction was quenched by the addition of aqueous ammonium chloride solution, and the mixture was extracted with ethyl acetate (3×150 mL). The organic layers were combined, dried over sodium sulfate, filtered and concentrated in vacuo. The residue was purified on silica, eluting with ethyl acetate/petroleum (1/1) to afford the title compound. LRMS (ESI) calc'd for $C_{14}H_{14}BrN_4$ [M+H]$^+$: 317, found 317.

Intermediate 109

4-Hydroxycyclohex-1-ene-1-carbonitrile

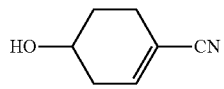

I-109

Step 1: 4-Oxocyclohex-1-ene-1-carbonitrile

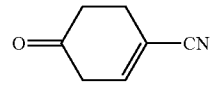

I-109a

In a sealed tube, {[(3E)-4-methoxybuta-1,3-dien-2-yl]oxy}(trimethyl)silane (5.65 mL, 29.0 mmol) and acrylonitrile (1.91 mL, 29.0 mmol) were combined in benzene (9.67 mL), heated to reflux, and allowed to stir for 16 hours. The reaction mixture was then cooled to ambient temperature and the volatiles concentrated in vacuo. The residue was stirred into a mixture of aqueous HCl (1.0 N; 29.0 mL, 29.0 mmol) and THF (9.7 mL). After being stirred at ambient temperature for 3 hours, the reaction mixture was extracted with diethyl ether. The organic layer was washed with de-ionized water (2×), brine, dried over anhydrous $Na_2SO_4$, filtered and concentrated in vacuo. The residue was purified on silica, eluting with 0-50% hexanes/acetone to afford the title compound. $^1$H NMR (600 MHz, CDCl$_3$): δ 6.68 (tt, J=4.0, 1.5 Hz, 1H), 3.05 (dt, J=4.3, 2.2 Hz, 2H), 2.71 (tq, J=6.9, 1.9 Hz, 2H), 2.57 (t, J=6.9 Hz, 2H).

Step 2: 4-Hydroxcyclohex-1-ene-1-carbonitrile

To a stirred solution of 4-oxocyclohex-1-ene-1-carbonitrile (170 mg, 1.40 mmol) in MeOH (2.3 mL) at −78° C. was added cerium (III) chloride (484 mg, 1.96 mmol) in MeOH (4.7 mL). The resulting mixture was allowed to stir for 5 minutes at −78° C. before NaBH$_4$ (48 mg, 1.3 mmol) was added in one portion. The mixture was stirred for 20 minutes and then allowed to warm to ambient temperature. After being stirred for 30 minutes, the reaction mixture was diluted with water and extracted with diethyl ether (3×). The combined organic extracts were washed with brine, dried over anhydrous $Na_2SO_4$, filtered, and concentrated in vacuo to afford the title compound. $^1$H NMR (600 MHz, CDCl$_3$): δ 6.50 (tt, J=3.9, 1.8 Hz, 1H), 4.03-3.98 (m, 1H), 3.50-3.42 (qd, J=11.4, 4.5 Hz, 1H), 2.50 (br d, J=19.2 Hz, 1H), 2.46-2.38 (m, 1H), 2.33-2.23 (m, 1H), 2.21-2.13 (m, 1H), 1.90-1.84 (m, 1H), 1.76-1.67 (m, 1H).

Intermediate 110

4-Bromo-2-(hydroxymethyl)benzenesulfonamide

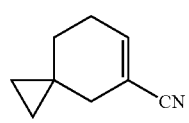
I-110

Step 1: 8-Methylene-1,4-dioxaspiro[4.5]decane

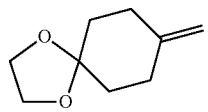
I-110a

To a suspension of PPh₃CH₃Br (17.2 g, 48.0 mmol) in THF (100 mL) was added t-BuONa (3.7 g, 38 mmol) at rt. The reaction mixture was stirred for 3 h at the same temperature, then to this mixture was added a solution of 1,4-dioxaspiro[4.5]decan-8-one (3.0 g, 19 mmol) in THF (50 mL). The reaction was stirred at rt for 5 h, then was quenched by saturated aqueous NH₄Cl (10 mL). The resulting mixture was extracted with CH₂Cl₂ (3×10 mL) and the combined organic layers were concentrated in vacuo. The residue was purified by column chromatography on silica gel (hexanes/EtOAc: 10/1) to give the title compound. $^1$H NMR (CDCl₃, 400 MHz): δ 4.65 (s, 2H), 3.96 (s, 4H), 2.27 (t, J=6.5 Hz, 4H), 1.69 (t, J=6.5 Hz, 4H).

Step 2: Spiro[2.5]octan-6-one ethylene ketone

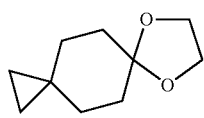
I-110b

To a solution of 8-methylene-1,4-dioxaspiro[4.5]decane (10 g, 65 mmol) and CH₂I₂ (56.0 g, 210 mmol) in THF (100 mL) was added Zn(Et)₂ (1.0 M, 110 mL, 110 mmol) under nitrogen at rt, and the mixture was stirred for 5 h at the same temperature. The reaction was quenched by careful addition of aqueous HCl (2.0 M; 150 mL), then was extracted with CH₂Cl₂ (3×20 mL). The organic layer was dried over MgSO₄, filtered and concentrated in vacuo. The residue was purified by column chromatography on silica gel (hexanes/EtOAc: 30/1) to afford the title compound. $^1$H NMR (CDCl₃, 400 MHz): δ 3.96 (s, 4H), 1.69 (t, J=6.4 Hz, 4H), 1.42 (t, J=6.4 Hz, 4H), 0.27 (s, 4H).

Step 3: Spiro[2.5]octan-6-one

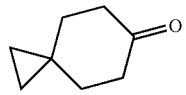
I-110c

To a solution of spiro[2.5]octan-6-one ethylene ketone (3.00 g, 17.9 mmol) in THF (100 mL) was added HCl (1.0 M; 100 mL), and the mixture was stirred at rt overnight. The reaction mixture was diluted with petroleum ether. The layers were separated, the organic layer was concentrated in vacuo, and the residue was purified by column chromatography on silica gel (hexanes/EtOAc: 10/1) to afford the title compound. $^1$H NMR (CDCl₃, 400 MHz): δ 2.39 (t, J=6.4 Hz, 4H), 1.65 (t, J=6.4 Hz, 4H), 0.46 (s, 4H).

Step 4: 6-Oxospiro[2.5]octane-5-carbonitrile

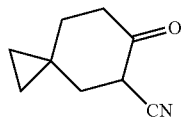
I-110d

To a solution of NH(i-Pr)₂ (1.2 g, 12 mmol) in THF (10 mL) was added n-BuLi (5.0 mL, 11.5 mmol) under nitrogen at −78° C. The resulting mixture was stirred at 0° C. for 30 min, then to the reaction was added a solution of spiro[2.5]octan-6-one (1.3 g, 10 mmol) in THF (10 mL) at −78° C. After stirring at this temperature for 30 min, this mixture was added to a solution of TsCN (3.7 g, 20 mmol) in THF (10 mL) at −78° C., and stirred for 30 min. The reaction was quenched carefully with concentrated ammonium hydroxide (10 mL), and the mixture was warmed to rt then acidified with HCl (1.0 M). The mixture was extracted with EtOAc (2×20 mL). The combined organic layers were concentrated in vacuo, and the residue purified by column chromatography on silica gel (hexanes/EtOAc: 10/1) to afford the title compound. $^1$H NMR (CDCl₃, 400 MHz): δ 3.46-3.42 (m, 1H), 2.46-2.40 (m, 1H), 2.33-2.26 (m, 1H), 2.19-2.13 (m, 1H), 1.94-1.83 (m, 1H), 1.59-1.53 (m, 1H), 1.26-1.17 (m, 1H), 0.54-0.44 (m, 2H), 0.36-0.33 (m, 2H).

Step 5: (trans)-6-Hydroxyspiro[2.5]octane-5-carbonitrile (racemic)

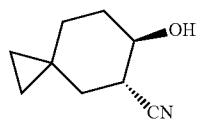
I-110e

A mixture of 6-oxospiro[2.5]octane-5-carbonitrile (3.0 g, 20 mmol) and LiBH₄ (1.8 g, 80 mmol) in THF (100 mL) was stirred at rt overnight. The mixture was quenched by the careful addition of aqueous HCl (1.0 M; 40 mL) and extracted with DCM (3×15 mL). The combined organic layers were concentrated in vacuo, and the residue purified by column chromatography on silica gel (hexanes/EtOAc: 5/1) to afford (trans)-6-hydroxyspiro[2.5]octane-5-carbonitrile (racemic). $^1$H NMR (CDCl$_3$, 400 MHz): δ 4.46-4.24 (m, 1H), 3.72 (br s, 1H), 3.54-3.46 (m, 1H), 2.29-2.18 (m, 3H), 2.12-1.68 (m, 3H), 1.08-0.95 (m, 1H), 0.88-0.81 (m, 1H), 0.8-0.73 (m, 2H).

Step 6: Spiro[2.5]oct-5-ene-6-carbonitrile

To a solution of (trans)-6-hydroxyspiro[2.5]octane-5-carbonitrile (racemic)(1.7 g, 11 mmol) and DIPEA (2.9 g, 22 mmol) in DCM (60 mL) was added MsCl (1.5 g, 12 mmol), and the mixture was stirred at rt for 3 h. DBU (6.9 g, 45 mmol) was added, and the resulting mixture was stirred at rt overnight. After being diluted with water, the mixture was extracted with EtOAc (3×20 mL), and the resulting organic layer was washed with aqueous HCl (1.0 M; 20 mL), saturated aqueous NaHCO$_3$ (20 mL) and brine. The organic layer was dried over MgSO$_4$, filtered and was concentrated in vacuo. The residue was purified by column chromatography on silica gel (hexanes/EtOAc: 80/1) to afford spiro[2.5]oct-5-ene-6-carbonitrile. $^1$H NMR (CDCl$_3$, 400 MHz): δ 6.70-6.68 (m, 1H), 2.31-2.35 (m, 2H), 2.08-2.04 (m, 2H), 1.43-1.4 (m, 2H), 0.44-0.34 (m, 4H).

Intermediate 111

1-Bromo-4-(tert-butylsulfonyl)benzene

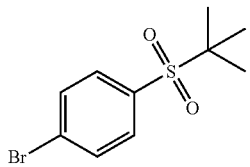

I-111

To a solution of (4-bromophenyl)(tert-butyl)sulfane (1.00 g, 4.08 mmol) in DCM (10 mL) was added m-CPBA (2.01 g, 8.97 mmol, 77 wt %. max) at room temperature. The resulting solution was stirred at room temperature for one hour, before being quenched by addition of saturated Na$_2$S$_2$O$_3$ and Na$_2$CO$_3$ solutions. The aqueous phase was extracted with DCM (×3), and the organic layers were dried over Na$_2$SO$_4$, filtered and concentrated in vacuo to give the title compound. $^1$H NMR (600 MHz, DMSO-d$_6$) δ 7.93 (d, 2H, J=8.5 Hz), 7.79 (d, 2H, J=8.5 Hz), 1.28 (s, 9H).

Intermediate 112

1-Bromo-4-((S and R)-propan-2-ylsulfonimidoyl)benzene

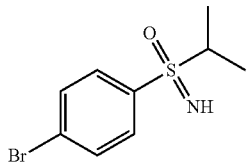

I-112

Step 1: (4-Bromophenyl)(isopropyl)sulfane

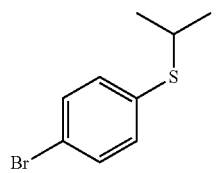

I-112a

To 4-bromothiophenol (1.00 g, 5.29 mmol) was added THF (17.6 mL) and then NaH (233 mg, 5.82 mmol, 60 wt %. in mineral oil) and the reaction was stirred at 0° C. for 1 hour before 2-bromopropane (1.24 g, 10.1 mmol) was added. The reaction was stirred overnight, then filtered through Celite and concentrated in vacuo. The residue was then purified on silica, eluting with 2-30% EtOAc/hexanes to afford the desired product. $^1$H NMR (600 MHz, CDCl$_3$) δ 7.41 (d, 2H, J=8.4 Hz), 7.25 (d, 2H, J=8.4 Hz), 3.34 (septet, 1H, J=6.6 Hz), 1.29 (d, 6H, J=6.6 Hz).

Step 2: 1-Bromo-4-(isopropylsulfinyl)benzene

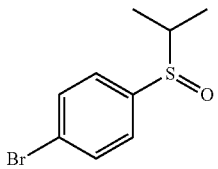

I-112b

To (4-bromophenyl)(isopropyl)sulfane (1.25 g, 5.40 mmol) was added CH$_2$Cl$_2$ (18.0 mL) and then m-CPBA (1.21 g, 5.40 mmol, 77 wt. % max) at 0° C. The reaction was stirred overnight, then quenched by addition of saturated NaHCO$_3$ and sodium sulfite solutions. The solution was then stirred for 15 minutes, extracted with DCM (×3), and the organic layers were dried over sodium sulfate, filtered and concentrated in vacuo. The crude product was purified on silica, eluting with 2-40% EtOAc/hexanes to afford the title compound. $^1$H NMR (600 MHz, CDCl$_3$) δ 7.65 (d, 2H, J=8.4 Hz), 7.46 (d, 2H, J=8.4 Hz), 2.81 (septet, 1H, J=6.6 Hz), 1.23 (d, 3H, J=6.6 Hz), 1.12 (d, 3H, J=6.6 Hz).

Step 3: 4-Methyl-N—[(R and S)-isopropyloxido-(4-bromophenyl)-λ$^4$-sulfanylidene]-benzenesulfonamide

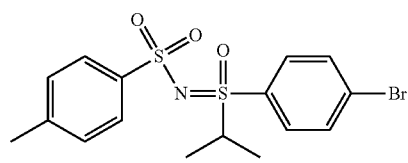

I-112c

Degassed copper(II) trifluoromethanesulfonate (21 mg, 0.057 mmol) and acetonitrile (17.2 mL) along with 1-bromo-4-(isopropylsulfinyl)benzene (175 mg, 0.708 mmol) were stirred under argon for 10 minutes before

[N-(p-toluenesulfonyl)imino]phenyliodinane (378 mg, 1.01 mmol) was added and the reaction was stirred at 25° C. overnight, and then at 50° C. for 7 hours. The reaction was concentrated in vacuo, and purified on silica, eluting with 0-40% EtOAc/hexanes to afford the title compound. LRMS (ESI) calc'd for $C_{16}H_{19}NO_3S_2Br$ [M+H]$^+$: 416, found 416. $^1$H NMR (600 MHz, CDCl$_3$) δ 7.80 (m, 4H), 7.73 (d, 2H, J=7.5 Hz), 7.24 (m, 2H), 3.60 (septet, 1H, J=6.6 Hz), 2.37 (s, 3H), 1.35 (d, 3H, J=6.6 Hz), 1.25 (d, 3H, J=6.6 Hz).

Step 4: 1-Bromo-4-((S and R)-propan-2-ylsulfonimidoyl)benzene

To 4-methyl-N—[(R and S)-isopropyloxido-(4-bromophenyl)-λ$^4$-sulfanylidene]-benzenesulfonamide (1.39 g, 3.34 mmol) was added concentrated sulfuric acid (20 mL) at 0° C. and the reaction was stirred at this temperature for 45 minutes, before being allowed to warm to room temperature over 15 minutes. The reaction was then diluted with CH$_2$Cl$_2$ and quenched by slow addition of saturated sodium bicarbonate solution. The neutralized solution was then extracted with CH$_2$Cl$_2$(×3), then EtOAc (×2), and the combined organic layers were dried over Na$_2$SO$_4$, filtered and concentrated in vacuo. Purification on silica, eluting with 5-80% EtOAc in hexanes afforded the title compound. $^1$H NMR (600 MHz, CDCl$_3$) δ 7.80 (m, 4H), 7.81 (d, 2H, J=8.4 Hz), 7.69 (d, 2H, J=8.4 Hz), 3.27 (septet, 1H, J=6.6 Hz), 1.33 (d, 3H, J=7.2 Hz), 1.28 (d, 3H, J=6.6 Hz).

Intermediate 113

1-(4-Bromophenyl)-N-ethyl-2,2,2-trifluoroethanamine

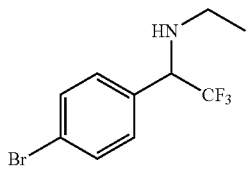

I-113

Step 1: 1-(4-Bromophenyl)-2,2,2-trifluoroethanol

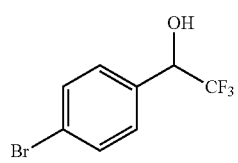

I-113a 1-(4-Bromophenyl)-2,2,2-trifluoroethanone (1.73 g, 6.84 mmol) was dissolved in THF (3.4 mL) and treated with sodium borohydride (0.285 g, 7.52 mmol) at 0° C. The reaction was then warmed to room temperature and stirred overnight. The reaction mixture was then diluted with DCM and washed with water and brine. The combined organic layers were dried over Na$_2$SO$_4$, filtered, and the filtrate was concentrated in vacuo. The residue was purified by silica chromatography, eluting with 5-30% EtOAc in hexanes and the desired fractions were concentrated in vacuo to afford 1-(4-bromophenyl)-2,2,2-trifluoroethanol. $^1$H NMR (500 MHz, CDCl$_3$) δ 7.56 (d, J=8.5 Hz, 2H), 7.36 (d, J=8.5 Hz, 2H), 5.06-4.96 (m, 1H), 2.63 (d, J=4.5 Hz, 1H).

Step 2: 1-(4-Bromophenyl)-2,2,2-trifluoroethyl trifluoromethanesulfonate

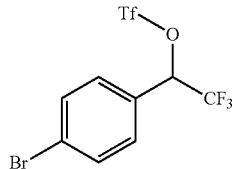

I-113b

A solution of 1-(4-bromophenyl)-2,2,2-trifluoroethanol (1.5 g, 5.9 mmol) and 2,6-lutidine (1.10 mL, 9.41 mmol) in DCE (12 mL) was cooled to −15° C. and triflic anhydride (8.82 mL, 8.82 mmol, in 1.0 M DCM) was added dropwise. The reaction stirred between −15° C. and room temperature for 1 hour. The reaction mixture was diluted with DCM and washed with water, HCl (1 N), and brine. The combined organic layers were dried over Na$_2$SO$_4$, filtered, and the filtrate was concentrated in vacuo to give 1-(4-bromophenyl)-2,2,2-trifluoroethyl trifluoromethanesulfonate. $^1$H NMR (500 MHz, CDCl$_3$) δ 7.64 (d, J=8.3 Hz, 2H), 7.37 (d, J=8.3 Hz, 2H), 5.85-5.74 (m, 1H).

Step 3: 1-(4-Bromophenyl)-N-ethyl-2,2,2-trifluoroethanamine 1-(4-Bromophenyl)-2,2,2-trifluoroethyl trifluoromethanesulfonate (1.0 g, 2.6 mmol) was dissolved in cyclohexane (10 mL) and ethylamine (3.88 mL, 7.75 mmol, in 2.0 M THF), and ground, dried potassium carbonate (0.714 g, 5.17 mmol) (dried over vacuum at 60° C. for one hour) was added. The reaction was heated to 75° C. and stirred overnight. The reaction mixture was diluted with dichloromethane and washed with water. The combined organic layers were dried over sodium sulfate, filtered, and concentrated in vacuo to afford 1-(4-bromophenyl)-N-ethyl-2,2,2-trifluoroethanamine which was carried onto the next step without further purification. LRMS (ESI) calc'd for $C_{10}H_{12}BrF_3N$ [M+H]$^+$: 282, 284 (1:1). found 282, 284 (1:1).

Following analogous methodology to that outlined for Intermediate 113 above, the following intermediate in Table 23 was synthesized. In select cases, the general procedure was modified to alternatively utilize 0.1 equivalents of DMAP.

TABLE 23

| Intermediate | Structure | Name | LRMS [M + H]$^+$ |
|---|---|---|---|
| I-114 | 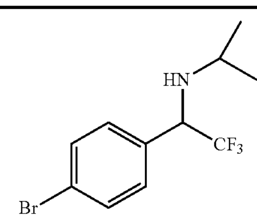 | N-(1-(4-bromophenyl)-2,2,2-trifluoroethyl)propan-2-amine | Calc'd 296, found 296 |

Intermediate 115

Ethyl 3-(4-bromophenyl)-4,4,4-trifluoro-3-hydroxy-2,2-dimethylbutanoate

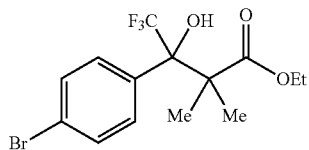

I-115

An oven dried round bottom flask with magnetic stir bar under an atmosphere of N$_2$ was charged with ethyl isobutyrate (689 mg, 5.90 mmol) and THF (2.5 mL). The solution was cooled to −78° C., and lithium diisopropylamide (3.0 mL, 5.9 mmol, 2.0 M in THF) was added. The reaction mixture stirred for 30 min followed by the addition of 1-(4-bromophenyl)-2,2,2-trifluoroethanone (0.5 g, 2 mmol). The reaction mixture was warmed to rt over 1-2 h, and was quenched by the addition of saturated aqueous NH$_4$Cl (10 mL). The resulting mixture was extracted with EtOAc (3×10 mL), and the combined organic layers were concentrated in vacuo and the residue was purified by column chromatography on silica gel (hexanes/EtOAc gradient) to afford ethyl 3-(4-bromophenyl)-4,4,4-trifluoro-3-hydroxy-2,2-dimethylbutanoate. LRMS (ESI) calc'd for C$_{14}$H$_{17}$BrF$_3$O$_3$[M+H]$^+$: 370, found 370. $^1$H NMR (CDCl$_3$, 500 MHz): δ 7.60 (d, J=8.2 Hz, 2H), 7.53 (d, J=8.5 Hz, 2H), 4.31-4.27 (m, 2H), 1.38 (d, J=3.5 Hz, 3H), 1.30 (s, 6H).

Table 24 discloses Intermediates that were prepared in an analogous manner to that of Intermediate 115.

Intermediate 117

5-Bromo-2,2-dimethyl-1-(trifluoromethyl)-2,3-dihydro-1H-inden-1-ol

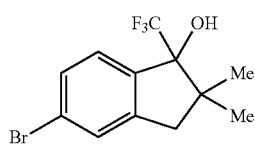

I-117

Step 1: 5-Bromo-2,2-dimethyl-2,3-dihydro-1H-inden-1-one

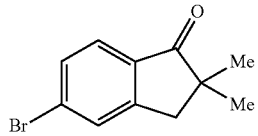

I-117a

An oven dried round bottom flask with magnetic stir bar under an atmosphere of N$_2$ was charged with 5-bromo-2,3-dihydro-1H-inden-1-one (500 mg, 2.40 mmol) and DMF (7.5 mL). The solution was cooled to 0° C., and sodium hydride (237 mg, 5.9 mmol, 60% wt) was added. The reaction mixture stirred for 30 min followed by the addition of iodomethane (0.37 mL, 5.9 mmol). The reaction mixture was warmed to rt over 1-2 h, and was quenched by the addition of saturated aqueous NH$_4$Cl (10 mL). The resulting mixture was extracted with Et$_2$O (3×20 mL), and the combined organic layers were concentrated in vacuo to afford a residue that was purified by column chromatography on silica gel (hexanes/EtOAc gradient) to yield 5-bromo-2,2-dimethyl-2,3-dihydro-1H-inden-1-one. LRMS (ESI) calc'd for C$_{11}$H$_{12}$BrO [M+H]$^+$: 240, found 240. $^1$H NMR (CDCl$_3$, 500 MHz): δ 7.64-7.61 (m, 2H), 7.53 (d, J=8.22 Hz, 1H), 2.99 (s, 2H), 1.26-1.24 (s, 6H).

Step 2: 5-Bromo-2,2-dimethyl-1-(trifluoromethyl)-2,3-dihydro-1H-inden-1-ol

An oven dried round bottom flask with magnetic stir bar under an atmosphere of N$_2$ was charged with 5-bromo-2,2-dimethyl-2,3-dihydro-1H-inden-1-one (2.2 g, 9.5 mmol) and THF (23 mL). The solution was cooled to 0° C., and (trifluoromethyl) trimethylsilane (7.0 mL, 47 mmol) was added. This was followed by the slow (exotherm) addition of

TABLE 24

| Intermediate | Structure | Compound Name | $^1$HNMR |
|---|---|---|---|
| I-116 | (structure shown) | Isopropyl 3-(4-bromophenyl)-4,4,4-trifluoro-3-hydroxy-2,2-dimethylbutanoate | (CDCl$_3$, 500 MHz): δ 7.60 (d, J = 8.2 Hz, 2H), 7.53 (d, J = 8.5 Hz, 2H), 4.31 (m, 1H), 1.30 (s, 6H), 1.27 (d, J = 1.2 Hz, 3H), 1.16 (d, J = 1.3 Hz, 3H) | tetrabutylammonium fluoride (11.9 mL, 11.9 mmol, 1.0 M in THF). The reaction mixture was warmed to rt over 1-2 h, and stirred overnight. The reaction was quenched by the addition of saturated aqueous NH$_4$Cl (10 mL), and the resulting mixture was extracted with EtOAc (3×40 mL). The combined organic layers were concentrated in vacuo to afford a residue that was purified by column chromatography on silica gel (hexanes/EtOAc gradient) to yield 5-bromo-2,2-dimethyl-1-(trifluoromethyl)-2,3-dihydro-1H-inden-1-ol. $^1$H NMR (CDCl$_3$, 500 MHz): δ 7.43-7.41 (m, 2H), 7.33 (d, J=8.11 Hz, 1H), 2.89 (d, J=15.69 Hz, 1H), 2.82 (d, J=15.64 Hz, 1H), 1.27 (s, 3H), 1.16 (s, 3H).

Table 25 discloses an Intermediate that was prepared in an analogous manner to that of Intermediate 117.

TABLE 25

| Intermediate | Structure | Compound Name | ¹HNMR |
|---|---|---|---|
| I-118 | ![structure] | 5'-Bromo-1'-(trifluoromethyl)-1',3'-dihydrospiro[cyclopropane-1,2'-inden]-1'-ol | (CDCl$_3$, 500 MHz): δ 7.46-7.38 (m, 2H), 7.35 (d, J = 15.78 Hz, 1H), 3.33 (d, J = 16.20 Hz, 1H), 2.66 (d, J = 16.20 Hz, 1H), 2.26 (br s, 1H), 1.08-1.01 (m, 2H), 0.98-0.88 (m, 2H). |

Intermediate 119

(R or S) 1-Bromo-4-1,-trifluoro-2-methoxypropan-2-yl)benzene

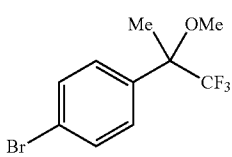

I-119

Step 1: (R or S) 2-(4-Bromophenyl)-1,1,1-trifluoropropan-2-ol and (R or S) 2-(4-Bromophenyl)-1,1,1-trifluoropropan-2-ol

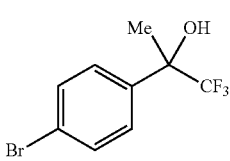

I-119a

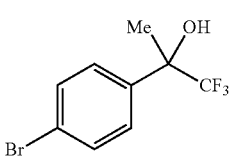

I-119b

An oven dried round bottom flask with magnetic stir bar under an atmosphere of N$_2$ was charged with 1-(4-bromophenyl)-2,2,2-trifluoroethanone (2.0 g, 7.9 mmol) and THF (13 mL). The solution was cooled to 0° C., and methyl magnesium bromide (17 mL, 23.7 mmol, 1.4 M) was added. The reaction mixture was warmed to rt over 1-2 h, and was quenched by the addition of saturated aqueous NH$_4$Cl (10 mL). The resulting mixture was extracted with Et$_2$O (3×20 mL), and the combined organic layers were concentrated in vacuo to afford a residue that was purified by column chromatography on silica gel (hexanes/EtOAc gradient) to yield racemic 2-(4-bromophenyl)-1,1,1-trifluoropropan-2-ol. ¹H NMR (CDCl$_3$, 500 MHz): δ 7.54 (d, J=8.31 Hz, 2H), 7.47 (d, J=8.26 Hz, 2H), 2.44 (s, 1H), 1.78 (s, 3H). Resolution of enantiomers was achieved by SFC purification using a Chiral Technology AZ-H 2.1×25 cm, 5 μM column, at 70 mL/min with 5%/95% (methanol/CO$_2$) solvent system. Retention times were 2.55 minutes for Intermediate 119a (LRMS (ESI) calc'd for C$_9$H$_9$BrF$_3$O [M+H]$^+$: 269, found 269) and 3.19 minutes for Intermediate 119b (LRMS (ESI) calc'd for C$_9$H$_9$BrF$_3$O [M+H]$^+$: 269, found 269).

Step 2: (R or S) 1-Bromo-4-(1,1,1-trifluoro-2-methoxypropan-2-yl)benzene

An oven dried round bottom flask with magnetic stir bar under an atmosphere of N$_2$ was charged with (R or S)-2-(4-bromophenyl)-1,1,1-trifluoropropan-2-ol (I-119a; 300 mg, 1.1 mmol) and DMF (3.5 mL). The solution was cooled to 0° C., and sodium hydride (67 mg, 1.7 mmol, 60% wt) was added. The reaction mixture stirred for 30 min followed by the addition of iodomethane (0.21 mL, 3.3 mmol). The reaction mixture was warmed to rt over 1-2 h, and was quenched by the addition of saturated aqueous NH$_4$Cl (10 mL). The resulting mixture was extracted with Et$_2$O (3×20 mL), and the combined organic layers were concentrated in vacuo to afford a residue that was purified by column chromatography on silica gel (hexanes/EtOAc gradient) to yield (R or S) 1-bromo-4-(1,1,1-trifluoro-2-methoxypropan-2-yl)benzene. ¹H NMR (CDCl$_3$, 500 MHz): δ 7.54 (d, J=8.19 Hz, 2H), 7.38 (d, J=8.14 Hz, 2H), 3.23 (s, 3H), 1.76 (s, 3H).

Intermediate 120

(4-Bromo-2-methylphenyl)(4,4-difluoropiperidin-1-yl)methanone

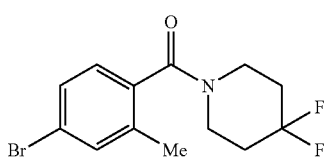

I-120

An oven dried round bottom flask with magnetic stir bar under an atmosphere of N$_2$ was charged with 4-bromo-2-methylbenzoic acid (750 mg, 3.50 mmol), DMF (9 mL), (1-[Bis(dimethylamino)methylene]-1H-1,2,3-triazolo[4,5-b]pyridinium 3-oxid hexafluorophosphate; HATU) (2.6 g, 7.0 mmol), Huenig's base (2.4 mL, 14 mmol), and 4,4-difluoropiperidine (840 mg, 7.0 mmol). The resulting reaction mixture was stirred for 12-16 h, and was concentrated in vacuo. The crude residue was purified by column chromatography on silica gel eluting with Hexanes/EtOAc gradient to yield (4-bromo-2-methylphenyl)(4,4-difluoropiperidin-1-yl)methanone. $^1$H NMR (500 MHz, CDCl$_3$): δ 7.42-7.37 (m, 2H), 7.05 (d, J=8.06 Hz, 1H), 4.02 (m, 1H), 3.82 (m, 1H), 3.38-3.34 (m, 2H), 2.30 (s, 3H), 2.11-2.07 (m, 2H), 1.90-1.86 (m, 2H).

line. $^1$H NMR (500 MHz, CDCl$_3$): δ 7.81 (d, J=9.19 Hz, 1H), 7.74 (s, 1H), 7.60-7.55 (m, 2H), 6.94 (d, J=9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H).

Table 26 discloses Intermediates that were prepared in an analogous manner to that of Intermediate 121.

TABLE 26

| Intermediate | Structure | Compound Name | $^1$HNMR |
|---|---|---|---|
| I-122 | ![structure] | (2S,5S)-4-(6-Bromoquinolin-2-yl)-2,5-dimethylmorpholine | (500 MHz, CDCl$_3$): δ 7.81 (d, J = 9.19 Hz, 1H), 7.74 (s, 1H), 7.60-7.55 (m, 2H), 6.94 (d, J = 9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H). |
| I-123 | ![structure] | (2R,5R)-4-(6-Bromoquinolin-2-yl)-2,5-dimethylmorpholine | (500 MHz, CDCl$_3$): δ 7.81 (d, J = 9.19 Hz, 1H), 7.74 (s, 1H), 7.60-7.55 (m, 2H), 6.94 (d, J = 9.22 Hz, 1H), 4.39 (m, 1H), 4.28 (m, 1H), 3.89-3.85 (m, 2H), 3.66 (m, 1H), 2.90 (m, 1H), 1.34-1.29 (m, 6H). |

Intermediate 121

(2R,5S)-4-(6-Bromoquinolin-2-yl)-2,5-dimethylmorpholine

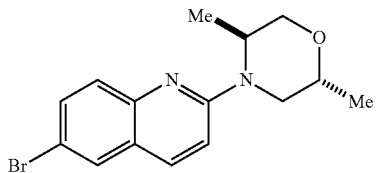 [SMILES: C[C@@H]1CN(c2ccc3cc(Br)ccc3n2)[C@H](C)CO1]

I-121

An oven dried microwave vial with magnetic stir bar under an atmosphere of N$_2$ was charged with 6-bromo-2-chloroquinoline (200 mg, 0.800 mmol), ACN (0.4 mL), triethylamine (0.80 mL, 5.8 mmol), and (2R,5S)-dimethylmorpholine (475 mg, 4.10 mmol). The reaction mixture was heated to 90° C. for 12-16 h, and was concentrated in vacuo. The crude residue was purified by column chromatography on silica gel eluting with Hexanes/EtOAc gradient to yield (2R,5S)-4-(6-bromoquinolin-2-yl)-2,5-dimethylmorpho-

Intermediate 124 tert-Butyl 4-(5-bromo-1-oxoisoindolin-2-yl)cyclohexanecarboxylate

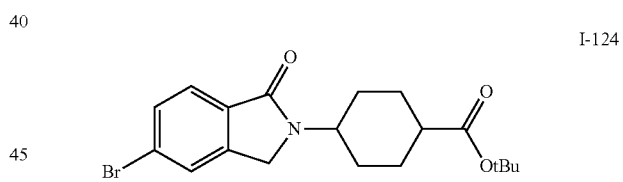

I-124

An oven dried round bottom flask with magnetic stir bar under an atmosphere of N$_2$ was charged with methyl 4-bromo-2-(bromomethyl)benzoate (500 mg, 1.60 mmol), THF (4.8 mL), triethylamine (0.60 mL, 4.1 mmol), and tert-butyl 4-aminocyclohexanecarboxylate (647 mg, 3.30 mmol). The reaction mixture was heated to reflux for 12-16 h, and was concentrated in vacuo. The crude residue was purified by column chromatography on silica gel eluting with Hexanes/EtOAc gradient to yield tert-butyl 4-(5-bromo-1-oxoisoindolin-2-yl)cyclohexanecarboxylate. $^1$H NMR (500 MHz, CDCl$_3$): δ 7.70 (d, J=7.92 Hz, 1H), 7.62-7.58 (m, 2H), 4.33-4.29 (m, 2H), 4.24 (m, 1H), 2.60 (m, 1H), 1.74-1.66 (m, 3H), 1.60-1.52 (m, 5H).

Table 27 discloses Intermediates prepared using similar procedures as described for Intermediate 124, using the appropriate amine. In select cases, the general procedure was modified by using toluene as the solvent.

TABLE 27

| Intermediate | Structure | Compound Name | LRMS [M + H]+ |
|---|---|---|---|
| I-125 | 5-Bromo-2-cyclopentyl-2,3-dihydro-1H-isoindol-1-one structure | 5-Bromo-2-cyclopentyl-2,3-dihydro-1H-isoindol-1-one | Calc'd 280, 282 (1:1), found 280, 282 (1:1) |
| I-126 | 5-Bromo-2-tert-butylisoindolin-1-one structure | 5-Bromo-2-tert-butylisoindolin-1-one | Calc'd 268, 270 (1:1), found 268, 270 (1:1) |
| I-127 | 5-Bromo-2-cyclohexyl-isoindolin-1-one structure | 5-Bromo-2-cyclohexyl-isoindolin-1-one | Calc'd 294, 296 (1:1), found 294, 296 (1:1) |
| I-128 | 5-Bromo-2-(tetrahydro-2H-thiopyran-4-yl)isoindolin-1-one structure | 5-Bromo-2-(tetrahydro-2H-thiopyran-4-yl)isoindolin-1-one | Calc'd 312, 314 (1:1), found 312, 314 (1:1) |
| I-129 | 5-Bromo-2-(tetrahydro-2H-pyran-4-yl)isoindolin-1-one structure | 5-Bromo-2-(tetrahydro-2H-pyran-4-yl)isoindolin-1-one | Calc'd 296, 298 (1:1), found 296, 298 (1:1) |
| I-130 | 5-bromo-2-(4-methyltetrahydro-2H-pyran-4-yl)isoindolin-1-one structure | 5-bromo-2-(4-methyltetrahydro-2H-pyran-4-yl)isoindolin-1-one | Calc'd 310, 312 (1:1), found 310, 312 (1:1) |

Intermediate 131

4-Bromo-N-(tert-butyl)-N-methylbenzenesulfonamide

I-131

To a solution of 4-bromo-N-(tert-butyl) benzenesulfonamide (I-35; 1.0 g, 3.4 mmol) and potassium carbonate (0.946 g, 6.84 mmol) in DMF (20 mL) was added methyl iodide (0.428 mL, 6.84 mmol) at room temperature. The reaction mixture was stirred for 6 h, then quenched with water (50 mL) and extracted with ethyl acetate (50 mL×3), dried over $Na_2SO_4$, filtered and concentrated in vacuo. The residue was purified by silica chromatography, eluting with 0-10% EtOAc/Hexanes to give 4-bromo-N-(tert-butyl)-N-methylbenzenesulfonamide. $^1$H NMR (600 MHz, $CDCl_3$): δ 7.65 (d, J=8.8 Hz, 2H), 7.58 (d, J=8.8 Hz, 2H), 2.94 (s, 3H), 1.32 (s, 9H).

Intermediate 132

4-(4-Bromo-2-chlorophenyl)-1-methyl-1H-pyrazole

I-132

4-Bromo-2-chloro-1-iodobenzene (500 mg, 1.58 mmol), 1-methyl-4-(4,4,5,5-tetramethyl-1,3,2-dioxaborolan-2-yl)-

1H-pyrazole (295 mg, 1.41 mmol), PdCl$_2$(dppf) (115 mg, 0.158 mmol), and potassium phosphate tribasic (1.03 g, 4.73 mmol) were combined in a 20 mL microwave vial and dissolved in dioxane (10 mL) and water (1.0 mL). The vial was sealed and flushed with argon. The reaction was stirred at 90° C. for 2 hours. The vial was then cooled to room temperature and diluted with ethyl acetate. The organic layer was washed with water and brine and then dried using magnesium sulfate. The solution was then filtered and concentrated in vacuo. The crude material was purified by silica chromatography, eluting with 10-50% EtOAc in hexanes and the desired fractions were concentrated in vacuo to give 4-(4-bromo-2-chlorophenyl)-1-methyl-1H-pyrazole. LRMS (ESI) calc'd for C$_{10}$H$_9$BrClN$_2$ [M+H]$^+$: 271, found 271.

Table 28 discloses an Intermediate that was prepared in an analogous manner to that of Intermediate 132.

TABLE 28

| Intermediate | Structure | Compound Name | LRMS [M + H]$^+$ |
|---|---|---|---|
| I-133 | 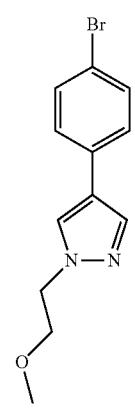 | 3-(4-(4-Bromo-2-methylphenyl)-1H-pyrazol-1-yl)propanenitrile | Calc'd 290, found 290 |

Intermediate 134

4-(4-Bromophenyl)-1-(2-methoxyethyl)-1H-pyrazole

I-134

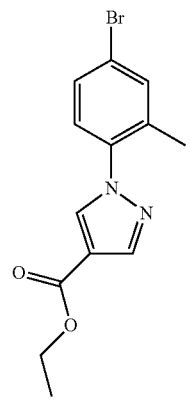

4-(4-Bromophenyl)pyrazole (150 mg, 0.672 mmol) and cesium carbonate (876 mg, 2.69 mmol) were combined in a 20 mL vial and dissolved in DMF (1.3 mL). 2-bromoethyl methyl ether (0.253 mL, 2.69 mmol) was then added. The reaction was stirred overnight at 60° C. The reaction was then diluted with ethyl acetate and washed with water (×2). The organic solution was dried with MgSO$_4$ and concentrated in vacuo to afford 4-(4-bromophenyl)-1-(2-methoxyethyl)-1H-pyrazole which was carried onto the next step without further purification. LRMS (ESI) calc'd for C$_{12}$H$_{14}$BrN$_2$O [M+H]$^+$: 281, found 281.

Intermediate 135

Ethyl 1-(4-bromo-2-methylphenyl)-1H-pyrazole-4-carboxylate

I-135

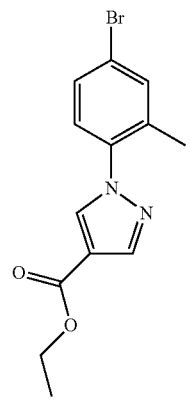

Ethyl 4-pyrazolecarboxylate (202 mg, 1.44 mmol), 5-bromo-2-iodotoluene (0.20 mL, 1.4 mmol), (1S,2S,N$^1$E,N$^2$E)-N$^1$,N$^2$-bis(pyridin-2-ylmethylene)cyclohexane-1,2-diamine (84 mg, 0.29 mmol), Copper(I) oxide (10 mg, 0.072 mmol), and cesium carbonate (939 mg, 2.88 mmol) were combined in a 5 mL microwave vial and dissolved in acetonitrile (3.0 mL). The reaction was stirred at 82° C. overnight. The reaction was then filtered through Celite rinsing with ethyl acetate. The solution was concentrated in vacuo and purified by silica chromatography, eluting with 10-25% ethyl acetate in hexanes to give ethyl 1-(4-bromo-2-methylphenyl)-1H-pyrazole-4-carboxylate. LRMS (ESI) calc'd for C$_{13}$H$_{14}$BrN$_2$O$_2$ [M+H]$^+$: 309, found 309.

Intermediate 136

Isopropyl 6-bromoquinoline-2-carboxylate

I-136

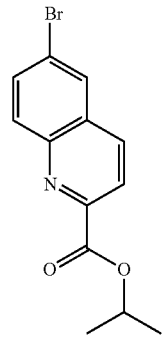

6-Bromoquinoline-2-carboxylic acid (40 mg, 0.16 mmol) and HATU (121 mg, 0.317 mmol) were dissolved in DMF (0.5 mL) in a 4 mL vial and allowed to stir at room temperature for 5 minutes. 2-Propanol (24 µL, 0.31 mmol) and N,N-diisopropylethylamine (83 µL, 0.48 mmol) in DMF (0.5 mL) was then added to the reaction. The reaction mixture was stirred at room temperature for 1 hour. The reaction was then diluted with ethyl acetate and washed with copious amounts of water. The organic layer was then dried using MgSO$_4$, filtered, and concentrated in vacuo to give isopropyl 6-bromoquinoline-2-carboxylate which was carried onto the next step without further purification. LRMS (ESI) calc'd for $C_{13}H_{13}BrNO_2$ [M+H]$^+$: 294, found 294.

Intermediate 137

Bromo-4-(1-bromo-2-methylpropyl)benzene

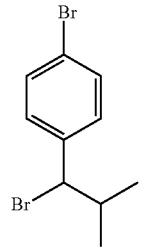

I-137

Step 1: 1-(4-Bromophenyl)-2-methylpropan-1-ol

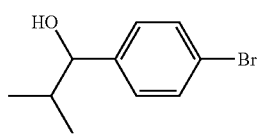

I-137a

To a solution of 4-bromobenzaldehyde (9.2 g, 0.048 mol) in THF (150 mL) cooled at 0–4° C. under nitrogen atmosphere was added isopropyl magnesium chloride (1.0 M in THF, 58.4 mL). The reaction was maintained at the same temperature for 30 min then warmed up to ambient temperature and stirred for 4 h then saturated aqueous sodium bicarbonate solution (150 mL) was added. The quenched reaction was extracted with EtOAc (200 mL) and the organic layer washed with brine, dried over anhydrous sodium sulfate and filtered. The filtrate was concentrated in vacuo and the residue purified on silica, eluting with ethyl acetate/petroleum ether (3:1) to afford the title compound. $^1$H NMR (300 MHz, DMSO-d$_6$) δ 7.49 (d, J=6.6 Hz, 2H), 7.30 (d, J=6.6 Hz, 2H), 5.18 (d, J=6.6 Hz, 1H), 4.26-4.21 (m, 1H), 1.82-1.71 (m, 1H), 0.85 (d, J=6.6 Hz, 3H), 0.75 (d, J=6.6 Hz, 3H).

Step 2: 1-Bromo-4-(1-bromo-2-methylpropyl)benzene

A solution of 1-(4-bromophenyl)-2-methylpropan-1-ol (2.50 g, 11.0 mmol) in hydrobromic acid (48%, 40 mL) was stirred at ambient temperature for 1 hour and then extracted with hexanes (3×40 mL). The combined organic layers were washed with water followed by saturated aqueous sodium hydrocarbonate, dried over anhydrous sodium sulfate and filtered. The filtrate was concentrated in vacuo to afford the title compound which was carried onto the next step without further purification. $^1$H NMR (300 MHz, CDCl$_3$) δ 7.49 (d, J=6.6 Hz, 2H), 7.27 (d, J=6.6 Hz, 2H), 4.68 (d, J=8.4 Hz, 1H), 2.34-2.23 (m, 1H), 1.17 (d, J=6.9 Hz, 3H), 0.91 (d, J=6.9 Hz, 3H).

Table 29 discloses an Intermediate that was prepared using similar procedures as described for Intermediate 137.

TABLE 29

| Intermediate | Structure | Compound Name | $^1$H NMR |
|---|---|---|---|
| I-138 | ![structure] | 4-bromo-1-(1-bromo-2-methylpropyl)-2-methylbenzene | (300 MHz, CDCl$_3$) δ7.38-7.25 (m, 3H), 4.89 (d, J = 9.3 Hz, 1H), 2.44-2.33 (m, 1H), 2.31 (s, 3H), 1.25 (d, J = 6.3 Hz, 3H), 0.87(d, J = 6.3 Hz, 3H) |

Intermediates 139 and 140

2-(1-(4-Bromophenyl)ethyl)-2H-1,2,3-triazole and 1-(1-(4-Bromophenyl)ethyl)-4,5-dihydro-1H-1,2,3-triazole

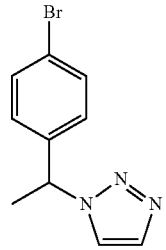

I-139

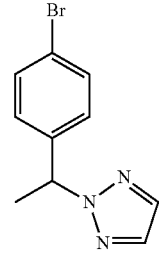

I-140

Step 1: 1-Bromo-4-(1-bromoethyl)benzene

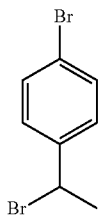

I-139a

To a 100 mL 3-necked round-bottom flask were placed 1-bromo-4-ethylbenzene (5.10 g, 27.6 mmol), N-bromosuccinimide (5.77 g, 32.4 mmol), and azo-bis-isobutyronitrile (0.89 g, 5.4 mmol) in chloroform (100 mL). The mixture was heated at reflux for 3 hours and cooled to ambient temperature. Then water (100 mL) was added and the organic layer was washed with brine, dried over anhydrous sodium sulfate and filtered. The filtrate was concentrated in vacuo and the residue purified on silica, eluting with ethyl acetate/petroleum ether (1:20) to afford the title compound. $^1$H NMR (300 MHz, CDCl$_3$) δ7.44 (d, J=8.4 Hz, 2H), 7.31 (d, J=8.4 Hz, 2H), 5.15 (q, J=6.9 Hz, 1H), 2.01 (d, J=6.9 Hz, 3H).

Step 2: 2-(1-(4-Bromophenyl)ethyl)-2H-1,2,3-triazole and 1-(1-(4-Bromophenyl)ethyl)-4,5-dihydro-1H-1,2,3-triazole In a 100 mL 3-necked round-bottom flask, 1-bromo-4-(1-bromoethyl)benzene (4.60 g, 17.5 mmol) was combined with N,N-dimethylformamide (60 mL) then 1H-1,2,3-triazole (1.45 g, 21.0 mmol) and potassium carbonate (6.04 g, 43.7 mmol) were added. The solution was heated at 80° C. for 5 hours then poured into water (100 mL). The resulting mixture was extracted with ethyl acetate (3×60 mL) and the organic layers combined, dried over anhydrous sodium sulfate and filtered. The filtrate was concentrated in vacuo and the resulting solid was triturated with ethyl acetate/petroleum ether (1:3, 10 mL) and filtered to give the two title compounds.

2-(1-(4-Bromophenyl)ethyl)-2H-1,2,3-triazole (I-139): LRMS (ESI) calc'd for C$_{10}$H$_{11}$BrN$_3$ [M+H]$^+$: 252, 254 (1:1). found 252, 254 (1:1); $^1$H NMR (300 MHz, CDCl$_3$) δ 7.62 (s, 2H), 7.44 (d, J=8.4 Hz, 2H), 7.16 (d, J=8.4 Hz, 2H), 5.82 (q, J=7.2 Hz, 1H), 1.96 (d, J=7.2 Hz, 3H).

1-(1-(4-Bromophenyl)ethyl)-4,5-dihydro-1H-1,2,3-triazole (I-140): LRMS (ESI) calc'd for C$_{10}$H$_{11}$BrN$_3$ [M+H]$^+$: 252, 254 (1:1). found 252, 254 (1:1); $^1$H NMR (300 MHz, CDCl$_3$) δ 7.72 (s, 1H), 7.49 (d, J=8.4 Hz, 2H), 7.44 (s, 1H), 7.14 (d, J=8.4 Hz, 2H), 5.81 (q, J=7.2 Hz, 1H), 1.98 (d, J=7.2 Hz, 3H).

Table 30 discloses Intermediates prepared in an analogous procedure to that for Intermediate 139, Step 2 using 1-bromo-4-(1-bromo-2-methylpropyl)benzene (Intermediate 137) or 4-bromo-1-(1-bromo-2-methylpropyl)-2-methylbenzene (Intermediate 138).

TABLE 30

| Intermediate | Structure | Compound Name | LRMS [M + H]$^+$/$^1$H NMR |
|---|---|---|---|
| I-141 | 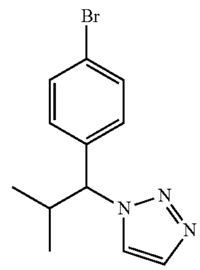 [SMILES: CC(C)C(c1ccc(Br)cc1)n1ccnn1] | 1-(1-(4-bromophenyl)-2-methylpropyl)-1H-1,2,3-triazole | Calc'd 280, 282 (1:1), found 280, 282 (1:1) |
| I-142 | 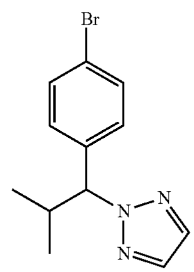 [SMILES: CC(C)C(c1ccc(Br)cc1)n1nccn1] | 2-(1-(4-bromophenyl)-2-methylpropyl)-2H-1,2,3-triazole | Calc'd 280, 282 (1:1), found 280, 282 (1:1) |
| I-143 | 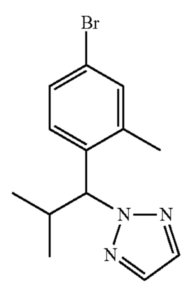 [SMILES: Cc1cc(Br)ccc1C(C(C)C)n1nccn1] | 2-(1-(4-bromo-2-methylphenyl)-2-methylpropyl)-2H-1,2,3-triazole | (300 MHz, CD$_3$OD) δ 7.62-7.58 (m, 3H), 7.33-7.30 (m, 2H), 5.54 (d, J = 11.1 Hz, 1H), 2.92-2.80 (m, 1H), 2.44 (s, 3H), 0.85 (d, J = 6.6 Hz, 3H), 0.79 (d, J = 6.6 Hz, 3H). |
| I-144 | 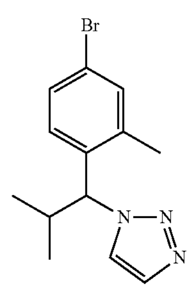 [SMILES: Cc1cc(Br)ccc1C(C(C)C)n1ccnn1] | 1-(1-(4-bromo-2-methylphenyl)-2-methylpropyl)-1H-1,2,3-triazole | (300 MHz, CD$_3$OD) δ 8.05 (d, J = 1.0 Hz, 1H), 7.67 (d, J = 1.0 Hz, 1H), 7.61 (d, J = 9.3 Hz, 1H), 7.39 (d, J = 7.2 Hz, 1H), 5.57 (d, J = 11.1 Hz, 1H), 2.90-2.78 (m, 1H), 2.41 (s, 3H), 0.90 (d, J = 6.6 Hz, 3H), 0.82 (d, J = 6.6 Hz, 3H). |

Intermediate 145

1-(1-(4-Bromophenyl)-2-methylpropyl)-4-tert-butyl-1H-1,2,3-triazole

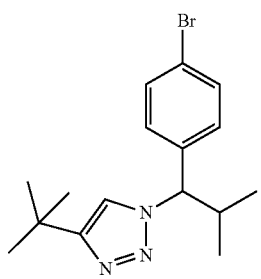

I-145

Step 1: 1-(1-Azido-2-methylpropyl)-4-bromobenzene

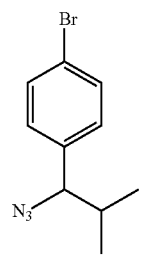

I-145a

To a solution of 1-bromo-4-(1-bromo-2-methylpropyl)benzene (I-137; 1.0 g, 3.4 mmol) in DMF (10.0 mL) was added sodium azide (0.45 g, 6.9 mmol). The mixture was heated at 90° C. for 4 hours and then diluted with water (50 mL) followed by extraction with EtOAc (2×50 mL). The combined organic layers were washed with brine (3×50 mL), dried over $Na_2SO_4$, and filtered. The filtrate was concentrated in vacuo and the residue purified on silica, eluting with petroleum ether to afford the title compound. LRMS (ESI) calc'd for $C_{10}H_{13}BrN_3$ $[M+H]^+$: 254, 256 (1:1). found 254, 256 (1:1); $^1$H NMR (400 MHz, $CDCl_3$) δ 7.50 (d, J=8.4 Hz, 2H), 7.16 (d, J=8.4 Hz, 2H), 4.17-4.15 (m, 1H), 2.05-1.90 (m, 1H), 1.04 (s, 3H), 0.94 (s, 3H).

Step 2: 1-(1-Azido-2-methylpropyl)-4-bromobenzene

A mixture of 1-(1-azido-2-methylpropyl)-4-bromobenzene (0.25 g, 0.98 mmol), $CuSO_4$ (31 mg, 0.20 mmol), 3,3-dimethylbut-1-yne (0.16 g, 2.0 mmol) and sodium ascorbate (0.40 g, 2.0 mmol) in water (3.0 mL) and n-butanol (3.00 mL) was stirred at ambient temperature for 24 hours. The mixture was then quenched with saturated ammonium hydroxide (10 mL) and extracted with EtOAc (2×20 mL). The combined organic layers were washed with brine (2×20 mL), dried over $Na_2SO_4$ and filtered. The filtrate was concentrated in vacuo and the residue purified on silica, eluting with DCM/petroleum ether (1:1) to afford the title compound. LRMS (ESI) calc'd for $C_{16}H_{23}BrN_3[M+H]^+$: 336, 338 (1:1). found 336, 338 (1:1); $^1$H NMR (400 MHz, $CDCl_3$) δ 7.52 (d, J=8.4 Hz, 2H), 7.36 (d, J=8.4 Hz, 2H), 7.30 (s, 1H), 5.01-4.98 (m, 1H), 2.82-2.76 (m, 1H), 1.35 (s, 9H), 0.91 (s, 6H).

Table 31 discloses an Intermediate prepared in an analogous procedure to that for Intermediate 145 using tert-butyl propiolate.

TABLE 31

| Intermediate | Structure | Compound Name | LRMS [M + H]$^+$ |
|---|---|---|---|
| I-146 | 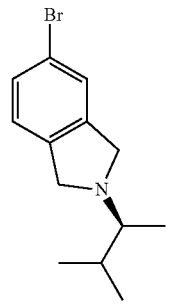 | tert-Butyl 1-(1-(4-bromophenyl)-2-methylpropyl)-1H-1,2,3-triazole-4-carboxylate | Calc'd 380, 382 (1:1), found 380, 382 (1:1) |

Intermediate 147

5-Bromo-2-[(2S)-3-methylbutan-2-yl]-2,3-dihydro-1H-isoindole

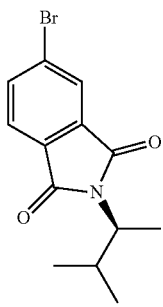

I-147

Step 1: (S)-5-Bromo-2-(3-methylbutan-2-yl)isoindoline-1,3-dione

I-147a

Into a 100 mL round bottom flask purged and maintained with an inert atmosphere of nitrogen, were placed 5-bromo-1,3-dihydro-2-benzofuran-1,3-dione (5.40 g, 23.8 mmol), (S)-3-methylbutan-2-amine (2.50 g, 28.7 mmol), diisopropyl amine (9.20 g, 71.2 mmol) and toluene (50 mL). The resulting solution was stirred for 5 hours at 110° C. The mixture was concentrated in vacuo and the residue purified on silica, eluting with ethyl acetate/petroleum ether (1:20) to afford the title compound. LRMS (ESI) calc'd for $C_{13}H_{14}BrNO_2$ [M]$^+$: 295, 297 (1:1). found 295, 297 (1:1); $^1$H NMR (300 MHz, CDCl$_3$) δ7.96 (s, 1H), 7.87-7.83 (m, 1H), 7.70-7.68 (m, 1H), 4.10-3.89 (m, 1H), 2.43-2.31 (m, 1H), 1.46 (d, J=7.2 Hz, 3H), 1.02 (d, J=6.9 Hz, 3H), 0.83 (d, J=6.9 Hz, 3H).

Step 2: 5-Bromo-2-[(2S)-3-methylbutan-2-yl]-2,3-dihydro-1H-isoindole

Into a 500 mL round bottom flask, were placed a solution of 5-bromo-2-[(2S)-3-methylbutan-2-yl]-2,3-dihydro-1H-isoindole-1,3-dione (2.00 g, 6.75 mmol) in tetrahydrofuran (20 mL) and borane dimethylsulfide (2.0 M in THF, 6.8 mL, 68 mmol). The resulting solution was stirred for 48 h at 80° C. The reaction was then quenched by hydrochloric acid (3.0 M, 100 mL) and the resulting solution extracted with ethyl acetate (3×100 mL). The combined organic layers were washed with water (2×50 mL), dried over anhydrous sodium sulfate and filtered. The filtrate was concentrated in vacuo and the residue purified on silica, eluting with ethyl acetate/petroleum ether (1:10) to afford 5-bromo-2-[(2S)-3-methylbutan-2-yl]-2,3-dihydro-1H-isoindole. LRMS (ESI) calc'd for $C_{13}H_{19}BrN$ [M+H]$^+$: 268, 270 (1:1). found 268, 270 (1:1).

Table 32 discloses an Intermediate that was prepared using similar procedures as described for Intermediate 147, using (R)-3-methylbutan-2-amine to replace (S)-3-methylbutan-2-amine.

TABLE 32

| Intermediate | Structure | Compound Name | LRMS [M + H]$^+$ |
|---|---|---|---|
| I-148 | Br-(structure) | 5-Bromo-2-[(2R)-3-methylbutan-2-yl]-2,3-dihydro-1H-isoindole | Calc'd 268, 270 (1:1), found 268, 270 (1:1) |

Intermediate 149 tert-Butyl 3-(5-bromo-1,1-dioxidobenzo[d]isothiazol-2(3H)-yl)propanoate

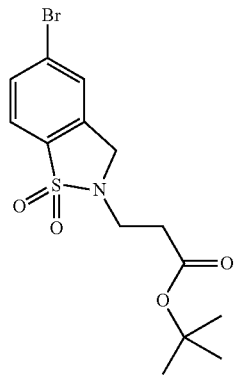

I-149

To a 50 mL 3-necked round bottom flask were placed potassium carbonate (0.33 g, 2.4 mmol), 5-bromo-2,3-dihydrobenzo[d]isothiazole 1,1-dioxide (0.20 g, 0.81 mmol), tert-butyl acrylate (0.10 g, 0.81 mmol) and N,N-dimethylformamide (10 mL). The mixture was stirred at 60° C. for 2 hours and cooled. Water (50 mL) was added and the mixture extracted with ethyl acetate (2×50 mL). The combined organic layers were washed with brine (50 mL), dried over anhydrous sodium sulfate and filtered. The filtrate was concentrated in vacuo and the residue purified on silica, eluting with ethyl acetate/petroleum ether (1:4) to afford tert-butyl 3-(5-bromo-1,1-dioxidobenzo[d]isothiazol-2(3H)-yl)propanoate. LRMS (ESI) calc'd for $C_{14}H_{19}BrNO_4S$ [M+H]$^+$: 376, 378 (1:1). found 376, 378 (1:1).

Table 33 discloses an Intermediate that was prepared using a similar procedure as described for Intermediate 149, starting with the appropriate benzothiazole or bromoisoindolinone. In select cases, the general procedure was modified to alternatively utilize between 3.0-4.0 equivalents $K_2CO_3$ or TEA base and DMF or t-BuOH as solvent.

TABLE 33

| Intermediate | Structure | Compound Name | LRMS [M + H]$^+$ |
|---|---|---|---|
| I-150 | Br-(structure) | tert-butyl 3-(5-bromoisoindolin-2-yl)propanoate | Calc'd 326, 328 (1:1), found 326, 328 (1:1) |

Intermediate 151

(5-Bromoisoindolin-2-yl)(5-(piperidin-1-yl)pyrazin-2-yl)methanone

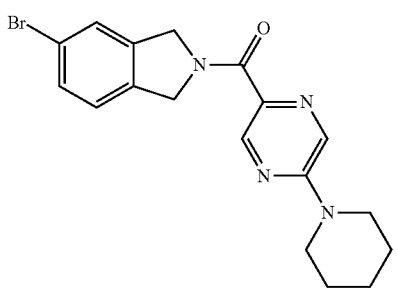

I-151

To a 50 mL 3-necked round bottom flask were placed 5-(piperidin-1-yl)pyrazine-2-carboxylic acid (1.57 g, 7.57 mmol), O-(7-azabenzotriazol-1-yl)-N,N,N',N'-tetramethyluronium hexafluorophosphate (2.88 g, 7.57 mmol), N,N-diisopropylethylamine (1.95 g, 15.2 mmol), 5-bromoisoindoline HCl salt (1.18 g, 5.05 mmol) and N,N-dimethylformamide (20 mL). The mixture was stirred at ambient temperature for 2 hours then water (20 mL) was added. The mixture was extracted with EtOAc (3×30 mL) and the combined organic layers were dried over anhydrous $Na_2SO_4$ and filtered. The filtrate was concentrated in vacuo to afford the title compound. LRMS (ESI) calc'd for $C_{18}H_{20}BrN_4O$ [M+H]$^+$: 387, 389 (1:1). found 387, 389 (1:1). $^1$H NMR (400 MHz, CDCl$_3$) δ 8.99 (s, 1H), 8.28 (s, 1H), 7.47-7.41 (m, 2H), 7.29-7.14 (m, 1H), 5.30 (d, J=16.0 Hz, 2H), 5.02 (d, J=16.0 Hz, 2H), 3.76-3.74 (m, 4H), 1.74-1.72 (m, 6H).

Intermediate 152

(5-Bromoisoindolin-2-yl)(piperidin-1-yl)methanone

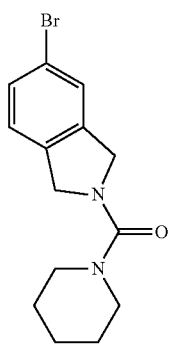

I-152

Into a 500 mL round bottom flask, were placed 5-bromoisoindoline hydrochloride (5.0 g, 21 mmol) and piperidine (2.72 g, 32.0 mmol) in DCM (300 mL). Triphosgene (3.16 g, 10.7 mmol) was added at 0° C. The mixture was stirred for 20 min at 0° C. then piperidine (2.72 g, 32.0 mmol) was added in the solution at 0° C. and stirred for 40 min. The mixture was quenched with water (100 mL) and extracted with ethyl acetate (3×1500 mL). The organic layers were combined, washed with brine (2×100 mL), dried over anhydrous sodium sulfate, filtered, and concentrated in vacuo. The residue was purified on silica, eluting with Petroleum ether/EtOAc (19:1) to afford (5-bromoisoindolin-2-yl)(piperidin-1-yl)methanone. LRMS (ESI) calc'd for $C_{14}H_{18}BrN_2O$ [M+H]$^+$: 309, 311 (1:1). found 309, 311 (1:1).

Intermediate 153

5-Bromo-1-(difluoromethyl)isoindoline HCl salt

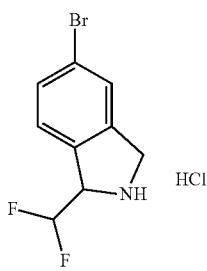

I-153

Step 1: (5-Bromo-2-iodophenyl)methanol

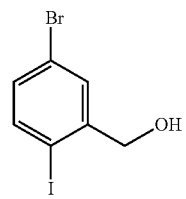

I-153a

A 1 L round-bottom flask was charged with a solution of 5-bromo-2-iodobenzoic acid (15.0 g, 45.9 mmol) in tetrahydrofuran (150 mL) then borane-tetrahydrofuran (459 mL, 0.460 mol, 1.0 M) was added dropwise. The reaction was stirred at ambient temperature for 16 hours then quenched by addition of water (200 mL). The resulting mixture was extracted with dichloromethane (3×100 mL) and the combined organic layers were dried over anhydrous sodium sulfate and filtered. The filtrate was concentrated in vacuo to afford the title compound. $^1$H NMR (400 MHz, CD$_3$OD) δ7.72 (d, J=8.4 Hz, 1H), 7.66 (d, J=2.4 Hz, 1H), 7.20-7.17 (m, 1H), 4.54 (s, 2H).

Step 2: (5-Bromo-2-iodobenzyl)oxy)(tert-butyl)dimethylsilane

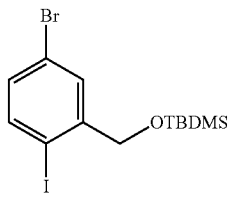

I-153b

In a 1 L 3-necked round-bottom flask (5-bromo-2-iodophenyl)methanol (14.0 g, 44.7 mmol) and 1H-imidazole (6.09 g, 89.0 mmol) were combined with dichloromethane (150 mL). Then tert-butylchlorodimethylsilane (10.1 g, 67.1 mmol) was added dropwise at 0-4° C. The resulting mixture was stirred at ambient temperature for 16 hours then water (50 mL) was added. The resulting mixture was extracted with ethyl acetate (3×50 mL) and the combined organic layers were washed with brine (50 mL), dried over anhydrous sodium sulfate and filtered. The filtrate was concentrated in vacuo and the residue purified on silica, eluting with 5-10% ethyl acetate in petroleum ether to afford the title compound. $^1$H NMR (400 MHz, CDCl$_3$) δ7.67-7.62 (m, 2H), 7.15-7.12 (m, 1H), 4.61 (s, 2H), 1.01 (s, 9H), 0.20 (s, 6H).

Step 3: 1-(4-Bromo-2-(((tert-butyldimethylsilyl)oxy) methyl)phenyl)-2,2-difluoroethanone

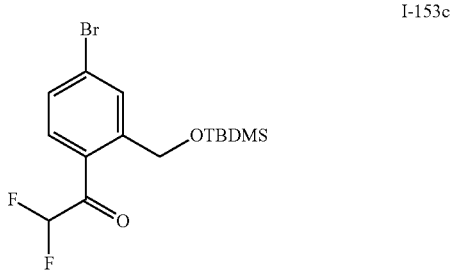 [SMILES: CC(C)(C)[Si](C)(C)OCc1cc(Br)ccc1C(=O)C(F)F]

I-153c

A 250 mL 3-necked round-bottom flask was charged under nitrogen with a solution of ((5-bromo-2-iodobenzyl) oxy)(tert-butyl)dimethylsilane (12.0 g, 28.1 mmol) in tetrahydrofuran (120 mL). Butyl lithium (11.2 mL, 28.1 mmol, 2.5 M in tetrahydrofuran) was added dropwise over 1 hour at −78° C. then ethyl 2,2-difluoroacetate (5.23 g, 42.1 mmol) was added. The reaction was stirred at −78° C. for 2 additional hours then quenched with water (100 mL). The resulting mixture was extracted with ethyl acetate (3×50 mL) and the combined organic layers dried over anhydrous sodium sulfate and filtered. The filtrate was concentrated in vacuo to afford the title compound. $^1$H NMR (400 MHz, CDCl$_3$) δ8.08 (s, 1H), 7.82 (d, J=8.0 Hz, 1H), 7.59-7.56 (m, 1H), 6.40-6.13 (m, 1H), 5.03 (s, 2H), 0.99 (s, 9H), 0.17 (s, 6H).

Step 4: N-(1-(4-Bromo-2-(((tert-butyldimethylsilyl) oxy)methyl)phenyl)-2,2-difluoroethyl)-2-methylpropane-2-sulfinamide

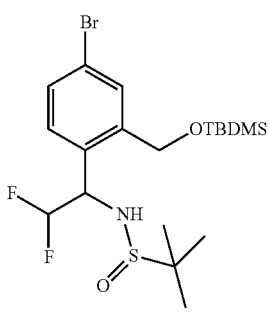

I-153d

A 500 mL round-bottom flask was charged at ambient temperature with THF (120 mL), 1-(4-bromo-2-(((tert-butyldimethylsilyl)oxy)methyl)phenyl)-2,2-difluoroethanone (10.0 g, 26.4 mmol), 2-methylpropane-2-sulfinamide (4.79 g, 39.5 mmol) and tetraethoxytitanium (12.0 g, 52.7 mmol). The reaction was heated at 80° C. for 16 hours then sodium borohydride (3.01 g, 79.2 mmol) was added. The mixture was stirred at ambient temperature for 2 additional hours then saturated aqueous ammonium chloride (100 mL) was added. The quenched reaction was extracted with ethyl acetate (3×50 mL) and the combined organic layers dried over anhydrous sodium sulfate and filtered. The filtrate was concentrated in vacuo to afford the title compound which was carried onto the next step without further purification. LRMS (ESI) calc'd for C$_{19}$H$_{33}$BrF$_2$NO$_2$SSi [M+H]$^+$: 484, 486 (1:1). found 484, 486 (1:1).

Step 5: N-(1-(4-Bromo-2-(hydroxymethyl)phenyl)- 2,2-difluoroethyl)-2-methylpropane-2-sulfinamide

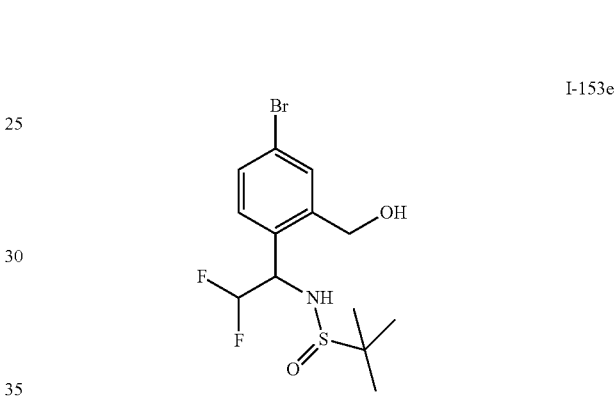

I-153e

A 250 mL round-bottom flask was charged with N-(1-(4-bromo-2-(((tert-butyldimethylsilyl)oxy)methyl)phenyl)-2, 2-difluoroethyl)-2-methylpropane-2-sulfinamide (12.00 g, 24.77 mmol), tetrabutylammonium fluoride THF solution (49.5 mL, 49.5 mmol) and THF (150 mL). The reaction was maintained at ambient temperature for 2 hours then was washed with water (3×50 mL). The organic layer was dried over anhydrous sodium sulfate and filtered. The filtrate was concentrated in vacuo and the residue purified on silica, eluting with dichloromethane/methanol (200:1) to afford the title compound. LRMS (ESI) calc'd for C$_{13}$H$_{19}$BrF$_2$NO$_2$S [M+H]$^+$: 370, 372 (1:1). found 370, 372 (1:1).

Step 6: 5-Bromo-1-(difluoromethyl)isoindoline HCl salt

N-(1-(4-bromo-2-(hydroxymethyl)phenyl)-2,2-difluoroethyl)-2-methylpropane-2-sulfinamide (0.50 g, 1.4 mmol) and thionyl chloride (0.41 mL, 5.6 mmol) were combined at ambient temperature with dichloromethane (5 mL). The reaction was stirred at the same temperature for 5 hours then concentrated in vacuo. The residue was dissolved in aqueous sodium hydroxide (5.0 M, 5.0 mL, 25 mmol) and isopropanol (5 mL). The resulting solution was then stirred at ambient temperature for 1 hour. The separated organic layer was treated with concentrated hydrochloric acid (12.0 M, 0.2 mL) and precipitation occurred. The solid was collected by filtration and dried in vacuo to give the hydrochloric acid salt of the title compound. LRMS (ESI) calc'd for C$_9$H$_9$BrF$_2$N [M+H]$^+$: 248, 250 (1:1). found 248, 250 (1:1).

Intermediate 154 tert-Butyl 5-bromo-1-methylisoindoline-2-carboxylate

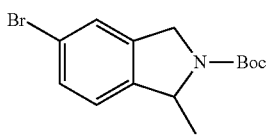

Step 1: 3-Hydroxy-3-methylisoindolin-1-one

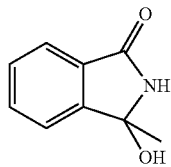

Into a 500 mL three-necked round bottom flask purged and maintained with an inert atmosphere of nitrogen, was placed isoindoline-1,3-dione (10.00 g, 68.03 mmol) in dichloromethane (300 mL). To this solution was added methylmagnesium iodide (100 mL, 2.0 M in ether, 0.200 mol) dropwise in an ice/water bath. After stirring for 5 h, the reaction was quenched by saturated aqueous ammonium chloride (100 mL). The resulting mixture was extracted with dichloromethane (3×100 mL). The organic layers were combined, washed with brine (150 mL), dried over sodium sulfate and filtered. The filtrate was concentrated in vacuo to afford 3-hydroxy-3-methylisoindolin-1-one. $^1$H NMR (300 MHz, DMSO-$d_6$) δ 8.80 (br, 1H), 7.62-7.56 (m, 3H), 7.49-7.44 (m, 1H), 6.09 (s, 1H), 1.59 (s, 3H).

Step 2: 3-Methylisoindolin-1-one

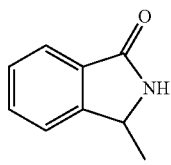

Into a 500 mL three necked round bottom flask purged and maintained with an inert atmosphere of nitrogen, was placed a solution of 3-hydroxy-3-methylisoindolin-1-one (5.70 g, 35.0 mmol) in dichloromethane (100 mL). Triethylsilane (40.6 g, 0.350 mol) and trifluoroborane ether complex (28 mL) were added dropwise respectively at −15° C. The resulting solution was stirred for 18 h at ambient temperature. The reaction was quenched by saturated aqueous sodium bicarbonate (40 mL) and extracted with dichloromethane (3×60 mL). The organic layers were combined, washed with brine (150 mL), dried over sodium sulfate and filtered. The filtrate was concentrated in vacuo and the residue purified on silica, eluting with 20-50% ethyl acetate in petroleum ether to afford 3-methylisoindolin-1-one. $^1$H NMR (300 MHz, DMSO-$d_6$) δ 8.61 (br s, 1H), 7.83-7.58 (m, 3H), 7.50-7.43 (m, 1H), 4.65-4.58 (m, 1H), 1.36 (d, J=6.6 Hz, 3H).

Step 3: 6-Bromo-3-methylisoindolin-1-one

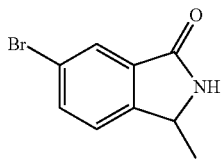

Into a 100 mL three necked round bottom flask purged and maintained with an inert atmosphere of nitrogen, were placed aluminum trichloride (4.98 g, 37.7 mmol) and a solution of 3-methylisoindolin-1-one (2.20 g, 15.0 mmol) in 1,2-dichloroethane (30 mL). Bromine (1.00 mL, 19.74 mmol) was added dropwise and the mixture was refluxed for 15 h. After cooling down to ambient temperature, the reaction was quenched by saturated aqueous sodium thiosulfate (10 mL). The mixture was extracted with ethyl acetate (100 mL) and the organic layer was dried over anhydrous sodium sulfate and filtered. The filtrate was concentrated in vacuo and the residue purified on silica, eluting with ethyl acetate/petroleum (1:1). The residue was triturated with ether to give 6-bromo-3-methylisoindolin-1-one. $^1$H NMR (300 MHz, DMSO-$d_6$) δ 8.00 (s, 1H), 7.72 (d, J=8.0 Hz, 1H), 7.52 (s, 1H), 7.34 (d, J=8.0 Hz, 1H), 4.73-4.68 (m, 1H), 1.53 (d, J=6.8 Hz, 3H).

Step 4: 5-Bromo-1-methylisoindoline

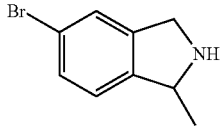

Into a 100-mL round-bottom flask were placed 6-bromo-3-methylisoindolin-1-one (0.80 g, 3.5 mmol), sodium borohydride (1.21 g, 31.8 mmol) and THF (40 mL). Trifluoroborane ether complex (6.02 g, 42.4 mmol) was added dropwise in an ice/water bath. The mixture was stirred for 16 h at 70° C. After cooling down to ambient temperature, the reaction was quenched with water (80 mL). Aqueous sodium hydroxide (5.0 M) was added to adjust the pH=10. The mixture was extracted with dichloromethane (3×60 mL). The organic layers were combined, washed with brine (30 mL), dried over anhydrous sodium sulfate and filtered. The filtrate was concentrated in vacuo and the residue was dissolved in hydrochloric acid (6.0 M, 60 mL) followed by addition of toluene (30 mL). The mixture was refluxed for 10 min and cooled to ambient temperature. The aqueous layer was separated and the pH adjusted to 10 with aqueous sodium hydroxide (5.0 M) then extracted with dichloromethane (3×40 mL). The organic layers were combined, dried over sodium sulfate and filtered. The filtrate was concentrated in vacuo to afford 5-bromo-1-methylisoindoline. $^1$H NMR (400 MHz, CDCl$_3$) δ 7.45-7.37 (m, 2H), 7.07 (d, J=8.0 Hz, 1H), 4.46-4.41 (m, 1H), 4.28-4.16 (m, 2H), 2.31 (br s, 1H), 1.45 (d, J=6.4 Hz, 3H).

Step 5: tert-Butyl 5-bromo-1-methylisoindoline-2-carboxylate

Into a 100-mL round-bottom flask were placed 5-bromo-1-methylisoindoline (0.45 g, 2.1 mmol), dichloromethane (30 mL), triethylamine (0.43 g, 4.3 mmol) and di-tert-butyl dicarbonate (0.93 g, 4.2 mmol). The mixture was stirred for 18 h at ambient temperature. The solvent was removed in vacuo and the residue purified on silica, eluting with ethyl acetate/petroleum (1:10) to afford tert-butyl 5-bromo-1-methylisoindoline-2-carboxylate. $^1$H NMR (400 MHz, CDCl$_3$) δ 7.43-7.38 (m, 2H), 7.11-7.08 (m, 1H), 5.13-4.92 (m, 1H), 4.82-4.58 (m, 2H), 1.55-1.48 (m, 12H).

Intermediate 155 tert-Butyl 3-(4-bromophenyl)-8-azabicyclo[3.2.1]oct-3-ene-8-carboxylate

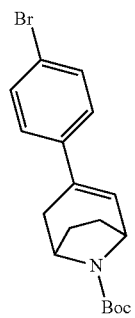

I-155

Step 1: tert-Butyl 3-(((trifluoromethyl)sulfonyl)oxy)-8-azabicyclo[3.2.1]oct-3-ene-8-carboxylate

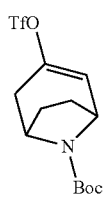

I-155a

To a 250 mL 3-necked round-bottom flask was placed a solution of (1R,5S)-tert-butyl 3-oxo-8-azabicyclo[3.2.1]octane-8-carboxylate (5.00 g, 22.2 mmol) in tetrahydrofuran (100 mL). Lithium bis(trimethylsilyl)amide (1.0 M in tetrahydrofuran, 26.6 mL, 26.6 mmol) was added dropwise at −78° C. The mixture was stirred at −78° C. for 1 hour. Then a solution of 1,1,1-trifluoro-N-phenyl-N-((trifluoromethyl)sulfonyl)methanesulfonamide (9.51 g, 26.6 mmol) in tetrahydrofuran (30 mL) was added at −78° C. The mixture was stirred for an additional 16 h at ambient temperature. The solvent was removed in vacuo and the residue dissolved in ethyl acetate (100 mL), washed with water (2×50 mL) and brine (50 mL), dried over anhydrous sodium sulfate and filtered. The filtrate was concentrated in vacuo and the residue purified on silica, eluting with ethyl acetate/petroleum ether (5:100) to afford the title compound. LRMS (ESI) calc'd for C$_{13}$H$_{19}$F$_3$NO$_5$S [M+H]$^+$: 358, found 358; 1H NMR (400 MHz, CDCl$_3$) δ6.08 (d, J=5.4 Hz, 1H), 4.59-4.33 (m, 2H), 3.12-2.94 (m, 1H), 2.31-2.13 (m, 1H), 2.09-1.93 (m, 3H), 1.79-1.63 (m, 1H), 1.46 (s, 9H).

Step 2: tert-Butyl 3-(4-bromophenyl)-8-azabicyclo[3.2.1]oct-3-ene-8-carboxylate A 100 mL 3-necked round-bottom flask was charged with tert-butyl 3-(((trifluoromethyl)sulfonyl)oxy)-8-azabicyclo[3.2.1]oct-3-ene-8-carboxylate (0.50 g, 1.1 mmol), (4-bromophenyl)boronic acid (0.25 g, 1.3 mmol), dichloro(1,1'-bis(diphenylphosphino)ferrocene)palladium(II) dichloromethane adduct (77 mg, 0.11 mmol), potassium phosphate (0.27 g, 1.3 mmol) and DMF (8 mL). The mixture was heated at 80° C. for 4 hours then water (30 mL) was added and the mixture extracted with ethyl acetate (3×30 mL). The organic layers were combined, washed with water (30 mL) and brine (30 mL), dried over anhydrous sodium sulfate and filtered. The filtrate was concentrated in vacuo and the residue purified on silica, eluting with ethyl acetate/petroleum ether (1:20) to afford the title compound. LRMS (ESI) calc'd for C$_{18}$H$_{23}$BrNO$_2$ [M+H]$^+$: 365, 367 (1:1). found 365, 367 (1:1); $^1$H NMR (400 MHz, CDCl$_3$) δ 7.42 (d, J=8.4 Hz, 2H), 7.21 (d, J=8.4 Hz, 2H), 6.43 (d, J=5.4 Hz, 1H), 4.52-4.48 (m, 2H), 3.09-3.01 (m, 1H), 2.28-1.92 (m, 4H), 1.76-1.65 (m, 1H), 1.46 (s, 9H).

Intermediate 156

(1S,4S)-tert-Butyl 4-(5-bromo-1,1-dioxidobenzo[d]isothiazol-2(3H)-yl)cyclohexanecarboxylate

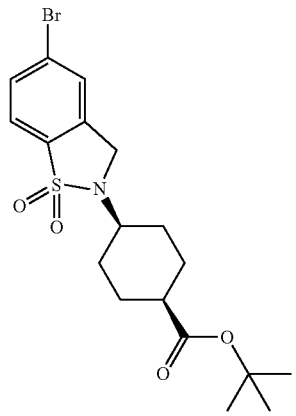

I-156

Step 1: (1R,4R)-tert-Butyl 4-hydroxycyclohexanecarboxylate

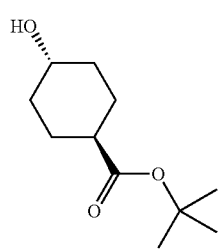

I-156a

The toluene solution (20 mL) of (1R,4R)-4-hydroxycyclohexanecarboxylic acid (0.50 g, 3.5 mmol) and 1,1-di-tert-butoxy-N,N-dimethylmethanamine (2.12 g, 10.4 mmol) was heated at 90° C. for 16 hours then cooled to ambient temperature. An aqueous NaOH solution (4.0 M, 50 mL) was added and the resulting mixture extracted with EtOAc (2×50 mL). The combined organic layers were washed with saturated aqueous NaOH (2×50 mL) followed by brine (2×50 mL), dried over anhydrous $Na_2SO_4$ and filtered. The filtrate was concentrated in vacuo to afford the crude title product. $^1$H NMR (300 MHz, $CDCl_3$) δ 3.88-3.85 (m, 1H), 2.31-2.26 (m, 1H), 1.68-1.62 (m, 4H), 1.44 (s, 9H), 1.25-1.22 (m, 4H).

Step 2: (1R,4R)-tert-Butyl 4-(tosyloxy)cyclohexanecarboxylate

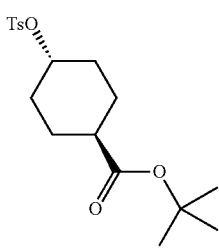

I-156b (1R,4R)-tert-Butyl 4-hydroxycyclohexanecarboxylate (0.70 g, 2.1 mmol), N,N-dimethylaminopyridine (3.0 mg, 0.021 mmol), triethylamine (424 mg, 4.19 mmol) and 4-methylbenzene-1-sulfonyl chloride (0.48 g, 2.5 mmol) were combined with DCM (20 mL) in a 50 mL round-bottom flask, under nitrogen atmosphere at ambient temperature. The mixture was stirred for 16 hours then water (50 mL) was added. The mixture was extracted with EtOAc (2×50 mL) and the combined organic layers washed with brine (2×50 mL), dried with anhydrous $Na_2SO_4$ and filtered. The filtrate was concentrated in vacuo and the residue purified on silica, eluting with petroleum ether/ethyl acetate (10:1) to afford the title compound. $^1$H NMR (300 MHz, $CDCl_3$) δ 7.78 (d, J=7.5 Hz, 2H), 7.32 (d, J=7.5 Hz, 2H), 4.41-4.36 (m, 1H), 2.47 (s, 3H), 2.16-2.14 (m, 1H), 1.95-1.86 (m, 4H), 1.51-1.45 (m, 4H), 1.44 (s, 9H).

Step 3: (1S,4S)-tert-Butyl 4-(5-bromo-1,1-dioxido-benzo[d]isothiazol-2(3H)-yl)cyclohexanecarboxylate To a 8 mL round-bottom flask were placed 5-bromo-2,3-dihydrobenzo[d]isothiazole 1,1-dioxide (50 mg, 0.20 mmol), potassium-2-methylpropan-2-olate (45 mg, 0.40 mmol) and (1R,4R)-tert-butyl-4-(tosyloxy)cyclohexanecarboxylate (86 mg, 0.24 mmol) in N,N-dimethyl formamide (0.50 mL) and benzene (0.50 mL). The reaction was heated at 100° C. for 16 hours. Water (10 mL) was added and the mixture extracted with EtOAc (2×10 mL). The combined organic layers were washed with brine (2×50 mL), dried over anhydrous $Na_2SO_4$ and filtered. The filtrate was concentrated in vacuo and the residue purified by prep-TLC (5:1 petroleum ether/EtOAc) to afford the title compound. LRMS (ESI) calc'd for $C_{18}H_{25}BrNO_4S$ [M+H]$^+$: 430, 432 (1:1) found 430, 432 (1:1); $^1$H NMR (300 MHz, $CDCl_3$) δ 7.68-7.66 (m, 2H), 7.59 (s, 1H), 4.36 (s, 2H), 3.73-3.70 (m, 1H), 2.56-2.53 (m, 1H), 2.19-2.16 (m, 2H), 1.96-1.91 (m, 4H), 1.75-1.61 (m, 2H), 1.58 (s, 9H).

Table 34 discloses an Intermediate that was prepared in an analogous manner to that for Intermediate 156.

TABLE 34

| Intermediate | Structure | Compound Name | LRMS [M + H]$^+$ |
|---|---|---|---|
| I-157 | Br | (1R,4R)-tert-Butyl 4-(5-bromo-1,1-dioxidobenzo[d]isothiazol-2(3H)-yl)cyclohexane carboxylate | Calc'd 430, 432 (1:1), found 430, 432 (1:1) |

Intermediates 158 and 159

(1S,4S and 1R,4R)-tert-Butyl 4-(4-bromophenyl)-4-hydroxycyclohexanecarboxylate and (1R,4S and 1S,4R)-tert-But 4-(4-bromophenyl)-4-hydroxycyclohexanecarboxylate

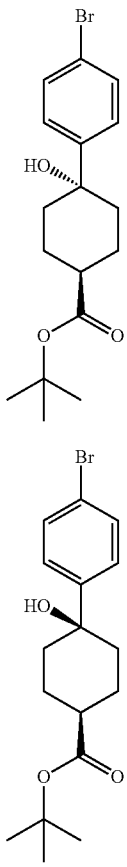

I-158

I-159

Step 1: 4-Oxocyclohexanecarboxylic acid

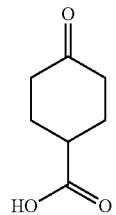

I-158a

To a solution of ethyl 4-oxocyclohexanecarboxylate (11.0 g, 64.6 mmol) in ethanol (80 mL) was added a solution of NaOH (2.58 g, 64.6 mmol) in water (40 mL). The reaction was stirred at ambient temperature for 2 hours then acidified to pH=1-3 with HCl (4.0 M). The resulting solution was extracted with EtOAc (2×150 mL) and the combined organic layers washed with brine (100 mL), dried over anhydrous $Na_2SO_4$ and filtered. The filtrate was concentrated in vacuo to afford the crude title compound. LRMS (ESI) calc'd for $C_7H_{11}O_3$ [M+H]$^+$: 143, found 143.

Step 2: tert-Butyl 4-oxocyclohexanecarboxylate

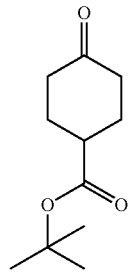

I-158b

A solution of 4-oxocyclohexanecarboxylic acid (8.0 g, 0.040 mol), 4-dimethylaminopyridine (6.88 g, 56.3 mmol) and di-tert-butyl dicarbonate (26.1 mL, 113 mmol) in tert-butyl alcohol (80 mL) was heated at 70° C. for 12 hours. The mixture was cooled and concentrated in vacuo and the residue purified on silica, eluting with petroleum ether/ethyl acetate (15:1) to afford the title compound. LRMS (ESI) calc'd for $C_{11}H_{19}O_3$[M+H]$^+$: 199, found 199.

Step 3: (1S,4S and 1R,4R)-tert-Butyl 4-(4-bromophenyl)-4-hydroxycyclohexanecarboxylate and (1S,4R and 1R,4S)-tert-Butyl 4-(4-bromophenyl)-4-hydroxycyclohexanecarboxylate To a solution of 1-bromo-4-iodobenzene (5.00 g, 17.7 mmol) in tetrahydrofuran (100 mL) cooled at −78° C. was added butyllithium (8.48 mL, 21.2 mmol, 2.0 M in THF) dropwise over 5 min. The reaction was stirred at −78° C. for 1 hour then tert-butyl 4-oxocyclohexanecarboxylate (2.80 g, 14.1 mmol) was added dropwise. The reaction was maintained at −78° C. for an additional hour then quenched with water (10 mL). The quenched reaction was extracted with ethyl acetate (2×80 mL) and the combined organic layers were washed with brine (50 mL), dried over anhydrous sodium sulfate and filtered. The filtrate was concentrated in vacuo and the residue purified on silica, eluting with petroleum ether/ethyl acetate (10:1) to afford the racemic title compound. The diastereomers were separated by mass triggered reverse phase HPLC (XBridge RP18; 38-70% acetonitrile/water containing 0.05% ammonia) to afford the title compounds (1S,4S and 1R,4R)-tert-Butyl 4-(4-bromophenyl)-4-hydroxycyclohexanecarboxylate (I-156). LRMS (ESI) calc'd for $C_{17}H_{24}BrO_3$ [M+H]$^+$: 355, 357 (1:1). found 355, 357 (1:1); $^1$H (400 MHz, DMSO-d$_6$) δ 7.53 (d, J=8.4 Hz, 2H), 7.37 (d, J=8.4 Hz, 2H), 4.94 (s, 1H), 2.55-2.52 (m, 1H), 1.94-1.86 (m, 4H), 1.74-1.72 (m, 2H), 1.56-1.52 (m, 2H), 1.41 (s, 9H) and (1S,4R and 1R,4S)-tert-Butyl 4-(4-bromophenyl)-4-hydroxycyclohexanecarboxylate (I-157). LRMS (ESI) calc'd for $C_{17}H_{24}BrO_3$ [M+H]$^+$: 355, 357 (1:1). found 355, 357 (1:1); $^1$H NMR (400 MHz, DMSO-d$_6$) δ 7.50 (d, J=8.8 Hz, 2H), 7.45 (d, J=8.8 Hz, 2H), 4.90 (s, 1H), 2.28-2.27 (m, 1H), 1.84-1.62 (m, 8H), 1.43 (s, 9H).

Table 35 discloses Intermediates that were prepared in an analogous manner to that for Intermediates 158 and 159.

TABLE 35

| Intermediate | Structure | Compound Name | LRMS [M + H]+ |
|---|---|---|---|
| I-160 | 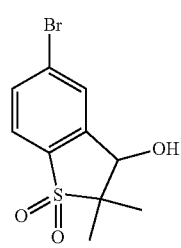 | (1S,4S and 1R,4R)-ethyl 4-(4-bromophenyl)-4-hydroxycyclo-hexanecarboxylate | Calc'd 327, 329 (1:1), found 327, 329 (1:1) |
| I-161 | 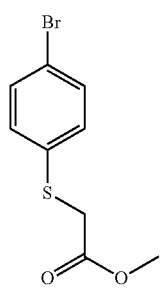 | (1R,4S and 1S,4R)-ethyl 4-(4-bromophenyl)-4-hydroxycyclo-hexanecarboxylate | Calc'd 327, 329 (1:1), found 327, 329 (1:1) |

Intermediate 162

Bromo-3-hydroxy-2,2-dimethyl-2,3-dihydrobenzo[b]thiophene-1,1-dioxide

I-162

Step 1: Methyl 2-((4-bromophenyl)thio)acetate

I-162a

To a 250 mL round-bottom flask were placed 4-bromobenzenethiol (5.00 g, 26.4 mmol), methyl-2-bromoacetate (6.07 g, 39.7 mmol), triethylamine (7.37 mL, 52.9 mmol) and tetrahydrofuran (130 mL). The mixture was heated at 70° C. for 4 hours then concentrated in vacuo. The residue was dissolved in water (100 mL) then extracted with ethyl acetate (3×150 mL). The organic layers were combined, washed with brine (100 mL), dried over anhydrous sodium sulfate and filtered. The filtrate was concentrated in vacuo to afford the crude title compound. GCMS (ES) calc'd for $C_9H_9BrO_2S$ [M]+: 260, 262 (1:1). found 260, 262 (1:1).

Step 2: 2-((4-Bromophenyl)thio)acetic acid

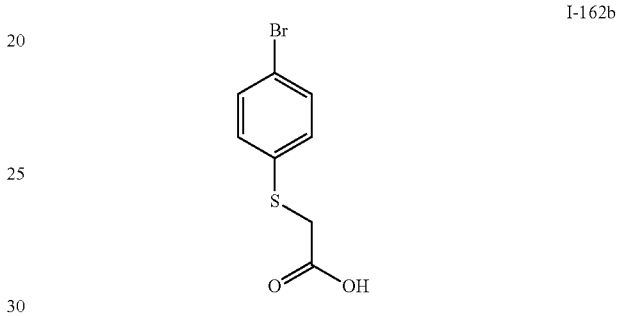

I-162b

To a 500 mL round-bottom flask were placed methyl 2-((4-bromophenyl)thio)acetate (7.40 g, 28.3 mmol), sodium hydroxide (2.26 g, 56.6 mmol) in methanol (200 mL) and water (20 mL). The mixture was stirred at ambient temperature for 16 hours then concentrated in vacuo. Water (100 mL) was added followed by hydrochloric acid (6.0 M) until pH=5. The mixture was extracted with ethyl acetate (3×100 mL) and the combined organic layers were washed with brine (100 mL), dried over anhydrous sodium sulfate and filtered. The filtrate was concentrated in vacuo to afford the crude title compound. GCMS (ES) calc'd for $C_8H_7BrO_2S$ [M]+: 246, 248 (1:1). found 246, 248 (1:1).

Step 3: 2-((4-Bromophenyl)thio)acetyl chloride

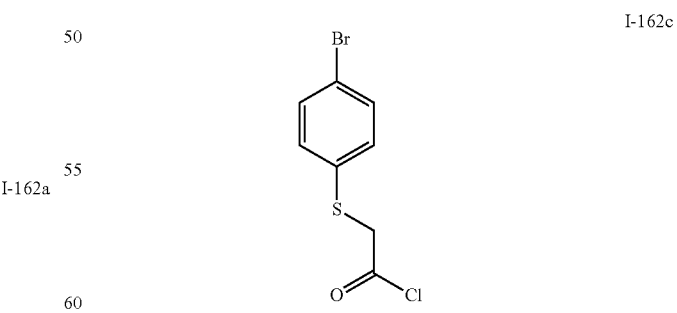

I-162c

A solution of 2-((4-bromophenyl)thio)acetic acid (6.20 g, 25.1 mmol) in thionyl chloride (150 mL) was heated at reflux for 1 hour then concentrated in vacuo to afford the crude title compound that was carried onto the next step without further purification.

Step 4: 5-Bromobenzo[b]thiophen-3(2H)-one

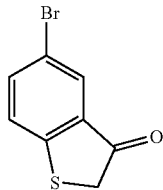

I-162d 2-((4-Bromophenyl)thio)acetyl chloride (21 g, 79 mmol) was added dropwise to a suspension of aluminum chloride (13.7 g, 103 mmol) in 1,2-dichloroethane (150 mL) at 0-4° C. The mixture was warmed and maintained at ambient temperature for 16 hours. The reaction mixture was added to hydrochloric acid (1.5 M, 150 mL) then extracted with 1,2-dichloroethane (3×300 mL). The combined organic layers were washed with brine (2×200 mL), dried over anhydrous sodium sulfate and filtered. The filtrate was concentrated in vacuo and the residue purified on silica, eluting with ethyl acetate/petroleum ether (1:30) to afford the title compound. $^1$H NMR (300 MHz, CDCl$_3$) δ 7.88 (d, J=2.1 Hz, 1H), 7.66-7.62 (m, 1H), 7.31 (d, J=8.4 Hz, 1H), 3.83 (s, 2H).

Step 5: 5-Bromobenzo[b]thiophen-3 (2H)-one 1,1-dioxide

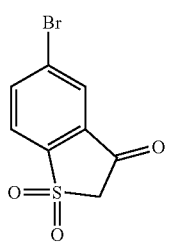

I-162e

To a 500 mL round-bottom flask was placed 5-bromobenzo[b]thiophen-3(2H)-one (10.0 g, 43.7 mmol) in 1,2-dichloroethane (200 mL) at 0-4° C., followed by 3-chlorobenzoperoxoic acid (22.6 g, 131 mmol). The reaction was stirred at ambient temperature for 5 hours and saturated sodium bicarbonate (150 mL) and water (200 mL) were added. The mixture was extracted with 1,2-dichloroethane (3×500 mL) and the combined organic layers were washed with brine (2×200 mL), dried over sodium sulfate and filtered. The filtrate was concentrated in vacuo and the residue purified on silica, eluting with ethyl acetate/petroleum ether (1:10) to give the title compound. $^1$H NMR (300 MHz, CDCl$_3$) δ 8.15 (d, J=1.8 Hz, 1H), 8.08-8.04 (m, 1H), 7.86 (d, J=8.4 Hz, 1H), 4.13 (s, 2H).

Step 6: 5-Bromo-2,2-dimethylbenzo[b]thiophen-3 (2H)-one 1,1-dioxide

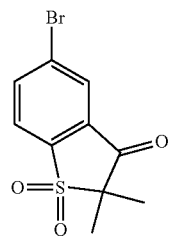

I-162f

To a 50 mL round-bottom flask were added 5-bromobenzo[b]thiophen-3(2H)-one 1,1-dioxide (0.51 g, 1.9 mmol), iodomethane (0.69 g, 4.9 mmol) and 1,5-diazabicyclo[4.3.0]non-5-ene (0.73 mL, 4.9 mmol) in tetrahydrofuran (20 mL). The mixture was heated at 70° C. for 3 hours then cooled to room temperature. Water (50 mL) was added and the resulting mixture extracted with ethyl acetate (3×50 mL). The organic layers were combined, washed with brine (2×100 mL), dried over anhydrous sodium sulfate and filtered. The filtrate was concentrated in vacuo and the residue purified on silica, eluting with ethyl acetate/petroleum ether (1:30) to afford the title compound. GCMS (ES) calc'd for C$_{10}$H$_9$BrO$_3$S [M]$^+$: 288, 290 (1:1). found 288, 290 (1:1); $^1$H NMR (400 MHz, CDCl$_3$) δ8.17 (d, J=1.8 Hz, 1H), 8.09-8.07 (m, 1H), 7.91 (d, J=6.4 Hz, 1H), 1.65 (s, 6H).

Step 7: Bromo-3-hydroxy-2,2-dimethyl-2,3-dihydrobenzo[b]thiophene-1,1-dioxide To a 50 mL round-bottom flask was placed 5-bromo-2,2-dimethylbenzo[b]thiophen-3 (2H)-one 1,1-dioxide (0.60 g, 2.1 mmol) in methanol (20 mL) then sodium borohydride (0.450 g, 10.4 mmol) was added. The reaction was stirred for 1 h then quenched by water (2 mL). The mixture was extracted with ethyl acetate (3×20 mL) and the organic layers combined, dried over anhydrous sodium sulfate and filtered. The filtrate was concentrated in vacuo to afford the title compound. $^1$H NMR (400 MHz, DMSO-d$_6$) δ 7.85-7.80 (m, 3H), 6.62 (d, J=6.0 Hz, 1H), 5.99 (d, J=6.0 Hz, 1H), 1.46 (s, 3H), 1.18 (s, 3H).

Table 36 discloses the Intermediates that were prepared in an analogous manner to that for Intermediate 162, using the appropriate electrophile.

TABLE 36

| Intermediate | Structure | Compound Name | $^1$H NMR |
|---|---|---|---|
| I-163 | ![structure] | 5-Bromo-3-hydroxy-3H-spiro[benzo[b]thiophene-2,1'-cyclohexane] 1,1-dioxide | (300 MHz, DMSO-d$_6$) δ 7.78-7.74 (m, 3H), 6.43 (d, J = 6.0 Hz, 1H), 5.96 (d, J = 5.4 Hz, 1H), 1.98-1.96 (m, 2H), 1.69-1.41 (m, 8H). |

TABLE 36-continued

| Intermediate | Structure | Compound Name | ¹H NMR |
|---|---|---|---|
| I-164 | 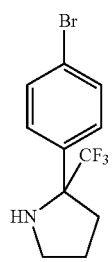 | 5-Bromo-3-hydroxy-2',3',5',6'-tetrahydro-3H-spiro[benzo[b]thiophene-2,4'-pyran] 1,1-dioxide | (400 MHz, CDCl$_3$) δ 7.78-7.64 (m, 3H), 4.96 (d, J = 5.4 Hz, 1H), 3.98-3.80 (m, 4H), 2.27-2.03 (m, 4H). |

Intermediate 165

(R and S)-2-(4-Bromophenyl)-2-(trifluoromethyl)pyrrolidine

I-165

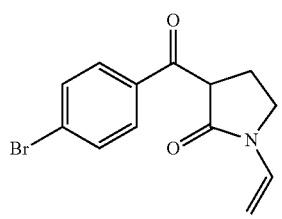

Step 1: 3-(4-Bromobenzoyl)-1-vinylpyrrolidin-2-one

I-165a

Potassium tert-butoxide (6.26 g, 55.8 mmol) was added to a solution of 1-vinylpyrrolidin-2-one (6.20 g, 55.8 mmol) and methyl 4-bromobenzoate (10.00 g, 46.50 mmol) in tetrahydrofuran (150 mL). The mixture was stirred at ambient temperature for 1 hour then water (200 mL) was added and the pH adjusted to 7 with hydrochloric acid (1.0 M). The resulting mixture was extracted with EtOAc (3×200 mL). The combined organic layers were dried over anhydrous Na$_2$SO$_4$, filtered and concentrated in vacuo. The residue was purified on silica, eluting with 0-25% EtOAc in petroleum ether to afford the title compound. LRMS (ESI) calc'd for C$_{13}$H$_{13}$BrNO$_2$ [M+H]$^+$: 294, 296 (1:1). found 294, 296 (1:1); ¹H NMR (300 MHz, CDCl$_3$) δ 7.90 (d, J=6.6 Hz, 2H), 7.65 (d, J=6.6 Hz, 2H), 7.06-6.97 (m, 1H), 4.55-4.50 (m, 3H), 3.77-3.68 (m, 1H), 3.62-3.55 (m, 1H), 2.80-2.71 (m, 1H), 2.37-2.28 (m, 1H).

Step 2: 5-(4-Bromophenyl)-3,4-dihydro-2H-pyrrole

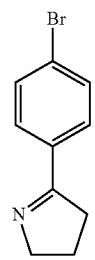

I-165b

A suspension of 3-(4-bromobenzoyl)-1-vinylpyrrolidin-2-one (5.0 g, 17.0 mmol) in HCl (8.0 M, 20.0 mL, 160 mmol) was heated at reflux for 16 hours. The mixture was cooled to ambient temperature and extracted with EtOAc (3×20 mL). The aqueous layer was basified to pH=13 with NaOH (15% aqueous solution) and extracted with DCM (5×20 mL). The combined organic layers were dried over anhydrous Na$_2$SO$_4$, filtered and concentrated in vacuo. The residue was purified on silica, eluting with 0-25% EtOAc in petroleum ether to afford the title compound. LRMS (ESI) calc'd for C$_{10}$H$_{11}$BrN [M+H]$^+$: 224, 226 (1:1). found 224, 226 (1:1); ¹H NMR (300 MHz, CDCl$_3$) δ 7.74-7.69 (m, 2H), 7.56-7.52 (m, 2H), 4.09-4.02 (m, 2H), 2.96-2.88 (m, 2H), 2.10-2.00 (m, 2H).

Step 3: (S and R)-2-(4-Bromophenyl)-2-(trifluoromethyl)pyrrolidine

To an ice-cooled solution of 5-(4-bromophenyl)-3,4-dihydro-2H-pyrrole (0.80 g, 3.6 mmol) in acetonitrile (3 mL) was added trifluoromethanesulfonic acid (0.67 g, 4.5 mmol), potassium hydrogen fluoride (0.84 g, 11 mmol) and trimethyl(trifluoromethyl)silane (5.08 g, 35.7 mmol) successively at 0° C. The mixture was warmed to ambient temperature and stirred for 48 hours then saturated aqueous NaHCO$_3$ was added until pH >7. The solution was extracted with EtOAc (3×10 mL) and the combined organic layers were dried over anhydrous Na$_2$SO$_4$, filtered and concentrated in vacuo. The residue was purified on silica, eluting with 0-20% DCM in petroleum ether to afford the title compound. LRMS (ESI) calc'd for C$_{11}$H$_{12}$BrF$_3$N [M+H]$^+$: 294, 296 (1:1). found 294, 296 (1:1); ¹H NMR (300 MHz, CDCl$_3$) δ 7.49 (d, J=5.4 Hz, 2H), 7.42 (d, J=5.4 Hz, 2H), 3.29-3.21 (m, 1H), 3.16-3.08 (m, 1H), 2.60-2.51 (m, 1H), 2.25-2.16 (m, 1H), 2.08-1.94 (m, 1H), 1.89-1.75 (m, 1H).

Intermediates 166 and 167

(R or S)-2-(4-Bromophenyl)-2-(trifluoromethyl)piperidine and (R or S)-2-(4-Bromophenyl)-2-(trifluoromethyl)piperidine

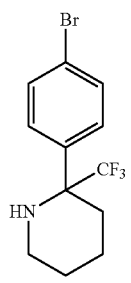
I-166

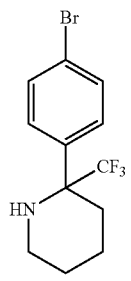
I-167

Step 1: 4-Bromobenzoyl chloride

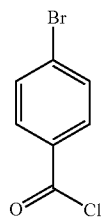
I-166a

A solution of 4-bromobenzoic acid (10.0 g, 49.7 mmol) in sulfurous dichloride (59 g, 0.50 mol) was heated at 80° C. for 16 hours. The mixture was then concentrated in vacuo to afford the title compound which was carried onto the next step without further purification.

Step 2: tert-Butyl 3-(4-bromobenzoyl)-2-oxopiperidine-1-carboxylate

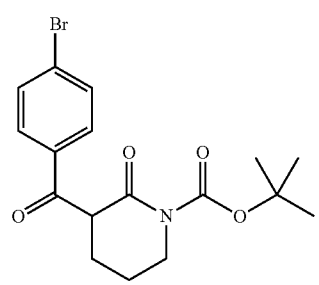
I-166b

Lithium bis(trimethylsilyl)amide (1.0 M in THF, 2.11 mL, 2.11 mmol) was added to a solution of tert-butyl 2-oxopiperidine-1-carboxylate (0.20 g, 1.0 mmol) in THF (2 mL) at −78° C. The resulting mixture was stirred for 10 min then 4-bromobenzoyl chloride (0.22 g, 1.0 mmol) was added. The reaction was warmed to ambient temperature and stirred for 1 hour then saturated aqueous ammonium chloride (20 mL) was added. The quenched reaction was extracted with EtOAc (3×10 mL) and the combined organic layers were dried over anhydrous $Na_2SO_4$, filtered and concentrated in vacuo. The residue was purified on silica, eluting with 0-1% EtOAc in petroleum ether to afford tert-butyl 3-(4-bromobenzoyl)-2-oxopiperidine-1-carboxylate. LRMS (ESI) calc'd for: $C_{17}H_{21}BrNO_4[M+H]^+$: 382, 384 (1:1). found 382, 384 (1:1).

Step 3: 6-(4-Bromophenyl)-2,3,4,5-tetrahydropyridine

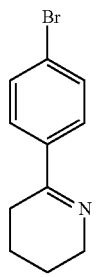
I-166c tert-Butyl 3-(4-bromobenzoyl)-2-oxopiperidine-1-carboxylate (2.00 g, 5.23 mmol) was combined with HCl (8.0 M, 43.6 mL, 0.520 mol) at ambient temperature. The resulting solution was heated at 80° C. for 16 hours. The reaction was then poured into saturated aqueous $Na_2CO_3$ (50 mL) and extracted with EtOAc (3×50 mL). The combined organic layers were dried over $Na_2SO_4$, filtered and concentrated in vacuo. The residue was purified on silica, eluting with 0-1% EtOAc in petroleum ether to afford the title compound. LRMS (ESI) calc'd for: $C_{11}H_{13}BrN$ $[M+H]^+$: 238, 240 (1:1). found 238, 240 (1:1).

Step 4: (R or S)-2-(4-Bromophenyl)-2-(trifluoromethyl)piperidine and (R or S)-2-(4-Bromophenyl)-2-(trifluoromethyl)piperidine To a solution of 6-(4-bromophenyl)-2,3,4,5-tetrahydropyridine (1.0 g, 4.2 mmol) in acetonitrile (10 mL), trifluoromethanesulfonic acid (3.30 g, 22.0 mmol), potassium hydrogen fluoride (3.94 g, 50.4 mmol) and trimethyl(trifluoromethyl)silane (5.97 g, 42.0 mmol) were added successively at 0-4° C. The resulted mixture was stirred at ambient temperature for 48 hours. The reaction was then quenched with saturated aqueous $NaHCO_3$ (50 mL) followed by extraction with EtOAc (3×30 mL). The combined organic layers were dried over anhydrous $Na_2SO_4$, filtered and concentrated in vacuo. The residue was purified on silica, eluting with 0-1% DCM in petroleum ether to afford the racemic title compound. The title compounds were then separated by Chiral SFC following the procedure below:

Column used: Chiralpak IA, 2×25 cm
Mobile phase: 15% iPrOH in $CO_2$
Peak A (I-166): (R or S)-2-(4-Bromophenyl)-2-(trifluoromethyl)piperidine. Tr=4.74 min. LRMS (ESI) calc'd for $C_{12}H_{14}BrF_3N\ [M+H]^+$: 308, 310 (1:1). found 308, 310 (1:1).
Peak B (I-167): (R or S)-2-(4-Bromophenyl)-2-(trifluoromethyl)piperidine. Tr=5.48 min. LRMS (ESI) calc'd for $C_{12}H_{14}BrF_3N\ [M+H]^+$: 308, 310 (1:1). found 308, 310 (1:1).

Example 1-1

(cis)-2-{3-[(4-Fluorophenyl)amino]-4-oxo-4,5-dihydro-1H-pyrazolo[4,3-c]pyridin-1-yl}cyclohexanecarbonitrile (racemate)

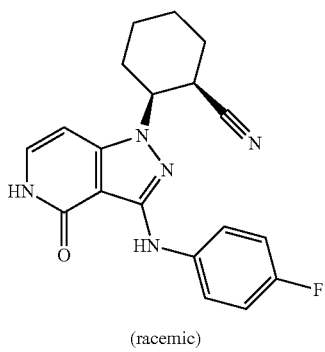

1-1

(racemic)

Step 1: cis-2-(4-(Benzyloxy)-3-((4-fluorophenyl)amino)-1H-pyrazolo[4,3-c]pyridin-1-yl)cyclohexanecarbonitrile (racemic)

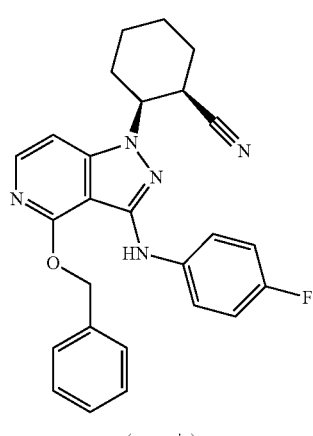

1-1a (racemic)

A vial was charged with (cis)-2-[3-amino-4-(benzyloxy)-1H-pyrazolo[4,3-c]pyridin-1-yl]cyclohexanecarbonitrile (I-2; 24 mg; 0.069 mmol), di-tert-butyl(2',4',6'-triisopropyl-3,4,5,6-tetramethyl-[1,1'-biphenyl]-2-yl)phosphine (20 mg, 0.041 mmol), Pd$_2$(dba)$_3$ (13 mg, 0.014 mmol), and potassium acetate (17 mg, 0.17 mmol). 2-propanol (0.75 mL) and 4-bromofluorobenzene (19 μL, 0.17 mmol) were added and the mixture was sparged with N$_2$. The vial was then sealed and heated at 85° C. for 2.5 hours. The reaction was cooled to room temperature, diluted with EtOAc (30 mL), and washed with water (10 mL) followed by brine (10 mL). The organic layer was dried over Na$_2$SO$_4$, filtered, and concentrated in vacuo to afford a residue that was purified by silica gel chromatography (0-100% EtOAc/hexanes) followed by further purification by preparatory thin layer chromatography (20% acetone/hexanes) to afford the title compound (racemate). LRMS (ESI) calc'd for C$_{26}$H$_{25}$FN$_5$O [M+H]$^+$: 442, found 442.

Step 2: (cis)-2-{3-[(4-Fluorophenyl)amino]-4-oxo-4,5-dihydro-1H-pyrazolo[4,3-c]pyridin-1-yl}cyclohexanecarbonitrile (racemate)

To a solution of cis-2-(4-(benzyloxy)-3-((4-fluorophenyl)amino)-1H-pyrazolo[4,3-c]pyridin-1-yl)cyclohexanecarbonitrile(racemic) (25 mg, 0.057 mmol) in EtOAc (2 mL) under nitrogen was added 10% Pd/C (10 mg). The reaction was placed under an atmosphere of H$_2$ (balloon) and stirred vigorously at room temperature for 2 hours. The balloon of H$_2$ was removed and EtOH (2 mL) and MeOH (2 mL) were added. The mixture was sonicated for several minutes and then the catalyst was removed by filtration. The filtrate was concentrated in vacuo and the residue was purified by mass triggered reverse phase HPLC (C-18; acetonitrile/water containing 0.1% TFA). Lyophilization of the fractions containing desired product afforded the title compound (racemate). LRMS (ESI) calc'd for C$_{19}$H$_{19}$FN$_5$O [M+H]$^+$: 352, found 352. $^1$H NMR (600 MHz, DMSO-d$_6$): δ 11.06 (d, J=5.4 Hz, 1H), 8.00 (s, 1H), 7.74 (m, 2H), 7.17 (m, 1H), 7.02 (m, 2H), 6.59 (d, J=7.2 Hz, 1H), 4.58 (m, 1H), 3.43 (m, 1H), 2.21 (m, 1H), 1.99 (m, 1H), 1.82-1.90 (m, 3H), 1.66 (m, 1H), 1.45-1.58 (m, 2H).

Example 2-1

(trans)-2-{3-[(4-Fluorophenyl)amino]-4-oxo-4,5-dihydro-1H-pyrazolo[4,3-c]pyridin-1-yl}cyclohexanecarbonitrile (racemate)

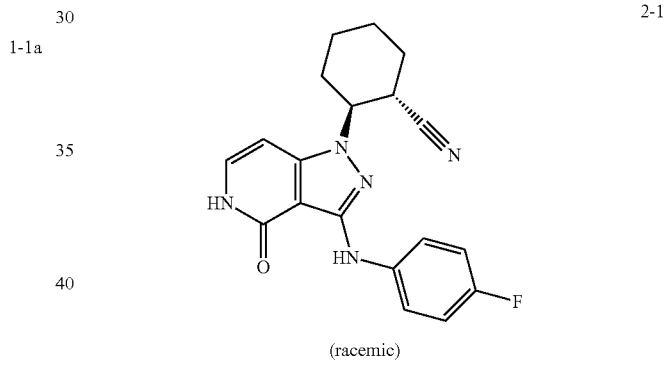

2-1

(racemic)

Step 1: (trans)-2-(4-(Benzyloxy)-3-((4-fluorophenyl)amino)-1H-pyrazolo[4,3-c]pyridin-1-yl)cyclohexanecarbonitrile (racemic)

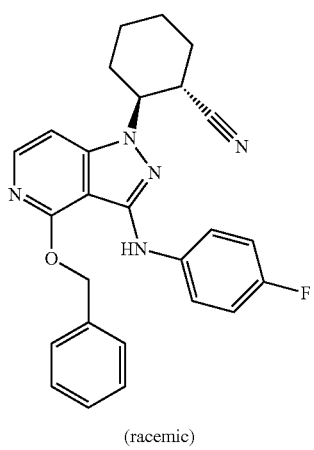

2-1a (racemic)

A vial was charged with (trans)-2-[3-amino-4-(benzyloxy)-1H-pyrazolo[4,3-c]pyridin-1-yl]cyclohexanecarbonitrile (I-3; 36.0 mg; 0.104 mmol), di-tert-butyl(2',4',6'-triisopropyl-3,4,5,6-tetramethyl-[1,1'-biphenyl]-2-yl)phosphine (30 mg, 0.062 mmol), Pd$_2$(dba)$_3$ (19 mg, 0.021 mmol), and potassium acetate (25 mg, 0.26 mmol). 2-propanol (1.0 mL) and 4-bromofluorobenzene (28 µL, 0.26 mmol) were added and the mixture was sparged with N$_2$. The vial was then sealed and heated at 85° C. for 2.5 hours. The reaction was cooled to room temperature, diluted with EtOAc (30 mL), and washed with water (10 mL) and brine (10 mL). The organic layer was dried over Na$_2$SO$_4$, filtered, and concentrated in vacuo. Purification of the residue by silica gel chromatography (0-100% EtOAc/hexanes) afforded the title compound (racemic). LRMS (ESI) calc'd for C$_{26}$H$_{25}$FN$_5$O [M+H]$^+$: 442, found 442.

Step 2: (trans)-2-{3-[(4-Fluorophenyl)amino]-4-oxo-4,5-dihydro-1H-pyrazolo[4,3-c]pyridin-1-yl}cyclohexanecarbonitrile (racemate)

To a solution of (trans)-2-(4-(benzyloxy)-3-((4-fluorophenyl)amino)-1H-pyrazolo[4,3-c]pyridin-1-yl)cyclohexanecarbonitrile(racemic) (45 mg, 0.057 mmol) in EtOAc (4 mL) was added EtOH (1 mL) and 10% Pd/C (10 mg). The reaction was placed under an atmosphere of H$_2$ (balloon) and stirred vigorously at room temperature for 2 hours. The balloon of H$_2$ was then removed and the catalyst was removed by filtration. The filtrate was concentrated in vacuo and the residue was purified by mass triggered reverse phase HPLC (C-18; acetonitrile/water containing 0.1% TFA). Lyophilization of the fractions containing desired product afforded the title compound (racemate). LRMS (ESI) calc'd for C$_{19}$H$_{19}$FN$_5$O [M+H]$^+$: 352, found 352. $^1$H NMR (600 MHz, DMSO-d$_6$): δ 11.05 (d, J=5.4 Hz, 1H), 8.07 (s, 1H), 7.66 (m, 2H), 7.18 (dd, J=7.2, 6.0 Hz, 1H), 7.09 (m, 2H), 6.63 (d, J=7.2 Hz, 1H), 4.64 (m, 1H), 3.28 (m, 1H), 2.15 (m, 1H), 1.68-1.87 (m, 5H), 1.45 (m, 1H), 1.33 (m, 1H).

Example 3-1

(1R,2R)-2-{3-[(2-Fluoropyridin-4-yl)amino]-4-oxo-4,5-dihydro-1H-pyrazolo[4,3-c]pyridin-1-yl}cyclohexanecarbonitrile 3-1

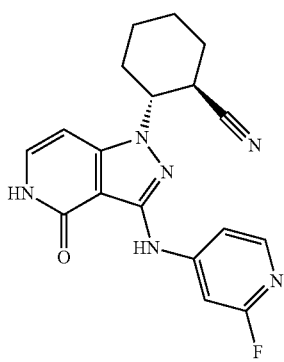

Step 1: (1R,2R)-2-(4-(Benzyloxy)-3-((2-fluoropyridin-4-yl)amino)-1H-pyrazolo[4,3-c]pyridin-1-yl)cyclohexanecarbonitrile 3-1a

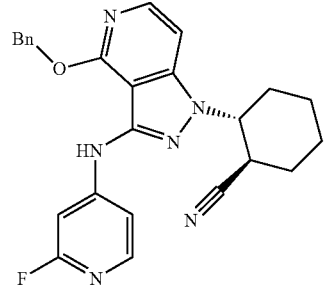

A vial was charged with (1R,2R)-2-[3-amino-4-(benzyloxy)-1H-pyrazolo[4,3-c]pyridin-1-yl]cyclohexanecarbonitrile (I-4; 28 mg; 0.082 mmol), di-tert-butyl(2',4',6'-triisopropyl-3,4,5,6-tetramethyl-[1,1'-biphenyl]-2-yl)phosphine (24 mg, 0.049 mmol), Pd$_2$(dba)$_3$ (15 mg, 0.016 mmol), 4-bromo-2-fluoropyridine (36.1 mg, 0.205 mmol), and potassium acetate (20.1 mg, 0.205 mmol). 2-propanol (1.0 mL) was added and the mixture was sparged with N$_2$. The vial was then sealed and heated at 85° C. for 2.5 hours. The reaction was cooled to room temperature, diluted with EtOAc (30 mL), and washed with water (10 mL) and brine (10 mL). The organic layer was dried over Na$_2$SO$_4$, filtered, and concentrated in vacuo. Purification of the residue by silica gel chromatography (0-100% EtOAc/hexanes) followed by further purification by preparatory thin layer chromatography (25% acetone/hexanes) afforded the title compound. LRMS (ESI) calc'd for C$_{25}$H$_{24}$FN$_6$O [M+H]$^+$: 443, found 443. $^1$H NMR (600 MHz, CDCl$_3$): δ 7.97 (d, J=5.4 Hz, 1H), 7.93 (d, J=6.0 Hz, 1H), 7.62 (s, 1H), 7.50 (d, J=7.2 Hz, 2H), 7.45 (t, J=7.2 Hz, 2H), 7.40 (t, J=7.2 Hz, 1H), 7.28 (s, 1H), 6.91 (d, J=6.6 Hz, 1H), 6.85 (d, J=5.4 Hz, 1H), 5.56 (s, 2H), 4.33 (m, 1H), 3.29 (m, 1H), 2.37 (m, 1H), 1.98-2.10 (m, 3H), 1.91 (m, 1H), 1.80 (m, 1H), 1.41-1.55 (m, 2H).

Step 2: (1R,2R)-2-{3-[(2-Fluoropyridin-4-yl)amino]-4-oxo-4,5-dihydro-1H-pyrazolo[4,3-c]pyridin-1-yl}cyclohexanecarbonitrile To a solution of (1R,2R)-2-(4-(Benzyloxy)-3-((2-fluoropyridin-4-yl)amino)-1H-pyrazolo[4,3-c]pyridin-1-yl)cyclohexanecarbonitrile (33 mg, 0.074 mmol) in EtOAc (3 mL) was added EtOH (0.5 mL) and 10% Pd/C (10 mg). The reaction was placed under an atmosphere of H$_2$ (balloon) and stirred vigorously at room temperature for 2 hours. The balloon of H$_2$ was then removed and the catalyst was removed by filtration. The filtrate was concentrated in vacuo and the residue was purified by silica gel chromatography (0-10% MeOH/CH$_2$Cl$_2$) to afford the title compound. LRMS (ESI) calc'd for C$_{18}$H$_{18}$FN$_6$O [M+H]$^+$: 353, found 353. $^1$H NMR (600 MHz, DMSO-d$_6$): δ 11.2 (s, 1H), 8.99 (s, 1H), 7.93 (d, J=6.0 Hz, 1H), 7.50 (d, J=6.0 Hz, 1H), 7.36 (s, 1H), 7.23 (m, 1H), 6.69 (d, J=7.2 Hz, 1H), 4.72 (m, 1H), 3.30 (m, 1H), 2.16 (m, 1H), 1.67-1.92 (m, 5H), 1.46 (m, 1H), 1.34 (m, 1H).

Table 37 discloses Examples that were prepared in analogy to Example 3-1, starting with the appropriate enantiopure carbonitrile. In select cases, the general procedure was modified to alternatively utilize between 1.75-2.7 equivalents K$_3$PO$_4$ or KOAc base and/or 0.11 mol % [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3), and/or 1.2-1.4 equivalents of the aryl bromide coupling partner at approximately 0.1 M in t-amyl alcohol, at 70-90° C. In select cases, the hydrogenolysis reaction was conducted using EtOAc, MeOH, or THF as solvent.

TABLE 37

| Example | Structure | Compound Name | LRMS [M + H]$^+$ |
| --- | --- | --- | --- |
| 3-2 | 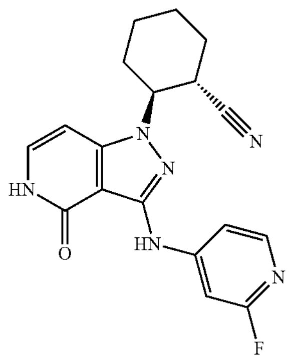 [SMILES: N#C[C@H]1CCCC[C@@H]1n1nc(Nc2ccnc(F)c2)c2c(=O)[nH]ccc21] | (1S,2S)-2-{3-[(2-fluoropyridin-4-yl)amino]-4-oxo-4,5-dihydro-1H-pyrazolo[4,3-c]pyridin-1-yl}cyclohexanecarbonitrile | Calc'd 353, found 353 |
| 3-3 | 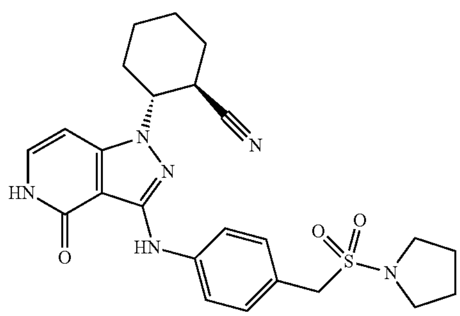 [SMILES: N#C[C@@H]1CCCC[C@H]1n1nc(Nc2ccc(CS(=O)(=O)N3CCCC3)cc2)c2c(=O)[nH]ccc21] | (1R,2R)-2-(4-oxo-3-((4-((pyrrolidin-1-ylsulfonyl)methyl)phenyl)amino)-4,5-dihydro-1H-pyrazolo[4,3-c]pyridin-1-yl)cyclohexanecarbonitrile | Calc'd 481, found 481 |
| 3-4 | 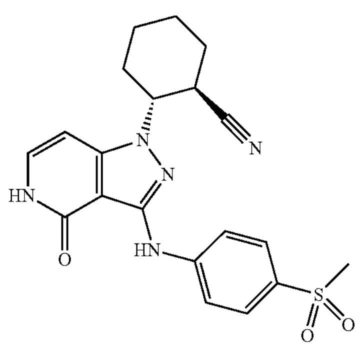 [SMILES: CS(=O)(=O)c1ccc(Nc2nn([C@@H]3CCCC[C@H]3C#N)c3cc[nH]c(=O)c23)cc1] | (1R,2R)-2-(3-{[4-(methylsulfonyl)phenyl]amino}-4-oxo-4,5-dihydro-1H-pyrazolo[4,3-c]pyridin-1-yl)cyclohexanecarbonitrile | Calc'd 412, found 412 |
| 3-5 | 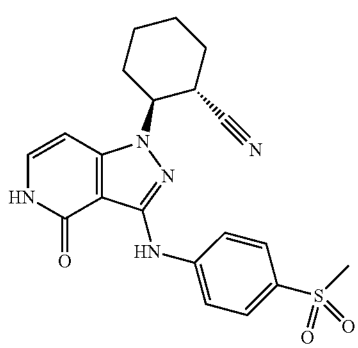 [SMILES: CS(=O)(=O)c1ccc(Nc2nn([C@H]3CCCC[C@@H]3C#N)c3cc[nH]c(=O)c23)cc1] | (1S,2S)-2-(3-{[4-(methylsulfonyl)phenyl]amino}-4-oxo-4,5-dihydro-1H-pyrazolo[4,3-c]pyridin-1-yl)cyclohexanecarbonitrile | Calc'd 412, found 412 |

TABLE 37-continued

| Example | Structure | Compound Name | LRMS [M + H]+ |
|---|---|---|---|
| 3-6 | 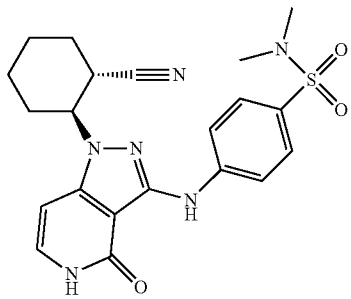 [SMILES: CN(C)S(=O)(=O)c1ccc(Nc2nn([C@H]3CCCC[C@@H]3C#N)c3cc[nH]c(=O)c23)cc1] | 4-({1-[(1S,2S)-2-cyanocyclohexyl]-4-oxo-4,5-dihydro-1H-pyrazolo[4,3-c]pyridin-3-yl}amino)-N,N-dimethylbenzenesulfonamide | Calc'd 441, found 441 |
| 3-7 | 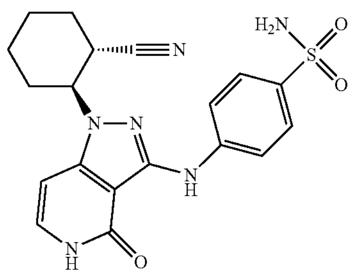 [SMILES: N#C[C@H]1CCCC[C@@H]1n1nc(Nc2ccc(S(N)(=O)=O)cc2)c2c(=O)[nH]ccc21] | 4-({1-[(1S,2S)-2-cyanocyclohexyl]-4-oxo-4,5-dihydro-1H-pyrazolo[4,3-c]pyridin-3-yl}amino)benzenesulfonamide | Calc'd 413, found 413 |
| 3-8 | 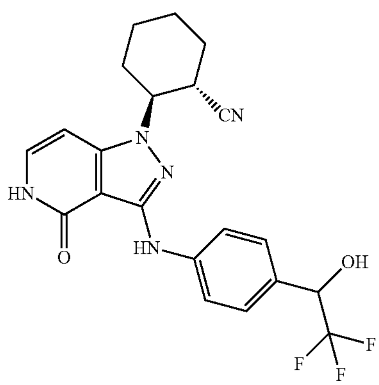 [SMILES: N#C[C@H]1CCCC[C@@H]1n1nc(Nc2ccc(C(O)C(F)(F)F)cc2)c2c(=O)[nH]ccc21] | (1S,2S)-2-[4-oxo-3-({4-[(1R or 1S))-2,2,2-trifluoro-1-hydroxyethyl]phenyl}amino)-4,5-dihydro-1H-pyrazolo[4,3-c]pyridin-1-yl]cyclohexanecarbonitrile (Derived from Peak A via SFC separation of pyridone final compound, AD-H, 25% MeOH in CO2, Tr = 2.9 mins) | Calc'd 432, found 432 |
| 3-9 | 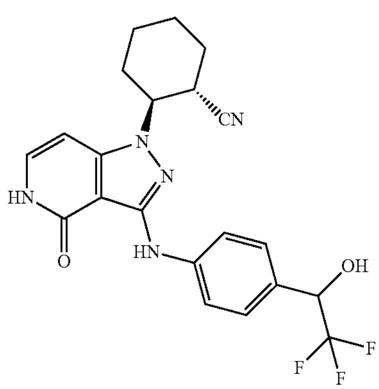 [SMILES: N#C[C@H]1CCCC[C@@H]1n1nc(Nc2ccc(C(O)C(F)(F)F)cc2)c2c(=O)[nH]ccc21] | (1S,2S)-2-[4-oxo-3-({4-[(1S or 1R)-2,2,2-trifluoro-1-hydroxyethyl]phenyl}amino)-4,5-dihydro-1H-pyrazolo[4,3-c]pyridin-1-yl]cyclohexanecarbonitrile (Derived from Peak B via SFC separation of pyridone final compound, AD-H, 25% MeOH in CO2, Tr = 6.59 mins) | Calc'd 432, found 432 |

TABLE 37-continued

| Example | Structure | Compound Name | LRMS [M + H]+ |
|---|---|---|---|
| 3-10 | 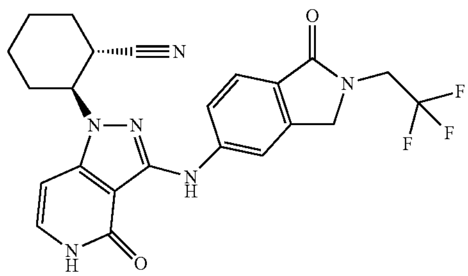 [SMILES: N#C[C@H]1CCCC[C@@H]1n1nc(Nc2ccc3c(c2)CN(CC(F)(F)F)C3=O)c2c(=O)[nH]ccc21] | (1S,2S)-2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclohexanecarbonitrile | Calc'd 471, found 471 |
| 3-11 | 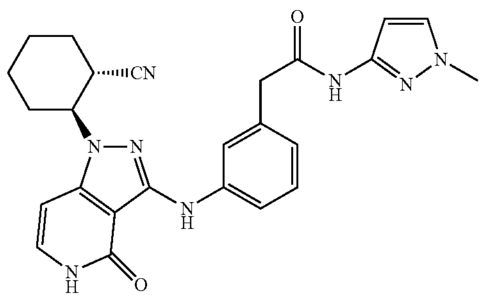 [SMILES: Cn1ccc(NC(=O)Cc2cccc(Nc3nn([C@H]4CCCC[C@@H]4C#N)c4cc[nH]c(=O)c34)c2)n1] | 2-[3-({1-[(1S,2S)-2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide | Calc'd 471, found 471 |
| 3-12 | 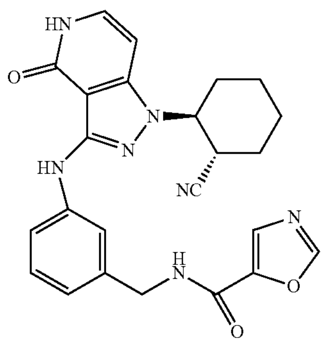 [SMILES: N#C[C@H]1CCCC[C@@H]1n1nc(Nc2cccc(CNC(=O)c3cnco3)c2)c2c(=O)[nH]ccc21] | N-[3-({1-[(1S,2S)-2-cyanocyclohexyl]-4-oxo-4,5-dihydro-1H-pyrazolo[4,3-c]pyridin-3-yl}amino)benzyl]-1,3-oxazole-5-carboxamide | Calc'd 458, found 458 |
| 3-13 | 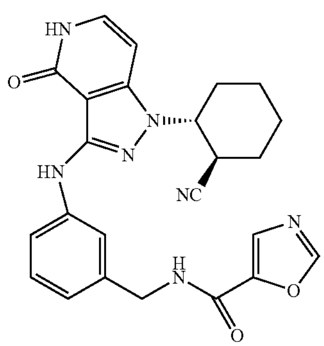 [SMILES: N#C[C@@H]1CCCC[C@H]1n1nc(Nc2cccc(CNC(=O)c3cnco3)c2)c2c(=O)[nH]ccc21] | N-[3-({1-[(1R,2R)-2-cyanocyclohexyl]-4-oxo-4,5-dihydro-1H-pyrazolo[4,3-c]pyridin-3-yl}amino)benzyl]-1,3-oxazole-5-carboxamide | Calc'd 458, found 458 |
| 3-14 | 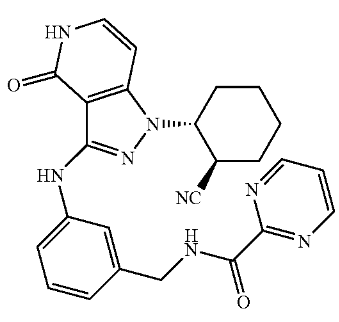 [SMILES: N#C[C@@H]1CCCC[C@H]1n1nc(Nc2cccc(CNC(=O)c3ncccn3)c2)c2c(=O)[nH]ccc21] | N-[3-({1-[(1R,2R)-2-cyanocyclohexyl]-4-oxo-4,5-dihydro-1H-pyrazolo[4,3-c]pyridin-3-yl}amino)benzyl]pyrimidine-2-carboxamide | Calc'd 469, found 469 |

TABLE 37-continued

| Example | Structure | Compound Name | LRMS [M + H]+ |
|---|---|---|---|
| 3-15 | 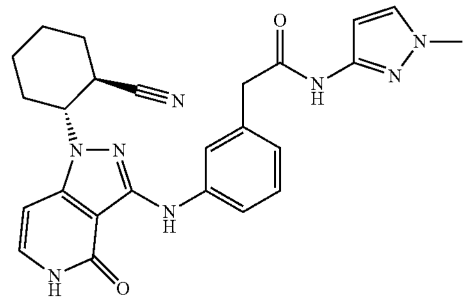 [SMILES: Cn1ccc(NC(=O)Cc2cccc(Nc3nn([C@@H]4CCCC[C@H]4C#N)c4cc[nH]c(=O)c34)c2)n1] | 2-[3-({1-[(1R,2R)-2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide | Calc'd 471, found 471 |
| 3-16 | 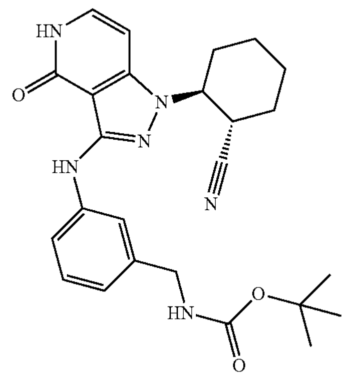 [SMILES: CC(C)(C)OC(=O)NCc1cccc(Nc2nn([C@H]3CCCC[C@@H]3C#N)c3cc[nH]c(=O)c23)c1] | tert-butyl [3-({1-[(1S,2S)-2-cyanocyclohexyl]-4-oxo-4,5-dihydro-1H-pyrazolo[4,3-c]pyridin-3-yl}amino)benzyl]carbamate | Calc'd 463, found 463 |
| 3-17 | 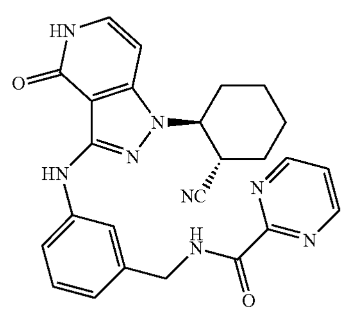 [SMILES: N#C[C@H]1CCCC[C@@H]1n1nc(Nc2cccc(CNC(=O)c3ncccn3)c2)c2c(=O)[nH]ccc21] | N-[3-({1-[(1S,2S)-2-cyanocyclohexyl]-4-oxo-4,5-dihydro-1H-pyrazolo[4,3-c]pyridin-3-yl}amino)benzyl]pyrimidine-2-carboxamide | Calc'd 469, found 469 |
| 3-18 | 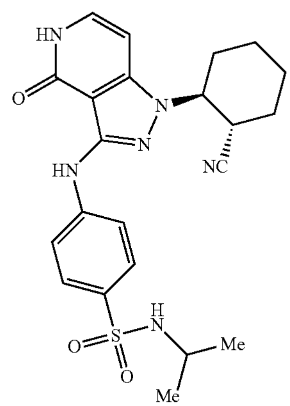 [SMILES: CC(C)NS(=O)(=O)c1ccc(Nc2nn([C@H]3CCCC[C@@H]3C#N)c3cc[nH]c(=O)c23)cc1] | 4-({1-[(1S,2S)-2-cyanocyclohexyl]-4-oxo-4,5-dihydro-1H-pyrazolo[4,3-c]pyridin-3-yl}amino)-N-(1-methylethyl)benzenesulfonamide | Calc'd 455, found 455 |

TABLE 37-continued

| Example | Structure | Compound Name | LRMS [M + H]+ |
|---|---|---|---|
| 3-19 | 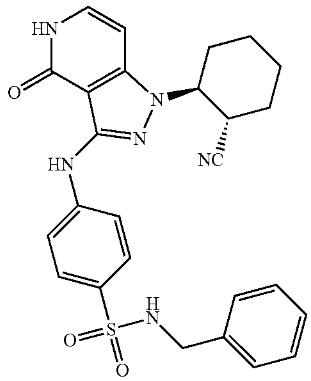 [SMILES: N#C[C@H]1CCCC[C@@H]1n1nc(Nc2ccc(S(=O)(=O)NCc3ccccc3)cc2)c2c(=O)[nH]ccc21] | N-benzyl-4-({1-[(1S,2S)-2-cyanocyclohexyl]-4-oxo-4,5-dihydro-1H-pyrazolo[4,3-c]pyridin-3-yl}amino)benzenesulfonamide | Calc'd 503, found 503 |
| 3-20 | 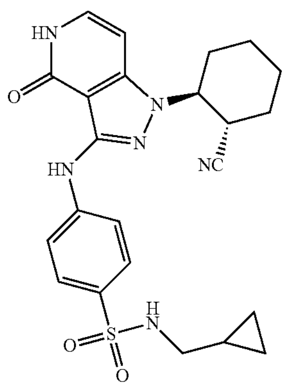 [SMILES: N#C[C@H]1CCCC[C@@H]1n1nc(Nc2ccc(S(=O)(=O)NCC3CC3)cc2)c2c(=O)[nH]ccc21] | 4-({1-[(1S,2S)-2-cyanocyclohexyl]-4-oxo-4,5-dihydro-1H-pyrazolo[4,3-c]pyridin-3-yl}amino)-N-(cyclopropylmethyl)benzenesulfonamide | Calc'd 467, found 467 |
| 3-21 | 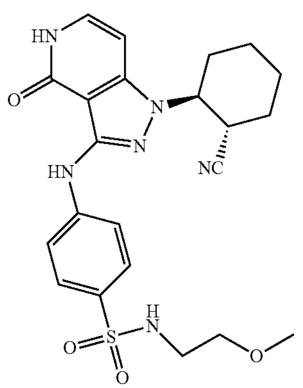 [SMILES: COCCNS(=O)(=O)c1ccc(Nc2nn([C@H]3CCCC[C@@H]3C#N)c3cc[nH]c(=O)c23)cc1] | 4-({1-[(1S,2S)-2-cyanocyclohexyl]-4-oxo-4,5-dihydro-1H-pyrazolo[4,3-c]pyridin-3-yl}amino)-N-(2-methoxyethyl)benzenesulfonamide | Calc'd 471, found 471 |
| 3-22 | 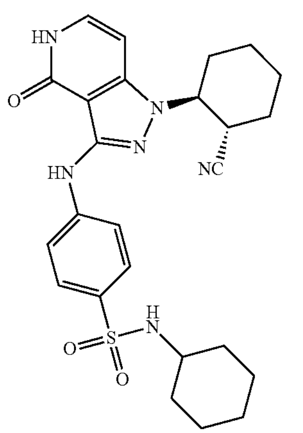 [SMILES: N#C[C@H]1CCCC[C@@H]1n1nc(Nc2ccc(S(=O)(=O)NC3CCCCC3)cc2)c2c(=O)[nH]ccc21] | 4-({1-[(1S,2S)-2-cyanocyclohexyl]-4-oxo-4,5-dihydro-1H-pyrazolo[4,3-c]pyridin-3-yl}amino)-N-cyclohexylbenzenesulfonamide | Calc'd 495, found 495 |

TABLE 37-continued

| Example | Structure | Compound Name | LRMS [M + H]+ |
|---|---|---|---|
| 3-23 | 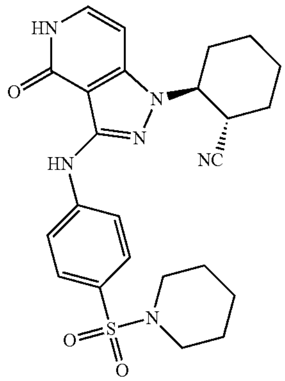 [SMILES: N#C[C@H]1CCCC[C@@H]1n1nc(Nc2ccc(S(=O)(=O)N3CCCCC3)cc2)c2c(=O)[nH]ccc21] | (1S,2S)-2-(4-oxo-3-{[4-(piperidin-1-ylsulfonyl)phenyl]amino}-4,5-dihydro-1H-pyrazolo[4,3-c]pyridin-1-yl)cyclohexanecarbonitrile | Calc'd 481, found 481 |
| 3-24 | 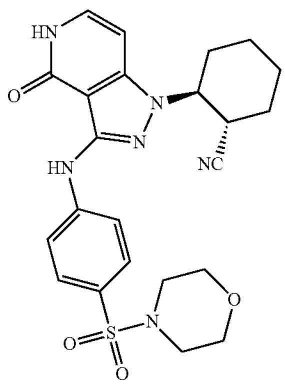 [SMILES: N#C[C@H]1CCCC[C@@H]1n1nc(Nc2ccc(S(=O)(=O)N3CCOCC3)cc2)c2c(=O)[nH]ccc21] | (1S,2S)-2-(3-{[4-(morpholin-4-ylsulfonyl)phenyl]amino}-4-oxo-4,5-dihydro-1H-pyrazolo[4,3-c]pyridin-1-yl)cyclohexanecarbonitrile | Calc'd 483, found 483 |
| 3-25 | 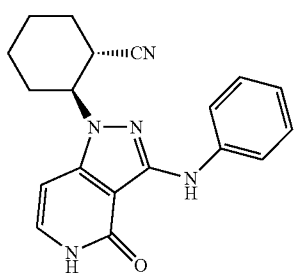 [SMILES: N#C[C@H]1CCCC[C@@H]1n1nc(Nc2ccccc2)c2c(=O)[nH]ccc21] | (1S,2S)-2-[4-oxo-3-(phenylamino)-4,5-dihydro-1H-pyrazolo[4,3-c]pyridin-1-yl]cyclohexanecarbonitrile | Calc'd 334, found 334 |
| 3-26 | 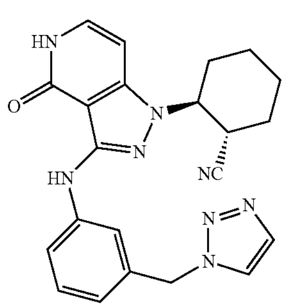 [SMILES: N#C[C@H]1CCCC[C@@H]1n1nc(Nc2cccc(Cn3ccnn3)c2)c2c(=O)[nH]ccc21] | (1S,2S)-2-(4-oxo-3-{[3-(1H-1,2,3-triazol-1-ylmethyl)phenyl]amino}-4,5-dihydro-1H-pyrazolo[4,3-c]pyridin-1-yl)cyclohexanecarbonitrile | Calc'd 415, found 415 |

TABLE 37-continued

| Example | Structure | Compound Name | LRMS [M + H]+ |
|---|---|---|---|
| 3-27 | 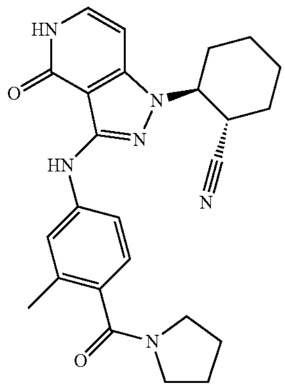 [SMILES: Cc1cc(Nc2nn([C@H]3CCCC[C@@H]3C#N)c3cc[nH]c(=O)c23)ccc1C(=O)N1CCCC1] | (1S,2S)-2-(3-{[3-methyl-4-(pyrrolidin-1-ylcarbonyl)phenyl]amino}-4-oxo-4,5-dihydro-1H-pyrazolo[4,3-c]pyridin-1-yl)cyclohexanecarbonitrile | Calc'd 445, found 445 |
| 3-28 | 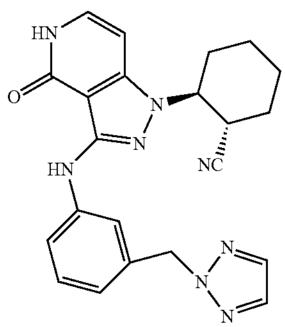 [SMILES: N#C[C@H]1CCCC[C@@H]1n1nc(Nc2cccc(Cn3nccn3)c2)c2c(=O)[nH]ccc21] | (1S,2S)-2-(4-oxo-3-{[3-(2H-1,2,3-triazol-2-ylmethyl)phenyl]amino}-4,5-dihydro-1H-pyrazolo[4,3-c]pyridin-1-yl)cyclohexanecarbonitrile | Calc'd 415, found 415 |
| 3-29 | 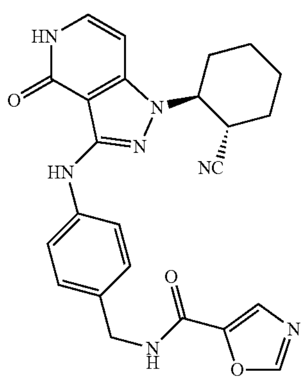 [SMILES: N#C[C@H]1CCCC[C@@H]1n1nc(Nc2ccc(CNC(=O)c3cnco3)cc2)c2c(=O)[nH]ccc21] | N-[4-({1-[(1S,2S)-2-cyanocyclohexyl]-4-oxo-4,5-dihydro-1H-pyrazolo[4,3-c]pyridin-3-yl}amino)benzyl]-1,3-oxazole-5-carboxamide | Calc'd 458, found 458 |
| 3-30 | 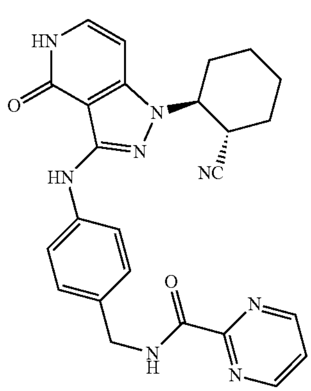 [SMILES: N#C[C@H]1CCCC[C@@H]1n1nc(Nc2ccc(CNC(=O)c3ncccn3)cc2)c2c(=O)[nH]ccc21] | N-[4-({1-[(1S,2S)-2-cyanocyclohexyl]-4-oxo-4,5-dihydro-1H-pyrazolo[4,3-c]pyridin-3-yl}amino)benzyl]pyrimidine-2-carboxamide | Calc'd 469, found 469 |

TABLE 37-continued

| Example | Structure | Compound Name | LRMS [M + H]+ |
|---|---|---|---|
| 3-31 | 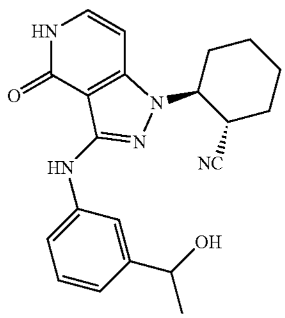 [SMILES: CC(O)c1cccc(Nc2nn([C@H]3CCCC[C@@H]3C#N)c3cc[nH]c(=O)c23)c1] | (1S,2S)-2-(3-{[3-(1-hydroxyethyl)phenyl]amino}-4-oxo-4,5-dihydro-1H-pyrazolo[4,3-c]pyridin-1-yl)cyclohexanecarbonitrile | Calc'd 378, found 378 |
| 3-32 | 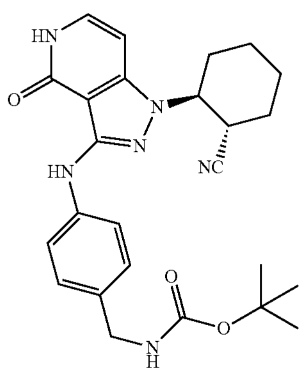 [SMILES: CC(C)(C)OC(=O)NCc1ccc(Nc2nn([C@H]3CCCC[C@@H]3C#N)c3cc[nH]c(=O)c23)cc1] | tert-butyl [4-({1-[(1S,2S)-2-cyanocyclohexyl]-4-oxo-4,5-dihydro-1H-pyrazolo[4,3-c]pyridin-3-yl}amino)benzyl]carbamate | Calc'd 463, found 463 |
| 3-33 | 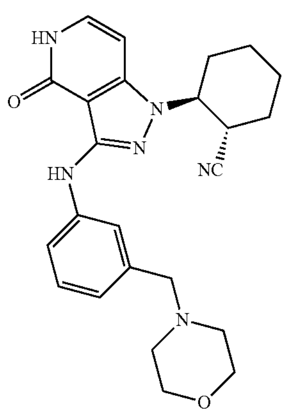 [SMILES: N#C[C@H]1CCCC[C@@H]1n1nc(Nc2cccc(CN3CCOCC3)c2)c2c(=O)[nH]ccc21] | (1S,2S)-2-(3-{[3-(morpholin-4-ylmethyl)phenyl]amino}-4-oxo-4,5-dihydro-1H-pyrazolo[4,3-c]pyridin-1-yl)cyclohexanecarbonitrile | Calc'd 433, found 433 |
| 3-34 | 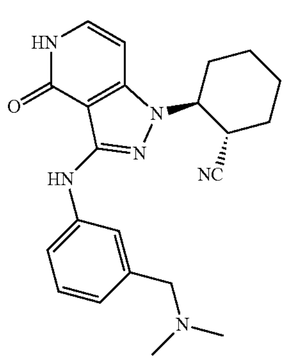 [SMILES: CN(C)Cc1cccc(Nc2nn([C@H]3CCCC[C@@H]3C#N)c3cc[nH]c(=O)c23)c1] | (1S,2S)-2-[3-({3-[(dimethylamino)methyl]phenyl}amino)-4-oxo-4,5-dihydro-1H-pyrazolo[4,3-c]pyridin-1-yl]cyclohexanecarbonitrile | Calc'd 391, found 391 |

TABLE 37-continued

| Example | Structure | Compound Name | LRMS [M + H]+ |
|---|---|---|---|
| 3-35 | 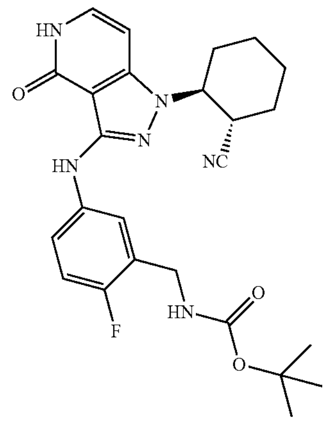 [SMILES: CC(C)(C)OC(=O)NCc1cc(Nc2nn([C@H]3CCCC[C@@H]3C#N)c3cc[nH]c(=O)c23)ccc1F] | tert-butyl [5-({1-[(1S,2S)-2-cyanocyclohexyl]-4-oxo-4,5-dihydro-1H-pyrazolo[4,3-c]pyridin-3-yl}amino)-2-fluorobenzyl]carbamate | Calc'd 481, found 425 [M − tBu] |
| 3-36 | 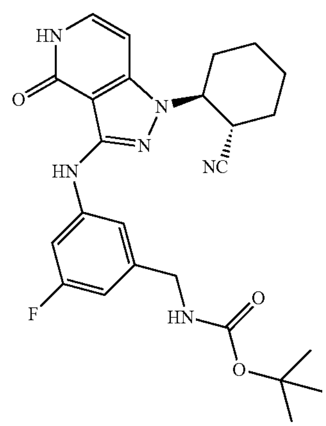 [SMILES: CC(C)(C)OC(=O)NCc1cc(F)cc(Nc2nn([C@H]3CCCC[C@@H]3C#N)c3cc[nH]c(=O)c23)c1] | tert-butyl [3-({1-[(1S,2S)-2-cyanocyclohexyl]-4-oxo-4,5-dihydro-1H-pyrazolo[4,3-c]pyridin-3-yl}amino)-5-fluorobenzyl]carbamate | Calc'd 481, found 425 [M − tBu] |
| 3-37 | 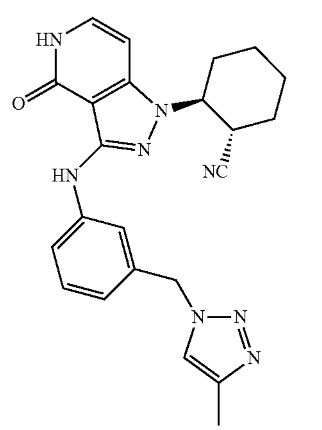 [SMILES: Cc1cn(Cc2cccc(Nc3nn([C@H]4CCCC[C@@H]4C#N)c4cc[nH]c(=O)c34)c2)nn1] | (1S,2S)-2-[3-({3-[(4-methyl-1H-1,2,3-triazol-1-yl)methyl]phenyl}amino)-4-oxo-4,5-dihydro-1H-pyrazolo[4,3-c]pyridin-1-yl]cyclohexanecarbonitrile | Calc'd 429, found 429 |

TABLE 37-continued

| Example | Structure | Compound Name | LRMS [M + H]+ |
|---|---|---|---|
| 3-38 | 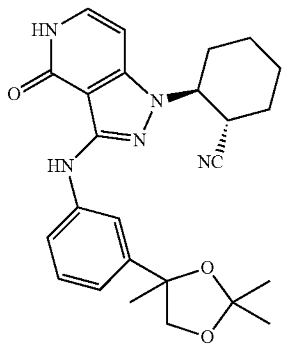 [SMILES: CC1(C)OCC(C)(c2cccc(Nc3nn([C@H]4CCCC[C@@H]4C#N)c4cc[nH]c(=O)c34)c2)O1] | (1S,2S)-2-(4-oxo-3-{[3-(2,2,4-trimethyl-1,3-dioxolan-4-yl)phenyl]amino}-4,5-dihydro-1H-pyrazolo[4,3-c]pyridin-1-yl)cyclohexanecarbonitrile | Calc'd 448, found 448 |
| 3-39 | 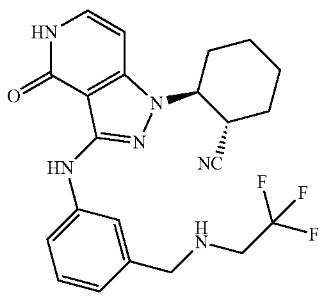 [SMILES: N#C[C@H]1CCCC[C@@H]1n1nc(Nc2cccc(CNCC(F)(F)F)c2)c2c(=O)[nH]ccc21] | (1S,2S)-2-{4-oxo-3-[(3-{[(2,2,2-trifluoroethyl)amino]methyl}phenyl)amino]-4,5-dihydro-1H-pyrazolo[4,3-c]pyridin-1-yl}cyclohexanecarbonitrile | Calc'd 445, found 445 |
| 3-40 | 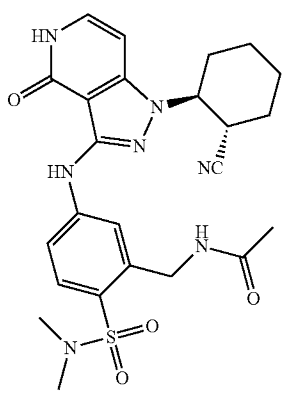 [SMILES: CC(=O)NCc1cc(Nc2nn([C@H]3CCCC[C@@H]3C#N)c3cc[nH]c(=O)c23)ccc1S(=O)(=O)N(C)C] | N-[5-({1-[(1S,2S)-2-cyanocyclohexyl]-4-oxo-4,5-dihydro-1H-pyrazolo[4,3-c]pyridin-3-yl}amino)-2-(dimethylsulfamoyl)benzyl]acetamide | Calc'd 512, found 512 |
| 3-41 | 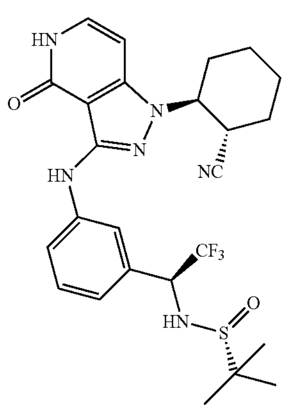 [SMILES: CC(C)(C)[S@@](=O)N[C@@H](c1cccc(Nc2nn([C@H]3CCCC[C@@H]3C#N)c3cc[nH]c(=O)c23)c1)C(F)(F)F] | N-{(1S)-1-[3-({1-[(1S,2S)-2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide (from I-65) | Calc'd 535, found 535 |

TABLE 37-continued

| Example | Structure | Compound Name | LRMS [M + H]+ |
|---|---|---|---|
| 3-42 | 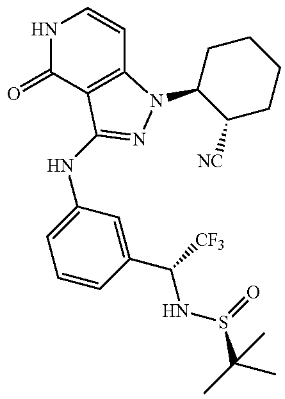 [SMILES: CC(C)(C)[S@](=O)N[C@H](c1cccc(Nc2nn([C@H]3CCCC[C@@H]3C#N)c3cc[nH]c(=O)c23)c1)C(F)(F)F] | N-{(1R)-1-[3-({1-[(1S,2S)-2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide (from I-66) | Calc'd 535, found 535 |
| 3-43 | 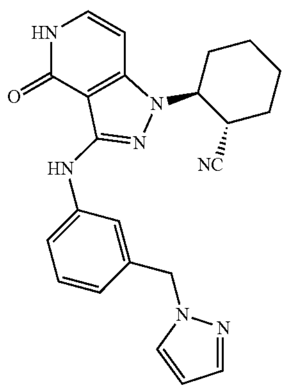 [SMILES: N#C[C@H]1CCCC[C@@H]1n1nc(Nc2cccc(Cn3cccn3)c2)c2c(=O)[nH]ccc21] | (1S,2S)-2-(4-oxo-3-{[3-(1H-pyrazol-1-ylmethyl)phenyl]amino}-4,5-dihydro-1H-pyrazolo[4,3-c]pyridin-1-yl)cyclohexanecarbonitrile | Calc'd 414, found 414 |
| 3-44 | 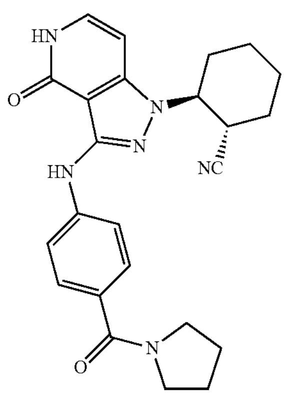 [SMILES: N#C[C@H]1CCCC[C@@H]1n1nc(Nc2ccc(C(=O)N3CCCC3)cc2)c2c(=O)[nH]ccc21] | (1S,2S)-2-(4-oxo-3-{[4-(pyrrolidin-1-ylcarbonyl)phenyl]amino}-4,5-dihydro-1H-pyrazolo[4,3-c]pyridin-1-yl)cyclohexanecarbonitrile | Calc'd 431, found 431 |
| 3-45 | 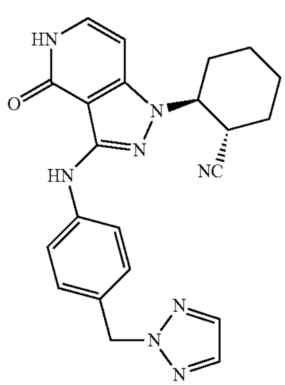 [SMILES: N#C[C@H]1CCCC[C@@H]1n1nc(Nc2ccc(Cn3nccn3)cc2)c2c(=O)[nH]ccc21] | (1S,2S)-2-(4-oxo-3-{[4-(2H-1,2,3-triazol-2-ylmethyl)phenyl]amino}-4,5-dihydro-1H-pyrazolo[4,3-c]pyridin-1-yl)cyclohexanecarbonitrile | Calc'd 415, found 415 |

TABLE 37-continued

| Example | Structure | Compound Name | LRMS [M + H]+ |
|---|---|---|---|
| 3-46 | 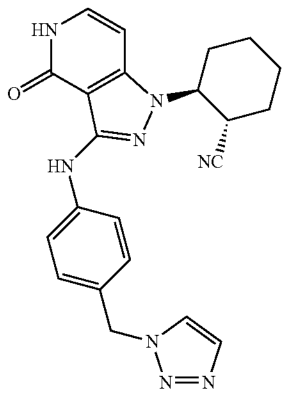 [SMILES: N#C[C@H]1CCCC[C@@H]1n1nc(Nc2ccc(Cn3ccnn3)cc2)c2c(=O)[nH]ccc21] | (1S,2S)-2-(4-oxo-3-{[4-(1H-1,2,3-triazol-1-ylmethyl)phenyl]amino}-4,5-dihydro-1H-pyrazolo[4,3-c]pyridin-1-yl)cyclohexanecarbonitrile | Calc'd 415, found 415 |
| 3-47 | 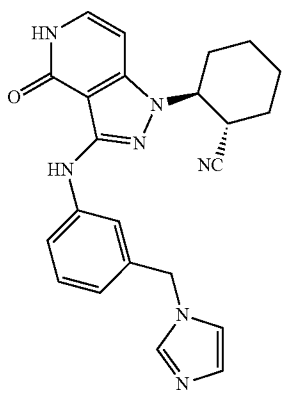 [SMILES: N#C[C@H]1CCCC[C@@H]1n1nc(Nc2cccc(Cn3ccnc3)c2)c2c(=O)[nH]ccc21] | (1S,2S)-2-(3-{[3-(1H-imidazol-1-ylmethyl)phenyl]amino}-4-oxo-4,5-dihydro-1H-pyrazolo[4,3-c]pyridin-1-yl)cyclohexanecarbonitrile | Calc'd 414, found 414 |
| 3-48 | 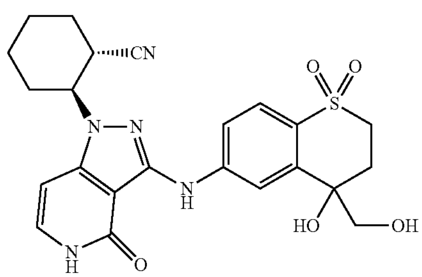 [SMILES: N#C[C@H]1CCCC[C@@H]1n1nc(Nc2ccc3c(c2)C(O)(CO)CCS3(=O)=O)c2c(=O)[nH]ccc21] | (1S,2S)-2-(3-{[4-hydroxy-4-(hydroxymethyl)-1,1-dioxido-3,4-dihydro-2H-thiochromen-6-yl]amino}-4-oxo-4,5-dihydro-1H-pyrazolo[4,3-c]pyridin-1-yl)cyclohexanecarbonitrile | Calc'd 484, found 484 |
| 3-49 | 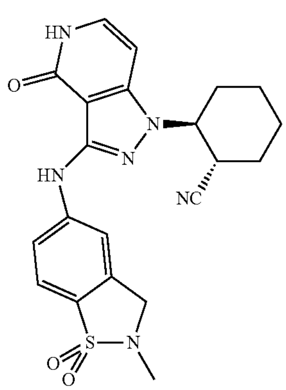 [SMILES: CN1Cc2cc(Nc3nn([C@H]4CCCC[C@@H]4C#N)c4cc[nH]c(=O)c34)ccc2S1(=O)=O] | (1S,2S)-2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile | Calc'd 439, found 439 |

TABLE 37-continued

| Example | Structure | Compound Name | LRMS [M + H]+ |
|---|---|---|---|
| 3-50 | 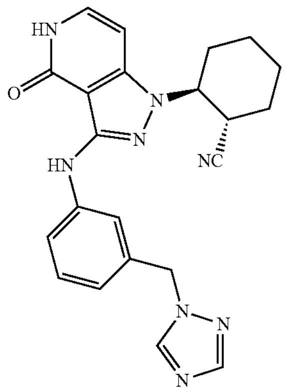 [SMILES: N#C[C@H]1CCCC[C@@H]1n1nc(Nc2cccc(Cn3cncn3)c2)c2c(=O)[nH]ccc21] | (1S,2S)-2-(4-oxo-3-{[3-(1H-1,2,4-triazol-1-ylmethyl)phenyl]amino}-4,5-dihydro-1H-pyrazolo[4,3-c]pyridin-1-yl)cyclohexanecarbonitrile | Calc'd 415, found 415 |
| 3-51 | 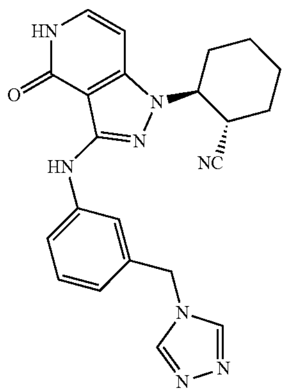 [SMILES: N#C[C@H]1CCCC[C@@H]1n1nc(Nc2cccc(Cn3cnnc3)c2)c2c(=O)[nH]ccc21] | (1S,2S)-2-(4-oxo-3-{[3-(4H-1,2,4-triazol-4-ylmethyl)phenyl]amino}-4,5-dihydro-1H-pyrazolo[4,3-c]pyridin-1-yl)cyclohexanecarbonitrile | Calc'd 415, found 415 |
| 3-52 | 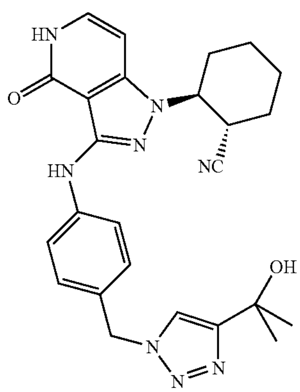 [SMILES: CC(C)(O)c1cn(Cc2ccc(Nc3nn([C@H]4CCCC[C@@H]4C#N)c4cc[nH]c(=O)c34)cc2)nn1] | (1S,2S)-2-{3-[(4-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile | Calc'd 473, found 473 |
| 3-53 | 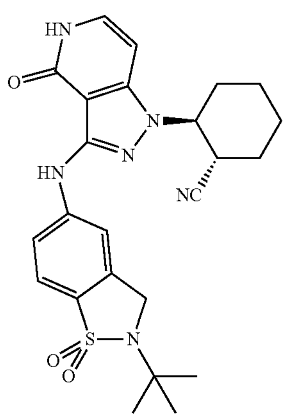 [SMILES: CC(C)(C)N1Cc2cc(Nc3nn([C@H]4CCCC[C@@H]4C#N)c4cc[nH]c(=O)c34)ccc2S1(=O)=O] | (1S,2S)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile | Calc'd 481, found 425 [M − tBu] |

TABLE 37-continued

| Example | Structure | Compound Name | LRMS [M + H]+ |
|---|---|---|---|
| 3-54 | 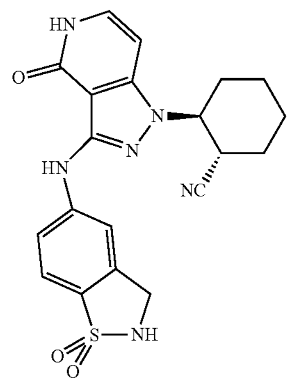 [SMILES: N#C[C@H]1CCCC[C@@H]1n1nc(Nc2ccc3c(c2)CNS3(=O)=O)c2c(=O)[nH]ccc21] | (1S,2S)-2-{3-[(1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile | Calc'd 425, found 425 |
| 3-55 | 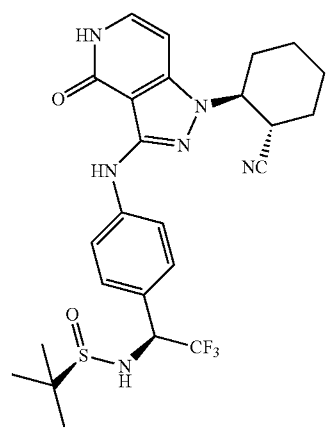 [SMILES: CC(C)(C)[S@@](=O)N[C@@H](c1ccc(Nc2nn([C@H]3CCCC[C@@H]3C#N)c3cc[nH]c(=O)c23)cc1)C(F)(F)F] | N-{(1S)-1-[4-({1-[(1S,2S)-2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide (from I-68) | Calc'd 535, found 535 |
| 3-56 | 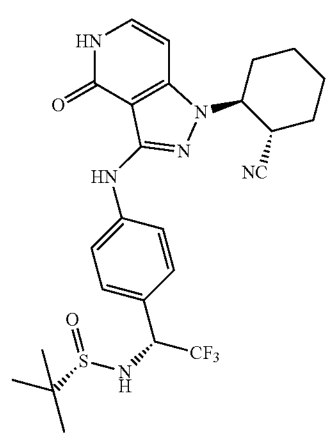 [SMILES: CC(C)(C)[S@](=O)N[C@H](c1ccc(Nc2nn([C@H]3CCCC[C@@H]3C#N)c3cc[nH]c(=O)c23)cc1)C(F)(F)F] | N-{(1R)-1-[4-({1-[(1S,2S)-2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide (from I-67) | Calc'd 535, found 535 |

TABLE 37-continued

| Example | Structure | Compound Name | LRMS [M + H]+ |
|---|---|---|---|
| 3-57 | 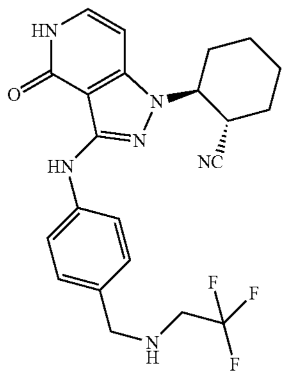 [SMILES: N#C[C@H]1CCCC[C@@H]1n1nc(Nc2ccc(CNCC(F)(F)F)cc2)c2c(=O)[nH]ccc21] | (1S,2S)-2-{4-oxo-3-[(4-{[(2,2,2-trifluoroethyl)amino]methyl}phenyl)amino]-4,5-dihydro-1H-pyrazolo[4,3-c]pyridin-1-yl}cyclohexanecarbonitrile | Calc'd 445, found: 445 |
| 3-58 | 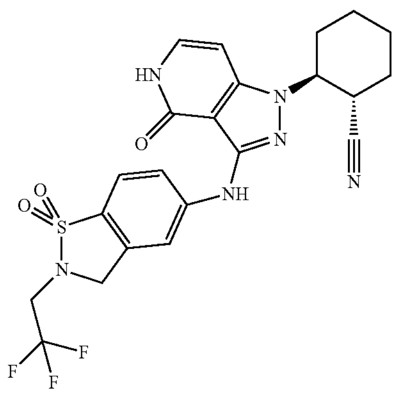 [SMILES: N#C[C@H]1CCCC[C@@H]1n1nc(Nc2ccc3c(c2)CN(CC(F)(F)F)S3(=O)=O)c2c(=O)[nH]ccc21] | (1S,2S)-2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 507, found 507 |
| 3-59 | 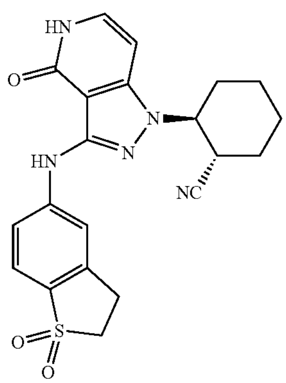 [SMILES: N#C[C@H]1CCCC[C@@H]1n1nc(Nc2ccc3c(c2)CCS3(=O)=O)c2c(=O)[nH]ccc21] | (1S,2S)-2-{3-[(1,1-dioxido-2,3-dihydro-1-benzothiophen-5-yl)amino]-4-oxo-4,5-dihydro-1H-pyrazolo[4,3-c]pyridin-1-yl}cyclohexanecarbonitrile | Calc'd 424, found 424 |
| 3-60 | 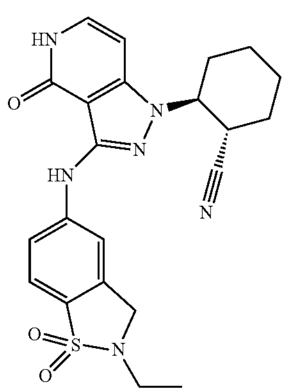 [SMILES: CCN1Cc2cc(Nc3nn([C@H]4CCCC[C@@H]4C#N)c4cc[nH]c(=O)c34)ccc2S1(=O)=O] | (1S,2S)-2-{3-[(2-ethyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile | Calc'd 453, found 453 |

TABLE 37-continued

| Example | Structure | Compound Name | LRMS [M + H]+ |
|---|---|---|---|
| 3-61 | 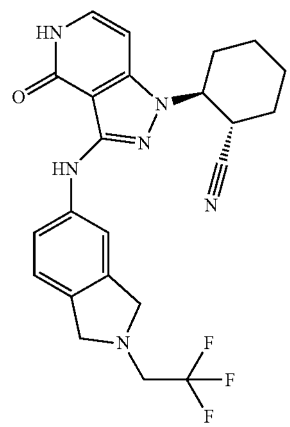 [SMILES: N#C[C@H]1CCCC[C@@H]1n1nc(Nc2ccc3c(c2)CN(CC(F)(F)F)C3)c2c(=O)[nH]ccc21] | (1S,2S)-2-(4-oxo-3-{[2-(2,2,2-trifluoroethyl)-2,3-dihydro-1H-isoindol-5-yl]amino}-4,5-dihydro-1H-pyrazolo[4,3-c]pyridin-1-yl}cyclohexanecarbonitrile | Calc'd 457, found 457 |
| 3-62 | 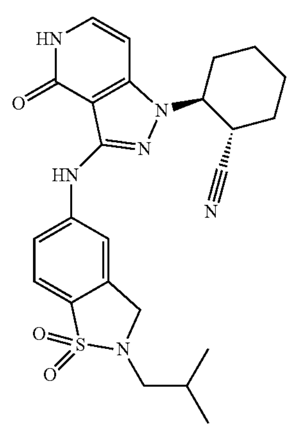 [SMILES: CC(C)CN1Cc2cc(Nc3nn([C@H]4CCCC[C@@H]4C#N)c4cc[nH]c(=O)c34)ccc2S1(=O)=O] | (1S,2S)-2-(3-{[2-(2-methylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 481, found 481 |
| 3-63 | 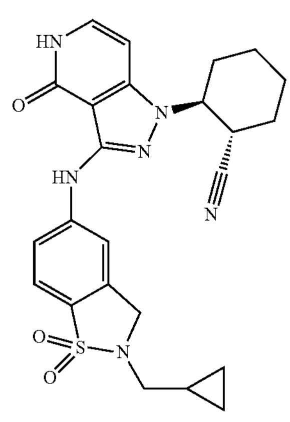 [SMILES: N#C[C@H]1CCCC[C@@H]1n1nc(Nc2ccc3c(c2)CN(CC2CC2)S3(=O)=O)c2c(=O)[nH]ccc21] | (1S,2S)-2-(3-{[2-(cyclopropylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 479, found 479 |

TABLE 37-continued

| Example | Structure | Compound Name | LRMS [M + H]+ |
|---|---|---|---|
| 3-64 | 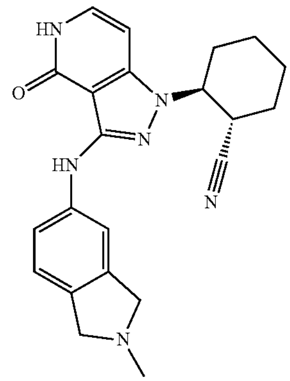 [SMILES: CN1Cc2ccc(Nc3nn([C@H]4CCCC[C@@H]4C#N)c4cc[nH]c(=O)c34)cc2C1] | (1S,2S)-2-{3-[(2-methyl-2,3-dihydro-1H-isoindol-5-yl)amino]-4-oxo-4,5-dihydro-1H-pyrazolo[4,3-c]pyridin-1-yl}cyclohexanecarbonitrile | Calc'd 389, found 389 |
| 3-65 | 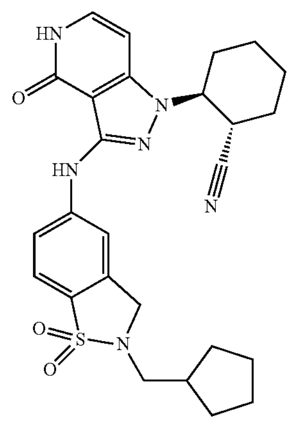 [SMILES: N#C[C@H]1CCCC[C@@H]1n1nc(Nc2ccc3c(c2)CN(CC2CCCC2)S3(=O)=O)c2c(=O)[nH]ccc21] | (1S,2S)-2-(3-{[2-(cyclopentylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 507, found 507 |
| 3-66 | 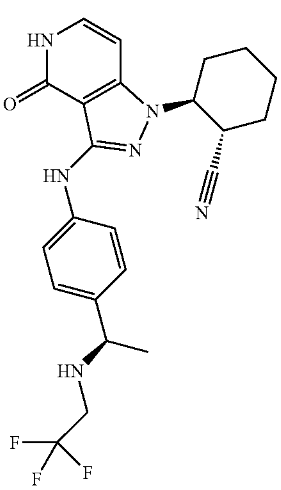 [SMILES: C[C@@H](NCC(F)(F)F)c1ccc(Nc2nn([C@H]3CCCC[C@@H]3C#N)c3cc[nH]c(=O)c23)cc1] | (1S,2S)-2-{4-oxo-3-[(4-{(1R)-1-[(2,2,2-trifluoroethyl)amino]ethyl}phenyl)amino]-4,5-dihydro-1H-pyrazolo[4,3-c]pyridin-1-yl}cyclohexanecarbonitrile (from I-49) | Calc'd 459, found 459 |

TABLE 37-continued

| Example | Structure | Compound Name | LRMS [M + H]+ |
|---|---|---|---|
| 3-67 | 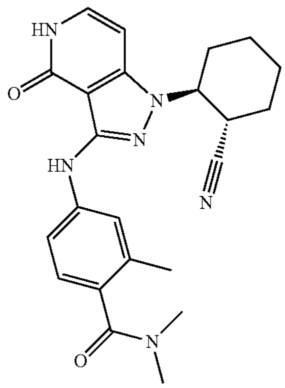 [SMILES: Cc1cc(Nc2nn([C@H]3CCCC[C@@H]3C#N)c3cc[nH]c(=O)c23)ccc1C(=O)N(C)C] | 4-({1-[(1S,2S)-2-cyanocyclohexyl]-4-oxo-4,5-dihydro-1H-pyrazolo[4,3-c]pyridin-3-yl}amino)-N,N,2-trimethylbenzamide | Calc'd 419, found 419 |
| 3-68 | 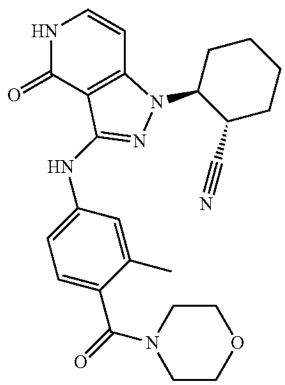 [SMILES: Cc1cc(Nc2nn([C@H]3CCCC[C@@H]3C#N)c3cc[nH]c(=O)c23)ccc1C(=O)N1CCOCC1] | (1S,2S)-2-(3-{[3-methyl-4-(morpholin-4-ylcarbonyl)phenyl]amino}-4-oxo-4,5-dihydro-1H-pyrazolo[4,3-c]pyridin-1-yl)cyclohexanecarbonitrile | Calc'd 461, found 461 |
| 3-69 | 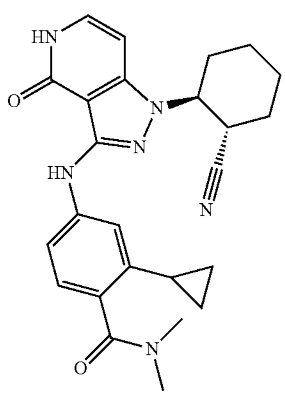 [SMILES: CN(C)C(=O)c1ccc(Nc2nn([C@H]3CCCC[C@@H]3C#N)c3cc[nH]c(=O)c23)cc1C1CC1] | 4-({1-[(1S,2S)-2-cyanocyclohexyl]-4-oxo-4,5-dihydro-1H-pyrazolo[4,3-c]pyridin-3-yl}amino)-2-cyclopropyl-N,N-dimethylbenzamide | Calc'd 445, found 445 |
| 3-70 | 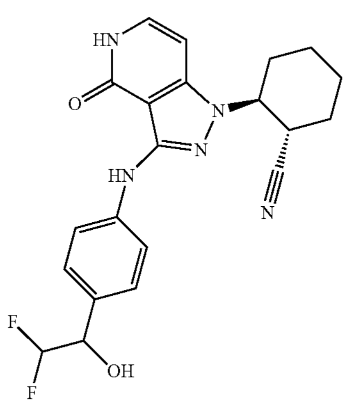 [SMILES: N#C[C@H]1CCCC[C@@H]1n1nc(Nc2ccc(C(O)C(F)F)cc2)c2c(=O)[nH]ccc21] | (1S,2S)-2-(3-{[4-(2,2-difluoro-1-hydroxyethyl)phenyl]amino}-4-oxo-4,5-dihydro-1H-pyrazolo[4,3-c]pyridin-1-yl)cyclohexanecarbonitrile (mix of diastereomers) | Calc'd 414, found 414 |

TABLE 37-continued

| Example | Structure | Compound Name | LRMS [M + H]+ |
|---|---|---|---|
| 3-71 | 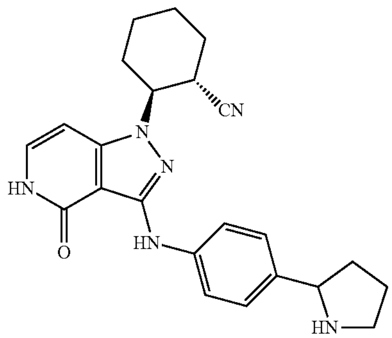 [SMILES: N#C[C@H]1CCCC[C@@H]1n1nc(Nc2ccc(C3CCCN3)cc2)c2c(=O)[nH]ccc21] | (1S,2S)-2-[4-oxo-3-({4-[(2S or 2R)-pyrrolidin-2-yl]phenyl}amino)-4,5-dihydro-1H-pyrazolo[4,3-c]pyridin-1-yl]cyclohexanecarbonitrile (Derived from Peak A via SFC separation of pyridone final compound, AD-H, 55% Hexanes in EtOH, Tr = 16 mins) | Calc'd 403, found 403 |
| 3-72 | 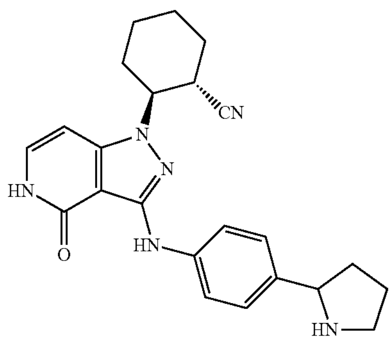 [SMILES: N#C[C@H]1CCCC[C@@H]1n1nc(Nc2ccc(C3CCCN3)cc2)c2c(=O)[nH]ccc21] | (1S,2S)-2-[4-oxo-3-({4-[(2R or 2S)-pyrrolidin-2-yl]phenyl}amino)-4,5-dihydro-1H-pyrazolo[4,3-c]pyridin-1-yl]cyclohexanecarbonitrile (Derived from Peak B via SFC separation of pyridone final compound, AD-H, 55% Hexanes in EtOH, Tr = 23 mins) | Calc'd 403, found 403 |
| 3-73 | 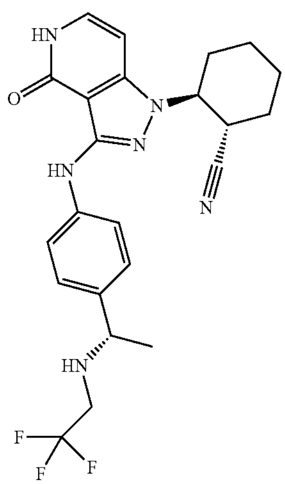 [SMILES: C[C@H](NCC(F)(F)F)c1ccc(Nc2nn([C@H]3CCCC[C@@H]3C#N)c3cc[nH]c(=O)c23)cc1] | (1S,2S)-2-{4-oxo-3-[(4-{(1S)-1-[(2,2,2-trifluoroethyl)amino]ethyl}phenyl)amino]-4,5-dihydro-1H-pyrazolo[4,3-c]pyridin-1-yl}cyclohexanecarbonitrile (from I-50) | Calc'd 459, found 459 |
| 3-74 | 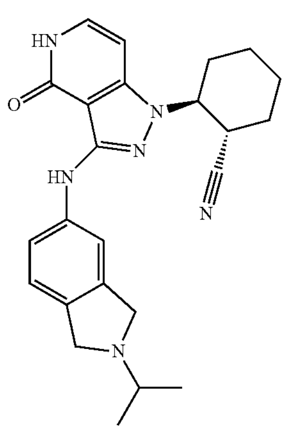 [SMILES: CC(C)N1Cc2ccc(Nc3nn([C@H]4CCCC[C@@H]4C#N)c4cc[nH]c(=O)c34)cc2C1] | (1S,2S)-2-(3-{[2-(1-methylethyl)-2,3-dihydro-1H-isoindol-5-yl]amino}-4-oxo-4,5-dihydro-1H-pyrazolo[4,3-c]pyridin-1-yl)cyclohexanecarbonitrile | Calc'd 417, found 417 |

TABLE 37-continued

| Example | Structure | Compound Name | LRMS [M + H]+ |
|---|---|---|---|
| 3-75 | 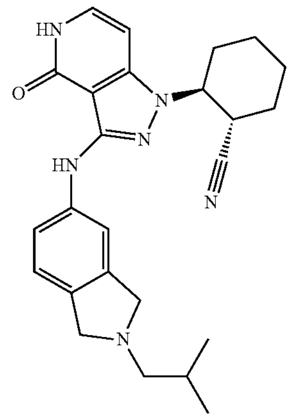 [SMILES: CC(C)CN1Cc2ccc(Nc3nn([C@H]4CCCC[C@@H]4C#N)c4cc[nH]c(=O)c34)cc2C1] | (1S,2S)-2-(3-{[2-(2-methylpropyl)-2,3-dihydro-1H-isoindol-5-yl]amino}-4-oxo-4,5-dihydro-1H-pyrazolo[4,3-c]pyridin-1-yl)cyclohexanecarbonitrile | Calc'd 431, found 431 |
| 3-76 | 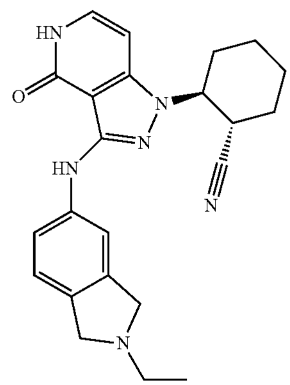 [SMILES: CCN1Cc2ccc(Nc3nn([C@H]4CCCC[C@@H]4C#N)c4cc[nH]c(=O)c34)cc2C1] | (1S,2S)-2-{3-[(2-ethyl-2,3-dihydro-1H-isoindol-5-yl)amino]-4-oxo-4,5-dihydro-1H-pyrazolo[4,3-c]pyridin-1-yl}cyclohexanecarbonitrile | Calc'd 403, found 403 |
| 3-77 | 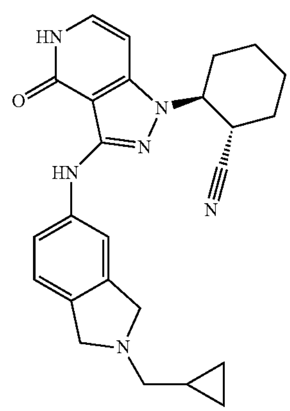 [SMILES: N#C[C@H]1CCCC[C@@H]1n1nc(Nc2ccc3c(c2)CN(CC2CC2)C3)c2c(=O)[nH]ccc21] | (1S,2S)-2-(3-{[2-(cyclopropylmethyl)-2,3-dihydro-1H-isoindol-5-yl]amino}-4-oxo-4,5-dihydro-1H-pyrazolo[4,3-c]pyridin-1-yl)cyclohexanecarbonitrile | Calc'd 429 found 429 |
| 3-78 | 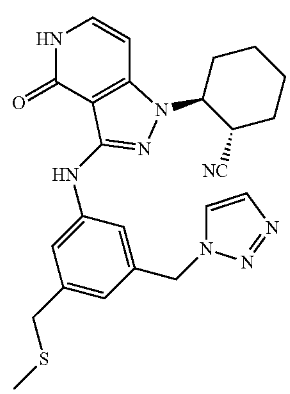 [SMILES: CSCc1cc(Cn2ccnn2)cc(Nc2nn([C@H]3CCCC[C@@H]3C#N)c3cc[nH]c(=O)c23)c1] | (1S,2S)-2-[3-({3-[(methylsulfanyl)methyl]-5-(1H-1,2,3-triazol-1-ylmethyl)phenyl}amino)-4-oxo-4,5-dihydro-1H-pyrazolo[4,3-c]pyridin-1-yl]cyclohexanecarbonitrile | Calc'd 475, found 475 |

TABLE 37-continued

| Example | Structure | Compound Name | LRMS [M + H]+ |
|---------|-----------|---------------|----------------|
| 3-79 | 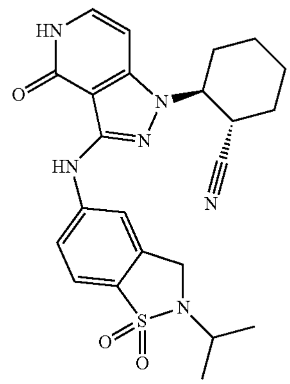 [SMILES: CC(C)N1Cc2cc(Nc3nn([C@H]4CCCC[C@@H]4C#N)c4cc[nH]c(=O)c34)ccc2S1(=O)=O] | (1S,2S)-2-(3-{[2-(1-methylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 467, found 467 |
| 3-80 | 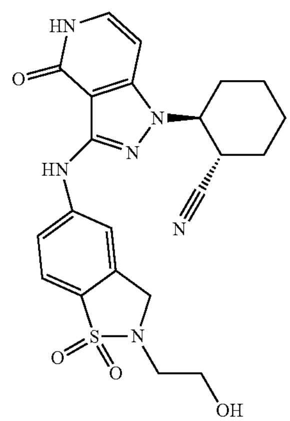 [SMILES: N#C[C@H]1CCCC[C@@H]1n1nc(Nc2ccc3c(c2)CN(CCO)S3(=O)=O)c2c(=O)[nH]ccc21] | (1S,2S)-2-(3-{[2-(2-hydroxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 469, found 469 |
| 3-81 | 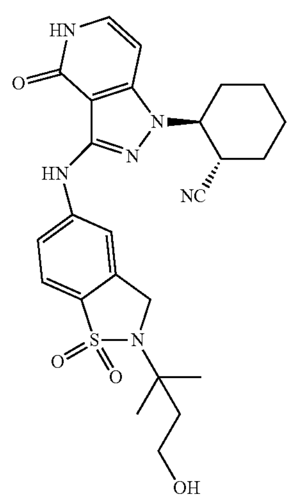 [SMILES: CC(C)(CCO)N1Cc2cc(Nc3nn([C@H]4CCCC[C@@H]4C#N)c4cc[nH]c(=O)c34)ccc2S1(=O)=O] | (1S,2S)-2-(3-{[2-(3-hydroxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 511, found 511 |

TABLE 37-continued

| Example | Structure | Compound Name | LRMS [M + H]+ |
|---|---|---|---|
| 3-82 | 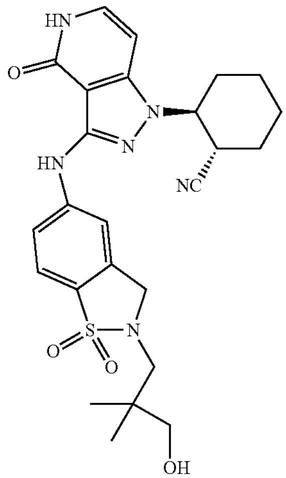 [SMILES: CC(C)(CO)CN1Cc2cc(Nc3nn([C@H]4CCCC[C@@H]4C#N)c4cc[nH]c(=O)c34)ccc2S1(=O)=O] | (1S,2S)-2-(3-{[2-(3-hydroxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 511, found 511 |
| 3-83 | 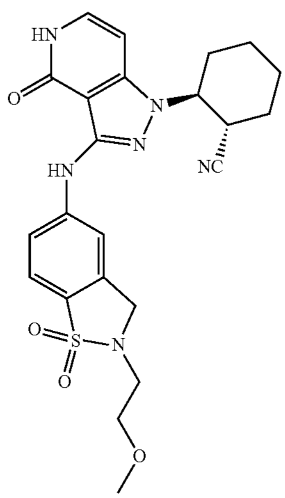 [SMILES: COCCN1Cc2cc(Nc3nn([C@H]4CCCC[C@@H]4C#N)c4cc[nH]c(=O)c34)ccc2S1(=O)=O] | (1S,2S)-2-(3-{[2-(2-methoxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 483, found 483 |
| 3-84 | 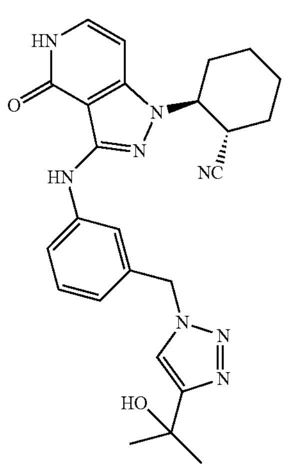 [SMILES: CC(C)(O)c1cn(Cc2cccc(Nc3nn([C@H]4CCCC[C@@H]4C#N)c4cc[nH]c(=O)c34)c2)nn1] | (1S,2S)-2-{3-[(3-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile | Calc'd 473, found 473 |

TABLE 37-continued

| Example | Compound Name | LRMS [M + H]+ |
|---|---|---|
| 3-85 | (1S,2S)-2-(3-{[3-(1-hydroxy-2-methoxy-1-methylethyl)-4-(methylsulfonyl)phenyl]amino}-4-oxo-4,5-dihydro-1H-pyrazolo[4,3-c]pyridin-1-yl)cyclohexanecarbonitrile | Calc'd 500, found 500 |
| 3-86 | (1S,2S)-2-(3-{[3-(1,3-dihydroxy-1-methylpropyl)-4-(methylsulfonyl)phenyl]amino}-4-oxo-4,5-dihydro-1H-pyrazolo[4,3-c]pyridin-1-yl)cyclohexanecarbonitrile | Calc'd 500, found 500 |
| 3-87 | (1S,2S)-2-(3-{[3-(1,2-dihydroxy-1-methylethyl)-4-(methylsulfonyl)phenyl]amino}-4-oxo-4,5-dihydro-1H-pyrazolo[4,3-c]pyridin-1-yl)cyclohexanecarbonitrile | Calc'd 486, found 486 |
| 3-88 | (1S,2S,5R)-5-hydroxy-2-(4-oxo-3-((4-(trifluoromethyl)phenyl)amino)-4,5-dihydro-1H-pyrazolo[4,3-c]pyridin-1-yl)cyclohexanecarbonitrile | Calc'd 508, found 508 |

TABLE 37-continued

| Example | Structure | Compound Name | LRMS [M + H]+ |
|---|---|---|---|
| 3-89 | 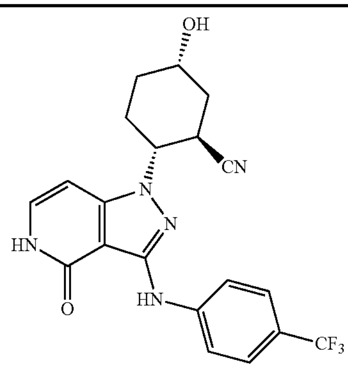 | (1R,2R,5S)-5-hydroxy-2-(4-oxo-3-((4-(trifluoromethyl)phenyl)amino)-4,5-dihydro-1H-pyrazolo[4,3-c]pyridin-1-yl)cyclohexanecarbonitrile | Calc'd 418, found 418 |
| 3-90 | 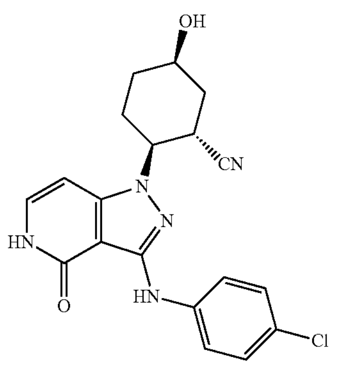 [SMILES: N#C[C@H]1C[C@H](O)CC[C@@H]1n1nc(Nc2ccc(Cl)cc2)c2c(=O)[nH]ccc21] | (1S,2S,5R)-2-(3-((4-chlorophenyl)amino)-4-oxo-4,5-dihydro-1H-pyrazolo[4,3-c]pyridin-1-yl)-5-hydroxycyclohexanecarbonitrile | Calc'd 384, found 384 |
| 3-91 | 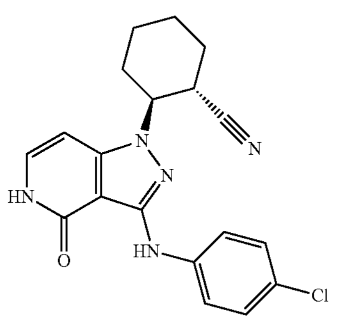 [SMILES: N#C[C@H]1CCCC[C@@H]1n1nc(Nc2ccc(Cl)cc2)c2c(=O)[nH]ccc21] | (1S,2S)-2-(3-((4-chlorophenyl)amino)-4-oxo-4,5-dihydro-1H-pyrazolo[4,3-c]pyridin-1-yl)cyclohexanecarbonitrile | Calc'd 368, found 368 |
| 3-92 | 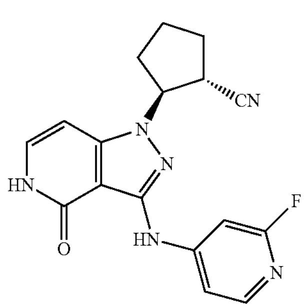 [SMILES: N#C[C@H]1CCC[C@@H]1n1nc(Nc2ccnc(F)c2)c2c(=O)[nH]ccc21] | (1S,2S)-2-{3-[(2-fluoropyridin-4-yl)amino]-4-oxo-4,5-dihydro-1H-pyrazolo[4,3-c]pyridin-1-yl}cyclopentanecarbonitrile | Calc'd 339, found 339 |

TABLE 37-continued

| Example | Structure | Compound Name | LRMS [M + H]+ |
|---------|-----------|---------------|---------------|
| 3-93 | 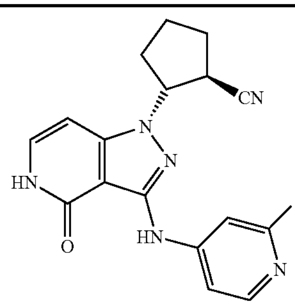 | (1R,2R)-2-{3-[(2-fluoropyridin-4-yl)amino]-4-oxo-4,5-dihydro-1H-pyrazolo[4,3-c]pyridin-1-yl}cyclopentanecarbonitrile | Calc'd 339, found 339 |
| 3-94 | 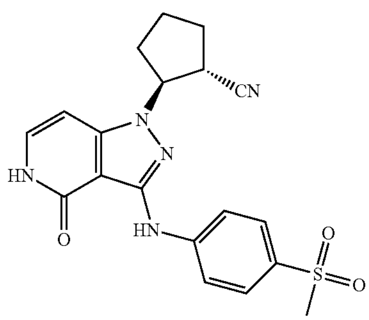 [SMILES: CS(=O)(=O)c1ccc(Nc2nn([C@H]3CCC[C@@H]3C#N)c3cc[nH]c(=O)c23)cc1] | (1S,2S)-2-(3-{[4-(methylsulfonyl)phenyl]amino}-4-oxo-4,5-dihydro-1H-pyrazolo[4,3-c]pyridin-1-yl)cyclopentanecarbonitrile | Calc'd 398, found 398 |
| 3-95 | 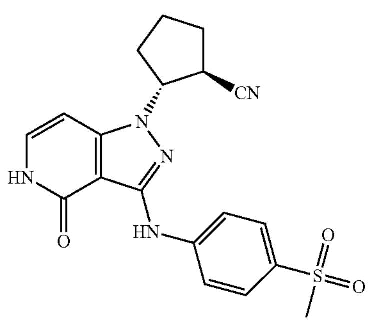 [SMILES: CS(=O)(=O)c1ccc(Nc2nn([C@@H]3CCC[C@H]3C#N)c3cc[nH]c(=O)c23)cc1] | (1R,2R)-2-(3-{[4-(methylsulfonyl)phenyl]amino}-4-oxo-4,5-dihydro-1H-pyrazolo[4,3-c]pyridin-1-yl)cyclopentanecarbonitrile | Calc'd 427, found 427 |
| 3-96 | 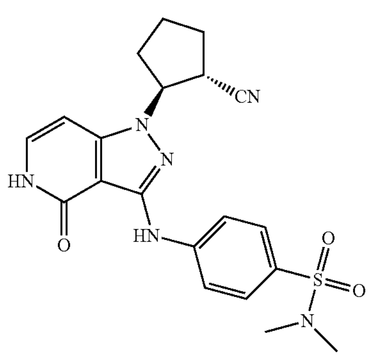 [SMILES: CN(C)S(=O)(=O)c1ccc(Nc2nn([C@H]3CCC[C@@H]3C#N)c3cc[nH]c(=O)c23)cc1] | 4-({1-[(1S,2S)-2-cyanocyclopentyl]-4-oxo-4,5-dihydro-1H-pyrazolo[4,3-c]pyridin-3-yl}amino)-N,N-dimethylbenzenesulfonamide | Calc'd 398, found 398 |
| 3-97 | 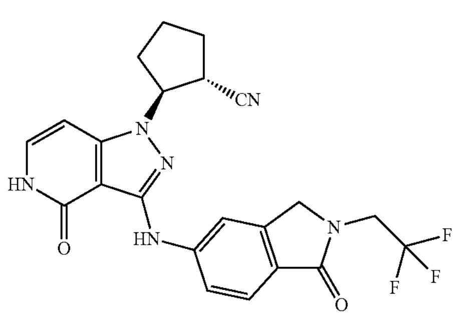 [SMILES: N#C[C@H]1CCC[C@@H]1n1nc(Nc2ccc3c(c2)CN(CC(F)(F)F)C3=O)c2c(=O)[nH]ccc21] | (1S,2S)-2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclopentanecarbonitrile | Calc'd 457, found 457 |

TABLE 37-continued

| Example | Structure | Compound Name | LRMS [M + H]+ |
|---|---|---|---|
| 3-98 | 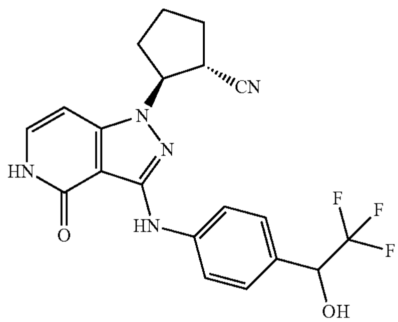 [SMILES: N#C[C@H]1CCC[C@@H]1n1nc(Nc2ccc(C(O)C(F)(F)F)cc2)c2c(=O)[nH]ccc21] | (1S,2S)-2-(4-oxo-3-{[4-(2,2,2-trifluoro-1-hydroxyethyl)phenyl]amino}-4,5-dihydro-1H-pyrazolo[4,3-c]pyridin-1-yl)cyclopentanecarbonitrile (mix of diastereomers) | Calc'd 418, found 418 |
| 3-99 | 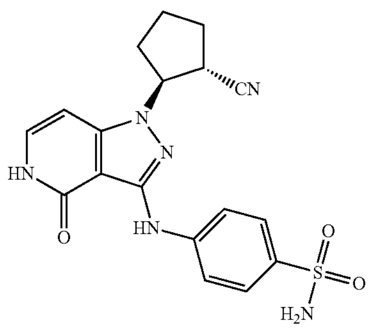 [SMILES: N#C[C@H]1CCC[C@@H]1n1nc(Nc2ccc(S(N)(=O)=O)cc2)c2c(=O)[nH]ccc21] | 4-({1-[(1S,2S)-2-cyanocyclopentyl]-4-oxo-4,5-dihydro-1H-pyrazolo[4,3-c]pyridin-3-yl}amino)benzenesulfonamide | Calc'd 399, found 399 |
| 3-100 | 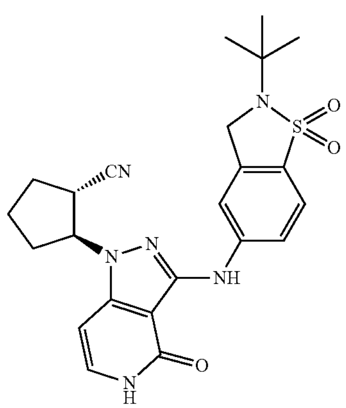 [SMILES: CC(C)(C)N1Cc2cc(Nc3nn([C@H]4CCC[C@@H]4C#N)c4cc[nH]c(=O)c34)ccc2S1(=O)=O] | (1S,2S)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile | Calc'd 467, found 467 |
| 3-101 | 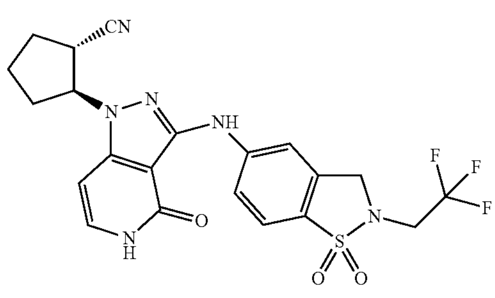 [SMILES: N#C[C@H]1CCC[C@@H]1n1nc(Nc2ccc3c(c2)CN(CC(F)(F)F)S3(=O)=O)c2c(=O)[nH]ccc21] | (1S,2S)-2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclopentanecarbonitrile | Calc'd 493, found 493 |

TABLE 37-continued

| Example | Structure | Compound Name | LRMS [M + H]+ |
|---|---|---|---|
| 3-102 | 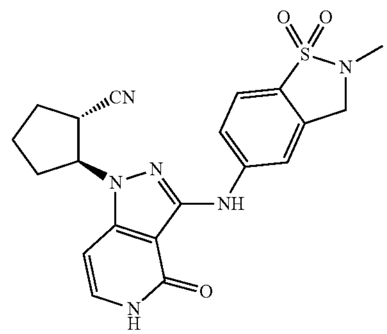 [SMILES: CN1Cc2cc(Nc3nn([C@H]4CCC[C@@H]4C#N)c4cc[nH]c(=O)c34)ccc2S1(=O)=O] | (1S,2S)-2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile | Calc'd 425, found 425 |
| 3-103 | 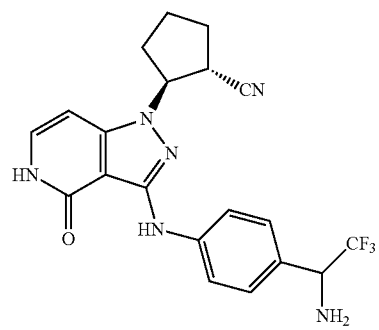 [SMILES: N#C[C@H]1CCC[C@@H]1n1nc(Nc2ccc(C(N)C(F)(F)F)cc2)c2c(=O)[nH]ccc21] | (1S,2S)-2-[3-({4-[(1R or 1S)-1-amino-2,2,2-trifluoroethyl]phenyl}amino)-4-oxo-4,5-dihydro-1H-pyrazolo[4,3-c]pyridin-1-yl]cyclopentanecarbonitrile | Calc'd 417, found 417 |
| 3-104 | 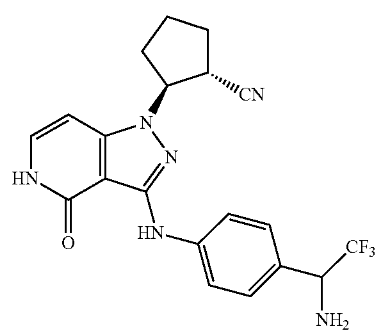 [SMILES: N#C[C@H]1CCC[C@@H]1n1nc(Nc2ccc(C(N)C(F)(F)F)cc2)c2c(=O)[nH]ccc21] | (1S,2S)-2-[3-({4-[(1S or 1R)-1-amino-2,2,2-trifluoroethyl]phenyl}amino)-4-oxo-4,5-dihydro-1H-pyrazolo[4,3-c]pyridin-1-yl]cyclopentanecarbonitrile | Calc'd 417, found 417 |
| 3-105 | 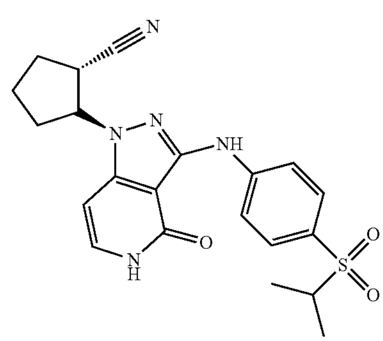 | (1S,2S)-2-[3-({4-[(1-methylethyl)sulfonyl]phenyl}amino)-4-oxo-4,5-dihydro-1H-pyrazolo[4,3-c]pyridin-1-yl]cyclopentanecarbonitrile | Calc'd 426, found 426 |

TABLE 37-continued

| Example | Structure | Compound Name | LRMS [M + H]+ |
|---|---|---|---|
| 3-106 | 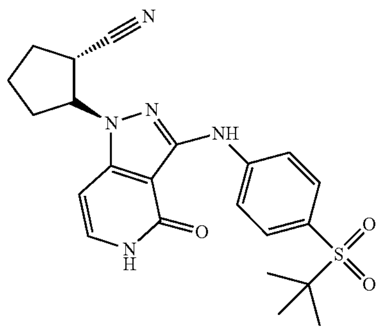 | (1S,2S)-2-(3-{[4-(tert-butylsulfonyl)phenyl]amino}-4-oxo-4,5-dihydro-1H-pyrazolo[4,3-c]pyridin-1-yl)cyclopentanecarbonitrile | Calc'd 440, found 440 |
| 3-107 | 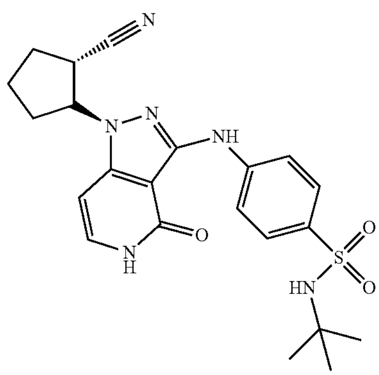 | N-tert-butyl-4-({1-[(1S,2S)-2-cyanocyclopentyl]-4-oxo-4,5-dihydro-1H-pyrazolo[4,3-c]pyridin-3-yl}amino)benzenesulfonamide | Calc'd 455, found 455 |
| 3-108 | 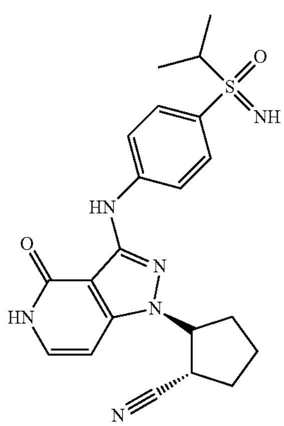 | (1S,2S)-2-[3-({4-[(S or R)-S-(1-methylethyl)sulfonimidoyl]phenyl}amino)-4-oxo-4,5-dihydro-yl]cyclopentanecarbonitrile (Derived from Peak B by SFC on OBn intermediate using AS-H, 20% MeOH in CO₂, Tr = 7.5 mins) | Calc'd 425, found 425 |
| 3-109 | 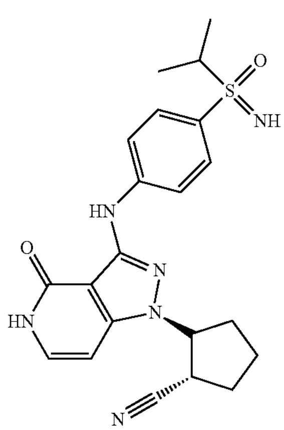 | (1S,2S)-2-[3-({4-[(S or R)-S-(1-methylethyl)sulfonimidoyl]phenyl}amino)-4-oxo-4,5-dihydro-1H-pyrazolo[4,3-c]pyridin-1-yl]cyclopentanecarbonitrile (Derived from Peak A by SFC on OBn intermediate using AS-H, 20% MeOH in CO₂, Tr = 6.8 mins) | Calc'd 425, found 425 |

TABLE 37-continued

| Example | Structure | Compound Name | LRMS [M + H]+ |
|---|---|---|---|
| 3-110 | 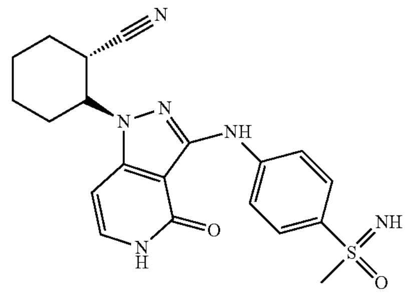 | (1S,2S)-2-(3-{[4-((S or R)-S-methylsulfonimidoyl)phenyl]amino}-4-oxo-4,5-dihydro-1H-pyrazolo[4,3-c]pyridin-1-yl)cyclohexanecarbonitrile (Derived from Peak A by SFC using OJ-H, 15% MeOH + 0.25% DMEA in CO₂, Tr = 6.0 mins) | Calc'd 411, found 411 |
| 3-111 | 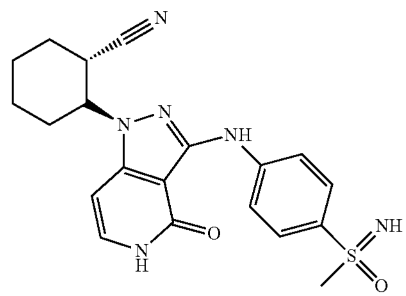 | (1S,2S)-2-(3-{[4-((S or R)-S-methylsulfonimidoyl)phenyl]amino}-4-oxo-4,5-dihydro-1H-pyrazolo[4,3-c]pyridin-1-yl)cyclohexanecarbonitrile (Derived from Peak B by SFC using OJ-H, 15% MeOH + 0.25% DMEA in CO₂, Tr = 6.9 mins) | Calc'd 411, found 411 |
| 3-112 | 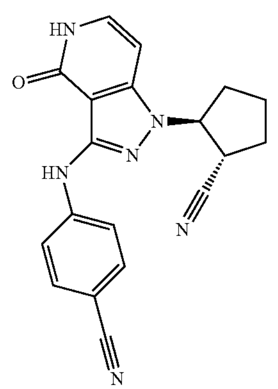 [SMILES: N#Cc1ccc(Nc2nn([C@H]3CCC[C@@H]3C#N)c3cc[nH]c(=O)c23)cc1] | 4-({1-[(1S,2S)-2-cyanocyclopentyl]-4-oxo-4,5-dihydro-1H-pyrazolo[4,3-c]pyridin-3-yl}amino)benzonitrile | Calc'd 345, found 345 |
| 3-113 | 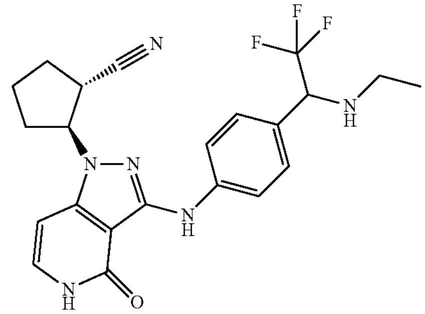 [SMILES: CCNC(c1ccc(Nc2nn([C@H]3CCC[C@@H]3C#N)c3cc[nH]c(=O)c23)cc1)C(F)(F)F] | (1S,2S)-2-[3-({4-[(1R or 1S)-1-(ethylamino)-2,2,2-trifluoroethyl]phenyl}amino)-4-oxo-4,5-dihydro-1H-pyrazolo[4,3-c]pyridin-1-yl]cyclopentanecarbonitrile (from I-113. Derived from Peak A by SFC, AS-H, 15% MeOH + 0.25% DMEA in CO₂, Tr = 4.89 mins) | Calc'd 445, found 445 |

TABLE 37-continued

| Example | Structure | Compound Name | LRMS [M + H]+ |
|---|---|---|---|
| 3-114 | 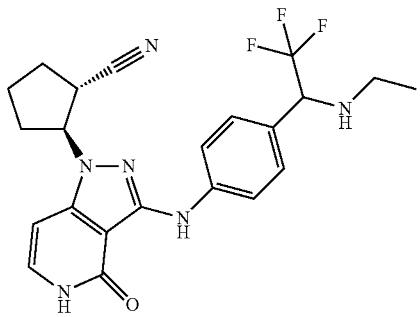 [SMILES: CCNC(c1ccc(Nc2nn([C@H]3CCC[C@@H]3C#N)c3cc[nH]c(=O)c23)cc1)C(F)(F)F] | (1S,2S)-2-[3-({4-[(1S or 1R)-1-(ethylamino)-2,2,2-trifluoroethyl]phenyl}amino)-4-oxo-4,5-dihydro-1H-pyrazolo[4,3-c]pyridin-1-yl]cyclopentanecarbonitrile (from I-113. Derived from Peak B by SFC, AS-H, 15% MeOH + 0.25% DMEA in $CO_2$, Tr = 7.63 mins) | Calc'd 445, found 445 |
| 3-115 | 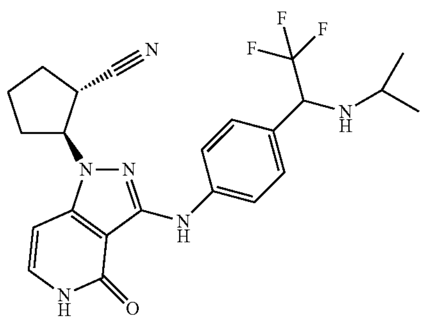 [SMILES: CC(C)NC(c1ccc(Nc2nn([C@H]3CCC[C@@H]3C#N)c3cc[nH]c(=O)c23)cc1)C(F)(F)F] | (1S,2S)-2-{4-oxo-3-[(4-{(1R or 1S)-2,2,2-trifluoro-1-[(1-methylethyl)amino]ethyl}phenyl)amino]-4,5-dihydro-1H-pyrazolo[4,3-c]pyridin-1-yl}cyclopentanecarbonitrile (from I-114. Derived from Peak A by SFC, AS-H, 15% MeOH + 0.25% DMEA in $CO_2$, Tr = 3.87 mins) | Calc'd 459, found 459 |
| 3-116 | 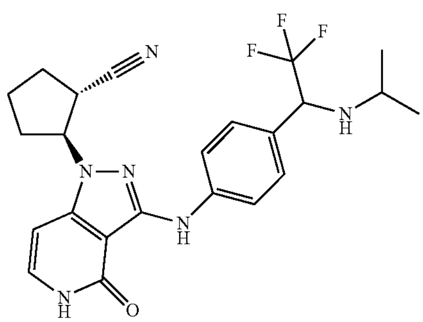 [SMILES: CC(C)NC(c1ccc(Nc2nn([C@H]3CCC[C@@H]3C#N)c3cc[nH]c(=O)c23)cc1)C(F)(F)F] | (1S,2S)-2-{4-oxo-3-[(4-{(1S or 1R)-2,2,2-trifluoro-1-[(1-methylethyl)amino]ethyl}phenyl)amino]-4,5-dihydro-1H-pyrazolo[4,3-c]pyridin-1-yl}cyclopentanecarbonitrile (from I-114. Derived from Peak B by SFC, AS-H, 15% MeOH + 0.25% DMEA in $CO_2$, Tr = 4.75 mins) | Calc'd 459, found 459 |
| 3-117 | 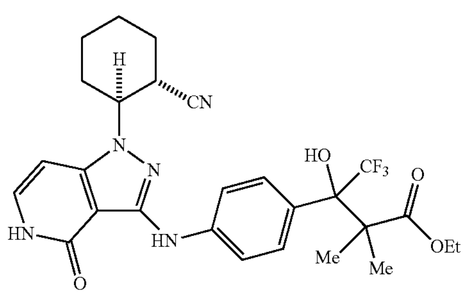 | (R or S) Ethyl 3-(4-((1-((1S,2S)-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-115. Derived from Peak A via SFC, Chiralpak IC, 30% MeOH in $CO_2$, Tr = 4.41 mins) | Calc'd 546, found 546. |
| 3-118 | 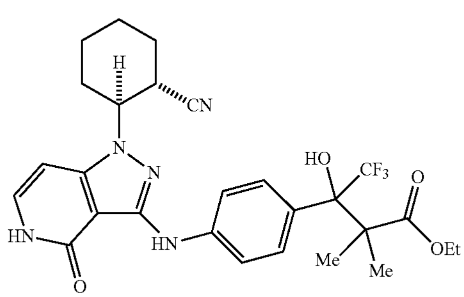 | (R or S) Ethyl 3-(4-((1-((1S,2S)-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-115. Derived from Peak B via SFC, Chiralpak IC, 30% MeOH in $CO_2$, Tr = 5.91 mins) | Calc'd 546, found 546. |

TABLE 37-continued

| Example | Structure | Compound Name | LRMS [M + H]+ |
|---|---|---|---|
| 3-119 | 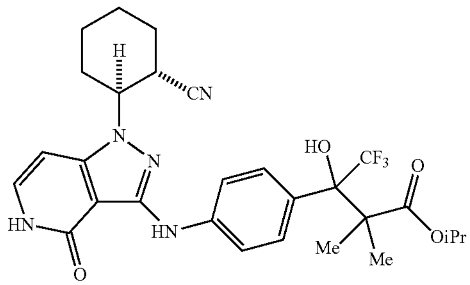 | (R or S) Isopropyl 3-(4-((1-((1S,2S)-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-116. Derived from Peak A via SFC, Chiralpak IC, 30% MeOH in $CO_2$, Tr = 3.57 mins) | Calc'd 560, found 560. |
| 3-120 | 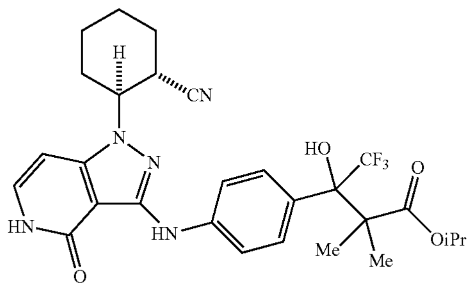 | (R or S) Isopropyl 3-(4-((1-((1S,2S)-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-116. Derived from Peak B via SFC, Chiralpak IC, 30% MeOH in $CO_2$, Tr = 4.87 mins) | Calc'd 560, found 560. |
| 3-121 | 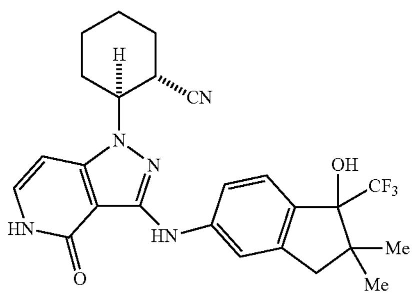 | (1S,2S)-2-(3-(((R or S)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)cyclohexanecarbonitrile (from I-117. Derived from Peak A via SFC, Lux-4, 35% MeOH in $CO_2$, Tr = 3.58 mins) | Calc'd 486, found 486. |
| 3-122 | 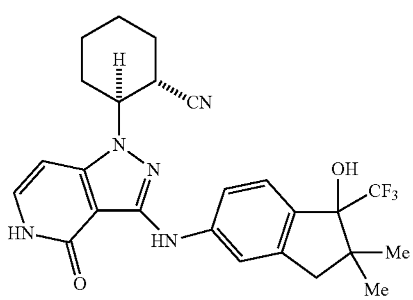 | (1S,2S)-2-(3-(((R or S)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)cyclohexanecarbonitrile (from I-117. Derived from Peak B via SFC, Lux-4, 35% MeOH in $CO_2$, Tr = 5.06 mins) | Calc'd 486, found 486. |
| 3-123 | 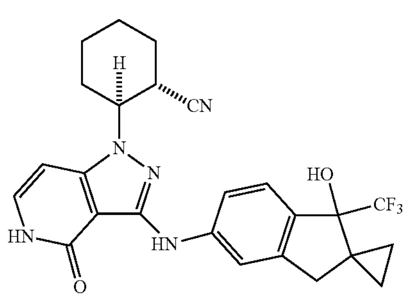 | (1S,2S)-2-(3-(((R or S)-1'-hydroxy-1'-(trifluoromethyl)-1',3'-dihydrospiro[cyclopropane-1,2'-inden]-5'-yl)amino)-4-oxo-4,5-dihydro-1H-pyrazolo[4,3-c]pyridin-1-yl)cyclohexanecarbonitrile (from I-118. Derived from Peak A via SFC, Lux-4, 25% MeOH in $CO_2$, Tr = 3.84 mins) | Calc'd 484, found 484. |

TABLE 37-continued

| Example | Structure | Compound Name | LRMS [M + H]+ |
|---|---|---|---|
| 3-124 | 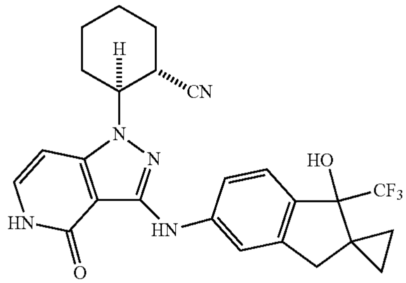 | (1S,2S)-2-(3-(((R or S)-1'-hydroxy-1'-(trifluoromethyl)-1',3'-dihydrospiro[cyclopropane-1,2'-inden]-5'-yl)amino)-4-oxo-4,5-dihydro-1H-pyrazolo[4,3-c]pyridin-1-yl)cyclohexanecarbonitrile (from I-118. Derived from Peak B via SFC: Lux-4, 25% MeOH in CO$_2$, Tr = 7.14 mins) | Calc'd 484, found 484. |
| 3-125 | 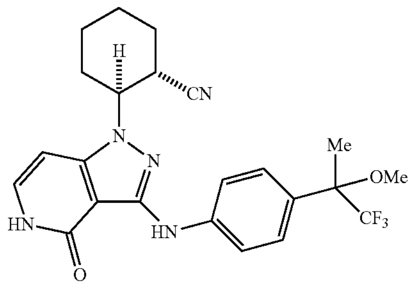 | (1S,2S)-2-(4-oxo-3-((4-((R or S)-1,1,1-trifluoro-2-methoxypropan-2-yl)phenyl)amino)-4,5-dihydro-1H-pyrazolo[4,3-c]pyridin-1-yl)cyclohexanecarbonitrile (from I-119) | Calc'd 460, found 460. |
| 3-126 | 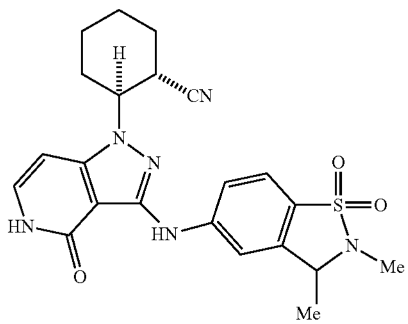 | (1S,2S)-2-(3-(((R or S)-2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile (from I-85) | Calc'd 454, found 454. |
| 3-127 | 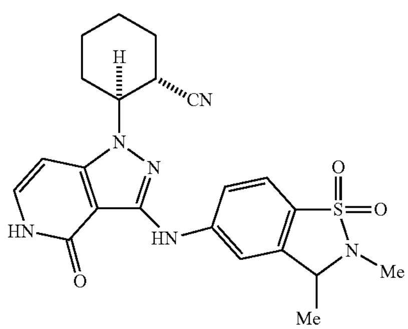 | (1S,2S)-2-(3-(((R or S)-2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile (from I-86) | Calc'd 454, found 454. |
| 3-128 | 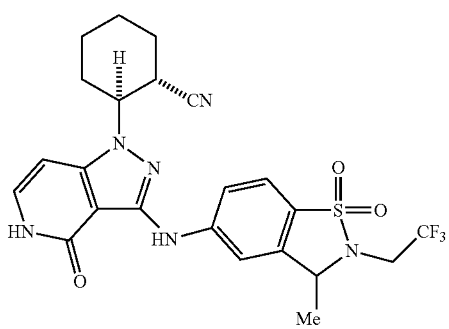 | (1S,2S)-2-(3-(((R or S)-3-methyl-1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)cyclohexanecarbonitrile (from I-83) | Calc'd 522, found 522. |

TABLE 37-continued

| Example | Structure | Compound Name | LRMS [M + H]+ |
|---|---|---|---|
| 3-129 | 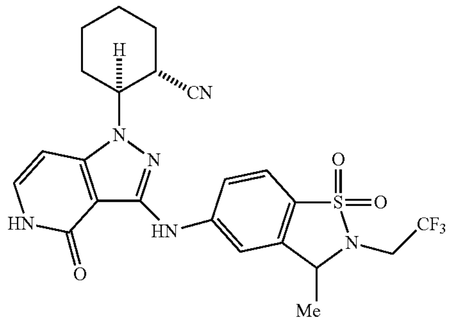 | (1S,2S)-2-(3-(((R or S)-3-methyl-1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)cyclohexanecarbonitrile (from I-84) | Calc'd 522, found 522. |
| 3-130 | 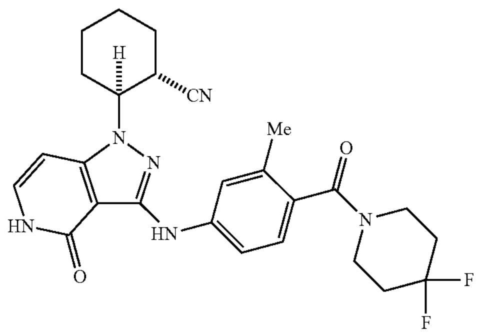 | (1S,2S)-2-(3-((4-(4,4-difluoropiperidine-1-carbonyl)-3-methylphenyl)amino)-4-oxo-4,5-dihydro-1H-pyrazolo[4,3-c]pyridin-1-yl)cyclohexanecarbonitrile (from I-120) | Calc'd 496, found 496. |
| 3-131 | 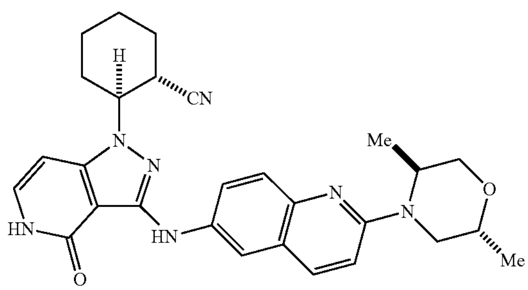 | (1S,2S)-2-(3-((2-((2R,5S)-2,5-dimethylmorpholino)quinolin-6-yl)amino)-4-oxo-4,5-dihydro-1H-pyrazolo[4,3-c]pyridin-1-yl)cyclohexanecarbonitrile (from I-121) | Calc'd 498, found 498. |
| 3-132 | 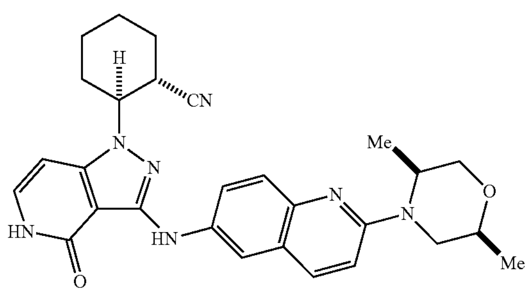 | (1S,2S)-2-(3-((2-((2S,5S)-2,5-dimethylmorpholino)quinolin-6-yl)amino)-4-oxo-4,5-dihydro-1H-pyrazolo[4,3-c]pyridin-1-yl)cyclohexanecarbonitrile (from I-122) | Calc'd 498, found 498. |
| 3-133 | 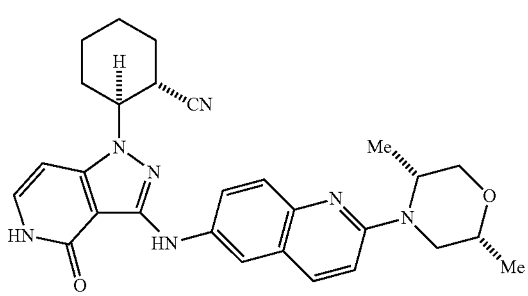 | (1S,2S)-2-(3-((2-((2R,5R)-2,5-dimethylmorpholino)quinolin-6-yl)amino)-4-oxo-4,5-dihydro-1H-pyrazolo[4,3-c]pyridin-1-yl)cyclohexanecarbonitrile (from I-123) | Calc'd 498, found 498. |

TABLE 37-continued

| Example | Structure | Compound Name | LRMS [M + H]+ |
|---|---|---|---|
| 3-134 | 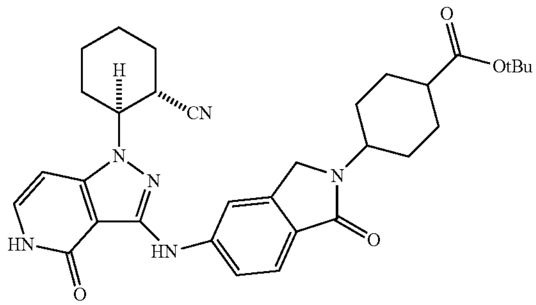 | (cis or trans)tert-butyl 4-(5-((1-((1S,2S)-2-cyanocyclohexyl)-4-oxo-4,5-dihydro-1H-pyrazolo[4,3-c]pyridin-3-yl)amino)-1-oxoisoindolin-2-yl)cyclohexanecarboxylate (from I-124. Derived from Peak A via SFC, ES Industries Basic, 20% MeOH in $CO_2$, Tr = 7.63 mins) | Calc'd 571, found 571. |
| 3-135 | 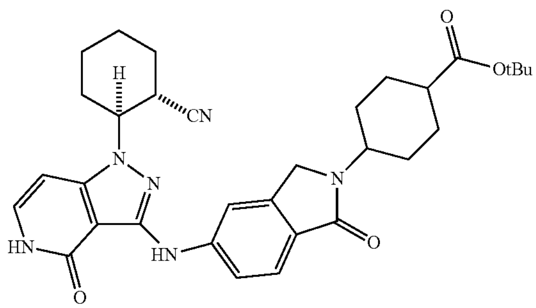 | (cis or trans)tert-butyl 4-(5-((1-((1S,2S)-2-cyanocyclohexyl)-4-oxo-4,5-dihydro-1H-pyrazolo[4,3-c]pyridin-3-yl)amino)-1-oxoisoindolin-2-yl)cyclohexanecarboxylate (from I-124. Derived from Peak B via SFC, ES Industries Basic, 20% MeOH in $CO_2$, Tr = 9.43 mins) | Calc'd 571, found 571. |
| 3-136 | 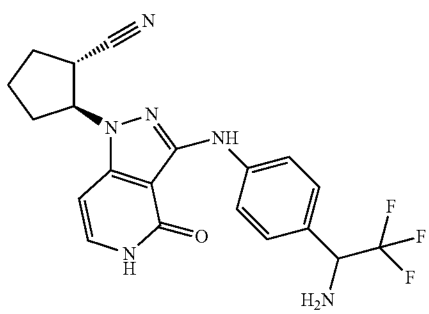 [SMILES: N#C[C@H]1CCC[C@@H]1n1nc(Nc2ccc(C(N)C(F)(F)F)cc2)c2c(=O)[nH]ccc21] | (1S,2S)-2-[3-({4-[(1R or 1S)-1-amino-2,2,2-trifluoroethyl]phenyl}amino)-4-oxo-4,5-dihydro-1H-pyrazolo[4,3-c]pyridin-1-yl]cyclopentanecarbonitrile (from I-69) | Calc'd 417, found 417 |
| 3-137 | 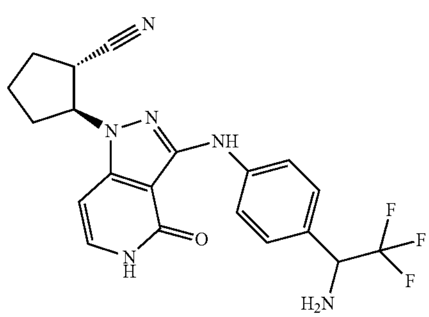 [SMILES: N#C[C@H]1CCC[C@@H]1n1nc(Nc2ccc(C(N)C(F)(F)F)cc2)c2c(=O)[nH]ccc21] | (1S,2S)-2-[3-({4-[(1S or 1R)-1-amino-2,2,2-trifluoroethyl]phenyl}amino)-4-oxo-4,5-dihydro-1H-pyrazolo[4,3-c]pyridin-1-yl]cyclopentanecarbonitrile (from I-70) | Calc'd 417, found 417 |
| 3-138 | 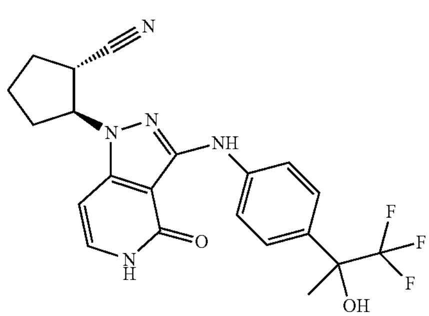 [SMILES: CC(O)(c1ccc(Nc2nn([C@H]3CCC[C@@H]3C#N)c3cc[nH]c(=O)c23)cc1)C(F)(F)F] | (1S,2S)-2-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]cyclopentanecarbonitrile (from I-119a) | Calc'd 432, found 432 |

TABLE 37-continued

| Example | Structure | Compound Name | LRMS [M + H]+ |
|---|---|---|---|
| 3-139 | 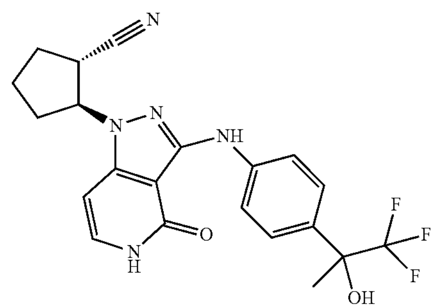 [SMILES: CC(O)(c1ccc(Nc2nn([C@H]3CCC[C@@H]3C#N)c3cc[nH]c(=O)c23)cc1)C(F)(F)F] | (1S,2S)-2-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]cyclopentanecarbonitrile (from I-119b) | Calc'd 432, found 432 |
| 3-140 | 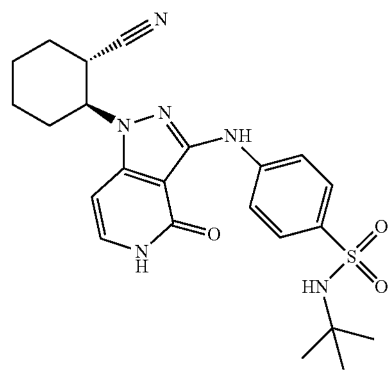 [SMILES: CC(C)(C)NS(=O)(=O)c1ccc(Nc2nn([C@H]3CCCC[C@@H]3C#N)c3cc[nH]c(=O)c23)cc1] | N-tert-butyl-4-({1-[(1S,2S)-2-cyanocyclohexyl]-4-oxo-4,5-dihydro-1H-pyrazolo[4,3-c]pyridin-3-yl}amino)benzenesulfonamide | Calc'd 469, found 469 |
| 3-141 | 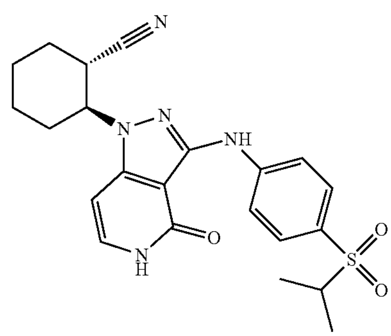 [SMILES: CC(C)S(=O)(=O)c1ccc(Nc2nn([C@H]3CCCC[C@@H]3C#N)c3cc[nH]c(=O)c23)cc1] | (1S,2S)-2-[3-({4-[(1-methylethyl)sulfonyl]phenyl}amino)-4-oxo-4,5-dihydro-1H-pyrazolo[4,3-c]pyridin-1-yl]cyclohexanecarbonitrile | Calc'd 440, found 440 |
| 3-142 | 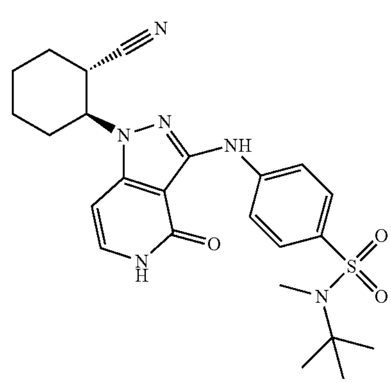 [SMILES: CN(C(C)(C)C)S(=O)(=O)c1ccc(Nc2nn([C@H]3CCCC[C@@H]3C#N)c3cc[nH]c(=O)c23)cc1] | N-tert-butyl-4-({1-[(1S,2S)-2-cyanocyclohexyl]-4-oxo-4,5-dihydro-1H-pyrazolo[4,3-c]pyridin-3-yl}amino)-N-methylbenzenesulfonamide | Calc'd 483, found 483 |

TABLE 37-continued

| Example | Structure | Compound Name | LRMS [M + H]+ |
|---------|-----------|---------------|---------------|
| 3-143 | 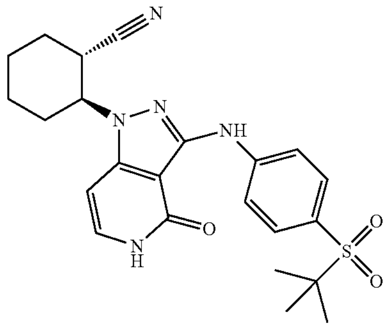 [SMILES: CC(C)(C)S(=O)(=O)c1ccc(Nc2nn([C@H]3CCCC[C@@H]3C#N)c3cc[nH]c(=O)c23)cc1] | (1S,2S)-2-(3-{[4-(tert-butylsulfonyl)phenyl]amino}-4-oxo-4,5-dihydro-1H-pyrazolo[4,3-c]pyridin-1-yl)cyclohexanecarbonitrile | Calc'd 454, found 454 |
| 3-144 | 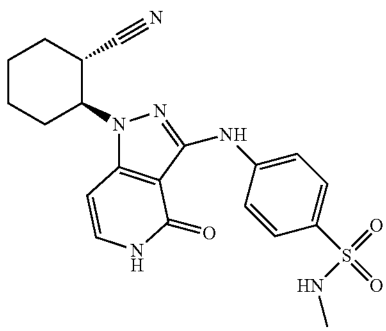 [SMILES: CNS(=O)(=O)c1ccc(Nc2nn([C@H]3CCCC[C@@H]3C#N)c3cc[nH]c(=O)c23)cc1] | 4-({1-[(1S,2S)-2-cyanocyclohexyl]-4-oxo-4,5-dihydro-1H-pyrazolo[4,3-c]pyridin-3-yl}amino)-N-methylbenzenesulfonamide | Calc'd 427, found 427 |
| 3-145 | 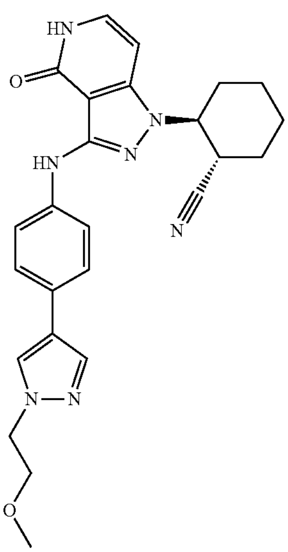 [SMILES: COCCn1cc(-c2ccc(Nc3nn([C@H]4CCCC[C@@H]4C#N)c4cc[nH]c(=O)c34)cc2)cn1] | (1S,2S)-2-[3-({4-[1-(2-methoxyethyl)-1H-pyrazol-4-yl]phenyl}amino)-4-oxo-4,5-dihydro-1H-pyrazolo[4,3-c]pyridin-1-yl]cyclohexanecarbonitrile | Calc'd 458, found 458 |

TABLE 37-continued

| Example | Structure | Compound Name | LRMS [M + H]+ |
|---|---|---|---|
| 3-146 | 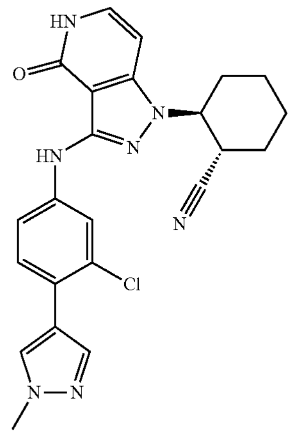 [SMILES: Cn1cc(-c2ccc(Nc3nn([C@H]4CCCC[C@@H]4C#N)c4cc[nH]c(=O)c34)cc2Cl)cn1] | (1S,2S)-2-(3-{[3-chloro-4-(1-methyl-1H-pyrazol-4-yl)phenyl]amino}-4-oxo-4,5-dihydro-1H-pyrazolo[4,3-c]pyridin-1-yl)cyclohexanecarbonitrile | Calc'd 448, found 448 |
| 3-147 | 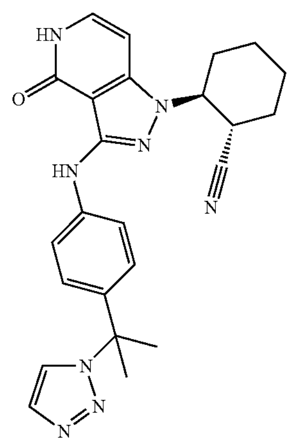 [SMILES: CC(C)(c1ccc(Nc2nn([C@H]3CCCC[C@@H]3C#N)c3cc[nH]c(=O)c23)cc1)n1ccnn1] | (1S,2S)-2-[3-({4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile | Calc'd 443, found 374 [M − 68] triazole |
| 3-148 | 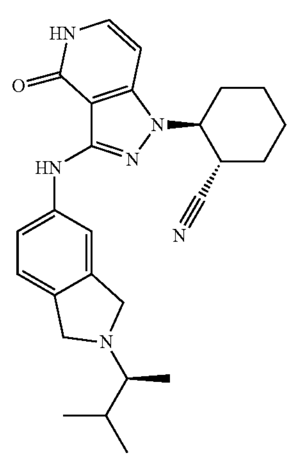 [SMILES: CC(C)[C@H](C)N1Cc2ccc(Nc3nn([C@H]4CCCC[C@@H]4C#N)c4cc[nH]c(=O)c34)cc2C1] | (1S,2S)-2-[3-({2-[(1S)-1,2-dimethylpropyl]-2,3-dihydro-1H-isoindol-5-yl}amino)-4-oxo-4,5-dihydro-1H-pyrazolo[4,3-c]pyridin-1-yl]cyclohexanecarbonitrile (from I-147) | Calc'd 445, found 445 |

TABLE 37-continued

| Example | Compound Name | LRMS [M + H]+ |
|---|---|---|
| 3-149 | (1S,2S)-2-[3-({2-[(1R)-1,2-dimethylpropyl]-2,3-dihydro-1H-isoindol-5-yl}amino)-4-oxo-4,5-dihydro-1H-pyrazolo[4,3-c]pyridin-1-yl]cyclohexanecarbonitrile (from I-148) | Calc'd 445, found 445 |
| 3-150 | tert-butyl 3-[5-({1-[(1S,2S)-2-cyanocyclohexyl]-4-oxo-4,5-dihydro-1H-pyrazolo[4,3-c]pyridin-3-yl}amino)-1,1-dioxido-1,2-benzisothiazol-2(3H)-yl]propanoate | Calc'd 553, found 553 |
| 3-151 | tert-butyl [5-({1-[(1S,2S)-2-cyanocyclohexyl]-4-oxo-4,5-dihydro-1H-pyrazolo[4,3-c]pyridin-3-yl}amino)-1,1-dioxido-1,2-benzisothiazol-2(3H)-yl]acetate | Calc'd 539, found 539 |

TABLE 37-continued

| Example | Structure | Compound Name | LRMS [M + H]+ |
|---|---|---|---|
| 3-152 | 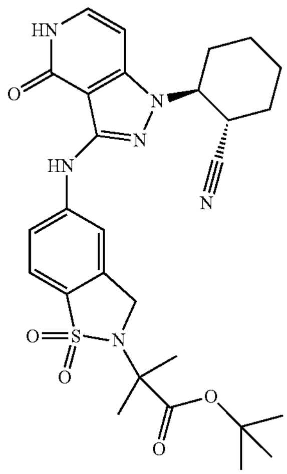 [SMILES: CC(C)(C)OC(=O)C(C)(C)N1Cc2cc(Nc3nn([C@H]4CCCC[C@@H]4C#N)c4cc[nH]c(=O)c34)ccc2S1(=O)=O] | tert-butyl 2-[5-({1-[(1S,2S)-2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-2-methylpropanoate | Calc'd 567, found 511 [M − tBu] |
| 3-153 | 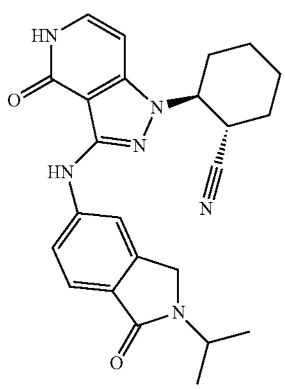 [SMILES: CC(C)N1Cc2cc(Nc3nn([C@H]4CCCC[C@@H]4C#N)c4cc[nH]c(=O)c34)ccc2C1=O] | (1S,2S)-2-(3-{[2-(1-methylethyl)-1-oxo-2,3-dihydro-1H-isoindol-5-yl]amino}-4-oxo-4,5-dihydro-1H-pyrazolo[4,3-c]pyridin-1-yl)cyclohexanecarbonitrile | Calc'd 431, found 431 |
| 3-154 | 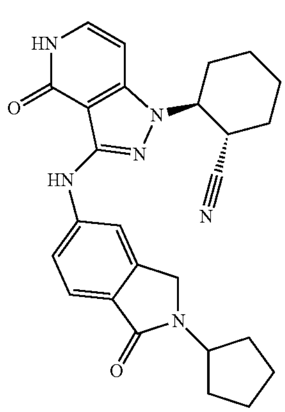 [SMILES: N#C[C@H]1CCCC[C@@H]1n1nc(Nc2ccc3c(c2)CN(C2CCCC2)C3=O)c2c(=O)[nH]ccc21] | (1S,2S)-2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cyclohexanecarbonitrile | Calc'd 457, found 457 |

TABLE 37-continued

| Example | Structure | Compound Name | LRMS [M + H]+ |
|---|---|---|---|
| 3-155 | 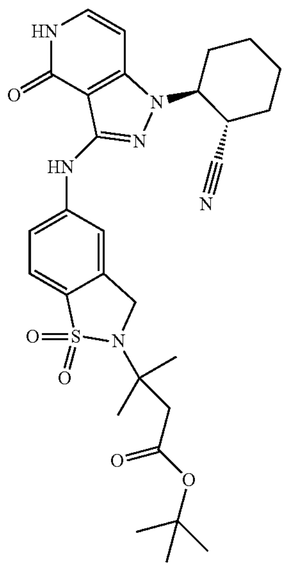 [SMILES: CC(C)(C)OC(=O)CC(C)(C)N1Cc2cc(Nc3nn([C@H]4CCCC[C@@H]4C#N)c4cc[nH]c(=O)c34)ccc2S1(=O)=O] | tert-butyl 3-[5-({1-[(1S,2S)-2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-3-methylbutanoate | Calc'd 581, found 581 |
| 3-156 | 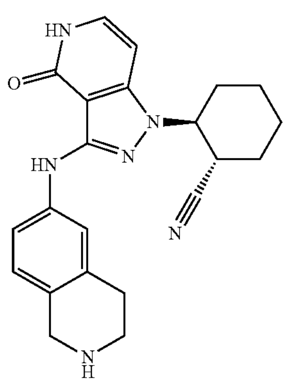 [SMILES: N#C[C@H]1CCCC[C@@H]1n1nc(Nc2ccc3c(c2)CCNC3)c2c(=O)[nH]ccc21] | (1S,2S)-2-[4-oxo-3-(1,2,3,4-tetrahydroisoquinolin-6-ylamino)-4,5-dihydro-1H-pyrazolo[4,3-c]pyridin-1-yl]cyclohexanecarbonitrile | Calc'd 389, found 389 |
| 3-157 | 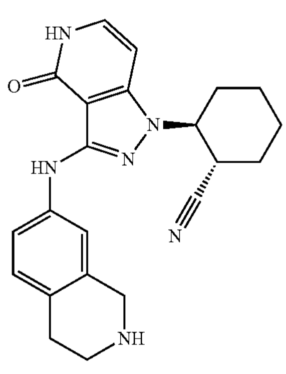 [SMILES: N#C[C@H]1CCCC[C@@H]1n1nc(Nc2ccc3c(c2)CNCC3)c2c(=O)[nH]ccc21] | (1S,2S)-2-[4-oxo-3-(1,2,3,4-tetrahydroisoquinolin-7-ylamino)-4,5-dihydro-1H-pyrazolo[4,3-c]pyridin-1-yl]cyclohexanecarbonitrile | Calc'd 389, found 389 |

TABLE 37-continued

| Example | Structure | Compound Name | LRMS [M + H]+ |
|---|---|---|---|
| 3-158 | 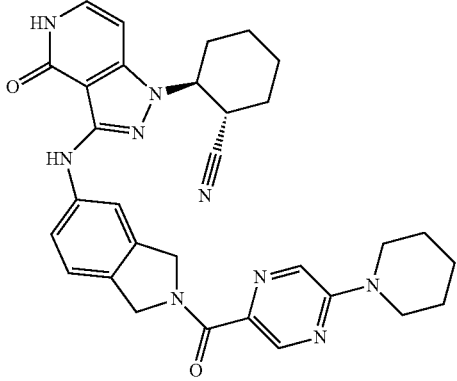 [SMILES: N#C[C@H]1CCCC[C@@H]1n1nc(Nc2ccc3c(c2)CN(C(=O)c2cnc(N4CCCCC4)cn2)C3)c2c(=O)[nH]ccc21] | (1S,2S)-2-[4-oxo-3-({2-[(5-piperidin-1-ylpyrazin-2-yl)carbonyl]-2,3-dihydro-1H-isoindol-5-yl}amino)-4,5-dihydro-1H-pyrazolo[4,3-c]pyridin-1-yl]cyclohexanecarbonitrile | Calc'd 564, found 564 |
| 3-159 | 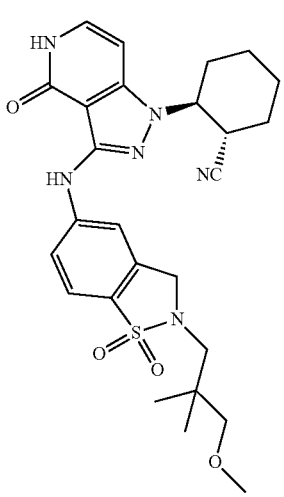 [SMILES: COCC(C)(C)CN1Cc2cc(Nc3nn([C@H]4CCCC[C@@H]4C#N)c4cc[nH]c(=O)c34)ccc2S1(=O)=O] | (1S,2S)-2-(3-((2-(3-methoxy-2,2-dimethylpropyl)-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile | Calc'd 525, found 525 |
| 3-160 | 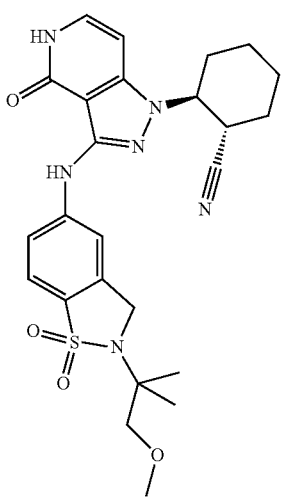 [SMILES: COCC(C)(C)N1Cc2cc(Nc3nn([C@H]4CCCC[C@@H]4C#N)c4cc[nH]c(=O)c34)ccc2S1(=O)=O] | (1S,2S)-2-(3-{[2-(2-methoxy-1,1-dimethylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 511, found 511 |

TABLE 37-continued

| Example | Structure | Compound Name | LRMS [M + H]+ |
|---|---|---|---|
| 3-161 | 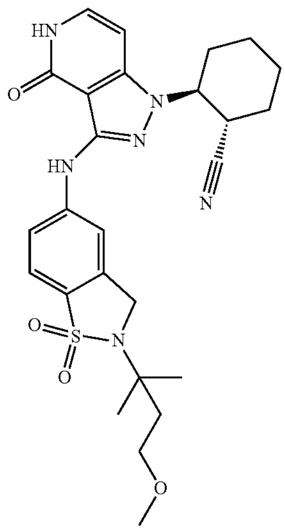 [SMILES: COCCC(C)(C)N1Cc2cc(Nc3nn([C@H]4CCCC[C@@H]4C#N)c4cc[nH]c(=O)c34)ccc2S1(=O)=O] | (1S,2S)-2-(3-{[2-(3-methoxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 525, found 525 |
| 3-162 | 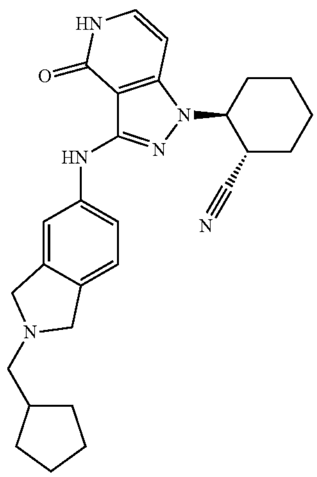 [SMILES: N#C[C@H]1CCCC[C@@H]1n1nc(Nc2ccc3c(c2)CN(CC2CCCC2)C3)c2c(=O)[nH]ccc21] | (1S,2S)-2-(3-{[2-(cyclopentylmethyl)-2,3-dihydro-1H-isoindol-5-yl]amino}-4-oxo-4,5-dihydro-1H-pyrazolo[4,3-c]pyridin-1-yl)cyclohexanecarbonitrile | Calc'd 457, found 457 |
| 3-163 | 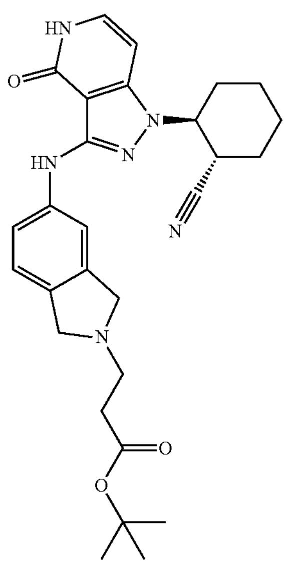 [SMILES: CC(C)(C)OC(=O)CCN1Cc2ccc(Nc3nn([C@H]4CCCC[C@@H]4C#N)c4cc[nH]c(=O)c34)cc2C1] | tert-butyl 3-[5-({1-[(1S,2S)-2-cyanocyclohexyl]-4-oxo-4,5-dihydro-1H-pyrazolo[4,3-c]pyridin-3-yl}amino)-1,3-dihydro-2H-isoindol-2-yl]propanoate | Calc'd 503, found 503 |

TABLE 37-continued

| Example | Structure | Compound Name | LRMS [M + H]+ |
|---|---|---|---|
| 3-164 | 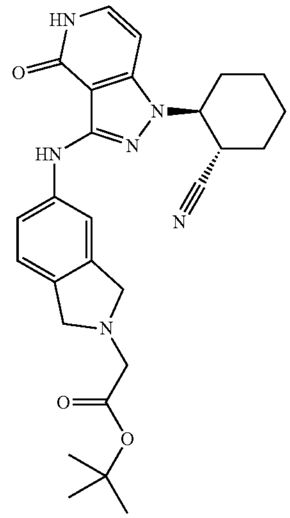 [SMILES: CC(C)(C)OC(=O)CN1Cc2ccc(Nc3nn([C@H]4CCCC[C@@H]4C#N)c4cc[nH]c(=O)c34)cc2C1] | tert-butyl [5-({1-[(1S,2S)-2-cyanocyclohexyl]-4-oxo-4,5-dihydro-1H-pyrazolo[4,3-c]pyridin-3-yl}amino)-1,3-dihydro-2H-isoindol-2-yl]acetate | Calc'd 489, found 489 |
| 3-165 | 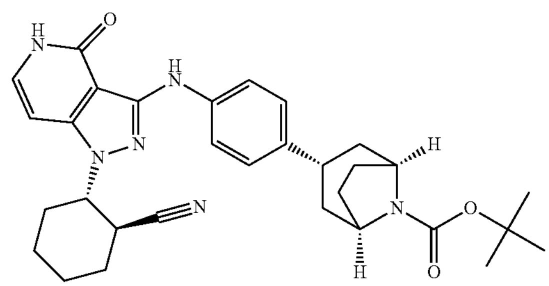 [SMILES: CC(C)(C)OC(=O)N1[C@@H]2CC[C@H]1C[C@@H](c1ccc(Nc3nn([C@H]4CCCC[C@@H]4C#N)c4cc[nH]c(=O)c34)cc1)C2] | (1R,3R,5S))-tert-butyl 3-(4-((1-((1S,2S)-2-cyanocyclohexyl)-4-oxo-4,5-dihydro-1H-pyrazolo[4,3-c]pyridin-3-yl)amino)phenyl)-8-azabicyclo[3.2.1]octane-8-carboxylate (from I-155 alkene reduced during OBn deprotection. Derived from Peak A by HPLC using IA, 10% EtOH in MTBE (with 0.1% TEA), Tr = 8.62 mins) | Calc'd 543, found 543 |
| 3-166 | 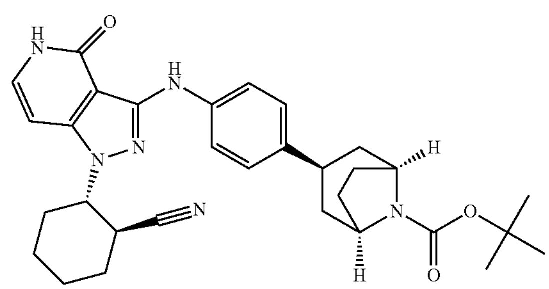 [SMILES: CC(C)(C)OC(=O)N1[C@@H]2CC[C@H]1C[C@H](c1ccc(Nc3nn([C@H]4CCCC[C@@H]4C#N)c4cc[nH]c(=O)c34)cc1)C2] | (1R,3S,5S)-tert-butyl 3-(4-((1-((1S,2S)-2-cyanocyclohexyl)-4-oxo-4,5-dihydro-1H-pyrazolo[4,3-c]pyridin-3-yl)amino)phenyl)-8-azabicyclo[3.2.1]octane-8-carboxylate (from I-155 alkene reduced during OBn deprotection. Derived from Peak B by HPLC using IA, 10% EtOH in MTBE (with 0.1% TEA), Tr = 10.68 mins) | Calc'd 543, found 543 |
| 3-167 | 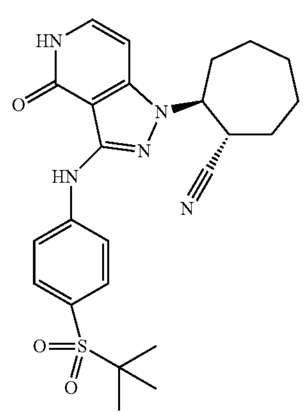 [SMILES: CC(C)(C)S(=O)(=O)c1ccc(Nc2nn([C@H]3CCCCC[C@@H]3C#N)c3cc[nH]c(=O)c23)cc1] | (1S,2S or 1R,2R)-2-(3-{[4-(tert-butylsulfonyl)phenyl]amino}-4-oxo-4,5-dihydro-1H-pyrazolo[4,3-c]pyridin-1-yl)cycloheptanecarbonitrile (from I-12. Derived from Peak B (trans racemic) HPLC using C-18, 30-70% ACN/Water (with 0.05% TFA), Tr = 6.1 mins followed by Peak B HPLC using IB, 15% EtOH (with 0.1% DEA) in Hexanes (with 0.1% DEA), Tr = 38.5 mins). | Calc'd 468, found 468 |

TABLE 37-continued

| Example | Structure | Compound Name | LRMS [M + H]+ |
|---|---|---|---|
| 3-168 | 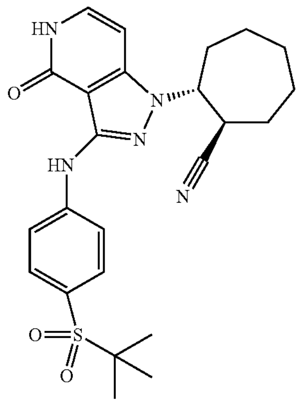 [SMILES: CC(C)(C)S(=O)(=O)c1ccc(Nc2nn([C@@H]3CCCCC[C@H]3C#N)c3cc[nH]c(=O)c23)cc1] | (1R,2R or 1S,2S)-2-(3-{[4-(tert-butylsulfonyl)phenyl]amino}-4-oxo-4,5-dihydro-1H-pyrazolo[4,3-c]pyridin-1-yl)cycloheptanecarbonitrile (from I-12. Derived from Peak B (trans racemic) HPLC using C-18, 30-70% ACN/Water (with 0.05% TFA), Tr = 6.1 mins followed by Peak A HPLC using IB, 15% EtOH (with 0.1% DEA) in Hexanes (with 0.1% DEA), Tr = 31.8 mins). | Calc'd 468, found 468 |
| 3-169 | 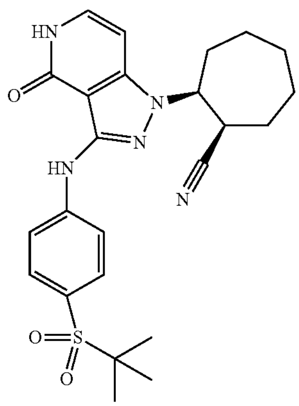 [SMILES: CC(C)(C)S(=O)(=O)c1ccc(Nc2nn([C@H]3CCCCC[C@H]3C#N)c3cc[nH]c(=O)c23)cc1] | (1R,2S or 1S,2R)-2-(3-{[4-(tert-butylsulfonyl)phenyl]amino}-4-oxo-4,5-dihydro-1H-pyrazolo[4,3-c]pyridin-1-yl)cycloheptanecarbonitrile (from I-12. Derived from Peak A (cis racemic) HPLC using C-18, 30-70% ACN/Water (with 0.05% TFA), Tr = 5.0 mins followed by Peak A HPLC using IA, 45% EtOH (with 0.1% DEA) in Hexanes (with 0.1% DEA), Tr = 12.1 mins). | Calc'd 468, found 468 |
| 3-170 | 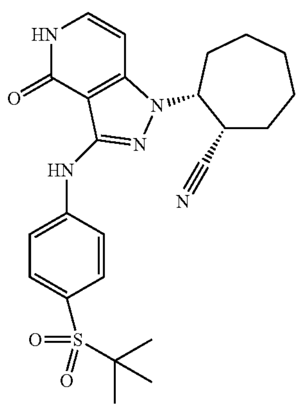 [SMILES: CC(C)(C)S(=O)(=O)c1ccc(Nc2nn([C@@H]3CCCCC[C@@H]3C#N)c3cc[nH]c(=O)c23)cc1] | (1S,2R or 1R,2S)-2-(3-{[4-(tert-butylsulfonyl)phenyl]amino}-4-oxo-4,5-dihydro-1H-pyrazolo[4,3-c]pyridin-1-yl)cycloheptanecarbonitrile (from I-12. Derived from Peak A (cis racemic) HPLC using C-18, 30-70% ACN/Water (with 0.05% TFA), Tr = 5.0 mins followed by Peak B HPLC using IA, 45% EtOH (with 0.1% DEA) in Hexanes (with 0.1% DEA), Tr = 15.6 mins). | Calc'd 468, found 468 |
| 3-171 | 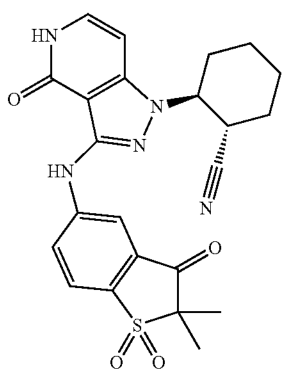 [SMILES: CC1(C)C(=O)c2cc(Nc3nn([C@H]4CCCC[C@@H]4C#N)c4cc[nH]c(=O)c34)ccc2S1(=O)=O] | (1S,2S)-2-{3-[(2,2-dimethyl-1,1-dioxido-3-oxo-2,3-dihydro-1-benzothiophen-5-yl)amino]-4-oxo-4,5-dihydro-1H-pyrazolo[4,3-c]pyridin-1-yl}cyclohexanecarbonitrile (from I-162f) | Calc'd 466, found 466 |

TABLE 37-continued

| Example | Structure | Compound Name | LRMS [M + H]+ |
|---|---|---|---|
| 3-172 | 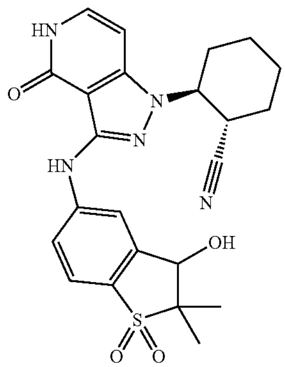 [SMILES: CC1(C)C(O)c2cc(Nc3nn([C@H]4CCCC[C@@H]4C#N)c4cc[nH]c(=O)c34)ccc2S1(=O)=O] | (1S,2S)-2-(3-{[(3S or 3R)-3-hydroxy-2,2-dimethyl-1,1-dioxido-2,3-dihydro-1-benzothiophen-5-yl]amino}-4-oxo-4,5-dihydro-1H-pyrazolo[4,3-c]pyridin-1-yl)cyclohexanecarbonitrile (Derived from Peak A by HPLC using IC, 20% EtOH in Hexanes (with 0.1% TEA), Tr = 24.9 mins) | Calc'd 468, found 468 |
| 3-173 | 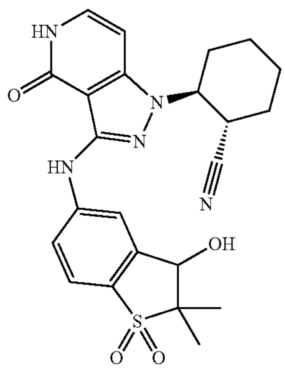 [SMILES: CC1(C)C(O)c2cc(Nc3nn([C@H]4CCCC[C@@H]4C#N)c4cc[nH]c(=O)c34)ccc2S1(=O)=O] | (1S,2S)-2-(3-{[(3R or 3S)-3-hydroxy-2,2-dimethyl-1,1-dioxido-2,3-dihydro-1-benzothiophen-5-yl]amino}-4-oxo-4,5-dihydro-1H-pyrazolo[4,3-c]pyridin-1-yl)cyclohexanecarbonitrile (Derived from Peak B by HPLC using IC, 20% EtOH in Hexanes (with 0.1% TEA), Tr = 31.19 mins) | Calc'd 468, found 468 |
| 3-174 | 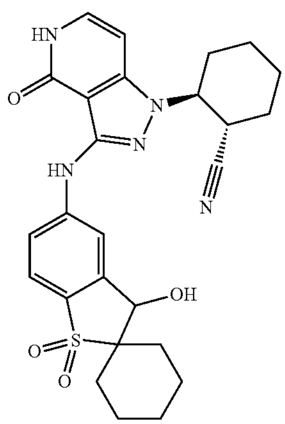 [SMILES: N#C[C@H]1CCCC[C@@H]1n1nc(Nc2ccc3c(c2)C(O)C2(CCCCC2)S3(=O)=O)c2c(=O)[nH]ccc21] | (1S,2S)-2-(3-{[(3S or 3R)-3-hydroxy-1,1-dioxido-3H-spiro[1-benzothiophene-2,1'-cyclohexan]-5-yl]amino}-4-oxo-4,5-dihydro-1H-pyrazolo[4,3-c]pyridin-1-yl)cyclohexanecarbonitrile (Derived from Peak A by HPLC using IA, 30% EtOH in Hexanes, Tr = 11.0 mins) | Calc'd 508, found 508 |
| 3-175 | 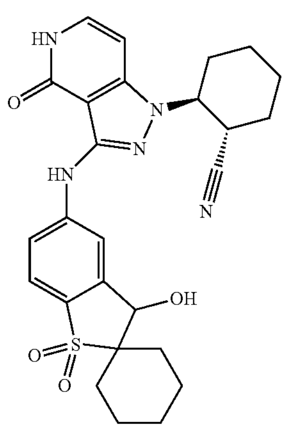 [SMILES: N#C[C@H]1CCCC[C@@H]1n1nc(Nc2ccc3c(c2)C(O)C2(CCCCC2)S3(=O)=O)c2c(=O)[nH]ccc21] | (1S,2S)-2-(3-{[(3R or 3S)-3-hydroxy-1,1-dioxido-3H-spiro[1-benzothiophene-2,1'-cyclohexan]-5-yl]amino}-4-oxo-4,5-dihydro-1H-pyrazolo[4,3-c]pyridin-1-yl)cyclohexanecarbonitrile (Derived from Peak B by HPLC using IA, 30% EtOH in Hexanes, Tr = 15.4 mins) | Calc'd 508, found 508 |

TABLE 37-continued

| Example | Structure | Compound Name | LRMS [M + H]+ |
|---------|-----------|---------------|---------------|
| 3-176 | 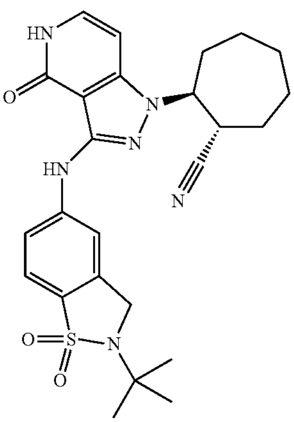 [SMILES: CC(C)(C)N1Cc2cc(Nc3nn([C@H]4CCCCC[C@@H]4C#N)c4cc[nH]c(=O)c34)ccc2S1(=O)=O] | (1S,2S or 1R,2R)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile (from I-12. Derived from Peak B (trans racemic) HPLC using C-18, 30-70% ACN/Water (with 0.05% TFA), Tr = 7.8 min followed by Peak A by HPLC using IC, 40% MeOH in Hexanes (with 0.1% DEA), Tr = 14.15 mins) | Calc'd 495, found 495 |
| 3-177 | 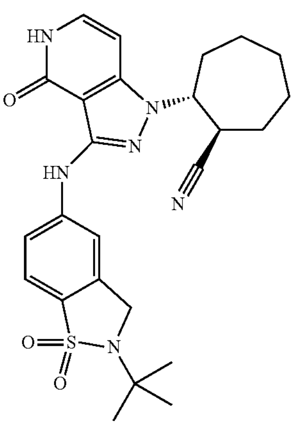 [SMILES: CC(C)(C)N1Cc2cc(Nc3nn([C@@H]4CCCCC[C@H]4C#N)c4cc[nH]c(=O)c34)ccc2S1(=O)=O] | (1R,2R or 1S,2S)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile (from I-12. Derived from Peak B (trans racemic) HPLC using C-18, 30-70% ACN/Water (with 0.05% TFA), Tr = 7.8 min followed by Peak B by HPLC using IC, 40% MeOH in Hexanes (with 0.1% DEA), Tr = 17.46 mins) | Calc'd 495, found 495 |
| 3-178 | 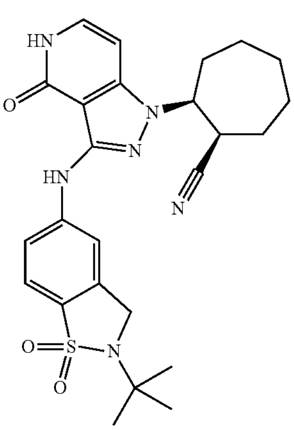 [SMILES: CC(C)(C)N1Cc2cc(Nc3nn([C@H]4CCCCC[C@H]4C#N)c4cc[nH]c(=O)c34)ccc2S1(=O)=O] | (1R,2S or 1S,2R)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile (from I-12. Derived from Peak A (cis racemic) HPLC using C-18, 30-70% ACN/Water (with 0.05% TFA), Tr = 6.5 min followed by Peak A by HPLC using IA, 50% EtOH (with 0.1% DEA) in Hexanes (with 0.1% DEA), Tr = 31.8 mins) | Calc'd 495, found 495 |

TABLE 37-continued

| Example | Structure | Compound Name | LRMS [M + H]+ |
|---|---|---|---|
| 3-179 | 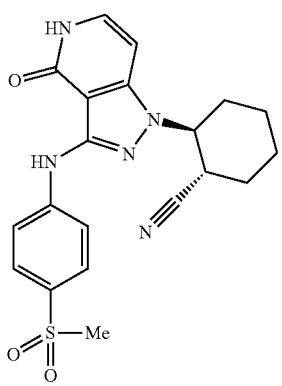 | (1S,2R or 1R,2S)-2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile (from I-12. Derived from Peak A (cis racemic) HPLC using C-18, 30-70% ACN/Water (with 0.05% TFA), Tr = 6.5 min followed by Peak B by HPLC using IA, 50% EtOH (with 0.1% DEA) in Hexanes (with 0.1% DEA), Tr = 74.0 mins) | Calc'd 495, found 495 |

Example 3-5

(1S,2S)-2-(3-{[4-(Methylsulfonyl)phenyl]amino}-4-oxo-4,5-dihydro-1H-pyrazolo[4,3-c]pyridin-1-yl)cyclohexanecarbonitrile 3-5

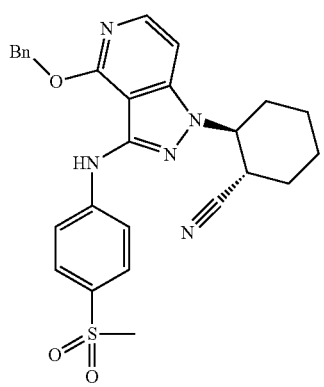

Step 1: (1S,2S)-2-(4-(Benzyloxy)-3-((4-(methylsulfonyl)phenyl)amino)-1H-pyrazolo[4,3-c]pyridin-1-yl)cyclohexanecarbonitrile 3-5a A mixture of (1S,2S)-2-(3-amino-4-(benzyloxy)-1H-pyrazolo[4,3-c]pyridin-1-yl)cyclohexanecarbonitrile (I-5; 6.24 g, 18.0 mmol), 1-bromo-4-(methylsulfonyl)benzene (8.44 g, 35.9 mmol), Pd$_2$(dba)$_3$ (1.64 g, 1.80 mmol) and 2-di-t-butylphosphino-3,4,5,6-tetramethyl-2',4',6'-tri-i-propylbiphenyl (tetramethyl-tBu-Xphos; 2.59 g, 5.38 mmol) in 2-Propanol (70 mL) was placed in a vial and sealed. The mixture was flushed with argon for 10 min, then was heated at 85° C. for 2 hours. The reaction mixture was cooled and diluted with EtOAc, filtered through celite, with the resulting filtrate concentrated in vacuo. The resulting residue was purified by silica gel chromatography (0-80% EtOAc/hexanes), to give the title compound. LRMS (ESI) calc'd for C$_{27}$H$_{28}$N$_5$O$_3$S [M+H]+: 502, found 502.

Step 2: (1S,2S)-2-(4-(Benzyloxy)-3-((4-(methylsulfonyl)phenyl)amino)-1H-pyrazolo[4,3-c]pyridin-1-yl)cyclohexanecarbonitrile (1S,2S)-2-(4-(benzyloxy)-3-((4-(methylsulfonyl)phenyl)amino)-1H-pyrazolo[4,3-c]pyridin-1-yl)cyclohexanecarbonitrile (8.58 g, 17.1 mmol) and Pd/C (10%; 0.85 g, 0.80 mmol) were combined in a flask and placed under nitrogen. Ethyl acetate (100 mL) and THF (100 mL) were added, and the mixture was evacuated in vacuo and back-filled with H$_2$ (3×). The reaction mixture was stirred at rt under hydrogen (balloon pressure) overnight. The catalyst was removed by filtration of the reaction mixture through celite rinsing with EtOAc. The resulting filtrate was concentrated in vacuo to afford a residue that was purified by silica gel chromatography (0-6% MeOH/DCM) and was triturated with MeOH to afford the title compound. LRMS (ESI) calc'd for C$_{20}$H$_{22}$N$_5$O$_3$S [M+H]+: 412, found 412. $^1$H NMR (600 MHz, DMSO-d$_6$): δ 11.1 (s, 1H), 8.66 (s, 1H), 7.85 (d, J=8.4 Hz, 2H), 7.75 (d, J=9.0 Hz, 2H), 7.22 (m, 1H), 6.68 (d, J=7.2 Hz, 1H), 4.70 (m, 1H), 3.35 (m, 1H), 3.10 (s, 3H), 2.16 (m, 1H), 1.68-1.91 (m, 5H), 1.46 (m, 1H), 1.33 (m, 1H).

Table 38 discloses intermediates utilized in synthesis of compounds of Examples 4 and 5. Intermediates I-168 through I-170 were made using procedures analogous to those utilized in the making of Intermediates I-8 and I-9 and using the general procedure to Example 3-1.

TABLE 38

| Intermediate | Structure | Compound Name | LRMS [M + H]+ |
|---|---|---|---|
| I-168 | 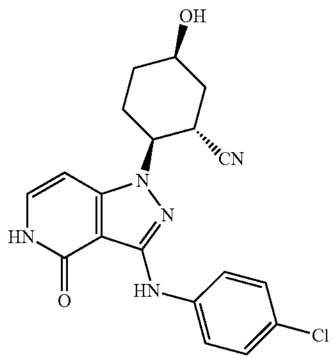 [SMILES: N#C[C@H]1C[C@H](O)CC[C@@H]1n1nc(Nc2ccc(Cl)cc2)c2c(=O)[nH]ccc21] | racemic-2-(3-((4-chlorophenyl)amino)-4-oxo-4,5-dihydro-1H-pyrazolo[4,3-c]pyridin-1-yl)-5-hydroxycyclohexanecarbonitrile | Calc'd 384, found 384 |
| I-169 | 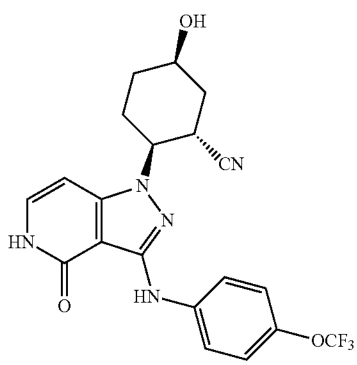 [SMILES: N#C[C@H]1C[C@H](O)CC[C@@H]1n1nc(Nc2ccc(OC(F)(F)F)cc2)c2c(=O)[nH]ccc21] | (1S,2S,5R)-5-hydroxy-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 434, found 434 |
| I-170 | 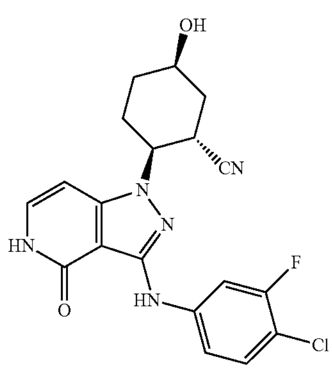 [SMILES: N#C[C@H]1C[C@H](O)CC[C@@H]1n1nc(Nc2ccc(Cl)c(F)c2)c2c(=O)[nH]ccc21] | (1S,2S,5R)-2-(3-((4-chloro-3-fluorophenyl)amino)-4-oxo-4,5-dihydro-1H-pyrazolo[4,3-c]pyridin-1-yl)-5-hydroxycyclohexanecarbonitrile | Calc'd 402, found 402 |

Examples 4-1, 4-2, 4-3, and 4-4

(1R,2R,5S)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile (4-1)

(1S,2S,5R)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile (4-2)

(1R,2R,5R)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile (4-3)

(1S,2S,5S)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile (4-4)

4-1
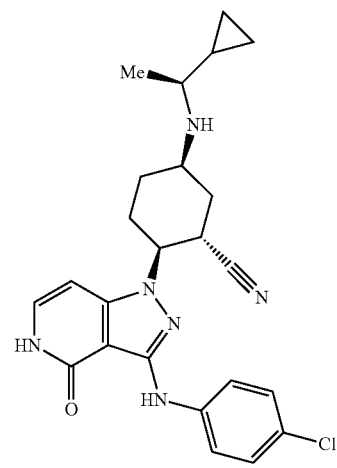

4-2
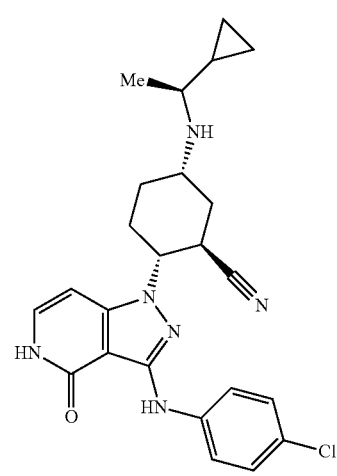

4-3
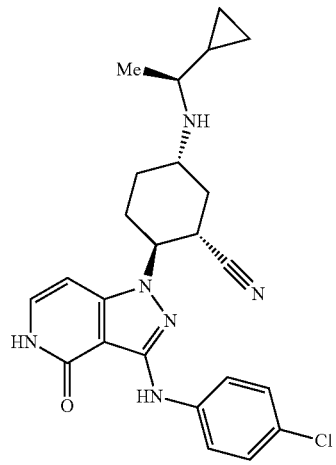

4-4
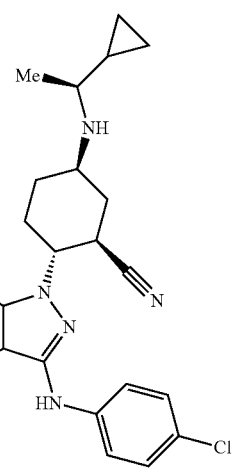

Step 1: (1R,2R)-2-(3-((4-Chlorophenyl)amino)-4-oxo-4,5-dihydro-1H-pyrazolo[4,3-c]pyridin-1-yl)-5-oxocyclohexanecarbonitrile and (1S,2S)-2-(3-((4-Chlorophenyl)amino)-4-oxo-4,5-dihydro-1H-pyrazolo[4,3-c]pyridin-1-yl)-5-oxocyclohexanecarbonitrile 4a
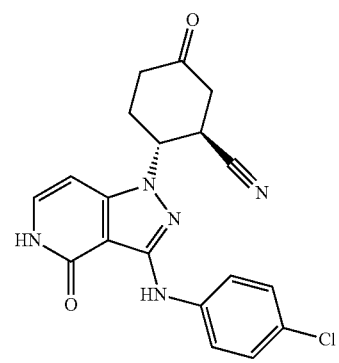

-continued

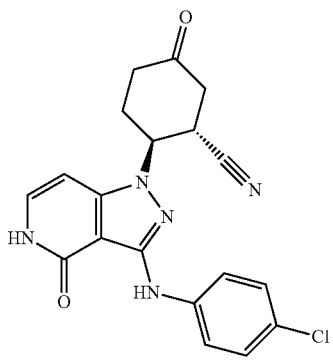

4b

To a solution of (racemic)-2-(3-((4-chlorophenyl)amino)-4-oxo-4,5-dihydro-1H-pyrazolo[4,3-c]pyridin-1-yl)-5-hydroxycyclohexanecarbonitrile (I-168; 77 mg, 0.20 mmol) in DMSO (2.0 mL) was added IBX (stabilized, 45% by weight; 312 mg, 0.502 mmol), and the mixture was heated at 50° C. for 3 h. The mixture was cooled to rt, stirred with sat $Na_2S_2O_3$ and sat $NaHCO_3$ for 30 min, extracted with ethyl acetate. The organic layer was washed with brine, dried over $Na_2SO_4$, filtered and concentrated in vacuo. The crude ketone, (4a and 4b) was used for the next step without purification.

Step 2: Title Compounds 4-1, 4-2, 4-3 and 4-4

$NaCNBH_4$ (28.8 mg, 0.458 mmol) was added to a mixture of the crude ketone from previous step (70.0 mg, 0.183 mmol), (s)-1-cyclopropylethylamine (150 μL, 1.47 mmol), and acetic acid (84.0 μL, 1.47 mmol) in MeOH/THF. The mixture was stirred at rt for 3 h, diluted with EtOAc and sat. $NaHCO_3$. The organic layer was separated, washed with brine, dried over $Na_2SO_4$, and concentrated in vacuo. The residue was purified by flash chromatography (dry loading, 0-20% MeOH/DCM) to give two mixtures, each containing two diastereomers. The two mixtures were submitted separately to chiral separation to give 4 diasteromers:
Column Used: Phenomenex Lux-4 IC, 2.1×25 cm, 5 μM.
Mobile phase: 39%/61% MeOH/$CO_2$ (with 0.25% dimethylamine modifier).
Flow rate: 62 mL/min, 7 min run time
Wavelength: 220 nm.
Diastereomer 1; Example 4-1: (1S,2S,5R)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile LRMS (ESI) calc'd for $C_{24}H_{28}ClN_6O$ [M+H]$^+$: 451, found 451. $^1$H NMR (600 MHz, Acetone-$d_6$): δ 10.1 (s, 1H), 8.09 (s, 1H), 7.78 (d, J=7.8 Hz, 2H), 7.27-7.29 (m, 3H), 6.60 (d, J=7.2 Hz, 1H), 4.64 (td, J=12.0, 3.6 Hz, 1H), 3.96 (t, J=12.0 Hz, 1H), 3.33 (d, J=21.0 Hz, 1H), 2.50-2.58 (m, 1H), 2.16-2.30 (m, 2H), 1.87-2.08 (m, 3H), 1.60-1.68 (m, 2H), 1.17 (s, 3H), 0.70-0.80 (m, 1H), 0.50-0.58 (m, 1H), 0.34-0.46 (m, 2H), 0.18-0.23 (m, 1H).
Diastereomer 2; Example 4-2: (1R,2R,5S)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile LRMS (ESI) calc'd for $C_{24}H_{28}ClN_6O$ [M+H]$^+$: 451, found 451.
Diastereomer 3; Example 4-3: (1S,2S,5S)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile LRMS (ESI) calc'd for $C_{24}H_{28}ClN_6O$ [M+H]$^+$: 451, found 451.
Diastereomer 4; Example 4-4: (1R,2R,5R)-2-(3-((4-Chlorophenyl)amino)-4-oxo-4,5-dihydro-1H-pyrazolo[4,3-c]pyridin-1-yl)-5-(((S)-1-cyclopropylethyl)amino)cyclohexanecarbonitrile LRMS (ESI) calc'd for $C_{24}H_{28}ClN_6O$ [M+H]$^+$: 451, found 451. $^1$H NMR (600 MHz, Acetone-$d_6$): δ 10.1 (s, 1H), 8.09 (s, 1H), 7.74 (d, J=9.0 Hz, 2H), 7.27-7.29 (m, 3H), 6.62 (d, J=7.2 Hz, 1H), 4.64-4.69 (m, 1H), 3.59 (t, J=10.2 Hz, 1H), 3.00-3.12 (m, 1H), 2.49-2.56 (m, 1H), 2.05-2.26 (m, 5H), 1.26-1.70 (m, 3H), 1.16 (s, 3H), 0.70-0.80 (m, 1H), 0.40-0.49 (m, 2H), 0.24-0.38 (m, 1H), 0.10-0.17 (m, 1H).

Examples 5-1 and 5-2

(1S,2S,5R)-2-(3-((4-Chlor-3-fluorophenyl)amino)-4-oxo-4,5-dihydro-1H-pyrazolo[4,3-c]pyridin-1-yl)-5-(dimethylamino)cyclohexanecarbonitrile (5-1) and (1S,2S,5S)-2-(3-((4-Chloro-3-fluorophenyl)amino)-4-oxo-4,5-dihydro-1H-pyrazolo[4,3-c]pyridin-1-yl)-5-(dimethylamino)cyclohexanecarbonitrile (5-2)

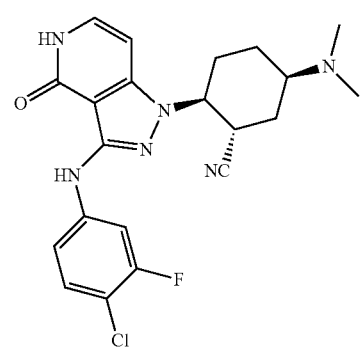

5-1

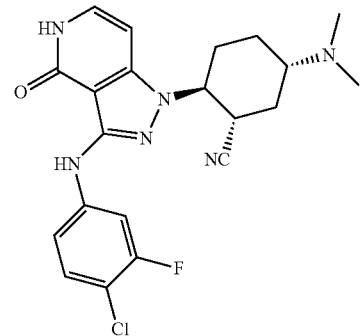

5-2

Step 1: (1S,2S)-2-(3-((4-Chloro-3-fluorophenyl)amino)-4-oxo-4,5-dihydro-1H-pyrazolo[4,3-c]pyridin-1-yl)-5-oxocyclohexanecarbonitrile

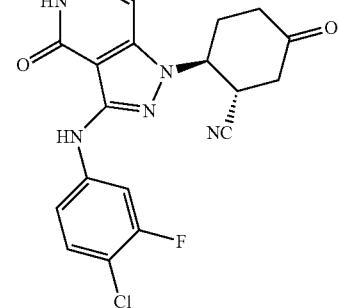

5a

To a solution of (1S,2S,5R)-2-(3-((4-chloro-3-fluorophenyl)amino)-4-oxo-4,5-dihydro-1H-pyrazolo[4,3-c]pyridin-1-yl)-5-hydroxycyclohexanecarbonitrile (I-170; 0.55 g, 1.4 mmol) in DMSO (14 mL) was added IBX (stabilized, 45% by weight; 2.1 g, 3.4 mmol). The mixture was heated at 50° C. and held for 2.5 hours. The reaction was cooled to room temperature, diluted with a mixture of water (70 mL), aqueous sodium thiosulphate (15 mL) and aqueous sodium bicarbonate (15 mL), and vigorously stirred for 20 minutes. The reaction mixture was extracted with EtOAc (50 mL). The organic layer was washed with water (15 mL) and brine (15 mL) then dried over $Na_2SO_4$ and concentrated in vacuo to afford the title compound. LRMS (ESI) calc'd for $C_{19}H_{16}ClFN_5O_2$ [M+H]$^+$: 400, found 400.

Step 2: (1S,2S,5R)-2-(3-((4-Chloro-3-fluorophenyl)amino)-4-oxo-4,5-dihydro-1H-pyrazolo[4,3-c]pyridin-1-yl)-5-(dimethylamino)cyclohexanecarbonitrile (5-1) and (1S,2S,5S)-2-(3-((4-Chloro-3-fluorophenyl)amino)-4-oxo-4,5-dihydro-1H-pyrazolo[4,3-c]pyridin-1-yl)-5-(dimethylamino)cyclohexanecarbonitrile (5-2)

To a suspension of (1S,2S)-2-(3-((4-chloro-3-fluorophenyl)amino)-4-oxo-4,5-dihydro-1H-pyrazolo[4,3-c]pyridin-1-yl)-5-oxocyclohexanecarbonitrile (0.18 g, 0.45 mmol) in a mixture of THF (2.3 mL) and MeOH (2.3 mL) was added dimethylamine (0.16 g, 3.6 mmol) and acetic acid (0.21 mL, 3.6 mmol). The reaction mixture was stirred at room temperature for 15 minutes then sodium cyanoborohydride (0.71 g, 1.1 mmol) was added and the reaction mixture was allowed to stir for an additional 18 hours at room temperature. The reaction mixture was concentrated in vacuo to afford a residue that was purified by column chromatography on silica gel (DCM/MeOH).

Peak A, Example 5-1. LRMS (ESI) calc'd for $C_{21}H_{23}ClFN_6O$ [M+H]$^+$: 429, found 429. $^1$H NMR (600 MHz, DMSO-$d_6$) δ 11.10 (d, J=5.6 Hz, 1H), 8.47 (s, 1H), 7.84-7.78 (m, 1H), 7.43-7.36 (m, 2H), 7.24-7.19 (m, 1H), 6.61 (d, J=7.4 Hz, 1H), 4.80-4.74 (m, 1H), 3.59-3.52 (m, 1H), 2.43-2.35 (m, 1H), 2.19 (s, 6H), 2.14-2.10 (m, 2H), 2.06-1.99 (m, 1H), 1.90-1.82 (m, 1H), 1.68-1.61 (m, 1H), 1.61-1.53 (m, 1H).

Peak B was further purified by reverse phase HPLC (C-18; acetonitrile/water containing 0.1% TFA). Fractions containing desired product were diluted with EtOAc, washed with saturated $NaHCO_3$, dried over $Na_2SO_4$, filtered, and concentrated in vacuo to afford Example 5-2. LRMS (ESI) calc'd for $C_{21}H_{23}ClFN_6O$ [M+H]$^+$: 429, found 429. $^1$H NMR (600 MHz, DMSO-$d_6$) δ 11.10 (d, J=5.7 Hz, 1H), 8.44 (s, 1H), 7.80 (dd, J=12.4, 2.5 Hz, 1H), 7.49 (dd, J=8.8, 2.3 Hz, 1H), 7.38 (t, J=8.7 Hz, 1H), 7.21 (dd, J=7.2, 6.0 Hz, 1H), 6.64 (d, J=7.3 Hz, 1H), 4.75-4.67 (m, 1H), 3.46-3.39 (m, 1H), 2.48-2.42 (m, 1H), 2.23-2.15 (m, 7H), 1.94-1.89 (m, 2H), 1.86-1.80 (m, 1H), 1.77-1.69 (m, 1H), 1.54-1.44 (m, 1H).

Table 39 contains Examples 5-3 through 5-28 that were prepared in an analogous fashion to that of Examples 5-1 and 5-2 starting with the appropriately substituted hydroxy-containing intermediate and amine through sequential oxidation and reductive amination reactions.

TABLE 39

| Example | Structure | Compound Name | LRMS [M + H]$^+$ |
|---|---|---|---|
| 5-3 | 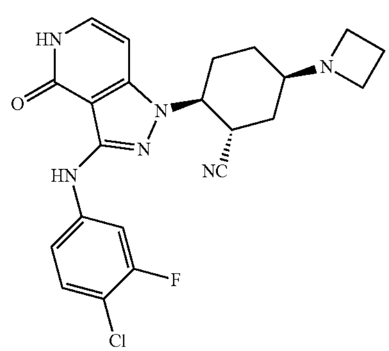 [SMILES: N#C[C@H]1C[C@H](N2CCC2)CC[C@@H]1n1nc(Nc2ccc(Cl)c(F)c2)c2c(=O)[nH]ccc21] | (1S,2S,5R)-5-(azetidin-1-yl)-2-(3-((4-chloro-3-fluorophenyl)amino)-4-oxo-4,5-dihydro-1H-pyrazolo[4,3-c]pyridin-1-yl)cyclohexanecarbonitrile | Calc'd 441, found 441 |
| 5-4 | 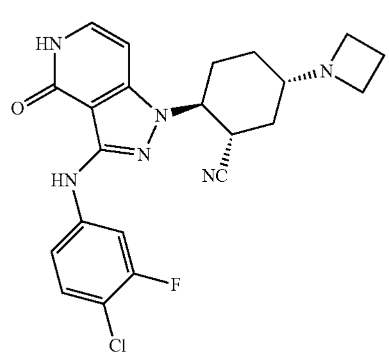 [SMILES: N#C[C@H]1C[C@@H](N2CCC2)CC[C@@H]1n1nc(Nc2ccc(Cl)c(F)c2)c2c(=O)[nH]ccc21] | (1S,2S,5S)-5-(azetidin-1-yl)-2-(3-((4-chloro-3-fluorophenyl)amino)-4-oxo-4,5-dihydro-1H-pyrazolo[4,3-c]pyridin-1-yl)cyclohexanecarbonitrile | Calc'd 441, found 441 |

TABLE 39-continued

| Example | Structure | Compound Name | LRMS [M + H]+ |
|---|---|---|---|
| 5-5 | 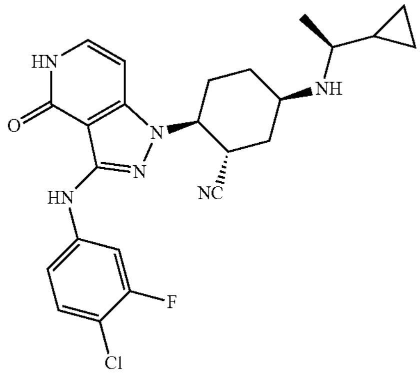 [SMILES: C[C@H](N[C@@H]1CC[C@H](n2nc(Nc3ccc(Cl)c(F)c3)c3c(=O)[nH]ccc32)[C@@H](C#N)C1)C1CC1] | (1S,2S,5R)-2-(3-((4-chloro-3-fluorophenyl)amino)-4-oxo-4,5-dihydro-1H-pyrazolo[4,3-c]pyridin-1-yl)-5-(((S)-1-cyclopropylethyl)amino)cyclohexane-carbonitrile | Calc'd 469, found 469 |
| 5-6 | 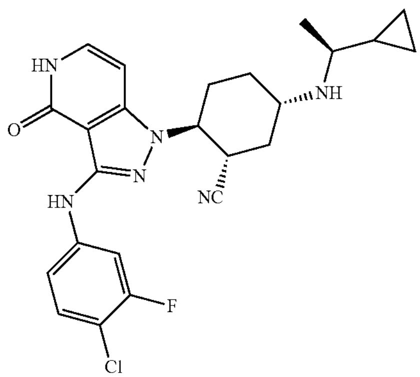 [SMILES: C[C@H](N[C@H]1CC[C@H](n2nc(Nc3ccc(Cl)c(F)c3)c3c(=O)[nH]ccc32)[C@@H](C#N)C1)C1CC1] | (1S,2S,5S)-2-(3-((4-chloro-3-fluorophenyl)amino)-4-oxo-4,5-dihydro-1H-pyrazolo[4,3-c]pyridin-1-yl)-5-(((S)-1-cyclopropylethyl)amino)cyclohexane-carbonitrile | Calc'd 469, found 469 |
| 5-7 | 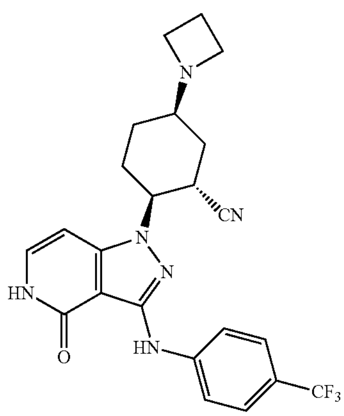 [SMILES: N#C[C@H]1C[C@H](N2CCC2)CC[C@@H]1n1nc(Nc2ccc(C(F)(F)F)cc2)c2c(=O)[nH]ccc21] | (1S,2S,5R)-5-(azetidin-1-yl)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 457, found 457 |
| 5-8 | 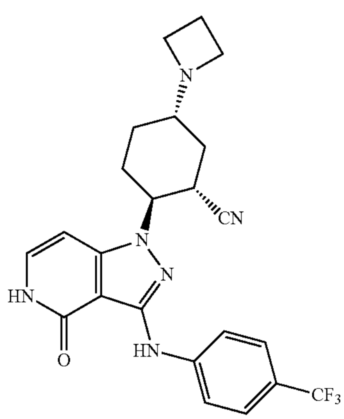 [SMILES: N#C[C@H]1C[C@@H](N2CCC2)CC[C@@H]1n1nc(Nc2ccc(C(F)(F)F)cc2)c2c(=O)[nH]ccc21] | (1S,2S,5S)-5-(azetidin-1-yl)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 457, found 457 |

TABLE 39-continued

| Example | Structure | Compound Name | LRMS [M + H]+ |
|---|---|---|---|
| 5-9 | 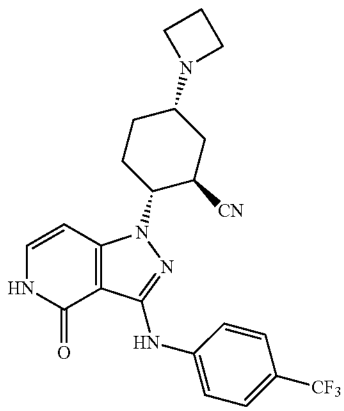 [SMILES: N#C[C@@H]1C[C@@H](N2CCC2)CC[C@H]1n1nc(Nc2ccc(C(F)(F)F)cc2)c2c(=O)[nH]ccc21] | (1R,2R,5S)-5-(azetidin-1-yl)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 457, found 457 |
| 5-10 | 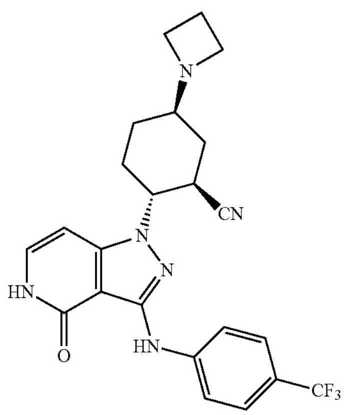 [SMILES: N#C[C@@H]1C[C@H](N2CCC2)CC[C@H]1n1nc(Nc2ccc(C(F)(F)F)cc2)c2c(=O)[nH]ccc21] | (1R,2R,5R)-5-(azetidin-1-yl)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 457, found 457 |
| 5-11 | 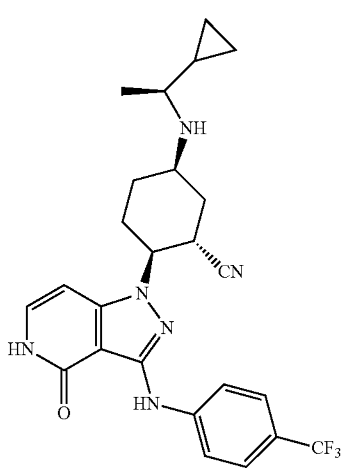 [SMILES: C[C@H](N[C@@H]1CC[C@H](n2nc(Nc3ccc(C(F)(F)F)cc3)c3c(=O)[nH]ccc32)[C@@H](C#N)C1)C1CC1] | (1S,2S,5R)-5-(((S)-1-cyclopropylethyl)amino)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 485, found 485 |

TABLE 39-continued

| Example | Structure | Compound Name | LRMS [M + H]+ |
|---|---|---|---|
| 5-12 | 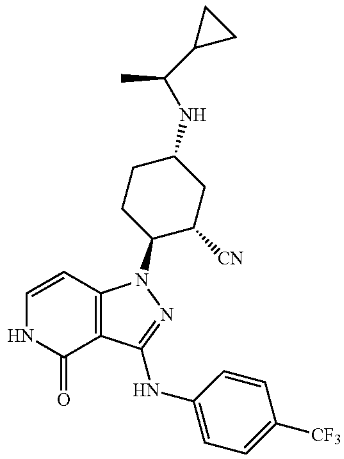 [SMILES: C[C@H](N[C@H]1CC[C@H](n2nc(Nc3ccc(C(F)(F)F)cc3)c3c(=O)[nH]ccc32)[C@@H](C#N)C1)C1CC1] | (1S,2S,5S)-5-(((S)-1-cyclopropylethyl)amino)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 485, found 485 |
| 5-13 | 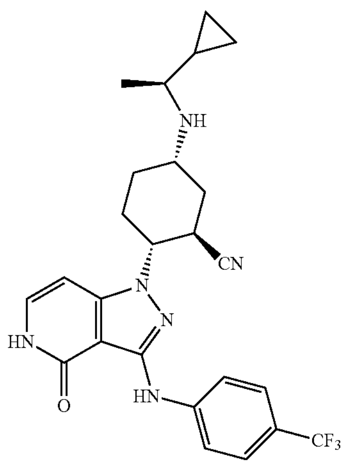 [SMILES: C[C@H](N[C@H]1CC[C@@H](n2nc(Nc3ccc(C(F)(F)F)cc3)c3c(=O)[nH]ccc32)[C@H](C#N)C1)C1CC1] | (1R,2R,5S)-5-(((S)-1-cyclopropylethyl)amino)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 485, found 485 |
| 5-14 | 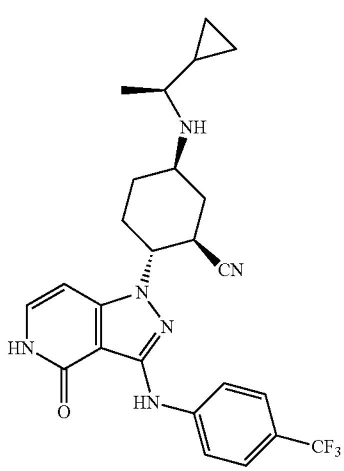 [SMILES: C[C@H](N[C@@H]1CC[C@@H](n2nc(Nc3ccc(C(F)(F)F)cc3)c3c(=O)[nH]ccc32)[C@H](C#N)C1)C1CC1] | (1R,2R,5R)-5-(((S)-1-cyclopropylethyl)amino)-2-(4-oxo-3-((4-(trifluoromethyl)phenyl)amino)-4,5-dihydro-1H-pyrazolo[4,3-c]pyridin-1-yl)cyclohexanecarbonitrile | Calc'd 485, found 485 |

TABLE 39-continued

| Example | Structure | Compound Name | LRMS [M + H]+ |
|---|---|---|---|
| 5-15 | 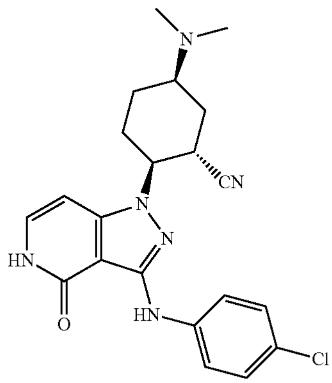 [SMILES: CN(C)[C@@H]1CC[C@H](n2nc(Nc3ccc(Cl)cc3)c3c(=O)[nH]ccc32)[C@@H](C#N)C1] | (1S,2S,5R)-2-(3-((4-chlorophenyl)amino)-4-oxo-4,5-dihydro-1H-pyrazolo[4,3-c]pyridin-1-yl)-5-(dimethylamino)cyclohexanecarbonitrile | Calc'd 411, found 411 |
| 5-16 | 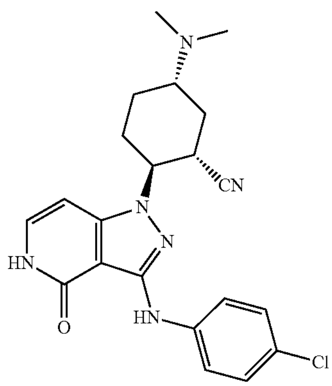 [SMILES: CN(C)[C@H]1CC[C@H](n2nc(Nc3ccc(Cl)cc3)c3c(=O)[nH]ccc32)[C@@H](C#N)C1] | (1S,2S,5S)-2-(3-((4-chlorophenyl)amino)-4-oxo-4,5-dihydro-1H-pyrazolo[4,3-c]pyridin-1-yl)-5-(dimethylamino)cyclohexanecarbonitrile | Calc'd 411, found 411 |
| 5-17 | 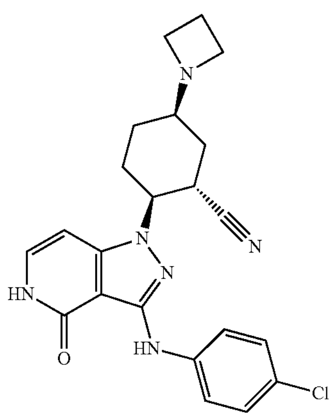 [SMILES: N#C[C@H]1C[C@H](N2CCC2)CC[C@@H]1n1nc(Nc2ccc(Cl)cc2)c2c(=O)[nH]ccc21] | (1S,2S,5R)-5-(azetidin-1-yl)-2-(3-((4-chlorophenyl)amino)-4-oxo-4,5-dihydro-1H-pyrazolo[4,3-c]pyridin-1-yl)cyclohexanecarbonitrile | Calc'd 423, found 423 |
| 5-18 | 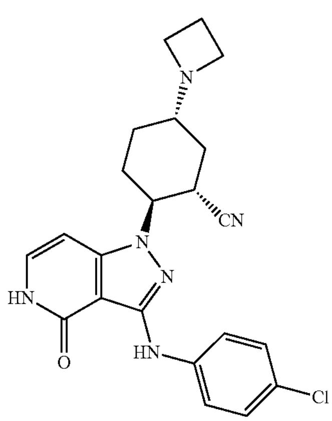 [SMILES: N#C[C@H]1C[C@@H](N2CCC2)CC[C@@H]1n1nc(Nc2ccc(Cl)cc2)c2c(=O)[nH]ccc21] | (1S,2S,5S)-5-(azetidin-1-yl)-2-(3-((4-chlorophenyl)amino)-4-oxo-4,5-dihydro-1H-pyrazolo[4,3-c]pyridin-1-yl)cyclohexanecarbonitrile | Calc'd 423, found 423 |

TABLE 39-continued

| Example | Structure | Compound Name | LRMS [M + H]+ |
|---|---|---|---|
| 5-19 | 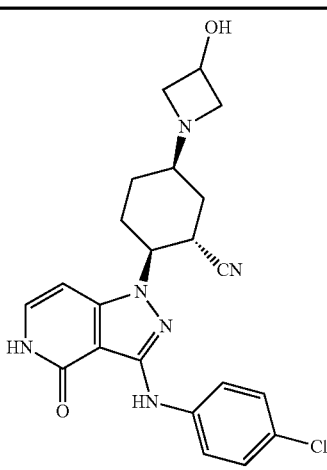 | (1S,2S,5R)-2-(3-((4-chlorophenyl)amino)-4-oxo-4,5-dihydro-1H-pyrazolo[4,3-c]pyridin-1-yl)-5-(3-hydroxyazetidin-1-yl)cyclohexanecarbonitrile | Calc'd 439 found 439, |
| 5-20 | 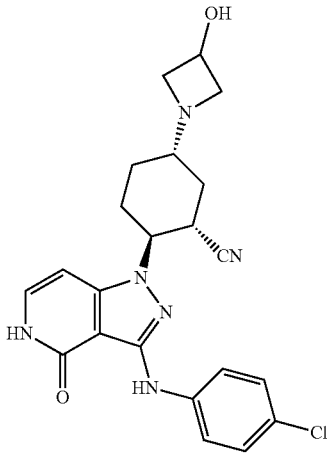 [SMILES: N#C[C@H]1C[C@@H](N2CC(O)C2)CC[C@@H]1n1nc(Nc2ccc(Cl)cc2)c2c(=O)[nH]ccc21] | (1S,2S,5S)-2-(3-((4-chlorophenyl)amino)-4-oxo-4,5-dihydro-1H-pyrazolo[4,3-c]pyridin-1-yl)-5-(3-hydroxyazetidin-1-yl)cyclohexanecarbonitrile | Calc'd 439, found 439 |
| 5-21 | 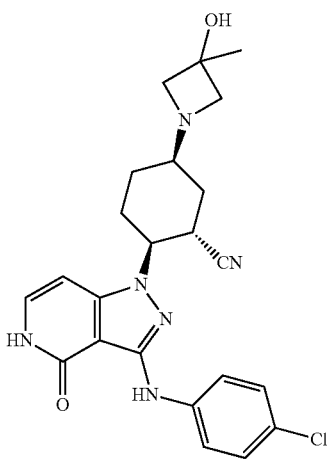 [SMILES: CC1(O)CN([C@@H]2CC[C@H](n3nc(Nc4ccc(Cl)cc4)c4c(=O)[nH]ccc43)[C@@H](C#N)C2)C1] | (1S,2S,5R)-2-(3-((4-chlorophenyl)amino)-4-oxo-4,5-dihydro-1H-pyrazolo[4,3-c]pyridin-1-yl)-5-(3-hydroxy-3-methylazetidin-1-yl)cyclohexanecarbonitrile | Calc'd 453, found 453 |

TABLE 39-continued

| Example | Structure | Compound Name | LRMS [M + H]+ |
|---|---|---|---|
| 5-22 | 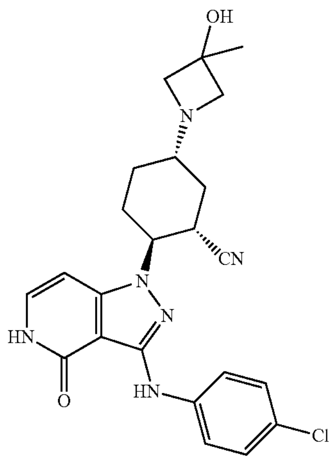 [SMILES: CC1(O)CN([C@H]2CC[C@H](n3nc(Nc4ccc(Cl)cc4)c4c(=O)[nH]ccc43)[C@@H](C#N)C2)C1] | (1S,2S,5S)-2-(3-((4-chlorophenyl)amino)-4-oxo-4,5-dihydro-1H-pyrazolo[4,3-c]pyridin-1-yl)-5-(3-hydroxy-3-methylazetidin-1-yl)cyclohexanecarbonitrile | Calc'd 453, found 453 |
| 5-23 | 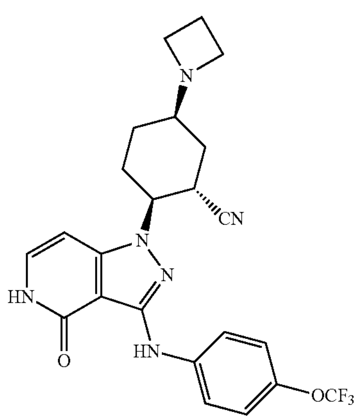 [SMILES: N#C[C@H]1C[C@H](N2CCC2)CC[C@@H]1n1nc(Nc2ccc(OC(F)(F)F)cc2)c2c(=O)[nH]ccc21] | (1S,2S,5R)-5-(azetidin-1-yl)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 473, found 473 |
| 5-24 | 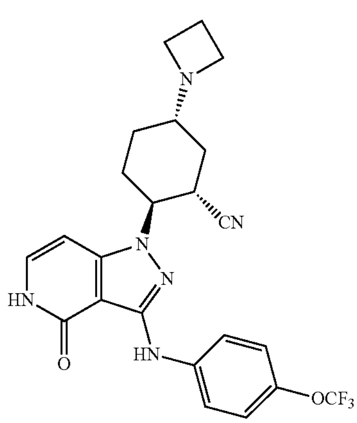 [SMILES: N#C[C@H]1C[C@@H](N2CCC2)CC[C@@H]1n1nc(Nc2ccc(OC(F)(F)F)cc2)c2c(=O)[nH]ccc21] | (1S,2S,5S)-5-(azetidin-1-yl)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 473, found 473 |

TABLE 39-continued

| Example | Structure | Compound Name | LRMS [M + H]+ |
|---|---|---|---|
| 5-25 | 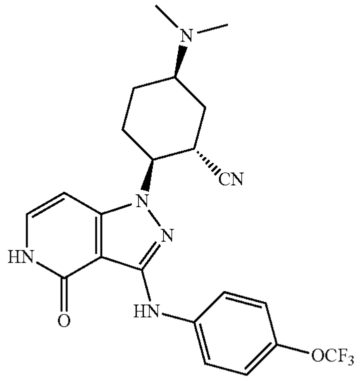 [SMILES: CN(C)[C@@H]1CC[C@H](n2nc(Nc3ccc(OC(F)(F)F)cc3)c3c(=O)[nH]ccc32)[C@@H](C#N)C1] | (1S,2S,5R)-5-(dimethylamino)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 461, found 461 |
| 5-26 | 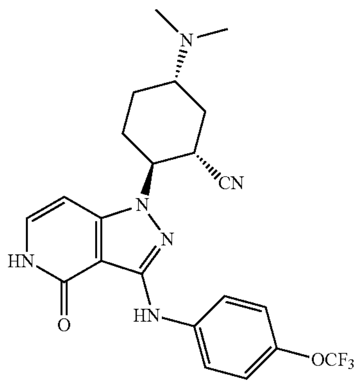 [SMILES: CN(C)[C@H]1CC[C@H](n2nc(Nc3ccc(OC(F)(F)F)cc3)c3c(=O)[nH]ccc32)[C@@H](C#N)C1] | (1S,2S,5S)-5-(dimethylamino)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 461, found 461 |
| 5-27 | 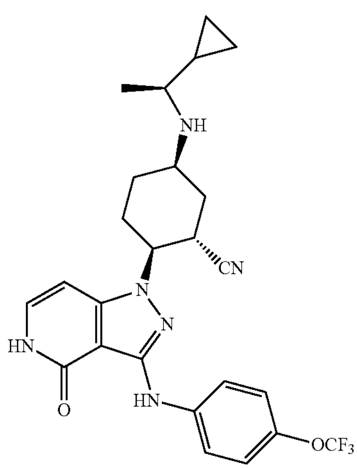 [SMILES: C[C@H](N[C@@H]1CC[C@H](n2nc(Nc3ccc(OC(F)(F)F)cc3)c3c(=O)[nH]ccc32)[C@@H](C#N)C1)C1CC1] | (1S,2S,5R)-5-(((S)-1-cyclopropylethyl)amino)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 501, found 501 |

TABLE 39-continued

| Example | Structure | Compound Name | LRMS [M + H]+ |
|---|---|---|---|
| 5-28 | 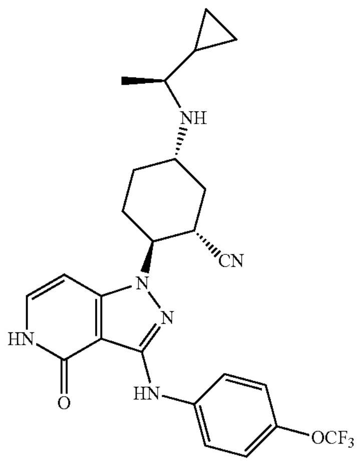 [SMILES: C[C@H](N[C@H]1CC[C@H](n2nc(Nc3ccc(OC(F)(F)F)cc3)c3c(=O)[nH]ccc32)[C@@H](C#N)C1)C1CC1] | (1S,2S,5S)-5-(((S)-1-cyclopropylethyl)amino)-2-(4-oxo-3-((4-(trifluoromethoxy)phenyl)amino)-4,5-dihydro-1H-pyrazolo[4,3-c]pyridin-1-yl)cyclohexanecarbonitrile | Calc'd 501, found 501 |

Example 6-1

(1S,2S)-2-(3-((3-(Aminomethyl)phenyl)amino)-4-oxo-4,5-dihydro-1H-pyrazolo[4,3-c]pyridin-1-yl)cyclohexanecarbonitrile

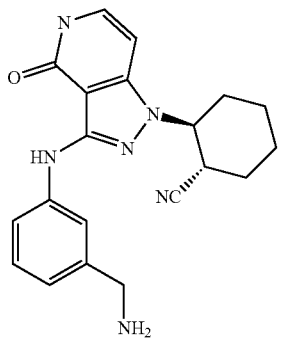

6-1

To a flask containing Example 3-16 (0.29 g, 0.63 mmol) was added HCl-MeOH solution, and the resulting mixture was stirred for 16 hours. The reaction mixture was concentrated in vacuo to afford (1S,2S)-2-(3-((3-(aminomethyl)phenyl)amino)-4-oxo-4,5-dihydro-1H-pyrazolo[4,3-c]pyridin-1-yl)cyclohexanecarbonitrile (HCl salt). LRMS (ESI) calc'd. for $C_{20}H_{23}N_6O$ [M+H]+: 363, found 363. $^1$H NMR (400 MHz, DMSO-$d_6$): δ 11.12 (d, J=5.6 Hz, 1H), 8.41 (br, 3H), 8.15 (s, 1H), 7.78-7.76 (m, 1H), 7.55 (s, 1H), 7.34-7.30 (m, 1H), 7.27-7.19 (m, 1H), 6.99-6.95 (m, 1H), 6.66 (d, J=7.2 Hz, 1H), 4.69-4.63 (m, 1H), 3.98 (d, J=5.2 Hz, 2H), 2.70-2.64 (m, 1H), 2.18-2.15 (m, 1H), 1.91-1.88 (m, 2H), 1.79-1.73 (m, 3H), 1.69-1.33 (m, 2H).

Table 40 contains Examples that were prepared in an analogous manner to that of Example 6-1.

TABLE 40

| Example | Structure | Compound Name | LRMS [M + H]+ |
|---|---|---|---|
| 6-2 | 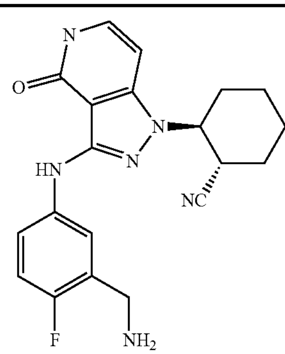 | (1S,2S)-2-(3-((3-(aminomethyl)-4-fluorophenyl)amino)-4-oxo-4,5-dihydro-1H-pyrazolo[4,3-c]pyridin-1-yl)cyclohexanecarbonitrile | Calc'd 381, found 381 |

TABLE 40-continued

| Example | Structure | Compound Name | LRMS [M + H]+ |
|---|---|---|---|
| 6-3 | 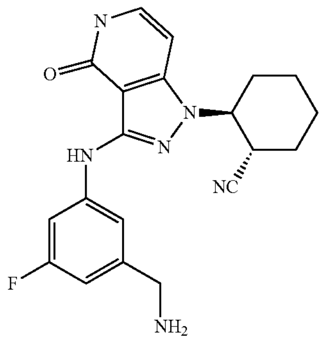 [SMILES: N#C[C@H]1CCCC[C@@H]1n1nc(Nc2cc(F)cc(CN)c2)c2c(=O)[nH]ccc21] | (1S,2S)-2-(3-((3-(aminomethyl)-5-fluorophenyl)amino)-4-oxo-4,5-dihydro-1H-pyrazolo[4,3-c]pyridin-1-yl)cyclohexanecarbonitrile | Calc'd 381, found 381 |
| 6-4 | 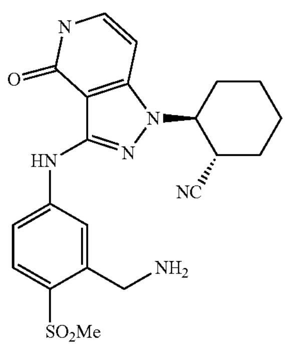 [SMILES: CS(=O)(=O)c1ccc(Nc2nn([C@H]3CCCC[C@@H]3C#N)c3cc[nH]c(=O)c23)cc1CN] | (1S,2S)-2-(3-((3-(aminomethyl)-4-(methylsulfonyl)phenyl)amino)-4-oxo-4,5-dihydro-1H-pyrazolo[4,3-c]pyridin-1-yl)cyclohexanecarbonitrile | Calc'd 441, found 441 |
| 6-5 | 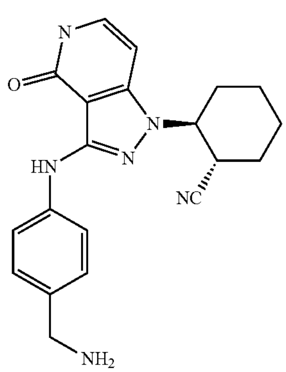 [SMILES: N#C[C@H]1CCCC[C@@H]1n1nc(Nc2ccc(CN)cc2)c2c(=O)[nH]ccc21] | (1S,2S)-2-(3-((4-(aminomethyl)phenyl)amino)-4-oxo-4,5-dihydro-1H-pyrazolo[4,3-c]pyridin-1-yl)cyclohexanecarbonitrile | Calc'd 363, found 363 |

Example 7-1

(1S,2S)-2-(3-((3-((S)-1-Amino-2,2,2-trifluoroethyl)phenyl)amino)-4-oxo-4,5-dihydro-H-pyrazolo[4,3-c]pyridin-1-yl)cyclohexanecarbonitrileecarbonitrile

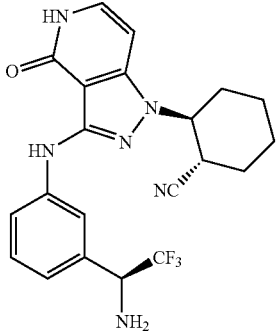

To a solution of HCl in EtOAc (1.0 M, 1.5 mL) was added (R)—N—((S)-1-(3-((4-(benzyloxy)-1-((1S,2S)-2-cyanocyclohexyl)-1H-pyrazolo[4,3-c]pyridin-3-yl)amino)phenyl)-2,2,2-trifluoroethyl)-2-methylpropane-2-sulfinamide (Example 3-55; 12 mg, 0.020 mmol), and the resulting mixture was stirred at rt overnight. After concentration in vacuo, the resulting residue was purified by prep. HPLC (Instrument: YMC-Actus, Column: Triart C-18 150×30 mm; 5 μM, Mobile phase A: water, Mobile phase B: acetonitrile) to afford the title compound. LRMS (ESI) calc'd. for $C_{21}H_{22}F_3N_6O$ [M+H]$^+$: 431, found 431.

Table 41 discloses Examples that were prepared in an analogous manner to Example 7-1.

TABLE 41

| Example | Structure | Compound Name | LRMS [M + H]$^+$ |
|---|---|---|---|
| 7-2 | 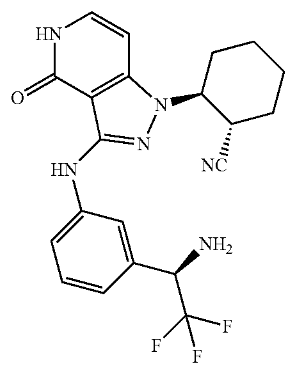 [SMILES: N#C[C@H]1CCCC[C@@H]1n1nc(Nc2cccc([C@@H](N)C(F)(F)F)c2)c2c(=O)[nH]ccc21] | (1S,2S)-2-[3-({3-[(1R)-1-amino-2,2,2-trifluoroethyl]phenyl}amino)-4-oxo-4,5-dihydro-1H-pyrazolo[4,3-c]pyridin-1-yl]cyclohexanecarbonitrile | Calc'd 431, found 431 |
| 7-3 | 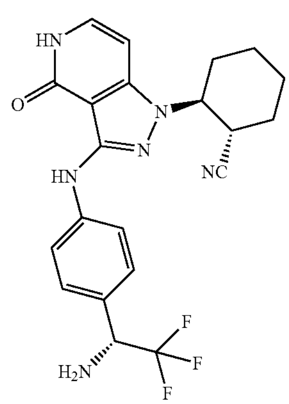 [SMILES: N#C[C@H]1CCCC[C@@H]1n1nc(Nc2ccc([C@@H](N)C(F)(F)F)cc2)c2c(=O)[nH]ccc21] | (1S,2S)-2-[3-({4-[(1R)-1-amino-2,2,2-trifluoroethyl]phenyl}amino)-4-oxo-4,5-dihydro-1H-pyrazolo[4,3-c]pyridin-1-yl]cyclohexanecarbonitrile | Calc'd 431, found 431 |

TABLE 41-continued

| Example | Structure | Compound Name | LRMS [M + H]+ |
|---|---|---|---|
| 7-4 | 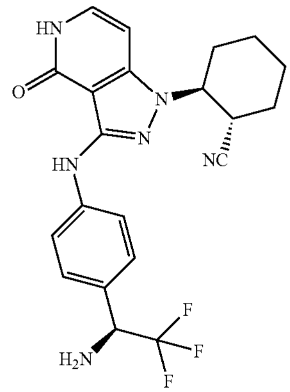 [SMILES: N#C[C@H]1CCCC[C@@H]1n1nc(Nc2ccc([C@H](N)C(F)(F)F)cc2)c2c(=O)[nH]ccc21] | (1S,2S)-2-[3-({4-[(1S)-1-amino-2,2,2-trifluoroethyl]phenyl}amino)-4-oxo-4,5-dihydro-1H-pyrazolo[4,3-c]pyridin-1-yl]cyclohexanecarbonitrile | Calc'd 431, found 431 |

Example 8-1

2-(Aminomethyl)-4-((1-((1S,2S)-2-cyanocyclohexyl)-4-oxo-4,5-dihydro-1H-pyrazolo[4,3-c]pyridin-3-yl)amino)-N,N-dimethylbenzenesulfonamide

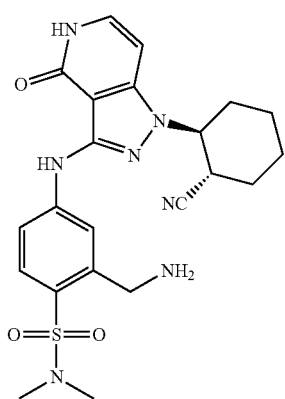

8-1

A mixture of Example 3-40 (10 mg, 0.020 mmol) in HCl (1.0 M, 10 mL) was refluxed for 4 h. After removal of solvent, the residue was purified by prep. HPLC to afford 2-(aminomethyl)-4-((1-((1S,2S)-2-cyanocyclohexyl)-4-oxo-4,5-dihydro-1H-pyrazolo[4,3-c]pyridin-3-yl)amino)-N,N-dimethylbenzenesulfonamide. LRMS (ESI) calc'd. for $C_{22}H_{28}N_7O_3S$ [M+H]+: 470, found 470.

Examples 9-1 and 9-2

(S or R)-2-(1-(3-(4-(1-Amino-2,2-difluoroethyl)phenylamino)-4-oxo-4,5-dihydro-1H-pyrazolo[4,3-c]pyridin-1-yl)cyclohexyl)acetonitrile and (R or S)-2-(1-(3-(4-(1-Amino(-2,2-difluoroethyl)phenylamino)-4-oxo-4,5-dihydro-1H-pyrazolo[4,3-c]pyridin-1-yl)cyclohexyl)acetonitrile

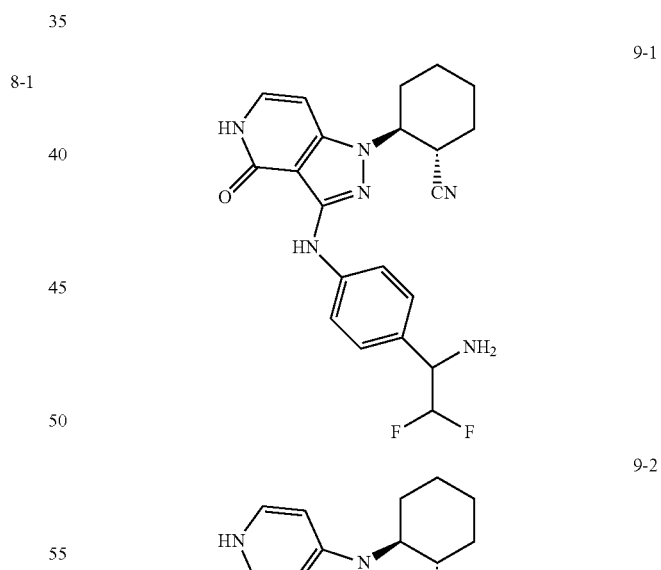

Step 1: 1-(4-Bromophenyl)-2,2-difluoroethanone

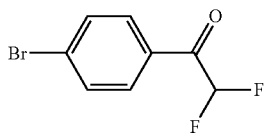
9a

Into an 100-mL 3-necked round-bottom flask was added a solution of 1,4-dibromobenzene (0.23 g, 0.99 mmol) in tetrahydrofuran (50 mL). The solution was placed under nitrogen and cooled to −78° C. n-Butyllithium (0.4 mL, 2.5 M) was added dropwise, and the resulting solution was stirred for 30 min at the same temperature. Ethyl 2,2-difluoroacetate (0.14 g, 1.1 mmol) was added dropwise to the mixture and the resulting solution was stirred for an additional 1 h at −78° C. The reaction was quenched by the careful addition of hydrochloric acid (2.0 mL, 1.0 M). The mixture was extracted with ethyl acetate (2×10 mL), and the organic layers were combined, dried over anhydrous sodium sulfate, and filtered. The filtrate was concentrated in vacuo to afford 1-(4-bromophenyl) 2,2-difluoroethan-1-one. GCMS calc'd for $C_8H_8BrF_2O[M]^+$: 234, found 234.

Step 2: (1S,2S)-2-(4-(Benzyloxy)-3-((4-(2,2-difluoroacetyl)phenyl)amino)-1H-pyrazolo[4,3-c]pyridin-1-yl)cyclohexanecarbonitrile

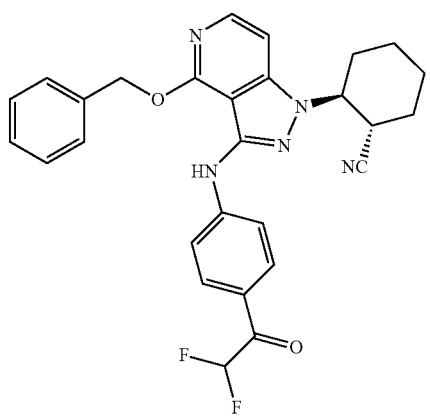
9b

Into an 100-mL round-bottom flask were placed (1S,2S)-2-[3-amino-4-(benzyloxy)-1H-pyrazolo[4,3-c]pyridin-1-yl]cyclohexane-1-carbonitrile (I-7; 0.50 g, 1.4 mmol), 1-(4-bromophenyl) 2,2-difluoroethan-1-one (0.67 g, 2.9 mmol), tris(dibenzylideneacetone)dipalladium(0) (0.33 g, 0.36 mmol), di-tert-butyl(2',4',6'-triisopropylbiphenyl-2-yl)phosphine (0.45 g, 1.0 mmol), potassium acetate (0.28 g, 2.8 mmol) and isopropanol (50 mL). The resulting mixture was stirred for 16 h at 80° C. The mixture was filtered and the filtrate was concentrated in vacuo. The resulting residue was purified by silica gel column chromatography (ethyl acetate/petroleum ether: 1:10) to afford the title compound. LRMS (ESI) calc'd for $C_{28}H_{26}F_2N_5O_2$ [M+H]$^+$: 502, found 502.

Step 3: N-(1-(4-((4-(Benzyloxy)-1-((1S,2S)-2-cyanocyclohexyl)-1H-pyrazolo[4,3-c]pyridin-3-yl)amino)phenyl)-2,2-difluoroethyl)-2-methylpropane-2-sulfinamide (diastereomers mixture)

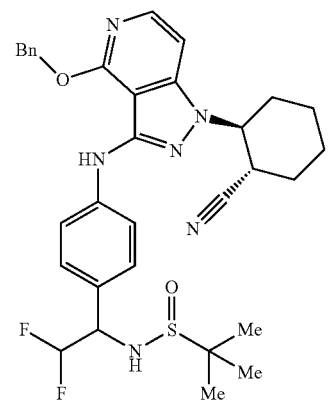
9c

Into an 100-mL round-bottom flask purged with nitrogen were placed (1S,2S)-2-(4-(benzyloxy)-3-((4-(2,2-difluoroacetyl)phenyl)amino)-1H-pyrazolo[4,3-c]pyridin-1-yl)cyclohexanecarbonitrile (0.25 g, 0.50 mmol), 2-methylpropane-2-sulfinamide (0.12 g, 0.99 mmol), titanium isopropoxide (0.28 g, 1.0 mmol) and tetrahydrofuran (40 mL). The mixture was stirred for 4 h at 80° C. and cooled down to ambient temperature. Sodium borohydride (93 mg, 1.5 mmol) was added portionwise. The mixture was stirred for 3 h at ambient temperature and quenched by water (50 mL). The solids were filtered off and the resulting filtrate was extracted with ethyl acetate (3×100 mL). The combined organic layers were combined, dried over anhydrous sodium sulfate and filtered. The filtrate was concentrated in vacuo to afford the title compound as a mixture of diastereomers. LRMS. (ESI) calc'd for $C_{32}H_{37}F_2N_6O_2S$ [M+H]$^+$: 607, found 607.

Step 4: (S or R)-2-(1-(3-(4-(1-Amino-2,2-difluoroethyl)phenylamino)-4-oxo-4,5-dihydro-1H-pyrazolo[4,3-c]pyridin-1-yl)cyclohexyl)acetonitrile and (S or R)-2-(1-(3-(4-(1-Amino-2,2-difluoroethyl)phenylamino)-4-oxo-4,5-dihydro-1H-pyrazolo[4,3-c]pyridin-1-yl)cyclohexyl)acetonitrile Into a 50-mL round-bottom flask were placed N-(1-(4-((4-(benzyloxy)-1-((1S,2S)-2-cyanocyclohexyl)-1H-pyrazolo[4,3-c]pyridin-3-yl)amino)phenyl)-2,2-difluoroethyl)-2-methylpropane-2-sulfinamide (diastereomers mixture) (0.25 g, 0.50 mmol), 10% palladium on carbon (0.20 g), ethyl acetate (20 mL), and hydrochloric acid (1 mL, 1 M). The resulting mixture was stirred for 5 h at ambient temperature under hydrogen (2 atm). The solid was removed by filtration. The filtrate was adjusted to pH=8 with saturated aqueous sodium carbonate, and the mixture was extracted with ethyl acetate (3×50 mL). The organic layers were combined, dried over sodium sulfate and filtered. The filtrate was concentrated in vacuo to afford (1S,2S)-2-(3-[[4-(1-amino-2,2-difluoroethyl)phenyl]amino]-4-oxo-1H,4H,5H-pyrazolo[4,3-c]pyridin-1-yl)cyclohexane-1-carbonitrile (mixture of diastereomers). The solid was purified by Chiral-Prep-HPLC with the following conditions: column, Chiralpak IA, 2×25 cm, 5 µm; mobile phase, hexane and ethanol (hold 40.0% ethanol in 30 min); detector, UV 254/220 nm. This affords (S or R)-2-(1-(3-(4-(1-Amino-2,2-difluoroethyl)phenylamino)-4-oxo-4,5-dihydro-1H-pyrazolo[4,3-c]pyridin-1-yl)cyclohexyl)acetonitrile (9-1) LRMS (ESI) calc'd for $C_{21}H_{23}F_2N_6O$ [M+H]$^+$: 413, found 413. $^1$H NMR (400 MHz, DMSO-d$_6$) δ11.10 (d, J=5.6 Hz, 1H), 8.07 (s, 1H), 7.64 (d, J=8.8 Hz, 2H), 7.33 (d, J=8.8 Hz, 2H), 7.24-7.21 (m, 1H), 5.93 (d, J=4.4 Hz, 1H), 4.81-4.61 (m, 1H), 4.12-3.95 (m, 1H), 3.33 (d, J=11.2 Hz, 1H), 2.21 (d, J=11.2 Hz, 3H), 1.91-1.75 (m, 5H), 1.77-1.33 (m, 3H) and (S or R)-2-(1-(3-(4-(1-Amino-2,2-difluoroethyl)phenylamino)-4-oxo-4,5-dihydro-1H-pyrazolo[4,3-c]pyridin-1-yl)cyclohexyl)acetonitrile (9-2) LRMS (ESI) calc'd for $C_{21}H_{23}F_2N_6O$ [M+H]$^+$: 413, found 413. $^1$H NMR (400 MHz, DMSO-d$_6$) δ 11.09 (d, J=5.6 Hz, 1H), 8.07 (s, 1H), 7.64 (d, J=8.8 Hz, 2H), 7.33 (d, J=8.8 Hz, 2H), 7.24-7.21 (m, 1H), 5.93 (d, J=4.4 Hz, 1H), 4.72-4.65 (m, 1H), 4.06-4.01 (m, 1H), 3.33 (d, J=11.2 Hz, 1H), 2.20 (d, J=11.8 Hz, 2H), 1.91-1.75 (m, 5H), 1.87-1.33 (m, 4H).

Table 42 reveals compounds that were prepared in similar procedures as described above in Examples 9-1 and 9-2, using dimethylamine instead of 2-methylpropane-2-sulfinamide.

TABLE 42

| Example | Structure | Compound Name | LRMS [M + H]$^+$ |
|---|---|---|---|
| 9-3 | 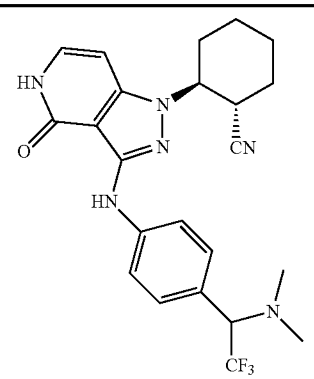 | (1S,2S)-2-(3-(4-((S or R)-1-(Dimethylamino)-2,2,2-trifluoroethyl)phenylamino)-4-oxo-4,5-dihydropyrazolo[4,3-c]pyridin-1-yl)cyclohexanecarbonitrile (Derived from Peak A via SFC separation of pyridone final compound, AD-H, 20% 2-propanol + 0.25% DMEA in CO$_2$, Tr = 7.36 mins) | Calc'd 459, found 459 |
| 9-4 | 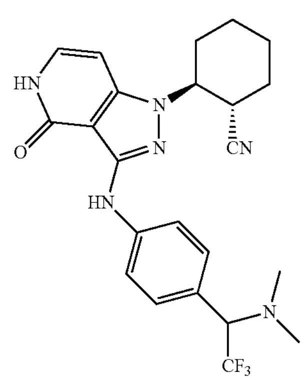 [SMILES: CN(C)C(c1ccc(Nc2nn([C@H]3CCCC[C@@H]3C#N)c3cc[nH]c(=O)c23)cc1)C(F)(F)F] | (1S,2S)-2-(3-(4-((R or S)-1-(Dimethylamino)-2,2,2-trifluoroethyl)phenylamino)-4-oxo-4,5-dihydropyrazolo[4,3-c]pyridin-1-yl)cyclohexanecarbonitrile (Derived from Peak B via SFC separation of pyridone final compound, AD-H, 20% 2-propanol + 0.25% DMEA in CO$_2$, Tr = 8.28 mins) | Calc'd 459, found 459 |

Example 10-1

Racemic-(1S,2S)-2-(3-((4-(2,2-difluoro-1-hydroxy-ethyl)phenyl)amino)-4-oxo-4,5-dihydro-1H-pyrazolo[4,3-c]pyridin-1-yl)cyclohexanecarbonitrile 10-1

Step 1: (1S,2S)-2-4-(Benzyloxy)-3-((4-(2,2-difluoro-1-hydroxyethyl)phenyl)amino)-1H-pyrazolo[4,3-c]pyridin-1-yl)cyclohexanecarbonitrile (mixture of diastereomers)

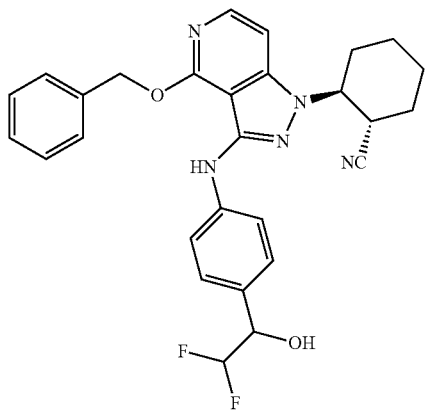

10-1a

Into an 100-mL round bottom flask was placed a solution of Example 9b (0.13 g, 0.26 mmol) in methanol (10 mL). Sodium borohydride (30 mg, 0.79 mmol) was added portionwise, and the resulting mixture was stirred for 3 h at ambient temperature. Water (20 mL) was added to the reaction and the mixture was extracted with ethyl acetate (3×50 mL). The combined organic layers were dried over anhydrous sodium sulfate and filtered. The filtrate was concentrated in vacuo to give racemic mixture of the title compound. LRMS (ESI) calc'd. for $C_{28}H_{28}F_2N_5O_2$ [M+H]$^+$: 504, found 504.

Step 2: (1S,2S)-2-(3-((4-(2,2-Difluoro-1-hydroxy-ethyl)phenyl)amino)-4-oxo-4,5-dihydro-1H-pyrazolo[4,3-c]pyridin-1-yl)cyclohexanecarbonitrile (mixture of diastereomers)

Deprotection was proceeded in a similar procedure as described above for Example 3-1 to afford a diastereomeric mixture of 10-1. LRMS (ESI) calc'd. for $C_{22}H_{22}F_2N_5O_2$ [M+H]$^+$: 414, found 414; $^1$H NMR (400 MHz, DMSO-d$_6$) δ 11.10 (d, J=5.6 Hz, 1H), 8.10 (s, 1H), 7.66 (d, J=8.4 Hz, 2H), 7.32 (d, J=8.4 Hz, 2H), 7.24-7.21 (m, 1H), 6.68 (d, J=7.2 Hz, 1H), 6.11-5.82 (m, 2H), 4.72-4.64 (m, 2H), 3.38-3.35 (m, 1H), 2.20 (d, J=10.0 Hz, 2H), 1.95-1.13 (m, 6H).

Example 11-1

(1S,2S)-2-(3-((3-(1,2-Dihydroxypropan-2-yl)phenyl)amino)-4-oxo-4,5-dihydro-1H-pyrazolo[4,3-c]pyridin-1-yl)cyclohexanecarbonitrile (mixture of diastereomer s)

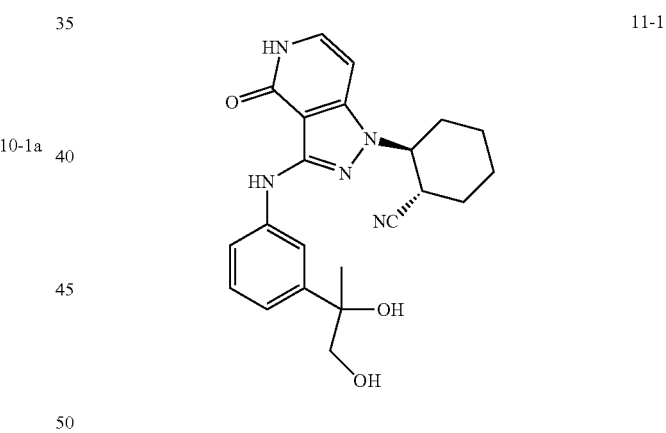

11-1

To a suspension of (1S,2S)-2-{4-Oxo-3-[3-(2,2,4-trimethyl-[1,3]dioxolan-4-yl)-phenylamino]-4,5-dihydro-pyrazolo[4,3-c]pyridin-1-yl}-cyclohexanecarbonitrile (diastereomeric mixture of Example 3-38; 10 mg, 0.022 mmol) in THF (1 mL) was added HCl (0.4 mL). The resulting suspension was stirred at room temperature for 8 hours. The mixture was concentrated in vacuo, and the resulting residue was purified by prep. HPLC (method below) to afford the title compound (mixture of diastereomers). LRMS (ESI) calc'd. for $C_{22}H_{25}N_5O_3$ [M+H]$^+$: 408, found 408.

Instrument: Gilson 215
Column: ASB C-18, 150×25 mm, 5 μM
Mobile phase A: Water (0.01 mol/L ammonium bicarbonate)
Mobile phase B: Acetonitrile (neutral)

Example 12-1

(1S,2S)-2-(3-(Isoindolin-5-ylamino)-4-oxo-4,5-di-hydro-H-pyrazolo[4,3-c]pyridin-1-yl)cyclohexanecarbonitrile (TFA salt)

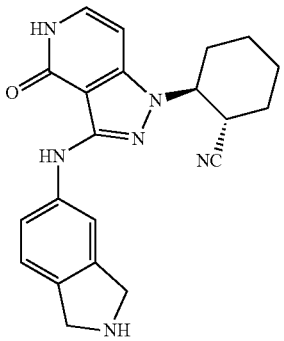

12-1

To a stirred solution of tert-butyl 5-((4-(benzyloxy)-1-((1S,2S)-2-cyanocyclohexyl)-1H-pyrazolo[4,3-c]pyridin-3-yl)amino)isoindoline-2-carboxylate (prepared in an analogous manner as described for Example 3-16; 35 mg, 0.062 mmol) in DCM (0.5 mL) was added TFA (0.5 mL). The resulting solution was stirred at rt for approximately 3 hr. The reaction was concentrated in vacuo to afford a crude residue that was taken up into MeOH (2 mL) and was purified by mass triggered reverse phase HPLC. Lyophilization of the fractions containing desired product afforded the title compound as a TFA salt. LRMS calc'd for $C_{21}H_{23}N_6O$ [M+H]$^+$: 375, found: 375. $^1$HNMR (600 MHz, DMSO-d$_6$): δ 11.07 (d, J=5.4 Hz, 1H), 9.24 (br s, 2H), 8.19 (s, 1H), 7.67 (s, 1H), 7.60 (d, J=8.4 Hz, 1H), 7.28 (d, J=7.8 Hz, 1H), 7.20 (t, J=7.8 Hz, 1H), 6.65 (d, J=7.2 Hz, 1H), 4.66 (dt, J=10.8, 4.2 Hz, 1H), 4.47 (br t, J=4.8 Hz, 2H), 4.41 (br t, J=5.4 Hz, 2H), 3.31 (m overlapping with water peak, 1H) 2.16 (br d, J=10.8 Hz, 1H), 1.86-1.71 (m, 4H), 1.47 (br q, J=12.6 Hz, 1H), 1.32 (br q, J=13.2 Hz, 1H).

Table 43 contains examples that were prepared in an analogous manner to that of Example 12-1.

TABLE 43

| Example | Structure | Compound Name | LRMS [M + H]$^+$ |
|---|---|---|---|
| 12-2 | 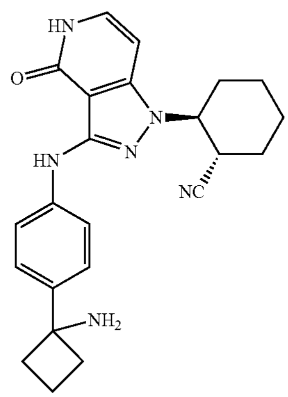 [SMILES: N#C[C@H]1CCCC[C@@H]1n1nc(Nc2ccc(C3(N)CCC3)cc2)c2c(=O)[nH]ccc21] | (1S,2S)-2-(3-((4-(1-aminocyclobutyl)phenyl)amino)-4-oxo-4,5-dihydro-1H-pyrazolo[4,3-c]pyridin-1-yl)cyclohexanecarbonitrile (TFA salt) | Calc'd [M + Na]: 425, found 425 |
| 12-3 | 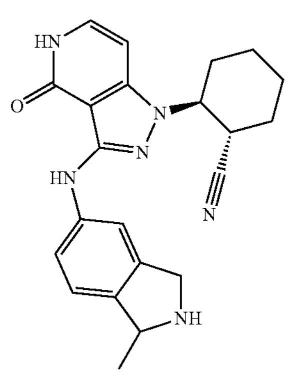 [SMILES: CC1NCc2cc(Nc3nn([C@H]4CCCC[C@@H]4C#N)c4cc[nH]c(=O)c34)ccc21] | (1S,2S)-2-(3-{[(1S and 1R)-1-methyl-2,3-dihydro-1H-isoindol-5-yl]amino}-4-oxo-4,5-dihydro-1H-pyrazolo[4,3-c]pyridin-1-yl)cyclohexanecarbonitrile | Calc'd 389, found 389 |

TABLE 43-continued

| Example | Structure | Compound Name | LRMS [M + H]+ |
|---|---|---|---|
| 12-4 | 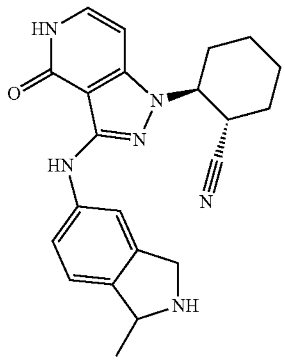 [SMILES: CC1NCc2cc(Nc3nn([C@H]4CCCC[C@@H]4C#N)c4cc[nH]c(=O)c34)ccc21] | (1S,2S)-2-(3-{[(1S or 1R)-1-methyl-2,3-dihydro-1H-isoindol-5-yl]amino}-4-oxo-4,5-dihydro-1H-pyrazolo[4,3-c]pyridin-1-yl)cyclohexanecarbonitrile (Derived from Peak A by HPLC using IC, 35% EtOH in Hexanes (with 0.1% DEA), Tr = 11 mins) | Calc'd 389, found 389 |
| 12-5 | 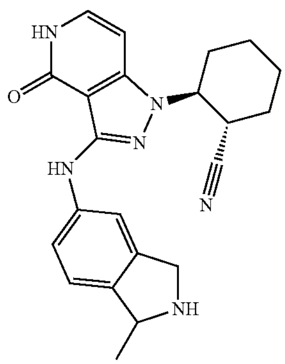 [SMILES: CC1NCc2cc(Nc3nn([C@H]4CCCC[C@@H]4C#N)c4cc[nH]c(=O)c34)ccc21] | (1S,2S)-2-(3-{[(1R or 1S)-1-methyl-2,3-dihydro-1H-isoindol-5-yl]amino}-4-oxo-4,5-dihydro-1H-pyrazolo[4,3-c]pyridin-1-yl)cyclohexanecarbonitrile (Derived from Peak B by HPLC using IC, 35% EtOH in Hexanes (with 0.1% DEA), Tr = 13.8 mins) | Calc'd 389, found 389 |

Example 13-1

5-((1-((1S,2S)-2-Cyanocyclohexyl)-4-oxo-4,5-dihydro-1H-pyrazolo[4,3-c]pyridin-3-yl)amino)-2,3-dihydro-1H-indene-2-carboxylic acid (mixture of diastereomers)

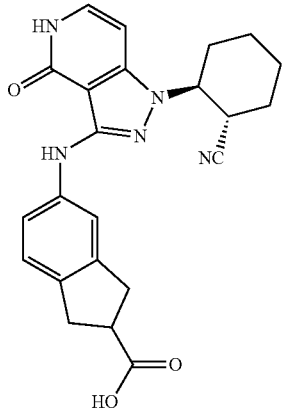

13-1

Step 1: Methyl 5-((4-(benzyloxy)-1-((1S,2S)-2-cyanocyclohexyl)-1H-pyrazolo[4,3-c]pyridin-3-yl)amino)-2,3-dihydro-1H-indene-2-carboxylate (mixture of diastereomers)

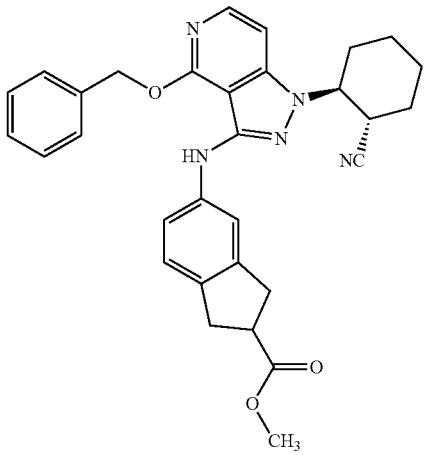

13-1a

Into a 50-mL round-bottom flask purged and maintained with an inert atmosphere of nitrogen, were placed I-3 (0.80 g, 2.3 mmol), I-106 (0.70 g, 2.7 mmol), di-tert-butyl(2',4', 6'-triisopropylbiphenyl-2-yl)phosphine (0.70 g, 1.6 mmol), tris(dibenzylideneacetone)dipalladium(0)-chloroform (0.70 g, 0.68 mmol), potassium acetate (0.30 g, 3.1 mmol) and isopropanol (20 mL). The resulting mixture was stirred for 6 h at 80° C. then was cooled and concentrated in vacuo. The residue was purified by silica gel column chromatography (ethyl acetate/petroleum ether: 1/3) to afford the title compound (mixture of diastereomers): LRMS (ESI) calc'd for $C_{31}H_{32}N_5O_3$ [M+H]$^+$: 522, found 522.

Step 2: 5-((4-(Benzyloxy)-1-((1S,2S)-2-cyanocyclohexyl)-1H-pyrazolo[4,3-c]pyridin-3-yl)amino)-2,3-dihydro-1H-indene-2-carboxylic acid (mixture of diastereomers)

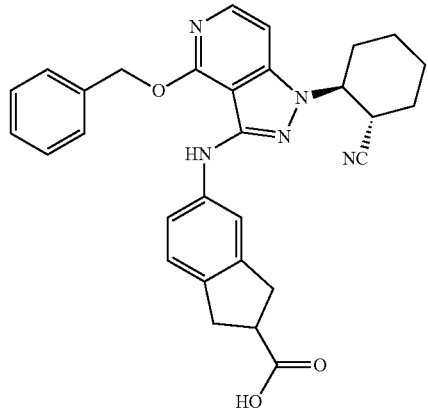

13-1b

Into a 25-mL round-bottom flask purged and maintained with an inert atmosphere of nitrogen were placed 13-1a (mixture of diastereomers; 0.15 g, 0.29 mmol), methanol (10 mL), sodium hydroxide (50.0 mg, 1.25 mmol) and water (10 mL). The resulting mixture was stirred for 3 h at 15° C., then was extracted with ethyl acetate (3×50 mL). The organic layers were combined, dried over anhydrous sodium sulfate and filtered. The filtrate was concentrated in vacuo to afford the title compound (mixture of diastereomers). LRMS (ESI) calc'd for $C_{30}H_{30}N_5O_3$ [M+H]$^+$: 508, found 508.

Step 3: 5-((1-((1S,2S)-2-Cyanocyclohexyl)-4-oxo-4,5-dihydro-1H-pyrazolo[4,3-c]pyridin-3-yl)amino)-2,3-dihydro-1H-indene-2-carboxylic acid (mixture of diastereomers)

Deprotection was similar to that described for Example 3-1 to afford 5-(1-((1S,2S)-2-cyanocyclohexyl)-4-oxo-4,5-dihydro-1H-pyrazolo[4,3-c]pyridin-3-ylamino)-2,3-dihydro-1H-indene-2-carboxylic acid (mixture of diastereomers). LRMS (ESI) calc'd for $C_{23}H_{24}N_5O_3$ [M+H]$^+$: 418, found 418; 1H NMR (400 MHz, DMSO-d$_6$) δ 11.04 (br s, 1H), 7.95 (br s, 1H), 7.47 (s, 1H), 7.41 (d, J=10.8 Hz, 1H), 7.21 (d, J=10.0 Hz, 1H), 7.11 (d, J=10.8 Hz, 1H), 6.66 (d, J=10.0 Hz, 1H), 4.71-4.62 (m, 1H), 3.14-3.04 (m, 4H), 2.27-2.14 (m, 1H), 1.89-1.75 (m, 5H), 1.64-1.38 (m, 3H).

Example 14-1

Racemic-trans-6-(3-((4-(methylsulfonyl)phenyl)amino)-4-oxo-4,5-dihydro-1H-pyrazolo[4,3-c]pyridin-1-yl)spiro[2.5]octane-5-carbonitrile 14-1

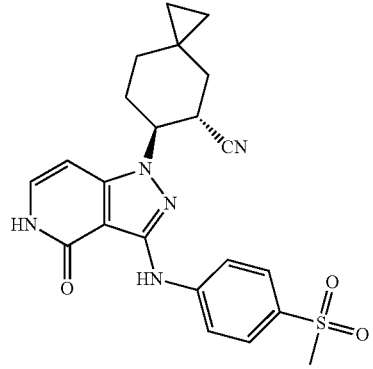

Step 1: cis and trans-6-(3-Amino-4-(benzyloxy)-1H-pyrazolo[4,3-c]pyridin-1-yl)spiro[2.5]octane-5-carbonitrile (racemic)

14-1a

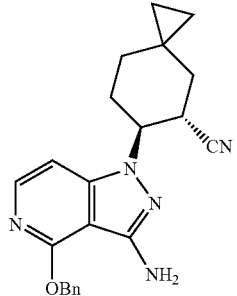

14-1b

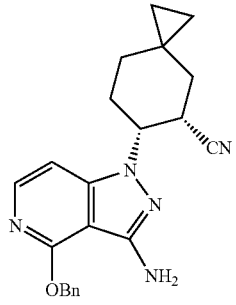

A mixture of spiro[2.5]oct-5-ene-6-carbonitrile (1-110; 1.38 g, 10.4 mmol), DBU (0.32 g, 2.2 mmol) and 4-(benzyloxy)-1H-pyrazolo[4,3-c]pyridin-3-amine (I-1; 0.25 g, 1.1 mmol) in EtOH (4 mL) was stirred at 100° C. in a sealed-vessel for 7 days. After removal of the solvent in vacuo, the residue was purified by column chromatography on silica gel (Hex:EtOAc=5:1) to give the individual cis/trans isomers of 6-(3-amino-4-(benzyloxy)-1H-pyrazolo[4,3-c]pyridin-1-yl)spiro[2.5]octane-5-carbonitrile (racemic).

Trans isomer 14-1a: $^1$H NMR (CDCl$_3$, 400 MHz): δ 7.48 (d, J=6.4 Hz, 1H), 7.11-6.96 (m, 5H), 6.43 (d, J=6.2 Hz, 1H), 5.14 (s, 2H), 4.11 (br, 2H), 3.92-3.85 (m, 1H), 3.05-2.98 (m, 1H), 1.93-1.77 (m, 2H), 1.66-1.55 (m, 2H), 1.07-1.02 (m, 1H), 0.69-0.66 (m, 1H), 0.16-0.10 (m, 2H), 0.03-0.00 (m, 2H).

Cis isomer 14-1b: $^1$H NMR (CDCl$_3$, 400 MHz): δ 7.76 (d, J=6.4 Hz, 1H), 7.42-7.4 (m, 2H), 7.35-7.25 (m, 3H), 6.78 (d, J=6.4 Hz, 1H), 5.46 (s, 2H), 4.42 (br, 2H), 4.31-4.26 (m, 1H), 3.31-3.27 (m, 1H), 2.71-2.61 (m, 1H), 2.14-2.06 (m, 2H), 1.85-1.78 (m, 1H), 1.57-1.46 (m, 1H), 1.33-1.21 (m, 1H), 0.81-0.72 (m, 2H), 0.56-0.52 (m, 1H), 0.34-0.31 (m, 2H).

Step 2: Racemic-trans-6-(4-(benzyloxy)-3-((4-(methylsulfonyl)phenyl)amino)-H-pyrazolo[4,3-c]pyridin-1-yl)spiro[2.5]octane-5-carbonitrile 14-1c

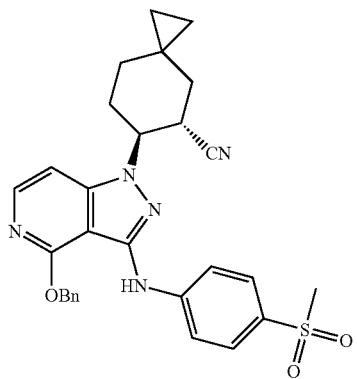

To a suspension of trans-6-(3-amino-4-(benzyloxy)-1H-pyrazolo[4,3-c]pyridin-1-yl)spiro[2.5]octane-5-carbonitrile (racemic; 50 mg, 0.13 mmol) and KOAc (34 mg, 0.34 mmol) in i-PrOH (0.5 mL) was added $Pd_2(dba)_3$ (27 mg, 0.030 mmol), tBuXPhos (34 mg, 0.080 mmol) and 1-bromo-4-(methylsulfonyl)benzene (40 mg, 0.16 mmol) under a nitrogen atmosphere. The resulting suspension was heated to 105° C. using microwave irradiation for 1 h, then cooled to room temperature and filtered. The filtrate was purified by prep. TLC (silica gel, Hex:EtOAc=1:1) to afford racemic-trans-6-(4-(benzyloxy)-3-((4-(methylsulfonyl)phenyl)amino)-1H-pyrazolo[4,3-c]pyridin-1-yl)spiro[2.5]octane-5-carbonitrile. LRMS calc'd for $C_{29}H_{30}N_5O_3S$ $[M+H]^+$: 528, found 528; $^1$H NMR (CDCl$_3$, 400 MHz): δ 7.95 (d, J=6.0 Hz, 1H), 7.89-7.87 (m, 2H), 7.63-7.59 (m, 3H), 7.55-7.53 (m, 2H), 7.48-7.4 (m, 3H), 6.94 (d, J=6.0 Hz, 1H), 5.6 (s, 2H), 4.45-4.38 (m, 1H), 3.52-3.45 (m, 1H), 3.03 (s, 3H), 2.37-2.23 (m, 2H), 2.11-2.01 (m, 2H), 1.51-1.47 (m, 1H), 1.14-1.08 (m, 1H), 0.59-0.47 (m, 4H).

Step 3: Racemic-trans-6-(3-((4-(methylsulfonyl)phenyl)amino)-4-oxo-4,5-dihydro-1H-pyrazolo[4,3-c]pyridin-1-yl)spiro[2.5]octane-5-carbonitrile A mixture of racemic 14-1c (37 mg, 0.070 mmol) and Pd/C (10 mg) in THF/EtOAc (1 mL, 1/1) was stirred at rt under H$_2$ (15 psi) overnight. The catalyst was removed by filtration, and the filtrate was concentrated in vacuo. The residue was washed with MeOH followed by THF to give racemic-trans-6-(3-((4-(methylsulfonyl)phenyl)amino)-4-oxo-4,5-dihydro-1H-pyrazolo[4,3-c]pyridin-1-yl)spiro[2.5]octane-5-carbonitrile. LRMS (ESI) calc'd. for $C_{22}H_{25}N_5O_3S$ $[M+H]^+$: 438, found 438. $^1$H NMR (DMSO-d$_6$, 400 MHz): δ 11.18 (s, 1H), 8.72 (s, 1H), 7.88-7.79 (m, 4H), 7.32-7.24 (m, 1H), 6.73 (d, J=7.3 Hz, 1H), 4.90-4.79 (m, 1H), 3.49-3.42 (m, 1H), 3.14 (s, 3H), 2.31-2.24 (m, 1H), 2.04-1.91 (m, 3H), 1.44-1.41 (m, 1H), 1.00-0.98 (m, 1H), 0.50-0.36 (m, 4H).

Table 44 discloses Examples that were prepared in an analogous manner to that described for Example 14-1, using the appropriate intermediates.

TABLE 44

| Example | Structure | Compound Name | LRMS [M + H]$^+$ |
| --- | --- | --- | --- |
| 14-2 | 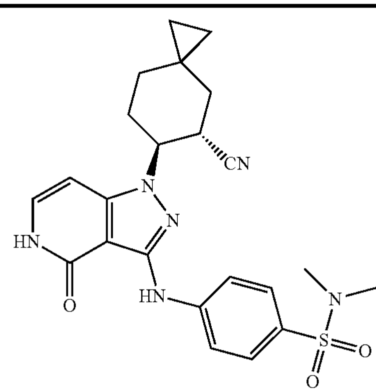 | Racemic-trans-4-((1-(5-cyanospiro[2.5]octan-6-yl)-4-oxo-4,5-dihydro-1H-pyrazolo[4,3-c]pyridin-3-yl)amino)-N,N-dimethylbenzenesulfonamide | Calc'd 467, found 467 |
| 14-3 | 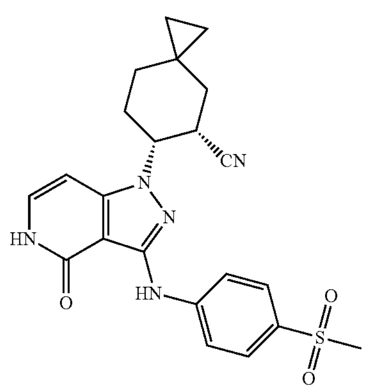 [SMILES: CS(=O)(=O)c1ccc(Nc2nn([C@@H]3CCC4(CC4)C[C@@H]3C#N)c3cc[nH]c(=O)c23)cc1] | Racemic-cis-6-(3-((4-(methylsulfonyl)phenyl)amino)-4-oxo-4,5-dihydro-1H-pyrazolo[4,3-c]pyridin-1-yl)spiro[2.5]octane-5-carbonitrile | Calc'd 438, found 438 |

Example 15

(1S,2S)-2-(3-{[4-(1,3-Oxazol-2-yl)phenyl]amino}-4-oxo-4,5-dihydro-1H-pyrazolo[4,3-c]pyridin-1-yl)cyclohexanecarbonitrile

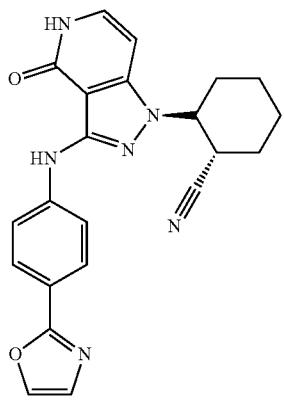

15-1

(1S,2S)-2-(3-amino-4-oxo-4,5-dihydro-1H-pyrazolo[4,3-c]pyridin-1-yl)cyclohexanecarbonitrile (I-10; 52 mg, 0.20 mmol), 2-(4-bromophenyl)oxazole (53.8 mg, 0.240 mmol), Pd$_2$(dba)$_3$ (22 mg, 0.024 mmol), t-Bu-XPhos (20.4 mg, 0.0480 mmol) and potassium acetate (39.3 mg, 0.400 mmol) and 2-propanol (2.50 mL) were added to a vial and the vial was sealed and degassed by evacuation/argon backfill. The resulting mixture was stirred at 85° C. for 2 hours, then cooled, concentrated in vacuo and purified by reverse-phase HPLC (5%-50% acetonitrile in water with 0.1% TFA modifier). The desired fractions were lyophilized to afford the title compound (TFA salt). LRMS(ESI) calc'd for C$_{22}$H$_{21}$N$_6$O$_2$ [M+H]$^+$: 401, found 401. $^1$H NMR (600 MHz, DMSO-d$_6$) δ 11.20 (d, 1H, J=5.7 Hz), 8.48 (s, 1H), 8.18 (s, 1H), 7.94 (d, 2H, J=8.5 Hz), 7.85 (d, 2H, J=8.5 Hz), 7.35 (s, 1H), 7.29 (dd, 1H, J=7.3, 5.8 Hz), 6.75 (d, 1H, J=7.4 Hz), 4.77 (m, 1H), 2.25 (d, 1H, J=11.1 Hz), 1.96 (m, 2H), 1.84 (m, 3H), 1.56 (m, 1H), 1.44 (m, 1H).

Table 45 discloses Examples that were prepared in analogy to Example 15-1, starting with the appropriate enantiopure carbonitrile pyridone and bromide. In select cases, the general procedure was modified to alternatively utilize Pd$_2$(dba)$_3$.CHCl$_3$ in DMF or a mixture of DMF and 2-propanol as solvent, at 70-90° C. For Examples 15-33, 15-37, and 15-38 negative ion mode LRMS was used for analysis with a mobile phase of 10% ACN in water (with NH$_4$HCO$_3$).

TABLE 45

| Example | Structure | Compound Name | LRMS [M + H]$^+$ |
|---|---|---|---|
| 15-2 | 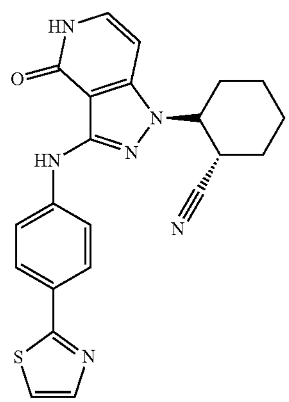 | (1S,2S)-2-(4-oxo-3-{[4-(1,3-thiazol-2-yl)phenyl]amino}-4,5-dihydro-1H-pyrazolo[4,3-c]pyridin-1-yl)cyclohexanecarbonitrile | Calc'd 417, found 417 |
| 15-3 | 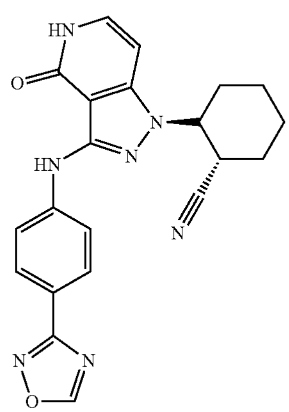 | (1S,2S)-2-(3-{[4-(1,2,4-oxadiazol-3-yl)phenyl]amino}-4-oxo-4,5-dihydro-1H-pyrazolo[4,3-c]pyridin-1-yl)cyclohexanecarbonitrile | Calc'd 402, found 402 |

TABLE 45-continued

| Example | Structure | Compound Name | LRMS [M + H]+ |
|---|---|---|---|
| 15-4 | 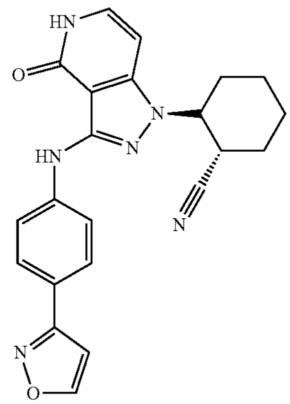 | (1S,2S)-2-{3-[(4-isoxazol-3-ylphenyl)amino]-4-oxo-4,5-dihydro-1H-pyrazolo[4,3-c]pyridin-1-yl}cyclohexanecarbonitrile | Calc'd 401, found 401 |
| 15-5 | 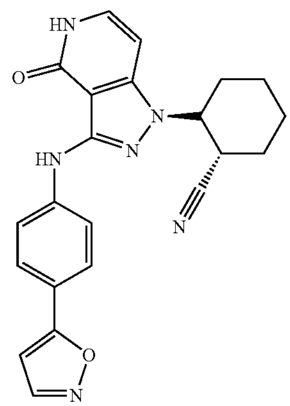 | (1S,2S)-2-{3-[(4-isoxazol-5-ylphenyl)amino]-4-oxo-4,5-dihydro-1H-pyrazolo[4,3-c]pyridin-1-yl}cyclohexanecarbonitrile | Calc'd 401, found 401 |
| 15-6 | 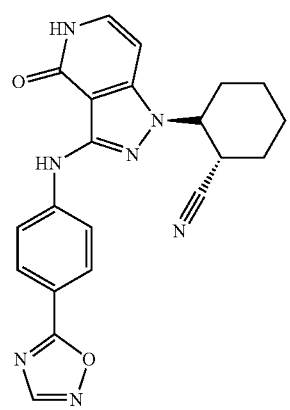 | (1S,2S)-2-(3-{[4-(1,2,4-oxadiazol-5-yl)phenyl]amino}-4-oxo-4,5-dihydro-1H-pyrazolo[4,3-c]pyridin-1-yl)cyclohexanecarbonitrile | Calc'd 402, found 402 |
| 15-7 | 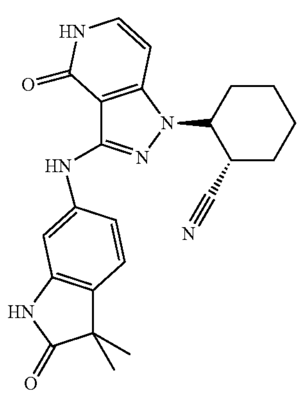 | (1S,2S)-2-{3-[(3,3-dimethyl-2-oxo-2,3-dihydro-1H-indol-6-yl)amino]-4-oxo-4,5-dihydro-1H-pyrazolo[4,3-c]pyridin-1-yl}cyclohexanecarbonitrile | Calc'd 417, found 417 |

TABLE 45-continued

| Example | Structure | Compound Name | LRMS [M + H]+ |
|---|---|---|---|
| 15-8 | 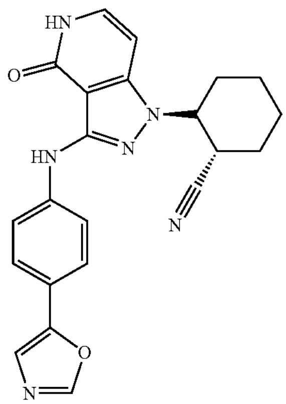 | (1S,2S)-2-(3-{[4-(1,3-oxazol-5-yl)phenyl]amino}-4-oxo-4,5-dihydro-1H-pyrazolo[4,3-c]pyridin-1-yl)cyclohexanecarbonitrile | Calc'd 401, found 401 |
| 15-9 | 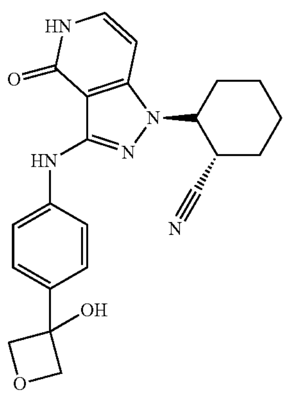 | (1S,2S)-2-(3-{[4-(3-hydroxyoxetan-3-yl)phenyl]amino}-4-oxo-4,5-dihydro-1H-pyrazolo[4,3-c]pyridin-1-yl)cyclohexanecarbonitrile | Calc'd 406, found 406 |
| 15-10 | 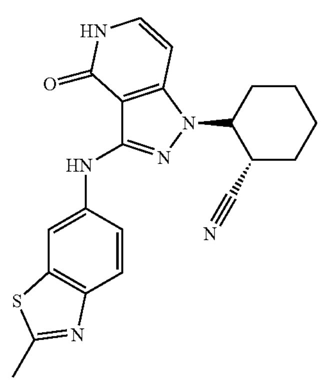 | (1S,2S)-2-{3-[(2-methyl-1,3-benzothiazol-6-yl)amino]-4-oxo-4,5-dihydro-1H-pyrazolo[4,3-c]pyridin-1-yl}cyclohexanecarbonitrile | Calc'd 405, found 405 |
| 15-11 | 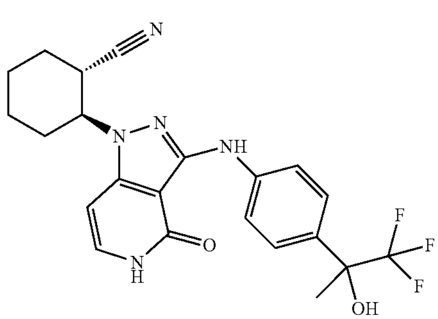 [SMILES: CC(O)(c1ccc(Nc2nn([C@H]3CCCC[C@@H]3C#N)c3cc[nH]c(=O)c23)cc1)C(F)(F)F] | (1S,2S)-2-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]cyclohexanecarbonitrile (from I-119a) | Calc'd 446, found 446 |

TABLE 45-continued

| Example | Structure | Compound Name | LRMS [M + H]+ |
|---|---|---|---|
| 15-12 | 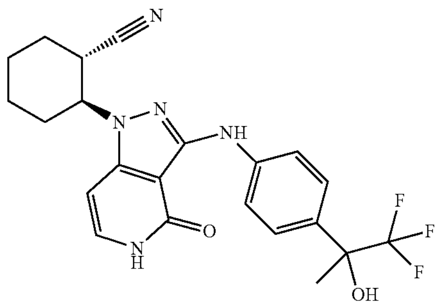 [SMILES: CC(O)(c1ccc(Nc2nn([C@H]3CCCC[C@@H]3C#N)c3cc[nH]c(=O)c23)cc1)C(F)(F)F] | (1S,2S)-2-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]cyclohexanecarbonitrile (from I-119b) | Calc'd 446, found 446 |
| 15-13 | 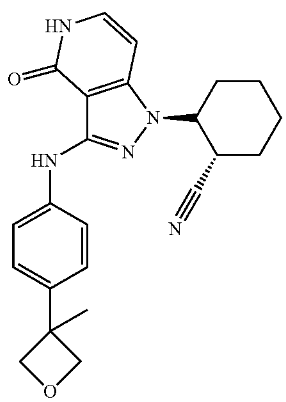 | (1S,2S)-2-(3-{[4-(3-methyloxetan-3-yl)phenyl]amino}-4-oxo-4,5-dihydro-1H-pyrazolo[4,3-c]pyridin-1-yl)cyclohexanecarbonitrile | Calc'd 404, found 404 |
| 15-14 | 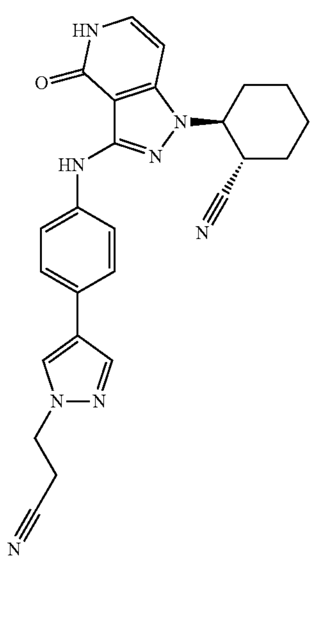 [SMILES: N#CCCn1cc(-c2ccc(Nc3nn([C@H]4CCCC[C@@H]4C#N)c4cc[nH]c(=O)c34)cc2)cn1] | (1S,2S)-2-[3-({4-[1-(2-cyanoethyl)-1H-pyrazol-4-yl]phenyl}amino)-4-oxo-4,5-dihydro-1H-pyrazolo[4,3-c]pyridin-1-yl]cyclohexanecarbonitrile | Calc'd 453, found 453 |

TABLE 45-continued

| Example | Structure | Compound Name | LRMS [M + H]+ |
|---|---|---|---|
| 15-15 | 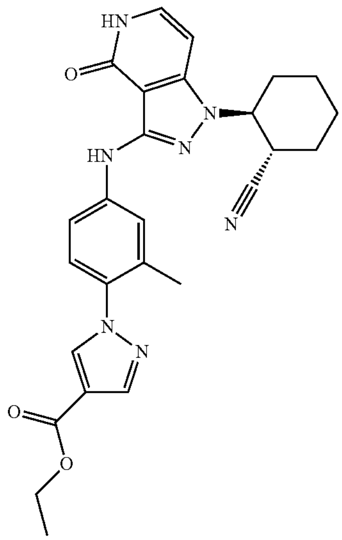 [SMILES: CCOC(=O)c1cnn(-c2ccc(Nc3nn([C@H]4CCCC[C@@H]4C#N)c4cc[nH]c(=O)c34)cc2C)c1] | ethyl 1-[4-({1-[(1S,2S)-2-cyanocyclohexyl]-4-oxo-4,5-dihydro-1H-pyrazolo[4,3-c]pyridin-3-yl}amino)-2-methylphenyl]-1H-pyrazole-4-carboxylate | Calc'd 486, found 486 |
| 15-16 | 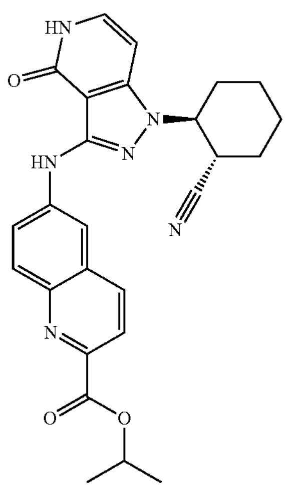 [SMILES: CC(C)OC(=O)c1ccc2cc(Nc3nn([C@H]4CCCC[C@@H]4C#N)c4cc[nH]c(=O)c34)ccc2n1] | isopropyl 6-((1-((1S,2S)-2-cyanocyclohexyl)-4-oxo-4,5-dihydro-1H-pyrazolo[4,3-c]pyridin-3-yl)amino)quinoline-2-carboxylate | Calc'd 471, found 471 |
| 15-17 | 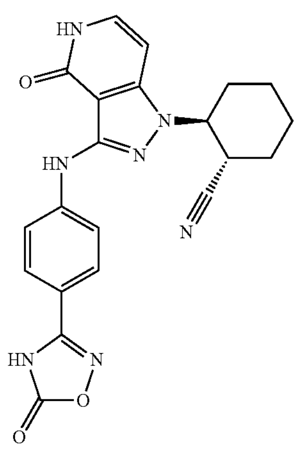 [SMILES: N#C[C@H]1CCCC[C@@H]1n1nc(Nc2ccc(-c3noc(=O)[nH]3)cc2)c2c(=O)[nH]ccc21] | (1S,2S)-2-(4-oxo-3-{[4-(5-oxo-4,5-dihydro-1,2,4-oxadiazol-3-yl)phenyl]amino}-4,5-dihydro-1H-pyrazolo[4,3-c]pyridin-1-yl)cyclohexanecarbonitrile | Calc'd 418, found 418 |

TABLE 45-continued

| Example | Structure | Compound Name | LRMS [M + H]+ |
|---|---|---|---|
| 15-18 | 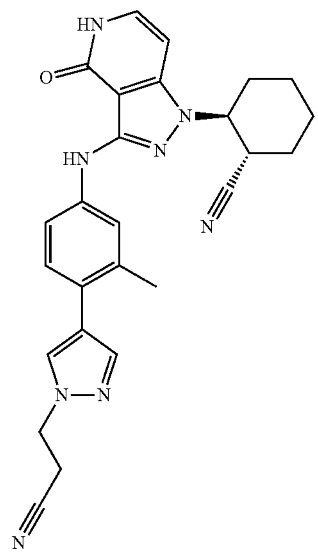 [SMILES: Cc1cc(Nc2nn([C@H]3CCCC[C@@H]3C#N)c3cc[nH]c(=O)c23)ccc1-c1cnn(CCC#N)c1] | (1S,2S)-2-[3-({4-[1-(2-cyanoethyl)-1H-pyrazol-4-yl]-3-methylphenyl}amino)-4-oxo-4,5-dihydro-1H-pyrazolo[4,3-c]pyridin-1-yl]cyclohexanecarbonitrile | Calc'd 467, found 467 |
| 15-19 | 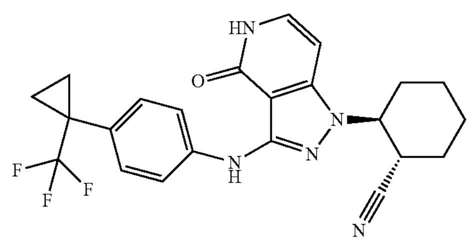 [SMILES: N#C[C@H]1CCCC[C@@H]1n1nc(Nc2ccc(C3(C(F)(F)F)CC3)cc2)c2c(=O)[nH]ccc21] | (1S,2S)-2-[4-oxo-3-({4-[1-trifluoromethyl)cyclopropyl]phenyl}amino)-4,5-dihydro-1H-pyrazolo[4,3-c]pyridin-1-yl]cyclohexanecarbonitrile | Calc'd 442, found 442 |
| 15-20 | 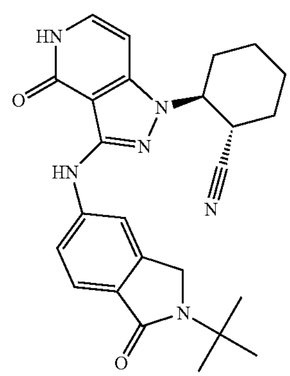 [SMILES: CC(C)(C)N1Cc2cc(Nc3nn([C@H]4CCCC[C@@H]4C#N)c4cc[nH]c(=O)c34)ccc2C1=O] | (1S,2S)-2-{3-[(2-tert-butyl-1-oxo-2,3-dihydro-1H-isoindol-5-yl)amino]-4-oxo-4,5-dihydro-1H-pyrazolo[4,3-c]pyridin-1-yl}cyclohexanecarbonitrile | Calc'd 445, found 445 |
| 15-21 | 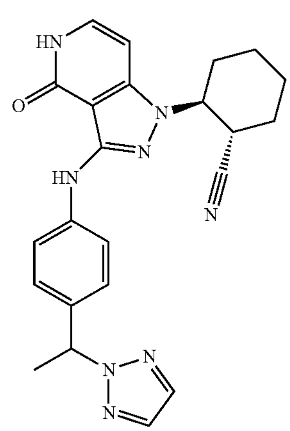 [SMILES: CC(c1ccc(Nc2nn([C@H]3CCCC[C@@H]3C#N)c3cc[nH]c(=O)c23)cc1)n1nccn1] | (1S,2S)-2-[4-oxo-3-({4-[(1S or 1R)-1-(2H-1,2,3-triazol-2-yl)ethyl]phenyl}amino)-4,5-dihydro-1H-pyrazolo[4,3-c]pyridin-1-yl]cyclohexanecarbonitrile (Derived from Peak A by HPLC using IB, 40% EtOH (with 0.1% DEA) in Hexanes (with 0.1% TEA), Tr = 10.8 mins) | Calc'd 429, found 360 [M − 68] triazole |

TABLE 45-continued

| Example | Structure | Compound Name | LRMS [M + H]+ |
|---|---|---|---|
| 15-22 | 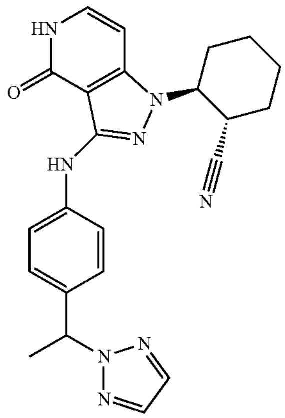 [SMILES: CC(c1ccc(Nc2nn([C@H]3CCCC[C@@H]3C#N)c3cc[nH]c(=O)c23)cc1)n1nccn1] | (1S,2S)-2-[4-oxo-3-({4-[(1R or 1S)-1-(2H-1,2,3-triazol-2-yl)ethyl]phenyl}amino)-4,5-dihydro-1H-pyrazolo[4,3-c]pyridin-1-yl]cyclohexanecarbonitrile (Derived from Peak B by HPLC using IB, 40% EtOH (with 0.1% DEA) in Hexanes (with 0.1% TEA), Tr = 14.2 mins) | Calc'd 429, found 360 [M − 68] triazole |
| 15-23 | 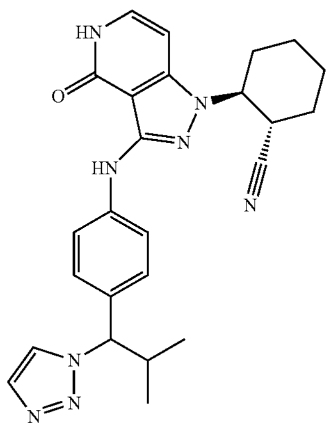 [SMILES: CC(C)C(c1ccc(Nc2nn([C@H]3CCCC[C@@H]3C#N)c3cc[nH]c(=O)c23)cc1)n1ccnn1] | (1S,2S)-2-[3-({4-[(1R or 1S)-2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile (Derived from Peak A by HPLC using IB, 30% EtOH (with 0.1% DEA) in Hexanes (with 0.1% TEA), Tr = 12.5 mins) | Calc'd 457, found 388 [M − 68] triazole |
| 15-24 | 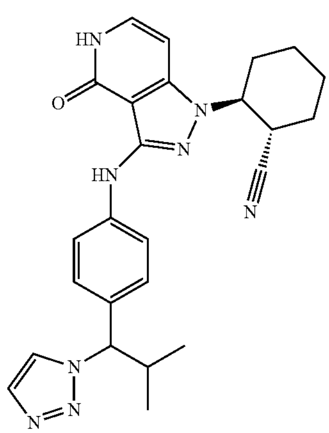 [SMILES: CC(C)C(c1ccc(Nc2nn([C@H]3CCCC[C@@H]3C#N)c3cc[nH]c(=O)c23)cc1)n1ccnn1] | (1S,2S)-2-[3-({4-[(1S or 1R)-2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile (Derived from Peak B by HPLC using IB, 4 = 30% EtOH (with 0.1% DEA) in Hexanes (with 0.1% TEA), Tr = 18 mins) | Calc'd 457, found 388 [M − 68] triazole |

TABLE 45-continued

| Example | Structure | Compound Name | LRMS [M + H]+ |
|---|---|---|---|
| 15-25 | 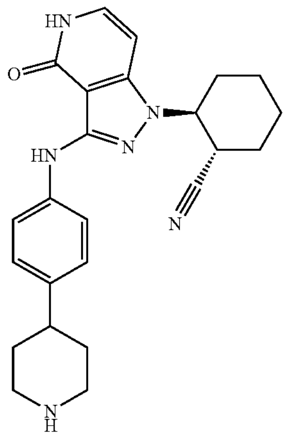 [SMILES: N#C[C@H]1CCCC[C@@H]1n1nc(Nc2ccc(C3CCNCC3)cc2)c2c(=O)[nH]ccc21] | (1S,2S)-2-{4-oxo-3-[(4-piperidin-4-ylphenyl)amino]-4,5-dihydro-1H-pyrazolo[4,3-c]pyridin-1-yl}cyclohexanecarbonitrile | Calc'd 417, found 417 |
| 15-26 | 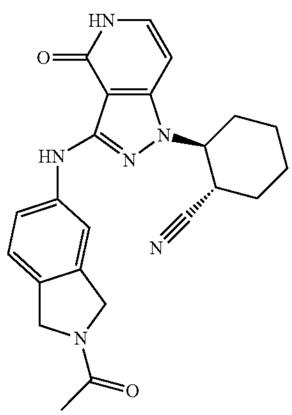 [SMILES: CC(=O)N1Cc2ccc(Nc3nn([C@H]4CCCC[C@@H]4C#N)c4cc[nH]c(=O)c34)cc2C1] | (1S,2S)-2-{3-[(2-acetyl-2,3-dihydro-1H-isoindol-5-yl)amino]-4-oxo-4,5-dihydro-1H-pyrazolo[4,3-c]pyridin-1-yl}cyclohexanecarbonitrile (from I-58a) | Calc'd 417, found 417 |
| 15-27 | 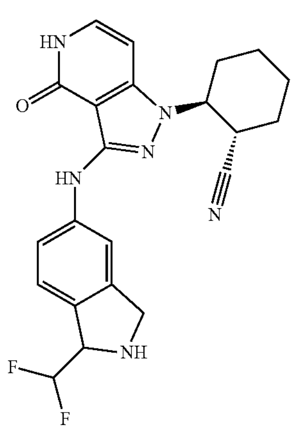 [SMILES: N#C[C@H]1CCCC[C@@H]1n1nc(Nc2ccc3c(c2)CNC3C(F)F)c2c(=O)[nH]ccc21] | (1S,2S)-2-(3-{[(1R or 1S)-1-(difluoromethyl)-2,3-dihydro-1H-isoindol-5-yl]amino}-4-oxo-4,5-dihydro-1H-pyrazolo[4,3-c]pyridin-1-yl)cyclohexanecarbonitrile (HCl salt) (Derived from Peak A by HPLC using IC, 30% EtOH in Hexanes (with 0.1% TEA), Tr = 19.29 mins) | Calc'd 425, found 425 |

TABLE 45-continued

| Example | Structure | Compound Name | LRMS [M + H]+ |
|---|---|---|---|
| 15-28 | 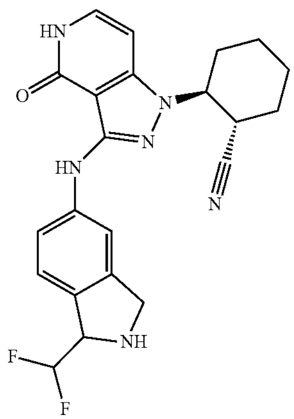 [SMILES: N#C[C@H]1CCCC[C@@H]1n1nc(Nc2ccc3c(c2)CNC3C(F)F)c2c(=O)[nH]ccc21] | (1S,2S)-2-(3-{[(1S or 1R)-1-(difluoromethyl)-2,3-dihydro-1H-isoindol-5-yl]amino}-4-oxo-4,5-dihydro-1H-pyrazolo[4,3-c]pyridin-1-yl)cyclohexanecarbonitrile (HCl salt) (Derived from Peak B by HPLC using IC, 30% EtOH in Hexanes (with 0.1% TEA), Tr = 22.3 mins) | Calc'd 425, found 425 |
| 15-29 | 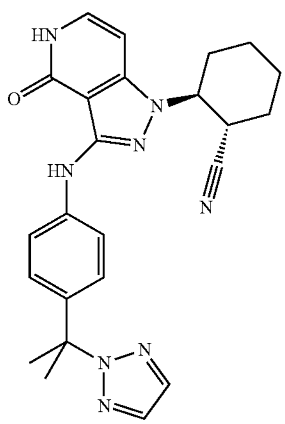 [SMILES: CC(C)(c1ccc(Nc2nn([C@H]3CCCC[C@@H]3C#N)c3cc[nH]c(=O)c23)cc1)n1nccn1] | (1S,2S)-2-[3-({4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile | Calc'd 443, found 374 [M − 68] triazole |
| 15-30 | 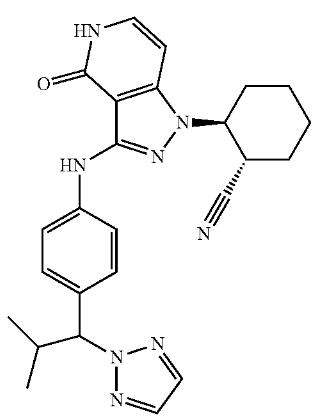 [SMILES: CC(C)C(c1ccc(Nc2nn([C@H]3CCCC[C@@H]3C#N)c3cc[nH]c(=O)c23)cc1)n1nccn1] | (1S,2S)-2-[3-({4-[(1S or 1R)-2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile (Derived from Peak A by HPLC using IA, 30% EtOH in Hexanes (with 0.1% TEA), Tr = 7.08 mins) | Calc'd 457, found 457 |

TABLE 45-continued

| Example | Compound Name | LRMS [M + H]+ |
|---|---|---|
| 15-31 | (1S,2S)-2-[3-({4-[(1R or 1S)-2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile (Derived from Peak B by HPLC using IA, 30% EtOH in Hexanes (with 0.1% TEA), Tr = 8.67 mins) | Calc'd 457, found 457 |
| 15-32 | (1S,2S)-2-[3-({3-methyl-4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile | Calc'd 457, found 457 |
| 15-33 | (1S,2S)-2-[3-({3-methyl-4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile | Calc'd [M − H] 455, found 455 |

TABLE 45-continued

| Example | Structure | Compound Name | LRMS [M + H]+ |
|---|---|---|---|
| 15-34 | 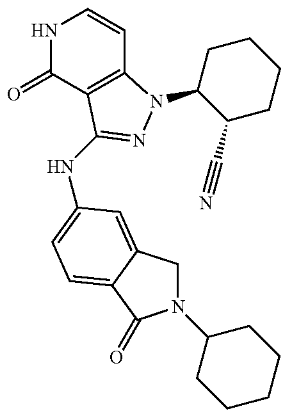 [SMILES: N#C[C@H]1CCCC[C@@H]1n1nc(Nc2ccc3c(c2)CN(C2CCCCC2)C3=O)c2c(=O)[nH]ccc21] | (1S,2S)-2-{3-[(2-cyclohexyl-1-oxo-2,3-dihydro-1H-isoindol-5-yl)amino]-4-oxo-4,5-dihydro-1H-pyrazolo[4,3-c]pyridin-1-yl}cyclohexanecarbonitrile | Calc'd 471, found 471 |
| 15-35 | 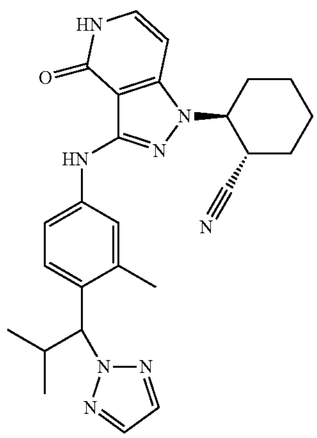 [SMILES: Cc1cc(Nc2nn([C@H]3CCCC[C@@H]3C#N)c3cc[nH]c(=O)c23)ccc1C(C(C)C)n1nccn1] | (1S,2S)-2-[3-({3-methyl-4-[(1S or 1R)-2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile (Derived from Peak A by HPLC using IA, 10% EtOH in Hexanes (with 0.1% TEA), Tr = 17.43 mins) | Calc'd 471, found 471 |
| 15-36 | 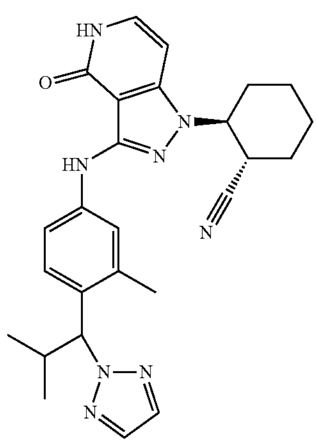 [SMILES: Cc1cc(Nc2nn([C@H]3CCCC[C@@H]3C#N)c3cc[nH]c(=O)c23)ccc1C(C(C)C)n1nccn1] | (1S,2S)-2-[3-({3-methyl-4-[(1R or 1S)-2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile (Derived from Peak B by HPLC using IA, 10% EtOH in Hexanes (with 0.1% TEA), Tr = 22.05 mins) | Calc'd 471, found 471 |

TABLE 45-continued

| Example | Structure | Compound Name | LRMS [M + H]+ |
|---|---|---|---|
| 15-37 | 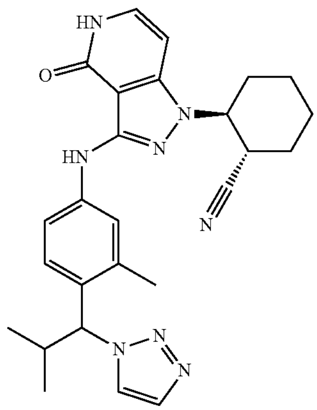 [SMILES: Cc1cc(Nc2nn([C@H]3CCCC[C@@H]3C#N)c3cc[nH]c(=O)c23)ccc1C(C(C)C)n1ccnn1] | (1S,2S)-2-[3-({3-methyl-4-[(1S or 1R)-2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile (Derived from Peak A by HPLC using IA, 20% EtOH in Hexanes (with 0.1% TEA), Tr = 4.36 mins) | Calc'd [M − H] 469, found 469 |
| 15-38 | 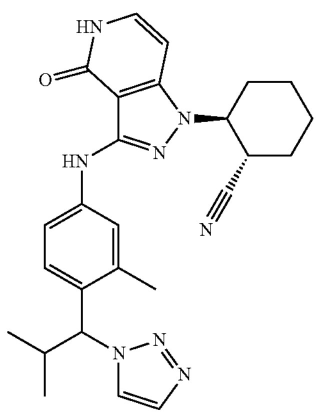 [SMILES: Cc1cc(Nc2nn([C@H]3CCCC[C@@H]3C#N)c3cc[nH]c(=O)c23)ccc1C(C(C)C)n1ccnn1] | (1S,2S)-2-[3-({3-methyl-4-[(1R or 1S)-2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile (Derived from Peak B by HPLC using IA, 20% EtOH in Hexanes (with 0.1% TEA), Tr = 6.11 mins) | Calc'd [M − H] 469, found 469 |
| 15-39 | 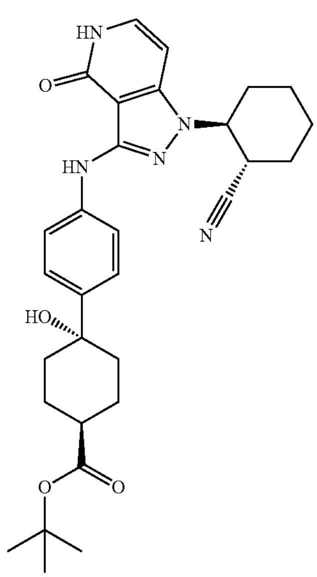 [SMILES: CC(C)(C)OC(=O)[C@H]1CC[C@@](O)(c2ccc(Nc3nn([C@H]4CCCC[C@@H]4C#N)c4cc[nH]c(=O)c34)cc2)CC1] | (1S,4S and 1R,4R)-tert-butyl 4-(4-((1-(((1S,2S)-2-cyanocyclohexyl)-4-oxo-4,5-dihydro-1H-pyrazolo[4,3-c]pyridin-3-yl)amino)phenyl)-4-hydroxycyclohexanecarboxylate (from I-158) | Calc'd 532, found 532 |

TABLE 45-continued

| Example | Structure | Compound Name | LRMS [M + H]+ |
|---|---|---|---|
| 15-40 | 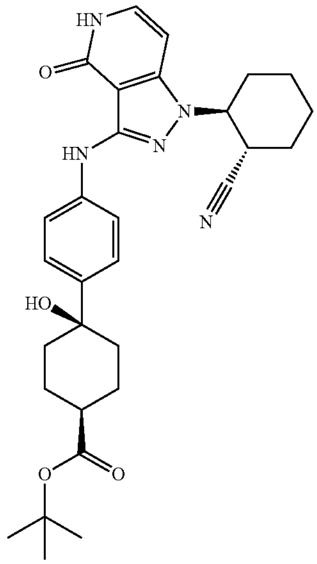 [SMILES: CC(C)(C)OC(=O)[C@H]1CC[C@](O)(c2ccc(Nc3nn([C@H]4CCCC[C@@H]4C#N)c4cc[nH]c(=O)c34)cc2)CC1] | (1S,4R and 1R,4S)-tert-butyl 4-(4-((1-((1S,2S)-2-cyanocyclohexyl)-4-oxo-4,5-dihydro-1H-pyrazolo[4,3-c]pyridin-3-yl)amino)phenyl)-4-hydroxycyclohexanecarboxylate (from I-159) | Calc'd 532, found 532 |
| 15-41 | 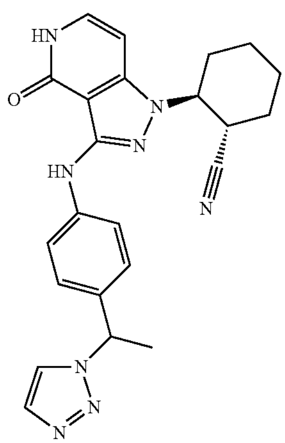 [SMILES: CC(c1ccc(Nc2nn([C@H]3CCCC[C@@H]3C#N)c3cc[nH]c(=O)c23)cc1)n1ccnn1] | (1S,2S)-2-[4-oxo-3-({4-[(1R or 1S)-1-(1H-1,2,3-triazol-1-yl)ethyl]phenyl}amino)-4,5-dihydro-1H-pyrazolo[4,3-c]pyridin-1-yl]cyclohexanecarbonitrile (Derived from Peak A by HPLC using IA, 30% EtOH in Hexanes, Tr = 26.1 mins) | Calc'd 429, found 360 [M − 68] triazole |
| 15-42 | 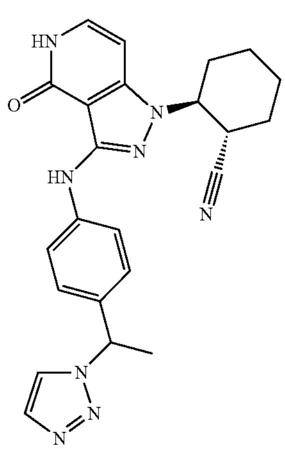 [SMILES: CC(c1ccc(Nc2nn([C@H]3CCCC[C@@H]3C#N)c3cc[nH]c(=O)c23)cc1)n1ccnn1] | (1S,2S)-2-[4-oxo-3-({4-[(1S or 1R)-1-(1H-1,2,3-triazol-1-yl)ethyl]phenyl}amino)-4,5-dihydro-1H-pyrazolo[4,3-c]pyridin-1-yl]cyclohexanecarbonitrile (Derived from Peak B by HPLC using IA, 30% EtOH in Hexanes, Tr = 33.8 mins) | Calc'd 429, found 360 [M − 68] triazole |

TABLE 45-continued

| Example | Structure | Compound Name | LRMS [M + H]+ |
|---|---|---|---|
| 15-43 | 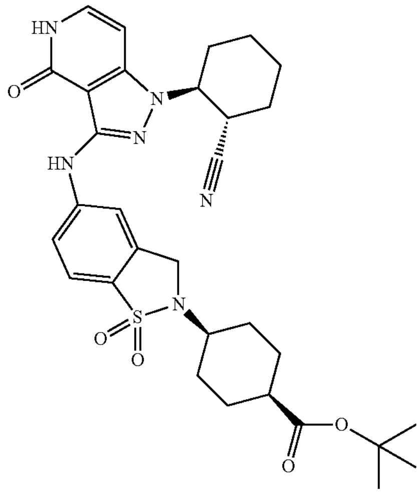 [SMILES: CC(C)(C)OC(=O)[C@H]1CC[C@@H](N2Cc3cc(Nc4nn([C@H]5CCCC[C@@H]5C#N)c5cc[nH]c(=O)c45)ccc3S2(=O)=O)CC1] | (1S,4S)-tert-butyl 4-(5-((1-((1S,2S)-2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylate (from I-156) | Calc'd 607, found 607 |
| 15-44 | 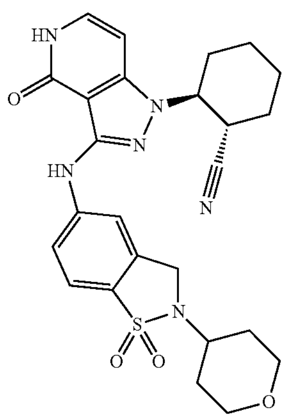 [SMILES: N#C[C@H]1CCCC[C@@H]1n1nc(Nc2ccc3c(c2)CN(C2CCOCC2)S3(=O)=O)c2c(=O)[nH]ccc21] | (1S,2S)-2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 509, found 509 |
| 15-45 | 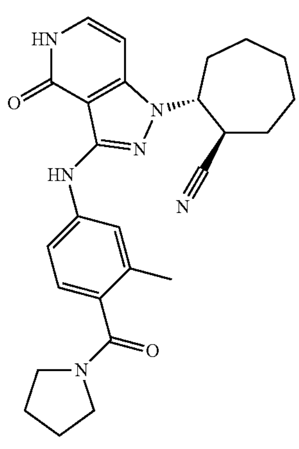 [SMILES: Cc1cc(Nc2nn([C@@H]3CCCCC[C@H]3C#N)c3cc[nH]c(=O)c23)ccc1C(=O)N1CCCC1] | (1R,2R or 1S,2S)-2-(3-{[3-methyl-4-(pyrrolidin-1-ylcarbonyl)phenyl]amino}-4-oxo-4,5-dihydro-1H-pyrazolo[4,3-c]pyridin-1-yl)cycloheptanecarbonitrile (from I-15) | Calc'd 459, found 459 |

TABLE 45-continued

| Example | Structure | Compound Name | LRMS [M + H]+ |
|---|---|---|---|
| 15-46 | 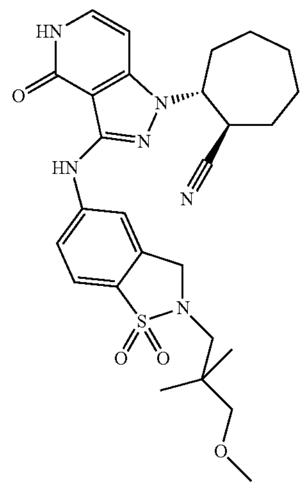 [SMILES: COCC(C)(C)CN1Cc2cc(Nc3nn([C@@H]4CCCCC[C@H]4C#N)c4cc[nH]c(=O)c34)ccc2S1(=O)=O] | (1R,2R or 1S,2S)-2-(3-{[2-(3-methoxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cycloheptanecarbonitrile (from I-15) | Calc'd 539, found 539 |
| 15-47 | 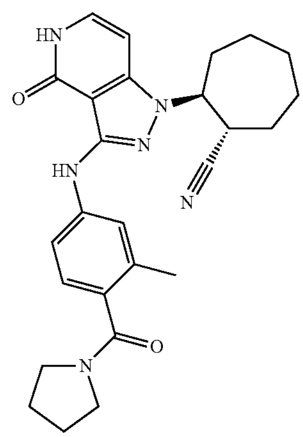 [SMILES: Cc1cc(Nc2nn([C@H]3CCCCC[C@@H]3C#N)c3cc[nH]c(=O)c23)ccc1C(=O)N1CCCC1] | (1S,2S or 1R,2R)-2-(3-{[3-methyl-4-(pyrrolidin-1-ylcarbonyl)phenyl]amino}-4-oxo-4,5-dihydro-1H-pyrazolo[4,3-c]pyridin-1-yl)cycloheptanecarbonitrile (from I-16) | Calc'd 459, found 459 |
| 15-48 | 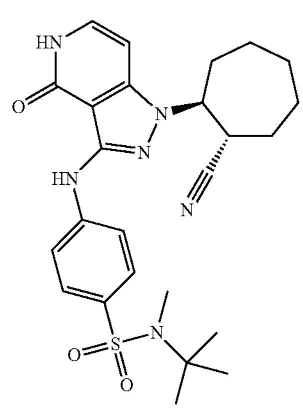 [SMILES: CN(C(C)(C)C)S(=O)(=O)c1ccc(Nc2nn([C@H]3CCCCC[C@@H]3C#N)c3cc[nH]c(=O)c23)cc1] | N-tert-butyl-4-({1-[(1S,2S or 1R,2R)-2-cyanocycloheptyl]-4-oxo-4,5-dihydro-1H-pyrazolo[4,3-c]pyridin-3-yl}amino)-N-methylbenzenesulfonamide (from I-16) | Calc'd 497, found 497 |

TABLE 45-continued

| Example | Structure | Compound Name | LRMS [M + H]+ |
|---------|-----------|---------------|---------------|
| 15-49 | 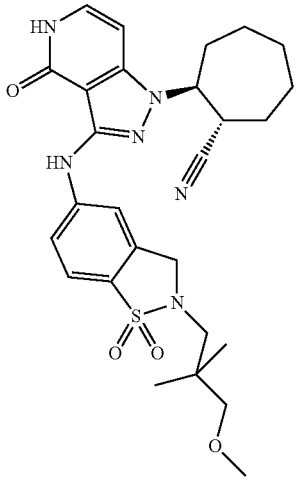 [SMILES: COCC(C)(C)CN1Cc2cc(Nc3nn([C@H]4CCCCC[C@@H]4C#N)c4cc[nH]c(=O)c34)ccc2S1(=O)=O] | (1S,2S or 1R,2R)-2-(3-{[2-(3-methoxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cycloheptanecarbonitrile (from I-16) | Calc'd 539, found 539 |
| 15-50 | 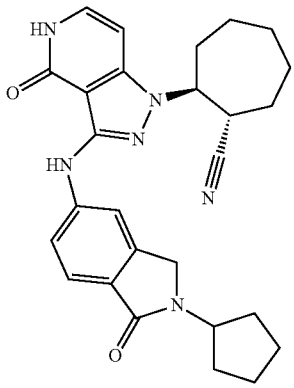 [SMILES: N#C[C@H]1CCCCC[C@@H]1n1nc(Nc2ccc3c(c2)CN(C2CCCC2)C3=O)c2c(=O)[nH]ccc21] | (1S,2S or 1R,2R)-2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cycloheptanecarbonitrile (from I-16) | Calc'd 471, found 471 |
| 15-51 | 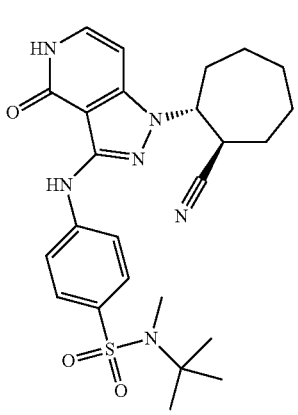 [SMILES: CN(C(C)(C)C)S(=O)(=O)c1ccc(Nc2nn([C@@H]3CCCCC[C@H]3C#N)c3cc[nH]c(=O)c23)cc1] | N-tert-butyl-4-({1-[(1R,2R or 1S,2S)-2-cyanocycloheptyl]-4-oxo-4,5-dihydro-1H-pyrazolo[4,3-c]pyridin-3-yl}amino)-N-methylbenzenesulfonamide (from I-15) | Calc'd 497, found 497 |

TABLE 45-continued

| Example | Structure | Compound Name | LRMS [M + H]+ |
|---|---|---|---|
| 15-52 | 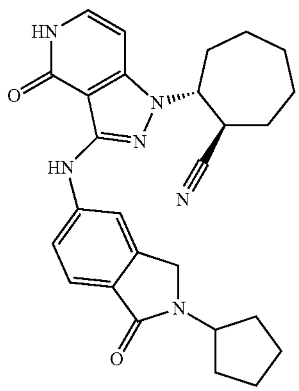 [SMILES: N#C[C@@H]1CCCCC[C@H]1n1nc(Nc2ccc3c(c2)CN(C2CCCC2)C3=O)c2c(=O)[nH]ccc21] | (1R,2R or 1S,2S)-2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cycloheptanecarbonitrile (from I-15) | Calc'd 471, found 471 |
| 15-53 | 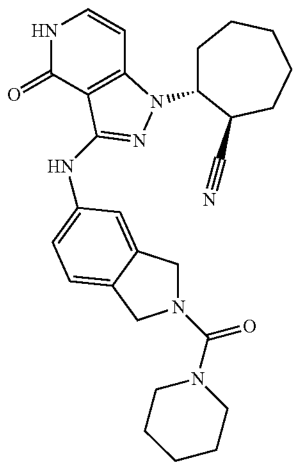 [SMILES: N#C[C@@H]1CCCCC[C@H]1n1nc(Nc2ccc3c(c2)CN(C(=O)N2CCCCC2)C3)c2c(=O)[nH]ccc21] | (1R,2R or 1S,2S)-2-(4-oxo-3-{[2-(piperidin-1-ylcarbonyl)-2,3-dihydro-1H-isoindol-5-yl]amino}-4,5-dihydro-1H-pyrazolo[4,3-c]pyridin-1-yl)cycloheptanecarbonitrile (from I-15) | Calc'd 500, found 500 |
| 15-54 | 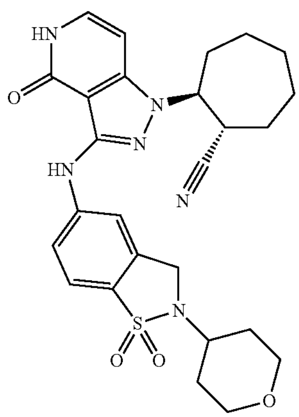 [SMILES: N#C[C@H]1CCCCC[C@@H]1n1nc(Nc2ccc3c(c2)CN(C2CCOCC2)S3(=O)=O)c2c(=O)[nH]ccc21] | (1S,2S or 1R,2R)-2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cycloheptanecarbonitrile (from I-16) | Calc'd 523, found 523 |

TABLE 45-continued

| Example | Structure | Compound Name | LRMS [M + H]+ |
|---|---|---|---|
| 15-55 | 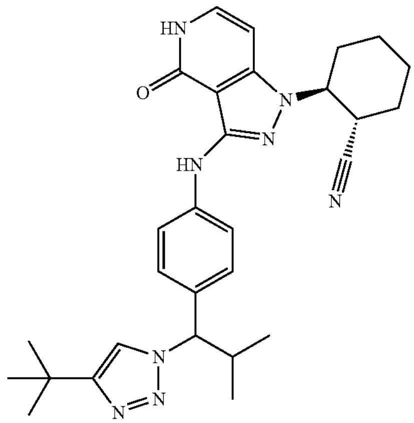 [SMILES: CC(C)C(c1ccc(Nc2nn([C@H]3CCCC[C@@H]3C#N)c3cc[nH]c(=O)c23)cc1)n1cc(C(C)(C)C)nn1] | (1S,2S)-2-[3-({4-[(1S or 1R)-1-(4-tert-butyl-1H-1,2,3-triazol-1-yl)-2-methylpropyl]phenyl}amino)-4-oxo-4,5-dihydro-1H-pyrazolo[4,3-c]pyridin-1-yl]cyclohexanecarbonitrile (Derived from Peak A by HPLC on free pyridone using Lux Cellulose-2, 25% EtOH in Hexanes (with 0.1% TEA), Tr = 12.98 mins) | Calc'd 513, found 388 [M − 124] triazole |
| 15-56 | 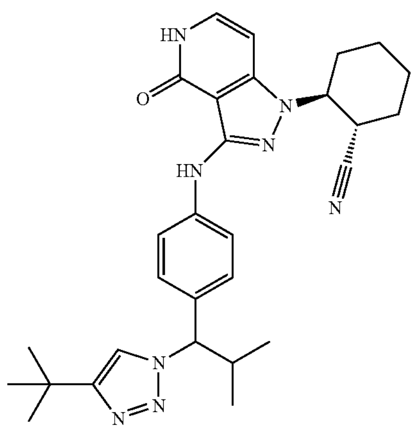 [SMILES: CC(C)C(c1ccc(Nc2nn([C@H]3CCCC[C@@H]3C#N)c3cc[nH]c(=O)c23)cc1)n1cc(C(C)(C)C)nn1] | (1S,2S)-2-[3-({4-[(1R or 1S)-1-(4-tert-butyl-1H-1,2,3-triazol-1-yl)-2-methylpropyl]phenyl}amino)-4-oxo-4,5-dihydro-1H-pyrazolo[4,3-c]pyridin-1-yl]cyclohexanecarbonitrile (Derived from Peak B by HPLC using Lux Cellulose-2, 25% EtOH in Hexanes (with 0.1% TEA), Tr = 15.49 mins) | Calc'd 513, found 388 [M − 124] triazole |
| 15-57 | 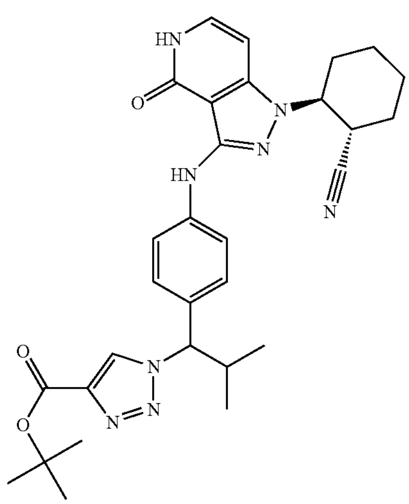 [SMILES: CC(C)C(c1ccc(Nc2nn([C@H]3CCCC[C@@H]3C#N)c3cc[nH]c(=O)c23)cc1)n1cc(C(=O)OC(C)(C)C)nn1] | tert-butyl 1-{(1S or 1R)-1-[4-({1-[(1S,2S)-2-cyanocyclohexyl]-4-oxo-4,5-dihydro-1H-pyrazolo[4,3-c]pyridin-3-yl}amino)phenyl]-2-methylpropyl}-1H-1,2,3-triazole-4-carboxylate (Derived from Peak A by HPLC using IA, 10% EtOH in MTBE, Tr = 8.42 mins) | Calc'd 557, found 388 [M − 124] triazole |

TABLE 45-continued

| Example | Structure | Compound Name | LRMS [M + H]+ |
|---|---|---|---|
| 15-58 | 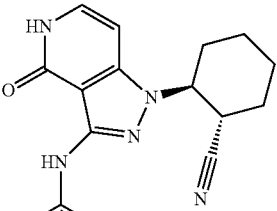 | tert-butyl 1-{(1R or 1S)-1-[4-({1-[(1S,2S)-2-cyanocyclohexyl]-4-oxo-4,5-dihydro-1H-pyrazolo[4,3-c]pyridin-3-yl}amino)phenyl]-2-methylpropyl}-1H-1,2,3-triazole-4-carboxylate (Derived from Peak B by HPLC using IA, 10% EtOH in MTBE, Tr = 10.15 mins) | Calc'd 557, found 388 [M − 124] triazole |
| 15-59 | 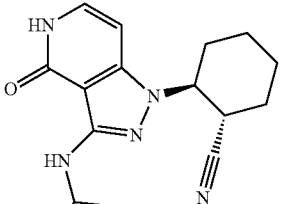 | (1S,2S)-2-(4-oxo-3-{[1-oxo-2-(tetrahydro-2H-pyran-4-yl)-2,3-dihydro-1H-isoindol-5-yl]amino}-4,5-dihydro-1H-pyrazolo[4,3-c]pyridin-1-yl)cyclohexanecarbonitrile | Calc'd 473, found 473 |
| 15-60 | 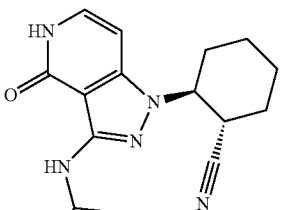 | (1S,2S)-2-(4-oxo-3-{[1-oxo-2-(tetrahydro-2H-thiopyran-4-yl)-2,3-dihydro-1H-isoindol-5-yl]amino}-4,5-dihydro-1H-pyrazolo[4,3-c]pyridin-1-yl)cyclohexanecarbonitrile | Calc'd 489, found 489 |

TABLE 45-continued

| Example | Structure | Compound Name | LRMS [M + H]+ |
|---|---|---|---|
| 15-61 | 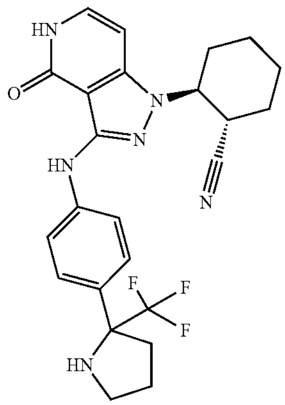 [SMILES: N#C[C@H]1CCCC[C@@H]1n1nc(Nc2ccc(C3(C(F)(F)F)CCCN3)cc2)c2c(=O)[nH]ccc21] | (1S,2S)-2-[4-oxo-3-({4-[(2R or 2S)-2-(trifluoromethyl)pyrrolidin-2-yl]phenyl}amino)-4,5-dihydro-1H-pyrazolo[4,3-c]pyridin-1-yl]cyclohexanecarbonitrile (Derived from Peak A by HPLC using OD-H, 10% EtOH in Hexanes, Tr = 25.24 mins) | Calc'd 471, found 471 |
| 15-62 | 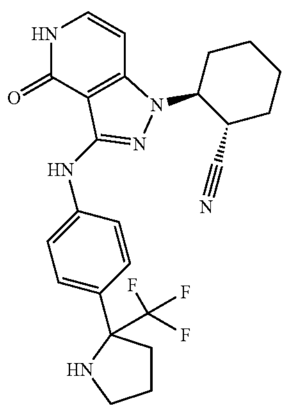 [SMILES: N#C[C@H]1CCCC[C@@H]1n1nc(Nc2ccc(C3(C(F)(F)F)CCCN3)cc2)c2c(=O)[nH]ccc21] | (1S,2S)-2-[4-oxo-3-({4-[(2S or 2R)-2-(trifluoromethyl)pyrrolidin-2-yl]phenyl}amino)-4,5-dihydro-1H-pyrazolo[4,3-c]pyridin-1-yl]cyclohexanecarbonitrile (Derived from Peak B by HPLC using OD-H, 10% EtOH in Hexanes, Tr = 30.36 mins) | Calc'd 471, found 471 |
| 15-63 | 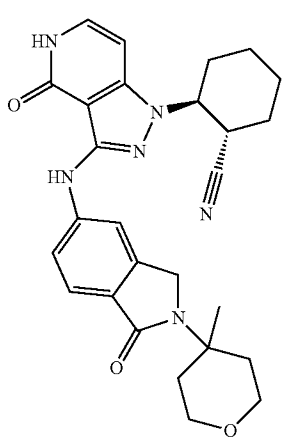 [SMILES: CC1(N2Cc3cc(Nc4nn([C@H]5CCCC[C@@H]5C#N)c5cc[nH]c(=O)c45)ccc3C2=O)CCOCC1] | (1S,2S)-2-(3-{[2-(4-methyltetrahydro-2H-pyran-4-yl)-1-oxo-2,3-dihydro-1H-isoindol-5-yl]amino}-4-oxo-4,5-dihydro-1H-pyrazolo[4,3-c]pyridin-1-yl)cyclohexanecarbonitrile | Calc'd 487, found 487 |

TABLE 45-continued

| Example | Structure | Compound Name | LRMS [M + H]+ |
|---|---|---|---|
| 15-64 | 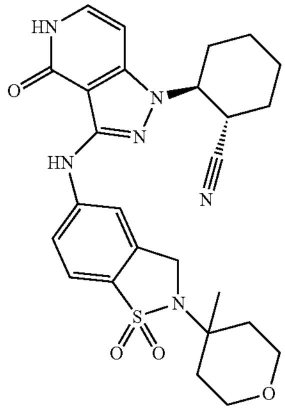 [SMILES: CC1(N2Cc3cc(Nc4nn([C@H]5CCCC[C@@H]5C#N)c5cc[nH]c(=O)c45)ccc3S2(=O)=O)CCOCC1] | (1S,2S)-2-(3-{[2-(4-methyltetrahydro-2H-pyran-4-yl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 523, found 523 |
| 15-65 | 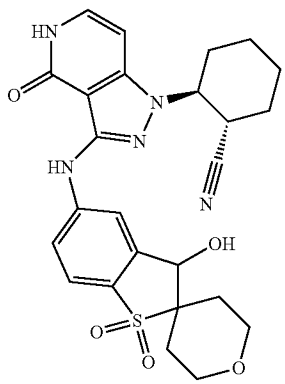 [SMILES: N#C[C@H]1CCCC[C@@H]1n1nc(Nc2ccc3c(c2)C(O)C2(CCOCC2)S3(=O)=O)c2c(=O)[nH]ccc21] | (1S,2S)-2-(3-{[(3S or 3R)-3-hydroxy-1,1-dioxido-2',3',5',6'-tetrahydro-3H-spiro[1-benzothiophene-2,4'-pyran]-5-yl]amino}-4-oxo-4,5-dihydro-1H-pyrazolo[4,3-c]pyridin-1-yl)cyclohexanecarbonitrile (Derived from Peak A by HPLC using IA, 30% EtOH (with 0.1% DEA) in Hexanes (with 0.1% DEA), Tr = 15 mins) | Calc'd 510, found 510 |
| 15-66 | 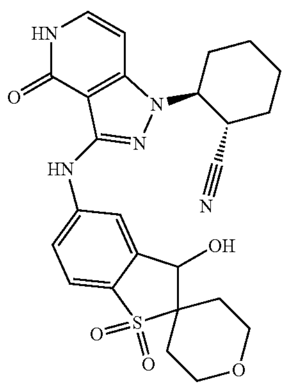 [SMILES: N#C[C@H]1CCCC[C@@H]1n1nc(Nc2ccc3c(c2)C(O)C2(CCOCC2)S3(=O)=O)c2c(=O)[nH]ccc21] | (1S,2S)-2-(3-{[(3R or 3S)-3-hydroxy-1,1-dioxido-2',3',5',6'-tetrahydro-3H-spiro[1-benzothiophene-2,4'-pyran]-5-yl]amino}-4-oxo-4,5-dihydro-1H-pyrazolo[4,3-c]pyridin-1-yl)cyclohexanecarbonitrile (Derived from Peak B by HPLC using IA, 30% EtOH (with 0.1% DEA) in Hexanes (with 0.1% DEA), Tr = 20.5 mins) | Calc'd 510, found 510 |
| 15-67 | 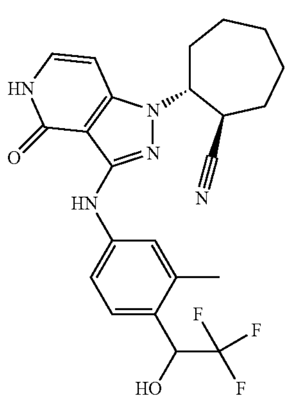 [SMILES: Cc1cc(Nc2nn([C@@H]3CCCCC[C@H]3C#N)c3cc[nH]c(=O)c23)ccc1C(O)C(F)(F)F] | (1R,2R or 1S,2S)-2-[3-({3-methyl-4-[(1S or 1R)-2,2,2-trifluoro-1-hydroxyethyl]phenyl}amino)-4-oxo-4,5-dihydro-1H-pyrazolo[4,3-c]pyridin-1-yl]cycloheptanecarbonitrile (from I-15. Derived from Peak A by HPLC using IA, 20% EtOH in Hexanes (with 0.1% TEA), Tr = 2.43 mins) | Calc'd 460, found 460 |

TABLE 45-continued

| Example | Structure | Compound Name | LRMS [M + H]+ |
|---|---|---|---|
| 15-68 | 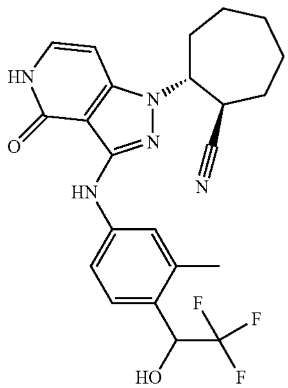 [SMILES: Cc1cc(Nc2nn([C@@H]3CCCCC[C@H]3C#N)c3cc[nH]c(=O)c23)ccc1C(O)C(F)(F)F] | (1R,2R or 1S,2S)-2-[3-({3-methyl-4-[(1R or 1S)-2,2,2-trifluoro-1-hydroxyethyl]phenyl}amino)-4-oxo-4,5-dihydro-1H-pyrazolo[4,3-c]pyridin-1-yl]cycloheptanecarbonitrile (from I-15. Derived from Peak B by HPLC using IA, 20% EtOH in Hexanes (with 0.1% TEA), Tr = 3.93 mins) | Calc'd 460, found 460 |
| 15-69 | 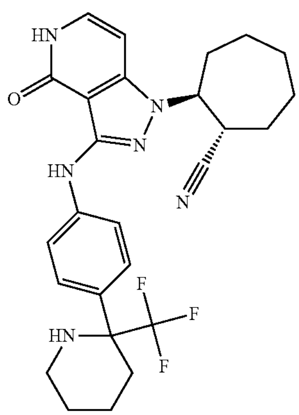 [SMILES: N#C[C@H]1CCCCC[C@@H]1n1nc(Nc2ccc(C3(C(F)(F)F)CCCCN3)cc2)c2c(=O)[nH]ccc21] | (1S,2S or 1R,2R)-2-[4-oxo-3-({4-[(2S or 2R)-2-(trifluoromethyl)piperidin-2-yl]phenyl}amino)-4,5-dihydro-1H-pyrazolo[4,3-c]pyridin-1-yl]cycloheptanecarbonitrile (from I-16 and I-167) | Calc'd 499, found 499 |
| 15-70 | 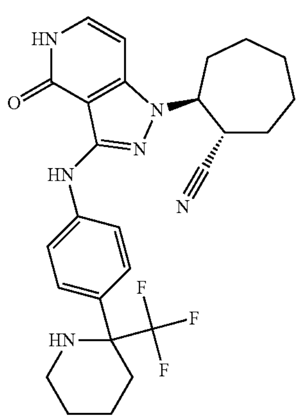 [SMILES: N#C[C@H]1CCCCC[C@@H]1n1nc(Nc2ccc(C3(C(F)(F)F)CCCCN3)cc2)c2c(=O)[nH]ccc21] | (1S,2S or 1R,2R)-2-[4-oxo-3-({4-[(2R or 2S)-2-(trifluoromethyl)piperidin-2-yl]phenyl}amino)-4,5-dihydro-1H-pyrazolo[4,3-c]pyridin-1-yl]cycloheptanecarbonitrile (from I-16 and I-166) | Calc'd 499, found 499 |

TABLE 45-continued

| Example | Structure | Compound Name | LRMS [M + H]+ |
|---------|-----------|---------------|---------------|
| 15-71 | 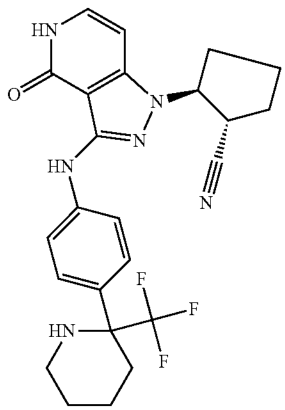 [SMILES: N#C[C@H]1CCC[C@@H]1n1nc(Nc2ccc(C3(C(F)(F)F)CCCCN3)cc2)c2c(=O)[nH]ccc21] | (1S,2S)-2-[4-oxo-3-({4-[(2S or 2R)-2-(trifluoromethyl)piperidin-2-yl]phenyl}amino)-4,5-dihydro-1H-pyrazolo[4,3-c]pyridin-1-yl]cyclopentanecarbonitrile (from I-167) | Calc'd 471, found 471 |
| 15-72 | 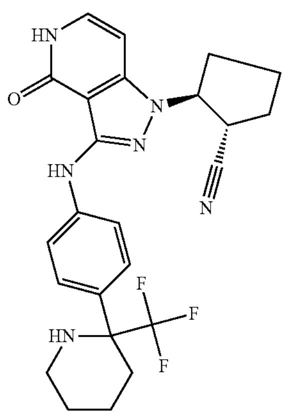 [SMILES: N#C[C@H]1CCC[C@@H]1n1nc(Nc2ccc(C3(C(F)(F)F)CCCCN3)cc2)c2c(=O)[nH]ccc21] | (1S,2S)-2-[4-oxo-3-({4-[(2R or 2S)-2-(trifluoromethyl)piperidin-2-yl]phenyl}amino)-4,5-dihydro-1H-pyrazolo[4,3-c]pyridin-1-yl]cyclopentanecarbonitrile (from I-166) | Calc'd 471, found 471 |
| 15-73 | 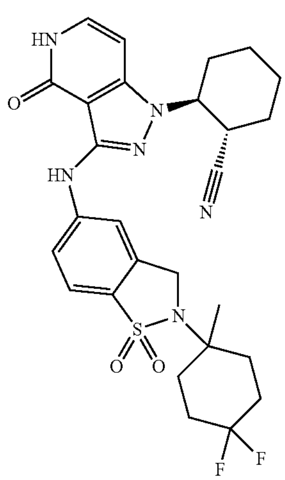 [SMILES: CC1(N2Cc3cc(Nc4nn([C@H]5CCCC[C@@H]5C#N)c5cc[nH]c(=O)c45)ccc3S2(=O)=O)CCC(F)(F)CC1] | (1S,2S)-2-(3-{[2-(4,4-difluoro-1-methylcyclohexyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile | Calc'd 557, found 557 |

TABLE 45-continued

| Example | Structure | Compound Name | LRMS [M + H]+ |
|---|---|---|---|
| 15-74 | 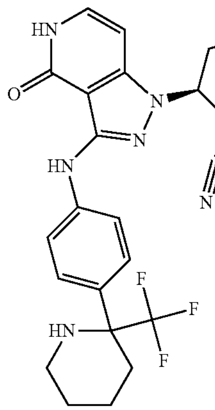 | (1S,2S)-2-[4-oxo-3-({4-[(2S or 2R)-2-(trifluoromethyl)piperidin-2-yl]phenyl}amino)-4,5-dihydro-1H-pyrazolo[4,3-c]pyridin-1-yl]cyclohexanecarbonitrile (from I-167) | Calc'd 485, found 485 |
| 15-75 | 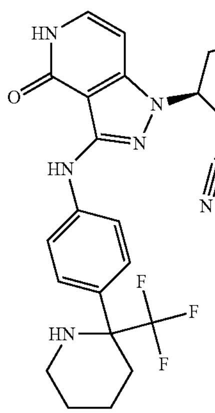 | (1S,2S)-2-[4-oxo-3-({4-[(2R or 2S)-2-(trifluoromethyl)piperidin-2-yl]phenyl}amino)-4,5-dihydro-1H-pyrazolo[4,3-c]pyridin-1-yl]cyclohexanecarbonitrile (from I-166) | Calc'd 485, found 485 |

Example 16-1

4-((1-((1S,2S)-2-Cyanocyclohexyl)-4-oxo-4,5-dihydro-1H-pyrazolo[4,3-c]pyridin-3-yl)amino)benzoic acid, HCl 16-1

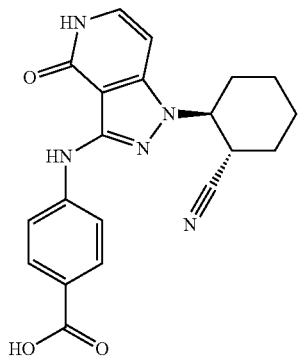

Step 1: tert-Butyl 4-((1-((1S,2S)-2-cyanocyclohexyl)-4-oxo-4,5-dihydro-1H-pyrazolo[4,3-c]pyridin-3-yl)amino)benzoate 16-1a

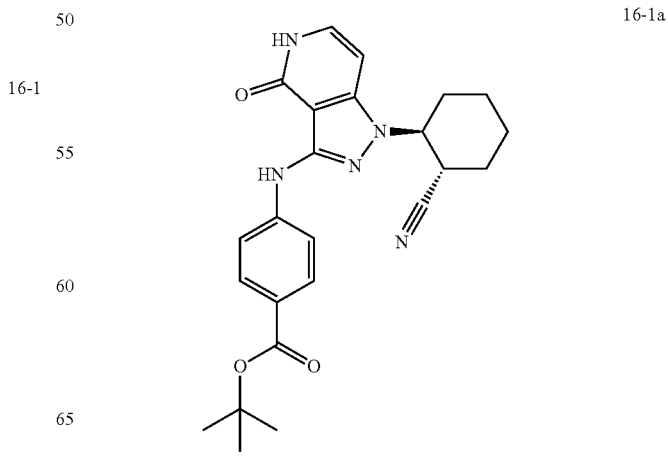

(1S,2S)-2-(3-amino-4-oxo-4,5-dihydro-1H-pyrazolo[4,3-c]pyridin-1-yl)cyclohexanecarbonitrile (I-10; 100 mg, 0.389 mmol), tert-butyl 4-bromobenzoate (90 μL, 0.47 mmol), 2-di-tert-butylphosphino-2',4',6'-triisopropylbiphenyl (33.0 mg, 0.078 mmol), and potassium acetate (114 mg, 1.17 mmol) were combined in a microwave vial and dissolved in 2-propanol (2 mL). Argon was bubbled through for 10 minutes followed by addition of $Pd_2(dba)_3$ (35.6 mg, 0.0390 mmol). The vial was then sealed and flushed with more argon. The reaction was stirred at 85° C. overnight. The reaction mixture was then filtered through Celite and concentrated in vacuo. The crude material was purified by silica chromatography, eluting with 25-75% ethyl acetate in hexanes. The desired fractions were concentrated in vacuo to give tert-butyl 4-((1-((1S,2S)-2-cyanocyclohexyl)-4-oxo-4,5-dihydro-1H-pyrazolo[4,3-c]pyridin-3-yl)amino)benzoate. LRMS (ESI) calc'd for $C_{24}H_{28}N_5O_3$ [M+H]$^+$: 434, found 434.

Step 2: 4-((1-((1S,2S)-2-Cyanocyclohexyl)-4-oxo-4,5-dihydro-1H-pyrazolo[4,3-c]pyridin-3-yl)amino) benzoic acid (HCl salt)

tert-Butyl 4-((1-((1S,2S)-2-cyanocyclohexyl)-4-oxo-4,5-dihydro-1H-pyrazolo[4,3-c]pyridin-3-yl)amino)benzoate (150 mg, 0.346 mmol) was dissolved in hydrochloric acid (5.0 mL, 20 mmol, 4.0 M in dioxane) and stirred at room temperature for 30 minutes. The reaction was concentrated in vacuo to give 4-((1-((1S,2S)-2-cyanocyclohexyl)-4-oxo-4,5-dihydro-1H-pyrazolo[4,3-c]pyridin-3-yl)amino)benzoic acid (HCl salt). LRMS (ESI) calc'd for $C_{20}H_{20}N_5O_3$ [M+H]$^+$: 378, found 378. $^1$H NMR (500 MHz, DMSO-$d_6$): δ 11.16 (s, 1H), 8.50 (s, 1H), 7.86 (d, J=8.5 Hz, 2H), 7.73 (d, J=8.5 Hz, 2H), 7.25 (t, J=6.0 Hz, 1H), 6.70 (d, J=7.0 Hz, 1H), 4.77-4.69 (m, 1H), 3.40-3.33 (m, 1H), 2.24-2.17 (m, 1H), 1.93-187 (m, 2H), 1.83-1.70 (m, 3H), 1.54-1.45 (m, 1H), 1.42-1.34 (m, 1H).

Table 46 contains Examples that were prepared in an analogous manner to that of Example 16-1. In select cases, the general procedure was modified to alternatively utilize HCl or TFA as the acid and DCM or Dioxane as solvent.

TABLE 46

| Example | Structure | Compound Name | LRMS [M + H]$^+$ |
|---|---|---|---|
| 16-2 | 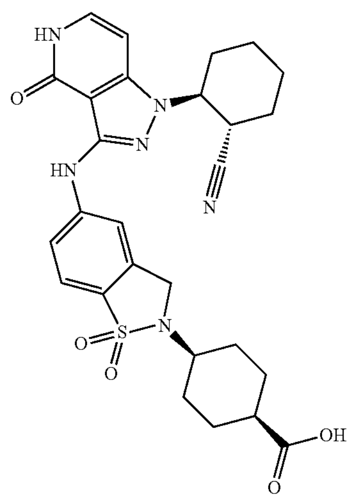 [SMILES: N#C[C@H]1CCCC[C@@H]1n1nc(Nc2ccc3c(c2)CN([C@H]2CC[C@@H](C(=O)O)CC2)S3(=O)=O)c2c(=O)[nH]ccc21] | (1S,4S)-4-(5-((1-((1S,2S)-2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylic acid (from I-156, 15-43) | Calc'd 551, found 551 |
| 16-3 | 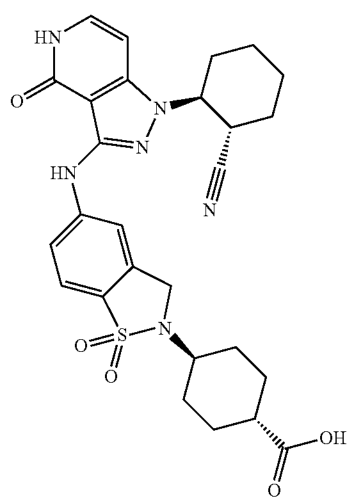 [SMILES: N#C[C@H]1CCCC[C@@H]1n1nc(Nc2ccc3c(c2)CN([C@H]2CC[C@H](C(=O)O)CC2)S3(=O)=O)c2c(=O)[nH]ccc21] | (1R,4R)-4-(5-((1-((1S,2S)-2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylic acid (from I-157) | Calc'd 551, found 551 |

Example 17-1

(1R,4S and 1S,4R)-4-(4-(1-(((1S,2S)-2-Cyanocyclo-hexyl)-4-oxo-4,5-dihydro-1H-pyrazolo[4,3-c]pyridin-3-ylamino)phenyl)-4-hydroxycyclohexanecarboxylic acid 17-1

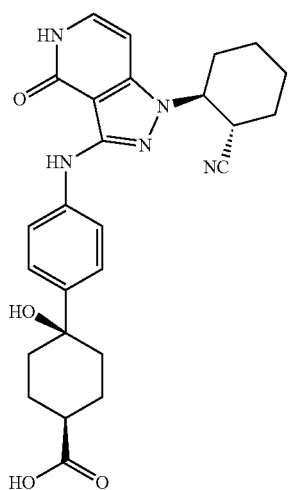

Step 1: (1R,4S and 1S,4R)-ethyl 4-(4-((1-(((1S,2S)-2-cyanocyclohexyl)-4-oxo-4,5-dihydro-1H-pyrazolo[4,3-c]pyridin-3-yl)amino)phenyl)-4-hydroxycyclohexanecarboxylate 17-1a

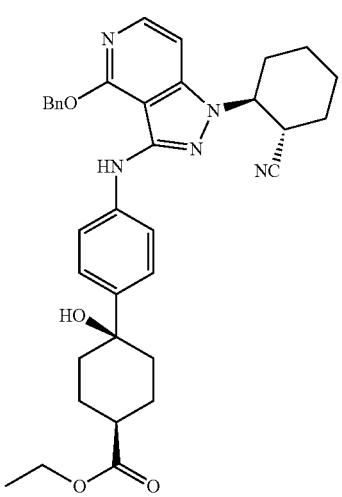

(1R,4S and 1S,4R)-ethyl 4-(4-((1-(((1S,2S)-2-cyanocyclohexyl)-4-oxo-4,5-dihydro-1H-pyrazolo[4,3-c]pyridin-3-yl)amino)phenyl)-4-hydroxycyclohexanecarboxylate was synthesized in a similar procedure described for tert-butyl 4-((1-(((1S,2S)-2-cyanocyclohexyl)-4-oxo-4,5-dihydro-1H-pyrazolo[4,3-c]pyridin-3-yl)amino)benzoate (Example 16-1a) from 1-161. LRMS (ESI) calc'd for $C_{35}H_{40}N_5O_4$ [M+H]$^+$: 594, found 594.

Step 2: (1R,4S and 1S,4R)-4-(4-(1-(((1S,2S)-2-Cyanocyclohexyl)-4-oxo-4,5-dihydro-1H-pyrazolo[4,3-c]pyridin-3-ylamino)phenyl)-4-hydroxycyclohexanecarboxylic acid To a mixture of (1R,4S and 1S,4R)-ethyl 4-(4-((1-((1S,2S)-2-cyanocyclohexyl)-4-oxo-4,5-dihydro-1H-pyrazolo[4,3-c]pyridin-3-yl)amino)phenyl)-4-hydroxycyclohexanecarboxylate (38 mg, 0.075 mmol) in tetrahydrofuran (1 mL) was added a solution of lithium hydroxide (9.04 mg, 0.377 mmol) in water (3 mL) dropwise at 0° C. The resulting mixture was stirred for 4 h at ambient temperature and then pH was adjusted to 6 with 1:19 buffer solution of 0.067 M disodium hydrogen phosphate and 0.067 M potassium phosphate monobasic. The solution was extracted with ethyl acetate (30 mL), washed with water (15 mL), dried over anhydrous sodium sulfate and filtered. The filtrate was concentrated in vacuo and the residue purified by mass triggered reverse phase HPLC (XBridge RP18; 40-56% acetonitrile/water) to afford (1R,4S and 1S,4R)-4-(4-((1-((1S,2S)-2-cyanocyclohexyl)-4-oxo-4,5-dihydro-1H-pyrazolo[4,3-c]pyridin-3-yl)amino)phenyl)-4-hydroxycyclohexanecarboxylic acid. LRMS (ESI) calc'd for $C_{26}H_{30}N_5O_4$ [M+H]$^+$: 476, found 476; $^1$H NMR (400 MHz, DMSO-$d_6$) δ 12.05 (br s, 1H), 11.10 (d, J=5.6 Hz, 1H), 8.00 (s, 1H), 7.60 (d, J=8.4 Hz, 2H), 7.42 (d, J=8.4 Hz, 2H), 7.24 (t, J=7.2 Hz, 1H), 6.69 (d, J=7.6 Hz, 1H), 4.73-4.65 (m, 2H), 2.25-2.22 (m, 2H), 1.94-1.70 (m, 14H), 1.65-1.35 (m, 2H).

Table 47 discloses an Example that was prepared in a similar method as described for Example 17.

TABLE 47

| Example | Structure | Compound Name | LRMS [M + H]+ |
|---|---|---|---|
| 17-2 | 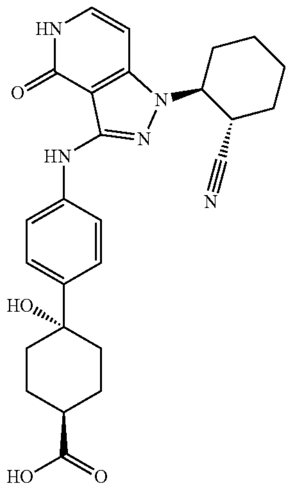 [SMILES: N#C[C@H]1CCCC[C@@H]1n1nc(Nc2ccc([C@]3(O)CC[C@H](C(=O)O)CC3)cc2)c2c(=O)[nH]ccc21] | (1S,4S and 1R,4R)-4-[4-({1-[(1S,2S)-2-cyanocyclohexyl]-4-oxo-4,5-dihydro-1H-pyrazolo[4,3-c]pyridin-3-yl}amino)phenyl]-4-hydroxycyclohexanecarboxylic acid (from I-160) | Calc'd 476, found 476 |

Example 18-1 tert-Butyl 5-((1-((1S,2S)-2-cyanocyclohexyl)-4-oxo-4,5-dihydro-1H-pyrazolo[4,3-c]pyridin-3-yl)amino)-1-methylisoindoline-2-carboxylate

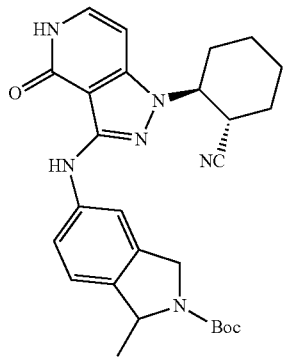

18-1

Into a 50 mL 3-necked round bottom flask, were placed (1S,2S)-2-(3-{[(1S and 1R)-1-methyl-2,3-dihydro-1H-isoindol-5-yl]amino}-4-oxo-4,5-dihydro-1H-pyrazolo[4,3-c]pyridin-1-yl)cyclohexanecarbonitrile (Example 12-3; 70 mg, 0.18 mmol), triethylamine (36.5 mg, 0.360 mmol), di-tert-butyl dicarbonate (59 mg, 0.27 mmol) and dichloromethane (10 mL). The mixture was stirred for 50 min at ambient temperature. The mixture was concentrated in vacuo and the residue purified by preparative TLC (100% ethyl acetate) to give tert-butyl 5-((1-((1S,2S)-2-cyanocyclohexyl)-4-oxo-4,5-dihydro-1H-pyrazolo[4,3-c]pyridin-3-yl)amino)-1-methylisoindoline-2-carboxylate. LRMS (ESI) calc'd for $C_{27}H_{33}N_6O_3$ [M+H]+: 489, found 489. $^1$H NMR (300 MHz, DMSO-d$_6$) δ 11.09 (br s, 1H), 8.04 (s, 1H), 7.55-7.53 (m, 2H), 7.20-7.15 (m, 2H), 6.63 (d, J=7.2 Hz, 1H), 4.90-4.81 (m, 1H), 4.69-4.41 (m, 3H), 3.38-3.31 (m, 1H), 2.19-2.11 (m, 1H), 1.89-1.35 (m, 10H), 1.42 (s, 9H).

Examples 19-1 and 19-2

(1S,2S)-2-(3-(((S or R)-2-Isopropyl-1-methylisoindolin-5-yl)amino)-4-oxo-4,5-dihydro-1H-pyrazolo[4,3-c]pyridin-1-yl)cyclohexanecarbonitrile and (1S,2S)-2-(3-(((S or R)-2-Isopropyl-1-methylisoindolin-5-yl)amino)-4-oxo-4,5-dihydro-1H-pyrazolo[4,3-c]pyridin-1-yl)cyclohexanecarbonitrile

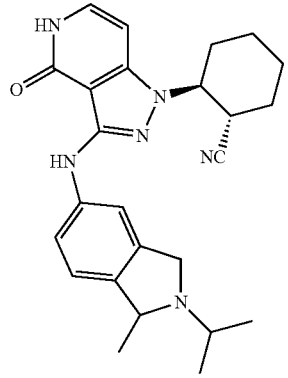

19-1

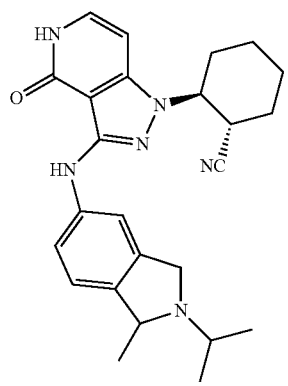

19-2

In a 50 mL 3-necked round bottom flask, (1S,2S)-2-(3-{[(1S and 1R)-1-methyl-2,3-dihydro-1H-isoindol-5-yl]amino}-4-oxo-4,5-dihydro-1H-pyrazolo[4,3-c]pyridin-1-yl)cyclohexanecarbonitrile (Example 12-3; 0.16 g, 0.41 mmol) was dissolved in methanol (10 mL) and propan-2-one (2.0 mL). The mixture was stirred for 40 min at ambient temperature. Sodium borohydride (0.31 g, 8.2 mmol) was added batchwise at 0° C. The mixture was stirred for an additional 16 h at ambient temperature. The reaction was quenched with water (10 mL) and extracted with dichloromethane (3×30 mL). The combined organic layers were dried over anhydrous sodium sulfate, filtered and concentrated in vacuo. The residue was purified on silica, eluting with 2-10% MeOH in DCM to afford (1S,2S)-2-(3-(2-isopropyl-1-methylisoindolin-5-ylamino)-4-oxo-4,5-dihydropyrazolo[4,3-c]pyridin-1-yl)cyclohexanecarbonitrile. The racemic product was separated by Chiral-Prep HPLC with the following conditions: column, Chiralpak IA, mobile phase, hexane (with 0.2% isopropanol) and isopropanol (hold 15%, hexane in 12 min); detector, UV 254/220 nm to afford (1S,2S)-2-(3-(((S or R)-2-isopropyl-1-methylisoindolin-5-yl)amino)-4-oxo-4,5-dihydro-1H-pyrazolo[4,3-c]pyridin-1-yl)cyclohexanecarbonitrile and (1S,2S)-2-(3-(((R or S)-2-isopropyl-1-methylisoindolin-5-yl)amino)-4-oxo-4,5-dihydro-1H-pyrazolo[4,3-c]pyridin-1-yl)cyclohexanecarbonitrile.

Peak A (19-1): Tr=9.72 mins. LRMS (ESI) calc'd for $C_{25}H_{31}N_6O$ [M+H]$^+$: 431, found 431; $^1$H NMR (400 MHz, CD$_3$OD) δ 7.69 (s, 1H), 7.57 (d, J=8.4 Hz, 1H), 7.24-7.19 (m, 2H), 6.71 (d, J=7.6 Hz, 1H), 4.61-4.54 (m, 2H), 4.36-4.18 (m, 2H), 3.48-3.33 (m, 2H), 2.34-2.31 (m, 1H), 2.14-1.82 (m, 5H), 1.67-1.45 (m, 5H), 1.30-1.28 (d, J=6.6 Hz, 3H), 1.21-1.19 (d, J=6.3 Hz, 3H).

Peak B (19-2): Tr=12.74 mins. LRMS (ESI) calc'd for $C_{25}H_{31}N_6O$ [M+H]$^+$: 431, found 431. $^1$H NMR (300 MHz, CD$_3$OD) δ 7.65 (s, 1H), 7.51 (d, J=8.1 Hz, 1H), 7.24-7.19 (m, 2H), 6.69 (d, J=7.2 Hz, 1H), 4.61-4.54 (m, 2H), 4.36-4.18 (m, 2H), 3.45-3.33 (m, 2H), 2.33-2.29 (m, 1H), 2.13-1.82 (m, 5H), 1.67-1.43 (m, 5H), 1.30-1.28 (d, J=6.6 Hz, 3H), 1.21-1.19 (d, J=6.3 Hz, 3H).

Example 20-1

(1S,2S)-2-(3-((4-((1R,3S,5S)-8-azabicyclo[3.2.1]octan-3-yl)phenyl)amino)-4-oxo-4,5-dihydro-1H-pyrazolo[4,3-c]pyridin-1-yl)cyclohexanecarbonitrile hydrochloride

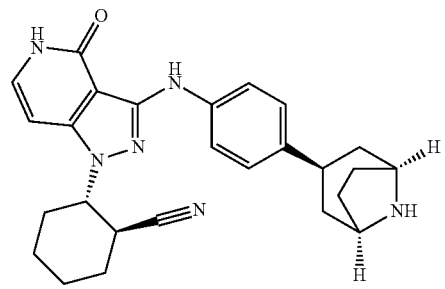 [SMILES: N#C[C@H]1CCCC[C@@H]1n1nc(Nc2ccc([C@H]3C[C@H]4CC[C@@H](C3)N4)cc2)c2c(=O)[nH]ccc21]

20-1

To a 25-mL 3-necked round-bottom flask, a solution of (1R,3S,5S)-tert-butyl 3-(4-((1-((1S,2S)-2-cyanocyclohexyl)-4-oxo-4,5-dihydro-1H-pyrazolo[4,3-c]pyridin-3-yl)amino)phenyl)-8-azabicyclo[3.2.1]octane-8-carboxylate (Example 3-166; 29 mg, 0.050 mmol) was dissolved in ethyl acetate (8 mL). Hydrogen chloride gas was bubbled into the solution to get a saturated solution then the mixture was stirred for 2 h at 0° C. The reaction was filtered and the solid washed with ether (50 mL) to afford (1S,2S)-2-(3-((4-((1R,3S,5S)-8-azabicyclo[3.2.1]octan-3-yl)phenyl)amino)-4-oxo-4,5-dihydro-1H-pyrazolo[4,3-c]pyridin-1-yl)cyclohexanecarbonitrile hydrochloride. LRMS (ESI) calc'd for $C_{26}H_{31}N_6O$ [M+H]$^+$: 443, found 443. $^1$H NMR (300 MHz, CD$_3$OD) δ 7.58 (d, J=8.7 Hz, 2H), 7.22-7.17 (m, 3H), 6.65 (d, J=7.5 Hz, 1H), 4.59-4.51 (m, 1H), 4.12-4.03 (m, 2H), 3.39-3.33 (m, 1H), 3.18-3.09 (m, 1H), 2.29-2.21 (m, 1H), 2.18-1.51 (m, 15H).

Table 48 discloses an Example that was prepared in analogy to Example 20-1, starting with Example 3-165.

TABLE 48

| Example | Structure | Compound Name | LRMS [M + H]$^+$ |
|---|---|---|---|
| 20-2 | 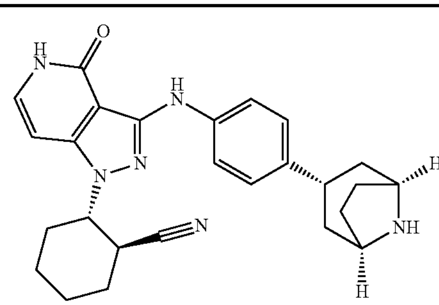 | (1S,2S)-2-(3-((4-((1R,3R,5S)-8-azabicyclo[3.2.1]octan-3-yl)phenyl)amino)-4-oxo-4,5-dihydro-1H-pyrazolo[4,3-c]pyridin-1-yl)cyclohexanecarbonitrile hydrochloride | Calc'd 443, found 443 |

Example 21-1

(1S,2S)-2-(3-((2,2-Dimethyl-1,1-dioxido-2,3-dihydrobenzo[b]thiophen-5-yl)amino)-4-oxo-4,5-dihydro-1H-pyrazolo[4,3-c]pyridin-1-yl)cyclohexanecarbonitrile

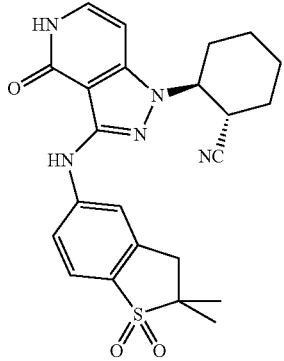

21-1

Step 1: (1S,2S)-2-(4-(Benzyloxy)-3-((2,2-dimethyl-1,1-dioxido-3-oxo-2,3-dihydrobenzo[b]thiophen-5-yl)amino)-1H-pyrazolo[4,3-c]pyridin-1-yl)cyclohexanecarbonitrile

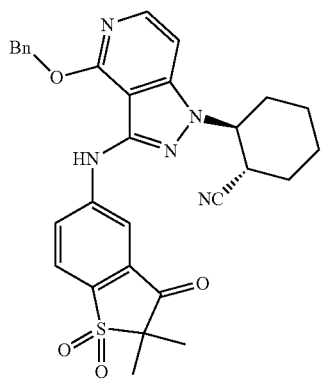

21-1a

To a 100 mL round bottom flask was added potassium acetate (56.5 mg, 0.576 mmol), 2-di-tert-butylphosphino-2'4'6-triisopropylbiphenyl (92 mg, 0.22 mmol), tris(dibenzyldeneacetone)dipalladium(0) chloroform adduct (75 mg, 0.072 mmol), 5-bromo-2,2-dimethylbenzo[b]thiophen-3(2H)-one 1,1-dioxide (I-162f; 0.10 g, 0.34 mmol), (1S,2S)-2-(3-amino-4-(benzyloxy)-1H-pyrazoles[4,3-c]pyridin-1-yl)cyclohexanecarbonitrile (I-1; 0.10 g, 0.29 mmol) and 2-propanol (30 mL). The mixture was stirred for 4 h at 80° C. under nitrogen atmosphere. The mixture was cooled and the solid filtered out. The filtrate was concentrated in vacuo and the residue purified on silica, eluting with ethyl acetate/petroleum (1:2) to afford (1S,2S)-2-(4-(benzyloxy)-3-((2,2-dimethyl-1,1-dioxido-3-oxo-2,3-dihydrobenzo[b]thiophen-5-yl)amino)-1H-pyrazolo[4,3-c]pyridin-1-yl)cyclohexanecarbonitrile. LRMS (ESI) calc'd for $C_{30}H_{30}N_5O_4S$ [M+H]$^+$: 556, found 556.

Step 2: (1S,2S)-2-(4-(Benzyloxy)-3-((3-hydroxy-2,2-dimethyl-1,1-dioxido-2,3-dihydrobenzo[b]thiophen-5-yl)amino)-1H-pyrazolo[4,3-c]pyridin-1-yl)cyclohexanecarbonitrile

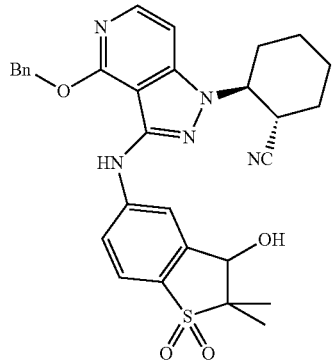

21-1b

To a 50 mL round bottom flask, sodium borohydride (22.5 mg, 0.594 mmol) was added to a solution of (1S,2S)-2-(4-(benzyloxy)-3-((2,2-dimethyl-1,1-dioxido-3-oxo-2,3-dihydrobenzo[b]thiophen-5-yl)amino)-1H-pyrazolo[4,3-c]pyridin-1-yl)cyclohexanecarbonitrile (0.11 g, 0.20 mmol) in methanol (20 mL). The mixture was stirred for 3 h at ambient temperature. The mixture was quenched by water (3 mL) and then extracted with ethyl acetate (3×10 mL). The combined organic layers were dried over anhydrous sodium sulfate and filtered. The filtrate was concentrated in vacuo and the residue purified on silica, eluting with ethyl acetate/petroleum (1:1) to afford (1S,2S)-2-(4-(benzyloxy)-3((3-hydroxy-2,2-dimethyl-1,1-dioxido-2,3-dihydrobenzo[b]thiophen-5-yl)amino)-1H-pyrazolo[4,3-c]pyridin-1-yl)cyclohexanecarbonitrile. LRMS (ESI) calc'd for $C_{30}H_{32}N_5O_4S$ [M+H]$^+$: 558, found 558.

Step 3: O-(5-((4-(Benzyloxy)-1-((1S,2S)-2-cyanocyclohexyl)-1H-pyrazolo[4,3-c]pyridin-3-yl)amino)-2,2-dimethyl-1,1-dioxido-2,3-dihydrobenzo[b]thiophen-3-yl)-1H-imidazole-1-carbothioate 21-1c To a 25 mL round bottom flask was placed a solution of (1S,2S)-2-(4-(benzyloxy)-3-((3-hydroxy-2,2-dimethyl-1,1-dioxido-2,3-dihydrobenzo[b]thiophen-5-yl)amino)-1H-pyrazolo[4,3-c]pyridin-1-yl)cyclohexanecarbonitrile (20 mg, 0.036 mmol) in dichloromethane (5 mL) followed by the addition of 4-dimethylaminopyridine (87 mg, 7.2 μmol) and di(1H-imidazol-1-yl)methanethione (9.6 mg, 0.054 mmol). The mixture was stirred for 30 min at ambient temperature. The mixture was concentrated in vacuo and the residue purified by prep-TLC, eluting with ethyl acetate/petroleum ether (1:1) to afford O-(5-((4-(benzyloxy)-1-((1S,2S)-2-cyanocyclohexyl)-1H-pyrazolo[4,3-c]pyridin-3-yl)amino)-2,2-dimethyl-1,1-dioxido-2,3-dihydrobenzo[b]thiophen-3-yl)-1H-imidazole-1-carbothioate. LRMS (ESI) calc'd for $C_{34}H_{34}N_7O_4S_2$ [M+H]$^+$: 668, found 668.

Step 4: (1S,2S)-2-(4-(Benzyloxy)-3-((2,2-dimethyl-1,1-dioxido-2,3-dihydrobenzo[b]thiophen-5-yl)amino)-1H-pyrazolo[4,3-c]pyridin-1-yl)cyclohexanecarbonitrile

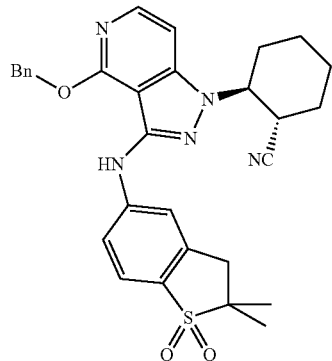

21-1d

To a 50 mL three-necked round bottom flask was placed a solution of 2,2'-azobis(2-methylpropionitrile) (26 mg, 0.16 mmol), O-(5-((4-(benzyloxy)-1-((1S,2S)-2-cyanocyclohexyl)-1H-pyrazolo[4,3-c]pyridin-3-yl)amino)-2,2-dimethyl-1,1-dioxido-2,3-dihydrobenzo[b]thiophen-3-yl)-1H-imidazole-1-carbothioate (0.10 g, 0.16 mmol) and tributylstannane (92 mg, 0.31 mmol) in toluene (20 mL) under nitrogen atmosphere. The solution was stirred for 1 h at 110° C. The mixture was concentrated in vacuo and the residue purified on silica, eluting with ethyl acetate to afford (1S,2S)-2-(4-(benzyloxy)-3-((2,2-dimethyl-1,1-dioxido-2,3-dihydrobenzo[b]thiophen-5-yl)amino)-1H-pyrazolo[4,3-c]pyridin-1-yl)cyclohexanecarbonitrile. LRMS (ESI) calc'd for $C_{30}H_{32}N_5O_3S$ [M+H]$^+$: 542, found 542.

Step 5: (1S,2S)-2-(3-((2,2-Dimethyl-1,1-dioxido-2,3-dihydroben(zo[b]thiophen-5-yl)amino)-4-oxo-4,5-dihydro-1H-pyrazolo[4,3-c]pyridin-1-yl)cyclohexanecarbonitrile To a 25 mL round bottom flask was added palladium on carbon (80 mg, 0.075 mmol, 10% wt), (1S,2S)-2-(4-(benzyloxy)-3-((2,2-dimethyl-1,1-dioxido-2,3-dihydrobenzo[b]thiophen-5-yl)amino)-1H-pyrazolo[4,3-c]pyridin-1-yl)cyclohexanecarbonitrile (75 mg, 0.14 mmol) and ethyl acetate (15 mL). The mixture was stirred for 16 h at ambient temperature under hydrogen atmosphere (1.5 atm). The solid was filtered and the filtrate concentrated in vacuo to afford (1S,2S)-2-(3-((2,2-dimethyl-1,1-dioxido-2,3-dihydroben(zo[b]thiophen-5-yl)amino)-4-oxo-4,5-dihydro-1H-pyrazolo[4,3-c]pyridin-1-yl)cyclohexanecarbonitrile. LRMS (ESI) calc'd for $C_{23}H_{26}N_5O_3S$ [M+H]$^+$: 452, found 452. $^1$H NMR (400 MHz, DMSO-d$_6$) δ11.18 (s, 1H), 8.64 (s, 1H), 7.75 (d, J=9.6 Hz, 2H), 7.63 (d, J=8.4 Hz, 2H), 7.28 (d, J=6.4 Hz, 1H), 6.73 (d, J=7.2 Hz, 1H), 4.76 (d, J=5.2 Hz, 1H), 3.38-3.33 (m, 1H), 3.15 (s, 2H), 2.36-2.21 (m, 1H), 1.94-1.78 (m, 3H), 1.38 (s, 6H), 0.65 (d, J=6.6 Hz, 3H).

Table 49 contains Examples that were prepared in an analogous fashion to that of Example 21-1 starting with the appropriate thiophene intermediate.

TABLE 49

| Example | Structure | Compound Name | LRMS [M + H]$^+$ |
|---|---|---|---|
| 21-2 | 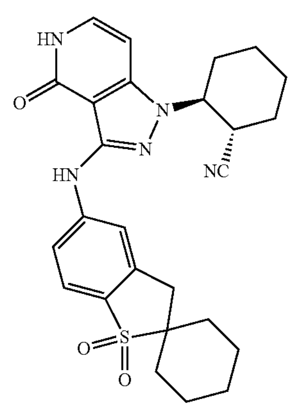 [SMILES: N#C[C@H]1CCCC[C@@H]1n1nc(Nc2ccc3c(c2)CC2(CCCCC2)S3(=O)=O)c2c(=O)[nH]ccc21] | (1S,2S)-2-(3-((1,1-Dioxido-3H-spiro[benzo[b]thiophene-2,1'-cyclohexan]-5-yl)amino)-4-oxo-4,5-dihydro-1H-pyrazolo[4,3-c]pyridin-1-yl)cyclohexanecarbonitrile | Calc'd 492, found 492 |

TABLE 49-continued

| Example | Structure | Compound Name | LRMS [M + H]+ |
|---|---|---|---|
| 21-3 | 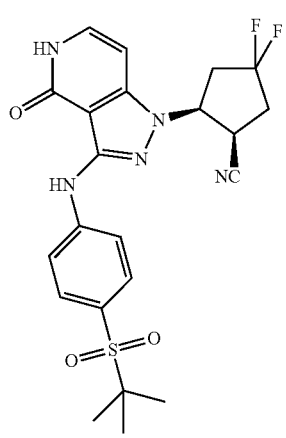 | (1S,2S)-2-{3-[(1,1-dioxido-2',3',5',6'-tetrahydro-3H-spiro[1-benzothiophene-2,4'-pyran]-5-yl)amino]-4-oxo-4,5-dihydro-1H-pyrazolo[4,3-c]pyridin-1-yl}cyclohexanecarbonitrile | Calc'd 494, found 494 |

Examples 22-1 and 22-2

(1R,2S or 1S,2R)-2-(3-((4-(tert-Butylsulfonyl)phenyl)amino)-4-oxo-4,5-dihydro-1H-pyrazolo[4,3-c]pyridin-1-yl)-4,4-difluorocyclopentanecarbonitrile and (1R,2S or 1S,2R)-2-(3-((4-(tert-Butylsulfonyl)phenyl)amino)-4-oxo-4,5-dihydro 1H-pyrazolo[4,3-c]pyridin-1-yl)-4,4-difluorocyclopentanecarbonitrile

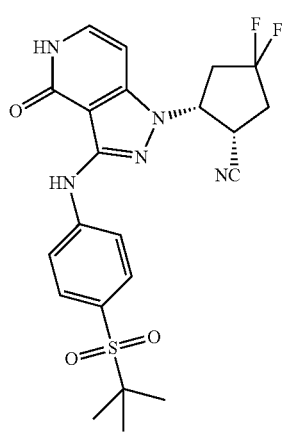

Step 1: (1S,2R and 1R,2S)-2-(3-Amino-4-(benzyloxy)-1H-pyrazolo[4,3-c]pyridin-1-yl)-4-hydroxycyclopentanecarbonitrile and (1S,2S and 1R,2R)-2-(3-Amino-4-(benzyloxy)-1H-pyrazolo[4,3-c]pyridin-1-yl)-4-hydroxycyclopentanecarbonitrile

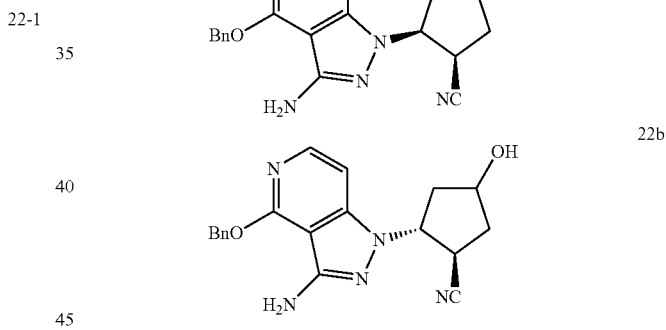

To a 25 mL round bottom flask, were placed 2,3,4,6,7,8,9,10-octahydropyrimido[1,2-a]azepine (1.90 g, 12.5 mmol), 4-hydroxycyclopent-1-enecarbonitrile (34.1 mg, 0.312 mmol), 4-(benzyloxy)-1H-pyrazolo[4,3-c]pyridin-3-amine (I-1; 1.50 g, 6.24 mmol) and acetonitrile (7 mL). The mixture was stirred for 6 h at 80° C. The mixture was cooled and water (20 mL) was added. The mixture was extracted with ethyl acetate (3×50 mL). The combined organic layers were washed with water (3×50 mL) and brine (3×50 mL), dried over anhydrous sodium sulfate and filtered. The filtrate was concentrated in vacuo and the residue purified on silica, eluting with petroleum ether/ethyl acetate (2:3) to afford (1S,2R and 1R,2S)-2-(3-amino-4-(benzyloxy)-1H-pyrazolo[4,3-c]pyridin-1-yl)-4-hydroxycyclopentanecarbonitrile (LRMS (ESI) calc'd for $C_{19}H_{20}N_5O_2$ [M+H]+: 350, found 350). and (1S,2S and 1R,2R)-2-(3-amino-4-(benzyloxy)-1H-pyrazolo[4,3-c]pyridin-1-yl)-4-hydroxycyclopentanecarbonitrile (LRMS (ESI) calc'd for $C_{19}H_{20}N_5O_2$ [M+H]+: 350, found 350). each as a racemic mixture of both R and S hydroxy diastereomers.

Step 2: (1S,2R and 1R,2S)-2-(4-(Benzyloxy)-3-((4-(tert-butylsulfonyl)phenyl)amino)-1H-pyrazolo[4,3-c]pyridin-1-yl)-4-hydroxycyclopentanecarbonitrile

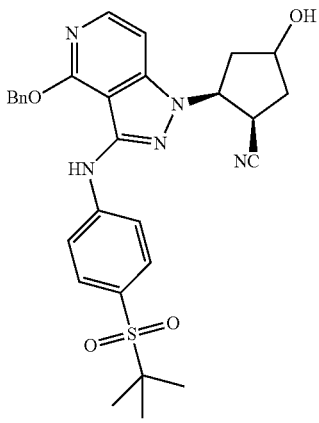

22c

To a 50 mL round flask, were placed potassium acetate (0.20 g, 2.0 mmol), di-tert-butyl(2',4',6'-triisopropyl-[1,1'-biphenyl]-2-yl)phosphine (85 mg, 0.20 mmol), tris(dibenzylideneacetone)dipalladium(0) chloroform adduct (0.10 g, 0.10 mmol), (1S,2R and 1R,2S)-2-(3-amino-4-(benzyloxy)-1H-pyrazolo[4,3-c]pyridin-1-yl)-4-hydroxycyclopentanecarbonitrile (0.35 g, 1.0 mmol), 1-bromo-4-(tert-butylsulfonyl)benzene (0.33 g, 1.2 mmol), isopropanol (40 mL) and N,N-dimethylformamide (1.5 mL). The mixture was degassed with nitrogen (×3) then stirred for 6 h at 80° C. The mixture was cooled, water (20 mL) was added, and extracted with ethyl acetate (2×20 mL). The combined organic layers were washed with brine (2×20 mL), dried over anhydrous sodium sulfate and filtered. The filtrate was concentrated in vacuo and the residue purified on silica, eluting with 10-50% EtOAc in petroleum ether to afford (1S,2R and 1R,2S)-2-(4-(benzyloxy)-3-((4-(tert-butylsulfonyl)phenyl)amino)-1H-pyrazolo[4,3-c]pyridin-1-yl)-4-hydroxycyclopentanecarbonitrile as a racemic mixture of both R and S hydroxy diastereomers. LRMS (ESI) calc'd for $C_{29}H_{32}N_5O_4S$ [M+H]$^+$: 546, found 546.

Step 3: (1S,2R and 1R,2S)-2-(4-(Benzyloxy)-3-(4-(tert-butylsulfonyl)phenylamino)-1H-pyrazolo[4,3-c]pyridin-1-yl)-4-oxocyclopentanecarbonitrile

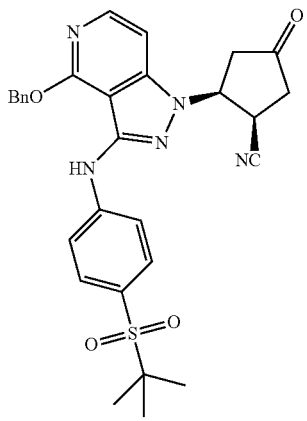

22d

To a 100 mL round bottom flask, were placed (1S,2R and 1R,2S)-2-(4-(benzyloxy)-3-((4-(tert-butylsulfonyl)phenyl)amino)-1H-pyrazolo[4,3-c]pyridin-1-yl)-4-hydroxycyclopentanecarbonitrile (0.46 g, 0.42 mmol) and Jones reagent (1.8 M in diluted sulfuric acid, 3.0 mL, 1.7 mmol) in acetone (50 mL). The mixture was stirred for 10 min at 0° C. The mixture was cooled and isopropanol (10 mL) was added. The mixture was stirred for 30 min at 0° C. and extracted with ethyl acetate (2×100 mL). The combined organic layers were washed with brine (2×200 mL), dried over anhydrous sodium sulfate and filtered. The filtrate was concentrated in vacuo and the residue purified on silica, eluting with petroleum ether/ethyl acetate (1.5:1) to afford the title compound. LRMS (ESI) calc'd for $C_{29}H_{30}N_5O_4S$ [M+H]$^+$: 544, found 544.

Step 4: (1S,2R and 1R,2S)-2-(4-(Benzyloxy)-3-((4-(tert-butylsulfonyl)phenyl)amino)-1H-pyrazolo[4,3-c]pyridin-1-yl)-4,4-difluorocyclopentanecarbonitrile

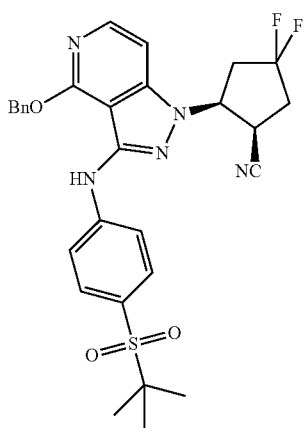

22e

To a 100 mL round bottom flask, were placed (1S,2R and 1R,2S)-2-(4-(benzyloxy)-3-((4-(tert-butylsulfonyl)phenyl)amino)-1H-pyrazolo[4,3-c]pyridin-1-yl)-4-oxocyclopentanecarbonitrile (0.24 g, 0.44 mmol) and DCM (15 mL). The mixture was degassed with nitrogen (×3) and bis(2-methoxyethyl)aminosulfur trifluoride (0.98 g, 4.4 mmol) was added dropwise at 0° C. The mixture was stirred for 4 h at 0° C. Water (20 mL) was added and the resulting solution extracted with ethyl acetate (2×50 mL). The combined organic layers were washed with brine (2×50 mL), dried over anhydrous sodium sulfate and filtered. The filtrate was concentrated in vacuo and the residue purified on silica, eluting with petroleum ether/ethyl acetate (3:1) to afford (1S,2R and 1R,2S)-2-(4-(benzyloxy)-3-((4-(tert-butylsulfonyl)phenyl)amino)-1H-pyrazolo[4,3-c]pyridin-1-yl)-4,4-difluorocyclopentanecarbonitrile. LRMS (ESI) calc'd for $C_{29}H_{30}F_2N_5O_3S$ [M+H]$^+$: 566, found 566.

Step 5: (1S,2R or 1R,2S)-2-(3-(4-(tert-Butylsulfonyl)phenylamino)-4-oxo-4,5-dihydropyrazolo[4,3-c]pyridin-1-yl)-4,4-difluorocyclopentanecarbonitrile and (1S,2R or 1R,2S)-2-(3-(4-(tert-Butylsulfonyl)phenylamino)-4-oxo-4,5-dihydropyrazolo[4,3-c]pyridin-1-yl)-4,4-difluorocyclopentanecarbonitrile To a 50 mL round bottom flask, were placed (1S,2R and 1R,2S)-2-(4-(benzyloxy)-3-((4-(tert-butylsulfonyl)phenyl)

amino)-1H-pyrazolo[4,3-c]pyridin-1-yl)-4,4-difluorocyclopentanecarbonitrile (0.16 g, 0.33 mmol), dichloromethane (5 mL) and 2,2,2-trifluoroacetic acid (1 mL). The mixture was stirred for 6 h at ambient temperature and then concentrated in vacuo and the residue purified by mass triggered reverse phase HPLC (XBridge RP18; 30-60% acetonitrile/water containing 0.05% ammonium bicarbonate) to afford (1S,2R and 1R,2S)-2-(3-(4-(tert-butylsulfonyl)phenylamino)-4-oxo-4,5-dihydropyrazolo[4,3-c]pyridin-1-yl)-4,4-difluoro-cyclopentanecarbonitrile. The racemic product was separated by Chiral-Prep HPLC with the following conditions: column, Chiralpak IB; mobile phase, hexane (0.1% DEA) in ethanol (0.1% DEA) (2:1 for 17 min); detector, UV 220/254 nm.

Peak A (22-1): (1R,2S or 1S,2R)-2-(3-((4-(tert-Butylsulfonyl)phenyl)amino)-4-oxo-4,5-dihydro-1H-pyrazolo[4,3-c]pyridin-1-yl)-4,4-difluorocyclopentanecarbonitrile. Tr=15 min. LRMS (ESI) calc'd for $C_{22}H_{24}F_2N_5O_3S$ [M+H]$^+$: 476, found 476; $^1$H NMR (300 MHz, DMSO-d$_6$) δ 11.26 (br s, 1H), 8.79 (br s, 1H), 7.91 (d, J=5.7 Hz, 2H), 7.66 (d, J=9.0 Hz, 2H), 7.34-7.30 (m, 1H), 6.64 (d, J=7.5 Hz, 1H), 5.60-5.54 (m, 1H), 3.95-3.89 (m, 1H), 3.01-2.73 (m, 4H), 1.24 (s, 9H).

Peak B (22-2): (1S,2R or 1R,2S)-2-(3-((4-(tert-Butylsulfonyl)phenyl)amino)-4-oxo-4,5-dihydro-1H-pyrazolo[4,3-c]pyridin-1-yl)-4,4-difluorocyclopentanecarbonitrile. Tr=18 min. LRMS (ESI) calc'd for $C_{22}H_{24}F_2N_5O_3S$ [M+H]$^+$: 476, found 476; $^1$H NMR (300 MHz, DMSO-d$_6$) δ 11.27 (br s, 1H), 8.79 (br s, 1H), 7.91 (d, J=5.7 Hz, 2H), 7.66 (d, J=9.0 Hz, 2H), 7.34-7.30 (m, 1H), 6.64 (d, J=7.5 Hz, 1H), 5.58-5.54 (m, 1H), 3.97-3.89 (m, 1H), 3.02-2.73 (m, 4H), 1.24 (s, 9H).

Table 50 contains Examples that were prepared in an analogous fashion to that of Examples 22-1 and 22-2 starting with the appropriate diastereomer of 2-(3-Amino-4-(benzyloxy)-1H-pyrazolo[4,3-c]pyridin-1-yl)-4-hydroxycyclopentanecarbonitrile and aryl bromide.

TABLE 50

| Example | Structure | Compound Name | LRMS [M + H]$^+$ |
|---|---|---|---|
| 22-3 | 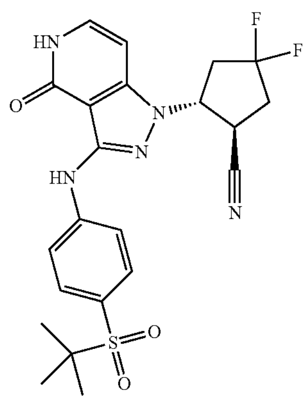 [SMILES: CC(C)(C)S(=O)(=O)c1ccc(Nc2nn([C@@H]3CC(F)(F)C[C@H]3C#N)c3cc[nH]c(=O)c23)cc1] | (1R,2R or 1S,2S)-2-(3-{[4-(tert-butylsulfonyl)phenyl]amino}-4-oxo-4,5-dihydro-1H-pyrazolo[4,3-c]pyridin-1-yl)-4,4-difluorocyclopentanecarbonitrile (Derived from Peak A by HPLC using IB, 40% EtOH (with 0.1% DEA) in Hexanes (with 0.1% DEA), Tr = 11 mins) | Calc'd 476, found 476 |
| 22-4 | 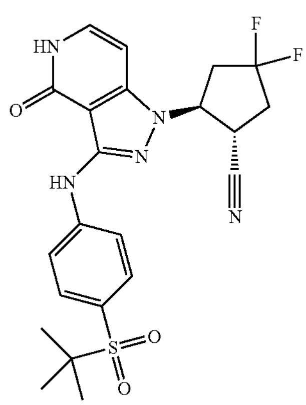 [SMILES: CC(C)(C)S(=O)(=O)c1ccc(Nc2nn([C@H]3CC(F)(F)C[C@@H]3C#N)c3cc[nH]c(=O)c23)cc1] | (1S,2S or 1R,2R)-2-(3-{[4-(tert-butylsulfonyl)phenyl]amino}-4-oxo-4,5-dihydro-1H-pyrazolo[4,3-c]pyridin-1-yl)-4,4-difluorocyclopentanecarbonitrile (Derived from Peak B by HPLC using IB, 40% EtOH (with 0.1% DEA) in Hexanes (with 0.1% DEA), Tr = 16 mins) | Calc'd 476, found 476 |

TABLE 50-continued

| Example | Structure | Compound Name | LRMS [M + H]+ |
|---|---|---|---|
| 22-5 | 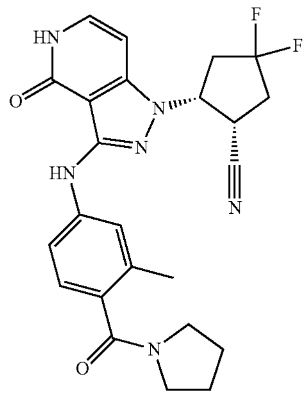 [SMILES: Cc1cc(Nc2nn([C@@H]3CC(F)(F)C[C@@H]3C#N)c3cc[nH]c(=O)c23)ccc1C(=O)N1CCCC1] | (1S,2R or 1R,2S)-4,4-difluoro-2-(3-{[3-methyl-4-(pyrrolidin-1-ylcarbonyl)phenyl]amino}-4-oxo-4,5-dihydro-1H-pyrazolo[4,3-c]pyridin-1-yl)cyclopentanecarbonitrile (Derived from Peak B by HPLC using IC, 35% EtOH in Hexanes (0.1% TEA), Tr = 7.21 mins) | Calc'd 467, found 467 |
| 22-6 | 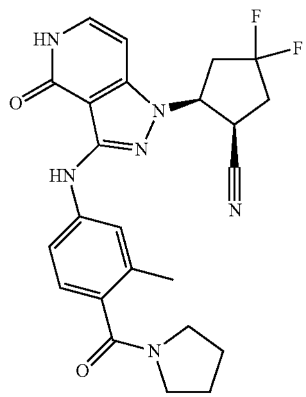 [SMILES: Cc1cc(Nc2nn([C@H]3CC(F)(F)C[C@H]3C#N)c3cc[nH]c(=O)c23)ccc1C(=O)N1CCCC1] | (1R,2S or 1S,2R)-4,4-difluoro-2-(3-{[3-methyl-4-(pyrrolidin-1-ylcarbonyl)phenyl]amino}-4-oxo-4,5-dihydro-1H-pyrazolo[4,3-c]pyridin-1-yl)cyclopentanecarbonitrile (Derived from Peak A by HPLC using IC, 35% EtOH in Hexanes (0.1% TEA), Tr = 4.28 mins) | Calc'd 467, found 467 |
| 22-7 | 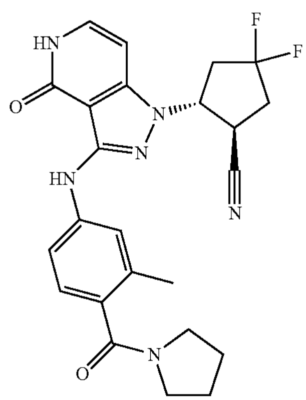 [SMILES: Cc1cc(Nc2nn([C@@H]3CC(F)(F)C[C@H]3C#N)c3cc[nH]c(=O)c23)ccc1C(=O)N1CCCC1] | (1R,2R or 1S,2S)-4,4-difluoro-2-(3-{[3-methyl-4-(pyrrolidin-1-ylcarbonyl)phenyl]amino}-4-oxo-4,5-dihydro-1H-pyrazolo[4,3-c]pyridin-1-yl)cyclopentanecarbonitrile (Derived from Peak A by HPLC using IA, 15% EtOH in Hexanes (0.1% DEA), Tr = 7.76 mins) | Calc'd 467, found 467 |
| 22-8 | 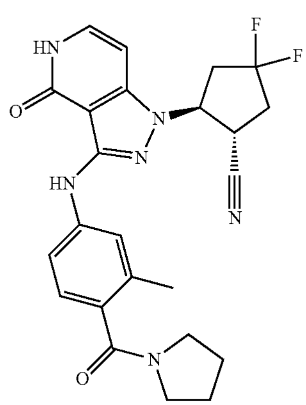 [SMILES: Cc1cc(Nc2nn([C@H]3CC(F)(F)C[C@@H]3C#N)c3cc[nH]c(=O)c23)ccc1C(=O)N1CCCC1] | (1S,2S or 1R,2R)-4,4-difluoro-2-(3-{[3-methyl-4-(pyrrolidin-1-ylcarbonyl)phenyl]amino}-4-oxo-4,5-dihydro-1H-pyrazolo[4,3-c]pyridin-1-yl)cyclopentanecarbonitrile (Derived from Peak B by HPLC using IA, 15% EtOH in Hexanes (0.1% DEA), Tr = 9.98 mins) | Calc'd 467, found 467 |

Biological Assays

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDEPEGDYFEWLW-NH$_2$ (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 µL of 1.11× enzyme and 1.11× substrate in 1× assay buffer (Invitrogen kinase buffer #PV3189, 2 mM DTT, 0.05% BSA) were added to the wells and shaken and then preincubated for 30 minutes at room temperature to allow compound binding to equilibrate. After equilibration, 2 µL of 10×ATP in 1× assay buffer was added to initiate the kinase reaction and the plates were shaken and then incubated at room temperature for 120 minutes. At the end of the incubation, 20 µL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 µs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate IC$_{50}$ values.

Final Reaction Conditions were:

| Enzyme | [E] (nM) | [S] (µM) | [ATP] (µM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK1 and JAK2 in vitro binding assays. The following table tabulates the biological data disclosed for the instant invention as JAK1 IC$_{50}$ and JAK2 IC$_{50}$ values.

| Example | JAK1 IC$_{50}$ | JAK2 IC$_{50}$ |
|---|---|---|
| 1-1 | 2.5 | 36 |
| 2-1 | 0.56 | 7.5 |
| 3-1 | 18 | 97 |
| 3-2 | 0.40 | 5.4 |
| 3-3 | 6.1 | 21 |
| 3-4 | 9.4 | 16 |
| 3-5 | 0.12 | 0.83 |
| 3-6 | 0.11 | 0.33 |
| 3-7 | 0.11 | 0.85 |
| 3-8 | 0.13 | 0.82 |
| 3-9 | 0.081 | 0.54 |
| 3-10 | 0.12 | 0.43 |
| 3-11 | 0.41 | 3.3 |
| 3-12 | 0.31 | 2.3 |
| 3-13 | 14 | 25 |
| 3-14 | 38 | 68 |
| 3-15 | 14 | 30 |
| 3-16 | 1.4 | 3.3 |
| 3-17 | 0.91 | 5.8 |
| 3-18 | 0.12 | 0.37 |
| 3-19 | 0.21 | 1.2 |
| 3-20 | 0.13 | 0.60 |
| 3-21 | 0.17 | 0.79 |
| 3-22 | 0.40 | 1.2 |
| 3-23 | 0.31 | 0.48 |
| 3-24 | 0.15 | 0.47 |
| 3-25 | 0.45 | 3.2 |
| 3-26 | 0.10 | 0.49 |
| 3-27 | 0.13 | 0.20 |
| 3-28 | 1.0 | 0.93 |
| 3-29 | 0.32 | 1.5 |
| 3-30 | 0.29 | 2.0 |
| 3-31 | 0.46 | 1.7 |
| 3-32 | 0.45 | 1.5 |
| 3-33 | 1.3 | 1.7 |
| 3-34 | 1.1 | 1.1 |
| 3-35 | 3.2 | 4.7 |
| 3-36 | 2.3 | 3.8 |
| 3-37 | 0.18 | 2.1 |
| 3-38 | 5.0 | 16 |
| 3-39 | 0.64 | 1.8 |
| 3-40 | 0.10 | 0.79 |
| 3-41 | 1.6 | 29 |
| 3-42 | 0.46 | 13 |
| 3-43 | 1.4 | 1.7 |
| 3-44 | 1.4 | 4.8 |
| 3-45 | 0.37 | 0.42 |
| 3-46 | 0.095 | 0.34 |
| 3-47 | 0.78 | 2.2 |
| 3-48 | 18 | 18 |
| 3-49 | 0.026 | 0.29 |
| 3-50 | 0.50 | 1.3 |
| 3-51 | 0.25 | 1.2 |
| 3-52 | 0.16 | 0.41 |
| 3-53 | 0.039 | 0.19 |
| 3-54 | 0.051 | 0.62 |
| 3-55 | 0.52 | 1.5 |
| 3-56 | 0.31 | 0.54 |
| 3-57 | 0.20 | 0.53 |
| 3-58 | 0.050 | 0.58 |
| 3-59 | 0.062 | 0.71 |
| 3-60 | 0.044 | 0.41 |
| 3-61 | 0.55 | 1.1 |
| 3-62 | 0.083 | 0.41 |
| 3-63 | 0.066 | 0.54 |
| 3-64 | 0.39 | 1.6 |
| 3-65 | 0.12 | 0.65 |
| 3-66 | 0.20 | 0.32 |
| 3-67 | 0.34 | 0.43 |
| 3-68 | 0.47 | 0.28 |
| 3-69 | 2.1 | 5.7 |
| 3-70 | 0.14 | 0.61 |
| 3-71 | 0.27 | 0.54 |
| 3-72 | 0.45 | 0.50 |
| 3-73 | 0.26 | 0.45 |
| 3-74 | 0.14 | 0.29 |
| 3-75 | 0.28 | 0.68 |
| 3-76 | 0.41 | 2.1 |
| 3-77 | 0.52 | 2.3 |
| 3-78 | 2.0 | 4.4 |
| 3-79 | 0.071 | 0.48 |
| 3-80 | 0.079 | 0.92 |
| 3-81 | 0.055 | 0.23 |
| 3-82 | 0.11 | 0.85 |
| 3-83 | 0.066 | 0.55 |
| 3-84 | 0.52 | 2.6 |

| Example | JAK1 IC$_{50}$ | JAK2 IC$_{50}$ | | Example | JAK1 IC$_{50}$ | JAK2 IC$_{50}$ |
|---|---|---|---|---|---|---|
| 3-85 | 3.0 | 4.2 | | 3-162 | 0.33 | 0.92 |
| 3-86 | 2.8 | 7.6 | | 3-163 | 0.49 | 3.0 |
| 3-87 | 0.25 | 0.95 | | 3-164 | 0.33 | 2.5 |
| 3-88 | 0.48 | 4.1 | | 3-165 | 2.6 | 7.9 |
| 3-89 | 9.8 | 117 | | 3-166 | 0.96 | 6.5 |
| 3-90 | 0.28 | 7.3 | | 3-167 | 6.9 | 8.6 |
| 3-91 | 0.45 | 10.3 | | 3-168 | 0.17 | 0.34 |
| 3-92 | 0.64 | 5.7 | | 3-169 | 1.2 | 0.95 |
| 3-93 | 12 | 48 | | 3-170 | 2.4 | 1.7 |
| 3-94 | 0.12 | 0.69 | | 3-171 | 1.16 | 5.5 |
| 3-95 | 4.7 | 16 | | 3-172 | 0.39 | 1.0 |
| 3-96 | 0.11 | 0.30 | | 3-173 | 0.094 | 0.49 |
| 3-97 | 0.082 | 0.44 | | 3-174 | 0.44 | 0.49 |
| 3-98 | 0.075 | 0.53 | | 3-175 | 0.10 | 0.26 |
| 3-99 | 0.090 | 0.51 | | 3-176 | 1.9 | 8.6 |
| 3-100 | 0.043 | 0.28 | | 3-177 | 0.046 | 0.31 |
| 3-101 | 0.056 | 0.50 | | 3-178 | 0.84 | 3.0 |
| 3-102 | 0.051 | 0.66 | | 3-179 | 0.46 | 2.2 |
| 3-103 | 0.28 | 0.70 | | 4-1 | 5.3 | 122 |
| 3-104 | 0.22 | 0.59 | | 4-2 | 84 | >1500 |
| 3-105 | 0.11 | 0.40 | | 4-3 | 0.30 | 13 |
| 3-106 | 0.12 | 0.36 | | 4-4 | 7.8 | 525 |
| 3-107 | 0.22 | 0.48 | | 5-1 | 1.5 | 19 |
| 3-108 | 0.40 | 0.50 | | 5-2 | 0.60 | 14 |
| 3-109 | 0.22 | 0.47 | | 5-3 | 1.7 | 40 |
| 3-110 | 0.42 | 1.1 | | 5-4 | 1.7 | 31 |
| 3-111 | 0.23 | 0.88 | | 5-5 | 7.1 | 113 |
| 3-112 | 0.25 | 1.2 | | 5-6 | 1.3 | 55 |
| 3-113 | 0.15 | 0.31 | | 5-7 | 1.4 | 60 |
| 3-114 | 0.19 | 0.28 | | 5-8 | 0.88 | 22 |
| 3-115 | 0.22 | 0.33 | | 5-9 | 25 | 660 |
| 3-116 | 0.18 | 0.20 | | 5-10 | 37 | 940 |
| 3-117 | 1.7 | 6.0 | | 5-11 | 3.0 | 106 |
| 3-118 | 0.50 | 0.88 | | 5-12 | 1.2 | 70 |
| 3-119 | 5.3 | 18.6 | | 5-13 | 97 | >1500 |
| 3-120 | 1.0 | 2.7 | | 5-14 | 9.4 | 580 |
| 3-121 | 0.12 | 0.24 | | 5-15 | 0.28 | 11 |
| 3-122 | 0.24 | 1.0 | | 5-16 | 0.34 | 11 |
| 3-123 | 0.18 | 0.29 | | 5-17 | 0.83 | 33 |
| 3-124 | 0.23 | 0.88 | | 5-18 | 0.54 | 13 |
| 3-125 | 0.32 | 0.86 | | 5-19 | 0.11 | 2.5 |
| 3-126 | 0.077 | 2.5 | | 5-20 | 0.14 | 3.0 |
| 3-127 | 0.33 | 2.6 | | 5-21 | 0.35 | 6.5 |
| 3-128 | 0.095 | 1.9 | | 5-22 | 0.24 | 4.0 |
| 3-129 | 1.1 | 2.6 | | 5-23 | 0.88 | 31 |
| 3-130 | 0.32 | 0.37 | | 5-24 | 0.88 | 31 |
| 3-131 | 0.32 | 3.3 | | 5-25 | 0.96 | 22 |
| 3-132 | 0.35 | 3.2 | | 5-26 | 0.33 | 7 |
| 3-133 | 0.32 | 3.6 | | 5-27 | 3.7 | 233 |
| 3-134 | 0.16 | 0.53 | | 5-28 | 0.50 | 37 |
| 3-135 | 0.22 | 1.2 | | 6-1 | 1.5 | 5.2 |
| 3-136 | 0.28 | 0.70 | | 6-2 | 0.75 | 2.3 |
| 3-137 | 0.22 | 0.59 | | 6-3 | 1.4 | 2.3 |
| 3-138 | 0.17 | 0.66 | | 6-4 | 1.0 | 2.9 |
| 3-139 | 0.093 | 0.35 | | 6-5 | 0.46 | 0.82 |
| 3-140 | 0.17 | 0.43 | | 7-1 | 0.61 | 1.5 |
| 3-141 | 0.15 | 0.69 | | 7-2 | 0.26 | 2.2 |
| 3-142 | 0.29 | 0.68 | | 7-3 | 0.12 | 0.37 |
| 3-143 | 0.12 | 0.44 | | 7-4 | 0.11 | 0.41 |
| 3-144 | 0.099 | 0.59 | | 8-1 | 0.78 | 1.6 |
| 3-145 | 0.12 | 1.8 | | 9-1 | 0.19 | 0.47 |
| 3-146 | 0.29 | 6.4 | | 9-2 | 0.22 | 0.51 |
| 3-147 | 0.17 | 0.50 | | 9-3 | 0.16 | 0.39 |
| 3-148 | 0.31 | 0.43 | | 9-4 | 0.11 | 0.25 |
| 3-149 | 0.48 | 0.61 | | 10-1 | 0.14 | 0.61 |
| 3-150 | 0.066 | 0.55 | | 11-1 | 2.5 | 4.0 |
| 3-151 | 0.041 | 0.52 | | 12-1 | 0.31 | 0.86 |
| 3-152 | 0.10 | 0.77 | | 12-2 | 0.36 | 0.32 |
| 3-153 | 0.057 | 0.36 | | 12-3 | 0.81 | 1.4 |
| 3-154 | 0.056 | 0.45 | | 12-4 | 0.58 | 1.8 |
| 3-155 | 0.12 | 0.71 | | 12-5 | 0.61 | 0.88 |
| 3-156 | 0.82 | 2.6 | | 13-1 | 0.47 | 3.4 |
| 3-157 | 0.45 | 0.88 | | 14-1 | 1.1 | 4.4 |
| 3-158 | 0.98 | 1.5 | | 14-2 | 0.80 | 2.2 |
| 3-159 | 0.059 | 0.44 | | 14-3 | 3.7 | 4.8 |
| 3-160 | 0.049 | 0.19 | | 15-1 | 0.13 | 1.9 |
| 3-161 | 0.067 | 0.15 | | 15-2 | 0.26 | 3.6 |

| Example | JAK1 IC$_{50}$ | JAK2 IC$_{50}$ |
| --- | --- | --- |
| 15-3 | 0.51 | 3.6 |
| 15-4 | 0.18 | 1.6 |
| 15-5 | 0.32 | 3.2 |
| 15-6 | 0.55 | 3.6 |
| 15-7 | 0.11 | 1.4 |
| 15-8 | 0.14 | 0.27 |
| 15-9 | 0.32 | 1.1 |
| 15-10 | 0.092 | 1.6 |
| 15-11 | 0.13 | 0.84 |
| 15-12 | 0.14 | 0.84 |
| 15-13 | 0.22 | 0.72 |
| 15-14 | 0.065 | 1.1 |
| 15-15 | 1.7 | 5.9 |
| 15-16 | 0.26 | 3.8 |
| 15-17 | 0.17 | 2.9 |
| 15-18 | 0.17 | 2.3 |
| 15-19 | 1.0 | 8.1 |
| 15-20 | 0.069 | 0.48 |
| 15-21 | 0.39 | 0.51 |
| 15-22 | 0.48 | 0.57 |
| 15-23 | 0.079 | 0.25 |
| 15-24 | 0.069 | 0.27 |
| 15-25 | 0.48 | 0.98 |
| 15-26 | 0.23 | 0.92 |
| 15-27 | 0.22 | 0.72 |
| 15-28 | 0.25 | 0.63 |
| 15-29 | 0.14 | 0.24 |
| 15-30 | 0.36 | 0.42 |
| 15-31 | 0.25 | 0.27 |
| 15-32 | 0.26 | 0.15 |
| 15-33 | 0.17 | 0.17 |
| 15-34 | 0.082 | 0.62 |
| 15-35 | 1.2 | 1.3 |
| 15-36 | 0.46 | 0.59 |
| 15-37 | 0.066 | 0.25 |
| 15-38 | 0.060 | 0.15 |
| 15-39 | 0.34 | 2.1 |
| 15-40 | 0.77 | 1.5 |
| 15-41 | 0.21 | 0.72 |
| 15-42 | 0.15 | 0.53 |
| 15-43 | 0.22 | 1.2 |
| 15-44 | 0.057 | 0.25 |
| 15-45 | 0.43 | 0.41 |
| 15-46 | 0.076 | 0.46 |
| 15-47 | 19 | 14 |
| 15-48 | 19 | 18 |
| 15-49 | 5.1 | 21 |
| 15-50 | 6.6 | 14 |
| 15-51 | 0.23 | 0.37 |
| 15-52 | 0.053 | 0.30 |
| 15-53 | 0.42 | 1.1 |
| 15-54 | 0.081 | 0.40 |
| 15-55 | 0.76 | 2.3 |
| 15-56 | 0.81 | 6.0 |
| 15-57 | 0.62 | 1.2 |
| 15-58 | 1.8 | 3.1 |
| 15-59 | 0.078 | 0.41 |
| 15-60 | 0.11 | 0.51 |
| 15-61 | 0.14 | 0.21 |
| 15-62 | 0.11 | 0.34 |
| 15-63 | 0.062 | 0.14 |
| 15-64 | 0.069 | 0.17 |
| 15-65 | 1.1 | 0.41 |
| 15-66 | 0.11 | 0.27 |
| 15-67 | 0.38 | 3.9 |
| 15-68 | 0.26 | 1.2 |
| 15-69 | 0.30 | 0.34 |
| 15-70 | 0.34 | 0.40 |
| 15-71 | 0.069 | 0.085 |
| 15-72 | 0.077 | 0.090 |
| 15-73 | 0.28 | 0.55 |
| 15-74 | 0.10 | 0.12 |
| 15-75 | 0.12 | 0.13 |
| 16-1 | 0.16 | 3.4 |
| 16-2 | 0.069 | 0.47 |
| 16-3 | 0.059 | 0.14 |
| 17-1 | 0.095 | 0.38 |
| 17-2 | 0.53 | 2.7 |
| 18-1 | 1.3 | 5.4 |
| 19-1 | 0.91 | 0.89 |
| 19-2 | 0.47 | 0.45 |
| 20-1 | 0.38 | 0.57 |
| 20-2 | 0.39 | 0.39 |
| 21-1 | 0.056 | 0.28 |
| 21-2 | 0.12 | 0.38 |
| 21-3 | 0.069 | 0.18 |
| 22-1 | 1.7 | 3.5 |
| 22-2 | 16 | 21 |
| 22-3 | 14 | 17 |
| 22-4 | 0.11 | 0.35 |
| 22-5 | 3.4 | 3.3 |
| 22-6 | 114 | 33 |
| 22-7 | 0.28 | 0.51 |
| 22-8 | 19 | 17 |

The invention claimed is:

1. A compound of formula I or a pharmaceutically acceptable salt, or a stereoisimer thereof:

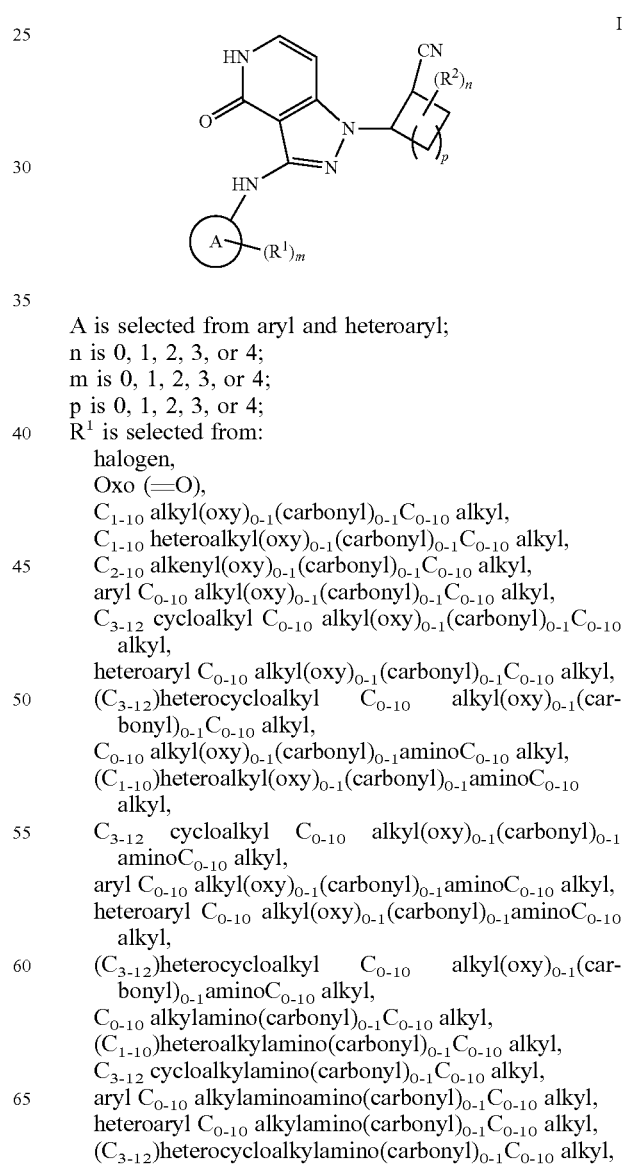

A is selected from aryl and heteroaryl;
n is 0, 1, 2, 3, or 4;
m is 0, 1, 2, 3, or 4;
p is 0, 1, 2, 3, or 4;
R$^1$ is selected from:
halogen,
Oxo (=O),
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
C$_{2-10}$ alkenyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
C$_{3-12}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-12}$)heterocycloalkyl C$_{0-10}$ alkyl(oxy)$_{0-1}$(carbonyl)$_{0-1}$C$_{0-10}$ alkyl,
C$_{0-10}$ alkyl(oxy)$_{0-1}$(carbonyl)$_{0-1}$aminoC$_{0-10}$ alkyl,
(C$_{1-10}$)heteroalkyl(oxy)$_{0-1}$(carbonyl)$_{0-1}$aminoC$_{0-10}$ alkyl,
C$_{3-12}$ cycloalkyl C$_{0-10}$ alkyl(oxy)$_{0-1}$(carbonyl)$_{0-1}$aminoC$_{0-10}$ alkyl,
aryl C$_{0-10}$ alkyl(oxy)$_{0-1}$(carbonyl)$_{0-1}$aminoC$_{0-10}$ alkyl,
heteroaryl C$_{0-10}$ alkyl(oxy)$_{0-1}$(carbonyl)$_{0-1}$aminoC$_{0-10}$ alkyl,
(C$_{3-12}$)heterocycloalkyl C$_{0-10}$ alkyl(oxy)$_{0-1}$(carbonyl)$_{0-1}$aminoC$_{0-10}$ alkyl,
C$_{0-10}$ alkylamino(carbonyl)$_{0-1}$C$_{0-10}$ alkyl,
(C$_{1-10}$)heteroalkylamino(carbonyl)$_{0-1}$C$_{0-10}$ alkyl,
C$_{3-12}$ cycloalkylamino(carbonyl)$_{0-1}$C$_{0-10}$ alkyl,
aryl C$_{0-10}$ alkylaminoamino(carbonyl)$_{0-1}$C$_{0-10}$ alkyl,
heteroaryl C$_{0-10}$ alkylamino(carbonyl)$_{0-1}$C$_{0-10}$ alkyl,
(C$_{3-12}$)heterocycloalkylamino(carbonyl)$_{0-1}$C$_{0-10}$ alkyl, $C_{0-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$C_{1-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkysulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$C_{1-10}$ alkylthio$C_{0-10}$ alkyl,
$(C_{0-10}$ alkyl$)_{1-2}$ amino,
—$CO_2(C_{0-10}$ alkyl),
—$(C_{0-10}$ alkyl$)CO_2H$,
—$SO_2NH_2$,
—$SO_2NH(C_{1-10}$ alkyl),
—$SO_2N(C_{1-10}$ alkyl$)_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
$(C_{3-12})$cycloalkyl$C_{0-10}$alkylsulfinyl$C_{0-10}$alkyl,
$(C_{3-12})$cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$alkyl,
$C_{0-10}$ alkylsulfinylamino$C_{0-10}$ alkyl,
$C_{1-4}$acylamino $C_{0-10}$ alkyl,
hydroxy,
—$(C_{1-10}$ alkyl)OH,
—$C_{1-10}$ alkylalkoxy,
cyano,
$(C_{1-6}$alkyl)cyano, and
$C_{1-6}$haloalkyl; and
wherein two $R^1$ may optionally join together with the ring atom to which they are attached to form a 3 to 6 membered ring;

$R^2$ is selected from:
halogen,
Oxo (=O),
$C_{1-10}$ alkyl(oxy)$_{0-1}$(carbonyl)$_{0-1}C_{0-10}$ alkyl,
$C_{3-12}$ cycloalkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkylamino$C_{0-10}$ alkyl,
$(C_{1-10})$heteroalkylamino$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$(C_{3-12})$cycloalkyl$C_{0-10}$alkylsulfonyl,
$(C_{3-12})$cycloheteroalkyl$C_{0-10}$alkylsulfonyl,
$(C_{0-10}$ alkyl$)_{1-2}$ amino,
—$CO_2(C_{0-10}$ alkyl),
—$(C_{0-10}$ alkyl$)CO_2H$,
—$SO_2CF_3$,
—$SO_2CF_2H$,
$C_{1-10}$ alkylsulfinyl,
hydroxy,
—$(C_{1-10}$ alkyl)OH,
—$C_{1-10}$ alkylalkoxy,
cyano,
$(C_{1-6}$alkyl)cyano, and
$C_{1-6}$haloalkyl, and
wherein two $R^2$ may optionally join together with the ring atom to which each is attached to form a 3 to 6 membered saturated ring; and
wherein $R^1$ and $R^2$ are each optionally substituted with 1, 2, 3, or 4 $R^3$ substituents;

$R^3$ is independently selected from:
halogen,
$C_{1-10}$ alkyl(oxy)$_{0-1}$(carbonyl)$_{0-1}C_{0-10}$ alkyl, and
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$((C_{0-10})$alkyl$)_{1-2}$aminocarbonyloxy,
aryl $(C_{0-10})$alkylaminocarbonyloxy,
—$CO_2(C_{0-10}$ alkyl),
—$(C_{0-10}$ alkyl$)CO_2H$,
Oxo (=O),
—$SO_2NH_2$,
—$SO_2NH(C_{1-10}$ alkyl),
—$SO_2N(C_{1-10}$ alkyl$)_2$,
—$SO_2CF_3$,
—$SO_2CF_2H$,
$C_{1-10}$ alkylsulfinyl,
amino,
$(C_{0-10}$ alkyl$)_{1-2}$ amino,
-(oxy)$_{0-1}$(carbonyl)$_{0-1}N(C_{0-10}$ alkyl$)_{1-2}$
hydroxy,
$(C_{1-10}$ alkyl)OH,
$C_{1-10}$ alkoxy,
$(C_{1-10}$ alkyl)cyano,
cyano, and
$C_{1-6}$haloalkyl; and
$R^3$ is optionally substituted with 1, 2, or 3 $R^4$ substituents selected from hydrogen, hydroxy, $(C_{1-6})$alkyl, $(C_{1-6})$alkoxy, $(C_{1-10}$ alkyl)OH, halogen, $CO_2H$, —$(C_{0-6})$alkylCN, —O(C=O)$C_1$-$C_6$ alkyl, $NO_2$, trifluoromethoxy, trifluoroethoxy, trifluoromethyl, trifluoroethyl, —N—C(O)O($C_{0-6}$)alkyl, $C_{1-10}$ alkylsulfonyl, oxo (O=), aminosulfonyl, —$SO_2NH_2$, —$SO_2NH(C_{1-10}$ alkyl), —$SO_2N(C_{1-10}$ alkyl$)_2$, —$SO_2C_{1-6}$alkyl, —$SO_2CF_3$, —$SO_2CF_2H$, —$C_{1-10}$ alkylsulfinyl, —$O_{(0-1)}(C_{1-10})$haloalkyl, amino($C_{1-6}$ alkyl)$_{0-2}$ and $NH_2$.

2. A compound of claim 1, where $R^1$ is selected from: halogen, Oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$ (carbonyl)$_{0-1}C_{0-10}$ alkyl, $(C_{3-12})$heterocycloalkyl $C_{0-10}$ alkyl(oxy)$_{0-1}$(carbonyl)$_{0-1}$ $C_{0-10}$ alkyl, $C_{0-10}$ alkyl(oxy)$_{0-1}$(carbonyl)$_{0-1}$amino$C_{0-10}$ alkyl, $(C_{1-10})$heteroalkyl(oxy)$_{0-1}$(carbonyl)$_{0-1}$amino$C_{0-10}$ alkyl, $(C_{3-12})$heterocycloalkyl $C_{0-10}$ alkyl(oxy)$_{0-1}$(carbonyl)$_{0-1}$amino$C_{0-10}$ alkyl, heteroaryl $C_{0-10}$ alkyl(oxy)$_{0-1}$(carbonyl)$_{0-1}$amino$C_{0-10}$alkyl, $C_{0-10}$ alkylsulfonyl$C_{0-10}$ alkyl, $(C_{3-12})$cycloheteroalkyl$C_{0-10}$alkylsulfonylalkyl)$C_{0-10}$ alkyl, $C_{1-10}$ alkylsulfamoyl$C_{0-10}$ alkyl, $(C_{3-12})$cycloalkyl $C_{0-10}$ alkylsulfamoyl$C_{0-10}$ alkyl, $(C_{3-12})$cycloheteroalkyl $C_{0-10}$alkylsulfamoyl$C_{0-10}$ alkyl, aryl$C_{0-10}$ alkylsulfamoyl $C_{0-10}$ alkyl, $C_{1-10}$ alkylsulfonimidoyl$C_{0-10}$ alkyl, $C_{1-10}$ alkylthio$C_{0-10}$ alkyl, $(C_{0-10}$ alkyl$)_{1-2}$ amino, —$CO_2(C_{0-10}$ alkyl$)$, —$(C_{0-10}$ alkyl$)CO_2H$, —$SO_2NH_2$, —$SO_2NH(C_{1-10}$ alkyl$)$, —$SO_2N(C_{1-10}$ alkyl$)_2$, hydroxy, —$(C_{1-10}$ alkyl$)OH$, —$C_{1-10}$ alkylalkoxy, cyano, and $C_{1-6}$haloalkyl; wherein two $R^1$ may optionally join together with the ring atoms to which they are attached to form a 3 to 6 membered ring; and wherein $R^1$ is optionally substituted with 1, 2, 3, or 4 $R^3$ substituents.

3. A compound of claim 2, wherein A is selected from: phenyl, isoindolinyl, 2,3-dihydro-1H-isoindolyl, quinolinyl, pyridinyl,

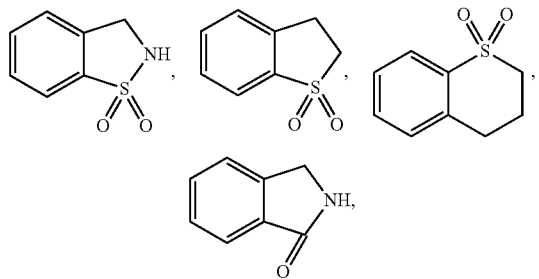

2,3-dihydro-1H-indenyl, benzothiazolyl, 1,3-benzothiazolyl, and 1,2,3,4-tetrahydroisoquinolinyl.

4. A compound of claim 3, wherein $R^1$ is selected from: fluoro, methylsulfonyl, chloro, trifluoromethyl, trifluoromethoxy, dimethylsulfamoyl, sulfamoyl, hydroxyethyl, trifluoroethyl, pyrazolylcarbamoylmethyl, pyrazolylcarbonylaminomethyl, tert-butyloxycarbonylaminomethyl, aminomethyl, isopropylsulfamoyl, benzylsulfamoyl, (cyclopropylmethyl)sulfamoyl, ethylsulfomoyl, cyclohexylsulfamoyl, piperidinylsulfonyl, morpholinylsulfonyl, triazolylmethyl, pyrrolidinylcarbonyl, oxazolylcarbonylaminomethyl, pyrimidinylcarbonylaminomethyl, hydroxyethyl, 1-hydroxyethyl, morpholinylmethyl, 1-hydroxymethylethyl, hydroxy(methylpropyl), 1-hydroxy(methylpropyl), hydroxypropyl, ethylhydroxy, (tert-butyl)sulfinylaminomethyl, dioxolanyl, methylaminomethyl, methylcarbonylaminomethyl, (dimethylamino)methyl, pyrazolylmethyl, imidazolylmethyl, oxo, hydroxy, hydroxymethyl, methyl, tert-butyl, (tert-butyl)sulfinylaminomethyl, (ethyl)aminomethyl, pyrrolidinylsulfonylmethyl, trifluoroethyl, (2,2,2,-trifluoroethyl), carboxy, cyclopropylmethyl, dimethylaminomethyl, cyclopentylmethyl, methylaminoethyl, 1-(methylamino)ethyl, ethylaminomethyl, dimethylaminocarbonyl, dimethylcarbamoyl, morpholinylcarbonyl, cyclopropyl, aminoethyl, 1-aminoethyl, pyrrolidinyl, methylethyl, isobutyl, cyclopropylmethyl, methylsulfanylmethyl, 3-hydroxy(dimethylpropyl), triazolylmethyl, 3-hydroxy-2,2,-dimethylpropyl, and methoxyethyl; wherein $R^1$ is optionally substituted with 1, 2, 3, or 4 $R^3$ substituents.

5. A compound of formula II or pharmaceutically acceptable salt, or stereoisomer thereof:

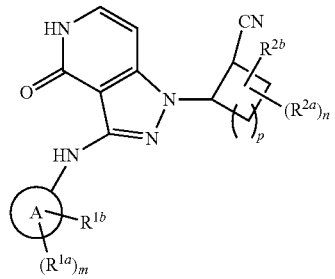

A is selected from aryl and heteroaryl;
n is 0, 1, or 2;
m is 0, 1, 2, or 3;
p is 0, 1, 2, 3, or 4;
$R^{1a}$ is selected from:
  halogen,
  Oxo (=O),
  $C_{1-10}$ alkyl(oxy)$_{0-1}$(carbonyl)$_{0-1}C_{0-10}$ alkyl,
  $C_{3-12}$ cycloalkyl $C_{0-10}$ alkyl(oxy)$_{0-1}$(carbonyl)$_{0-1}C_{0-10}$ alkyl,
  $C_{0-10}$ alkyl(oxy)$_{0-1}$(carbonyl)$_{0-1}$amino$C_{0-10}$ alkyl,
  $(C_{1-10})$heteroalkyl(oxy)$_{0-1}$ (carbonyl)$_{0-1}$amino$C_{0-10}$ alkyl,
  $C_{0-10}$ alkylamino(carbonyl)$_{0-1}C_{0-10}$ alkyl,
  $(C_{0-10}$ alkyl$)_{1-2}$ amino,
  $C_{1-10}$ alkylthio$C_{0-10}$ alkyl,
  $C_{0-10}$ alkylsulfonyl$C_{0-10}$ alkyl,
  —$SO_2NH_2$,
  —$SO_2NH(C_{1-10}$ alkyl$)$,
  —$SO_2N(C_{1-10}$ alkyl$)_2$,
  hydroxy,
  —$(C_{1-10}$ alkyl$)OH$,
  —$C_{1-10}$ alkylalkoxy, and
  $C_{1-6}$haloalkyl, and
  wherein two $R^{1a}$ may optionally join together with the ring atoms to which they are attached to form a 3 to 6 membered saturated ring;
$R^{2a}$ is selected from
  halogen,
  Oxo (=O),
  $C_{1-10}$ alkyl(oxy)$_{0-1}$(carbonyl)$_{0-1}C_{0-10}$ alkyl,
  $C_{0-10}$ alkylamino$C_{0-10}$ alkyl,
  $(C_{3-12})$heterocycloalkyl $C_{0-10}$ alkylamino$C_{0-10}$ alkyl,
  $(C_{0-10}$ alkyl$)_{1-2}$ amino,
  —$CO_2(C_{0-10}$ alkyl$)$,
  —$(C_{0-10}$ alkyl$)CO_2H$,
  hydroxy,
  —$(C_{1-10}$ alkyl$)OH$,
  —$C_{1-10}$ alkylalkoxy, and
  $C_{1-6}$haloalkyl, wherein two $R^{2a}$ may optionally join together with the ring atom to which each is attached to form a 3 to 6 membered saturated ring;
wherein $R^{1a}$ and $R^{2a}$ are independently optionally substituted with 1, 2, 3, or 4 $R^{3a}$ substituents;
$R^{3a}$ is independently selected from:
  halogen,
  $C_{1-10}$ alkyl(oxy)$_{0-1}$(carbonyl)$_{0-1}C_{0-10}$ alkyl, and
  $C_{1-10}$ heteroalkyl(oxy)$_{0-1}$(carbonyl)$_{0-1}C_{0-10}$ alkyl,
  Oxo (=O),
  hydroxy,
  $(C_{1-10}$ alkyl$)OH$,
  $C_{1-10}$ alkoxy, and
  $C_{1-6}$haloalkyl;

$R^{3a}$ is optionally substituted with 1, 2, or 3 $R^{4a}$ substituents selected from hydrogen, hydroxy, $(C_{1-6})$alkyl, $(C_{1-6})$alkoxy, $(C_{1-10}$ alkyl)OH, halogen, $CO_2H$, —$(C_{0-6})$alkylCN, —O(C=O)$C_1$-$C_6$ alkyl, $NO_2$, trifluoroethoxy, trifluoromethyl, trifluoroethyl, —N—C(O)O($C_{0-6}$)alkyl, $C_{1-10}$ alkylsulfonyl, oxo (O=), aminosulfonyl,
—$SO_2NH_2$, —$SO_2NH(C_{1-10}$ alkyl), —$SO_2N(C_{1-10}$ alkyl)$_2$, —$SO_2C_{1-6}$alkyl, —$SO_2CF_3$, —$SO_2CF_2H$, —$C_{1-10}$ alkylsulfinyl, —$O_{(0-1)}(C_{1-10})$haloalkyl, amino($C_{1-6}$alkyl)$_{0-2}$ and $NH_2$;

$R^{1b}$ is selected from:
hydrogen,
halogen,
Oxo (=O),
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
$C_{3-12}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkyl(oxy)$_{0-1}$(carbonyl)$_{0-1}$amino$C_{0-10}$ alkyl,
$(C_{1-10})$heteroalkyl(oxy)$_{0-1}$(carbonyl)$_{0-1}$amino$C_{0-10}$ alkyl,
$C_{3-12}$ cycloalkyl $C_{0-10}$ alkyl(oxy)$_{0-1}$(carbonyl)$_{0-1}$amino$C_{0-10}$ alkyl,
aryl $C_{0-10}$ alkyl(oxy)$_{0-1}$(carbonyl)$_{0-1}$amino$C_{0-10}$ alkyl,
heteroaryl $C_{0-10}$ alkyl(oxy)$_{0-1}$(carbonyl)$_{0-1}$amino$C_{0-10}$ alkyl,
$(C_{3-12})$heterocycloalkyl $C_{0-10}$ alkyl(oxy)$_{0-1}$(carbonyl)$_{0-1}$amino$C_{0-10}$ alkyl,
$C_{0-10}$ alkylamino(carbonyl)$_{0-1}C_{0-10}$ alkyl,
$(C_{1-10})$heteroalkylamino(carbonyl)$_{0-1}C_{0-10}$ alkyl,
$C_{3-12}$ cycloalkylamino(carbonyl)$_{0-1}C_{0-10}$ alkyl,
aryl $C_{0-10}$ alkylaminoamino(carbonyl)$_{0-1}C_{0-10}$ alkyl,
heteroaryl $C_{0-10}$ alkylamino(carbonyl)$_{0-1}C_{0-10}$ alkyl,
$(C_{3-12})$heterocycloalkylamino(carbonyl)$_{0-1}C_{0-10}$ alkyl,
$C_{0-10}$ alkylsulfonyl$C_{0-10}$ alkyl,
$C_{1-10}$ heteroalkylsulfonyl$C_{0-10}$ alkyl,
$(C_{3-12})$cycloalkyl$C_{0-10}$alkylsulfonyl$C_{0-10}$ alkyl,
$(C_{3-12})$cycloheteroalkyl$C_{0-10}$alkylsulfonyl$C_{0-10}$ alkyl,
heteroaryl$C_{0-10}$ alkylsulfonyl$C_{0-10}$ alkyl,
aryl$C_{0-10}$ alkylsulfonyl$C_{0-10}$ alkyl,
$C_{1-10}$ alkylsulfamoyl$C_{0-10}$ alkyl,
$C_{1-10}$ heteroalkylsulfamoyl$C_{0-10}$ alkyl,
$(C_{3-12})$cycloalkyl$C_{0-10}$ alkylsulfamoyl$C_{0-10}$ alkyl,
$(C_{3-12})$cycloheteroalkyl$C_{0-10}$alkylsulfamoyl$C_{0-10}$ alkyl,
heteroaryl$C_{0-10}$ alkylsulfamoyl$C_{0-10}$ alkyl,
aryl$C_{0-10}$ alkylsulfamoyl$C_{0-10}$ alkyl,
$C_{1-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkysulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$C_{1-10}$ alkylthio$C_{0-10}$ alkyl,
$(C_{0-10}$ alkyl$)_{1-2}$ amino,
—$CO_2(C_{0-10}$ alkyl),
—$(C_{0-10}$ alkyl)$CO_2H$,
—$SO_2NH_2$,
—$SO_2NH(C_{1-10}$ alkyl),
—$SO_2N(C_{1-10}$ alkyl)$_2$,
—$SO_2CF_3$,
—$SO_2CF_2H$,
$C_{1-10}$ alkylsulfinyl$C_{0-10}$ alkyl,
$C_{1-10}$ heteroalkylsulfinyl$C_{0-10}$alkyl,
$(C_{3-12})$cycloalkyl$C_{0-10}$alkylsulfinyl$C_{0-10}$alkyl,
$(C_{3-12})$cycloheteroalkyl$C_{0-10}$alkylsulfinyl$C_{0-10}$alkyl,
heteroaryl$C_{0-10}$ alkylsulfinyl$C_{0-10}$alkyl,
aryl$C_{0-10}$alkylsulfinyl$C_{0-10}$ alkyl,
$C_{0-10}$ alkylsulfinylamino$C_{0-10}$ alkyl,
$C_{1-4}$acylamino $C_{0-10}$ alkyl,
hydroxy,
—$(C_{1-10}$ alkyl)OH,
—$C_{1-10}$ alkylalkoxy,
cyano,
$(C_{1-6}$alkyl)cyano, and
$C_{1-6}$haloalkyl;

$R^{2b}$ is selected from:
hydrogen,
halogen,
Oxo (=O),
$C_{1-10}$ alkyl(oxy)$_{0-1}$(carbonyl)$_{0-1}C_{0-10}$ alkyl,
$C_{3-12}$ cycloalkyl,
$(C_{3-12})$heterocycloalkyl $C_{0-10}$ alkyl(oxy)$_{0-1}$(carbonyl)$_{0-1}C_{0-10}$ alkyl,
$C_{0-10}$ alkylamino$C_{0-10}$ alkyl,
$(C_{1-10})$heteroalkylamino$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$(C_{3-12})$cycloalkyl$C_{0-10}$alkylsulfonyl,
$(C_{3-12})$cycloheteroalkyl$C_{0-10}$ alkylsulfonyl,
$(C_{0-10}$ alkyl)$_{1-2}$ amino,
—$CO_2(C_{0-10}$ alkyl),
—$(C_{0-10}$ alkyl)$CO_2H$,
—$SO_2CF_3$,
—$SO_2CF_2H$,
$C_{1-10}$ alkylsulfinyl,
hydroxy,
—$(C_{1-10}$ alkyl)OH,
—$C_{1-10}$ alkylalkoxy,
cyano,
$(C_{1-6}$alkyl)cyano, and
$C_{1-6}$haloalkyl; wherein $R^{1b}$ and $R^{2b}$ are each optionally substituted with 1, 2, or 3 $R^{3b}$ substituents;

$R^{3b}$ is independently selected from: is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, —$CO_2(C_{0-10}$ alkyl), Oxo (=O), $C_{1-10}$ alkylsulfinyl, amino, $(C_{0-10}$ alkyl)$_{1-2}$ amino, hydroxy, $(C_{1-10}$ alkyl)OH, $C_{1-10}$ alkoxy, $(C_{1-10}$ alkyl)cyano, cyano, and $C_{1-6}$haloalkyl, halogen, $C_{1-10}$ alkyl(oxy)$_{0-1}$(carbonyl)$_{0-1}C_{0-10}$ alkyl, Oxo (=O), amino, hydroxy, $(C_{1-10}$ alkyl)OH, $C_{1-10}$alkoxy, and $C_{1-6}$haloalkyl; wherein $R^{3b}$ is optionally substituted with 1, 2, or 3 $R^{4b}$ substituents; and $R^{4b}$ is independently selected from hydrogen, hydroxy, $(C_{1-6})$alkyl, $(C_{1-6})$alkoxy, $(C_{1-10}$ alkyl)OH, halogen, —O(C=O)$C_1$-$C_6$ alkyl, trifluoroethoxy, trifluoroethoxy, trifluoromethyl, trifluoroethyl, oxo (O=), —$O_{(0-1)}(C_{1-10})$haloalkyl, amino($C_{1-6}$alkyl)$_{0-2}$ and $NH_2$.

6. A compound according to claim 5, wherein: $R^{1b}$ is selected from: halogen, Oxo (=O), $C_{1-10}$ alkyl(oxy)$_{0-1}$(carbonyl)$_{0-1}$C$_{0-10}$ alkyl, C$_{1-10}$ heteroalkyl(oxy)$_{0-1}$(carbonyl)$_{0-1}$ C$_{0-10}$ alkyl, C$_{3-12}$ cycloalkyl C$_{0-10}$ alkyl(oxy)$_{0-1}$(carbonyl)$_{0-1}$ C$_{0-10}$ alkyl, heteroaryl C$_{0-10}$ alkyl(oxy)$_{0-1}$(carbonyl)$_{0-1}$ C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkyl(oxy)$_{0-1}$(carbonyl)$_{0-1}$ aminoC$_{0-10}$ alkyl, (C$_{1-10}$)heteroalkyl(oxy)$_{0-1}$(carbonyl)$_{0-1}$aminoC$_{0-10}$ alkyl, (C$_{3-12}$)heterocycloalkyl C$_{0-10}$ alkyl(oxy)$_{0-1}$(carbonyl)$_{0-1}$aminoC$_{0-10}$ alkyl, heteroaryl C$_{0-10}$ alkyl(oxy)$_{0-1}$(carbonyl)$_{0-1}$aminoC$_{0-10}$ alkyl, C$_{0-10}$ alkylamino(carbonyl)$_{0-1}$C$_{0-10}$ alkyl, heteroaryl C$_{0-10}$ alkylamino (carbonyl)$_{0-1}$C$_{0-10}$ alkyl, C$_{0-10}$ alkylsulfonylC$_{0-10}$ alkyl, (C$_{3-12}$)cycloheteroalkylC$_{0-10}$alkylsulfonylC$_{0-10}$ alkyl, C$_{1-10}$ alkylsulfamoylC$_{0-10}$ alkyl, (C$_{3-12}$)cycloalkylC$_{0-10}$ alkylsulfamoylC$_{0-10}$ alkyl, (C$_{3-12}$)cycloheteroalkylC$_{0-10}$alkylsulfamoylC$_{0-10}$ alkyl, arylC$_{0-10}$ alkylsulfamoylC$_{0-10}$ alkyl, C$_{1-10}$ alkylsulfonimidoylC$_{0-10}$ alkyl, C$_{1-10}$ alkylthioC$_{0-10}$ alkyl, (C$_{0-10}$ alkyl)$_{1-2}$ amino, —CO$_2$(C$_{0-10}$ alkyl), —(C$_{0-10}$ alkyl)CO$_2$H, —SO$_2$NH$_2$, —SO$_2$NH(C$_{1-10}$ alkyl), —SO$_2$N(C$_{1-10}$ alkyl)$_2$, hydroxy, —(C$_{1-10}$ alkyl)OH, —C$_{1-10}$ alkylalkoxy, cyano, and C$_{1-6}$haloalkyl;

R$^{2b}$ is selected from: hydrogen, halogen, C$_{1-10}$ alkyl (oxy)$_{0-1}$(carbonyl)$_{0-1}$C$_{0-10}$ alkyl, C$_{3-12}$ cycloalkyl, (C$_{3-12}$)heterocycloalkyl C$_{0-10}$ alkyl(oxy)$_{0-1}$(carbonyl)$_{0-1}$ C$_{0-10}$ alkyl, C$_{0-10}$ alkylaminoC$_{0-10}$ alkyl, C$_{3-12}$ cycloalkyl C$_{0-10}$ alkylaminoC$_{0-10}$ alkyl, (C$_{0-10}$ alkyl)$_{1-2}$ amino, and hydroxy; and wherein R$^{1b}$ and R$^{2b}$ are each independently optionally substituted with 1, 2, 3, or 4 R$^{3b}$ substituents.

7. A compound of claim 1 or a pharmaceutically acceptable salt, or a stereoisomer thereof selected from:

2-{3-[(4-fluorophenyl)amino]-4-oxo-4,5-dihydro-1H-pyrazolo[4,3-c]pyridin-1-yl}cyclohexanecarbonitrile;
2-(3-{[4-(methylsulfonyl)phenyl]amino}-4-oxo-4,5-dihydro-1H-pyrazolo[4,3-c]pyridin-1-yl)cyclohexanecarbonitrile;
2-{3-[(2-fluoropyridin-4-yl)amino]-4-oxo-4,5-dihydro-1H-pyrazolo[4,3-c]pyridin-1-yl}cyclohexanecarbonitrile;
2-{3-[(4-chlorophenyl)amino]-4-oxo-4,5-dihydro-1H-pyrazolo[4,3-c]pyridin-1-yl}cyclohexanecarbonitrile;
2-{3-[(4-chlorophenyl)amino]-4-oxo-4,5-dihydro-1H-pyrazolo[4,3-c]pyridin-1-yl}-5-{[1-cyclopropylethyl]amino}cyclohexanecarbonitrile;
5-hydroxy-2-(4-oxo-3-{[4-(trifluoromethyl)phenyl]amino}-4,5-dihydro-1H-pyrazolo[4,3-c]pyridin-1-yl)cyclohexanecarbonitrile;
5-azetidin-1-yl-2-(4-oxo-3-{[4-(trifluoromethyl)phenyl]amino}-4,5-dihydro-1H-pyrazolo[4,3-c]pyridin-1-yl)cyclohexanecarbonitrile;
5-{[1-cyclopropylethyl]amino}-2-(4-oxo-3-{[4-(trifluoromethyl)phenyl]amino}-4,5-dihydro-1H-pyrazolo[4,3-c]pyridin-1-yl)cyclohexanecarbonitrile;
5-{[1-cyclopropylethyl]amino}-2-(4-oxo-3-{[4-(trifluoromethyl)phenyl]amino}-4,5-dihydro-1H-pyrazolo[4,3-c]pyridin-1-yl)cyclohexanecarbonitrile;
5-azetidin-1-yl-2-{3-[(4-chloro-3-fluorophenyl)amino]-4-oxo-4,5-dihydro-1H-pyrazolo[4,3-c]pyridin-1-yl}cyclohexanecarbonitrile;
2-{3-[(4-chloro-3-fluorophenyl)amino]-4-oxo-4,5-dihydro-1H-pyrazolo[4,3-c]pyridin-1-yl}-5-(dimethylamino)cyclohexanecarbonitrile;
2-{3-[(4-chloro-3-fluorophenyl)amino]-4-oxo-4,5-dihydro-1H-pyrazolo[4,3-c]pyridin-1-yl}-5-{[1-cyclopropylethyl]amino}cyclohexanecarbonitrile;
5-azetidin-1-yl-2-{3-[(4-chlorophenyl)amino]-4-oxo-4,5-dihydro-1H-pyrazolo[4,3-c]pyridin-1-yl}cyclohexanecarbonitrile;
2-{3-[(4-chlorophenyl)amino]-4-oxo-4,5-dihydro-1H-pyrazolo[4,3-c]pyridin-1-yl}-5-(dimethylamino)cyclohexanecarbonitrile;
5-azetidin-1-yl-2-(4-oxo-3-{[4-(trifluoromethoxy)phenyl]amino}-4,5-dihydro-1H-pyrazolo[4,3-c]pyridin-1-yl)cyclohexanecarbonitrile;
5-{[1-cyclopropylethyl]amino}-2-(4-oxo-3-{[4-(trifluoromethoxy)phenyl]amino}-4,5-dihydro-1H-pyrazolo[4,3-c]pyridin-1-yl)cyclohexanecarbonitrile;
5-(dimethylamino)-2-(4-oxo-3-{[4-(trifluoromethoxy)phenyl]amino}-4,5-dihydro-1H-pyrazolo[4,3-c]pyridin-1-yl)cyclohexanecarbonitrile;
2-{3-[(4-chlorophenyl)amino]-4-oxo-4,5-dihydro-1H-pyrazolo[4,3-c]pyridin-1-yl}-5-(3-hydroxy-3-methylazetidin-1-yl)cyclohexanecarbonitrile;
2-{3-[(4-chlorophenyl)amino]-4-oxo-4,5-dihydro-1H-pyrazolo[4,3-c]pyridin-1-yl}-5-(3-hydroxyazetidin-1-yl)cyclohexanecarbonitrile;
4-({1-[2-cyanocyclohexyl]-4-oxo-4,5-dihydro-1H-pyrazolo[4,3-c]pyridin-3-yl}amino)-N,N-dimethylbenzenesulfonamide;
4-({1-[2-cyanocyclohexyl]-4-oxo-4,5-dihydro-1H-pyrazolo[4,3-c]pyridin-3-yl}amino)benzenesulfonamide;
(2-{3-[(2-fluoropyridin-4-yl)amino]-4-oxo-4,5-dihydro-1H-pyrazolo[4,3-c]pyridin-1-yl}cyclopentanecarbonitrile;
(2-(3-{[4-(methylsulfonyl)phenyl]amino}-4-oxo-4,5-dihydro-1H-pyrazolo[4,3-c]pyridin-1-yl)cyclopentanecarbonitrile;
2-[4-oxo-3-({4-[2,2,2-trifluoro-1-hydroxyethyl]phenyl}amino)-4,5-dihydro-1H-pyrazolo[4,3-c]pyridin-1-yl]cyclohexanecarbonitrile;
2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclohexanecarbonitrile;
4-({1-[2-cyanocyclopentyl]-4-oxo-4,5-dihydro-1H-pyrazolo[4,3-c]pyridin-3-yl}amino)-N,N-dimethylbenzenesulfonamide;
2-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)cyclopentanecarbonitrile;
2-(4-oxo-3-{[4-(2,2,2-trifluoro-1-hydroxyethyl)phenyl]amino}-4,5-dihydro-1H-pyrazolo[4,3-c]pyridin-1-yl)cyclopentanecarbonitrile;
4-({1-[2-cyanocyclopentyl]-4-oxo-4,5-dihydro-1H-pyrazolo[4,3-c]pyridin-3-yl}amino)benzenesulfonamide;
2-[3-({1-[2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide;
N-[3-({1-[2-cyanocyclohexyl]-4-oxo-4,5-dihydro-1H-pyrazolo[4,3-c]pyridin-3-yl}amino)benzyl]-1,3-oxazole-5-carboxamide;
N-[3-({1-[2-cyanocyclohexyl]-4-oxo-4,5-dihydro-1H-pyrazolo[4,3-c]pyridin-3-yl}amino)benzyl]pyrimidine-2-carboxamide;
2-[3-({1-[2-cyanocyclohexyl]-4-oxo-4,5-dihydro-1H-pyrazolo[4,3-c]pyridin-3-yl}amino)phenyl]-N-(1-methyl-1H-pyrazol-3-yl)acetamide;
tert-butyl [3-({1-[2-cyanocyclohexyl]-4-oxo-4,5-dihydro-1H-pyrazolo[4,3-c]pyridin-3-yl}amino)benzyl] carbamate;
2-(3-{[3-(aminomethyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-N-(1-methylethyl)benzenesulfonamide;

N-benzyl-4-({1-[2-cyanocyclohexyl]-4-oxo-4,5-dihydro-1H-pyrazolo[4,3-c]pyridin-3-yl}amino)benzenesulfonamide;

4-({1-[2-cyanocyclohexyl]-4-oxo-4,5-dihydro-1H-pyrazolo[4,3-c]pyridin-3-yl}amino)-N-(cyclopropylmethyl)benzenesulfonamide;

4-({1-[2-cyanocyclohexyl]-4-oxo-4,5-dihydro-1H-pyrazolo[4,3-c]pyridin-3-yl}amino)-N-(2-methoxyethyl)benzenesulfonamide;

4-({1-[2-cyanocyclohexyl]-4-oxo-4,5-dihydro-1H-pyrazolo[4,3-c]pyridin-3-yl}amino)-N-cyclohexylbenzenesulfonamide;

2-(3-{[4-(morpholin-4-yl sulfonyl)phenyl]amino}-4-oxo-4,5-dihydro-1H-pyrazolo[4,3-c]pyridin-1-yl)cyclohexanecarbonitrile;

2-[4-oxo-3-(phenylamino)-4,5-dihydro-1H-pyrazolo[4,3-c]pyridin-1-yl]cyclohexanecarbonitrile;

2-(3-{[3-methyl-4-(pyrrolidin-1-ylcarbonyl)phenyl]amino}-4-oxo-4,5-dihydro-1H-pyrazolo[4,3-c]pyridin-1-yl)cyclohexanecarbonitrile;

2-(4-oxo-3-{[3-(2H-1,2,3-triazol-2-ylmethyl)phenyl]amino}-4,5-dihydro-1H-pyrazolo[4,3-c]pyridin-1-yl)cyclohexanecarbonitrile;

N-[4-({1-[2-cyanocyclohexyl]-4-oxo-4,5-dihydro-1H-pyrazolo[4,3-c]pyridin-3-yl}amino)benzyl]-1,3-oxazole-5-carboxamide;

N-[4-({1-[2-cyanocyclohexyl]-4-oxo-4,5-dihydro-1H-pyrazolo[4,3-c]pyridin-3-yl}amino)benzyl]pyrimidine-2-carboxamide;

2-(3-{[3-(1-hydroxyethyl)phenyl]amino}-4-oxo-4,5-dihydro-1H-pyrazolo[4,3-c]pyridin-1-yl)cyclohexanecarbonitrile;

tert-butyl [4-({1-[2-cyanocyclohexyl]-4-oxo-4,5-dihydro-1H-pyrazolo[4,3-c]pyridin-3-yl}amino)benzyl]carbamate;

2-(3-{[4-(aminomethyl)phenyl]amino}-4-oxo-4,5-dihydro-1H-pyrazolo[4,3-c]pyridin-1-yl)cyclohexanecarbonitrile;

2-(3-{[3-(aminomethyl)-4-fluorophenyl]amino}-4-oxo-4,5-dihydro-1H-pyrazolo[4,3-c]pyridin-1-yl)cyclohexanecarbonitrile;

2-(3-{[3-(morpholin-4-ylmethyl)phenyl]amino}-4-oxo-4,5-dihydro-1H-pyrazolo[4,3-c]pyridin-1-yl)cyclohexanecarbonitrile;

tert-butyl [5-({1-[2-cyanocyclohexyl]-4-oxo-4,5-dihydro-1H-pyrazolo[4,3-c]pyridin-3-yl}amino)-2-fluorobenzyl]carbamate;

tert-butyl [3-({1-[2-cyanocyclohexyl]-4-oxo-4,5-dihydro-1H-pyrazolo[4,3-c]pyridin-3-yl}amino)-5-fluorobenzyl]carbamate;

2-{3-[(3-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile;

2-(3-{[3-(1-hydroxy-2-methoxy-1-methylethyl)-4-(methylsulfonyl)phenyl]amino}-4-oxo-4,5-dihydro-1H-pyrazolo[4,3-c]pyridin-1-yl)cyclohexanecarbonitrile;

2-(3-{[3-(1,3-dihydroxy-1-methylpropyl)-4-(methylsulfonyl)phenyl]amino}-4-oxo-4,5-dihydro-1H-pyrazolo[4,3-c]pyridin-1-yl)cyclohexanecarbonitrile;

2-(3-{[3-(1,2-dihydroxy-1-methylethyl)-4-(methylsulfonyl)phenyl]amino}-4-oxo-4,5-dihydro-1H-pyrazolo[4,3-c]pyridin-1-yl)cyclohexanecarbonitrile;

2-[3-(2,3-dihydro-1H-isoindol-5-ylamino)-4-oxo-4,5-dihydro-1H-pyrazolo[4,3-c]pyridin-1-yl]cyclohexanecarbonitrile;

2-[3-({3-[(4-methyl-1H-1,2,3-triazol-1-yl)methyl]phenyl}amino)-4-oxo-4,5-dihydro-1H-pyrazolo[4,3-c]pyridin-1-yl]cyclohexanecarbonitrile;

2-[3-({3-[1-amino-2,2,2-trifluoroethyl]phenyl}amino)-4-oxo-4,5-dihydro-1H-pyrazolo[4,3-c]pyridin-1-yl]cyclohexanecarbonitrile;

N-{1-[3-({1-[2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide;

2-(4-oxo-3-{[3-(2,2,4-trimethyl-1,3-dioxolan-4-yl)phenyl]amino}-4,5-dihydro-1H-pyrazolo[4,3-c]pyridin-1-yl)cyclohexanecarbonitrile;

2-{4-oxo-3-[(3-{[(2,2,2-trifluoroethyl)amino]methyl}phenyl)amino]-4,5-dihydro-1H-pyrazolo[4,3-c]pyridin-1-yl}cyclohexanecarbonitrile;

2-(3-{[3-(aminomethyl)-4-(methylsulfonyl)phenyl]amino}-4-oxo-4,5-dihydro-1H-pyrazolo[4,3-c]pyridin-1-yl)cyclohexanecarbonitrile;

6-(3-{[4-(methylsulfonyl)phenyl]amino}-4-oxo-4,5-dihydro-1H-pyrazolo[4,3-c]pyridin-1-yl)spiro[2.5]octane-5-carbonitrile;

N-[5-({1-[2-cyanocyclohexyl]-4-oxo-4,5-dihydro-1H-pyrazolo[4,3-c]pyridin-3-yl}amino)-2-(dimethyl sulfamoyl)benzyl]acetamide;

2-[3-({3-[(dimethylamino)methyl]phenyl}amino)-4-oxo-4,5-dihydro-1H-pyrazolo[4,3-c]pyridin-1-yl]cyclohexanecarbonitrile;

2-(3-{[3-(1,2-dihydroxy-1-methylethyl)phenyl]amino}-4-oxo-4,5-dihydro-1H-pyrazolo[4,3-c]pyridin-1-yl)cyclohexanecarbonitrile;

4-{[1-(5-cyanospiro[2.5]oct-6-yl)-4-oxo-4,5-dihydro-1H-pyrazolo[4,3-c]pyridin-3-yl]amino}-N,N-dimethylbenzenesulfonamide;

2-(aminomethyl)-4-({1-[2-cyanocyclohexyl]-4-oxo-4,5-dihydro-1H-pyrazolo[4,3-c]pyridin-3-yl}amino)-N,N-dimethylbenzenesulfonamide;

2-(4-oxo-3-{[3-(1H-pyrazol-1-ylmethyl)phenyl]amino}-4,5-dihydro-1H-pyrazolo[4,3-c]pyridin-1-yl)cyclohexanecarbonitrile;

2-(4-oxo-3-{[4-(pyrrolidin-1-ylcarbonyl)phenyl]amino}-4,5-dihydro-1H-pyrazolo[4,3-c]pyridin-1-yl)cyclohexanecarbonitrile;

2-(4-oxo-3-{[4-(1H-1,2,3-triazol-1-ylmethyl)phenyl]amino}-4,5-dihydro-1H-pyrazolo[4,3-c]pyridin-1-yl)cyclohexanecarbonitrile;

2-(3-{[3-(1H-imidazol-1-ylmethyl)phenyl]amino}-4-oxo-4,5-dihydro-1H-pyrazolo[4,3-c]pyridin-1-yl)cyclohexanecarbonitrile;

6-(3-{[4-(methylsulfonyl)phenyl]amino}-4-oxo-4,5-dihydro-1H-pyrazolo[4,3-c]pyridin-1-yl)spiro[2.5]octane-5-carbonitrile;

2-(3-{[4-hydroxy-4-(hydroxymethyl)-1,1-dioxido-3,4-dihydro-2H-thiochromen-6-yl]amino}-4-oxo-4,5-dihydro-1H-pyrazolo[4,3-c]pyridin-1-yl)cyclohexanecarbonitrile;

2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-(4-oxo-3-{[3-(1H-1,2,4-triazol-1-ylmethyl)phenyl]amino}-4,5-dihydro-1H-pyrazolo[4,3-c]pyridin-1-yl)cyclohexanecarbonitrile;

2-(4-oxo-3-{[3-(1H-1,2,4-triazol-4-ylmethyl)phenyl]amino}-4,5-dihydro-1H-pyrazolo[4,3-c]pyridin-1-yl)cyclohexanecarbonitrile;

2-{3-[(4-{[4-(1-hydroxy-1-methylethyl)-1H-1,2,3-triazol-1-yl]methyl}phenyl)amino]-4-oxo-4,5-dihydro-1H-pyrazolo[4,3-c]pyridin-1-yl}cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-{3-[(1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

N-{1-[4-({1-[2-cyanocyclohexyl]-4-oxo-4,5-dihydro-1H-pyrazolo[4,3-c]pyridin-3-yl}amino)phenyl]-2,2,2-trifluoroethyl}-2-methylpropane-2-sulfinamide;

2-[3-({4-[1-amino-2,2,2-trifluoroethyl]phenyl}amino)-4-oxo-4,5-dihydro-1H-pyrazolo[4,3-c]pyridin-1-yl]cyclopentanecarbonitrile;

2-{4-oxo-3-[(4-{[(2,2,2-trifluoroethyl)amino]methyl}phenyl)amino]-4,5-dihydro-1H-pyrazolo[4,3-c]pyridin-1-yl}cyclohexanecarbonitrile;

2-[4-oxo-3-({4-[(pyrrolidin-1-yl sulfonyl)methyl]phenyl}amino)-4,5-dihydro-1H-pyrazolo[4,3-c]pyridin-1-yl]cyclohexanecarbonitrile;

2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{3-[(1,1-dioxido-2,3-dihydro-1-benzothiophen-5-yl)amino]-4-oxo-4,5-dihydro-1H-pyrazolo[4,3-c]pyridin-1-yl}cyclohexanecarbonitrile;

2-{3-[(2-ethyl-1,1-dioxido-2,3-dihydro-1,2-benzisothiazol-5-yl)amino]-4-oxo-4,5-dihydro-1H-pyrazolo[4,3-c]pyridin-1-yl}cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile;

2-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)cyclopentanecarbonitrile;

2-(4-oxo-3-{[2-(2,2,2-trifluoroethyl)-2,3-dihydro-1H-isoindol-5-yl]amino}-4,5-dihydro-1H-pyrazolo[4,3-c]pyridin-1-yl)cyclohexanecarbonitrile;

5-({1-[2-cyanocyclohexyl]-4-oxo-4,5-dihydro-1H-pyrazolo[4,3-c]pyridin-3-yl}amino)-2,3-dihydro-1H-indene-2-carboxylic acid;

2-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}cyclopentanecarbonitrile;

2-(3-{[2-(cyclopropylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{3-[(2-methyl-2,3-dihydro-1H-isoindol-5-yl)amino]-4-oxo-4,5-dihydro-1H-pyrazolo[4,3-c]pyridin-1-yl}cyclohexanecarbonitrile;

2-[3-({4-[1-(dimethylamino)-2,2,2-trifluoroethyl]phenyl}amino)-4-oxo-4,5-dihydro-1H-pyrazolo[4,3-c]pyridin-1-yl]cyclohexanecarbonitrile;

2-(3-{[2-(cyclopentylmethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-{4-oxo-3-[(4-{1-[(2,2,2-trifluoroethyl)amino]ethyl}phenyl)amino]-4,5-dihydro-1H-pyrazolo[4,3-c]pyridin-1-yl}cyclohexanecarbonitrile;

4-({1-[2-cyanocyclohexyl]-4-oxo-4,5-dihydro-1H-pyrazolo[4,3-c]pyridin-3-yl}amino)-N,N,2-trimethylbenzamide;

2-(3-{[3-methyl-4-(morpholin-4-ylcarbonyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-2-cyclopropyl-N,N-dimethylbenzamide;

2-[3-({4-[1-amino-2,2-difluoroethyl]phenyl}amino)-4-oxo-4,5-dihydro-1H-pyrazolo[4,3-c]pyridin-1-yl]cyclohexanecarbonitrile;

2-(3-{[4-(2,2-difluoro-1-hydroxyethyl)phenyl]amino}-4-oxo-4,5-dihydro-1H-pyrazolo[4,3-c]pyridin-1-yl)cyclohexanecarbonitrile;

2-[4-oxo-3-({4-[pyrrolidin-2-yl]phenyl}amino)-4,5-dihydro-1H-pyrazolo[4,3-c]pyridin-1-yl]cyclohexanecarbonitrile;

2-(3-{[2-(1-methylethyl)-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[2-(2-methylpropyl)-2,3-dihydro-1H-isoindol-5-yl]amino}-4-oxo-4,5-dihydro-1H-pyrazolo[4,3-c]pyridin-1-yl)cyclohexanecarbonitrile;

2-{3-[(2-ethyl-2,3-dihydro-1H-isoindol-5-yl)amino]-4-oxo-4,5-dihydro-1H-pyrazolo[4,3-c]pyridin-1-yl}cyclohexanecarbonitrile;

2-(3-{[2-(cyclopropylmethyl)-2,3-dihydro-1H-isoindol-5-yl]amino}-4-oxo-4,5-dihydro-1H-pyrazolo[4,3-c]pyridin-1-yl)cyclohexanecarbonitrile;

2-[3-({3-[(methylsulfanyl)methyl]-5-(1H-1,2,3-triazol-1-ylmethyl)phenyl}amino)-4-oxo-4,5-dihydro-1H-pyrazolo[4,3-c]pyridin-1-yl]cyclohexanecarbonitrile;

2-(3-{[2-(1-methylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(2-hydroxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(3-hydroxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-[4-oxo-3-({4-[1-(1H-1,2,3-triazol-1-yl)ethyl]phenyl}amino)-4,5-dihydro-1H-pyrazolo[4,3-c]pyridin-1-yl]cyclohexanecarbonitrile;

2-[3-({4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile;

2-(3-{[2-(3-hydroxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-[3-({4-[1-amino-2,2,2-trifluoroethyl]phenyl}amino)-4-oxo-4,5-dihydro-1H-pyrazolo[4,3-c]pyridin-1-yl]cyclopentanecarbonitrile;

2-(3-{[2-(2-methoxyethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-(aminomethyl)phenyl]amino}-4-oxo-4,5-dihydro-1H-pyrazolo[4,3-c]pyridin-1-yl)cyclohexanecarbonitrile;

2-[3-({4-[(1-methylethyl)sulfonyl]phenyl}amino)-4-oxo-4,5-dihydro-1H-pyrazolo[4,3-c]pyridin-1-yl]cyclopentanecarbonitrile;

2-(3-{[4-(tert-butylsulfonyl)phenyl]amino}-4-oxo-4,5-dihydro-1H-pyrazolo[4,3-c]pyridin-1-yl)cyclopentanecarbonitrile;

N-tert-butyl-4-({1-[2-cyanocyclopentyl]-4-oxo-4,5-dihydro-1H-pyrazolo[4,3-c]pyridin-3-yl}amino)benzenesulfonamide;

2-(4-oxo-3-((4-(propan-2-methylsulfonimidoyl)phenyl)amino)-4,5-dihydro-1H-pyrazolo[4,3-c]pyridin-1-yl)cyclopentanecarbonitrile;

2-(3-{[4-(methylsulfonimidoyl)phenyl]amino}-4-oxo-4,5-dihydro-1H-pyrazolo[4,3-c]pyridin-1-yl)cyclohexanecarbonitrile;

4-({1-[2-cyanocyclopentyl]-4-oxo-4,5-dihydro-1H-pyrazolo[4,3-c]pyridin-3-ylamino)benzonitrile;

2-[3-({4-[1-(ethylamino)-2,2,2-trifluoroethyl]phenylamino)-4-oxo-4,5-dihydro-1H-pyrazolo[4,3-c]pyridin-1-yl]cyclopentanecarbonitrile;

2-(4-oxo-3-((4-(2,2,2-trifluoro-1-(isopropylamino)ethyl)phenyl)amino)-4,5-dihydro-1H-pyrazolo[4,3-c]pyridin-1-yl)cyclopentanecarbonitrile;

ethyl 3-(4-((1-(2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate;

isopropyl 3-(4-((1-2-cyanocyclohexyl)-4-oxo-4,5-dihydro-1H-pyrazolo[4,3-c]pyridin-3-yl)amino)phenyl)-4,4,4-trifluoro-3-hydroxy-2,2-dimethylbutanoate;

2-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)cyclohexanecarbonitrile;

2-(3-((1'-hydroxy-1'-(trifluoromethyl)-1',3'-dihydrospiro[cyclopropane-1,2'-inden]-5'-yl)amino)-4-oxo-4,5-dihydro-1H-pyrazolo[4,3-c]pyridin-1-yl)cyclohexanecarbonitrile 2-(4-oxo-3-((4-(1,1,1-trifluoro-2-methoxypropan-2-yl)phenyl)amino)-4,5-dihydro-1H-pyrazolo[4,3-c]pyridin-1-yl)cyclohexanecarbonitrile;

2-(3-((2,3-dimethyl-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-((3-methyl-1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-((4-(4,4-difluoropiperidine-1-carbonyl)-3-methylphenyl)amino)-4-oxo-4,5-dihydro-1H-pyrazolo[4,3-c]pyridin-1-yl)cyclohexanecarbonitrile;

2-(3-((2-(2,5-dimethylmorpholino)quinolin-6-yl)amino)-4-oxo-4,5-dihydro-1H-pyrazolo[4,3-c]pyridin-1-yl)cyclohexanecarbonitrile;

tert-butyl 4-(5-((1-(2-cyanocyclohexyl)-4-oxo-4,5-dihydro-1H-pyrazolo[4,3-c]pyridin-3-yl)amino)-1-oxoisoindolin-2-yl)cyclohexanecarboxylate;

2-[3-({4-[1-amino-2,2,2-trifluoroethyl]phenylamino)-4-oxo-4,5-dihydro-1H-pyrazolo[4,3-c]pyridin-1-yl]cyclopentanecarbonitrile;

2-(4-oxo-3-((4-(1,1,1-trifluoro-2-hydroxypropan-2-yl)phenyl)amino)-4,5-dihydro-1H-pyrazolo[4,3-c]pyridin-1-yl)cyclopentanecarbonitrile;

N-tert-butyl-4-({1-2-cyanocyclohexyl]-4-oxo-4,5-dihydro-1H-pyrazolo[4,3-c]pyridin-3-yl}amino)benzenesulfonamide;

2-[3-({4-[(1-methylethyl)sulfonyl]phenyl}amino)-4-oxo-4,5-dihydro-1H-pyrazolo[4,3-c]pyridin-1-yl]cyclohexanecarbonitrile;

N-tert-butyl-4-({1-[2-cyanocyclohexyl]-4-oxo-4,5-dihydro-1H-pyrazolo[4,3-c]pyridin-3-yl}amino)-N-methylbenzenesulfonamide;

2-(3-{[4-(tert-butylsulfonyl)phenyl]amino}-4-oxo-4,5-dihydro-1H-pyrazolo[4,3-c]pyridin-1-yl)cyclohexanecarbonitrile;

4-({1-[2-cyanocyclohexyl]-4-oxo-4,5-dihydro-1H-pyrazolo[4,3-c]pyridin-3-yl}amino)-N-methylbenzenesulfonamide;

2-[3-({4-[1-(2-methoxyethyl)-1H-pyrazol-4-yl]phenyl}amino)-4-oxo-4,5-dihydro-1H-pyrazolo[4,3-c]pyridin-1-yl]cyclohexanecarbonitrile;

2-(3-{[3-chloro-4-(1-methyl-1H-pyrazol-4-yl)phenyl]amino}-4-oxo-4,5-dihydro-1H-pyrazolo[4,3-c]pyridin-1-yl)cyclohexanecarbonitrile;

2-[3-({4-[1-methyl-1-(1H-1,2,3-triazol-1-yl)ethyl]phenyl}amino)-4-oxo-4,5-dihydro-1H-pyrazolo[4,3-c]pyridin-1-yl]cyclohexanecarbonitrile;

2-[3-({2-[1,2-dimethylpropyl]-2,3-dihydro-1H-isoindol-5-yl}amino)-4-oxo-4,5-dihydro-1H-pyrazolo[4,3-c]pyridin-1-yl]cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]propanoate;

tert-butyl [5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]acetate;

tert-butyl 2-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-2-methylpropanoate;

2-(3-{[2-(1-methylethyl)-1-oxo-2,3-dihydro-1H-isoindol-5-yl]amino}-4-oxo-4,5-dihydro-1H-pyrazolo[4,3-c]pyridin-1-yl)cyclohexanecarbonitrile;

2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,1-dioxido-1,2-benzisothiazol-2(3H)-yl]-3-methylbutanoate;

2-[4-oxo-3-(1,2,3,4-tetrahydroisoquinolin-6-ylamino)-4,5-dihydro-1H-pyrazolo[4,3-c]pyridin-1-yl]cyclohexanecarbonitrile;

2-[4-oxo-3-(1,2,3,4-tetrahydroisoquinolin-7-ylamino)-4,5-dihydro-1H-pyrazolo[4,3-c]pyridin-1-yl]cyclohexanecarbonitrile;

2-[4-oxo-3-({2-[(5-piperidin-1-ylpyrazin-2-yl)carbonyl]-2,3-dihydro-1H-isoindol-5-yl}amino)-4,5-dihydro-1H-pyrazolo[4,3-c]pyridin-1-yl]cyclohexanecarbonitrile;

2-(3-((2-(3-methoxy-2,2-dimethylpropyl)-1,1-dioxido-2,3-dihydrobenzo[d]isothiazol-5-yl)amino)-4-oxo-4,5-dihydro-1H-pyrazolo[4,3-c]pyridin-1-yl)cyclohexanecarbonitrile;

2-(3-{[2-(2-methoxy-1,1-dimethylethyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(3-methoxy-1,1-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[2-(cyclopentylmethyl)-2,3-dihydro-1H-isoindol-5-yl]amino}-4-oxo-4,5-dihydro-1H-pyrazolo[4,3-c]pyridin-1-yl)cyclohexanecarbonitrile;

tert-butyl 3-[5-({1-[2-cyanocyclohexyl]-4-oxo-4,5-dihydro-1H-pyrazolo[4,3-c]pyridin-3-yl}amino)-1,3-dihydro-2H-isoindol-2-yl]propanoate;

tert-butyl [5-({1-[2-cyanocyclohexyl]-4-oxo-4,5-dihydro-1H-pyrazolo[4,3-c]pyridin-3-yl}amino)-1,3-dihydro-2H-isoindol-2-yl]acetate;

tert-butyl 3-(4-((1-(2-cyanocyclohexyl)-4-oxo-4,5-dihydro-1H-pyrazolo[4,3-c]pyridin-3-yl)amino)phenyl)-8-azabicyclo[3.2.1]octane-8-carboxylate;

2-(3-{[4-(tert-butylsulfonyl)phenyl]amino}-4-oxo-4,5-dihydro-1H-pyrazolo[4,3-c]pyridin-1-yl)cycloheptanecarbonitrile;

2-{3-[(2,2-dimethyl-1,1-dioxido-3-oxo-2,3-dihydro-1-benzothiophen-5-yl)amino]-4-oxo-4,5-dihydro-1H-pyrazolo[4,3-c]pyridin-1-yl}cyclohexanecarbonitrile;

2-(3-{[3-hydroxy-2,2-dimethyl-1,1-dioxido-2,3-dihydro-1-benzothiophen-5-yl]amino}-4-oxo-4,5-dihydro-1H-pyrazolo[4,3-c]pyridin-1-yl)cyclohexanecarbonitrile;

2-(3-{[3-hydroxy-1,1-dioxido-3H-spiro[1-benzothiophene-2,1'-cyclohexan]-5-yl]amino}-4-oxo-4,5-dihydro-1H-pyrazolo[4,3-c]pyridin-1-yl)cyclohexanecarbonitrile;

2-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}cycloheptanecarbonitrile;

2-(3-{[1-methyl-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[4-(1,3-oxazol-2-yl)phenyl]amino}-4-oxo-4,5-dihydro-1H-pyrazolo[4,3-c]pyridin-1-yl)cyclohexanecarbonitrile;

2-(4-oxo-3-{[4-(1,3-thiazol-2-yl)phenyl]amino}-4,5-dihydro-1H-pyrazolo[4,3-c]pyridin-1-yl)cyclohexanecarbonitrile;

2-(3-{[4-(1,2,4-oxadiazol-3-yl)phenyl]amino}-4-oxo-4,5-dihydro-1H-pyrazolo[4,3-c]pyridin-1-yl)cyclohexanecarbonitrile;

2-{3-[(4-isoxazol-3-ylphenyl)amino]-4-oxo-4,5-dihydro-1H-pyrazolo[4,3-c]pyridin-1-yl}cyclohexanecarbonitrile;

2-{3-[(4-isoxazol-5-ylphenyl)amino]-4-oxo-4,5-dihydro-1H-pyrazolo[4,3-c]pyridin-1-yl}cyclohexanecarbonitrile;

2-(3-{[4-(1,2,4-oxadiazol-5-yl)phenyl]amino}-4-oxo-4,5-dihydro-1H-pyrazolo[4,3-c]pyridin-1-yl)cyclohexanecarbonitrile;

2-{3-[(3,3-dimethyl-2-oxo-2,3-dihydro-1H-indol-6-yl)amino]-4-oxo-4,5-dihydro-1H-pyrazolo[4,3-c]pyridin-1-yl}cyclohexanecarbonitrile;

2-(3-{[4-(1,3-oxazol-5-yl)phenyl]amino}-4-oxo-4,5-dihydro-1H-pyrazolo[4,3-c]pyridin-1-yl)cyclohexanecarbonitrile;

2-(3-{[4-(3-hydroxyoxetan-3-yl)phenyl]amino}-4-oxo-4,5-dihydro-1H-pyrazolo[4,3-c]pyridin-1-yl)cyclohexanecarbonitrile;

2-{3-[(2-methyl-1,3-benzothiazol-6-yl)amino]-4-oxo-4,5-dihydro-1H-pyrazolo[4,3-c]pyridin-1-yl}cyclohexanecarbonitrile;

2-(4-oxo-3-((4-(1,1,1-trifluoro-2-hydroxypropan-2-yl)phenyl)amino)-4,5-dihydro-1H-pyrazolo[4,3-c]pyridin-1-yl)cyclohexanecarbonitrile;

2-(3-{[4-(3-methyloxetan-3-yl)phenyl]amino}-4-oxo-4,5-dihydro-1H-pyrazolo[4,3-c]pyridin-1-yl)cyclohexanecarbonitrile;

2-[3-({4-[1-(2-cyanoethyl)-1H-pyrazol-4-yl]phenyl}amino)-4-oxo-4,5-dihydro-1H-pyrazolo[4,3-c]pyridin-1-yl]cyclohexanecarbonitrile;

ethyl 1-[4-({1-[2-cyanocyclohexyl]-4-oxo-4,5-dihydro-1H-pyrazolo[4,3-c]pyridin-3-yl}amino)-2-methylphenyl]-1H-pyrazole-4-carboxylate;

isopropyl 6-((1-(2-cyanocyclohexyl)-4-oxo-4,5-dihydro-1H-pyrazolo[4,3-c]pyridin-3-yl)amino)quinoline-2-carboxylate;

2-(4-oxo-3-{[4-(5-oxo-4,5-dihydro-1,2,4-oxadiazol-3-yl)phenyl]amino}-4,5-dihydro-1H-pyrazolo[4,3-c]pyridin-1-yl)cyclohexanecarbonitrile;

2-[3-({4-[1-(2-cyanoethyl)-1H-pyrazol-4-yl]-3-methylphenyl}amino)-4-oxo-4,5-dihydro-1H-pyrazolo[4,3-c]pyridin-1-yl]cyclohexanecarbonitrile;

2-[4-oxo-3-({4-[1-trifluoromethyl)cyclopropyl]phenyl}amino)-4,5-dihydro-1H-pyrazolo[4,3-c]pyridin-1-yl]cyclohexanecarbonitrile;

2-{3-[(2-tert-butyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

2-[4-oxo-3-({4-[1-(2H-1,2,3-triazol-2-yl)ethyl]phenyl}amino)-4,5-dihydro-1H-pyrazolo[4,3-c]pyridin-1-yl]cyclohexanecarbonitrile;

2-[3-({4-[2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile;

2-{4-oxo-3-[(4-piperidin-4-ylphenyl)amino]-4,5-dihydro-1H-pyrazolo[4,3-c]pyridin-1-yl}cyclohexanecarbonitrile;

2-{3-[(2-acetyl-2,3-dihydro-1H-isoindol-5-yl)amino]-4-oxo-4,5-dihydro-1H-pyrazolo[4,3-c]pyridin-1-yl}cyclohexanecarbonitrile;

2-(3-{[1-(difluoromethyl)-2,3-dihydro-1H-isoindol-5-yl]amino}-4-oxo-4,5-dihydro-1H-pyrazolo[4,3-c]pyridin-1-yl)cyclohexanecarbonitrile;

2-[3-({4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile;

2-[3-({4-[2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile;

2-[3-({3-methyl-4-[1-methyl-1-(2H-1,2,3-triazol-2-yl)ethyl]phenyl}amino)-4-oxo-4,5-dihydro-1H-pyrazolo[4,3-c]pyridin-1-yl]cyclohexanecarbonitrile;

2-{3-[(2-cyclohexyl-1-oxo-2,3-dihydro-1H-isoindol-5-yl)amino]-4-oxo-4,5-dihydro-1H-pyrazolo[4,3-c]pyridin-1-yl}cyclohexanecarbonitrile;

2-[3-({3-methyl-4-[2-methyl-1-(2H-1,2,3-triazol-2-yl)propyl]phenyl}amino)-4-oxo-4,5-dihydro-1H-pyrazolo[4,3-c]pyridin-1-yl]cyclohexanecarbonitrile;

2-[3-({3-methyl-4-[2-methyl-1-(1H-1,2,3-triazol-1-yl)propyl]phenyl}amino)-4-oxo-4,5-dihydro-1H-pyrazolo[4,3-c]pyridin-1-yl]cyclohexanecarbonitrile;

tert-butyl 4-(4-((1-(2-cyanocyclohexyl)-4-oxo-4,5-dihydro-1H-pyrazolo[4,3-c]pyridin-3-yl)amino)phenyl)-4-hydroxycyclohexanecarboxylate;

2-[4-oxo-3-({4-[1-(1H-1,2,3-triazol-1-yl)ethyl]phenyl}amino)-4,5-dihydro-1H-pyrazolo[4,3-c]pyridin-1-yl]cyclohexanecarbonitrile;

tert-butyl 4-(5-((1-(2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylate;

2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-methyl-4-(pyrrolidin-1-ylcarbonyl)phenyl]amino}-4-oxo-4,5-dihydro-1H-pyrazolo[4,3-c]pyridin-1-yl)cycloheptanecarbonitrile;

2-(3-{[2-(3-methoxy-2,2-dimethylpropyl)-1,1-dioxido-2,3-dihydro-1,2-benzisothiazol-5-yl]amino}-4-oxo-4,5-dihydro-1H-pyrazolo[4,3-c]pyridin-1-yl)cycloheptanecarbonitrile;

N-tert-butyl-4-({1-[2-cyanocycloheptyl]-4-oxo-4,5-dihydro-1H-pyrazolo[4,3-c]pyridin-3-yl}amino)-N-methylbenzenesulfonamide;

2-{3-[(2-cyclopentyl-1-oxo-2,3-dihydro-1H-isoindol-5-yl)amino]-4-oxo-4,5-dihydro-1H-pyrazolo[4,3-c]pyridin-1-yl}cycloheptanecarbonitrile;

2-(4-oxo-3-{[2-(piperidin-1-ylcarbonyl)-2,3-dihydro-1H-isoindol-5-yl]amino-4,5-dihydro-1H-pyrazolo[4,3-c]pyridin-1-yl)cycloheptanecarbonitrile;

2-(3-{[1,1-dioxido-2-(tetrahydro-2H-pyran-4-yl)-2,3-dihydro-1,2-benzisothiazol-5-yl]amino}-4-oxo-4,5-dihydro-1H-pyrazolo[4,3-c]pyridin-1-yl)cycloheptanecarbonitrile;

2-[3-({4-[1-(4-tert-butyl-1H-1,2,3-triazol-1-yl)-2-methylpropyl]phenyl}amino)-4-oxo-4,5-dihydro-1H-pyrazolo[4,3-c]pyridin-1-yl]cyclohexanecarbonitrile;

tert-butyl 1-{1-[4-({1-[2-cyanocyclohexyl]-4-oxo-4,5-dihydro-1H-pyrazolo[4,3-c]pyridin-3-yl}amino)phenyl]-2-methylpropyl 1-1H-1,2,3-triazole-4-carboxylate;

2-(4-oxo-3-{[1-oxo-2-(tetrahydro-2H-pyran-4-yl)-2,3-dihydro-1H-isoindol-5-yl]amino}-4,5-dihydro-1H-pyrazolo[4,3-c]pyridin-1-yl)cyclohexanecarbonitrile;

2-(4-oxo-3-{[1-oxo-2-(tetrahydro-2H-thiopyran-4-yl)-2,3-dihydro-1H-isoindol-5-yl]amino}-4,5-dihydro-1H-pyrazolo[4,3-c]pyridin-1-yl)cyclohexanecarbonitrile;

2-[4-oxo-3-({4-[2-(trifluoromethyl)pyrrolidin-2-yl]phenyl}amino)-4,5-dihydro-1H-pyrazolo[4,3-c]pyridin-1-yl]cyclohexanecarbonitrile;

2-(3-{[2-(4-methyltetrahydro-2H-pyran-4-yl)-1-oxo-2,3-dihydro-1H-isoindol-5-yl]amino}-4-oxo-4,5-dihydro-1H-pyrazolo[4,3-c]pyridin-1-yl)cyclohexanecarbonitrile;

2-(3-{[2-(4-methyltetrahydro-2H-pyran-4-yl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile;

2-(3-{[3-hydroxy-1,1-dioxido-2',3',5',6'-tetrahydro-3H-spiro[1-benzothiophene-2,4'-pyran]-5-yl]amino}-4-oxo-4,5-dihydro-1H-pyrazolo[4,3-c]pyridin-1-yl)cyclohexanecarbonitrile;

2-(3-((3-methyl-4-(2,2,2-trifluoro-1-hydroxyethyl)phenyl)amino)-4-oxo-4,5-dihydro-1H-pyrazolo[4,3-c]pyridin-1-yl)cycloheptanecarbonitrile;

4-((1-(2-cyanocyclohexyl)-4-oxo-4,5-dihydro-1H-pyrazolo[4,3-c]pyridin-3-yl)amino)benzoic acid;

4-(5-((1-(2-cyanocyclohexyl)-4-oxo-4,5-dihydro-1H-pyrazolo[4,3-c]pyridin-3-yl)amino)-1,1-dioxidobenzo[d]isothiazol-2(3H)-yl)cyclohexanecarboxylic acid;

4-(4-(1-(2-cyanocyclohexyl)-4-oxo-4,5-dihydro-1H-pyrazolo[4,3-c]pyridin-3-ylamino)phenyl)-4-hydroxycyclohexanecarboxylic acid;

tert-butyl 5-((1-(2-cyanocyclohexyl)-4-oxo-4,5-dihydro-1H-pyrazolo[4,3-c]pyridin-3-yl)amino)-1-methylisoindoline-2-carboxylate;

2-(3-((2-isopropyl-1-methylisoindolin-5-yl)amino)-4-oxo-4,5-dihydro-1H-pyrazolo[4,3-c]pyridin-1-yl)cyclohexanecarbonitrile;

2-(3-((4-(8-azabicyclo[3.2.1]octan-3-yl)phenyl)amino)-4-oxo-4,5-dihydro-1H-pyrazolo[4,3-c]pyridin-1-yl)cyclohexanecarbonitrile;

2-(3-((2,2-dimethyl-1,1-dioxido-2,3-dihydrobenzo[b]thiophen-5-yl)amino)-4-oxo-4,5-dihydro-1H-pyrazolo[4,3-c]pyridin-1-yl)cyclohexanecarbonitrile;

2-(3-((1,1-dioxido-3H-spiro[benzo[b]thiophene-2,1'-cyclohexan]-5-yl)amino)-4-oxo-4,5-dihydro-1H-pyrazolo[4,3-c]pyridin-1-yl)cyclohexanecarbonitrile;

2-{3-[(1,1-dioxido-2',3',5',6'-tetrahydro-3H-spiro[1-benzothiophene-2,4'-pyran]-5-yl)amino]-4-oxo-4,5-dihydro-1H-pyrazolo[4,3-c]pyridin-1-yl}cyclohexanecarbonitrile;

2-(3-((4-(tert-butylsulfonyl)phenyl)amino)-4-oxo-4,5-dihydro-1H-pyrazolo[4,3-c]pyridin-1-yl)-4,4-difluorocyclopentanecarbonitrile;

4,4-difluoro-2-(3-{[3-methyl-4-(pyrrolidin-1-ylcarbonyl)phenyl]amino}-4-oxo-4,5-dihydro-1H-pyrazolo[4,3-c]pyridin-1-yl)cyclopentanecarbonitrile;

2-[4-oxo-3-({4-2-(trifluoromethyl)piperidin-2-yl]phenyl}amino)-4,5-dihydro-1H-pyrazolo[4,3-c]pyridin-1-yl]cycloheptanecarbonitrile;

2-[4-oxo-3-({4-2-(trifluoromethyl)piperidin-2-yl]phenyl}amino)-4,5-dihydro-1H-pyrazolo[4,3-c]pyridin-1-yl]cyclopentanecarbonitrile;

2-(3-{[2-(4,4-difluoro-1-methylcyclohexyl)-1,1-dioxido-2,3-dihydro-1,2-benzisothiazol-5-yl]amino}-4-oxo-4,5-dihydro-1H-pyrazolo[4,3-c]pyridin-1-yl)cyclohexanecarbonitrile; and 2-[4-oxo-3-({4-[2-(trifluoromethyl)piperidin-2-yl]phenyl}amino)-4,5-dihydro-1H-pyrazolo[4,3-c]pyridin-1-yl]cyclohexanecarbonitrile.

8. A pharmaceutical composition comprising a compound of claim 1 or a pharmaceutically acceptable salt thereof and a pharmaceutically acceptable carrier.

9. A method for the treatment of a JAK-mediated disease comprising administering to a patient in need thereof a therapeutically effective amount of a compound of claim 1 or a pharmaceutically acceptable thereof.

10. A method of treating a condition in a mammal that can be ameliorated by the inhibition of Janus kinases JAK1 and JAK 2 which condition is selected from, arthritis, asthma and obstructive airways diseases, autoimmune diseases or disorders, and cancer comprising administering to the mammal in need of such treatment, a therapeutically effective amount of a compound according to claim for a pharmaceutically acceptable salt or a stereoisomer thereof.

11. A method according to claim 10, wherein said condition is arthritis.

12. A method according to claim 11, wherein said condition is selected from rheumatoid arthritis, juvenile arthritis, and psoriatic arthritis.

13. A method according to claim 10, wherein said condition is asthma or obstructive airways diseases.

14. A method according to claim 13, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease (COPD), and emphysema.

15. A method according to claim 10, wherein said condition is autoimmune diseases or disorders.

16. A method of treating asthma characterized by JAK activation in a mammal in need thereof, comprising administering a therapeutically effective amount of a compound according to claim 1 or a pharmaceutically acceptable salt thereof.

17. A method of treating arthritis characterized by JAK activation in a mammal in need thereof, comprising administering a therapeutically effective amount of a compound according to claim 1 or a pharmaceutically acceptable salt thereof.

* * * * *